US006537751B1

(12) United States Patent
Cohen et al.

(10) Patent No.: US 6,537,751 B1
(45) Date of Patent: Mar. 25, 2003

(54) BIALLELIC MARKERS FOR USE IN CONSTRUCTING A HIGH DENSITY DISEQUILIBRIUM MAP OF THE HUMAN GENOME

(75) Inventors: Daniel Cohen, Neuilly-sur-Seine (FR); Ilya Chumakov, Vaux-le-Pénil (FR); Marta Blumenfeld, Paris (FR)

(73) Assignee: Genset S.A. (FR)

( * ) Notice: Subject to any disclaimer, the term of this patent is extended or adjusted under 35 U.S.C. 154(b) by 553 days.

(21) Appl. No.: 09/422,978

(22) Filed: Oct. 20, 1999

Related U.S. Application Data

(63) Continuation-in-part of application No. 09/298,850, filed on Apr. 21, 1999, now abandoned, and a continuation-in-part of application No. PCT/IB99/00822, filed on Apr. 21, 1999.
(60) Provisional application No. 60/109,732, filed on Nov. 23, 1998, and provisional application No. 60/082,614, filed on Apr. 21, 1998.

(51) Int. Cl.$^7$ ............................ C07H 21/04; C12Q 1/68

(52) U.S. Cl. ........................ 435/6; 435/91.2; 536/23.1; 536/24.3; 536/23.4

(58) Field of Search ................... 435/6, 91.2; 536/23.1, 536/24.3, 23.4

(56) References Cited

U.S. PATENT DOCUMENTS 5,589,136 A 12/1996 Northrup et al.

FOREIGN PATENT DOCUMENTS

| EP | 0 785 280 A2 | 7/1997 |
|---|---|---|
| WO | WO 91 13075 A | 9/1991 |
| WO | WO 95/12607 | 5/1996 |
| WO | WO 98/20165 | 5/1998 |
| WO | WO 99/04038 | 1/1999 |
| WO | WO 99/32644 | 7/1999 |

OTHER PUBLICATIONS

Gyapay, G., et al., "The 1993–94 Généthon Human Genetic Linkage Map", Nature Genetics, vol. 7, pp. 246–249, Jun. 1994.
Hillier et al. Genbank Accession No. AA143179, May 1997.*
Freitas et al. Genbank Accession No. AF050154, "Homo sapiens clonse F19374 Apo E–C2 gene cluster" Mar. 1999.*
Freitas et al. "Sequencing of 42kb of the APO E–C2 gene cluster reveals a new gene : PEREC1". DNA Sequence. vol. 9, No. 2, pp. 89–100, 1998.*
Benham, F., et al., "A Method for Generating Hybrids Containing Nonselected Fragments of Human Chromosomes". Gennomics, vol. 4 pp. 509–517.
Ches, M., et al., "Accessing Genetic Information with High–Density DNA Arrays", Science, vol. 274. pp. 610–614, Oct. 25, 1996.

Cherif, D., et al., "Simultaneous Localization of Cosmids and Chromosome R–banding by Fluorescence Microscopy: Application to Regional Mapping of Human Chromosome 11". Proc. Natl. Acad. Sci., vol. 87, pp. 6639–6643, Sep. 1990.
Chumakov, I. M., et al., "A YAC Contig Map of the Human Genome". Nature, vol. 377, pp. 175–287, Sep. 28, 1995.
Cox. D. et al., "Radiation Hybrid Mapping: A somatic Cell Genetic Method for Constructing High–Resolution Maps of Mammalian Chromosomes". Scinece. vol. 250. pp. 245–250, Oct. 12, 1990.
Cox, et al., "Assessing Mapping Progress in the Human Genome Project". Science. vol. 265, pp. 2031–2032, 1994.
Excoffier. L.. et al., "Maximum–Likelihood Estimation of Molecular Haplotype Frequencies in a Diploid Population", Mol. Biol. Evol., 1(15):921–927, 1995.
Fan, J., et al., "Genetic Mapping: Finding and Analyzing Single–Nucleotide Polymorphisms with High–Density DNA Arrays", Am. J. Human Genetics, vol. 71. No. 4, 1997.
Foster, J., et al., "High–Resolution Whole Genome Radiation Hybrid Map of Human Chromosome 17q22–q25.3 Across the Genes for GM and TK", Genomics, vol. 33, pp. 185–192, 1996.
Frazier, K., et al., "A Radiation Hybrid Map of the Region on Human Chromosome 22 Containing the Neurolibromatosis Type 2 Locus", Genomics, vol. 14, pp. 574–584. 1992.
Hudson. T., et al., "An STS–Based Map of the Human Genome", Science. vol. 270, pp. 1945–1954, Dec. 22, 1995.
Kim. et al., "Construction and Characterization of a Human Bacterial Artificial Chromosome Library", Genomics, vol. 34, pp. 213–218, 1996.
Kruglyak, L., "The Use of a Genetic Map of Biallelic Markers in Linkage Studies", Nature Genetics, vol. 17, Sep. 17, 1997.
Ledbetler, S., et al., Rapid Isolation of DNA Probes within Specific Chromosome Regions by Interspersed Repetitive Sequence Polymerase Chain Reaction. Genomics. vol. 5, pp. 475–481, 1990.

(List continued on next page.)

*Primary Examiner*—W. Gary Jones
*Assistant Examiner*—Jeanine Goldberg
(74) *Attorney, Agent, or Firm*—Saliwanchik, Lloyd & Saliwanchik

(57) ABSTRACT

The present invention relates to genomic maps comprising biallelic markers, new biallelic markers, and methods of using biallelic markers. Primers hybridizing to regions flanking these biallelic markers are also provided. This invention provides polynucleotides and methods suitable for genotyping a nucleic acid containing sample for one or more biallelic markers of the invention. Further, the invention provides a number of methods utilizing the biallelic markers of the invention including methods to detect a statistical correlation between a biallelic marker allele and a phenotype and/or between a biallelic marker haplotype and a phenotype.

5 Claims, 18 Drawing Sheets

OTHER PUBLICATIONS

Noether. Goulned E., "Introduction to Statistics. The Nonparametric Way", Springer–Verlag.

Obermayr. F., "A High–Resolution Radiation Hybrid Map of the Region Surrounding the Gorlin Syndrome Gene". Eur. J. Hum. Gene vol. 4. pp. 242–245, 1996.

Raeymaekers, P., et al., "A Radiation Hybrid Map with 60 Loci Covering the Entire Short Arm of Chromosome 12", Gennomics, vol. pp. 170–178, 1995.

Sapolsky, R., et al., "High–Throughput Polymorphism Screening and Genotyping with High–Density Oligonucleotide Arrays", Genetic Analysis, vol. 14, pp 187–192, 1999.

Schork, N., et al., "Linkage Disequilibrium Mapping Quantitative Traits within Case/Control Settings", Am. J. Human Genetics. vol. 61, No. 4, Suppl. p. A293, 1997.

Schuler, G.D., et al., A Gene Map of the Human Genome, Science, vol. 274, pp. 540–546, Oct. 25, 1996.

Syvanen, A., et al., "Identification of Individuals by Analysis Biallelic DNA Markers, Using PCR and Solid–Phase Minisequencing", J. Hum. Genet. 52:46–59, 1993.

Wang, D., et al., "Toward a Third Generation Genetic Map of the Human Genome Based on Bi–Allelic Polymorphisms", Am. J. Human Genet., vol. 59, p. A3. 1996.

Wang, D., et al., "Large–Scale Identification, Mapping and Genotyping of Single–Nucleotide Polymorphisms in the Human Genome", Science, vol. 280, pp. 1077–1082, May 15, 1998.

Warrington, J.A., et al., "Radiation Hybrid Map of 13 Loci on the Long Arm of Chromosome 5", Genomics, vol. 11, pp. 701–708, 1999.

Xiong, Li Jin. Bialletic Markers in Genelics Studies of Human Diseases: Their Power, Accuracy, and Density in Population–based Linkage Analyses.

Chumakov I., et al., "Continuum of Overlapping Clones Spanning the Entire Human Chromosome 21q", Nature, vol. 359, pp. 380–.

Cohen. D., et al., "A Fast–Generation Physical Map of the Human Genome", Nature, vol. 366, pp. 698–701, Mar. 14, 1996.

Dib C., et al., "A Comprehensive Genetic Map of the Human Genome Based on 5,264 Microsatellites", Nature, vol. 380, pp. 152–154, Mar. 14, 1996.

Doggett, N.A., et al., "An Integrated Physical Map of Human Chromosome 16", Nature, vol. 377, pp. 335–365, Sep. 28, 1995.

EMBL Database Accession No. HS448E20, Nov. 23, 1999.

Hacia, J.G., et al., "Detection of Heterozygous Mutations in BRCA1 Using High Density Oligonucleotide Arrays and Two–Colour Fluores cence Analysis", Nature, vol. 14, pp. 441–447, Dec. 14, 1996.

Hawley, M.E., et al., HAPLO: A Program Using the EM Algorithm to Estimate the Frequencies of Multi–Site Haplotypes. J. Or Heredity, 86(5): 409–411 (1995).

Kozai, M.J., et al., "Extensive Polymorphisms Observed in HIV–1 Clade B Protease Gene Using High–Density Oligonucleotide Array", Nature, vol. 2, pp. 753–759, Jul. 1996.

Larin, Z., "Fluorescence in Situ Hybridisatin of Multiple Probes on a Single Microscope Slide", Nucleic Acids Research vol. 22, No. 16, pp. 3589–3692, 1994.

Risch, N., et al., "The Futrue of Genetic Studies of Complex Human Diseases", Science, vol. 273, pp. 1516–1517, Sep. 13, 1996.

Shoemaker, D.D., et al., "Quantitative Phenotypic Analysis of Yeast Deletion Mutants Using a Highly Parallel Molecular Bar–Coding Strategy", Nature vol. 14, pp. 450–456, Dec. 14, 1996.

Wang D., et al., "Abstracts of papers presented at the 1997 meeting on Genome Mapping & Sequencing", Cold Spring Harbor Laboratory, p. 17, May 14–18, 1997.

Woo. Sung–Sick, et al., "Construction and Characterization of a Bacterial Artificial Chromosome Library of Sorghum Bicolor", Nucleic Acids Research. vol. 22, No. 22, pp. 4922–4931, 1994.

* cited by examiner

FIG. 3

| # aff | 150 | | | | | |
|---|---|---|---|---|---|---|
| # non aff | 150 | | | | | |
| pAi non aff | | 0 | 0,1 | 0,2 | 0,3 | 0,4 | 0,5 |
| Δ pAi | 0,05 | 8,7699E-05 | 0,06407752 | 0,14252002 | 0,19106311 | 0,21543442 | 0,22009395 |
| Δ pAi | 0,1 | 1,9149E-08 | 0,00060364 | 0,00467774 | 0,01023571 | 0,01382303 | 0,01382303 |
| Δ pAi | 0,15 | 3,0618E-12 | 1,3319E-06 | 3,8827E-05 | 0,0001478 | 0,0002343 | 0,00020218 |
| Δ pAi | 0,2 | 3,2153E-16 | 9,1413E-10 | 9,0305E-08 | 5,733E-07 | 9,6336E-07 | 5,733E-07 |
| Δ pAi | 0,25 | 2,0791E-20 | 2,2614E-13 | 6,2679E-11 | 5,873E-10 | 8,7113E-10 | 2,5396E-10 |
| Δ pAi | 0,3 | 7,8245E-25 | 2,152E-17 | 1,3261E-14 | 1,5189E-13 | 1,5189E-13 | 1,3261E-14 |
| Δ pAi | 0,35 | 1,6192E-29 | 7,9823E-22 | 8,4152E-19 | 9,1669E-18 | 4,2713E-18 | 5,5844E-20 |
| Δ pAi | 0,4 | 1,7336E-34 | 1,1282E-26 | 1,524E-23 | 1,1488E-22 | 1,524E-23 | 1,1282E-26 |

| # aff | 200 | | | | | |
|---|---|---|---|---|---|---|
| # non aff | 200 | | | | | |
| pAi non aff | | 0 | 0,1 | 0,2 | 0,3 | 0,4 | 0,5 |
| Δ pAi | 0,05 | 5,9233E-06 | 0,03250945 | 0,09039173 | 0,13111935 | 0,15260313 | 0,15678006 |
| Δ pAi | 0,1 | 8,649E-11 | 7,4765E-05 | 0,00109084 | 0,00302686 | 0,00447365 | 0,00447365 |
| Δ pAi | 0,15 | 8,0215E-16 | 2,3653E-08 | 2,0257E-06 | 1,1771E-05 | 2,1573E-05 | 1,7772E-05 |
| Δ pAi | 0,2 | 4,1762E-21 | 1,5375E-12 | 6,7374E-10 | 7,764E-09 | 1,5417E-08 | 7,764E-09 |
| Δ pAi | 0,25 | 1,1282E-26 | 2,525E-17 | 4,4025E-14 | 8,5532E-13 | 1,4423E-12 | 2,8149E-13 |
| Δ pAi | 0,3 | 1,4722E-32 | 1,1488E-22 | 5,8424E-19 | 1,4886E-17 | 1,4886E-17 | 5,842E-19 |
| Δ pAi | 0,35 | 8,6169E-39 | 1,4784E-28 | 1,5457E-24 | 3,6958E-23 | 1,3394E-23 | 4,197E-26 |
| Δ pAi | 0,4 | 2,0885E-45 | 5,2308E-35 | 7,6438E-31 | 1,1224E-29 | 7,6438E-31 | 5,2308E-35 |

| # aff | 500 | | | | | |
|---|---|---|---|---|---|---|
| # non aff | 500 | | | | | |
| pAi non aff | | 0 | 0,1 | 0,2 | 0,3 | 0,4 | 0,5 |
| Δ pAi | 0,05 | 8,0004E-13 | 0,00072323 | 0,00741965 | 0,0169842 | 0,02371865 | 0,02516449 |
| Δ pAi | 0,1 | 1,0695E-24 | 3,7948E-10 | 2,4176E-07 | 2,7579E-06 | 6,9679E-06 | 6,9679E-06 |
| Δ pAi | 0,15 | 3,813E-37 | 1,0719E-18 | 5,8344E-14 | 4,2622E-12 | 1,8601E-11 | 1,1611E-11 |
| Δ pAi | 0,2 | 2,9626E-50 | 5,0895E-29 | 1,6881E-22 | 6,9321E-20 | 3,7441E-19 | 6,9321E-20 |
| Δ pAi | 0,25 | 4,2697E-64 | 7,2043E-41 | 7,7528E-33 | 1,194E-29 | 4,3462E-29 | 7,6438E-31 |
| Δ pAi | 0,3 | 9,6976E-79 | 3,9328E-54 | 6,3017E-45 | 1,9429E-41 | 1,9429E-41 | 6,3017E-45 |
| Δ pAi | 0,35 | 2,911E-94 | 8,8513E-69 | 8,7879E-59 | 2,3478E-55 | 1,8839E-56 | 1,1206E-62 |
| Δ pAi | 0,4 | 9505E-111 | 7,7199E-85 | 1,8063E-74 | 1,4484E-71 | 1,8063E-74 | 7,7199E-85 |

| # aff | 150 | | | | | |
|---|---|---|---|---|---|---|
| # non aff | 850 | | | | | |
| pAi non aff | | 0 | 0,1 | 0,2 | 0,3 | 0,4 | 0,5 |
| Δ pAi | 0,05 | 2,1561E-20 | 0,00994614 | 0,04896055 | 0,08358651 | 0,10417953 | 0,11025423 |
| Δ pAi | 0,1 | 2,0126E-39 | 5,571E-07 | 0,00010149 | 0,00058665 | 0,00119145 | 0,00139743 |
| Δ pAi | 0,15 | 1,1091E-58 | 2,7555E-13 | 8,462E-09 | 2,9851E-07 | 1,2395E-06 | 1,6229E-06 |
| Δ pAi | 0,2 | 3,2726E-78 | 2,1683E-21 | 3,2211E-14 | 1,1049E-11 | 1,111E-10 | 1,5638E-10 |
| Δ pAi | 0,25 | 4,9576E-98 | 4,4952E-31 | 6,5226E-21 | 3,1015E-17 | 2,5169E-16 | 1,1763E-15 |
| Δ pAi | 0,3 | 3,749E-118 | 3,6987E-42 | 8,129E-29 | 6,9335E-24 | 5,4331E-22 | 6,5657E-22 |
| Δ pAi | 0,35 | 1,383E-138 | 1,6797E-54 | 7,1058E-38 | 1,2938E-31 | 2,9415E-29 | 2,5869E-29 |
| Δ pAi | 0,4 | 2,435E-159 | 5,4915E-68 | 4,8846E-48 | 2,1003E-40 | 1,3332E-37 | 6,8178E-38 |

| # aff | 200 | | | | | |
|---|---|---|---|---|---|---|
| # non aff | 500 | | | | | |
| pAi non aff | | 0 | 0,1 | 0,2 | 0,3 | 0,4 | 0,5 |
| Δ pAi | 0,05 | 1,0628E-12 | 0,00789803 | 0,03942584 | 0,06867566 | 0,08621572 | 0,09083704 |
| Δ pAi | 0,1 | 3,4525E-24 | 4,4217E-07 | 5,6883E-05 | 0,00031976 | 0,0006363 | 0,00070881 |
| Δ pAi | 0,15 | 5,9036E-36 | 4,3025E-13 | 3,3635E-09 | 9,2134E-08 | 3,319E-07 | 3,5871E-07 |
| Δ pAi | 0,2 | 4,7325E-48 | 1,5566E-20 | 1,0346E-14 | 1,7218E-12 | 1,1512E-11 | 1,0047E-11 |
| Δ pAi | 0,25 | 1,6694E-60 | 3,5436E-29 | 2,0473E-21 | 2,2178E-18 | 1,1498E-17 | 1,3524E-17 |
| Δ pAi | 0,3 | 2,4613E-73 | 7,2498E-39 | 3,0748E-29 | 2,0601E-25 | 3,4525E-24 | 7,4807E-25 |
| Δ pAi | 0,35 | 1,4447E-86 | 1,6945E-49 | 3,9559E-38 | 1,4118E-33 | 2,662E-32 | 1,4118E-33 |
| Δ pAi | 0,4 | 3,214E-100 | 5,3051E-61 | 4,7325E-48 | 7,1282E-43 | 1,0691E-41 | 7,2652E-44 |

| # aff | 500 | | | | | |
|---|---|---|---|---|---|---|
| # non aff | 1000 | | | | | |
| pAi non aff | | 0 | 0,1 | 0,2 | 0,3 | 0,4 | 0,5 |
| Δ pAi | 0,05 | 6,4766E-24 | 5,7827E-05 | 0,00172627 | 0,00551541 | 0,00882876 | 0,00978249 |
| Δ pAi | 0,1 | 6,5309E-47 | 3,065E-14 | 1,0301E-09 | 4,3205E-08 | 1,8833E-07 | 2,2731E-07 |
| Δ pAi | 0,15 | 1,1969E-70 | 2,0716E-27 | 3,7441E-19 | 4,6626E-16 | 6,9719E-15 | 6,9719E-15 |
| Δ pAi | 0,2 | 3,3252E-95 | 1,1636E-43 | 1,6614E-31 | 8,5632E-27 | 4,1421E-25 | 1,9885E-25 |
| Δ pAi | 0,25 | 1,227E-120 | 1,7683E-62 | 1,5329E-46 | 3,1722E-40 | 8,6765E-39 | 3,6071E-39 |
| Δ pAi | 0,3 | 5,303E-147 | 1,526E-83 | 4,2697E-64 | 2,5968E-56 | 3,9328E-54 | 2,5968E-56 |
| Δ pAi | 0,35 | 2,36E-174 | 1,184E-106 | 4,5658E-84 | 4,7426E-75 | 4,2624E-73 | 4,0958E-77 |
| Δ pAi | 0,4 | 9,446E-203 | 1,082E-131 | 2,137E-106 | 1,8014E-96 | 3,3252E-95 | 6,725E-102 |

| markers | 99-366 | 99-344 | 99-359 | 99-355 | haplotype frequencies | | odds-ratio | P value |
| --- | --- | --- | --- | --- | --- | --- | --- | --- |
| p value | 3.01E-01 | 1.11E-01 | 6.63E-01 | 1.38E-01 | cases | controls | | |
| haplotype 1 | C | G | | | 0.404 | 0.308 | 1.52 | 3.05E-03 *** |
| haplotype 2 | | G | A | | 0.203 | 0.165 | 1.29 | 1.24E-01 * |
| haplotype 3 | | | G | G | 0.375 | 0.306 | 1.36 | 2.83E-02 ** |
| haplotype 4 | C | G | A | | 0.264 | 0.209 | 1.36 | 5.95E-02 ** |
| haplotype 5 | | | | A | 0.115 | 0.071 | 1.70 | 1.64E-02 ** |
| haplotype 6 | C | | | A | 0.15 | 0.129 | 1.19 | 3.59E-01 * |
| haplotype 7 | T | | G | G | 0.225 | 0.122 | 2.09 | 4.76E-05 ***** |
| haplotype 8 | T | A | G | G | 0.228 | 0.108 | 2.44 | 2.05E-06 ****** |

POPULATIONS: AD CASES (225) | AD CONTROLS (248)

Figure 7

| | PROSTATE CANCER | NON-AFFECTED |
|---|---|---|
| | CASES (281) | CONTROLS (130) |
| characteristics of populations | 143 sporadic cases + 138 familial cases | > 65 years PSA<4 |

| markers | 99-123 | 4-26 | 4-14 | 4-77 | 99-217 | 4-67 | 99-213 | 99-221 | 99-135 | haplotype frequencies | | relative risk | pvalue | |
|---|---|---|---|---|---|---|---|---|---|---|---|---|---|---|
| bacs | H0287B09 | B0189E08 | | | | B0463F01 | | | B0725B12 | | | | | |
| genes | | | | <----------PG1----------> | | | | | | | | | | |
| p value | 2.00E-01 | 1.00E-01 | 1.00E-01 | 2.00E-02 | 2.00E-02 | 6.00E-04 | 9.00E-02 | 7.00E-01 | 2.00E-01 | cases | controls | | | |
| haplotype 8 >304kb< | C | A | C | G | T | T | C | A | A | 0.075 | 0.018 | 4.42 | 9.00E-04 | *** |
| haplotype 7 >286kb< | | A | C | G | T | T | C | A | A | 0.095 | 0.016 | 6.46 | 6.00E-05 | **** |
| haplotype 6 <186kb> | | A | C | G | T | T | C | A | | 0.116 | 0.019 | 6.78 | 1.00E-05 | ***** |
| haplotype 5 <171kb> | | | C | G | T | T | C | A | | 0.117 | 0.013 | 10.06 | 9.00E-07 | ****** |
| haplotype 4 <83kb> | | | | G | T | T | C | A | | 0.117 | 0.025 | 5.17 | 2.00E-05 | ***** |
| haplotype 3.1 <54kb> | | | | | T | T | C | A | | 0.117 | 0.027 | 4.78 | 2.00E-05 | ***** |
| haplotype 3.2 <54kb> | | | | G | T | T | C | | | 0.222 | 0.109 | 2.33 | 4.00E-05 | ***** |
| haplotype 2.2 <39kb> | | | | G | T | T | C | | | 0.251 | 0.134 | 2.17 | 2.00E-04 | **** |
| haplotype 2 <32kb> | | | | | T | T | C | | | 0.226 | 0.112 | 2.32 | 1.00E-04 | *** |
| haplotype 1.1 <17 kb> | | | | | | T | | | | 0.256 | 0.146 | 2.01 | 3.00E-04 | **** |
| haplotype 1.2 <15 kb> | | | | | | T | C | | | 0.233 | 0.129 | 2.05 | 6.00E-04 | *** |

Figure 12

PROSTATE CANCER HAPLOTYPE SIMULATIONS (100 ITERATIONS)
| markers | 4-14 | 4-77 | 99-217 | 4-67 | 99-213 | 99-221 | haplotype frequencies | | relative risk | pvalue |
| --- | --- | --- | --- | --- | --- | --- | --- | --- | --- | --- |
| | | | | | | | cases | controls | | |
| haplotype | C | G | T | T | G | A | 0.117 | 0.013 | 10.06 | 9.00E-07 |
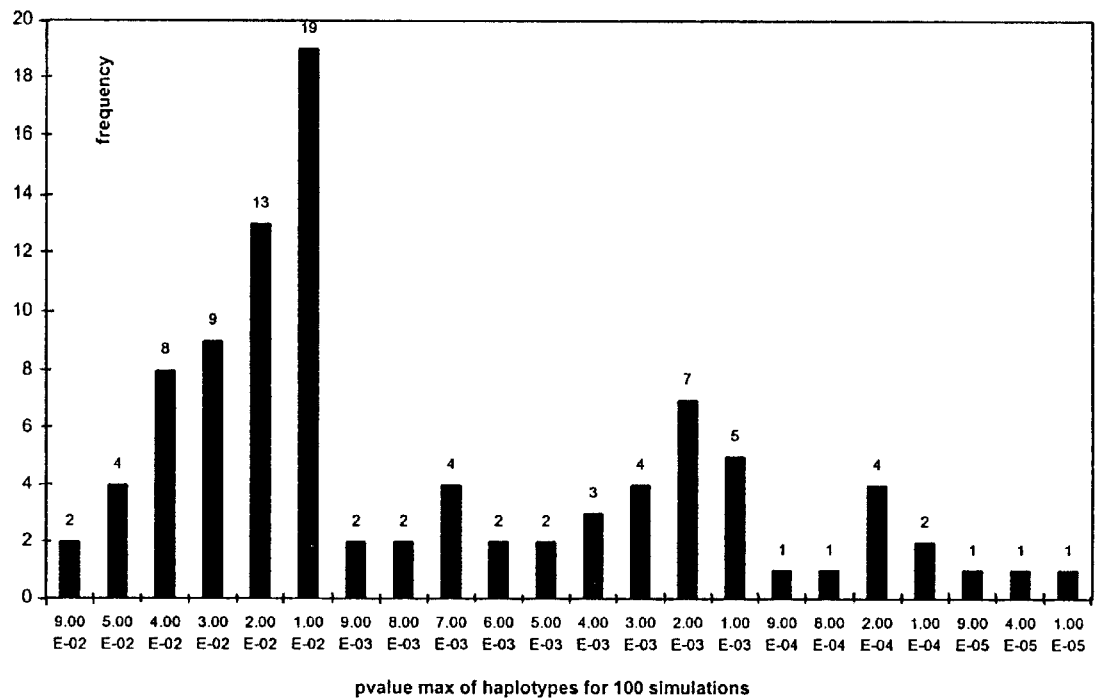
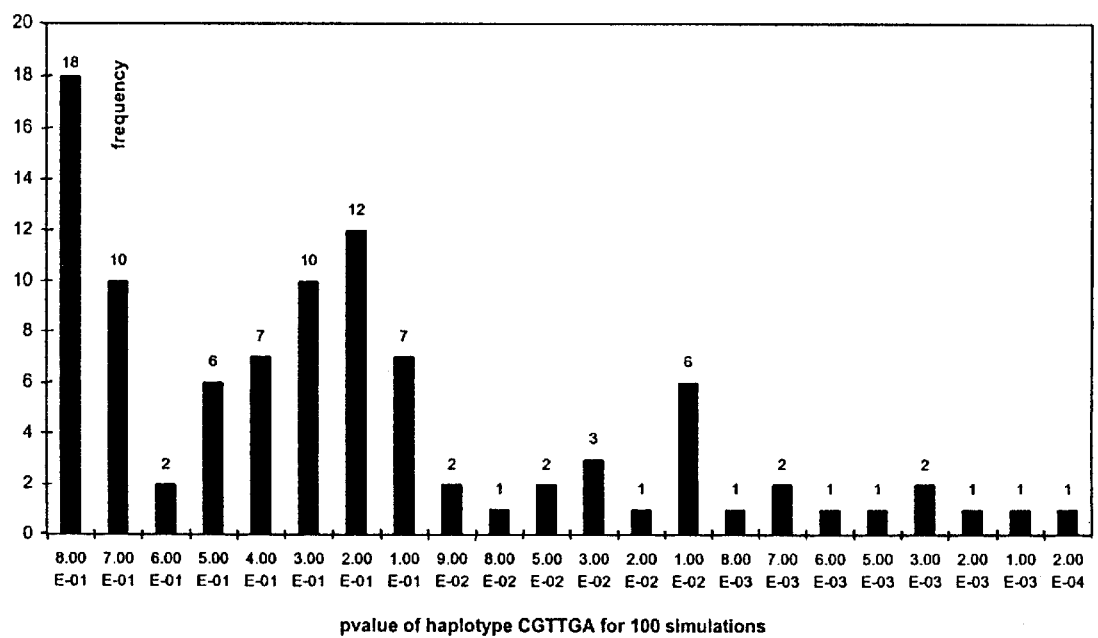
Figure 13

BIALLELIC MARKERS FOR USE IN CONSTRUCTING A HIGH DENSITY DISEQUILIBRIUM MAP OF THE HUMAN GENOME

RELATED APPLICATIONS

The present application is a Continuation-in-Part application of U.S. patent application Ser. No. 09/298,850, filed Apr. 21, 1999, now abandoned, and International Patent Application No. PCT/IB99/00822, filed Apr. 21, 1999, which both claim priority to U.S. Provisional Patent Application Serial No. 60/082,614, filed Apr. 21, 1998 and U.S. Provisional Patent Application Serial No. 60/109,732, filed Nov. 23, 1998, the disclosures of each of which are incorporated herein by reference in their entireties.

BACKGROUND OF THE INVENTION

Recent advances in genetic engineering and bioinformatics have enabled the manipulation and characterization of large portions of the human genome. While efforts to obtain the full sequence of the human genome are rapidly progressing, there are many practical uses for genetic information which can be implemented with partial knowledge of the sequence of the human genome.

As the full sequence of the human genome is assembled, the partial sequence information available can be used to identify genes responsible for detectable human traits, such as genes associated with human diseases, and to develop diagnostic tests capable of identifying individuals who express a detectable trait as the result of a specific genotype or individuals whose genotype places them at risk of developing a detectable trait at a subsequent time. Each of these applications for partial genomic sequence information is based upon the assembly of genetic and physical maps which order the known genomic sequences along the human chromosomes.

The present invention relates to an ordered set of human genomic sequences comprising single nucleotide polymorphisms, as well as the use of these polymorphisms as a high resolution map of the human genome, methods of identifying genes associated with detectable human traits, and diagnostics for identifying individuals who carry a gene which causes them to express a detectable trait or which places them at risk of expressing a detectable trait in the future.

Advantages of the Biallelic Markers of the Present Invention

The map-related biallelic markers of the present invention offer a number of important advantages over other genetic markers such as RFLP (Restriction fragment length polymorphism), VNTR (Variable Number of Tandem Repeats) markers and earlier STS-(sequence tagged sites) derived markers.

The first generation of markers, RFLPs, are variations that modify the length of a restriction fragment. However, methods used to identify and type RFLPs are relatively wasteful of materials, effort, and time. Since they are biallelic markers (they present only two alleles, the restriction site being either present or absent), their maximum heterozygosity is 0.5. The theoretical number of RFLPs distributed along the entire human genome is more than $10^5$, which leads to a potential average inter-marker distance of 30 kilobases. However, in reality, the number of evenly distributed RFLPs which occurs at a sufficient frequency in the population to make them useful for tracking of genetic polymorphisms is very limited.

The second generation of genetic markers were VNTRs, which can be categorized as either minisatellites or microsatellites. Minisatellites are tandemly repeated DNA sequences present in units of 5–50 repeats which are distributed along regions of the human chromosomes ranging from 0.1 to 20 kilobases in length. Since they present many possible alleles, their informative content is very high. Minisatellites are scored by performing Southern blots to identify the number of tandem repeats present in a nucleic acid sample from the individual being tested. However, there are only $10^4$ potential VNTRs that can be typed by Southern blotting. Thus, the number of easily typed informative markers in these maps is far too small for the average distance between informative markers to fulfill the requirements for a useful genetic map. Moreover, both RFLP and VNTR markers are costly and time-consuming to develop and assay in large numbers.

Initial attempts to construct genetic maps based on non-RFLP biallelic markers have focused on identifying biallelic markers lying within sequence tagged sites (STS), pieces of genomic DNA having a known sequence and averaging about 250 bases in length. More than 30,000 STSs have been identified and ordered along the genome (Hudson et al., *Science* 270:1945–1954 (1995); Schuler et al., *Science* 274:540–546 (1996), the disclosures of which are incorporated herein by reference in their entireties). For example, the Whitehead Institute and Genethon's integrated map contains 15,086 STSs.

These sequence tagged sites can be screened to identify polymorphisms, preferably Single Nucleotide Polymorphisms (SNPs), more preferably non RFLP biallelic markers therein. Generally polymorphisms are identified by determining the sequence of the STSs in 5 to 10 individuals.

Wang et al. (Cold Spring Harbor Laboratory: *Abstracts of Papers Presented on Genome Mapping and Sequencing* p. 17 (May 14–18, 1997), the disclosure of which is incorporated herein by reference in its entirety) recently announced the identification and mapping of 750 Single Nucleotide Polymorphisms issued from the sequencing of 12,000 STSs from the Whitehead/MIT map, in eight unrelated individuals. The map was assembled using a high throughput system based on the utilization of DNA chip technology available from Affymetrix (Chee et al., *Science* 274:610–614 (1996), the disclosure of which is incorporated herein by reference in its entirety).

However, according to experimental data and statistical calculations, less than one out of 10 of all STSs mapped today will contain an informative Single Nucleotide Polymorphism. This is primarily due to the short length of existing STSs (usually less than 250 bp). If one assumes $10^6$ informative SNPs spread along the human genome, there would on average be one marker of interest every $3\times10^9/10^6$, i.e. every 3,000 bp. The probability that one such marker is present on a 250 bp stretch is thus less than $\frac{1}{10}$.

While it could produce a high density map, the STS approach based on currently existing markers does not put any systematic effort into making sure that the markers obtained are optimally distributed throughout the entire genome. Instead, polymorphisms are limited to those locations for which STSs are available.

The even distribution of markers along the chromosomes is critical to the future success of genetic analyses. In particular, a high density map having appropriately spaced markers is essential for conducting association studies on sporadic cases, aiming at identifying genes responsible for detectable traits such as those which are described below.

As will be further explained below, genetic studies have mostly relied in the past on a statistical approach called linkage analysis, which took advantage of microsatellite markers to study their inheritance pattern within families from which a sufficient number of individuals presented the studied trait. Because of intrinsic limitations of linkage analysis, which will be further detailed below, and because these studies necessitate the recruitment of adequate family pedigrees, they are not well suited to the genetic analysis of all traits, particularly those for which only sporadic cases are available (e.g. drug response traits), or those which have a low penetrance within the studied population.

Association studies enabled by the biallelic markers of the present invention offer an alternative to linkage analysis. Combined with the use of a high density map of appropriately spaced, sufficiently informative markers, association studies, including linkage disequilibrium-based genome wide association studies, will enable the identification of most genes involved in complex traits.

Single nucleotide polymorphism or biallelic markers can be used in the same manner as RFLPs and VNTRs but offer several advantages. Single nucleotide polymorphisms are densely spaced in the human genome and represent the most frequent type of variation. An estimated number of more than $10^7$ sites are scattered along the $3 \times 10^9$ base pairs of the human genome. Therefore, single nucleotide polymorphisms occur at a greater frequency and with greater uniformity than RFLP or VNTR markers which means that there is a greater probability that such a marker will be found in close proximity to a genetic locus of interest. Single nucleotide polymorphisms are less variable than VNTR markers but are mutationally more stable.

Also, the different forms of a characterized single nucleotide polymorphism, such as the biallelic markers of the present invention, are often easier to distinguish and can therefore be typed easily on a routine basis. Biallelic markers have single nucleotide based alleles and they have only two common alleles, which allows highly parallel detection and automated scoring. The biallelic markers of the present invention offer the possibility of rapid, high-throughput genotyping of a large number of individuals.

Biallelic markers are densely spaced in the genome, sufficiently informative and can be assayed in large numbers. The combined effects of these advantages make biallelic markers extremely valuable in genetic studies. Biallelic markers can be used in linkage studies in families, in allele sharing methods, in linkage disequilibrium studies in populations, in association studies of case-control populations. An important aspect of the present invention is that biallelic markers allow association studies to be performed to identify genes involved in complex traits. Association studies examine the frequency of marker alleles in unrelated case- and control-populations and are generally employed in the detection of polygenic or sporadic traits. Association studies may be conducted within the general population and are not limited to studies performed on related individuals in affected families (linkage studies). Biallelic markers in different genes can be screened in parallel for direct association with disease or response to a treatment. This multiple gene approach is a powerful tool for a variety of human genetic studies as it provides the necessary statistical power to examine the synergistic effect of multiple genetic factors on a particular phenotype, drug response, sporadic trait, or disease state with a complex genetic etiology.

The present invention relates to a high density linkage disequilibrium-based genetic maps of the human genome which comprise the map-related biallelic markers of the invention and will allow the identification of genes responsible for detectable traits using genome-wide association studies and linkage disequilibrium mapping.

SUMMARY OF THE INVENTION

The present invention is based on the discovery of a set of novel map-related biallelic markers (See Table 1). The position of these markers and knowledge of the surrounding sequence have been used to design polynucleotide compositions which are useful in high density mapping of the human genome as well as in determining the identity of nucleotides at the marker position, and more complex association and haplotyping studies which are useful in determining the genetic basis for disease states. In addition, the compositions and methods of the invention find use in the identification of the targets for the development of pharmaceutical agents and diagnostic methods, as well as in the characterization of the differential efficacious responses to and side effects from pharmaceutical agents acting on a disease as well as other treatments.

A first embodiment of the present invention is a map of the human genome comprising an ordered array of biallelic markers, wherein at least 1, 2, 5, 10, 20, 25, 30, 50, 100, 200, 500, 1000, 2000 or 3000 of said biallelic markers are map-related biallelic markers. In addition, the maps of the present invention encompass maps with any further limitation described in this disclosure, or those following, specified alone or in any combination: optionally, said map-related biallelic marker may be selected individually or in any combination from the group consisting of the biallelic markers of SEQ ID Nos. 1 to 3908, 1 to 2260, 2261 to 3734, 3734 to 3908 and the complements thereof; optionally said ordered array comprises at least 20,000, 40,000, 60,000, 80,000, 100,000, or 120,000 biallelic markers; optionally, wherein said biallelic markers are separated from one another by an average distance of 10 kb–200 kb, 15 kb–150 kb, 20 kb–100 kb, 100 kb–150 kb, 50–100 kb, or 25 kb–50 kb in the human genome; optionally, said biallelic markers are distributed at an average density of at least one biallelic marker every 150 kb, 50 kb, or 30 kb in the human genome; or optionally, wherein, all of said biallelic markers are selected to have a heterozygosity rates of at least about 0.18, 0.32, or 0.42.

A second embodiment of the invention encompasses isolated, purified or recombinant polynucleotides consisting of, consisting essentially of, or comprising a contiguous span of nucleotides of a sequence selected as an individual or in any combination from the group consisting of SEQ ID No. 1 to 3908, 1 to 2260, 2261 to 3734, 3734 to 3908, 3935 to 7842, 7866 to 11773, 3935 to 6194, 6195 to 7668, 7669 to 7842, 7866 to 10125, 10126 to 11599, and 11600 to 11773, or the complements thereof, wherein said contiguous span is at least 8, 10, 12, 15, 18, 19, 20, 21, 22, 23, 24, 25, 30, 35, 43, 44, 45, 46 or 47 nucleotides in length, to the extent that a contiguous span of these lengths is consistent with the lengths of the particular Sequence ID. The present invention also relates to polynucleotides hybridizing under stringent or intermediate conditions to a sequence selected from the group consisting of SEQ ID No. 1 to 3908, 1 to 2260, 2261 to 3734, 3734 to 3908, 3935 to 7842, 7866 to 11773, 3935 to 6194, 6195 to 7668, 7669 to 7842, 7866 to 10125, 10126 to 11599, and 11600 to 11773 and the complements thereof. In addition, the polynucleotides of the invention encompass polynucleotides with any further limitation described in this disclosure, or those following, specified alone or in any combination: said contiguous span may optionally comprise a map-related biallelic marker; optionally either the 1st or the 2nd allele of the respective SEQ ID No., as indicated in Table 1, may be specified as being present at said map-related biallelic marker; optionally, said biallelic marker may be within 6, 5, 4, 3, 2, or 1 nucleotides of the center of said polynucleotide or at the center of said polynucleotide; optionally, said polynucleotide may comprise, consist of, or consist essentially of a contiguous span which ranges in length from 8, 10, 12, 15, 18 or 20 to 21, 25, 35, 40, 43, or 47 nucleotides; optionally, said polynucleotide may comprise, consist of, or consist essentially of a contiguous span which ranges in length from 8, 10, 12, 15, 18 or 20 to 21, 25, 35, 40, 43, or 47 nucleotides, or be specified as being 12, 15, 18, 20, 25, 35, 40, 43, or 47 nucleotides in length and including an map-related biallelic marker of said sequence, and optionally the 1st allele of Table 1 is present at said biallelic marker; optionally, the 3' end of said contiguous span may be present at the 3' end of said polynucleotide; optionally, biallelic marker may be present at the 3' end of said polynucleotide; optionally, the 3' end of said polynucleotide may be located within or at least 2, 4, 6, 8, or 10 nucleotides upstream of a map-related biallelic marker in said sequence, to the extent that such a distance is consistent with the lengths of the particular Sequence ID; optionally, the 3' end of said polynucleotide may be located 1 nucleotide upstream of a map-related biallelic marker in said sequence; and optionally, said polynucleotide may further comprise a label.

A third embodiment of the invention encompasses any polynucleotide of the invention attached to a solid support. In addition, the polynucleotides of the invention which are attached to a solid support encompass polynucleotides with any further limitation described in this disclosure, or those following, specified alone or in any combination: optionally, said polynucleotides may be specified as attached individually or in groups of at least 2, 5, 8, 10, 12, 15, 20, 25, 50, 100, 200, or 500 distinct polynucleotides of the inventions to a single solid support; optionally, polynucleotides other than those of the invention may attached to the same solid support as polynucleotides of the invention; optionally, when multiple polynucleotides are attached to a solid support they may be attached at random locations, or in an ordered array; optionally, said ordered array may be addressable.

A fourth embodiment of the invention encompasses the use of any polynucleotide for, or any polynucleotide for use in, determining the identity of nucleotides at a map-related biallelic marker. In addition, the polynucleotides of the invention for use in determining the identity of nucleotides at a map-related biallelic marker encompass polynucleotides with any further limitation described in this disclosure, or those following, specified alone or in any combination: optionally, said map-related biallelic marker may be selected individually or in any combination from the group consisting of the biallelic markers of SEQ ID No. 1 to 3908, 1 to 2260, 2261 to 3734, 3734 to 3908 and the complements thereof; optionally, said polynucleotide may comprise a sequence disclosed in the present specification; optionally, said polynucleotide may comprise, consist of, or consist essentially of any polynucleotide described in the present specification; optionally, said determining may be performed in a hybridization assay, sequencing assay, microsequencing assay, or an enzyme-based mismatch detection assay; optionally, said polynucleotide may be attached to a solid support, array, or addressable array; optionally, said polynucleotide may be labeled.

A fifth embodiment of the invention encompasses the use of any polynucleotide for, or any polynucleotide for use in, amplifying a segment of nucleotides comprising a map-related biallelic marker. In addition, the polynucleotides of the invention for use in amplifying a segment of nucleotides comprising a map-related biallelic marker encompass polynucleotides with any further limitation described in this disclosure, or those following, specified alone or in any combination: optionally, said map-related biallelic marker may be selected individually or in any combination from the group consisting of the biallelic markers of SEQ ID Nos. 1 to 3908, 1 to 2260, 2261 to 3734, 3734 to 3908 and the complements thereof; optionally, said polynucleotide may comprise, consist of, consist essentially of, or comprise a sequence selected individually or in any combination from the group consisting of SEQ ID Nos. 3935 to 7842, 7866 to 11773, 3935 to 6194, 6195 to 7668, 7669 to 7842, 7866 to 10125, 10126 to 11599, and 11600 to 11773; optionally, said polynucleotide may comprise, consist of, or consist essentially of any polynucleotide described in the present specification; optionally, said amplifying may be performed by a PCR or LCR. Optionally, said polynucleotide may be attached to a solid support, array, or addressable array. Optionally, said polynucleotide may be labeled.

A sixth embodiment of the invention encompasses methods of genotyping a biological sample comprising determining the identity of a nucleotide at a map-related biallelic marker. In addition, the genotyping methods of the invention encompass methods with any further limitation described in this disclosure, or those following, specified alone or in any combination: optionally, said map-related biallelic marker may be selected individually or in any combination from the group consisting of the biallelic markers of SEQ ID No. 1 to 3908, 1 to 2260, 2261 to 3734, 3734 to 3908 and the complements thereof; optionally, said method further comprises determining the identity of a second nucleotide at said biallelic marker, wherein said first nucleotide and second nucleotide are not base paired (by Watson & Crick base pairing) to one another; optionally, said biological sample is derived from a single individual or subject; optionally, said method is performed in vitro; optionally, said biallelic marker is determined for both copies of said biallelic marker present in said individual's genome; optionally, said biological sample is derived from multiple subjects or individuals; optionally, said method further comprises amplifying a portion of said sequence comprising the biallelic marker prior to said determining step; optionally, wherein said amplifying is performed by PCR, LCR, or replication of a recombinant vector comprising an origin of replication and said portion in a host cell; optionally, wherein said determining is performed by a hybridization assay, sequencing assay, microsequencing assay, or an enzyme-based mismatch detection assay.

A seventh embodiment of the invention comprises methods of estimating the frequency of an allele in a population comprising genotyping individuals from said population for a map-related biallelic marker and determining the proportional representation of said biallelic marker in said population. In addition, the methods of estimating the frequency of an allele in a population of the invention encompass methods with any further limitation described in this disclosure, or those following, specified alone or in any combination: optionally, said map-related biallelic marker may be selected individually or in any combination from the group consisting of the biallelic markers of SEQ ID Nos. 1 to 3908, 1 to 2260, 2261 to 3734, 3734 to 3908 and the complements thereof; optionally, determining the frequency of a biallelic marker allele in a population may be accomplished by determining the identity of the nucleotides for both copies of said biallelic marker present in the genome of each individual in said population and calculating the proportional representation of said nucleotide at said map-related biallelic marker for the population; optionally, determining the frequency of a biallelic marker allele in a population may be accomplished by performing a genotyping method on a pooled biological sample derived from a representative number of individuals, or each individual, in said population, and calculating the proportional amount of said nucleotide compared with the total.

An eighth embodiment of the invention comprises methods of detecting an association between an allele and a phenotype, comprising the steps of a) determining the frequency of at least one map-related biallelic marker allele in a trait positive population, b) determining the frequency of said map-related biallelic marker allele in a control population and; c) determining whether a statistically significant association exists between said genotype and said phenotype. In addition, the methods of detecting an association between an allele and a phenotype of the invention encompass methods with any further limitation described in this disclosure, or those following, specified alone or in any combination: optionally, said map-related biallelic marker may be selected individually or in any combination from the group consisting of the biallelic markers of SEQ ID Nos. 1 to 3908, 1 to 2260, 2261 to 3734, 3734 to 3908 and the complements thereof, optionally, said control population may be a trait-negative population, or a random population; optionally, wherein said phenotype is selected from the group consisting of disease, treatment response, treatment efficacy, drug response, drug efficacy, and drug toxicity; optionally, the determining steps a) and b) are performed on all of the biallelic markers of SEQ ID Nos. 1 to 3908.

An ninth embodiment of the present invention encompasses methods of estimating the frequency of a haplotype for a set of biallelic markers in a population, comprising the steps of: a) genotyping each individual in said population for at least one map-related biallelic marker, b) genotyping each individual in said population for a second biallelic marker by determining the identity of the nucleotides at said second biallelic marker for both copies of said second biallelic marker present in the genome; and c) applying a haplotype determination method to the identities of the nucleotides determined in steps a) and b) to obtain an estimate of said frequency. In addition, the methods of estimating the frequency of a haplotype of the invention encompass methods with any further limitation described in this disclosure, or those following, specified alone or in any combination: optionally said haplotype determination method is selected from the group consisting of asymmetric PCR amplification, double PCR amplification of specific alleles, the Clark method, or an expectation maximization algorithm; optionally, said map-related biallelic marker may be selected individually or in any combination from the group consisting of the biallelic markers of SEQ ID Nos. 1 to 3908, 1 to 2260, 2261 to 3734, 3734 to 3908 and the complements thereof; optionally, said second biallelic marker is a map-related biallelic marker; optionally, the identity of the nucleotides at the biallelic markers in every one of the sequences of SEQ ID No. 1 to 3908 is determined in steps a) and b).

A tenth embodiment of the present invention encompasses methods of detecting an association between a haplotype and a phenotype, comprising the steps of: a) estimating the frequency of at least one haplotype in a trait positive population according to a method of estimating the frequency of a haplotype of the invention; b) estimating the frequency of said haplotype in a control population according to the method of estimating the frequency of a haplotype of the invention; and c) determining whether a statistically significant association exists between said haplotype and said phenotype. In addition, the methods of detecting an association between a haplotype and a phenotype of the invention encompass methods with any further limitation described in this disclosure, or those following, specified alone or in any combination: optionally, said map-related biallelic marker may be in a sequence selected individually or in any combination from the group consisting of SEQ ID No. 1 to 3908, 1 to 2260, 2261 to 3734, 3734 to 3908 and the complements thereof; optionally, said control population may be a trait-negative population, or a random population; optionally, wherein said phenotype is selected from the group consisting of disease, treatment response, treatment efficacy, drug response, drug efficacy, and drug toxicity; optionally, the identity of the nucleotides at the biallelic markers in every one of the following sequences: SEQ ID No. 1 to 3908 is included in the estimating steps a) and b).

An eleventh embodiment of the present invention is a method of identifying a gene associated with a detectable trait comprising the steps of: a) determining the frequency of each allele of at least one map-related biallelic marker in individuals having the detectable trait and individuals lacking the detectable trait; b) identifying at least one alleles of one or biallelic markers having a statistically significant association with the detectable trait; and c) identifying a gene in linkage disequilibrium with said allele. In addition, the methods of the present invention for identifying a gene associated with a detectable trait encompass methods with any further limitation described in this disclosure, or those following, specified alone or in any combination: optionally, wherein the method further comprises d) identifying a mutation in the gene identified in step c) which is associated with the detectable trait; optionally, wherein the individuals having the detectable trait and the individuals lacking the detectable trait are readily distinguishable from one another; optionally, wherein the individuals having the detectable trait and the individuals lacking the detectable trait are selected from a bimodal population; optionally, wherein the individuals having the detectable trait are at one extreme of the population and the individuals lacking the detectable trait are at the other extreme of the population; optionally, said map-related biallelic marker may be in a sequence selected individually or in any combination from the group consisting of SEQ ID No. 1 to 3908, 1 to 2260, 2261 to 3734, 3734 to 3908 and the complements thereof; optionally, wherein said detectable trait is selected from the group consisting of disease, treatment response, treatment efficacy, drug response, drug efficacy, and drug toxicity.

A twelfth embodiment of the present invention is a method of identifying biallelic markers associated with a detectable trait comprising the steps of: a) determining the frequencies of a set of biallelic markers comprising at least one map-related biallelic marker in individuals who express said detectable trait and individuals who do not express said detectable trait; and b) identifying one or more biallelic markers in said set which are statistically associated with the expression of said detectable trait. In addition, the methods of the present invention for identifying biallelic markers associated with a detectable trait encompass methods with any further limitation described in this disclosure, or those following, specified alone or in any combination: optionally, said map-related biallelic marker may be in a sequence selected individually or in any combination from the group consisting of SEQ ID No. 1 to 3908, 1 to 2260, 2261 to 3734, 3734 to 3908 and the complements thereof; optionally, wherein said detectable trait is selected from the group consisting of disease, treatment response, treatment efficacy, drug response, drug efficacy, and drug toxicity.

A thirteenth embodiment of the present invention is a method of identifying biallelic marker(s) in linkage disequilibrium with a trait causing allele or in linkage disequilibrium with a trait-associated biallelic marker comprising the steps of: a) selecting at least one map-related biallelic marker which is in the genomic region suspected of containing the trait-causing allele or the trait-associated biallelic marker; and b) determining which of the map-related biallelic markers are associated with the trait-causing allele or in linkage disequilibrium with the trait-associated biallelic marker. In addition, the methods of the present invention for identifying biallelic marker(s) in linkage disequilibrium with a trait causing allele or in linkage disequilibrium with a trait-associated biallelic marker encompass methods with any further limitation described in this disclosure, or those following, specified alone or in any combination: optionally, said map-related biallelic marker may be in a sequence selected individually or in any combination from the group consisting of SEQ ID No. 1 to 3908, 1 to 2260, 2261 to 3734, 3734 to 3908 and the complements thereof; optionally, wherein said detectable trait is selected from the group consisting of disease, treatment response, treatment efficacy, drug response, drug efficacy, and drug toxicity.

A fourteenth embodiment of the present invention is a method for determining whether an individual is at risk of developing a detectable trait or suffers from a detectable trait comprising the steps of: a) obtaining a nucleic acid sample from the individual; b) screening the nucleic acid sample with at least one map-related biallelic marker; and c) determining whether the nucleic acid sample contains at least one allele of said map-related biallelic marker statistically associated with the detectable trait. In addition, the methods of the present invention for determining whether an individual is at risk of developing a detectable trait or suffers from a detectable trait encompass methods with any further limitation described in this disclosure, or those following, specified alone or in any combination: optionally, said map-related biallelic marker may be in a sequence selected individually or in any combination from the group consisting of SEQ ID No. 1 to 3908, 1 to 2260, 2261 to 3734, 3734 to 3908 and the complements thereof; optionally, wherein said detectable trait is selected from the group consisting of disease, treatment response, treatment efficacy, drug response, drug efficacy, and drug toxicity.

A fifteenth embodiment of the present invention is a method of administering a drug or a treatment comprising the steps of: a) obtaining a nucleic acid sample from an individual; b) determining the identity of the polymorphic base of at least one map-related biallelic marker which is associated with a positive response to the treatment or the drug; or at least one biallelic map-related marker which is associated with a negative response to the treatment or the drug; and c) administering the treatment or the drug to the individual if the nucleic acid sample contains said biallelic marker associated with a positive response to the treatment or the drug or if the nucleic acid sample lacks said biallelic marker associated with a negative response to the treatment or the drug. In addition, the methods of the present invention for administering a drug or a treatment encompass methods with any further limitation described in this disclosure, or those following, specified alone or in any combination: optionally, said map-related biallelic marker may be in a sequence selected individually or in any combination from the group consisting of SEQ ID No. 1 to 3908, 1 to 2260, 2261 to 3734, 3734 to 3908 and the complements thereof; or optionally, the administering step comprises administering the drug or the treatment to the individual if the nucleic acid sample contains said biallelic marker associated with a positive response to the treatment or the drug and the nucleic acid sample lacks said biallelic marker associated with a negative response to the treatment or the drug.

A sixteenth embodiment of the present invention is a method of selecting an individual for inclusion in a clinical trial of a treatment or drug comprising the steps of: a) obtaining a nucleic acid sample from an individual; b) determining the identity of the polymorphic base of at least one map-related biallelic marker which is associated with a positive response to the treatment or the drug, or at least one map-related biallelic marker which is associated with a negative response to the treatment or the drug in the nucleic acid sample, and c) including the individual in the clinical trial if the nucleic acid sample contains said map-related biallelic marker associated with a positive response to the treatment or the drug or if the nucleic acid sample lacks said biallelic marker associated with a negative response to the treatment or the drug. In addition, the methods of the present invention for selecting an individual for inclusion in a clinical trial of a treatment or drug encompass methods with any further limitation described in this disclosure, or those following, specified alone or in any combination: optionally, said map-related biallelic marker may be in a sequence selected individually or in any combination from the group consisting of SEQ ID No. 1 to 3908, 1 to 2260, 2261 to 3734, 3734 to 3908 and the complements thereof; optionally, the including step comprises administering the drug or the treatment to the individual if the nucleic acid sample contains said biallelic marker associated with a positive response to the treatment or the drug and the nucleic acid sample lacks said biallelic marker associated with a negative response to the treatment or the drug.

A seventeenth embodiment of the present invention is a method of identifying a gene associated with a detectable trait comprising the steps of: a) selecting a gene suspected of being associated with a detectable trait; and b) identifying at least one map-related biallelic marker within said gene which is associated with said detectable trait. In addition, the methods of the present invention for identifying a gene associated with a detectable trait encompass methods with any further limitation described in this disclosure, or those following, specified alone or in any combination: optionally, said map-related biallelic marker may be in a sequence selected individually or in any combination from the group consisting of SEQ ID No. 1 to 3908, 1 to 2260, 2261 to 3734, 3734 to 3908 and the complements thereof; optionally, the identifying step comprises determining the frequencies of the map-related biallelic marker(s) in individuals who express said detectable trait and individuals who do not express said detectable trait and identifying one or more biallelic markers which are statistically associated with the expression of the detectable trait.

Additional embodiments are set forth in the Detailed Description of the Invention and in the Examples.

BRIEF DESCRIPTION OF THE DRAWINGS

FIG. 3 shows, for a series of hypothetical sample sizes, the p-value significance obtained in association studies performed using individual markers from the high-density biallelic map, according to various hypotheses regarding the difference of allelic frequencies between the trait-positive and trait-negative samples.

FIG. 7 is a haplotype analysis using biallelic markers in the Apo E region.

FIG. 12 is a haplotype analysis using the biallelic markers in the genomic region of the gene associated with prostate cancer.

FIG. 13 is a simulated haplotype using the six markers included in haplotype 5 of FIG. 12.

BRIEF DESCRIPTION OF THE SEQUENCE LISTINGS

Figure 1:
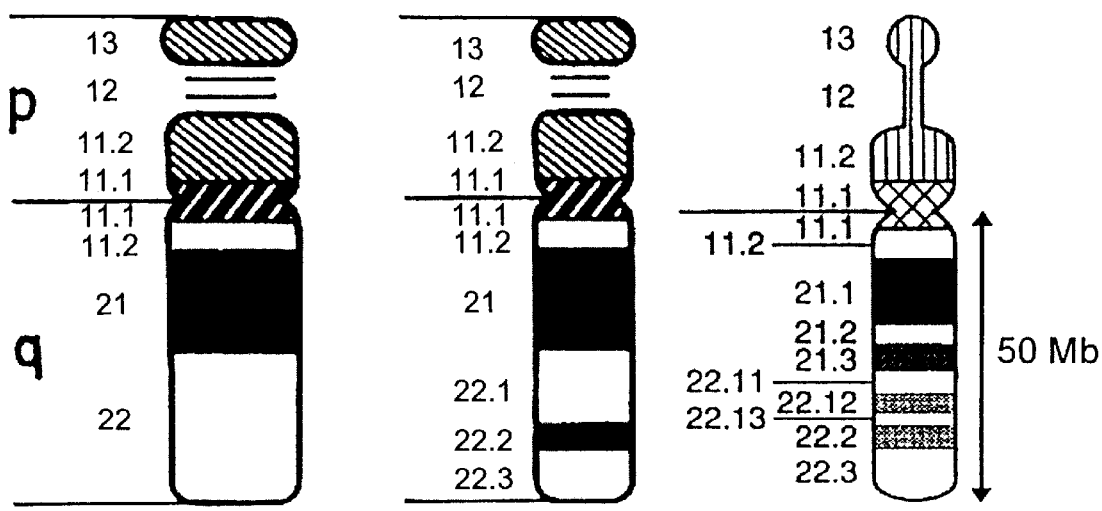
FIG. 1 is a cytogenetic map of chromosome 21.

SEQ ID Nos. 1 to 3908 contain nucleotide sequences comprising a portion of the map-related biallelic markers of the invention.

SEQ ID Nos. 3909 to 3934 contain nucleotide sequences comprising a portion of the map-related biallelic markers which are shown to be associated with Alzheimer's disease, prostate cancer or asthma as described in the Examples.

SEQ ID Nos. 3935 to 7842 contain nucleotide sequences of upstream amplification primers (PU) designed to amplify sequences containing the biallelic markers of SEQ ID Nos. 1 to 3908.

SEQ ID Nos. 7843 to 7865 contain nucleotide sequences of upstream amplification primers (PU) designed to amplify sequences containing the biallelic markers of SEQ ID Nos. 3909 to 3934.

SEQ ID Nos. 7866 to 11773 contain nucleotide sequences of downstream amplification primers (RP) designed to amplify sequences containing the biallelic markers of SEQ ID Nos. 1 to 3908.

SEQ ID Nos. 11774 to 11796 contain nucleotide sequences of downstream amplification primers (RP) designed to amplify sequences containing the biallelic markers of SEQ ID Nos. 3909 to 3934.

DETAILED DESCRIPTION OF THE EMBODIMENTS

Before describing the invention in greater detail, the following definitions are set forth to illustrate and define the meaning and scope of the terms used to describe the invention herein.

Definitions

As used interchangeably herein, the terms "nucleic acids" "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. However, the polynucleotides of the invention are preferably comprised of greater than 50% conventional deoxyribose nucleotides, and most preferably greater than 90% conventional deoxyribose nucleotides. The polynucleotide sequences of the invention may be prepared by any known method, including synthetic, recombinant, ex vivo generation, or a combination thereof, as well as utilizing any purification methods known in the art.

The term "purified" is used herein to describe a polynucleotide or polynucleotide vector of the invention which has been separated from other compounds including, but not limited to other nucleic acids, carbohydrates, lipids and proteins (such as the enzymes used in the synthesis of the polynucleotide), or the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polynucleotide typically comprises about 50%, preferably 60 to 90% weight/weight of a nucleic acid sample, more usually about 95%, and preferably is over about 99% pure. Polynucleotide purity or homogeneity may be indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., polynucleotide as defined herein) which can be used to identify a specific polynucleotide sequence present in samples, said nucleic acid segment comprising a nucleotide sequence complementary of the specific polynucleotide sequence to be identified.

The terms "detectable trait" "trait" and "phenotype" are used interchangeably herein and refer to any visible, detectable or otherwise measurable property of an organism such as symptoms of, or susceptibility to a disease for example. Typically the terms "detectable trait" "trait" or "phenotype" are used herein to refer to symptoms of, or susceptibility to a disease; or to refer to an individual's response to an agent, drug, or treatment acting on a disease; or to refer to symptoms of, or susceptibility to side effects to an agent acting on a disease.

The term "treatment" is used herein to encompass any medical intervention known in the art including, for example, the administration of pharmaceutical agents, medically prescribed changes in diet, or habits such as a reduction in smoking or drinking, surgery, the application of medical devices, and the application or reduction of certain physical conditions, for example, light or radiation.

The term "allele" is used herein to refer to variants of a nucleotide sequence. A biallelic polymorphism has two forms; designated herein as the $1^{ST}$ allele and the $2^{ND}$ allele. Diploid organisms may be homozygous or heterozygous for an allelic form.

The term "heterozygosity rate" is used herein to refer to the incidence of individuals in a population, which are heterozygous at a particular allele. In a biallelic system the heterozygosity rate is on average equal to $2P_a(1-P_a)$, where $P_a$ is the frequency of the least common allele. In order to be useful in genetic studies a genetic marker should have an adequate level of heterozygosity to allow a reasonable probability that a randomly selected person will be heterozygous.

The term "genotype" as used herein refers the identity of the alleles present in an individual or a sample. In the context of the present invention a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "mutation" as used herein refers to a difference in DNA sequence between or among different genomes or individuals which has a frequency below 1%.

The term "haplotype" refers to a combination of alleles present in an individual or a sample. In the context of the present invention a haplotype preferably refers to a combination of biallelic marker alleles found in a given individual and which may be associated with a phenotype.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is a single base pair change. Typically a single nucleotide polymorphism is the replacement of one nucleotide by another nucleotide at the polymorphic site. Deletion of a single nucleotide or insertion of a single nucleotide, also give rise to single nucleotide polymorphisms. In the context of the present invention "single nucleotide polymorphism" preferably refers to a single nucleotide substitution. Typically, between different genomes or between different individuals, the polymorphic site may be occupied by two different nucleotides.

The terms "biallelic polymorphism" and "biallelic marker" are used interchangeably herein to refer to a polymorphism having two alleles at a fairly high frequency in the population, preferably a single nucleotide polymorphism. A "biallelic marker allele" refers to the nucleotide variants present at a biallelic marker site. Typically the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker."

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on.

The term "upstream" is used herein to refer to a location which, is toward the 5' end of the polynucleotide from a specific reference point.

The terms "base paired" and "Watson & Crick base paired" are used interchangeably herein to refer to nucleotides which can be hydrogen bonded to one another be virtue of their sequence identities in a manner like that found in double-helical DNA with thymine or uracil residues linked to adenine residues by two hydrogen bonds and cytosine and guanine residues linked by three hydrogen bonds (See Stryer, L., *Biochemistry*, 4th edition, 1995).

The terms "complementary" or "complement thereof" are used herein to refer to the sequences of polynucleotides which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

As used herein the term "map-related biallelic marker" relates to a biallelic marker in linkage disequilibrium with any of the sequences disclosed in SEQ ID Nos. 1 to 3908 which contain a biallelic marker of the map. The term map-related biallelic marker encompasses all of the biallelic markers disclosed in SEQ ID Nos. 1 to 3908, 1 to 2260, 2261 to 3374, 3735 to 3908. The preferred map-related biallelic marker alleles of the present invention include each one of the alleles selected individually or in any combination from the biallelic markers of SEQ ID Nos. 1 to 3908, 1 to 2260, 2261 to 3374, and 3735 to 3908, as identified in field <223> of the allele feature in the appended Sequence Listing, individually or in groups consisting of all the possible combinations of the alleles.

The terms "$1^{ST}$ allele" and "$2^{ND}$ allele" refer to the nucleotide located at the polymorphic base of a polynucleotide sequence containing a biallelic marker, as identified in field <222> of the allele feature in the appended Sequence Listing for each Sequence ID number. As used herein, the polymorphic base is located at nucleotide position 24 for each of SEQ ID Nos. 1 to 3908, with the exception of SEQ ID Nos. 914, 1013, 2544, 3434, 3795, and 3028. The polymorphic base is located at nucleotide position 23 for SEQ ID Nos. 914, 1013 and 2544, at nucleotide position 21 for SEQ ID No. 3028, at nucleotide position 20 for SEQ ID No. 3434.

I. Biallelic Markers And Polynucleotides Comprising Biallelic Markers Polynucleotides of the Present Invention The present invention encompasses polynucleotides for use as primers and probes in the methods of the invention. All of the polynucleotides of the invention may be specified as being isolated, purified or recombinant. These polynucleotides may consist of, consist essentially of, or comprise a contiguous span of nucleotides of a sequence from any sequence in the Sequence Listing as well as sequences which are complementary thereto ("complements thereof"). The "contiguous span" may be at least 8, 10, 12, 15, 18, 19, 20, 22, 23, 24, 25, 30, 35, 43, 44, 45, 46 or 47 nucleotides in length, to the extent that a contiguous span of these lengths is consistent with the lengths of the particular Sequence ID. It should be noted that the polynucleotides of the present invention are not limited to having the exact flanking sequences surrounding the polymorphic bases which are enumerated in the Sequence Listing. Rather, it will be appreciated that the flanking sequences surrounding the biallelic markers, or any of the primers of probes of the invention which, are more distant from the markers, may be lengthened or shortened to any extent compatible with their intended use and the present invention specifically contemplates such sequences. It will be appreciated that the polynucleotides referred to in the Sequence Listing may be of any length compatible with their intended use. Also the flanking regions outside of the contiguous span need not be homologous to native flanking sequences which actually occur in human subjects. The addition of any nucleotide sequence, which is compatible with the nucleotides intended use is specifically contemplated. The contiguous span may optionally include the map-related biallelic marker in said sequence. Biallelic markers generally consist of a polymorphism at one single base position. Each biallelic marker therefore corresponds to two forms of a polynucleotide sequence which, when compared with one another, present a nucleotide modification at one position. Usually, the nucleotide modification involves the substitution of one nucleotide for another. Optionally either the $1^{ST}$ allele or the $2^{ND}$ allele of the biallelic markers of SEQ ID Nos. 1 to 3908, 1 to 2260, 2261 to 3374, and 3735 to 3908 may be specified as being present at the map-related biallelic marker.

Preferred polynucleotides may consist of, consist essentially of, or comprise a contiguous span of nucleotides of a sequence from SEQ ID Nos. 1 to 2260 as well as sequences which are complementary thereto. The "contiguous span" may be at least 8, 10, 12, 15, 18, 19, 20, 22, 23, 24, 25, 30, 35, 43, 44, 45, 46 or 47 nucleotides in length, to the extent that a contiguous span of these lengths is consistent with the lengths of the particular Sequence ID. Particularly preferred are polynucleotides which consist of, consist essentially of, or comprise a contiguous span of nucleotides of a sequence of any of SEQ ID Nos. 1 to 2260, or the complements thereof, wherein the $1^{ST}$ allele of the biallelic marker of the SEQ ID No. is present at the map-related biallelic marker. Other preferred polynucleotides consist of, consist essentially of, or comprise a contiguous span of nucleotides of any of SEQ ID Nos. 1 to 2260, or the complements thereof, wherein the $2^{ND}$ allele of the biallelic marker of the SEQ ID No. is present at the map-related biallelic marker. Preferred polynucleotides may consist of, consist essentially of, or comprise a contiguous span of at least 8, 10, 12, 15, 18, 19, 20, 22, 23, 24, 25, 30, 35, 43, 44, 45, 46 or 47 nucleotides in length, to the extent that a contiguous span of these lengths is consistent with the lengths of the particular Sequence ID No., of a sequence from SEQ ID Nos. 2261 to 3734 as well as sequences which are complementary thereto. Particularly preferred are polynucleotides which consist of, consist essentially of, or comprise a contiguous span of nucleotides of a sequence of any of SEQ ID Nos. 2261 to 3734, or the complements thereof, wherein the $1^{ST}$ allele of the biallelic marker of the SEQ ID No. is present at the map-related biallelic marker. Other preferred polynucleotides consist of, consist essentially of, or comprise a contiguous span of nucleotides of any of SEQ ID Nos. 2261 to 3734, or the complements thereof, wherein the $2^{ND}$ allele of the biallelic marker of the SEQ ID No. is present at the map-related biallelic marker. Preferred polynucleotides may consist of, consist essentially of, or comprise a contiguous span of at least 8, 10, 12, 15, 18, 19, 20, 22, 23, 24, 25, 30, 35, 43, 44, 45, 46 or 47 nucleotides in length, to the extent that a contiguous span of these lengths is consistent with the lengths of the particular Sequence ID No., of a sequence from SEQ ID Nos. 3735 to 3908 as well as sequences which are complementary thereto. Particularly preferred are polynucleotides which consist of, consist essentially of, or comprise a contiguous span of nucleotides of a sequence of any of SEQ ID Nos. 3735 to 3908, or the complements thereof, wherein the $1^{ST}$ allele of the biallelic marker of the SEQ ID No. is present at the map-related biallelic marker. Other preferred polynucleotides consist of, consist essentially of, or comprise a contiguous span of nucleotides of any of SEQ ID Nos. 3735 to 3908, or the complements thereof, wherein the $2^{ND}$ allele of the biallelic marker of the SEQ ID No. is present at the map-related biallelic marker. Also encompassed by the polynucleotides of the present invention are polynucleotides which consist of, consist essentially of, or comprise a contiguous span at least 8, 10, 12, 15, 18, 19, 20, 22, 23, 24, 25, 30, 35, 43, 44, 45, 46 or 47 nucleotides in length, to the extent that a contiguous span of these lengths is consistent with the lengths of the particular Sequence ID, of a sequence from SEQ ID Nos. 1201, 3242, 3907 and 3908 as well as sequences which are complementary thereto, wherein said contiguous span of SEQ ID Nos. 1201 or 3242 contains a "G" at the polymorphic base, or wherein said contiguous span of SEQ ID Nos. 3907 or 3908 contain an "A" at the polymorphic base.

The present invention also relates to a biallelic marker or set of biallelic markers of the invention comprising:

(a) at least one of SEQ ID Nos. 583, 620, 1277 to 1279, 1281, 1375 to 1377, 1379 to 1382, 1676 to 1681, 3106, 3547, 3548, 3889; and/or (b) at least one of SEQ ID Nos. 86, 105, 109, 110, 185, 284, 381, 414, 428, 441, 445, 446, 453, 464, 467, 487, 489, 520, 3915 to 3918, 3920, and 3923 to 3926; and/or (c) at least one of SEQ ID Nos. 232 to 237, 340, 346, and 3927–3934; and/or (d) at least one of SEQ ID Nos. 607, 616, 619, 623, 626, 627, 645, 646, 650, 651, 1899 and 2721; and/or (e) at least one of SEQ ID Nos. 2694 to 2697, 3494 to 3496 and 3882; and/or (f) at least one of SEQ ID Nos. 204, 205, 225, 273, 274, 1723, 1732, 1743.

Thus, in said embodiment, the polynucleotides and nucleic acid codes of the invention may comprise a nucleotide sequence or group of nucleotide sequences of said SEQ ID numbers listed above in (a) to (f), the amplification primers related to said SEQ ID Numbers, as described in Table 1, and the sequences complementary thereto. Optionally, any biallelic markers, sets of biallelic markers, polynucleotides or nucleic acid codes described throughout the present specification may be selected from a group specifically excluding one or more of said SEQ ID numbers listed above in (a) to (f). The biallelic markers, sets of biallelic markers, polynucleotides or nucleic acid codes of the invention may be selected from a group which specifically excludes one or more of said SEQ ID numbers listed above in (a) to (f) individually or in any combination.

The invention also relates to polynucleotides that hybridize, under conditions of high or intermediate stringency, to a polynucleotide of a sequence from any of SEQ ID Nos. 1 to 3908, 1 to 2260, 2261 to 3374, and 3735 to 3908 as well as sequences which are complementary thereto. Preferably such polynucleotides are at least 8, 10, 12, 15, 18, 19, 20, 22, 23, 24, 25, 30, 35, 43, 44, 45, 46 or 47 nucleotides in length, to the extent that a polynucleotide of these lengths is consistent with the lengths of the particular Sequence ID. Preferred polynucleotides comprise a map-related biallelic marker. Optionally either the $1^{ST}$ or the $2^{ND}$ allele of the biallelic markers disclosed in the SEQ ID No. may be specified as being present at the map-related biallelic marker. Conditions of high and intermediate stringency are further described in III.C.4.

The primers of the present invention may be designed from the disclosed sequences using any method known in the art. A preferred set of primers is fashioned such that the 3' end of the contiguous span of identity with the sequences of the Sequence Listing is present at the 3' end of the primer. Such a configuration allows the 3' end of the primer to hybridize to a selected nucleic acid sequence and dramatically increases the efficiency of the primer for amplification or sequencing reactions.

In a preferred set of primers, the contiguous span is found in one of the sequences described in SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 or the complements thereof. The invention also relates to polynucleotides consisting of, consisting essentially of, or comprising a contiguous span of nucleotides of a sequence from SEQ ID Nos. 3935 to 7842, 3935 to 6194, 6195 to 7668, 7669 to 7842, 7866 to 11773, 7866 to 10125, 10126 to 11599, and 11600 to 11773, as well as sequences which are complementary thereto, wherein the "contiguous span" may be at least 8, 10, 12, 15, 18, 19, 20, or 21 nucleotides in length, to the extent that a contiguous span of these lengths is consistent with the lengths of the particular Sequence ID No.

Allele specific primers may be designed such that a biallelic marker is at the 3' end of the contiguous span and the contiguous span is present at the 3' end of the primer. Such allele specific primers tend to selectively prime an amplification or sequencing reaction so long as they are used with a nucleic acid sample that contains one of the two alleles present at a biallelic marker. The 3' end of primer of the invention may be located within or at least 2, 4, 6, 8, 10, to the extent that this distance is consistent with the particular Sequence ID, nucleotides upstream of a map-related biallelic marker in said sequence or at any other location which is appropriate for their intended use in sequencing, amplification or the location of novel sequences or markers. Primers with their 3' ends located 1 nucleotide upstream of a map-related biallelic marker have a special utility as microsequencing assays. Preferred microsequencing primers are described in SEQ ID Nos. 1 to 3908, 1 to 2260, 2261 to 3374, and 3735 to 3908, where for each of SEQ ID Nos. 1 to 3908, 1 to 2260, 2261 to 3374, and 3735 to 3908, the sense microsequencing primer contains the complement of the 19 nucleotides having their 3' ends located 1 nucleotide upstream of the polymorphic base of the respective SEQ ID No, and where the antisense microsequencing primer contains the complement of the 19 nucleotides of the complementary strand, nucleotides of the primer having their 3' end located 1 nucleotide upstream of the polymorphic base on the complementary strand to the respective SEQ ID No. The most preferred of said microsequencing primers for each of SEQ ID Nos. 1 to 3908, 1 to 2260, 2261 to 3374, and 3735 to 3908 are microsequencing primers indicated as "A" or "S" in Table 1, which have been validated in microsequencing experiments.

The probes of the present invention may be designed from the disclosed sequences for any method known in the art, particularly methods which allow for testing if a particular sequence or marker disclosed herein is present. A preferred set of probes may be designed for use in the hybridization assays of the invention in any manner known in the art such that they selectively bind to one allele of a biallelic marker, but not the other under any particular set of assay conditions. Preferred hybridization probes may consist of, consist essentially of, or comprise a contiguous span of SEQ ID Nos. 1 to 3908, 1 to 2260, 2261 to 3374, and 3735 to 3908, or the complement thereof, which ranges in length from least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID No., or be specified as being 12, 15, 18, 19, 20, 25, 35, 40, 43, 44, 45, 46 or 47 nucleotides in length and including the map-related biallelic marker of said sequence. Optionally the 1 st allele or 2nd allele of SEQ ID Nos. 1 to 3908, 1 to 2260, 2261 to 3374, and 3735 to 3908 may be specified as being present at the biallelic marker site. Optionally, said biallelic marker may be within 6, 5, 4, 3, 2, or 1 nucleotides of the center of the hybridization probe or at the center of said probe.

Any of the polynucleotides of the present invention can be labeled, if desired, by incorporating a label detectable by spectroscopic, photochemical, biochemical, immunochemical, or chemical means. For example, useful labels include radioactive substances, fluorescent dyes or biotin. Preferably, polynucleotides are labeled at their 3' and 5' ends. A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes® and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the inventions to a single solid support. In addition, polynucleotides other than those of the invention may attached to the same solid support as one or more polynucleotides of the invention.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092, the disclosures of which are incorporated herein by reference in their entireties. These arrays may generally be produced using mechanical synthesis methods or light directed synthesis methods, which incorporate a combination of photolithographic methods and solid phase oligonucleotide synthesis (Fodor et al., Science, 251:767–777, 1991, the disclosure of which is incorporated herein by reference in its entirety). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854 and 5,412,087 and in PCT Publications WO 90/15070, WO 92/10092 and WO 95/11995, the disclosures of which are incorporated herein by reference in their entirety, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated herein by reference in their entireties.

Oligonucleotide arrays may comprise at least one of the sequences selected from the group consisting of SEQ ID Nos. 1 to 3908, 1 to 2260, 2261 to 3374, and 3735 to 3908 and the sequences complementary thereto, or a fragment thereof of at least 8, 10, 12, 15, 18, 19, 20, 22, 23, 24, 25, 30, 35, 43, 44, 45, 46 or 47 consecutive nucleotides, to the extent that fragments of these lengths is consistent with the lengths of the particular Sequence ID, for determining whether a sample contains one or more alleles of the biallelic markers of the present invention. Oligonucleotide arrays may also comprise at least one of the sequences selected from the group consisting of SEQ ID Nos. 1 to 3908, 1 to 2260, 2261 to 3374, and 3735 to 3908, and the sequences complementary thereto, or a fragment thereof of at least 8, 10, 12, 15, 18, 19, 20, 22, 23, 24, 25, 30, 35, 43, 44, 45, 46 or 47 consecutive nucleotides, to the extent that fragments of these lengths is consistent with the lengths of the particular Sequence ID, for amplifying one or more alleles of the biallelic markers of SEQ ID Nos. 1 to 3908, 1 to 2260, 2261 to 3374, and 3735 to 3908. In other embodiments, arrays may also comprise at least one of the sequences selected from the group consisting of SEQ ID Nos. 1 to 3908, 1 to 2260, 2261 to 3374, and 3735 to 3908 and the sequences complementary thereto, or a fragment thereof of at 8, 10, 12, 15, 18, 19, 20, 22, 23, 24, 25, 30, 35, 43, 44, 45, 46 or 47 consecutive nucleotides, to the extent that fragments of these lengths is consistent with the lengths of the particular Sequence ID, for conducting microsequencing analyses to determine whether a sample contains one or more alleles of the biallelic markers of the invention. In still further embodiments, the oligonucleotide array may comprise at least one of the sequences selected from the group consisting of SEQ ID Nos. 1 to 3908, 1 to 2260, 2261 to 3374, and 3735 to 3908 and the sequences complementary thereto, or a fragment thereof of at least 8, 10, 12, 15, 18, 19, 20, 22, 23, 24, 25, 30, 35, 43, 44, 45, 46 or 47 nucleotides in length, to the extent that fragments of these lengths is consistent with the lengths of the particular Sequence ID, for determining whether a sample contains one or more alleles of the biallelic markers of the present invention.

In designing strategies aimed at providing arrays of nucleotides immobilized on solid supports, further presentation strategies were developed to order and display the probe arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated herein by reference in their entireties.

Each DNA chip can contain thousands to millions of individual synthetic DNA probes arranged in a grid-like pattern and miniaturized to the size of a dime. In some embodiments, the efficiency of hybridization of nucleic acids in the sample with the probes attached to the chip may be improved by using polyacrylamide gel pads isolated from one another by hydrophobic regions in which the DNA probes are covalently linked to an acrylamide matrix.

The polymorphic bases present in the biallelic marker or markers of the sample nucleic acids are determined as follows. Probes which contain at least a portion of one or more of the biallelic markers of the present invention are synthesized either in situ or by conventional synthesis and immobilized on an appropriate chip using methods known to the skilled technician.

Any one or more alleles of the biallelic markers described herein (SEQ ID Nos. 1 to 3908, 1 to 2260, 2261 to 3374, 3735 to 3908 or the sequences complementary thereto) or fragments thereof containing the polymorphic bases, may be fixed to a solid support, such as a microchip or other immobilizing surface. The fragments of these nucleic acids may comprise at least 10, at least 15, at least 20, at least 25, or more than 25 consecutive nucleotides of the biallelic markers described herein. Preferably, the fragments include the polymorphic bases of the biallelic markers.

A nucleic acid sample is applied to the immobilizing surface and analyzed to determine the identities of the polymorphic bases of one or more of the biallelic markers. In some embodiments, the solid support may also include one or more of the amplification primers described herein, or fragments comprising at least 10, at least 15, or at least 20 consecutive nucleotides thereof, for generating an amplification product containing the polymorphic bases of the biallelic markers to be analyzed in the sample.

Another embodiment of the present invention is a solid support which includes one or more of the microsequencing primers of the invention, or fragments comprising at least 10, at least 15, or at least 20 consecutive nucleotides thereof and having a 3' terminus immediately upstream of the polymorphic base of the corresponding biallelic marker, for determining the identity of the polymorphic base of the one or more biallelic markers fixed to the solid support.

For example, one embodiment of the present invention is an array of nucleic acids fixed to a solid support, such as a microchip, bead, or other immobilizing surface, comprising one or more of the biallelic markers in the maps of the present invention or a fragment comprising at least 10, at least 15, at least 20, at least 25, or more than 25 consecutive nucleotides thereof including the polymorphic base. For example, the array may comprise 1, 5, 10, 20, 50, 100, 200, 500, 1000, 2000, or 3000 of the biallelic markers selected from the group consisting of SEQ ID Nos.: 1 to 3908, 1 to 2260, 2261 to 3374, 3735 to 3908 or the sequences complementary thereto, or a fragment comprising at least 10, at least 15, at least 20, at least 25, or more than 25 consecutive nucleotides thereof including the polymorphic base.

Another embodiment of the present invention is an array comprising amplification primers for generating amplification products containing the polymorphic bases of one or more, at least five, at least 10, at least 20, at least 100, at least 200, at least 300, at least 400, or more than 400 of the biallelic markers in the maps of the present invention. For example, the array may comprise amplification primers for generating amplification products containing the polymorphic bases of at least 1,5, 10, 20, 50, 100, 200, 300, 400, 500, 1000, 2000, or 3000, of the biallelic markers selected from the group consisting of SEQ ID Nos.: 1 to 3908, 1 to 2260, 2261 to 3374, 3735 to 3908 or the sequences complementary thereto. In such arrays, the amplification primers included in the array are capable of amplifying the biallelic marker sequences to be detected in the nucleic acid sample applied to the array (i.e. the amplification primers correspond to the biallelic markers affixed to the array—see Table 1). Thus, the arrays may include one or more of the amplification primers of SEQ ID Nos.: 3935 to 7842, 7866 to 11773, 3935 to 6194, 6195 to 7668, 7669 to 7842, 7866 to 10125, 10126 to 11599, and 11600 to 11773 corresponding to the one or more biallelic markers of SEQ ID Nos. 1 to 3908, 1 to 2260, 2261 to 3374, and 3735 to 3908 which are included in the array.

Another embodiment of the present invention is an array which includes microsequencing primers capable of determining the identity of the polymorphic bases of at least 1, 5, 10, 20, 50, 100, 200, 300, 500, 1000, 2000, or 3000 of the present invention. For example, the array may comprise microsequencing primers capable of determining the identity of the polymorphic bases of one or more, at least five, at least 10, at least 20, at least 100, at least 200, at least 300, at least 400, or more than 400 of the biallelic markers of SEQ ID Nos. 1 to 3908, 1 to 2260, 2261 to 3374, 3735 to 3908 or the sequences complementary thereto.

Arrays containing any combination of the above nucleic acids which permits the specific detection or identification of the polymorphic bases of the biallelic markers in the maps of the present invention, including any combination of biallelic markers of SEQ ID Nos. 1 to 3908, 1 to 2260, 2261 to 3374, 3735 to 3908 or the sequences complementary thereto are also within the scope of the present invention. For example, the array may comprise both the biallelic markers and amplification primers capable of generating amplification products containing the polymorphic bases of the biallelic markers. Alternatively, the array may comprise both amplification primers capable of generating amplification products containing the polymorphic bases of the biallelic markers and microsequencing primers capable of determining the identities of the polymorphic bases of these markers.

Although the above examples describe arrays comprising specific groups of biallelic markers and, in some embodiments, specific amplification primers and microsequencing primers, it will be appreciated that the present invention encompasses arrays including any biallelic marker, group of biallelic markers, amplification primer, group of amplification primers, microsequencing primer, or group of amplification primers described herein, as well as any combination of the preceding nucleic acids.

The present invention also encompasses diagnostic kits comprising one or more polynucleotides of the invention, optionally with a portion or all of the necessary reagents and instructions for genotyping a test subject by determining the identity of a nucleotide at a map-related biallelic marker. The polynucleotides of a kit may optionally be attached to a solid support, or be part of an array or addressable array of polynucleotides. The kit may provide for the determination of the identity of the nucleotide at a marker position by any method known in the art including, but not limited to, a sequencing assay method, a microsequencing assay method, a hybridization assay method, or an allele specific amplification method. Optionally,such a kit may include instructions for scoring the results of the determination with respect to the test subjects' risk of contracting a diseases involving a disease, likely response to an agent acting on a disease, or chances of suffering from side effects to an agent acting on a disease.

II. Methods For De Novo Identification Of Biallelic Markers

Any of a variety of methods can be used to screen a genomic fragment for single nucleotide polymorphisms such as differential hybridization with oligonucleotide probes, detection of changes in the mobility measured by gel electrophoresis or direct sequencing of the amplified nucleic acid. A preferred method for identifying biallelic markers involves comparative sequencing of genomic DNA fragments from an appropriate number of unrelated individuals.

In a first embodiment, DNA samples from unrelated individuals are pooled together, following which the genomic DNA of interest is amplified and sequenced. The nucleotide sequences thus obtained are then analyzed to identify significant polymorphisms. One of the major advantages of this method resides in the fact that the pooling of the DNA samples substantially reduces the number of DNA amplification reactions and sequencing reactions, which must be carried out. Moreover, this method is sufficiently sensitive so that a biallelic marker obtained thereby usually demonstrates a sufficient frequency of its less common allele to be useful in conducting association studies. Usually, the frequency of the least common allele of a biallelic marker identified by this method is at least 10%.

In a second embodiment, the DNA samples are not pooled and are therefore amplified and sequenced individually. This method is usually preferred when biallelic markers need to be identified in order to perform association studies within candidate genes. Preferably, highly relevant gene regions such as promoter regions or exon regions may be screened for biallelic markers. A biallelic marker obtained using this method may show a lower degree of informativeness for conducting association studies, e.g. if the frequency of its less frequent allele may be less than about 10%. Such a biallelic marker will however be sufficiently informative to conduct association studies and it will further be appreciated that including less informative biallelic markers in the genetic analysis studies of the present invention, may allow in some cases the direct identification of causal mutations, which may, depending on their penetrance, be rare mutations.

The following is a description of the various parameters of a preferred method used by the inventors for the identification of the biallelic markers of the present invention.

II.A. Genomic DNA Samples

The genomic DNA samples from which the biallelic markers of the present invention are generated are preferably obtained from unrelated individuals corresponding to a heterogeneous population of known ethnic background. The number of individuals from whom DNA samples are obtained can vary substantially, preferably from about 10 to about 1000, more preferably from about 50 to about 200 individuals. Usually, DNA samples are collected from at least about 100 individuals in order to have sufficient polymorphic diversity in a given population to identify as many markers as possible and to generate statistically significant results.

As for the source of the genomic DNA to be subjected to analysis, any test sample can be foreseen without any particular limitation. These test samples include biological samples, which can be tested by the methods of the present invention described herein, and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the present invention is from peripheral venous blood of each donor. Techniques to prepare genomic DNA from biological samples are well known to the skilled technician. Details of a preferred embodiment are provided in Example 27. The person skilled in the art can choose to amplify pooled or unpooled DNA samples.

II.B. DNA Amplification

The identification of biallelic markers in a sample of genomic DNA may be facilitated through the use of DNA amplification methods. DNA samples can be pooled or unpooled for the amplification step. DNA amplification techniques are well known to those skilled in the art. Various methods to amplify DNA fragments carrying biallelic markers are further described hereinafter in III.B. The PCR technology is the preferred amplification technique used to identify new biallelic markers.

In a first embodiment, biallelic markers are identified using genomic sequence information generated by the inventors. Genomic DNA fragments, such as the inserts of the BAC clones described above, are sequenced and used to design primers for the amplification of 500 bp fragments. These 500 bp fragments are amplified from genomic DNA and are scanned for biallelic markers. Primers may be designed using the OSP software (Hillier L. and Green P., 1991, the entire disclosure of which is incorporated by reference herein in its entirety). All primers may contain, upstream of the specific target bases, a common oligonucleotide tail that serves as a sequencing primer. Those skilled in the art are familiar with primer extensions, which can be used for these purposes.

In another embodiment of the invention, genomic sequences of candidate genes are available in public databases allowing direct screening for biallelic markers. Preferred primers, useful for the amplification of genomic sequences encoding the candidate genes, focus on promoters, exons and splice sites of the genes. A biallelic marker present in these functional regions of the gene have a higher probability to be a causal mutation.

Preferred primers include those disclosed in SEQ ID Nos. 3935 to 7842, 3935 to 6194, 6195 to 7668, 7669 to 7842, 7866 to 11773, 7866 to 10125, 10126 to 11599, and 11600 to 11773.

II.C. Sequencing Of Amplified Genomic DNA And Identification Of Single Nucleotide Polymorphisms The amplification products generated as described above, are then sequenced using any method known and available to the skilled technician. Methods for sequencing DNA using either the dideoxy-mediated method (Sanger method) or the Maxam-Gilbert method are widely known to those of ordinary skill in the art. Such methods are for example disclosed in Maniatis et al. (Molecular Cloning, A Laboratory Manual, Cold Spring Harbor Press, Second Edition, 1989 the disclosure of which is incorporated herein by reference in its entirety). Alternative approaches include hybridization to high-density DNA probe arrays as described in Chee et al. (Science 274, 610, 1996, the disclosure of which is incorporated herein by reference in its entirety).

Preferably, the amplified DNA is subjected to automated dideoxy terminator sequencing reactions using a dye-primer cycle sequencing protocol. The products of the sequencing reactions are run on sequencing gels and the sequences are determined using gel image analysis. The polymorphism search is based on the presence of superimposed peaks in the electrophoresis pattern resulting from different bases occurring at the same position. Because each dideoxy terminator is labeled with a different fluorescent molecule, the two peaks corresponding to a biallelic site present distinct colors corresponding to two different nucleotides at the same position on the sequence. However, the presence of two peaks can be an artifact due to background noise. To exclude such an artifact, the two DNA strands are sequenced and a comparison between the peaks is carried out. In order to be registered as a polymorphic sequence, the polymorphism has to be detected on both strands.

The above procedure permits those amplification products, which contain biallelic markers to be identified.

The detection limit for the frequency of biallelic polymorphisms detected by sequencing pools of 100 individuals is approximately 0.1 for the minor allele, as verified by sequencing pools of known allelic frequencies. However, more than 90% of the biallelic polymorphisms detected by the pooling method have a frequency for the minor allele higher than 0.25. Therefore, the biallelic markers selected by this method have a frequency of at least 0.1 for the minor allele and less than 0.9 for the major allele. Preferably at least 0.2 for the minor allele and less than 0.8 for the major allele, more preferably at least 0.3 for the minor allele and less than 0.7 for the major allele, thus a heterozygosity rate higher than 0.18, preferably higher than 0.32, more preferably higher than 0.42.

In another embodiment, biallelic markers are detected by sequencing individual DNA samples, the frequency of the minor allele of such a biallelic marker may be less than 0.1.

The markers carried by the same fragment of genomic DNA, such as the insert in a BAC clone, need not necessarily be ordered with respect to one another within the genomic fragment to conduct association studies. However, in some embodiments of the present invention, the order of biallelic markers carried by the same fragment of genomic DNA are determined.

II.D. Validation of the Biallelic Markers of the Present Invention

The polymorphisms are evaluated for their usefulness as genetic markers by validating that both alleles are present in a population. Validation of the biallelic markers is accomplished by genotyping a group of individuals by a method of the invention and demonstrating that both alleles are present. Microsequencing is a preferred method of genotyping alleles. The validation by genotyping step may be performed on individual samples derived from each individual in the group or by genotyping a pooled sample derived from more than one individual. The group can be as small as one individual if that individual is heterozygous for the allele in question. Preferably the group contains at least three individuals, more preferably the group contains five or six individuals, so that a single validation test will be more likely to result in the validation of more of the biallelic markers that are being tested. It should be noted, however, that when the validation test is performed on a small group it may result in a false negative result if as a result of sampling error none of the individuals tested carries one of the two alleles. Thus, the validation process is less useful in demonstrating that a particular initial result is an artifact, than it is at demonstrating that there is a bonafide biallelic marker at a particular position in a sequence. All of the genotyping, haplotyping, association, and interaction study methods of the invention may optionally be performed solely with validated biallelic markers.

II.E. Evaluation of the Frequency of the Biallelic Markers of the Present Invention The validated biallelic markers are further evaluated for their usefulness as genetic markers by determining the frequency of the least common allele at the biallelic marker site. The determination of the least common allele is accomplished by genotyping a group of individuals by a method of the invention and demonstrating that both alleles are present. This determination of frequency by genotyping step may be performed on individual samples derived from each individual in the group or by genotyping a pooled sample derived from more than one individual. The group must be large enough to be representative of the population as a whole. Preferably the group contains at least 20 individuals, more preferably the group contains at least 50 individuals, most preferably the group contains at least 100 individuals. Of course the larger the group the greater the accuracy of the frequency determination because of reduced sampling error. A biallelic marker wherein the frequency of the less common allele is 30% or more is termed a "high quality biallelic marker." All of the genotyping, haplotyping, association, and interaction study methods of the invention may optionally be performed solely with high quality biallelic markers.

III. Methods Of Genotyping An Individual For Biallelic Markers

Methods are provided to genotype a biological sample for one or more biallelic markers of the present invention, all of which may be performed in vitro. Such methods of genotyping comprise determining the identity of a nucleotide at a map-related biallelic marker by any method known in the art. These methods find use in genotyping case-control populations in association studies as well as individuals in the context of detection of alleles of biallelic markers which, are known to be associated with a given trait, in which case both copies of the biallelic marker present in individual's genome are determined so that an individual may be classified as homozygous or heterozygous for a particular allele.

These genotyping methods can be performed nucleic acid samples derived from a single individual or pooled DNA samples.

Genotyping can be performed using similar methods as those described above for the identification of the biallelic markers, or using other genotyping methods such as those further described below. In preferred embodiments, the comparison of sequences of amplified genomic fragments from different individuals is used to identify new biallelic markers whereas microsequencing is used for genotyping known biallelic markers in diagnostic and association study applications.

III.A. Source of DNA for Genotyping

Any source of nucleic acids, in purified or non-purified form, can be utilized as the starting nucleic acid, provided it contains or is suspected of containing the specific nucleic acid sequence desired. DNA or RNA may be extracted from cells, tissues, body fluids and the like as described above in II.A. While nucleic acids for use in the genotyping methods of the invention can be derived from any mammalian source, the test subjects and individuals from which nucleic acid samples are taken are generally understood to be human.

III.B. Amplification Of DNA Fragments Comprising Biallelic Markers

Methods and polynucleotides are provided to amplify a segment of nucleotides comprising one or more biallelic marker of the present invention. It will be appreciated that amplification of DNA fragments comprising biallelic markers may be used in various methods and for various purposes and is not restricted to genotyping. Nevertheless, many genotyping methods, although not all, require the previous amplification of the DNA region carrying the biallelic marker of interest. Such methods specifically increase the concentration or total number of sequences that span the biallelic marker or include that site and sequences located either distal or proximal to it. Diagnostic assays may also rely on amplification of DNA segments carrying a biallelic marker of the present invention.

Amplification of DNA may be achieved by any method known in the art. The established PCR (polymerase chain reaction) method or by developments thereof or alternatives. Amplification methods which can be utilized herein include but are not limited to Ligase Chain Reaction (LCR) as described in EP A 320 308 and EP A 439 182, Gap LCR (Wolcott, M. J., Clin. Mcrobiol. Rev. 5:370–386), the so-called "NASBA" or "3SR" technique described in Guatelli J. C. et al. (*Proc. Natl. Acad. Sci. USA* 87:1874–1878, 1990) and in Compton J. (*Nature* 350:91–92, 1991), Q-beta amplification as described in European Patent Application no 4544610, strand displacement amplification as described in Walker et al. (*Clin. Chem.* 42:9–13, 1996) and EP A 684 315 and, target mediated amplification as described in PCT Publication WO 9322461, the disclosures of which are incorporated herein by reference in their entireties.

LCR and Gap LCR are exponential amplification techniques, both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3'hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227, the disclosure of which is incorporated herein by reference in its entirety). Gap LCR (GLCR) is a version of LCR where the probes are not adjacent but are separated by 2 to 3 bases.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, the disclosure of which is incorporated herein by reference in its entirety, or, to use Asymmetric Gap LCR (RT-AGLCR) as described by Marshall R. L. et al. (*PCR Methods and Applications* 4:80–84, 1994, the disclosure of which is incorporated herein by reference in its entirety). AGLCR is a modification of GLCR that allows the amplification of RNA.

Some of these amplification methods are particularly suited for the detection of single nucleotide polymorphisms and allow the simultaneous amplification of a target sequence and the identification of the polymorphic nucleotide as it is further described in III.C.

The PCR technology is the preferred amplification technique used in the present invention. A variety of PCR techniques are familiar to those skilled in the art. For a review of PCR technology, see Molecular Cloning to Genetic Engineering White, B.A. Ed. in *Methods in Molecular Biology* 67: Humana Press, Totowa (1997) and the publication entitled "PCR Methods and Applications" (1991, Cold Spring Harbor Laboratory Press, the disclosures of which are incorporated herein by reference in their entireties). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188, the disclosures of which are incorporated herein by reference in their entireties.

The identification of biallelic markers as described above allows the design of appropriate oligonucleotides, which can be used as primers to amplify DNA fragments comprising the biallelic markers of the present invention. Amplification can be performed using the primers initially used to discover new biallelic markers which are described herein or any set of primers allowing the amplification of a DNA fragment comprising a biallelic marker of the present invention. Primers can be prepared by any suitable method. As for example, direct chemical synthesis by a method such as the phosphodiester method of Narang S. A. et al. (*Methods Enzymol*. 68:90–98, 1979), the phosphodiester method of Brown E. L. et al. (*Methods Enzymol*. 68:109–151, 1979), the diethylphosphoramidite method of Beaucage et al. (*Tetrahedron Lett*. 22:1859–1862, 1981) and the solid support method described in EP 0 707 592, the disclosures of which are incorporated herein by reference in their entireties.

In some embodiments the present invention provides primers for amplifying a DNA fragment containing one or more biallelic markers of the present invention. Preferred amplification primers are listed in SEQ ID Nos. 3935 to 7842, 3935 to 6194, 6195 to 7668, 7669 to 7842, 7866 to 11773, 7866 to 10125, 10126 to 11599, and 11600 to 11773. It will be appreciated that the primers listed are merely exemplary and that any other set of primers which produce amplification products containing one or more biallelic markers of the present invention.

The primers are selected to be substantially complementary to the different strands of each specific sequence to be amplified. The length of the primers of the present invention can range from 8 to 100 nucleotides, preferably from 8 to 50, 8 to 30 or more preferably 8 to 25 nucleotides. Shorter primers tend to lack specificity for a target nucleic acid sequence and generally require cooler temperatures to form sufficiently stable hybrid complexes with the template. Longer primers are expensive to produce and can sometimes self-hybridize to form hairpin structures. The formation of stable hybrids depends on the melting temperature (Tm) of the DNA. The Tm depends on the length of the primer, the ionic strength of the solution and the G+C content. The higher the G+C content of the primer, the higher is the melting temperature because G:C pairs are held by three H bonds whereas A:T pairs have only two. The G+C content of the amplification primers of the present invention preferably ranges between 10 and 75%, more preferably between 35 and 60%, and most preferably between 40 and 55%. The appropriate length for primers under a particular set of assay conditions may be empirically determined by one of skill in the art.

The spacing of the primers determines the length of the segment to be amplified. In the context of the present invention amplified segments carrying biallelic markers can range in size from at least about 25 bp to 35 kbp. Amplification fragments from 25–3000 bp are typical, fragments from 50–1000 bp are preferred and fragments from 100–600 bp are highly preferred. It will be appreciated that amplification primers for the biallelic markers may be any sequence which allow the specific amplification of any DNA fragment carrying the markers. Amplification primers may be labeled or immobilized on a solid support as described in I.

III.C. Methods of Genotyping DNA Samples for Biallelic Markers

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods. Methods well-known to those skilled in the art that can be used to detect biallelic polymorphisms include methods such as, conventional dot blot analyzes, single strand conformational polymorphism analysis (SSCP) described by Orita et al. (*Proc. Natl. Acad. Sci. U.S.A* 86:27776–2770, 1989, the disclosure of which is incorporated herein by reference in its entirety), denaturing gradient gel electrophoresis (DGGE), heteroduplex analysis, mismatch cleavage detection, and other conventional techniques as described in Sheffield, V. C. et al. (*Proc. Natl. Acad. Sci. USA* 49:699–706, 1991), White et al. (*Genomics* 12:301–306, 1992), Grompe, M. et al. (*Proc. Natl. Acad. Sci. USA* 86:5855–5892, 1989) and Grompe, M. (*Nature Genetics* 5:111–117, 1993, the disclosures of which are incorporated herein by reference in their entireties). Another method for determining the identity of the nucleotide present at a particular polymorphic site employs a specialized exonuclease-resistant nucleotide derivative as described in U.S. Pat. No. 4,656,127, the disclosure of which is incorporated herein by reference in its entirety.

Preferred methods involve directly determining the identity of the nucleotide present at a biallelic marker site by sequencing assay, enzyme-based mismatch detection assay, or hybridization assay. The following is a description of some preferred methods. A highly preferred method is the microsequencing technique. The term "sequencing assay" is used herein to refer to polymerase extension of duplex primer/template complexes and includes both traditional sequencing and microsequencing.

1) Sequencing Assays

The nucleotide present at a polymorphic site can be determined by sequencing methods. In a preferred embodiment, DNA samples are subjected to PCR amplification before sequencing as described above. DNA sequencing methods are described in IIC.

Preferably, the amplified DNA is subjected to automated dideoxy terminator sequencing reactions using a dye-primer cycle sequencing protocol. Sequence analysis allows the identification of the base present at the biallelic marker site.

2) Microsequencing Assays

In microsequencing methods, a nucleotide at the polymorphic site that is unique to one of the alleles in a target DNA is detected by a single nucleotide primer extension reaction. This method involves appropriate microsequencing primers which, hybridize just upstream of a polymorphic base of interest in the target nucleic acid. A polymerase is used to specifically extend the 3' end of the primer with one single ddNTP (chain terminator) complementary to the selected nucleotide at the polymorphic site. Next the identity of the incorporated nucleotide is determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883, the disclosure of which is incorporated herein by reference in its entirety. Alternatively capillary electrophoresis can be used in order to process a higher number of assays simultaneously. An example of a typical microsequencing procedure that can be used in the context of the present invention is provided in Example 8.

Different approaches can be used to detect the nucleotide added to the microsequencing primer. A homogeneous phase detection method based on fluorescence resonance energy transfer has been described by Chen and Kwok (*Nucleic Acids Research* 25:347–353 1997) and Chen et al. (*Proc. Natl. Acad. Sci. USA* 94/20 10756–10761,1997, the disclosures of which are incorporated herein by reference in their entireties). In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All of these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff L. A. and Smirnov I. P., *Genome Research*, 7:378–388, 1997, the disclosure of which is incorporated herein by reference in its entirety).

Microsequencing may be achieved by the established microsequencing method or by developments or derivatives thereof. Alternative methods include several solid-phase microsequencing techniques. The basic microsequencing protocol is the same as described previously, except that the method is conducted as a heterogenous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystyrene particles. In the same manner oligonucleotides or templates may be attached to a solid support in a high-density format. In such solid phase microsequencing reactions, incorporated ddNTPs can be radiolabeled (Syvänen, *Clinica Chimica Acta* 226:225–236, 1994, the disclosure of which is incorporated herein by reference in its entirety), or linked to fluorescein (Livak and Hainer, *Human Mutation* 3:379–385,1994, the disclosure of which is incorporated herein by reference in its entirety). The detection of radiolabeled ddNTPs can be achieved through scintillation-based techniques. The detection of fluorescein-linked ddNTT's can be based on the binding of antifluorescein antibody conjugated with alkaline phosphatase, followed by incubation with a chromogenic substrate (such asp-nitrophenyl phosphate). Other possible reporter-detection pairs include: ddNTP linked to dinitrophenyl (DNP) and anti-DNP alkaline phosphatase conjugate (Harju et al., *Clin. Chem.* 39/11 2282–2287, 1993, the disclosure of which is incorporated herein by reference in its entirety), or biotinylated ddNTP and horseradish peroxidase-conjugated streptavidin with o-phenylenediamine as a substrate (WO 92/15712, the disclosure of which is incorporated herein by reference in its entirety). As yet another alternative solid-phase microsequencing procedure, Nyren et al. (*Analytical Biochemistry* 208:171–175, 1993, the disclosure of which is incorporated herein by reference in its entirety), described a method relying on the detection of DNA polymerase activity by an enzymatic luminometric inorganic pyrophosphate detection assay (ELIDA).

Pastinen et al. (*Genome Research* 7:606–614, 1997, the disclosure of which is incorporated herein by reference in its entirety), describe a method for multiplex detection of single nucleotide polymorphism in which the solid phase minisequencing principle is applied to an oligonucleotide array format. High-density arrays of DNA probes attached to a solid support (DNA chips) are further described in III.C.5.

In one aspect, the present invention provides polynucleotides and methods to genotype one or more biallelic markers of the present invention by performing a microsequencing assay. In the preferred embodiment, it will be appreciated that any primer having a 3' end immediately adjacent to a polymorphic nucleotide may be used as a microsequencing primer. Similarly, it will be appreciated that microsequencing analysis may be performed for any biallelic marker or any combination of biallelic markers of the present invention. One aspect of the present invention is a solid support which includes one or more microsequencing primers comprising nucleotides complementary to the nucleotide sequences of SEQ ID Nos. 1 to 3908, 1 to 2260, 2261 to 3374, and 3735 to 3908 or the complements thereof, or fragments comprising at least 8, at least 12, at least 15, or at least 20 consecutive nucleotides thereof and having a 3' terminus immediately upstream of the corresponding biallelic marker, for determining the identity of a nucleotide at biallelic marker site.

3) Mismatch Detection Assays Based on Polymerases and Ligases

In one aspect the present invention provides polynucleotides and methods to determine the allele of one or more biallelic markers of the present invention in a biological sample, by mismatch detection assays based on polymerases and/or ligases. These assays are based on the specificity of polymerases and ligases. Polymerization reactions places particularly stringent requirements on correct base pairing of the 3' end of the amplification primer and the joining of two oligonucleotides hybridized to a target DNA sequence is quite sensitive to mismatches close to the ligation site, especially at the 3' end. The terms "enzyme based mismatch detection assay" are used herein to refer to any method of determining the allele of a biallelic marker based on the specificity of ligases and polymerases. Preferred methods are described below. Methods, primers and various parameters to amplify DNA fragments comprising biallelic markers of the present invention are further described above in III.B.

Allele Specific Amplification

Discrimination between the two alleles of a biallelic marker can also be achieved by allele specific amplification, a selective strategy, whereby one of the alleles is amplified without amplification of the other allele. This is accomplished by placing a polymorphic base at the 3' end of one of the amplification primers. Because the extension forms from the 3' end of the primer, a mismatch at or near this position has an inhibitory effect on amplification. Therefore, under appropriate amplification conditions, these primers only direct amplification on their complementary allele. Designing the appropriate allele-specific primer and the corresponding assay conditions are well with the ordinary skill in the art.

Ligation/Amplification Based Methods

The "Oligonucleotide Ligation Assay" (OLA) uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting biallelic markers and may be advantageously combined with PCR as described by Nickerson D. A. et al. (*Proc. Natl. Acad. Sci. U.S.A.* 87:8923–8927, 1990, the disclosure of which is incorporated herein by reference in its entirety). In this method, PCR is used to achieve the exponential amplification of target DNA, which is then detected using OLA.

Other methods which are particularly suited for the detection of biallelic markers include LCR (ligase chain reaction), Gap LCR (GLCR) which are described above in III.B. As mentioned above LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide(s) that is complementary to the biallelic marker on the oligonucleotide. In an alternative embodiment, the oligonucleotides will not include the biallelic marker, such that when they hybridize to the target molecule, a "gap" is created as described in WO 90/01069, the disclosure of which is incorporated herein by reference in its entirety. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271, the disclosure of which is incorporated herein by reference in its entirety). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay may be used including Southern hybridization, Northern hybridization, dot blot hybridization and solid-phase hybridization (see Sambrook et al., Molecular Cloning—A Laboratory Manual, Second Edition, Cold Spring Harbor Press, N.Y., 1989, the disclosure of which is incorporated herein by reference in its entirety).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., Molecular Cloning—A Laboratory Manual, Second Edition, Cold Spring Harbor Press, N.Y., 1989, the disclosure of which is incorporated herein by reference in its entirety). Stringent conditions are sequence dependent and will be different in different circumstances. Generally, stringent conditions are selected to be about 5° C. lower than the thermal melting point (Tm) for the specific sequence at a defined ionic strength and pH. By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in prehybridization mixture containing 100 µg/ml denatured salmon sperm DNA and 5–20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. By way of example and not limitation, procedures using conditions of intermediate stringency are as follows: Filters containing DNA are prehybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of high and intermediate stringency which may be used are well known in the art and as cited in Sambrook et al. (Molecular Cloning—A Laboratory Manual, Second Edition, Cold Spring Harbor Press, N.Y., 1989) and Ausubel et al. (Current Protocols in Molecular Biology, Green Publishing Associates and Wiley Interscience, N.Y., 1989, the disclosure of which is incorporated herein by reference in its entirety).

Although such hybridizations can be performed in solution, it is preferred to employ a solid-phase hybridization assay. The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe. Standard heterogeneous assay formats are suitable for detecting the hybrids using the labels present on the primers and probes.

Two recently developed assays allow hybridization-based allele discrimination with no need for separations or washes (see Landegren U. et al., *Genome Research*, 8:769–776, 1998, the disclosure of which is incorporated herein by reference in its entirety). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., *Nature Genetics*, 9:341–342, 1995, the disclosure of which is incorporated herein by reference in its entirety). In an alternative homogeneous hybridization-based procedure, molecular beacons are used for allele discriminations. Molecular beacons are hairpin-shaped oligonucleotide probes that report the presence of specific nucleic acids in homogeneous solutions. When they bind to their targets, they undergo a conformational reorganization that restores the fluorescence of an internally quenched fluorophore (Tyagi et al., *Nature Biotechnology*, 16:49–53, 1998, the disclosure of which is incorporated herein by reference in its entirety).

The polynucleotides provided herein can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. The GC content in the probes of the invention usually ranges between 10 and 75%, preferably between 35 and 60%, and more preferably between 40 and 55%. The length of these probes can range from 10, 15, 20, or 30 to at least 100 nucleotides, preferably from 10 to 50, more preferably from 18 to 35 nucleotides. A particularly preferred probe is 25 nucleotides in length. Preferably the biallelic marker is within 4 nucleotides of the center of the polynucleotide probe. In particularly preferred probes the biallelic marker is at the center of said polynucleotide. Shorter probes may lack specificity for a target nucleic acid sequence and generally require cooler temperatures to form sufficiently stable hybrid complexes with the template. Longer probes are expensive to produce and can sometimes self-hybridize to form hairpin structures. Methods for the synthesis of oligonucleotide probes have been described above and can be applied to the probes of the present invention.

Preferably, the probes of the-present invention are labeled or immobilized on a solid support. Labels and solid supports are further described in I. Detection probes are generally nucleic acid sequences or uncharged nucleic acid analogs such as, for example peptide nucleic acids which are disclosed in International Patent Application WO 92/20702, the disclosure of which is hereby incorporated herein by reference in its entirety, and morpholino analogs which are described in U.S. Pat. Nos. 5,185,444; 5,034,506 and 5,142,047, the disclosures of which are hereby incorporated herein by reference in their entireties. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be finctionalized with the capture or detection label to thereby consume or otherwise block the hydroxyl group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

The probes of the present invention are useful for a number of purposes. They can be used in Southern hybridization to genomic DNA or Northern hybridization to mRNA. The probes can also be used to detect PCR amplification products. By assaying the hybridization to an allele specific probe, one can detect the presence or absence of a biallelic marker allele in a given sample.

High-throughput parallel hybridizations in array format are specifically encompassed within "hybridization assays" and are described below.

Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in *S. cerevisiae* mutant strains, and in the protease gene of HIV-1 virus (Hacia et al., *Nature Genetics*, 14(4):441–447, 1996; Shoemaker et al., *Nature Genetics*, 14(4):450–456, 1996; Kozal et al., *Nature Medicine*, 2:753–759, 1996, the disclosures of which are incorporated herein by reference in their entireties). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual which, target sequences include a polymorphic marker. EP785280, the disclosure of which is incorporated herein by reference in its entirety, describes a tiling strategy for the detection of single nucleotide polymorphisms. Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of monomers, i.e. nucleotides. Tiling strategies are further described in PCT application No. WO 95/11995, the disclosure of which is incorporated herein by reference in its entirety. In a particular aspect, arrays are tiled for a number of specific, identified biallelic marker sequences. In particular the array is tiled to include a number of detection blocks, each detection block being specific for a specific biallelic marker or a set of biallelic markers. For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92/10092 and WO 95/11995 and U.S. Pat. No. 5,424,186, the disclosures of which are incorporated herein by reference in their entireties.

Thus, in some embodiments, the chips may comprise an array of nucleic acid sequences of fragments of about 15 nucleotides in length. In further embodiments, the chip may comprise an array including at least one of the sequences selected from the group consisting of SEQ ID No. 1 to 3908, 1 to 2260, 2261 to 3374, and 3735 to 3908 and the sequences complementary thereto, or a fragment thereof at least about 8 consecutive nucleotides, preferably 10, 15, 20, more preferably least 30, 35, 43, 44, 45, 46 or 47 consecutive nucleotides, to the extent that a contiguous span of these lengths is consistent with the lengths of the particular Sequence ID. In some embodiments, the chip may comprise an array of at least 2, 3, 4, 5, 6, 7, 8 or more of these polynucleotides of the invention. Solid supports and polynucleotides of the present invention attached to solid supports are further described in I.

5) Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, the disclosure of which is hereby incorporated herein by reference in its entirety, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip. For genotyping biallelic markers, the microfluidic system may integrate nucleic acid amplification, microsequencing, capillary electrophoresis and a detection method such as laser-induced fluorescence detection.

IV. Methods Of Genetic Analysis Using The Biallelic Markers Of The Present Invention Different methods are available for the genetic analysis of complex traits (see Lander and Schork, *Science*, 265, 2037–2048, 1994, the disclosure of which is hereby incorporated herein by reference in its entirety). The search for disease-susceptibility genes is conducted using two main methods: the linkage approach in which evidence is sought for cosegregation between a locus and a putative trait locus using family studies, and the association approach in which evidence is sought for a statistically significant association between an allele and a trait or a trait causing allele (Khoury J. et al., *Fundamentals of Genetic Epidemiology*, Oxford University Press, New York, 1993, the disclosure of which is incorporated herein by reference in its entirety). In general, the biallelic markers of the present invention find use in any method known in the art to demonstrate a statistically significant correlation between a genotype and a phenotype. The biallelic markers may be used in parametric and non-parametric linkage analysis methods. Preferably, the biallelic markers of the present invention are used to identify genes associated with detectable traits using association studies, an approach which does not require the use of affected families and which permits the identification of genes associated with complex and sporadic traits.

The genetic analysis using the biallelic markers of the present invention may be conducted on any scale. The whole set of biallelic markers of the present invention or any subset of biallelic markers of the present invention may be used. In some embodiments a subset of biallelic markers corresponding to one or several candidate genes may be used. In other embodiments a subset of biallelic markers corresponding to candidate genes from a particular disease pathway may be used. Alternatively, a subset of biallelic markers of the present invention localised on a specific chromosome segment may be used. Further, any set of genetic markers including a biallelic marker of the present invention may be used. A set of biallelic polymorphisms that, could be used as genetic markers in combination with the biallelic markers of the present invention, has been described in WO 98/20165, the disclosure of which is incorporated herein by reference in its entirety. As mentioned above, it should be noted that the biallelic markers of the present invention may be included in any complete or partial genetic map of the human genome. These different uses are specifically contemplated in the present invention and claims.

IV.A. Linkage Analysis

Linkage analysis is based upon establishing a correlation between the transmission of genetic markers and that of a specific trait throughout generations within a family. Thus, the aim of linkage analysis is to detect marker loci that show cosegregation with a trait of interest in pedigrees.

Parametric Methods

When data are available from successive generations there is the opportunity to study the degree of linkage between pairs of loci. Estimates of the recombination fraction enable loci to be ordered and placed onto a genetic map. With loci that are genetic markers, a genetic map can be established, and then the strength of linkage between markers and traits can be calculated and used to indicate the relative positions of markers and genes affecting those traits (Weir, B. S., *Genetic data Analysis II: Methods for Discrete population genetic Data*, Sinauer Assoc., Inc., Sunderland, Mass., USA, 1996, the disclosure of which is incorporated herein by reference in its entirety). The classical method for linkage analysis is the logarithm of odds (lod) score method (see Morton N. E., *Am. J. Hum. Genet.*, 7:277–318, 1955; Ott J., *Analysis of Human Genetic Linkage*, John Hopkins University Press, Baltimore, 1991, the disclosures of which are incorporated herein by reference in their entireties). Calculation of lod scores requires specification of the mode of inheritance for the disease (parametric method). Generally, the length of the candidate region identified using linkage analysis is between 2 and 20 Mb. Once a candidate region is identified as described above, analysis of recombinant individuals using additional markers allows further delineation of the candidate region. Linkage analysis studies have generally relied on the use of a maximum of 5,000 microsatellite markers, thus limiting the maximum theoretical attainable resolution of linkage analysis to about 600 kb on average.

Linkage analysis has been successfully applied to map simple genetic traits that show clear Mendelian inheritance patterns and which have a high penetrance (i.e., the ratio between the number of trait positive carriers of allele a and the total number of a carriers in the population). However, parametric linkage analysis suffers from a variety of drawbacks. First, it is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis. In addition, parametric linkage analysis approaches have proven difficult when applied to complex genetic traits, such as those due to the combined action of multiple genes and/or environmental factors. It is very difficult to model these factors adequately in a lod score analysis. In such cases, too large an effort and cost are needed to recruit the adequate number of affected families required for applying linkage analysis to these situations, as recently discussed by Risch, N. and Merikangas, K. (*Science*, 273:1516–1517, 1996, the disclosure of which is incorporated herein by reference in its entirety).

Non-parametric Methods

The advantage of the so-called non-parametric methods for linkage analysis is that they do not require specification of the mode of inheritance for the disease, they tend to be more useful for the analysis of complex traits. In non-parametric methods, one tries to prove that the inheritance pattern of a chromosomal region is not consistent with random Mendelian segregation by showing that affected relatives inherit identical copies of the region more often than expected by chance. Affected relatives should show excess "allele sharing" even in the presence of incomplete penetrance and polygenic inheritance. In non-parametric linkage analysis the degree of agreement at a marker locus in two individuals can be measured either by the number of alleles identical by state (IBS) or by the number of alleles identical by descent (IBD). Affected sib pair analysis is a well-known special case and is the simplest form of these methods.

The biallelic markers of the present invention may be used in both parametric and non-parametric linkage analysis. Preferably biallelic markers may be used in non-parametric methods which allow the mapping of genes involved in complex traits. The biallelic markers of the present invention may be used in both IBD- and IBS-methods to map genes affecting a complex trait. In such studies, taking advantage of the high density of biallelic markers, several adjacent biallelic marker loci may be pooled to achieve the efficiency attained by multi-allelic markers (Zhao et al., *Am. J. Hum. Genet.*, 63:225–240, 1998, the disclosure of which is incorporated herein by reference in its entirety).

However, both parametric and non-parametric linkage analysis methods analyse affected relatives, they tend to be of limited value in the genetic analysis of drug responses or in the analysis of side effects to treatments. This type of analysis is impractical in such cases due to the lack of availability of familial cases. In fact, the likelihood of having more than one individual in a family being exposed to the same drug at the same time is extremely low.

IV.B. Population Association Studies

The present invention comprises methods for identifying one or several genes among a set of candidate genes that are associated with a detectable trait using the biallelic markers of the present invention. In one embodiment the present invention comprises methods to detect an association between a biallelic marker allele or a biallelic marker haplotype and a trait. Further, the invention comprises methods to identify a trait causing allele in linkage disequilibrium with any biallelic marker allele of the present invention.

As described above, alternative approaches can be employed to perform association studies: genome-wide association studies, candidate region association studies and candidate gene association studies. In a preferred embodiment, the biallelic markers of the present invention are used to perform candidate gene association studies. Further, the biallelic markers of the present invention may be incorporated in any map of genetic markers of the human genome in order to perform genome-wide association studies. Methods to generate a high-density map of biallelic markers has been described in US Provisional Patent application serial No. 60/082,614. The biallelic markers of the present invention may further be incorporated in any map of a specific candidate region of the genome (a specific chromosome or a specific chromosomal segment for example).

As mentioned above, association studies may be conducted within the general population and are not limited to studies performed on related individuals in affected families. Association studies are extremely valuable as they permit the analysis of sporadic or multifactor traits. Moreover, association studies represent a powerful method for fine-scale mapping enabling much finer mapping of trait causing alleles than linkage studies. Studies based on pedigrees often only narrow the location of the trait causing allele. Association studies using the biallelic markers of the present invention can therefore be used to refine the location of a trait causing allele in a candidate region identified by Linkage Analysis methods. Moreover, once a chromosome segment of interest has been identified, the presence of a candidate gene such as a candidate gene of the present invention, in the region of interest can provide a shortcut to the identification of the trait causing allele. Biallelic markers of the present invention can be used to demonstrate that a candidate gene is associated with a trait. Such uses are specifically contemplated in the present invention and claims.

1) Determining the Frequency of a Biallelic Marker Allele or of a Biallelic Marker Haplotype in a Population Association studies explore the relationships among frequencies for sets of alleles between loci.

Determining the Frequency of an Allele in a Population

Allelic frequencies of the biallelic markers in a population can be determined using one of the methods described above under the heading "Methods for genotyping an individual for biallelic markers", or any genotyping procedure suitable for this intended purpose. Genotyping pooled samples or individual samples can determine the frequency of a biallelic marker allele in a population. One way to reduce the number of genotypings required is to use pooled samples. A major obstacle in using pooled samples is in terms of accuracy and reproducibility for determining accurate DNA concentrations in setting up the pools. Genotyping individual samples provides higher sensitivity, reproducibility and accuracy and; is the preferred method used in the present invention. Preferably, each individual is genotyped separately and simple gene counting is applied to determine the frequency of an allele of a biallelic marker or of a genotype in a given population.

Determining the Frequency of a Haplotype in a Population

The gametic phase of haplotypes is unknown when diploid individuals are heterozygous at more than one locus. Using genealogical information in families gametic phase can sometimes be inferred (Perlin et al., *Am. J. Hum. Genet.*, 55:777–787, 1994, the disclosure of which is incorporated herein by reference in its entirety). When no genealogical information is available different strategies may be used. One possibility is that the multiple-site heterozygous diploids can be eliminated from the analysis, keeping only the homozygotes and the single-site heterozygote individuals, but this approach might lead to a possible bias in the sample composition and the underestimation of low-frequency haplotypes. Another possibility is that single chromosomes can be studied independently, for example, by asymmetric PCR amplification (see Newton et al., *Nucleic Acids Res.*, 17:2503–2516, 1989; Wu et al., *Proc. Natl. Acad. Sci. USA*, 86:2757, 1989, the disclosures of which are incorporated herein by reference in their entireties) or by isolation of single chromosome by limit dilution followed by PCR amplification (see Ruano et al., *Proc. Natl. Acad. Sci. USA*, 87:6296–6300, 1990, the disclosure of which is incorporated herein by reference in its entirety). Further, a sample may be haplotyped for sufficiently close biallelic markers by double PCR amplification of specific alleles (Sarkar, G. and Sommer S. S., *Biotechniques*, 1991, the disclosure of which is incorporated herein by reference in its entirety). These approaches are not entirely satisfying either because of their technical complexity, the additional cost they entail, their lack of generalisation at a large scale, or the possible biases they introduce. To overcome these difficulties, an algorithm to infer the phase of PCR-amplified DNA genotypes introduced by Clark A. G. (*Mol. Biol. Evol*, 7:111–122, 1990, the disclosure of which is incorporated herein by reference in its entirety) may be used. Briefly, the principle is to start filling a preliminary list of haplotypes present in the sample by examining unambiguous individuals, that is, the complete homozygotes and the single-site heterozygotes. Then other individuals in the same sample are screened for the possible occurrence of previously recognised haplotypes. For each positive identification, the complementary haplotype is added to the list of recognised haplotypes, until the phase information for all individuals is either resolved or identified as unresolved. This method assigns a single haplotype to each multiheterozygous individual, whereas several haplotypes are possible when there are more than one heterozygous site. Alternatively, one can use methods estimating haplotype frequencies in a population without assigning haplotypes to each individual. Preferably, a method based on an expectation-maximization (EM) algorithm (Dempster et al., *J. R. Stat. Soc.*, 39B: 1–38, 1977, the disclosure of which is incorporated herein by reference in its entirety) leading to maximum-likelihood estimates of haplotype frequencies under the assumption of Hardy-Weinberg proportions (random mating) is used (see Excoffier L. and Slatkin M., *Mol. Biol. Evol.*, 12(5): 921–927, 1995, the disclosure of which is incorporated herein by reference in its entirety). The EM algorithm is a generalised iterative maximum-likelihood approach to estimation that is useful when data are ambiguous and/or incomplete. The EM algorithm is used to resolve heterozygotes into haplotypes. Haplotype estimations are further described below under the heading "Statistical methods". Any other method known in the art to determine or to estimate the frequency of a haplotype in a population may also be used.

2) Linkage Disequilibrium Analysis

Linkage disequilibrium is the non-random association of alleles at two or more loci and represents a powerful tool for mapping genes involved in disease traits (see Ajioka R. S. et al., *Am. J. Hum. Genet.*, 60:1439–1447, 1997, the disclosure of which is incorporated herein by reference in its entirety). Biallelic markers, because they are densely spaced in the human genome and can be genotyped in more numerous numbers than other types of genetic markers (such as RFLP or VNTR markers), are particularly useful in genetic analysis based on linkage disequilibrium. The biallelic markers of the present invention may be used in any linkage disequilibrium analysis method known in the art.

Briefly, when a disease mutation is first introduced into a population (by a new mutation or the immigration of a mutation carrier), it necessarily resides on a single chromosome and thus on a single "background" or "ancestral" haplotype of linked markers. Consequently, there is complete disequilibrium between these markers and the disease mutation: one finds the disease mutation only in the presence of a specific set of marker alleles. Through subsequent generations recombinations occur between the disease mutation and these marker polymorphisms, and the disequilibrium gradually dissipates. The pace of this dissipation is a function of the recombination frequency, so the markers closest to the disease gene will manifest higher levels of disequilibrium than those that are further away. When not broken up by recombination, "ancestral" haplotypes and linkage disequilibrium between marker alleles at different loci can be tracked not only through pedigrees but also through populations. Linkage disequilibrium is usually seen as an association between one specific allele at one locus and another specific allele at a second locus.

The pattern or curve of disequilibrium between disease and marker loci is expected to exhibit a maximum that occurs at the disease locus. Consequently, the amount of linkage disequilibrium between a disease allele and closely linked genetic markers may yield valuable information regarding the location of the disease gene. For fine-scale mapping of a disease locus, it is useful to have some knowledge of the patterns of linkage disequilibrium that exist between markers in the studied region. As mentioned above the mapping resolution achieved through the analysis of linkage disequilibrium is much higher than that of linkage studies. The high density of biallelic markers combined with linkage disequilibrium analysis provides powerful tools for fine-scale mapping. Different methods to calculate linkage disequilibrium are described below under the heading "Statistical Methods".

3) Population-based Case-control Studies of Trait-marker Associations

As mentioned above, the occurrence of pairs of specific alleles at different loci on the same chromosome is not random and the deviation from random is called linkage disequilibrium. Association studies focus on population frequencies and rely on the phenomenon of linkage disequilibrium. If a specific allele in a given gene is directly involved in causing a particular trait, its frequency will be statistically increased in an affected (trait positive) population, when compared to the frequency in a trait negative population or in a random control population. As a consequence of the existence of linkage disequilibrium, the frequency of all other alleles present in the haplotype carrying the trait-causing allele will also be increased in trait positive individuals compared to trait negative individuals or random controls. Therefore, association between the trait and any allele (specifically a biallelic marker allele) in linkage disequilibrium with the trait-causing allele will suffice to suggest the presence of a trait-related gene in that particular region. Case-control populations can be genotyped for biallelic markers to identify associations that narrowly locate a trait causing allele. As any marker in linkage disequilibrium with one given marker associated with a trait will be associated with the trait. Linkage disequilibrium allows the relative frequencies in case-control populations of a limited number of genetic polymorphisms (specifically biallelic markers) to be analysed as an alternative to screening all possible functional polymorphisms in order to find trait-causing alleles. Association studies compare the frequency of marker alleles in unrelated case-control populations, and represent powerful tools for the dissection of complex traits.

Case-control Populations (Inclusion Criteria)

Population-based association studies do not concern familial inheritance but compare the prevalence of a particular genetic marker, or a set of markers, in case-control populations. They are case-control studies based on comparison of unrelated case (affected or trait positive) individuals and unrelated control (unaffected or trait negative or random) individuals. Preferably the control group is composed of unaffected or trait negative individuals. Further, the control group is ethnically matched to the case population. Moreover, the control group is preferably matched to the case-population for the main known confusion factor for the trait under study (for example age-matched for an age-dependent trait). Ideally, individuals in the two samples are paired in such a way that they are expected to differ only in their disease status. In the following "trait positive population", "case population" and "affected population" are used interchangeably.

An important step in the dissection of complex traits using association studies is the choice of case-control populations (see Lander and Schork, *Science*, 265, 2037–2048, 1994, the disclosure of which is incorporated herein by reference in its entirety). A major step in the choice of case-control populations is the clinical definition of a given trait or phenotype. Any genetic trait may be analysed by the association method proposed here by carefully selecting the individuals to be included in the trait positive and trait negative phenotypic groups. Four criteria are often useful: clinical phenotype, age at onset, family history and severity. The selection procedure for continuous or quantitative traits (such as blood pressure for example) involves selecting individuals at opposite ends of the phenotype distribution of the trait under study, so as to include in these trait positive and trait negative populations individuals with non-overlapping phenotypes. Preferably, case-control populations consist of phenotypically homogeneous populations. Trait positive and trait negative populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and selected among individuals exhibiting non-overlapping phenotypes. The clearer the difference between the two trait phenotypes, the greater the probability of detecting an association with biallelic markers. The selection of those drastically different but relatively uniform phenotypes enables efficient comparisons in association studies and the possible detection of marked differences at the genetic level, provided that the sample sizes of the populations under study are significant enough.

In preferred embodiments, a first group of between 50 and 300 trait positive individuals, preferably about 100 individuals, are recruited according to their phenotypes. A similar number of trait negative individuals are included in such studies.

Association Analysis

The general strategy to perform association studies using biallelic markers derived from a region carrying a candidate gene is to scan two groups of individuals (case-control populations) in order to measure and statistically compare the allele frequencies of the biallelic markers of the present invention in both groups.

If a statistically significant association with a trait is identified for at least one or more of the analysed biallelic markers, one can assume that: either the associated allele is directly responsible for causing the trait (the associated allele is the trait causing allele), or more likely the associated allele is in linkage disequilibrium with the trait causing allele. The specific characteristics of the associated allele with respect to the candidate gene function usually gives further insight into the relationship between the associated allele and the trait (causal or in linkage disequilibrium). If the evidence indicates that the associated allele within the candidate gene is most probably not the trait causing allele but is in linkage disequilibrium with the real trait causing allele, then the trait causing allele can be found by sequencing the vicinity of the associated marker.

Association studies are usually run in two successive steps. In a first phase, the frequencies of a reduced number of biallelic markers from one or several candidate genes are determined in the trait positive and trait negative populations. In a second phase of the analysis, the identity of the candidate gene and the position of the genetic loci responsible for the given trait is further refined using a higher density of markers from the relevant region. However, if the candidate gene under study is relatively small in length, as it is the case for many of the candidate genes analysed included in the present invention, a single phase may be sufficient to establish significant associations.

Haplotype Analysis

As described above, when a chromosome carrying a disease allele first appears in a population as a result of either mutation or migration, the mutant allele necessarily resides on a chromosome having a set of linked markers: the ancestral haplotype. This haplotype can be tracked through populations and its statistical association with a given trait can be analysed. Complementing single point (allelic) association studies with multi-point association studies also called haplotype studies increases the statistical power of association studies. Thus, a haplotype association study allows one to define the frequency and the type of the ancestral carrier haplotype. A haplotype analysis is important in that it increases the statistical power of an analysis involving individual markers.

In a first stage of a haplotype frequency analysis, the frequency of the possible haplotypes based on various combinations of the identified biallelic markers of the invention is determined. The haplotype frequency is then compared for distinct populations of trait positive and control individuals. The number of trait positive individuals, which should be, subjected to this analysis to obtain statistically significant results usually ranges between 30 and 300, with a preferred number of individuals ranging between 50 and 150. The same considerations apply to the number of unaffected individuals (or random control) used in the study. The results of this first analysis provide haplotype frequencies in case-control populations, for each evaluated haplotype frequency a p-value and an odd ratio are calculated. If a statistically significant association is found the relative risk for an individual carrying the given haplotype of being affected with the trait under study can be approximated.

Interaction Analysis

The biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate level of statistical significance can be considered as a haplotype analysis. Interaction analysis consists in stratifying the case-control populations with respect to a given haplotype for the first loci and performing a haplotype analysis with the second loci with each subpopulation.

Statistical methods used in association studies are further described below in IV.C.

4) Testing for Linkage in the Presence of Association

The biallelic markers of the present invention may further be used in TDT (transmission/disequilibrium test). TDT tests for both linkage and association and is not affected by population stratification. TDT requires data for affected individuals and their parents or data from unaffected sibs instead of from parents (see Spielmann S. et al., *Am. J. Hum. Genet.*, 52:506–516, 1993; Schaid D. J. et al., *Genet. Epidemiol.*, 13:423–450, 1996, Spielmann S. and Ewens W. J., *Am. J. Hum. Genet.*, 62:450–458, 1998, the disclosures of which are incorporated herein by reference in their entireties). Such combined tests generally reduce the false—positive errors produced by separate analyses.

IV.C. Statistical Methods

In general, any method known in the art to test whether a trait and a genotype show a statistically significant correlation may be used.

1) Methods in Linkage Analysis

Statistical methods and computer programs useful for linkage analysis are well-known to those skilled in the art (see Terwilliger J. D. and Ott J., *Handbook of Human Genetic Linkage*, John Hopkins University Press, London, 1994; Ott J., *Analysis of Human Genetic Linkage*, John Hopkins University Press, Baltimore, 1991, the disclosures of which are incorporated herein by reference in their entireties).

2) Methods to Estimate Haplotype Frequencies in a Population

As described above, when genotypes are scored, it is often not possible to distinguish heterozygotes so that haplotype frequencies cannot be easily inferred. When the gametic phase is not known, haplotype frequencies can be estimated from the multilocus genotypic data. Any method known to person skilled in the art can be used to estimate haplotype frequencies (see Lange K., *Mathematical and Statistical Methods for Genetic Analysis*, Springer, N.Y. 1997; Weir, B. S., *Genetic data Analysis II: Methods for Discrete population genetic Data*, Sinauer Assoc., Inc., Sunderland, Mass., USA, 1996, the disclosures of which are incorporated herein by reference in their entireties) Preferably, maximum-likelihood haplotype frequencies are computed using an Expectation-Maximization (EM) algorithm (see Dempster et al., *J. R. Stat. Soc.*, 39B:1–38, 1977; Excoffier L. and Slatkin M., *Mol. Biol. Evol.*, 12(5): 921–927, 1995, the disclosures of which are incorporated herein by reference in their entireties). This procedure is an iterative process aiming at obtaining maximum-likelihood estimates of haplotype frequencies from multi-locus genotype data when the gametic phase is unknown. Haplotype estimations are usually performed by applying the EM algorithm using for example the EM-HAPLO program (Hawley M. E. et al., *Am. J. Phys. Anthropol.*, 18:104, 1994, the disclosure of which is incorporated herein by reference in its entirety) or the Arlequin program (Schneider et al., *Arlequin: a software for population genetics data analysis*, University of Geneva, 1997, the disclosure of which is incorporated herein by reference in its entirety). The EM algorithm is a generalised iterative maximum likelihood approach to estimation and is briefly described below.

In the following part of this text, phenotypes will refer to multi-locus genotypes with unknown phase. Genotypes will refer to known-phase multi-locus genotypes.

Suppose a sample of N unrelated individuals typed for K markers. The data observed are the unknown-phase K-locus phenotypes that can categorised in F different phenotypes. Suppose that we have H underlying possible haplotypes (in case of K biallelic markers, $H=2^K$). For phenotype j, suppose that $c_j$ genotypes are possible. We thus have the following equation $$Pj = \sum_{i=1}^{c_j} pr(genotype_i) = \sum_{i=1}^{c_j} pr(h_k, h_l) \qquad \text{Equation 1}$$

where $P_j$ is the probability of the phenotypes, $h_k$ and $h_l$ are the two haplotypes constituent the genotype i. Under the Hardy-Weinberg equilibrium, $pr(h_k h_l)$ becomes:

$$pr(h_k,h_l)=pr(h_k)^2 \text{ if } h_k=h_l, pr(h_k,h_l)=$$
$$2pr(h_k).pr(h_l) \text{ if } h_k \neq h_l. \qquad \text{Equation 2}$$

The successive steps of the E-M algorithm can be described as follows: Starting with initial values of the of haplotypes frequencies, noted $p_1^{(0)}$, $p_2^{(0)}$, ... $P_H^{(0)}$, these initial values serve to estimate the genotype frequencies (Expectation step) and then estimate another set of haplotype frequencies (Maximisation step), noted $p_1^{(1)}$, $p_2^{(1)}$, ...

$p_H^{(1)}$, these two steps are iterated until changes in the sets of haplotypes frequency are very small.

A stop criterion can be that the maximum difference between haplotype frequencies between two iterations is less than $10^{-7}$. These values can be adjusted according to the desired precision of estimations.

In details, at a given iteration s, the Expectation step consists in calculating the genotypes frequencies by the following equation:

$$pr(genotype_i)^{(s)} = \qquad \text{Equation 3}$$
$$pr(phenotype_j) \cdot pr(genotype_i \mid phenotype_j)^{(s)} =$$
$$\frac{n_j}{N} \cdot \frac{pr(h_k, h_l)^{(s)}}{p_j^{(s)}}$$

where genotype i occurs in phenotype j, and where $h_k$ and $h_l$ constitute genotype i. Each probability is derived according to eq.1, and eq.2 described above.

Then the Maximisation step simply estimates another set of haplotype frequencies given the genotypes frequencies. This approach is also known as gene-counting method (Smith, *Ann. Hum. Genet.*, 21:254–276, 1957, the disclosure of which is incorporated herein by reference in its entirety).

$$p_t^{(s+1)} = \frac{1}{2} \sum_{j=1}^{F} \sum_{i=1}^{c_j} \delta_{it} \cdot pr(genotype_i)^{(s)} \qquad \text{Equation 4}$$

Where $\delta_{it}$ is an indicator variable which count the number of time haplotype t in genotype i. It takes the values of 0, 1 or 2.

To ensure that the estimation finally obtained is the maximum-likelihood estimation several values of departures are required. The estimations obtained are compared and if they are different the estimations leading to the best likelihood are kept.

3) Methods to Calculate Linkage Disequilibrium Between Markers

A number of methods can be used to calculate linkage disequilibrium between any two genetic positions, in practice linkage disequilibrium is measured by applying a statistical association test to haplotype data taken from a population.

Linkage disequilibrium between any pair of biallelic markers comprising at least one of the biallelic markers of the present invention ($M_i$, $M_j$) having alleles ($a_i/b_i$) at marker $M_i$ and alleles ($a_j/b_j$) at marker $M_j$ can be calculated for every allele combination ($a_i,a_j$; $a_i,b_j$; $b_i,a_j$ and $b_i,b_j$), according to the Piazza formula:

$$\Delta_{a_ia_j} = \sqrt{\theta 4} - \sqrt{(\theta 4 + \theta 3)(\theta 4 + \theta 2)}, \text{ where:}$$

θ4=−−=frequency of genotypes not having allele $a_i$ at $M_i$ and not having allele $a_j$ at $M_j$ θ3=−+=frequency of genotypes not having allele $a_i$ at $M_i$ and having allele $a_j$ at $M_j$ θ2=−+=frequency of genotypes having allele $a_i$ at $M_i$ and not having allele $a_j$ at $M_j$ Linkage disequilibrium (LD) between pairs of biallelic markers ($M_i$, $M_j$) can also be calculated for every allele combination ($a_i,a_j$; $a_i,b_j$; $b_i,a_j$ and $b_i,b_j$), according to the maximum-likelihood estimate (MLE) for delta (the composite genotypic disequilibrium coefficient), as described by Weir (Weir B. S., *Genetic Data Analysis, Sinauer Ass. Eds*, 1996, the disclosure of which is incorporated herein by reference in its entirety). The MLE for the composite linkage disequilibrium is:

$$D_{a_ia_j} = (2n_1 + n_2 + n_3 + n_4/2)/N - 2(pr(a_i) \cdot pr(a_j))$$

Where $n_1 = \Sigma$ phenotype ($a_i/a_i$, $a_j/a_j$), $n_2 = \Sigma$ phenotype ($a_i/a_i$, $a_j/b_j$), $n_3 = \Sigma$ phenotype ($a_i/b_i$, $a_j/a_j$), $n_4 = \Sigma$ phenotype ($a_i/b_i$, $a_j/b_j$) and N is the number of individuals in the sample. This formula allows linkage disequilibrium between alleles to be estimated when only genotype, and not haplotype, data are available.

Another means of calculating the linkage disequilibrium between markers is as follows. For a couple of biallelic markers, $M_i$ ($a_i/b_i$) and $M_j$ ($a_j/b_j$), fitting the Hardy-Weinberg equilibrium, one can estimate the four possible haplotype frequencies in a given population according to the approach described above.

The estimation of gametic disequilibrium between $a_i$ and $a_j$ is simply:

$$D_{a_ia_j} = pr(\text{haplotype}(a_i,a_j)) - pr(a_i) \cdot pr(a_j).$$

Where $pr(a_i)$ is the probability of allele $a_i$ and $pr(a_j)$ is the probability of allele $a_j$ and where pr(haplotype ($a_i,a_j$)) is estimated as in Equation 3 above. For a couple of biallelic marker only one measure of disequilibrium is necessary to describe the association between $M_i$ and $M_j$.

Then a normalised value of the above is calculated as follows:

$$D'_{a_ia_j} = D_{a_ia_j}/\max(-pr(a_i) \cdot pr(a_j), -pr(b_i) \cdot pr(b_j)) \text{ with } D_{a_ia_j} < 0$$

$$D'_{a_ia_j} = D_{a_ia_j}/\max(pr(b_i) \cdot pr(a_j), pr(a_i) \cdot pr(b_j)) \text{ with } D_{a_ia_j} < 0$$

The skilled person will readily appreciate that other LD calculation methods can be used without undue experimentation.

Linkage disequilibrium among a set of biallelic markers having an adequate heterozygosity rate can be determined by genotyping between 50 and 1000 unrelated individuals, preferably between 75 and 200, more preferably around 100.

4) Testing for Association

Methods for determining the statistical significance of a correlation between a phenotype and a genotype, in this case an allele at a biallelic marker or a haplotype made up of such alleles, may be determined by any statistical test known in the art and with any accepted threshold of statistical significance being required. The application of particular methods and thresholds of significance are well with in the skill of the ordinary practitioner of the art.

Testing for association is performed by determining the frequency of a biallelic marker allele in case and control populations and comparing these frequencies with a statistical test to determine if their is a statistically significant difference in frequency which would indicate a correlation between the trait and the biallelic marker allele under study. Similarly, a haplotype analysis is performed by estimating the frequencies of all possible haplotypes for a given set of biallelic markers in case and control populations, and comparing these frequencies with a statistical test to determine if their is a statistically significant correlation between the haplotype and the phenotype (trait) under study. Any statistical tool useful to test for a statistically significant association between a genotype and a phenotype may be used. Preferably the statistical test employed is a chi-square test with one degree of freedom. A p-value is calculated (the p-value is the probability that a statistic as large or larger than the observed one would occur by chance).

Statistical Significance

In preferred embodiments, significance for diagnosis purposes, either as a positive basis for further diagnostic tests or as a preliminary starting point for early preventive therapy, the p value related to a biallelic marker association is preferably about $1 \times 10^{-2}$ or less, more preferably about $1 \times 10^{-4}$ or less, for a single biallelic marker analysis and about $1 \times 10^{-3}$ or less, still more preferably $1 \times 10^{-6}$ or less and most preferably of about $1 \times 10^{-8}$ or less, for a haplotype analysis involving several markers. These values are believed to be applicable to any association studies involving single or multiple marker combinations.

The skilled person can use the range of values set forth above as a starting point in order to carry out association studies with biallelic markers of the present invention. In doing so, significant associations between the biallelic markers of the present invention and diseases can be revealed.

Phenotypic Permutation

In order to confirm the statistical significance of the first stage haplotype analysis described above, it might be suitable to perform further analyses in which genotyping data from case-control individuals are pooled and randomised with respect to the trait phenotype. Each individual genotyping data is randomly allocated to two groups, which contain the same number of individuals as the case-control populations used to compile the data obtained in the first stage. A second stage haplotype analysis is preferably run on these artificial groups, preferably for the markers included in the haplotype of the first stage analysis showing the highest relative risk coefficient. This experiment is reiterated preferably at least between 100 and 10000 times. The repeated iterations allow the determination of the percentage of obtained haplotypes with a significant p-value level.

Assessment of Statistical Association

To address the problem of false positives similar analysis may be performed with the same case-control populations in random genomic regions. Results in random regions and the candidate region are compared as described in US Provisional Patent Application entitled "Methods, software and apparati for identifying genomic regions harbouring a gene associated with a detectable trait".

5) Evaluation of Risk Factors

The association between a risk factor (in genetic epidemiology the risk factor is the presence or the absence of a certain allele or haplotype at marker loci) and a disease is measured by the odds ratio (OR) and by the relative risk (RR). If $P(R^+)$ is the probability of developing the disease for individuals with R and $P(R^-)$ is the probability for individuals without the risk factor, then the relative risk is simply the ratio of the two probabilities, that is:

$$RR=P(R^+)/P(R^-)$$

In case-control studies, direct measures of the relative risk cannot be obtained because of the sampling design. However, the odds ratio allows a good approximation of the relative risk for low-incidence diseases and can be calculated:

$$OR = \left[\frac{F^+}{1-F^+}\right] / \left[\frac{F^-}{(1-F^-)}\right]$$

$F^+$ is the frequency of the exposure to the risk factor in cases and $F^-$ is the frequency of the exposure to the risk factor in controls. $F^+$ and $F^-$ are calculated using the allelic or haplotype frequencies of the study and further depend on the underlying genetic model (dominant, recessive, additive . . .).

One can further estimate the attributable risk (AR) which describes the proportion of individuals in a population exhibiting a trait due to a given risk factor. This measure is important in quantitating the role of a specific factor in disease etiology and in terms of the public health impact of a risk factor. The public health relevance of this measure lies in estimating the proportion of cases of disease in the population that could be prevented if the exposure of interest were absent. AR is determined as follows:

$$AR=P_E(RR-1)/(P_E(RR-1)+1)$$

AR is the risk attributable to a biallelic marker allele or a biallelic marker haplotype. $P_E$ is the frequency of exposure to an allele or a haplotype within the population at large; and RR is the relative risk which, is approximated with the odds ratio when the trait under study has a relatively low incidence in the general population.

IV.F. Identification Of Biallelic Markers In Linkage Disequilibrium With The Biallelic Markers of the Invention Once a first biallelic marker has been identified in a genomic region of interest, the practitioner of ordinary skill in the art, using the teachings of the present invention, can easily identify additional biallelic markers in linkage disequilibrium with this first marker. As mentioned before any marker in linkage disequilibrium with a first marker associated with a trait will be associated with the trait. Therefore, once an association has been demonstrated between a given biallelic marker and a trait, the discovery of additional biallelic markers associated with this trait is of great interest in order to increase the density of biallelic markers in this particular region. The causal gene or mutation will be found in the vicinity of the marker or set of markers showing the highest correlation with the trait.

Identification of additional markers in linkage disequilibrium with a given marker involves: (a) amplifying a genomic fragment comprising a first biallelic marker from a plurality of individuals; (b) identifying of second biallelic markers in the genomic region harboring said first biallelic marker; (c) conducting a linkage disequilibrium analysis between said first biallelic marker and second biallelic markers; and (d) selecting said second biallelic markers as being in linkage disequilibrium with said first marker. Subcombinations comprising steps (b) and (c) are also contemplated.

Methods to identify biallelic markers and to conduct linkage disequilibrium analysis are described herein and can be carried out by the skilled person without undue experimentation. The present invention then also concerns biallelic markers which are in linkage disequilibrium with any of the specific biallelic markers of SEQ ID Nos. 1 to 3908, 1 to 2260, 2261 to 3374, and 3735 to 3908 and which are expected to present similar characteristics in terms of their respective association with a given trait.

Example 5 illustrates the measurement of linkage disequilibrium between a publicly known biallelic marker, the "ApoE Site A", located within the Alzheimer's related ApoE gene, and other biallelic markers randomly derived from the genomic region containing the ApoE gene.

IV.G. Identification Of Functional Mutations

Once a positive association is confirmed with a biallelic marker of the present invention, the associated candidate gene can be scanned for mutations by comparing the sequences of a selected number of trait positive and trait negative individuals. In a preferred embodiment, functional regions such as exons and splice sites, promoters and other regulatory regions of the candidate gene are scanned for mutations. Preferably, trait positive individuals carry the haplotype shown to be associated with the trait and trait negative individuals do not carry the haplotype or allele associated with the trait. The mutation detection procedure is essentially similar to that used for biallelic site identification.

The method used to detect such mutations generally comprises the following steps: (a) amplification of a region of the candidate gene comprising a biallelic marker or a group of biallelic markers associated with the trait from DNA samples of trait positive patients and trait negative controls; (b) sequencing of the amplified region; (c) comparison of DNA sequences from trait-positive patients and trait-negative controls; and (d) determination of mutations specific to trait-positive patients. Subcombinations which comprise steps (b) and (c) are specifically contemplated.

It is preferred that candidate polymorphisms be then verified by screening a larger population of cases and controls by means of any genotyping procedure such as those described herein, preferably using a microsequencing technique in an individual test format. Polymorphisms are considered as candidate mutations when present in cases and controls at frequencies compatible with the expected association results.

V. Biallelic Markers Of The Invention In Methods Of Genetic Diagnostics

The biallelic markers of the present invention can also be used to develop diagnostics tests capable of identifying individuals who express a detectable trait as the result of a specific genotype or individuals whose genotype places them at risk of developing a detectable trait at a subsequent time. The trait analyzed using the present diagnostics may be any detectable trait, including a disease, a response to an agent acting on a disease, or side effects to an agent acting on a disease.

The diagnostic techniques of the present invention may employ a variety of methodologies to determine whether a test subject has a biallelic marker pattern associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids.

The present invention provides diagnostic methods to determine whether an individual is at risk of developing a disease or suffers from a disease resulting from a mutation or a polymorphism in a candidate gene of the present invention. The present invention also provides methods to determine whether an individual is likely to respond positively to an agent acting on a disease or whether an individual is at risk of developing an adverse side effect to an agent acting on a disease.

These methods involve obtaining a nucleic acid sample from the individual and, determining, whether the nucleic acid sample contains at least one allele or at least one biallelic marker haplotype, indicative of a risk of developing the trait or indicative that the individual expresses the trait as a result of possessing a particular candidate gene polymorphism or mutation (trait-causing allele).

Preferably, in such diagnostic methods, a nucleic acid sample is obtained from the individual and this sample is genotyped using methods described above in III. The diagnostics may be based on a single biallelic marker or a on group of biallelic markers.

In each of these methods, a nucleic acid sample is obtained from the test subject and the biallelic marker pattern of one or more of the biallelic markers of SEQ ID Nos. 1 to 3908, 1 to 2260, 2261 to 3374, and 3735 to 3908 is determined.

In one embodiment, a PCR amplification is conducted on the nucleic acid sample to amplify regions in which polymorphisms associated with a detectable phenotype have been identified. The amplification products are sequenced to determine whether the individual possesses one or more polymorphisms associated with a detectable phenotype. The primers used to generate amplification products may comprise the primers of SEQ ID Nos. 3935 to 7842, 3935 to 6194, 6195 to 7668, 7669 to 7842, 7866 to 11773, 7866 to 10125, 10126 to 11599, and 11600 to 11773. Alternatively, the nucleic acid sample is subjected to microsequencing reactions as described above to determine whether the individual possesses one or more polymorphisms associated with a detectable phenotype resulting from a mutation or a polymorphism in a candidate gene. In another embodiment, the nucleic acid sample is contacted with one or more allele specific oligonucleotide probes which, specifically hybridize to one or more candidate gene alleles associated with a detectable phenotype.

These diagnostic methods are extremely valuable as they can, in certain circumstances, be used to initiate preventive treatments or to allow an individual carrying a significant haplotype to foresee warning signs such as minor symptoms. In diseases in which attacks may be extremely violent and sometimes fatal if not treated on time, such as disease, the knowledge of a potential predisposition, even if this predisposition is not absolute, might contribute in a very significant manner to treatment efficacy. Similarly, a diagnosed predisposition to a potential side effect could immediately direct the physician toward a treatment for which such side effects have not been observed during clinical trials.

Diagnostics, which analyze and predict response to a drug or side effects to a drug, may be used to determine whether an individual should be treated with a particular drug. For example, if the diagnostic indicates a likelihood that an individual will respond positively to treatment with a particular drug, the drug may be administered to the individual. Conversely, if the diagnostic indicates that an individual is likely to respond negatively to treatment with a particular drug, an alternative course of treatment may be prescribed. A negative response may be defined as either the absence of an efficacious response or the presence of toxic side effects.

Clinical drug trials represent another application for the markers of the present invention. One or more markers indicative of response to an agent acting on a disease or to side effects to an agent acting on a disease may be identified using the methods described above. Thereafter, potential participants in clinical trials of such an agent may be screened to identify those individuals most likely to respond favorably to the drug and exclude those likely to experience side effects. In that way, the effectiveness of drug treatment may be measured in individuals who respond positively to the drug, without lowering the measurement as a result of the inclusion of individuals who are unlikely to respond positively in the study and without risking undesirable safety problems.

VI. Computer-Related Embodiments

In some embodiments of the present invention a computer to based system may support the on-line coordination between the identification of biallelic markers and the corresponding analysis of their frequency in the different groups.

As used herein the term "nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773" encompasses the nucleotide sequences of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773, fragments of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773, nucleotide sequences homologous to SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 or homologous to fragments of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773, and sequences complementary to all of the preceding sequences. As used herein the term "nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773" further encompasses the nucleotide sequences comprising, consisting essentially of, or consisting of any one of the following:

a) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 1 to 2260 or the complements thereof;

b) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 1 to 2260 or the complements thereof, further comprising the $1^{ST}$ allele of the polymorphic base of the respective SEQ ID number;

c) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 1 to 2260 or the complements thereof, further comprising the $2^{ND}$ allele of the polymorphic base of the respective SEQ ID number;

d) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 2261 to 3734 or the complements thereof;

e) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 2261 to 3734 or the complements thereof, further comprising the $1^{ST}$ allele of the polymorphic base of the respective SEQ ID number;

f) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 2261 to 3734 or the complements thereof, further comprising the $2^{ND}$ allele of the polymorphic base of the respective SEQ ID number;

g) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 3735 to 3908 or the complements thereof;

h) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 3735 to 3908 or the complements thereof, further comprising the $1^{ST}$ allele of the polymorphic base of the respective SEQ ID number;

i) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 3735 to 3908 or the complements thereof, further comprising the $2^{ND}$ allele of the polymorphic base of the respective SEQ ID number; and j) a contiguous span of at least 8, 10, 12, 15, 18, 19, 20, or 21 nucleotides, to the extent that a contiguous span of these lengths is consistent with the lengths of the particular Sequence ID, of any of SEQ ID Nos. 3935 to 7842, 3935 to 6194, 6195 to 7668, 7669 to 7842, 7866 to 11773, 7866 to 10125, 10126 to 11599, and 11600 to 11773 or the complements thereof.

The "nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773" further encompass nucleotide sequences homologous to:

a) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 1 to 2260 or the complements thereof;

b) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 1 to 2260 or the complements thereof, further comprising the $1^{ST}$ allele of the polymorphic base of the respective SEQ ID number;

c) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 1 to 2260 or the complements thereof, further comprising the $2^{ND}$ allele of the polymorphic base of the respective SEQ ID number;

d) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 2261 to 3734 or the complements thereof;

e) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 2261 to 3734 or the complements thereof, further comprising the $1^{ST}$ allele of the polymorphic base of the respective SEQ ID number;

f) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 2261 to 3734 or the complements thereof, further comprising the $2^{ND}$ allele of the polymorphic base of the respective SEQ ID number;

g) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 3735 to 3908 or the complements thereof;

h) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 3735 to 3908 or the complements thereof, further comprising the $1^{ST}$ allele of the polymorphic base of the respective SEQ ID number;

i) a contiguous span of at least 8, 10, 12, 15, 18, 19, 20, 22, 23, 24, 25, 30, 35, 43, 44, 45, 46 or 47 nucleotides, to the extent that a contiguous span of these lengths is consistent with the lengths of the particular Sequence ID, of any of SEQ ID Nos. 3735 to 3908 or the complements thereof, further comprising the $2^{ND}$ allele of the polymorphic base of the respective SEQ ID number; and j) a contiguous span of at least 8, 10, 12, 15, 18, 19, 20, or 21 nucleotides, to the extent that a contiguous span of these lengths is consistent with the lengths of the particular Sequence ID, of any of SEQ ID Nos. 3935 to 7842, 3935 to 6194, 6195 to 7668, 7669 to 7842, 7866 to 11773, 7866 to 10125, 10126 to 11599, and 11600 to 11773 or the complements thereof.

Homologous sequences refer to a sequence having at least 99%, 98%, 97%, 96%, 95%, 90%, 85%, 80%, or 75% homology to these contiguous spans. Homology may be determined using any method described herein, including BLAST2N with the default parameters or with any modified parameters. Homologous sequences also may include RNA sequences in which uridines replace the thymines in the nucleic acid codes of the invention. It will be appreciated that the nucleic acid codes of the invention can be represented in the traditional single character format (See the inside back cover of Stryer, Lubert. *Biochemistry*, $3^{rd}$ edition. W. H Freeman & Co., New York.) or in any other format or code which records the identity of the nucleotides in a sequence.

It should be noted that the nucleic acid codes of the invention further encompass all of the polynucleotides disclosed, described or claimed in the present application. Moveover, the present invention specifically contemplates computer readable media and computer systems wherein such codes are stored individually or in any combination.

It will be appreciated by those skilled in the art that the nucleic acid codes of SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate embodiments comprising one or more of the nucleic acid codes of SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773. A particularly preferred embodiment of the present invention is a computer readable medium having recorded thereon at least 2, 5, 10, 15, 20, 25, 30, 50, 100, 200, 500, 1000, 2000, or 5000 nucleic acid codes of SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 14:
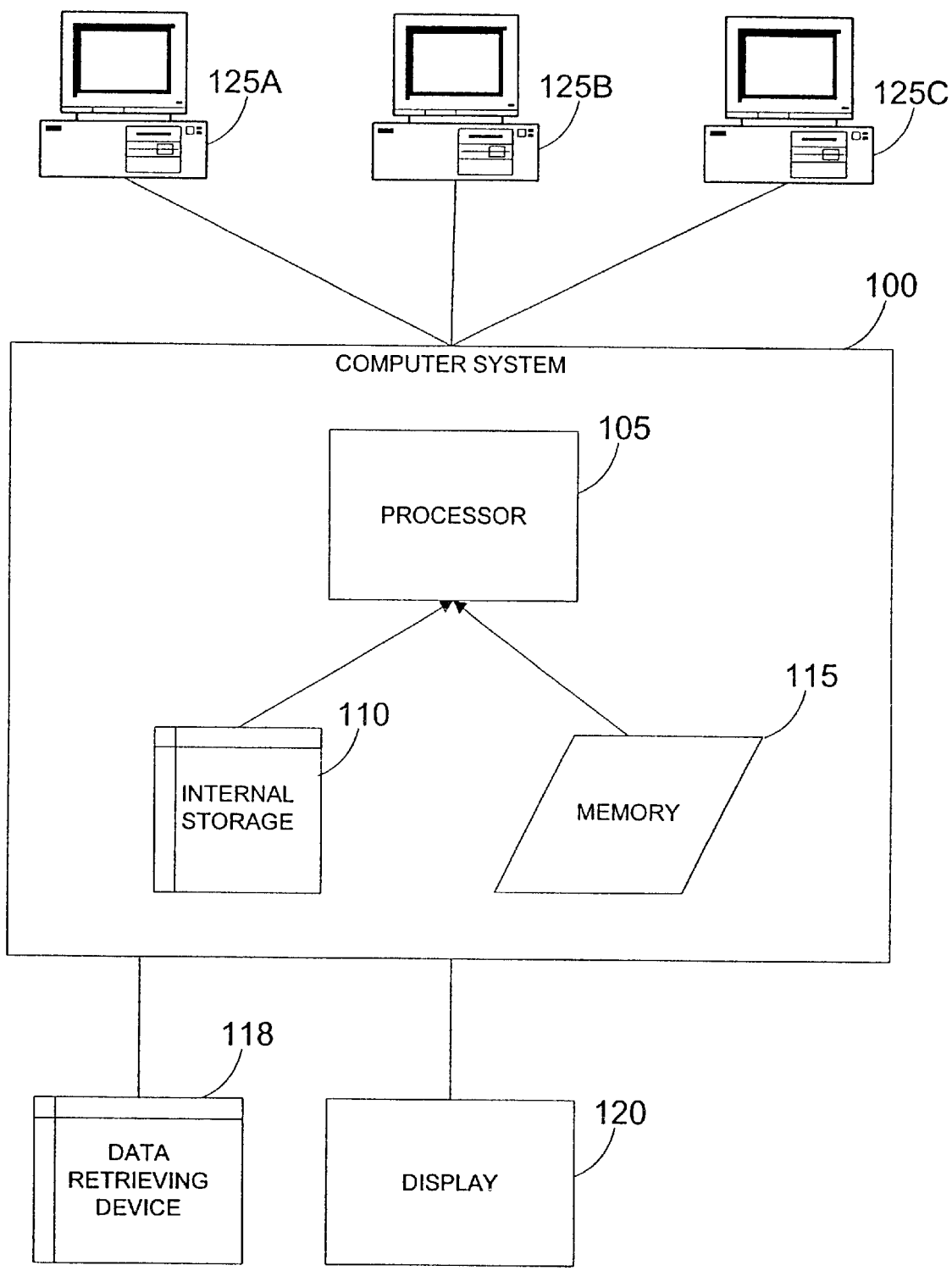
FIG. 14 is a block diagram of an exemplary computer system.

Embodiments of the present invention include systems, particularly computer systems which store and manipulate the sequence information described herein. One example of a computer system 100 is illustrated in block diagram form in FIG. 14. As used herein, "a computer system" refers to the hardware components, software components, and data storage components used to analyze the nucleotide sequences of the nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773. In one embodiment, the computer system 100 is a Sun Enterprise 1000 server (Sun Microsystems, Palo Alto, Calif.). The computer system 100 preferably includes a processor for processing, accessing and manipulating the sequence data. The processor 105 can be any well-known type of central processing unit, such as the Pentium III from Intel Corporation, or similar processor from Sun, Motorola, Compaq or International Business Machines.

Preferably, the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125*a–c* in a network or wide area network to provide centralized access to the computer system 100.

Software for accessing and processing the nucleotide sequences of the nucleic acid codes of SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 (such as search tools, compare tools, and modeling tools etc.) may reside in main memory 115 during execution.

In some embodiments, the computer system 100 may further comprise a sequence comparer for comparing the above-described nucleic acid codes of SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 stored on a computer readable medium to reference nucleotide or polypeptide sequences stored on a computer readable medium. A "sequence comparer" refers to one or more programs which are implemented on the computer system 100 to compare a nucleotide sequence with other nucleotide sequences and/or compounds stored within the data storage means. For example, the sequence comparer may compare the nucleotide sequences of the nucleic acid codes of SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 stored on a computer readable medium to reference sequences stored on a computer readable medium to identify homologies or structural motifs. The various sequence comparer programs identified elsewhere in this patent specification are particularly contemplated for use in this aspect of the invention.

Figure 15:
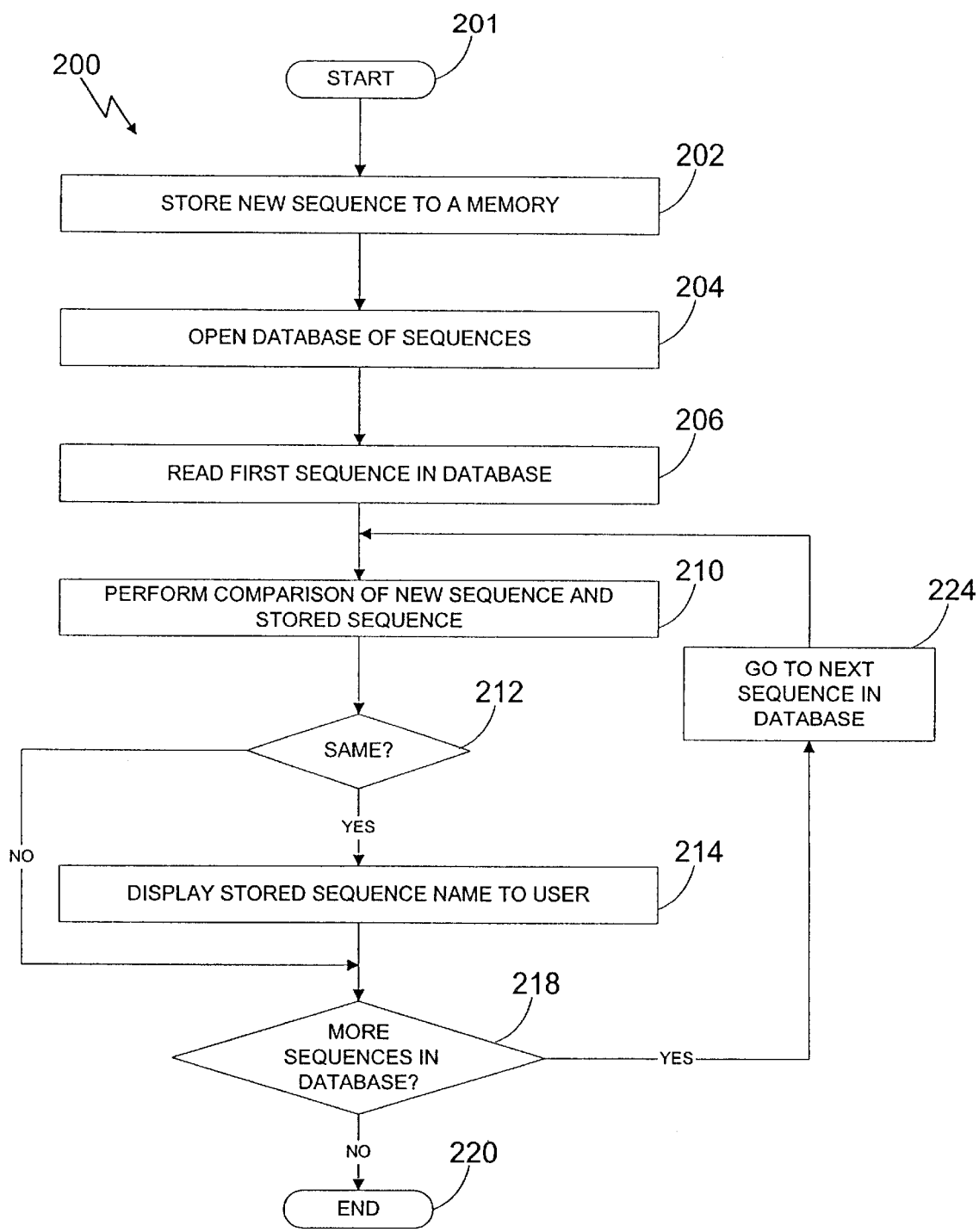
FIG. 15 is a flow diagram illustrating one embodiment of a process 200 for comparing a new nucleotide or protein sequence with a database of sequences in order to determine the homology levels between the new sequence and the sequences in the database.

FIG. 15 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the present invention is a computer system comprising a processor, a data storage device having stored thereon a nucleic acid code of SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773, a data storage device having retrievably stored thereon reference nucleotide sequences or polypeptide sequences to be compared to the nucleic acid code of SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 and a sequence comparer for conducting the comparison. The sequence comparer may indicate a homology level between the sequences compared or identify structural motifs in the above described nucleic acid code of SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 or it may identify structural motifs in sequences which are compared to these nucleic acid codes and polypeptide codes. In some embodiments, the data storage device may have stored thereon the sequences of at least 2, 5, 10, 15, 20, 25, 30, 50, 100, 200, 500, 1000, 2000, or 5000 of the nucleic acid codes of SEQ ID Nos. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773.

Another aspect of the present invention is a method for determining the level of homology between a nucleic acid code of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 and a reference nucleotide sequence, comprising the steps of reading the nucleic acid code and the reference nucleotide sequence through the use of a computer program which determines homology levels and determining homology between the nucleic acid code and the reference nucleotide sequence with the computer program. The computer program may be any of a number of computer programs for determining homology levels, including those specifically enumerated herein, including BLAST2N with the default parameters or with any modified parameters. The method may be implemented using the computer systems described above. The method may also be performed by reading at least 2, 5, 10, 15, 20, 25, 30, 50, 100, 200, 500, 1000, 2000, or 5000 of the above described nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 through use of the computer program and determining homology between the nucleic acid codes and reference nucleotide sequences.

Figure 16:
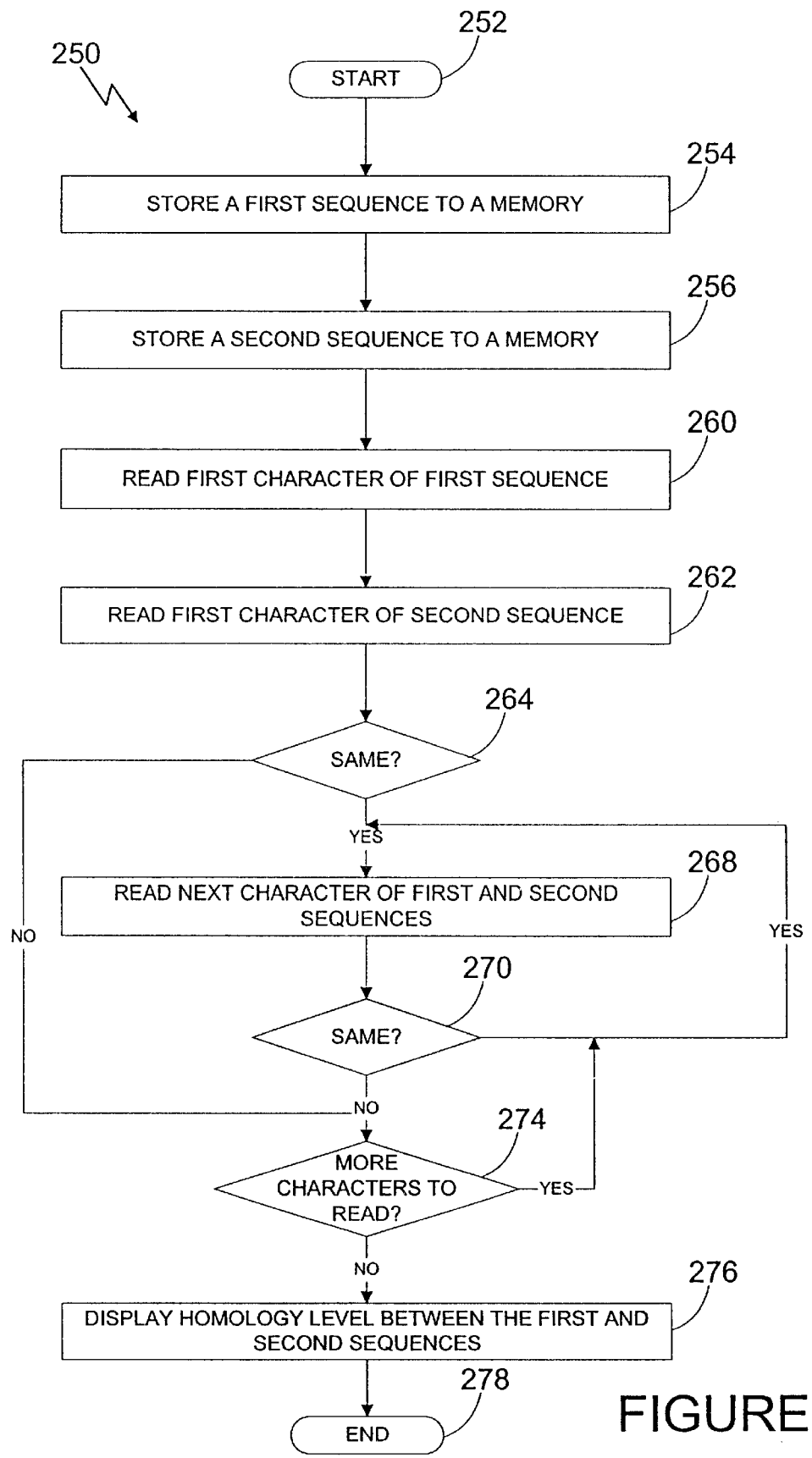
FIG. 16 is a flow diagram illustrating one embodiment of a process 250 in a computer for determining whether two sequences are homologous.

FIG. 16 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it should be in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there aren't any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of the nucleic acid codes of the present invention, to reference nucleotide sequences in order to determine whether the nucleic acid code of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 differs from a reference nucleic acid sequence at one or more positions. Optionally such a program records the length and identity of inserted, deleted or substituted nucleotides with respect to the sequence of either the reference polynucleotide or the nucleic acid code of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773. In one embodiment, the computer program may be a program which determines whether the nucleotide sequences of the nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 contain a biallelic marker or single nucleotide polymorphism (SNP) with respect to a reference nucleotide sequence. This single nucleotide polymorphism may comprise a single base substitution, insertion, or deletion, while this biallelic marker may comprise about one to ten consecutive bases substituted, inserted or deleted.

Accordingly, another aspect of the present invention is a method for determining whether a nucleic acid code of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 16. The method may also be performed by reading at least 2, 5, 10, 15, 20, 25, 30, 50, 100, 200, 500, 1000, 2000, or 5000 of the nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 and the reference nucleotide sequences through the use of the computer program and identifying differences between the nucleic acid codes and the reference nucleotide sequences with the computer program. In other embodiments the computer based system may further comprise an identifier for identifying features within the nucleotide sequences of the nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773.

An "identifier" refers to one or more programs which identifies certain features within the above-described nucleotide sequences of the nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773. In one embodiment, the identifier may comprise a program which identifies an open reading frame in the cDNAs codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773.

Figure 17:
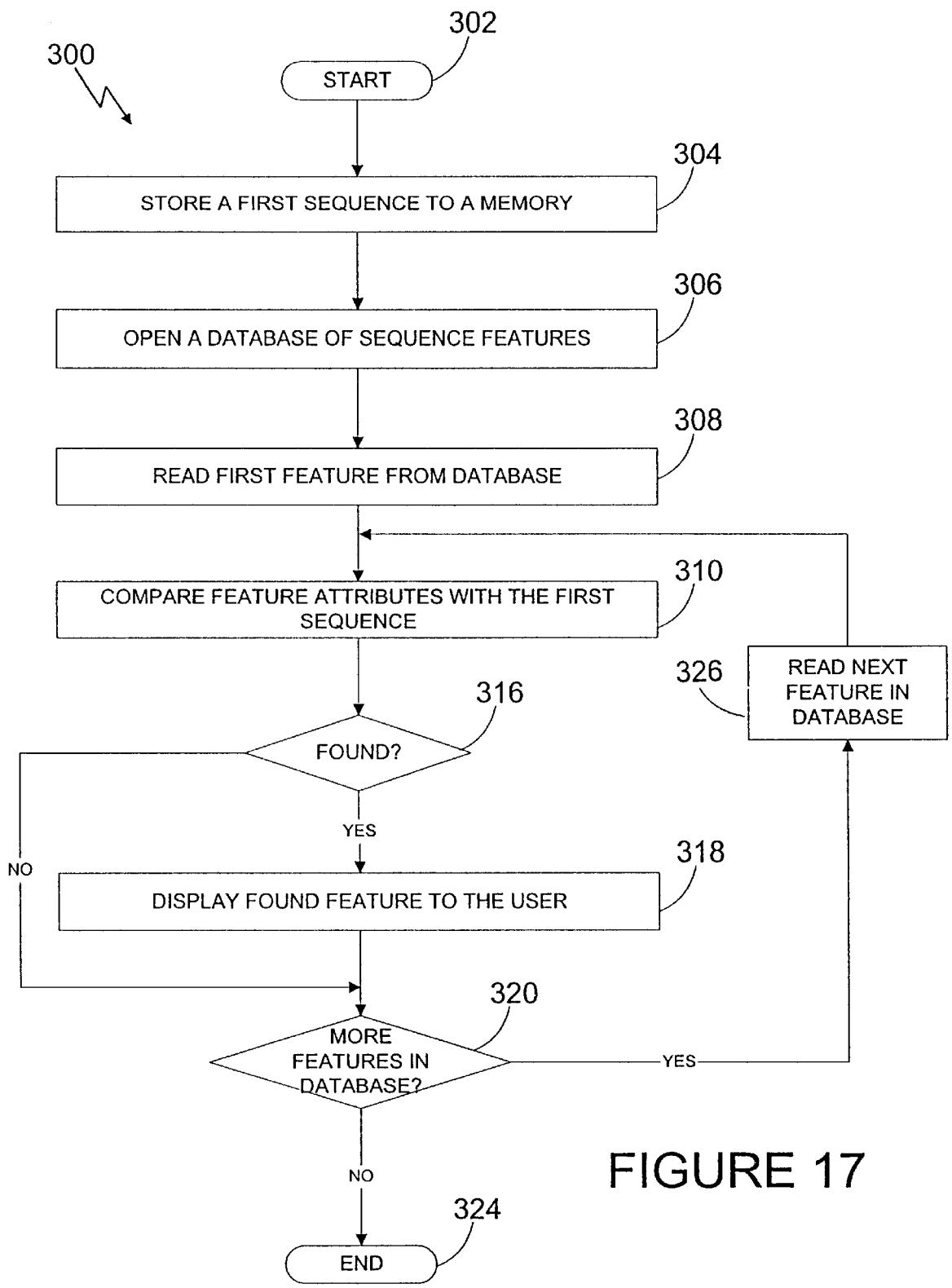
FIG. 17 is a flow diagram illustrating one embodiment of an identifier process 300 for detecting the presence of a feature in a sequence.

FIG. 17 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (www.gcg.com).

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

Accordingly, another aspect of the present invention is a method of identifying a feature within the nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 comprising reading the nucleic acid code(s) through the use of a computer program which identifies features therein and identifying features within the nucleic acid code(s) with the computer program. In one embodiment, computer program comprises a computer program which identifies open reading frames. The method may be performed by reading a single sequence or at least 2, 5, 10, 15, 20, 25, 30, 50, 100, 200, 500, 1000, 2000, or 5000 of the nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 through the use of the computer program and identifying features within the nucleic acid codes with the computer program.

The nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 may be stored and manipulated in a variety of data processor programs in a variety of formats. For example, the nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773 may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide sequences to be compared to the nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773. The following list is intended not to limit the invention but to provide guidance to programs and databases which are useful with the nucleic acid codes of SEQ ID NOs. 1 to 3908, 1 to 2260, 2261 to 3374, 3735 to 3908, 3935 to 7842, 3935 to 6194, 6195 to 7668, 7669 to 7842, 7866 to 11773, 7866 to 10125, 10126 to 11599, and 11600 to 11773.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990)), FASTA (Pearson and Lipman, *Proc. Natl. Acad. Sci. USA*, 85: 2444 (1988)), FASTDB (Brutlag et al. Comp. App. Biosci. 6:237–245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

It should be noted that the nucleic acid codes of the invention further encompass all of the polynucleotides disclosed, described or claimed in the present application. Moreover, the present invention specifically contemplates the storage of such codes on computer readable media and computer systems individually or in any combination, as well as the use of such codes and combinations in the methods of VI.

VII. Mapping and Maps Comprising the Biallelic Markers of the Invention

The human haploid genome contains an estimated 80,000 to 100,000 or more genes scattered on a $3\times10^9$ base-long double stranded DNA shared among the 24 chromosomes. Each human being is diploid, i.e. possesses two haploid genomes, one from paternal origin, the other from maternal origin. The sequence of the human genome varies among individuals in a population About $10^7$ sites scattered along the $3\times10^9$ base pairs of DNA are polymorphic, existing in at least two variant forms called alleles. Most of these polymorphic sites are generated by single base substitution mutations and are biallelic. Less than $10^5$ polymorphic sites are due to more complex changes and are very often multi-allelic, i.e. exist in more than two allelic forms. At a given polymorphic site, any individual (diploid), can be either homozygous (twice the same allele) or heterozygous (two different alleles). A given polymorphism or rare mutation can be either neutral (no effect on trait), or functional, i.e. responsible for a particular genetic trait.

Genetic Maps

The first step towards the identification of genes associated with a detectable trait, such as a disease or any other detectable trait, consists in the localization of genomic regions containing trait-causing genes using genetic mapping methods. The preferred traits contemplated within the present invention relate to fields of therapeutic interest; in particular embodiments, they will be disease traits and/or drug response traits, reflecting drug efficacy or toxicity. Traits can either be "binary", e.g. diabetic vs. non diabetic, or "quantitative", e.g. elevated blood pressure. Individuals affected by a quantitative trait can be classified according to an appropriate scale of trait values, e.g. blood pressure ranges. Each trait value range can then be analyzed as a binary trait. Patients showing a trait value within one such range will be studied in comparison with patients showing a trait value outside of this range. In such a case, genetic analysis methods will be applied to subpopulations of individuals showing trait values within defined ranges.

Genetic mapping involves the analysis of the segregation of polymorphic loci in trait positive and trait-negative populations. Polymorphic loci constitute a small fraction of the human genome (less than 1%), compared to the vast majority of human genomic DNA which is identical in sequence among the chromosomes of different individuals. Among all existing human polymorphic loci, genetic markers can be defined as genome-derived polynucleotides which are sufficiently polymorphic to allow a reasonable probability that a randomly selected person will be heterozygous, and thus informative for genetic analysis by methods such as linkage analysis or association studies.

A genetic map consists of a collection of polymorphic markers which have been positioned on the human chromosomes. Genetic maps may be combined with physical maps, collections of ordered overlapping fragments of genomic DNA whose arrangement along the human chromosomes is known. The optimal genetic map should possess the following characteristics:

the density of the genetic markers scattered along the genome should be sufficient to allow the identification and localization of any trait-related polymorphism, each marker should have an adequate level of heterozygosity, so as to be informative in a large percentage of different meioses, all markers should be easily typed on a routine basis, at a reasonable expense, and in a reasonable amount of time, the entire set of markers per chromosome should be ordered in a highly reliable fashion.

However, while the above maps are optimal, it will be appreciated that the maps of the present invention may be used in the individual marker and haplotype association analyses described below without the necessity of determining the order of biallelic markers derived from a single BAC with respect to one another.

Construction of a Physical Map

The first step in constructing a high density genetic map of biallelic markers is the construction of a physical map. Physical maps consist of ordered, overlapping cloned fragments of genomic DNA covering a portion of the genome, preferably covering one or all chromosomes. Obtaining a physical map of the genome entails constructing and ordering a genomic DNA library. For an example of a complete explanation of the construction of a physical map from a BAC library see related PCT Application No. PCT/IB98/00193 filed Jul. 17, 1998, the disclosure of which is incorporated herein by reference in its entirety. The methods disclosed therein can be used to generate larger more complete sets of markers and entire maps of the human genome comprising the map-relate biallelic markers of the invention.

Biallelic Markers

It will be appreciated that the ordered DNA fragments containing these groups of biallelic markers need not completely cover the genomic regions of these lengths but may instead be incomplete contigs having one or more gaps therein. As discussed in further detail below, biallelic markers may be used in single maker and haplotype association analyses regardless of the completeness of the corresponding physical contig harboring them.

Using the procedures above, 3908 biallelic markers, each having two alleles, were identified using sequences obtained from BACs which had been localized on the genome. In some cases, markers were identified using pooled BACs and thereafter reassigned to individual BACs using STS screening procedures such as those described in Examples 1 and 2. The sequences of these biallelic markers are provided in the accompanying Sequence Listing as SEQ ID Nos. 1 to 3908. Although the sequences of SEQ ID Nos. 1 to 3908 will be used as exemplary markers throughout the present application, these markers are not limited to markers having the exact flanking sequences surrounding the polymorphic bases which are enumerated in SEQ ID Nos. 1 to 3908. Rather, it will be appreciated that the flanking sequences surrounding the polymorphic bases of SEQ ID Nos. 1 to 3908 may be lengthened or shortened to any extent compatible with their intended use and the present invention specifically contemplates such sequences. The sequences of these biallelic markers may be used to construct genomic maps as well as in the gene identification and diagnostic techniques described herein. It will be appreciated that the biallelic markers referred to herein may be of any length compatible with their intended use provided that the markers include the polymorphic base, and the present invention specifically contemplates such sequences.

Some of the markers of SEQ ID Nos: 1 to 3908 as well as related amplification and microsequencing primers were disclosed in the instant priority documents. However, some of the earlier described amplification primers and microsequencing primers did not have the precise sequence lengths disclosed in the instant application. It will be appreciated that either length of primers may be used in the methods disclosed in the present application.

In addition, the internal identification numbers used to identify the biallelic markers disclosed in U.S. Provisional Patent Application Serial No. 60/082,614 filed Apr. 21, 1998 have been revised to include additional numbers on the end. For example, the marker formerly given the internal identification number 99-1091 was given the revised internal identification number 99-1091-446. Therefore, it will be appreciated that shortened identification numbers and extended identification numbers which overlap one another refer to the same markers.

Ordering of Biallelic Markers

Biallelic markers can be ordered to determine their positions along chromosomes, preferably subchromosomal regions, by methods known in the art as well as those disclosed in PCT Application No. PCT/IB98/00193 filed Jul. 17, 1998, and U.S. Provisional Patent Application Serial No. 60/082,614 filed Apr. 21, 1998.

The positions of the biallelic markers along chromosomes may be determined using a variety of methodologies. In one approach, radiation hybrid mapping is used. Radiation hybrid (RH) mapping is a somatic cell genetic approach that can be used for high resolution mapping of the human genome. In this approach, cell lines containing one or more human chromosomes are lethally irradiated, breaking each chromosome into fragments whose size depends on the radiation dose. These fragments are rescued by fusion with cultured rodent cells, yielding subclones containing different portions of the human genome. This technique is described by Benham et al. (*Genomics* 4:509–517, 1989) and Cox et al., (*Science* 250:245–250, 1990), the entire contents of which are hereby incorporated by reference. The random and independent nature of the subclones permits efficient mapping of any human genome marker. Human DNA isolated from a panel of 80–100 cell lines provides a mapping reagent for ordering biallelic markers. In this approach, the frequency of breakage between markers is used to measure distance, allowing construction of fine resolution maps as has been done for ESTs (Schuler et al., *Science* 274:540–546, 1996, hereby incorporated herein by reference in its entirety).

RH mapping has been used to generate a high-resolution whole genome radiation hybrid map of human chromosome 17q22-q25.3 across the genes for growth hormone (GH) and thymidine kinase (TK) (Foster et al., *Genomics* 33:185–192, 1996), the region surrounding the Gorlin syndrome gene (Obermayr et al., *Eur. J. Hum. Genet.* 4:242–245, 1996), 60 loci covering the entire short arm of chromosome 12 (Raeymaekers et al., *Genomics* 29:170–178, 1995), the region of human chromosome 22 containing the neurofibromatosis type 2 locus (Frazer et al., *Genomics* 14:574–584, 1992) and 13 loci on the long arm of chromosome 5 (Warrington et al., *Genomics* 11:701–708, 1991, the disclosure of which is hereby incorporated herein by reference in its entirety).

Alternatively, PCR based techniques and human-rodent somatic cell hybrids may be used to determine the positions of the biallelic markers on the chromosomes. In such approaches, oligonucleotide primer pairs which are capable of generating amplification products containing the polymorphic bases of the biallelic markers are designed. Preferably, the oligonucleotide primers are 18–23 bp in length and are designed for PCR amplification. The creation of PCR primers from known sequences is well known to those with skill in the art. For a review of PCR technology see Erlich, H. A., *PCR Technology: Principles and Applications for DNA Amplification*. 1992. W. H. Freeman and Co., New York, the disclosure of which is hereby incorporated herein by reference in its entirety.

The primers are used in polymerase chain reactions (PCR) to amplify templates from total human genomic DNA. PCR conditions are as follows: 60 ng of genomic DNA is used as a template for PCR with 80 ng of each oligonucleotide primer, 0.6 unit of Taq polymerase, and 1 mCu of a $^{32}$P-labeled deoxycytidine triphosphate. The PCR is performed in a microplate thermocycler (Techne) under the following conditions: 30 cycles of 94° C., 1.4 min; 55° C., 2 min; and 72° C., 2 min; with a final extension at 72° C. for 10 min. The amplified products are analyzed on a 6% polyacrylamide sequencing gel and visualized by autoradiography. If the length of the resulting PCR product is identical to the length expected for an amplification product containing the polymorphic base of the biallelic marker, then the PCR reaction is repeated with DNA templates from two panels of human-rodent somatic cell hybrids, BIOS PCRable DNA (BIOS Corporation) and NIGMS Human-Rodent Somatic Cell Hybrid Mapping Panel Number 1 (NIGMS, Camden, N.J.).

PCR is used to screen a series of somatic cell hybrid cell lines containing defined sets of human chromosomes for the presence of a given biallelic marker. DNA is isolated from the somatic hybrids and used as starting templates for PCR reactions using the primer pairs from the biallelic marker. Only those somatic cell hybrids with chromosomes containing the human sequence corresponding to the biallelic marker will yield an amplified fragment. The biallelic markers are assigned to a chromosome by analysis of the segregation pattern of PCR products from the somatic hybrid DNA templates. The single human chromosome present in all cell hybrids that give rise to an amplified fragment is the chromosome containing that biallelic marker. For a review of techniques and analysis of results from somatic cell gene mapping experiments. (See Ledbetter et al., *Genomics* 6:475–481 (1990 the disclosure of which is incorporated herein by reference in its entirety).)

Example 2 describes a preferred method for positioning of biallelic markers on clones, such as BAC clones, obtained from genomic DNA libraries. Using such procedures, a number of BAC clones carrying selected biallelic markers can be isolated. The position of these BAC clones on the human genome can be defined by performing STS screening as described in Example 1. Preferably, to decrease the number of STSs to be tested, each BAC can be localized on chromosomal or subchromosomal regions by procedures such as those described in Examples 3 and 4. This localization will allow the selection of a subset of STSs corresponding to the identified chromosomal or subchromosomal region. Testing each BAC with such a subset of STSs and taking account of the position and order of the STSs along the genome will allow a refined positioning of the corresponding biallelic marker along the genome.

In other embodiments, if the DNA library used to isolate BAC inserts or any type of genomic DNA fragments harboring the selected biallelic markers already constitute a physical map of the genome or any portion thereof, using the known order of the DNA fragments will allow the order of the biallelic markers to be established.

As discussed above, it will be appreciated that markers carried by the same fragment of genomic DNA, such as the insert in a BAC clone, need not necessarily be ordered with respect to one another within the genomic fragment to conduct single point or haplotype association analyses. However, in other embodiments of the present maps, the order of biallelic markers carried by the same fragment of genomic DNA may be determined.

The positions of the biallelic markers used to construct the maps of the present invention, including the map-related biallelic markers of the invention, may be assigned to subchromosomal locations using Fluorescence In Situ Hybridization (FISH) (Cherif et al., *Proc. Natl. Acad. Sci. U.S.A.*, 87:6639–6643 (1990), the disclosure of which is incorporated herein by reference in its entirety). FISH analysis is described in Example 3.

The ordering analyses may be conducted to generate an integrated genome wide genetic map comprising about 20,000, 40,000, 60,000, 80,000, 100,000, 120,000 biallelic markers with a roughly consistent number of biallelic marker per BAC. In some embodiments, the map includes one or more markers selected from the group consisting of the sequences of SEQ ID Nos. 1 to 3908, 1 to 2260, 2261 to 3374, 3735 to 3908 or the sequences complementary thereto.

Alternatively, maps having the above-specified average numbers of biallelic markers per BAC which comprise smaller portions of the genome, such as a set of chromosomes, a single chromosome, a particular subchromosomal region, or any other desired portion of the genome, may also be constructed using the procedures provided herein.

In some embodiments, the biallelic markers in the map are separated from one another by an average distance of 10–200 kb, 15–150 kb, 20–100 kb, 100–150 kb, 50–100 kb, or 25–50 kb. Maps having the above-specified intermarker distances which comprise smaller portions of the genome, such as a set of chromosomes, a single chromosome, a particular subchromosomal region, or any other desired portion of the genome, may also be constructed using the procedures provided herein.

FIG. 2, showing the results of computer simulations of the distribution of inter-marker spacing on a randomly distributed set of biallelic markers, indicates the percentage of biallelic markers which will be spaced a given distance apart for a given number of markers/BAC in the genomic map (assuming 20,000 BACs constituting a minimally overlapping array covering the entire genome are evaluated). One hundred iterations were performed for each simulation (20,000 marker map, 40,000 marker map, 60,000 marker map, 120,000 marker map).

Figure 2A:
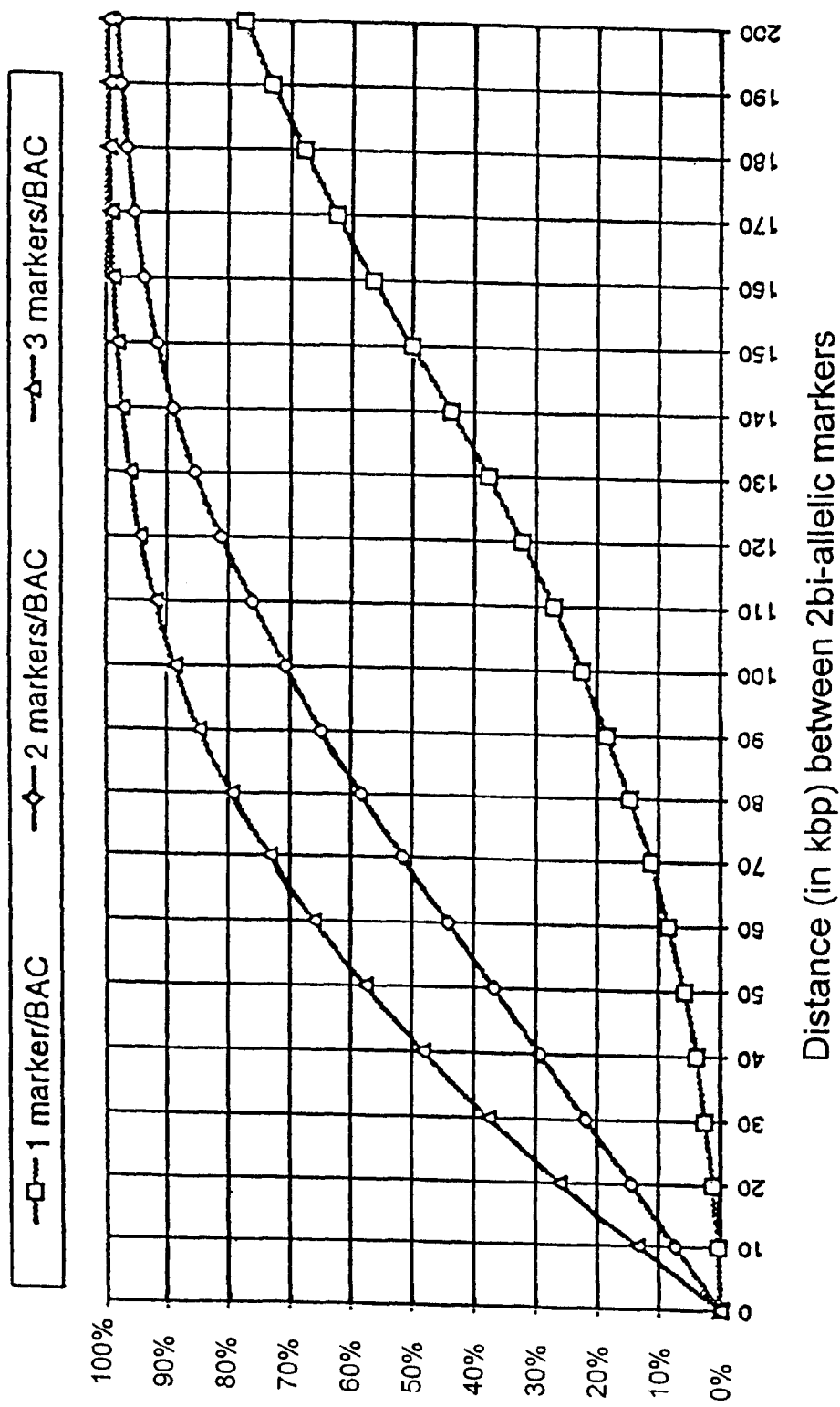
FIG. 2a shows the results of a computer simulation of the distribution of inter-marker spacing on a randomly distributed set of biallelic markers indicating the percentage of biallelic markers which will be spaced a given distance apart for 1, 2, or 3 markers/BAC in a genomic map (assuming a set of 20,000 minimally overlapping BACs covering the genome are evaluated).

As illustrated in FIG. 2a, 98% of inter-marker distances will be lower than 150 kb provided 60,000 evenly distributed markers are generated (3 per BAC); 90% of inter-marker distances will be lower than 150 kb provided 40,000 evenly distributed markers are generated (2 per BAC); and 50% of inter-marker distances will be lower than 150 kb provided 20,000 evenly distributed markers are generated (1 per BAC).

Figure 2B:
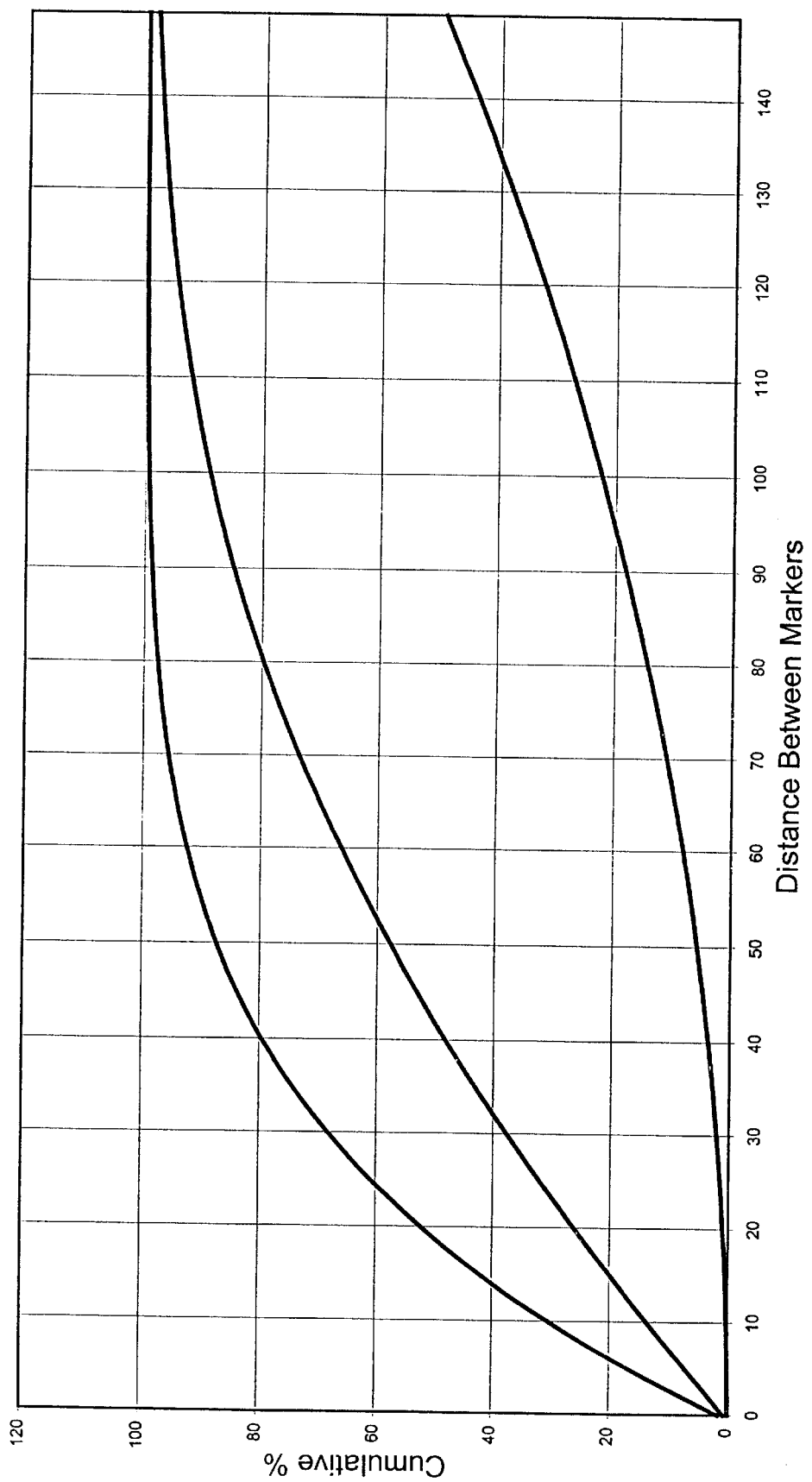
FIG. 2b shows the results of a computer simulation of the distribution of inter-marker spacing on a randomly distributed set of biallelic markers indicating the percentage of biallelic markers which will be spaced a given distance apart for 1, 3, or 6 markers/BAC in a genomic map (assuming a set of 20,000 minimally overlapping BACs covering the genome are evaluated).

As illustrated in FIG. 2b, 98% of inter-marker distances will be lower than 80 kb provided 120,000 evenly distributed markers are generated (6 per BAC); 80% of inter-marker distances will be lower than 80 kb provided 60,000 evenly distributed markers are generated (3 per BAC); and 15% of inter-marker distances will be lower than 80 kb provided 20,000 evenly distributed markers are generated (1 per BAC).

As already mentioned, high density biallelic marker maps allow association studies to be performed to identify genes involved in complex traits.

Tables 9 to 11 provide the genomic location of biallelic markers described herein. Listed are chromosomal regions and subregions to which biallelic markers were assigned using the methods of Example 3 and by screening BAC sequences against published and unpublished STSs.

In particular, the locations of markers listed in table 9 are locations for which adjacent STSs are publicly available. The column "adjacent STS" provides the public accession numbers of STSs localised on the same BAC with the subject biallelic marker as well as aliases for said STSs. As noted above, all of the marker localisations provided in Table 9 are confirmed by fluorescence in situ hybridization methods and public STS screening.

Table 10 describes chromosomal locations for biallelic markers for which no public adjacent STSs were available. Thus, Table 10 provides biallelic markers for which chromosomal localisations obtained by methods of FISH were confirmed by unpublished STSs, localisations which were obtained only by FISH, and localisations obtained by FISH which were discordant with localisations obtained from unpublished STSs.

Biallelic markers for which localisation were unconfirmed due to discordant localisation from STS screening and FISH methods are further provided in Table 11. The 204, 205, 225, 273, 274, 1723, 1732, 1743 localisations of these biallelic markers listed in Table 11 are those obtained by FISH methods, and may thus be considered as potential localisations. Table 11 includes certain markers also listed in Table 10.

Linkage Disequilibrium

The present invention then also concerns biallelic markers in linkage disequilibrium with the specific biallelic markers described above and which are expected to present similar characteristics in terms of their respective association with a given trait. In a preferred embodiment, the present invention concerns the biallelic markers that are in linkage disequilibrium with the biallelic markers of SEQ ID Nos. 1 to 3908, 1 to 2260, 2261 to 3374, 3735 to 3908 or the sequences complementary thereto.

LD among a set of biallelic markers having an adequate heterozygosity rate can be determined by genotyping between 50 and 1000 unrelated individuals, preferably between 75 and 200, more preferably around 100. Genotyping a biallelic marker consists of determining the specific allele carried by an individual at the given polymorphic base of the biallelic marker. Genotyping can be performed using similar methods as those described above for the generation of the biallelic markers, or using other genotyping methods such as those further described below.

Genome-wide linkage disequilibrium mapping aims at identifying, for any trait-causing allele being searched, at least one biallelic marker in linkage disequilibrium with said trait-causing allele. Preferably, in order to enhance the power of linkage disequilibrium maps, in some embodiments, the biallelic markers therein have average inter-marker distances of 150 kb or less, 75 kb or less, or 50 kb or less, 30 kb or less, or 25 kb or less to accommodate the fact that, in some regions of the genome, the detection of linkage disequilibrium requires lower inter-marker distances.

The present invention provides methods to generate biallelic marker maps with average inter-marker distances of 150 kb or less. In some embodiments, the mean distance between biallelic markers constituting the high density map will be less than 75 kb, preferably less than 50 kb. Further preferred maps according to the present invention contain markers that are less than 37.5 kb apart. In highly preferred embodiments, the average inter-marker spacing for the biallelic markers constituting very high density maps is less than 30 kb, most preferably less than 25 kb.

Genetic maps containing biallelic markers (including the biallelic markers of SEQ ID Nos. 1 to 3908, 1 to 2260, 2261 to 3374, 3735 to 3908 or the sequences complementary thereto) may be used to identify and isolate genes associated with detectable traits. The use of the genetic maps of the present invention is described in more detail below.

VIII. Use of High Density Biallelic Marker Maps to Identify Genes Associated with Detectable Traits One embodiment of the present invention comprises methods for identifying and isolating genes associated with a detectable trait using the biallelic marker maps of the present invention.

In the past, the identification of genes linked with detectable traits has relied on a statistical approach called linkage analysis. Linkage analysis is based upon establishing a correlation between the transmission of genetic markers and that of a specific trait throughout generations within a family. In this approach, all members of a series of affected families are genotyped with a few hundred markers, typically microsatellite markers, which are distributed at an average density of one every 10 Mb. By comparing genotypes in all family members, one can attribute sets of alleles to parental haploid genomes (haplotyping or phase determination). The origin of recombined fragments is then determined in the offsping of all families. Those that co-segregate with the trait are tracked. After pooling data from all families, statistical methods are used to determine the likelihood that the marker and the trait are segregating independently in all families. As a result of the statistical analysis, one or several regions having a high probability of harboring a gene linked to the trait are selected as candidates for further analysis. The result of linkage analysis is considered as significant (i.e. there is a high probability that the region contains a gene involved in a detectable trait) when the chance of independent segregation of the marker and the trait is lower than 1 in 1000 (expressed as a LOD score>3). Generally, the length of the candidate region identified using linkage analysis is between 2 and 20 Mb.

Once a candidate region is identified as described above, analysis of recombinant individuals using additional markers allows further delineation of the candidate linked region.

Linkage analysis studies have generally relied on the use of a maximum of 5,000 microsatellite markers, thus limiting the maximum theoretical attainable resolution of linkage analysis to ca. 600 kb on average.

Linkage analysis has been successfully applied to map simple genetic traits that show clear Mendelian inheritance patterns and which have a high penetrance (penetrance is the ratio between the number of trait-positive carriers of allele a and the total number of a carriers in the population). About 100 pathological trait-causing genes were discovered using linkage analysis over the last 10 years. In most of these cases, the majority of affected individuals had affected relatives and the detectable trait was rare in the general population (frequencies less than 0.1%). In about 10 cases, such as Alzheimer's Disease, breast cancer, and Type II diabetes, the detectable trait was more common but the allele associated with the detectable trait was rare in the affected population. Thus, the alleles associated with these traits were not responsible for the trait in all sporadic cases.

Linkage analysis suffers from a variety of drawbacks. First, linkage analysis is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis.

In addition, linkage analysis approaches have proven difficult when applied to complex genetic traits, such as those due to the combined action of multiple genes and/or environmental factors. In such cases, too large an effort and cost are needed to recruit the adequate number of affected families required for applying linkage analysis to these situations, as recently discussed by Risch, N. and Merikangas, K. (*Science* 273:1516–1517 (1996), the disclosure of which is incorporated herein by reference in its entirety).

Finally, linkage analysis cannot be applied to the study of traits for which no large informative families are available. Typically, this will be the case in any attempt to identify trait-causing alleles involved in sporadic cases, such as alleles associated with positive or negative responses to drug treatment.

The present genetic maps and biallelic markers (including the biallelic markers of SEQ ID Nos. 1 to 3908, 1 to 2260, 2261 to 3374, 3735 to 3908 or the sequences complementary thereto) may be used to identify and isolate genes associated with detectable traits using association studies, an approach which does not require the use of affected families and which permits the identification of genes associated with sporadic traits.

Association Studies

As already mentioned, any gene responsible or partly responsible for a given trait will be in linkage disequilibrium with some flanking markers. To map such a gene, specific alleles of these flanking markers which are associated with the gene or genes responsible for the trait are identified. Although the following discussion of techniques for finding the gene or genes associated with a particular trait using linkage disequilibrium mapping, refers to locating a single gene which is responsible for the trait, it will be appreciated that the same techniques may also be used to identify genes which are partially responsible for the trait.

Association studies may be conducted within the general population (as opposed to the linkage analysis techniques discussed above which are limited to studies performed on related individuals in one or several affected families).

Association between a biallelic marker A and a trait T may primarily occur as a result of three possible relationships between the biallelic marker and the trait.

First, allele a of biallelic marker A may be directly responsible for trait T (e.g., Apo E ε 4 site A and Alzheimer's disease). However, since the majority of the biallelic markers used in genetic mapping studies are selected randomly, they mainly map outside of genes. Thus, the likelihood of allele a being a functional mutation directly related to trait T is very low.

Second, an association between a biallelic marker A and a trait T may also occur when the biallelic marker is very closely linked to the trait locus. In other words, an association occurs when allele a is in linkage disequilibrium with the trait-causing allele. When the biallelic marker is in close proximity to a gene responsible for the trait, more extensive genetic mapping will ultimately allow a gene to be discovered near the marker locus which carries mutations in people with trait T (i.e. the gene responsible for the trait or one of the genes responsible for the trait). As will be further exemplified below, using a group of biallelic markers which are in close proximity to the gene responsible for the trait the location of the causal gene can be deduced from the profile of the association curve between the biallelic markers and the trait. The causal gene will usually be found in the vicinity of the marker showing the highest association with the trait.

Finally, an association between a biallelic marker and a trait may occur when people with the trait and people without the trait correspond to genetically different subsets of the population who, coincidentally, also differ in the frequency of allele a (population stratification). This phenomenon may be avoided by using ethnically matched large heterogeneous samples.

Association studies are particularly suited to the efficient identification of genes that present common polymorphisms, and are involved in multifactorial traits whose frequency is relatively higher than that of diseases with monofactorial inheritance.

Association studies mainly consist of four steps: recruitment of trait-positive (T+) and control populations, preferably trait-negative (T−) populations with well-defined phenotypes, identification of a candidate region suspected of harboring a trait causing gene, identification of said gene among candidate genes in the region, and finally validation of mutation(s) responsible for the trait in said trait causing gene.

In a first step, the trait-positive should be well-defined, preferably the control phenotype is a well-defined trait-negative phenotype as well. In order to perform efficient and significant association studies such as those described herein, the trait under study should preferably follow a bimodal distribution in the population under study, presenting two clear non-overlapping phenotypes, trait-positive and trait-negative.

Nevertheless, in the absence of such a bimodal distribution (as may in fact be the case for complex genetic traits), any genetic trait may still be analyzed using the association method proposed herein by carefully selecting the individuals to be included in the trait-positive group and preferably the trait-negative phenotypic group as well. The selection procedure ideally involves selecting individuals at opposite ends of the non-bimodal phenotype spectrum of the trait under study, so as to include in these trait-positive and trait-negative populations individuals who clearly represent non-overlapping, preferably extreme phenotypes.

As discussed above, the definition of the inclusion criteria for the trait-positive and control populations is an important aspect of the present invention.

FIG. 3 shows, for a series of hypothetical sample sizes, the p-value significance obtained in association studies performed using individual markers from the high-density biallelic map, according to various hypotheses regarding the difference of allelic frequencies between the trait-positive and trait-negative samples. It indicates that, in all cases, samples ranging from 150 to 500 individuals are numerous enough to achieve statistical significance. It will be appreciated that bigger or smaller groups can be used to perform association studies according to the methods of the present invention.

In a second step, a marker/trait association study is performed that compares the genotype frequency of each biallelic marker in the above described trait-positive and trait-negative populations by means of a chi square statistical test (one degree of freedom). In addition to this single marker association analysis, a haplotype association analysis is performed to define the frequency and the type of the ancestral carrier haplotype. Haplotype analysis, by combining the informativeness of a set of biallelic markers increases the power of the association analysis, allowing false positive and/or negative data that may result from the single marker studies to be eliminated.

Genotyping can be performed using any method described in III, including the microsequencing procedure described in Example 8.

If a positive association with a trait is identified using an array of biallelic markers having a high enough density, the causal gene will be physically located in the vicinity of the associated markers, since the markers showing positive association with the trait are in linkage disequilibrium with the trait locus. Regions harboring a gene responsible for a particular trait which are identified through association studies using high density sets of biallelic markers will, on average, be 20–40 times shorter in length than those identified by linkage analysis.

Once a positive association is confirmed as described above, a third step consists of completely sequencing the BAC inserts harboring the markers identified in the association analyzes. These BACs are obtained through screening human genomic libraries with the markers probes and/or primers, as described above. Once a candidate region has been sequenced and analyzed, the functional sequences within the candidate region (e.g. exons, splice sites, promoters, and other potential regulatory regions) are scanned for mutations which are responsible for the trait by comparing the sequences of the functional regions in a selected number of trait-positive and trait-negative individuals using appropriate software. Tools for sequence analysis are further described in Example 9.

Finally, candidate mutations are then validated by screening a larger population of trait-positive and trait-negative individuals using genotyping techniques described below. Polymorphisms are confirmed as candidate mutations when the validation population shows association results compatible with those found between the mutation and the trait in the test population.

In practice, in order to define a region bearing a candidate gene, the trait-positive and trait-negative populations are genotyped using an appropriate number of biallelic markers. The markers may include one or more of the markers of SEQ ID Nos: 1 to 3908, 1 to 2260, 2261 to 3374, 3735 to 3908 or the sequences complementary thereto.

The markers used to define a region bearing a candidate gene may be distributed at an average density of 1 marker per 10–200 kb. Preferably, the markers used to define a region bearing a candidate gene are distributed at an average density of 1 marker every 15–150 kb. In further preferred embodiments, the markers used to define a region bearing a candidate gene are distributed at an average density of 1 marker every 20–100 kb. In yet another preferred embodiment, the markers used to define a region bearing a candidate gene are distributed at an average density of 1 marker every 100 to 150 kb. In a further highly preferred embodiment, the markers used to define a region bearing a candidate gene are distributed at an average density of 1 marker every 50 to 100 kb. In yet another embodiment, the biallelic markers used to define a region bearing a candidate gene are distributed at an average density of 1 marker every 25–50 kilobases. As mentioned above, in order to enhance the power of linkage disequilibrium based maps, in a preferred embodiment, the marker density of the map will be adapted to take the linkage disequilibrium distribution in the genomic region of interest into account.

In some embodiments, the initial identification of a candidate genomic region harboring a gene associated with a detectable phenotype may be conducted using a preliminary map containing a few thousand biallelic markers. Thereafter, the genomic region harboring the gene responsible for the detectable trait may be better delineated using a map containing a larger number of biallelic markers. Furthermore, the genomic region harboring the gene responsible for the detectable trait may be further delineated using a high density map of biallelic markers. Finally, the gene associated with the detectable trait may be identified and isolated using a very high density biallelic marker map.

Example 6 describes a procedure for identifying a candidate region harboring a gene associated with a detectable trait and provides simulated results for this procedure. It will be appreciated that although Example 6 compares the results of simulated analyzes using markers derived from maps having 3,000, 20,000, and 60,000 markers, the number of markers contained in the map is not restricted to these exemplary figures. Rather, Example 6 exemplifies the increasing refinement of the candidate region with increasing marker density. As increasing numbers of markers are used in the analysis, points in the association analysis become broad peaks. The gene associated with the detectable trait under investigation will lie within or near the region under the peak.

The statistical power of linkage disequilibrium mapping using a high density marker map is also reinforced by complementing the single point association analysis described above with a multi-marker association analysis of haplotype analysis described in IV. To improve the statistical power of the individual marker association analyses conducted as described above using maps of increasing marker densities, haplotype studies can be performed using groups of markers located in proximity to one another within regions of the genome. For example, using the methods described above in which the association of an individual marker with a detectable phenotype was analyzed using maps of 3,000 markers, 20,000 markers, and 60,000 markers, a series of haplotype studies can be performed using groups of contiguous markers from such maps or from maps having higher marker densities.

In a preferred embodiment, a series of successive haplotype studies including groups of markers spanning regions of more than 1 Mb may be performed. In some embodiments, the biallelic markers included in each of these groups may be located within a genomic region spanning less than 1 kb, from 1 to 5 kb, from 5 to 10 kb, from 10 to 25 kb, from 25 to 50 kb, from 50 to 150 kb, from 150 to 250 kb, from 250 to 500 kb, from 500 kb to 1 Mb, or more than 1 Mb. Preferably, the genomic regions containing the groups of biallelic markers used in the successive haplotype analyses are overlapping. It will be appreciated that the groups of biallelic markers need not completely cover the genomic regions of the above-specified lengths but may instead be obtained from incomplete contigs having one or more gaps therein. As discussed in further detail below, biallelic markers may be used in single point and haplotype association analyses regardless of the completeness of the corresponding physical contig harboring them.

Genome-wide mapping using association studies with dense enough arrays of markers permit a case-by-case best estimate of p-value significance thresholds. Given a test population comprising two ethnically matched trait-positive and control groups of about 50 to about 500 individuals or more, conducting the above described association studies will allow a p-value "cut-off" to be established by, for example, analyzing significant numbers of allele frequency differences or, in some cases where appropriate, running computer simulations or control studies as described in Examples 6, 15, and 26.

For a p-value above the threshold, a corresponding association between the trait and a studied marker will be deemed not significant, while for a p-value below such a threshold, said association will be deemed significant. If the p-value is significant, the genomic region around the marker will be further scrutinized for a trait-causing gene.

It is preferred that p-value significance thresholds be assessed for each case/control population comparison. Both the genetic distance between sampled population—"stratification"—and the dispersion due to random selection of samples may indeed influence the p-value significance thresholds.

It will be appreciated that the above approaches may be conducted on any scale (i.e. over the whole genome, a set of chromosomes, a single chromosome, a particular subchromosomal region, or any other desired portion of the genome). As mentioned above, once significance thresholds have been assessed, population sample sizes may be adapted as exemplified in FIG. 3.

Example 7 below illustrates the increase in statistical power brought to an association study by a haplotype analysis.

The results described in Examples 5 and 7, generated from individual and haplotype studies using a biallelic marker set of an average density equal to ca. 40 kb in the region of an Alzheimer's disease trait causing gene, indicate that all biallelic markers of sufficient informative content located within a ca. 200 kb genomic region around a trait-causing allele can potentially be successfully used to localize a trait causing gene with the methods provided by the present invention. This conclusion is further supported by the results obtained through measuring the linkage disequilibrium between markers 99-365-344 or 99-359-308 and ApoE 4 Site A marker within Alzheimer's patients: as one could predict since linkage disequilibrium is the supporting basis for association studies, linkage disequilibrium between these pairs of markers was enhanced in the diseased population vs. the control population. In a similar way as the haplotype analysis enhanced the significance of the corresponding association studies.

Once a given polymorphic site has been found and characterized as a biallelic marker according to the methods of the present invention, several methods can be used in order to determine the specific allele carried by an individual at the given polymorphic base as described in III.

Location of a Gene Associated with Detectable Traits

Once the candidate region has been delineated using the high density biallelic marker map, a sequence analysis process will allow the detection of all genes located within said region, together with a potential functional characterization of said genes. The identified functional features may allow preferred trait-causing candidates to be chosen from among the identified genes. More biallelic markers may then be generated within said candidate genes, and used to perform refined association studies that will support the identification of the trait causing gene. Sequence analysis processes are described in Example 9.

Examples 10–18 illustrate the application of the above methods using biallelic markers to identify a gene associated with a complex disease, prostate cancer, within a ca. 450 kb candidate region. Additional details of the identification of the gene associated with prostate cancer are provided in the U.S. patent application entitled "Prostate Cancer Gene" Ser. No. 08/996,306, the disclosure of which is incorporated herein by reference in its entirety.

The above methods were also used to identify biallelic markers in a gene which was an attractive candidate for a gene associated with asthma. Examples 19–26 show how the use of methods of the present invention allowed this gene to be identified as a gene responsible, at least partially, for asthma in the studied populations. Additional details of the identification of the gene associated with asthma are provided in U.S. Provisional Application Serial Nos. 60/081, 893, the disclosure of which are incorporated herein by reference in its entirety Alternatively, genes associated with detectable traits may be identified as follows. Candidate genomic regions suspected of harboring a gene associated with the trait may be identified using techniques such as those described herein. In such techniques, the allelic frequencies of biallelic markers are compared in nucleic acid samples derived from individuals expressing the detectable trait and individuals who do not express the detectable trait. In this manner, candidate genomic regions suspected of harboring a gene associated with the detectable trait under investigation are identified.

The existence of one or more genes associated with the detectable trait within the candidate region is confirmed by identifying more biallelic markers lying in the candidate region. A first haplotype analysis is performed for each possible combination of groups of biallelic markers within the genomic region suspected of harboring a trait-associated gene. For % example, each group may comprise three biallelic markers. For each of the groups of markers, the frequency of each possible haplotype (for groups of three markers there are 8 possible haplotypes) in individuals expressing the trait and individuals who do not express the trait is estimated. For example, the a haplotype estimation method is applied as described in IV. for example the haplotype frequencies may be estimated using the Expectation-Maximization method of Excoffier L and Slatkin M, *Mol. Biol. Evol.* 12:921–927 (1995), the disclosure of which is incorporated herein by reference in its entirety.

The frequencies of each of the possible haplotypes of the grouped markers (or each allele of individual markers) in individuals expressing the trait and individuals who do not express the trait are compared. For example, the frequencies may be compared by performing a chi-squared analysis. Within each group, the haplotype (or the allele of each individual marker) having the greatest association with the trait is selected. This process is repeated for each group of biallelic markers (or each allele of the individual markers) to generate a distribution of association values, which will be referred to herein as the "trait-associated" distribution.

A second haplotype analysis is performed for each possible combination of groups of biallelic markers within the genomic regions which are not suspected of harboring a trait-associated gene. For example, each group may comprise three biallelic markers. For each of the groups of markers, the frequency of each possible haplotype (for groups of three markers there are 8 possible haplotypes) in individuals expressing the trait and individuals who do not express the trait is estimated.

The frequencies of each of the possible haplotypes of the grouped markers (or each allele of individual markers) in individuals expressing the trait and individuals who do not express the trait are compared. For example, the frequencies may be compared by performing a chi-squared analysis. Within each group, the haplotype (or the allele of each individual marker) having the greatest association with the trait is selected. This process is repeated for each group of biallelic markers (or each allele of the individual markers) to generate a distribution of association values, which will be referred to herein as the "random" distribution.

The trait-associated distribution and the random distribution are then compared to one another to determine if there are significant differences between them. For example, the trait-associated distribution and the random distribution can be compared using either the Wilcoxon rank test (Noether, G. E. (1991) Introduction to statistics: "The nonparametric way", Springer-Verlag, New York, Berlin, the disclosure of which is incorporated herein by reference in its entirety) or the Kolmogorov-Smirnov test (Saporta, G. (1990) "Probalites, analyse des donnees et statistiques" Technip editions, Paris, the disclosure of which is incorporated herein by reference in its entirety) or both the Wilcoxon rank test and the Kolmogorov-Smirnov test.

If the trait-associated distribution and the random distribution are found to be significantly different, the candidate genomic region is highly likely to contain a gene associated with the detectable trait. Accordingly, the candidate genomic region is evaluated more fully to isolate the trait-associated gene. Alternatively, if the trait-associated distribution and the random distribution are equal using the above analyses, the candidate genomic region is unlikely to contain a gene associated with the detectable trait. Accordingly, no further analysis of the candidate genomic region is performed.

While Examples 10 to 26 illustrate the use of the maps and markers of the present invention for identifying a new gene associated with a complex disease within a 2 Mb genomic region for establishing that a candidate gene is, at least partially, responsible for a disease, the maps and markers of the present invention may also be used to identify one or more biallelic markers or one or more genes associated with other detectable phenotypes, including drug response, drug toxicity, or drug efficacy. The biallelic markers used in such drug response analyses or shown, using the methods of the present invention to be associated with such traits, may lie within or near genes responsible for or partly responsible for a particular disease, for example a disease against which the drug is meant to act, or may lie within genomic regions which are not responsible for or partly responsible for a disease. In the context of the present invention, a "positive response" to a medicament can be defined as comprising a reduction of the symptoms related to the disease or condition to be treated. In the context of the present invention, a "negative response" to a medicament can be defined as comprising either a lack of positive response to the medicament which does not lead to a symptom reduction or to a side-effect observed following administration of the medicament.

Drug efficacy, response and tolerance/toxicity can be considered as multifactorial traits involving a genetic component in the same way as complex diseases such as Alzheimer's disease, prostate cancer, hypertension or diabetes. As such, the identification of genes involved in drug efficacy and toxicity could be achieved following a positional cloning approach, e.g. performing linkage analysis within families in order to obtain the subchromosomal location of the gene(s). However, this type of analysis is actually impractical in the case of drug responsiveness, due to the lack of availability of familial cases. In fact, the likelihood of having more than one individual in a particular family being exposed to the same drug at the same time is very low. Therefore, drug efficacy and toxicity can only be analyzed as sporadic traits.

In order to conduct association studies to analyze the individual response to a given drug in groups of patients affected with a disease, up to four groups are screened to determine their patterns of biallelic markers using the techniques described above. The four groups are:

Non-diseased or random controls,

Diseased patients/drug responders,

Diseased patients/drug non-responders, and

Diseased patients/drug side effects.

In preferred embodiments, the above mentioned groups are recruited according to phenotyping criteria having the characteristics described above, so that the phenotypes defining the different groups are non-overlapping, preferably extreme phenotypes. In highly preferred embodiments, such phenotyping criteria have the bimodal distribution described above.

The final number and composition of the groups for each drug association study is adapted to the distribution of the above described phenotypes within the studied population.

After selecting a suitable population, association and haplotype analyses may be performed as described herein to identify one or more biallelic markers associated with drug response, preferably drug toxicity or drug efficacy. The identification of such one or more biallelic markers allows one to conduct diagnostic tests to determine whether the administration of a drug to an individual will result in drug response, preferably drug toxicity, or drug efficacy.

The methods described above for identifying a gene associated with prostate cancer and biallelic markers indicative of a risk of suffering from asthma may be utilized to identify genes associated with other detectable phenotypes. In particular, the above methods may be used with any marker or combination of markers included in the maps of the present invention, including the biallelic markers of SEQ ID Nos.: 1 to 3809 or the sequences complementary thereto. As described above, the general strategy to perform the association studies using the maps and markers of the present invention is to scan two groups of individuals (trait-positive individuals and trait-negative controls) characterized by a well defined phenotype in order to measure the allele frequencies of the biallelic markers in each of these groups. Preferably, the frequencies of markers with inter-marker spacing of about 150 kb are determined in each group. More preferably, the frequencies of markers with inter-marker spacing of about 75 kb are determined in each group. Even more preferably, markers with inter-marker spacing of about 50 kb, about 37.5 kb, about 30 kb, or about 25 kb will be tested in each population.

In some embodiments, the frequencies of 1, 5, 10, 20, 50, 100, 500, 1000, 2000, 3000, or all of the biallelic markers of SEQ ID Nos.: 1 to 3908 or the sequences complementary thereto are measured in each population. In another embodiment, the frequencies of 1, 5, 10, 20, 50, 100, 500, 1000, 2000, or 3000 biallelic markers selected from the group consisting of biallelic markers which are in linkage disequilibrium with the biallelic markers of 1 to 3908 or the sequences complementary thereto are measured in each population. In some embodiments the frequencies of 1, 5, 10, 20, 50, 100, 500, 1000, 2000, or all of the biallelic markers of SEQ ID Nos.: 1 to 2260 or the sequences complementary thereto are measured in each population. In another embodiment, the frequencies of 1, 5, 10, 20, 50, 100, 500, 1000, or 2000 biallelic markers selected from the group consisting of biallelic markers which are in linkage disequilibrium with the biallelic markers of 1 to 2260 or the sequences complementary thereto are measured in each population. In some embodiments the frequencies of 1, 5, 10, 20, 50, 100, 500, 1000, or all of the biallelic markers of SEQ ID Nos.: 2261 to 3734 or the sequences complementary thereto are measured in each population. In another embodiment, the frequencies of 1, 5, 10, 20, 50, 100, 500, 1000 biallelic markers selected from the group consisting of biallelic markers which are in linkage disequilibrium with the biallelic markers of 2261 to 3734 or the sequences complementary thereto are measured in each population. In some embodiments the frequencies of 1, 5, 10, 20, 50, 100, or all of the biallelic markers of SEQ ID Nos.: 3735 to 3908 or the sequences complementary thereto are measured in each population. In another embodiment, the frequencies of 1, 5, 10, 20, 50, or 100 biallelic markers selected from the group consisting of biallelic markers which are in linkage disequilibrium with the biallelic markers of 3735 to 3908 or the sequences complementary thereto are measured in each population.

In some embodiments, the frequencies of about 20,000, or about 40,000 biallelic markers are determined in each population. In a highly preferred embodiment, the frequencies of about 60,000, about 80,000, about 100,000, or about 120,000 biallelic markers are determined in each population. In some embodiments, haplotype analyses may be run using groups of markers located within regions spanning less than 1 kb, from 1 to 5 kb, from 5 to 100 kb, from 10 to 25 kb, from 25 to 50 kb, from 50 to 150 kb, from 150 to 250 kb, from 250 to 500 kb, from 500 kb to 1 Mb, or more than 1 Mb.

Allele frequency can be measured using any genotyping method described herein including microsequencing techniques; preferred high throughput microsequencing procedures are further exemplified in III; it will be further appreciated that any other large scale genotyping method suitable with the intended purpose contemplated herein may also be used.

It will be appreciated that it is not necessary to use a full high density biallelic marker map in order to start a genome-wide association study. Maps having higher densities of biallelic markers (two or more markers per BAC, average inter-marker spacing of about 75 kb or less) may then be generated by starting first on those BACs for which a candidate association has been established at the first step.

In cases when one or more candidate regions have previously been delineated, such as cases where a particular gene or genomic region is suspected of being associated with a trait, local excerpts of biallelic marker maps having densities above one marker per 150 kb may be exploited using BACs harboring said genomic regions, or genes, or portions thereof. In these cases also, successive association studies may be performed using sets of biallelic markers showing increasing densities, preferably from about one every 150 kb to about one every 75 kb; more preferably, sets of markers with inter-marker spacing below about 50 kb, below about 37.5 kb, below about 30 kb, most preferably below about 25 kb, will be used.

Haplotype analyses may also be conducted using groups of biallelic markers within the candidate region. The biallelic markers included in each of these groups may be located within a genomic region spanning less than 1 kb, from 1 to 5 kb, from 5 to 10 kb, from 10 to 25 kb, from 25 to 50 kb, from 50 to 150 kb, from 150 to 250 kb, from 250 to 500 kb, from 500 kb to 1 Mb, or more than 1 Mb. It will be appreciated that the ordered DNA fragments containing these groups of biallelic markers need not completely cover the genomic regions of these lengths but may instead be incomplete contigs having one or more gaps therein. As discussed in further detail below, biallelic markers may be used in association studies and haplotype analyses regardless of the completeness of the corresponding physical contig harboring them, provided linkage disequilibrium between the markers can be assessed.

As described above, if a positive association with a trait, such as a disease, or a drug efficacy and/or toxicity, is identified using the biallelic markers and maps of the present invention, the maps will provide not only the confirmation of the association, but also a shortcut towards the identification of the gene involved in the trait under study. As described above, since the markers showing positive association to the trait are in linkage disequilibrium with the trait loci, the causal gene will be physically located in the vicinity of these markers. Regions identified through association studies using high density maps will on average have a 20–40 times shorter length than those identified by linkage analysis (2 to 20 Mb).

As described above, once a positive association is confirmed with the high density biallelic marker maps of the present invention, BACs from which the most highly associated markers were derived are completely sequenced and the mutations in the causal gene are searched by applying genomic analysis tools. As described above, once a region harboring a gene associated with a detectable trait has been sequenced and analyzed, the candidate functional regions (e.g. exons and splice sites, promoters and other regulatory regions) are scanned for mutations by comparing the sequences of a selected number of controls and cases, using adequate software.

In some embodiments, trait-positive samples being compared to identify causal mutations are selected among those carrying the ancestral haplotype; in these embodiments, control samples are chosen from individuals not carrying said ancestral haplotype.

In further embodiments, trait-positive samples being compared to identify causal mutations are selected among those showing haplotypes that are as close as possible to the ancestral haplotype; in these embodiments, control samples are chosen from individuals not carrying any of the haplotypes selected for the case population.

The maps and biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate p-values can be considered as a haplotype analysis, similar to those described in further details within the present invention.

IX. Use of Biallelic Markers to Identify Individuals Likely to Exhibit a Detectable Trait Associated with a Particular Allele of a Known Gene In addition to their utility in searches for genes associated with detectable traits on a genome-wide, chromosome-wide, or subchromosomal level, the maps and biallelic markers of the present invention may be used in more targeted approaches for identifying individuals likely to exhibit a particular detectable trait or individuals who exhibit a particular detectable trait as a consequence of possessing a particular allele of a gene associated with the detectable trait. For example, the biallelic markers and maps of the present invention may be used to identify individuals who carry an allele of a known gene that is suspected of being associated with a particular detectable trait. In particular, the target genes may be genes having alleles which predispose an individual to suffer from a specific disease state. In other cases, the target genes may be genes having alleles that predispose an individual to exhibit a desired or undesired response to a drug or other pharmaceutical composition, a food, or any administered compound. The known gene may encode any of a variety of types of biomolecules. For example, the known genes targeted in such analyzes may be genes known to be involved in a particular step in a metabolic pathway in which disruptions may cause a detectable trait. Alternatively, the target genes may be genes encoding receptors or ligands which bind to receptors in which disruptions may cause a detectable trait, genes encoding transporters, genes encoding proteins with signaling activities, genes encoding proteins involved in the immune response, genes encoding proteins involved in hematopoesis, or genes encoding proteins involved in wound healing. It will be appreciated that the target genes are not limited to those specifically enumerated above, but may be any gene known to be or suspected of being associated with a detectable trait.

As previously mentioned, the maps and markers of the present invention may be used to identify genes associated with drug response. The biallelic markers of the present invention may also be used to select individuals for inclusion in the clinical trials of a drug. In some embodiments, the markers of SEQ ID Nos.: 1 to 3908, 1 to 2260, 2261 to 3374, 3735 to 3908 or the sequences complementary thereto may be used in targeted approaches to identify individuals at risk of developing a detectable trait, for example a complex disease or desired/undesired drug response, or to identify individuals exhibiting said trait. The present invention provides methods to establish putative associations between any of the biallelic markers described herein and any detectable traits, including those specifically described herein.

To use the maps and markers of the present invention in further targeted approaches, biallelic markers which are in linkage disequilibrium with any of the above disclosed markers may be identified. In cases where one or more biallelic markers of the present invention have been shown to be associated with a detectable trait, more biallelic markers in linkage disequilibrium with said associated biallelic markers may be generated and used to perform targeted approaches aiming at identifying individuals exhibiting, or likely to exhibit, said detectable trait, according to the methods provided herein.

Furthermore, in cases where a candidate gene is suspected of being associated with a particular detectable trait or suspected of causing the detectable trait, biallelic markers in linkage disequilibrium with said candidate gene may be identified and used in targeted approaches, such as the approaches utilized above for the asthma-associated gene and the Apo E gene.

Biallelic markers that are in linkage disequilibrium with markers associated with a detectable trait, or with genes associated with a detectable trait, or suspected of being so, are identified by performing single marker analyzes, haplotype association analyzes, or linkage disequilibrium measurements on samples from trait-positive and trait-negative individuals as described above using biallelic markers lying in the vicinity of the target marker or gene. In this manner, a single biallelic marker or a group of biallelic markers may be identified which indicate that an individual is likely to possess the detectable trait or does possess the detectable trait as a consequence of a particular allele of the target marker or gene.

Nucleic acid samples from individuals to be tested for predisposition to a detectable trait or possession of a detectable trait as a consequence of a particular allele of the target gene may be examined using the diagnostic methods described above.

Throughout this application, various publications, patents, and published patent applications are cited. The disclosures of the publications, patents, and published patent specifications referenced in this application are hereby incorporated by reference into the present disclosure in their entireties to more fully describe the state of the art to which this invention pertains.

EXAMPLES

Several of the methods of the present invention are described in the following examples, which are offered by way of illustration and not by way of limitation. Many other modifications and variations of the invention as herein set forth can be made without departing from the spirit and scope thereof and therefore only such limitations should be imposed as are indicated by the appended claims.

Example 1

Ordering of a BAC Library: Screening Clones with STSs

The BAC library is screened with a set of PCR-typeable STSs to identify clones containing the STSs. To facilitate PCR screening of several thousand clones, for example 200,000 clones, pools of clones are prepared.

Three-dimensional pools of the BAC libraries are prepared as described in Chumakov et al. and are screened for the ability to generate an amplification fragment in amplification reactions conducted using primers derived from the ordered STSs. (Chumakov et al. (1995), supra). A BAC library typically contains 200,000 BAC clones. Since the average size of each insert is 100–300 kb, the overall size of such a library is equivalent to the size of at least about 7 human genomes. This library is stored as an array of individual clones in 518 384-well plates. It can be divided into 74 primary pools (7 plates each). Each primary pool can then be divided into 48 subpools prepared by using a three-dimensional pooling system based on the plate, row and column address of each clone (more particularly, 7 subpools consisting of all clones residing in a given microtiter plate; 16 subpools consisting of all clones in a given row; 24 subpools consisting of all clones in a given column).

Amplification reactions are conducted on the pooled BAC clones using primers specific for the STSs. For example, the three dimensional pools may be screened with 45,000 STSs whose positions relative to one another and locations along the genome are known. Preferably, the three dimensional pools are screened with about 30,000 STSs whose positions relative to one another and locations along the genome are known. In a highly preferred embodiment, the three dimensional pools are screened with about 20,000 STSs whose positions relative to one another and locations along the genome are known.

Amplification products resulting from the amplification reactions are detected by conventional agarose gel electrophoresis combined with automatic image capturing and processing. PCR screening for a STS involves three steps: (1) identifying the positive primary pools; (2) for each positive primary pool, identifying the positive plate, row and column 'subpools' to obtain the address of the positive clone; (3) directly confirming the PCR assay on the identified clone. PCR assays are performed with primers specifically defining the STS.

Screening is conducted as follows. First BAC DNA containing the genomic inserts is prepared as follows. Bacteria containing the BACs are grown overnight at 37° C. in 120 μl of LB containing chloramphenicol (12 μg/ml). DNA is extracted by the following protocol:

Centrifuge 10 min at 4° C. and 2000 rpm

Eliminate supernatant and resuspend pellet in 120 μl TE 10-2 (Tris HCl 10 mM, EDTA 2 mM)

Centrifuge 10 min at 4° C. and 2000 rpm

Eliminate supernatant and incubate pellet with 20 μl lyzozyme 1 mg/ml during 15 min at room temperature Add 20 μl proteinase K 100 μg/ml and incubate 15 min at 60° C.

Add 8 μl DNAse 2U/μl and incubate 1 hr at room temperature

Add 100 μl TE 10-2 and keep at −80° C.

PCR assays are performed using the following protocol:

| Final volume | 15 μl |
| Final volume | 15 μl |
| BAC DNA | 1.7 ng/μl |
| MgCl$_2$ | 2 mM |
| dNTP (each) | 200 μM |
| primer (each) | 2.9 ng/μl |
| Ampli Taq Gold DNA polymerase | 0.05 unit/μl |
| PCR buffer (10× = 0.1 M TrisHCl pH 8.3 0.5 M KCl | 1× |

The amplification is performed on a Genius II thermocycler. After heating at 95° C. for 10 min, 40 cycles are performed. Each cycle comprises: 30 sec at 95° C., 54° C. for 1 min, and 30 sec at 72° C. For final elongation, 10 min at 72° C. end the amplification. PCR products are analyzed on 1% agarose gel with 0.1 mg/ml ethidium bromide.

Alternatively, a YAC (Yeast Artificial Chromosome) library can be used. The very large insert size, of the order of 1 megabase, is the main advantage of the YAC libraries. The library can typically include about 33,000 YAC clones as described in Chumakov et al. (1995, supra). The YAC screening protocol may be the same as the one used for BAC screening.

The known order of the STSs is then used to align the BAC inserts in an ordered array (contig) spanning the whole human genome. If necessary new STSs to be tested can be generated by sequencing the ends of selected BAC inserts. Subchromosomal localization of the BACs can be established and/or verified by fluorescence in situ hybridization (FISH), performed on metaphasic chromosomes as described by Cherif et al. 1990 and in Example 3 below. BAC insert size may be determined by Pulsed Field Gel Electrophoresis after digestion with the restriction enzyme NotI.

Finally, a minimally overlapping set of BAC clones, with known insert size and subchromosomal location, covering the entire genome, a set of chromosomes, a single chromosome, a particular subchromosomal region, or any other desired portion of the genome is selected from the DNA library. For example, the BAC clones may cover at least 100 kb of contiguous genomic DNA, at least 250 kb of contiguous genomic DNA, at least 500 kb of contiguous genomic DNA, at least 2 Mb of contiguous genomic DNA, at least 5 Mb of contiguous genomic DNA, at least 10 Mb of contiguous genomic DNA, or at least 20 Mb of contiguous genomic DNA.

Example 2

Screening BAC Libraries with Biallelic Markers

Amplification primers enabling the specific amplification of DNA fragments carrying the biallelic markers, including the map-related biallelic markers of the invention, may be used to screen clones in any genomic DNA library, preferably the BAC libraries described above for the presence of the biallelic markers.

Pairs of primers of SEQ ID Nos: 3935 to 7842, 3935 to 6194, 6195 to 7668, 7669 to 7842, 7866 to 11773, 7866 to 10125, 10126 to 11599, and 11600 to 11773 were designed which allow the amplification of fragments carrying the biallelic markers of SEQ ID Nos: 1 to 3908, 1 to 2260, 2261 to 3374, 3735 to 3908 or the sequences complementary thereto. The amplification primers of SEQ ID Nos: 3935 to 7842, 3935 to 6194, 6195 to 7668, 7669 to 7842, 7866 to 11773, 7866 to 10125, 10126 to 11599, and 11600 to 11773 may be used to screen clones in a genomic DNA library for the presence of the biallelic markers of SEQ ID Nos: 1 to 3908, 1 to 2260, 2261 to 3374, 3735 to 3908 or the sequences complementary thereto.

It will be appreciated that amplification primers for the biallelic markers of SEQ ID Nos: 1 to 3908, 1 to 2260, 2261 to 3374, 3735 to 3908 need not be identical to the primers of SEQ ID Nos: 3935 to 7842, 3935 to 6194, 6195 to 7668, 7669 to 7842, 7866 to 11773, 7866 to 10125, 10126 to 11599, and 11600 to 11773. Rather, they can be any other primers allowing the specific amplification of any DNA fragment carrying the markers and may be designed using techniques familiar to those skilled in the art. The amplification primers may be oligonucleotides of 8, 10, 15, 20 or more bases in length which enable the amplification of any fragment carrying the polymorphic site in the markers. The polymorphic base may be in the center of the amplification product or, alternatively, it may be located off-center. For example, in some embodiments, the amplification product produced using these primers may be at least 100 bases in length (i.e. 50 nucleotides on each side of the polymorphic base in amplification products in which the polymorphic base is centrally located). In other embodiments, the amplification product produced using these primers may be at least 500 bases in length (i.e. 250 nucleotides on each side of the polymorphic base in amplification products in which the polymorphic base is centrally located). In still further embodiments, the amplification product produced using these primers may be at least 1000 bases in length (i.e. 500 nucleotides on each side of the polymorphic base in amplification products in which the polymorphic base is centrally located). Amplification primers such as those described above are included within the scope of the present invention.

The localization of biallelic markers on BAC clones is performed essentially as described in Example 1.

The BAC clones to be screened are distributed in three dimensional pools as described in Example 1.

Amplification reactions are conducted on the pooled BAC clones using primers specific for the biallelic markers to identify BAC clones which contain the biallelic markers, using procedures essentially similar to those described in Example 1.

Amplification products resulting from the amplification reactions are detected by conventional agarose gel electrophoresis combined with automatic image capturing and processing. PCR screening for a biallelic marker involves three steps: (1) identifying the positive primary pools; (2) for each positive primary pools, identifying the positive plate, row and column 'subpools' to obtain the address of the positive clone; (3) directly confirming the PCR assay on the identified clone. PCR assays are performed with primers defining the biallelic marker.

Screening is conducted as follows. First BAC DNA is isolated as follows. Bacteria containing the genomic inserts are grown overnight at 37° C. in 120 µl of LB containing chloramphenicol (12 µg/ml). DNA is extracted by the following protocol:

Centrifuge 10 min at 4° C. and 2000 rpm
Eliminate supernatant and resuspend pellet in 120 µl TE 10-2 (Tris HCl 10 mM, EDTA 2 mM)
Centrifuge 10 min at 4° C. and 2000 rpm
Eliminate supernatant and incubate pellet with 20 µl lyzozyme 1 mg/ml during 15 min at room temperature
Add 20 µl proteinase K 100 µg/ml and incubate 15 min at 60° C.
Add 8 µl DNAse 2U/µl and incubate 1 hr at room temperature
Add 100 µl TE 10-2 and keep at −80° C.

PCR assays are performed using the following protocol:

| | |
|---|---|
| Final volume | 15 µl |
| BAC DNA | 1.7 ng/µl |
| MgCl₂ | 2 mM |
| dNTP (each) | 200 µM |
| primer (each) | 2.9 ng/µl |
| Ampli Taq Gold DNA polymerase | 0.05 unit/µl |
| PCR buffer (10× = 0.1 M TrisHCl pH 8.3 0.5 M KCl | 1× |

The amplification is performed on a Genius II thermocycler. After heating at 95° C. for 10 min, 40 cycles are performed. Each cycle comprises: 30 sec at 95° C., 54° C. for 1 min, and 30 sec at 72° C. For final elongation, 10 min at 72° C. end the amplification. PCR products are analyzed on 1% agarose gel with 0.1 mg/ml ethidium bromide.

Example 3

Assignment of Biallelic Markers to Subchromosomal Regions

Metaphase chromosomes are prepared from phytohemagglutinin (PHA)-stimulated blood cell donors. PHA-stimulated lymphocytes from healthy males are cultured for 72 h in RPMI-1640 medium. For synchronization, methotrexate (10 mM) is added for 17 h, followed by addition of 5-bromodeoxyuridine (5-BudR, 0.1 mM) for 6 h. Colcemid (1 mg/ml) is added for the last 15 min before harvesting the cells. Cells are collected, washed in RPMI, incubated with a hypotonic solution of KCl (75 mM) at 37° C. for 15 min and fixed in three changes of methanol:acetic acid (3:1). The cell suspension is dropped onto a glass slide and air-dried.

BAC clones carrying the biallelic markers used to construct the maps of the present invention (including the biallelic markers of SEQ ID Nos: 1 to 3908, 1 to 2260, 2261 to 3374, 3735 to 3908 or the sequences complementary thereto) can be isolated as described above. These BACs or portions thereof, including fragments carrying said biallelic markers, obtained for example from amplification reactions using pairs of primers of SEQ ID Nos: 3935 to 7842, 3935 to 6194, 6195 to 7668, 7669 to 7842, 7866 to 11773, 7866 to 10125, 10126 to 11599, and 11600 to 11773, can be used as probes to be hybridized with metaphasic chromosomes. It will be appreciated that the hybridization probes to be used in the contemplated method may be generated using alternative methods well known to those skilled in the art. Hybridization probes may have any length suitable for this intended purpose.

Probes are then labeled with biotin-16 dUTP by nick translation according to the manufacturer's instructions (Bethesda Research Laboratories, Bethesda, Md.), purified using a Sephadex G-50 column (Pharmacia, Upssala, Sweden) and precipitated. Just prior to hybridization, the DNA pellet is dissolved in hybridization buffer (50% formamide, 2×SSC, 10% dextran sulfate, 1 mg/ml sonicated salmon sperm DNA, pH 7) and the probe is denatured at 70° C. for 5–10 min.

Slides kept at −20° C. are treated for 1 h at 37° C. with RNase A (100 mg/ml), rinsed three times in 2×SSC and dehydrated in an ethanol series. Chromosome preparations are denatured in 70% formamide, 2×SSC for 2 min at 70° C., then dehydrated at 4° C. The slides are treated with proteinase K (10 mg/100 ml in 20 mM Tris-HCl, 2 mM CaCl₂) at 37° C. for 8 min and dehydrated. The hybridization mixture containing the probe is placed on the slide, covered with a coverslip, sealed with rubber cement and incubated overnight in a humid chamber at 37° C. After hybridization and post-hybridization washes, the biotinylated probe is detected by avidin-FITC and amplified with additional layers of biotinylated goat anti-avidin and avidin-FITC. For chromosomal localization, fluorescent R-bands are obtained as previously described (Cherif et al., (1990) supra.). The slides are observed under a LEICA fluorescence microscope (DMRXA). Chromosomes are counterstained with propidium iodide and the fluorescent signal of the probe appears as two symmetrical yellow-green spots on both chromatids of the fluorescent R-band chromosome (red). Thus, a particular biallelic marker may be localized to a particular cytogenetic R-band on a given chromosome.

The above procedure was used to confirm the subchromosomal location of many of the BAC clones harboring the markers obtained above. In particular, several of the markers were assigned to subchromosomal regions of chromosome 21. Simple identification numbers were attributed to each BAC from which the markers are derived. FIG. 1 is a cytogenetic map of chromosome 21 indicating the subchromosomal regions therein. Amplification primers for generating amplification products containing the polymorphic bases of these markers are also provided in the accompanying sequence listing. In addition, microsequencing primers for use in determining the identities of the polymorphic bases of these biallelic markers are provided in the accompanying Sequence Listing.

The rate at which biallelic markers may be assigned to subchromosomal regions may be enhanced through automation. For example, probe preparation may be performed in a microtiter plate format, using adequate robots. The rate at which biallelic markers may be assigned to subchromosomal regions may be enhanced using techniques which permit the in situ hybridization of multiple probes on a single microscope slide, such as those disclosed in Larin et al., *Nucleic Acids Research* 22: 3689–3692 (1994), the disclosure of which is incorporated herein by reference in its entirety. In the largest test format described, different probes were hybridized simultaneously by applying them directly from a 96-well microtiter dish which was inverted on a glass plate. Software for image data acquisition and analysis that is adapted to each optical system, test format, and fluorescent probe used, can be derived from the system described in Lichter et al. *Science* 247: 64–69 (1990), the disclosure of which is incorporated herein by reference in its entirety. Such software measures the relative distance between the center of the fluorescent spot corresponding to the hybridized probe and the telomeric end of the short arm of the corresponding chromosome, as compared to the total length of the chromosome. The rate at which biallelic markers are assigned to subchromosomal locations may be further enhanced by simultaneously applying probes labeled with different flourescent tags to each well of the 96 well dish. A further benefit of conducting the analysis on one slide is that it facilitates automation, since a microscope having a moving stage and the capability of detecting fluorescent signals in different metaphase chromosomes could provide the coordinates of each probe on the metaphase chromosomes distributed on the 96 well dish.

Example 4 below describes an alternative method to position biallelic markers which allows their assignment to human chromosomes.

Example 4

Assignment of Biallelic Markers to Human Chromosomes

The biallelic markers used to construct the maps of the present invention, including the biallelic markers of SEQ ID Nos. 1 to 3908, 1 to 2260, 2261 to 3374, 3735 to 3908 or the sequences complementary thereto, may be assigned to a human chromosome using monosomal analysis as described below.

The chromosomal localization of a biallelic marker can be performed through the use of somatic cell hybrid panels. For example 24 panels, each panel containing a different human chromosome, may be used (Russell et al., *Somat Cell Mol. Genet* 22:425–431 (1996); Drwinga et al., *Genomics* 16:311–314 (1993), the disclosures of which are incorporated herein by reference in their entireties).

The biallelic markers are localized as follows. The DNA of each somatic cell hybrid is extracted and purified. Genomic DNA samples from a somatic cell hybrid panel are prepared as follows. Cells are lysed overnight at 42° C. with 3.7 ml of lysis solution composed of:

3 ml TE 10-2 (Tris HCl 10 mM, EDTA 2 mM)/NaCl 0.4 M

200 µl SDS 10%

500 µl K-proteinase (2 mg K-proteinase in TE 10-2/NaCl 0.4 M)

For the extraction of proteins, 1 ml saturated NaCl (6M) (1/3.5 v/v) is added. After vigorous agitation, the solution is centrifuged for 20 min at 10,000 rpm. For the precipitation of DNA, 2 to 3 volumes of 100% ethanol are added to the previous supernatant, and the solution is centrifuged for 30 min at 2,000 rpm. The DNA solution is rinsed three times with 70% ethanol to eliminate salts, and centrifuged for 20 min at 2,000 rpm. The pellet is dried at 37° C., and resuspended in 1 ml TE 10-1 or 1 ml water. The DNA concentration is evaluated by measuring the OD at 260 nm (1 unit OD=50 µg/ml DNA). To determine the presence of proteins in the DNA solution, the $OD_{260}/OD_{280}$ ratio is determined. Only DNA preparations having a $OD_{260}/OD_{280}$ ratio between 1.8 and 2 are used in the PCR assay.

Then, a PCR assay is performed on genomic DNA with primers defining the biallelic marker. The PCR assay is performed as described above for BAC screening. The PCR products are analyzed on a 1% agarose gel containing 0.2 mg/ml ethidium bromide.

Example 5

Measurement of Linkage Disequilibrium

As originally reported by Strittmater et al. and by Saunders et al. in 1993, the Apo E e4 allele is strongly associated with both late-onset familial and sporadic Alzheimer's disease. (Saunders, A. M. Lancet 342: 710–711 (1993) and Strittmater, W. J. et al., Proc. Natl. Acad. Sci. U.S.A. 90: 1977–1981 (1993), the disclosures of which are incorporated herein by reference in their entireties). The 3 major isoforms of human Apolipoprotein E (apoE2, -E3, and -E4), as identified by isoelectric focusing, are coded for by 3 alleles (e 2, 3, and 4). The e 2, e 3, and e 4 isoforms differ in amino acid sequence at 2 sites, residue 112 (called site A) and residue 158 (called site B). The ancestral isoform of the protein is Apo E3, which at sites A/B contains cysteine/arginine, while ApoE2 and -E4 contain cysteine/cysteine and arginine/arginine, respectively (Weisgraber, K. H. et al., J. Biol. Chem. 256: 9077–9083 (1981); Rall, S. C. et al., Proc. Natl. Acad. Sci. U.S.A. 79: 4696–4700 (1982), the disclosures of which are incorporated herein by reference in their entireties).

Apo E e 4 is currently considered as a major susceptibility risk factor for Alzheimer's disease development in individuals of different ethnic groups (specially in Caucasians and Japanese compared to Hispanics or African Americans), across all ages between 40 and 90 years, and in both men and women, as reported recently in a study performed on 5930 Alzheimer's disease patients and 8607 controls (Farrer et al., *JAMA* 278:1349–1356 (1997), the disclosure of which is incorporated herein by reference in its entirety). More specifically, the frequency of a C base coding for arginine 112 at site A is significantly increased in Alzheimer's disease patients.

Although the mechanistic link between Apo E e 4 and neuronal degeneration characteristic of Alzheimer's disease remains to be established, current hypotheses suggest that the Apo E genotype may influence neuronal vulnerability by increasing the deposition and/or aggregation of the amyloid beta peptide in the brain or by indirectly reducing energy availability to neurons by promoting atherosclerosis.

Using the methods of the present invention, biallelic markers that are in the vicinity of the Apo E site A were generated and the association of one of their alleles with Alzheimer's disease was analyzed. An Apo E public marker (stSG94) was used to screen a human genome BAC library as previously described. A BAC, which gave a unique FISH hybridization signal on chromosomal region 19q13.2.3, the chromosomal region harboring the Apo E gene, was selected for finding biallelic markers in linkage disequilibrium with the Apo E gene as follows.

This BAC contained an insert of 205 kb that was subcloned as previously described. Fifty BAC subclones were randomly selected and sequenced. Twenty five subclone sequences were selected and used to design twenty five pairs of PCR primers allowing 500 bp-amplicons to be generated. These PCR primers were then used to amplify the corresponding genomic sequences in a pool of DNA from 100 unrelated individuals (blood donors of French origin) as already described.

Amplification products from pooled DNA were sequenced and analyzed for the presence of biallelic polymorphisms, as already described. Five amplicons were shown to contain a polymorphic base in the pool of 100 unrelated individuals, and therefore these polymorphisms were selected as random biallelic markers in the vicinity of the Apo E gene. The sequences of both alleles of these biallelic markers (99-344-439; 99-366-274, 99-359-308; 99-355-219; 99-365-344;) correspond to SEQ ID Nos: 3909 to 3913. Corresponding pairs of amplification primers for generating amplicons containing these biallelic markers can be chosen from those listed as SEQ ID Nos: 7843 to 7847 and 11774 to 11778.

An additional pair of primers (SEQ ID Nos: 3124 and 4169) was designed that allows amplification of the genomic fragment carrying the biallelic polymorphism corresponding to the ApoE marker (99-2452-54; C/T; designated SEQ ID NO: 3914 in the accompanying Sequence Listing; publicly known as Apo E site A (Weisgraber et al. (1981), supra; Rall et al. (1982), supra) to be amplified.

The five random biallelic markers plus the Apo E site A marker were physically ordered by PCR screening of the corresponding amplicons using all available BACs originally selected from the genomic DNA libraries, as previously described, using the public Apo E marker stSG94. The amplicon's order derived from this BAC screening is as follows: (99-344-439/99-366-274)-(99-365-344/99-2452-54)-99-359-308-99-355-219, where parentheses indicate that the exact order of the respective amplicons couldn't be established.

Linkage disequilibrium among the six biallelic markers (five random markers plus the Apo E site A) was determined by genotyping the same 100 unrelated individuals from whom the random biallelic markers were identified.

DNA samples and amplification products from genomic PCR were obtained in similar conditions as those described above for the generation of biallelic markers, and subjected to automated microsequencing reactions using fluorescent ddNTPs (specific fluorescence for each ddNTP) and the appropriate microsequencing primers having a 3' end immediately upstream of the polymorphic base in the biallelic markers. Once specifically extended at the 3' end by a DNA polymerase using the complementary fluorescent dideoxynucleotide analog (thermal cycling), the microsequencing primer was precipitated to remove the unincorporated fluorescent ddNTPs. The reaction products were analyzed by electrophoresis on ABI 377 sequencing machines. Results were automatically analyzed by an appropriate software further described in Example 8.

Linkage disequilibrium (LD) between all pairs of biallelic markers ($M_i$, $M_j$) was calculated for every allele combination (Mi1,Mj1; Mi1,Mj2; Mi2,Mj1; Mi2,Mj2) according to the maximum likelihood estimate (MLE) for delta (the composite linkage disequilibrium coefficient). The results of the linkage disequilibrium analysis between the Apo E Site A marker and the five new biallelic markers (99-344-439; 99-355-219; 99-359-308; 99-365-344; 99-366-274) are summarized in Table 2 below:

TABLE 2

| Markers | d × 100 APOE Site A 99-2452-54 | SEQ ID Nos of the biallelic Markers | SEQ ID Nos of the amplification Primers |
|---|---|---|---|
| ApoE Site A 99-2452-54 | | 3914 | 7848; 11779 |
| 99-344-439 | 1 | 3909 | 7843, 11774 |
| 99-366-274 | 1 | 3910 | 7844, 11775 |
| 99-365-344 | 8 | 3913 | 7847, 11778 |
| 99-359-308 | 2 | 3911 | 7845, 11776 |
| 99-355-219 | 1 | 3912 | 7846, 11777 |

The above linkage disequilibrium results indicate that among the five biallelic markers randomly selected in a region of about 200 kb containing the Apo E gene, marker 99-365-344T is in relatively strong linkage disequilibrium with the Apo E site A allele (99-2452-54C).

Therefore, since the Apo E site A allele is associated with Alzheimer's disease, one can predict that the T allele of marker 99-365-344 will probably be found associated with Alzheimer's disease. In order to test this hypothesis, the biallelic markers of SEQ ID Nos: 3909 to 3913 were used in association studies as described below.

225 Alzheimer's disease patients were recruited according to clinical inclusion criteria based on the MMSE test. The 248 control cases included in this study were both ethnically- and age-matched to the affected cases. Both affected and control individuals corresponded to unrelated cases. The identities of the polymorphic bases of each of the biallelic markers was determined in each of these individuals using the methods described above. Techniques for conducting association studies are further described below.

The results of this study are summarized in Table 3 below:

TABLE 3

| | ASSOCIATION DATA | |
|---|---|---|
| MARKER | Difference in allele frequency between individuals with Alzheimer's and control individuals | Corresponding p-value |
| 99-344-439 | 3.3% | 9.54 E-02 |
| 99-366-274 | 1.6% | 2.09 E-01 |
| 99-365-344 | 17.7% | 6.9 E-10 |
| 99-2452-54 (ApoE Site A) | 23.8% | 3.95 E-21 |
| 99-359-308 | 0.4% | 9.2 E-01 |
| 99-355-219 | 2.5% | 2.54 E-01 |

The frequency of the Apo E site A allele in both Alzheimer's disease cases and controls was found in agreement with that previously reported (ca. 10% in controls and ca. 34% in Alzheimer's disease cases, leading to a 24% difference in allele frequency), thus validating the Apo E e4 association in the populations used for this study.

Moreover, as predicted from the linkage disequilibrium analysis (Table 3), a significant association of the T allele of marker 99-365/344 with Alzheimer's disease cases (18% increase in the T allele frequency in Alzheimer's disease cases compared to controls, p value for this difference=6.9 E-10) was observed.

The above results indicate that any marker in linkage disequilibrium with one given marker associated with a trait will be associated with the trait. It will be appreciated that, though in this case the ApoE Site A marker is the trait-causing allele (TCA) itself, the same conclusion could be drawn with any other non trait-causing allele marker associated with the studied trait.

These results further indicate that conducting association studies with a set of biallelic markers randomly generated within a candidate region at a sufficient density (here about one biallelic marker every 40 kb on average), allows the identification of at least one marker associated with the trait.

In addition, these results correlate with the physical order of the six biallelic markers contemplated within the present example (see above): marker 99-365/344, which had been found to be the closest in terms of physical distance to the ApoE Site A marker, also shows the strongest linkage disequilibrium with the Apo E site A marker.

In order to further refine the relationship between physical distance and linkage disequilibrium between biallelic markers, a ca. 450 kb fragment from a genomic region on chromosome 8 was fully sequenced.

LD within ca. 230 pairs of biallelic markers derived therefrom was measured in a random French population and analyzed as a function of the known physical inter-marker spacing. This analysis confirmed that, on average, linkage disequilibrium between 2 biallelic markers correlates with the physical distance that separates them. It further indicated that linkage disequilibrium between 2 biallelic markers tends to decrease when their spacing increases. More particularly, linkage disequilibrium between 2 biallelic markers tends to decrease when their inter-marker distance is greater than 50 kb, and is further decreased when the inter-marker distance is greater than 75 kb. It was further observed that when 2 biallelic markers were further than 150 kb apart, most often no significant linkage disequilibrium between them could be evidenced. It will be appreciated that the size and history of the sample population used to measure linkage disequilibrium between markers may influence the distance beyond which linkage disequilibrium tends not to be detectable. Assuming that linkage disequilibrium can be measured between markers spanning regions up to an average of 150 kb long, biallelic marker maps will allow genome-wide linkage disequilibrium mapping, provided they have an average inter-marker distance lower than 150 kb.

Example 6

Identification of a Candidate Region Harboring a Gene Associated with a Detectable Trait The initial identification of a candidate genomic region harboring a gene associated with a detectable trait may be conducted using a genome-wide map comprising about 20,000 biallelic markers. The candidate genomic region may be further defined using a map having a higher marker density, such as a map comprising about 40,000 markers, about 60,000 markers, about 80,000 markers, about 100,000 markers, or about 120,000 markers.

The use of high density maps such as those described above allows the identification of genes which are truly associated with detectable traits, since the coincidental associations will be randomly distributed along the genome while the true associations will map within one or more discrete genomic regions. Accordingly, biallelic markers located in the vicinity of a gene associated with a detectable trait will give rise to broad peaks in graphs plotting the frequencies of the biallelic markers in trait-positive individuals versus control individuals. In contrast, biallelic markers which are not in the vicinity of the gene associated with the detectable trait will produce unique points in such a plot. By determining the association of several markers within the region containing the gene associated with the detectable trait, the gene associated with the detectable trait can be identified using an association curve which reflects the difference between the allele frequencies within the trait-positive and control populations for each studied marker. The gene associated with the detectable trait will be found in the vicinity of the marker showing the highest association with the trait.

Figure 4:
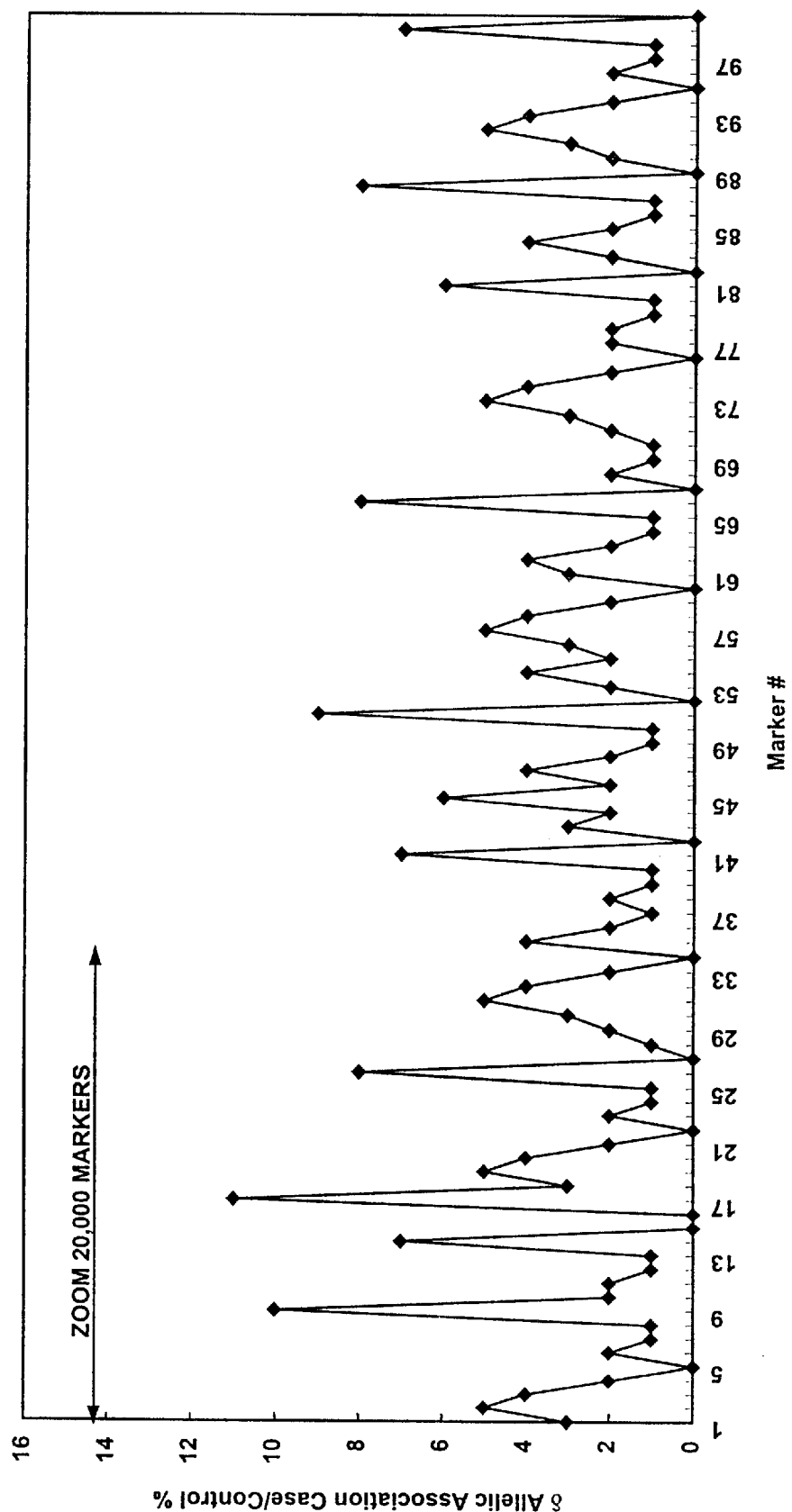
FIG. 4 is a hypothetical association analysis conducted with a map comprising about 3,000 biallelic markers.
Figure 5:
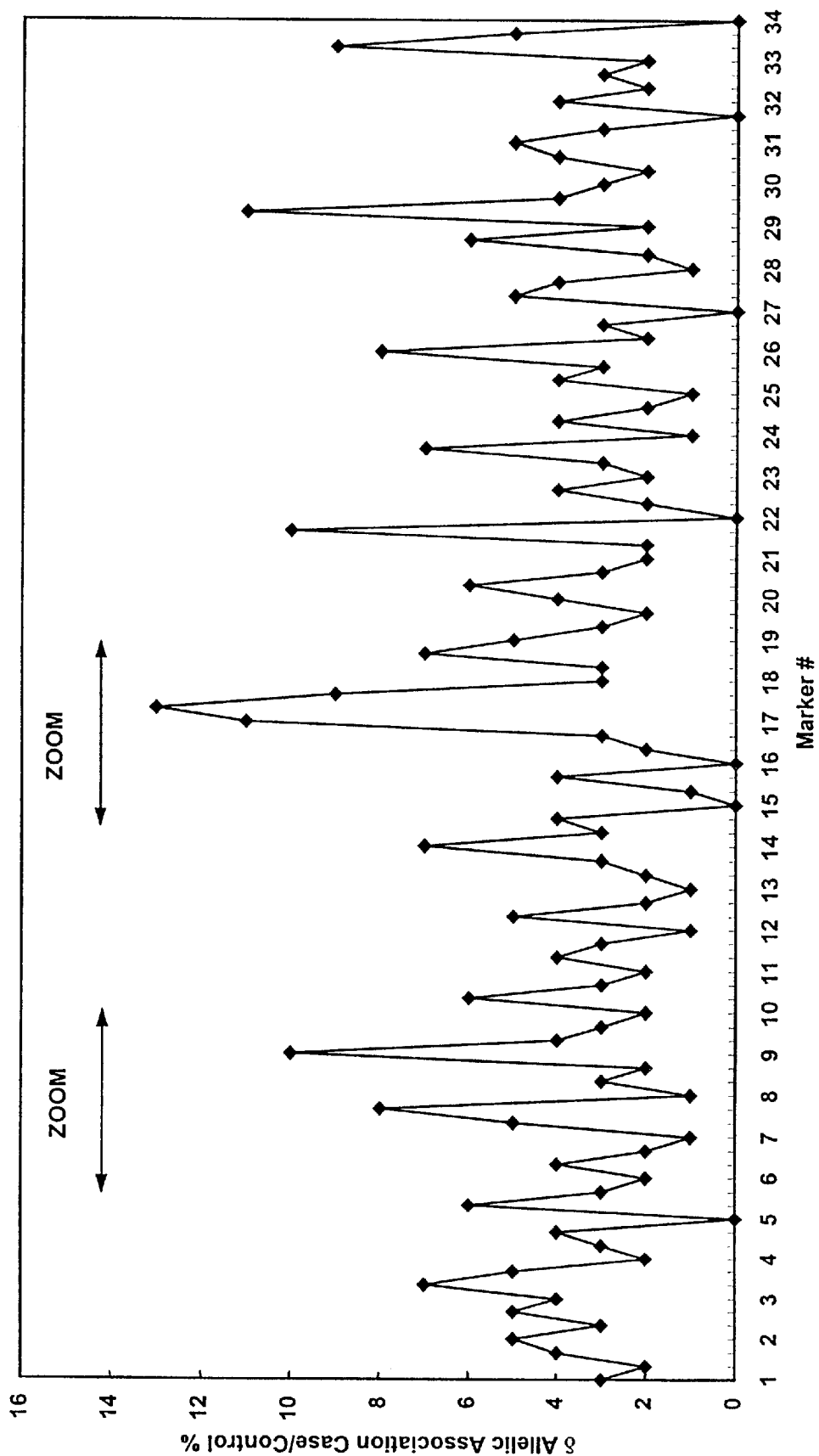
FIG. 5 is a hypothetical association analysis conducted with a map comprising about 20,000 biallelic markers.
Figure 6:
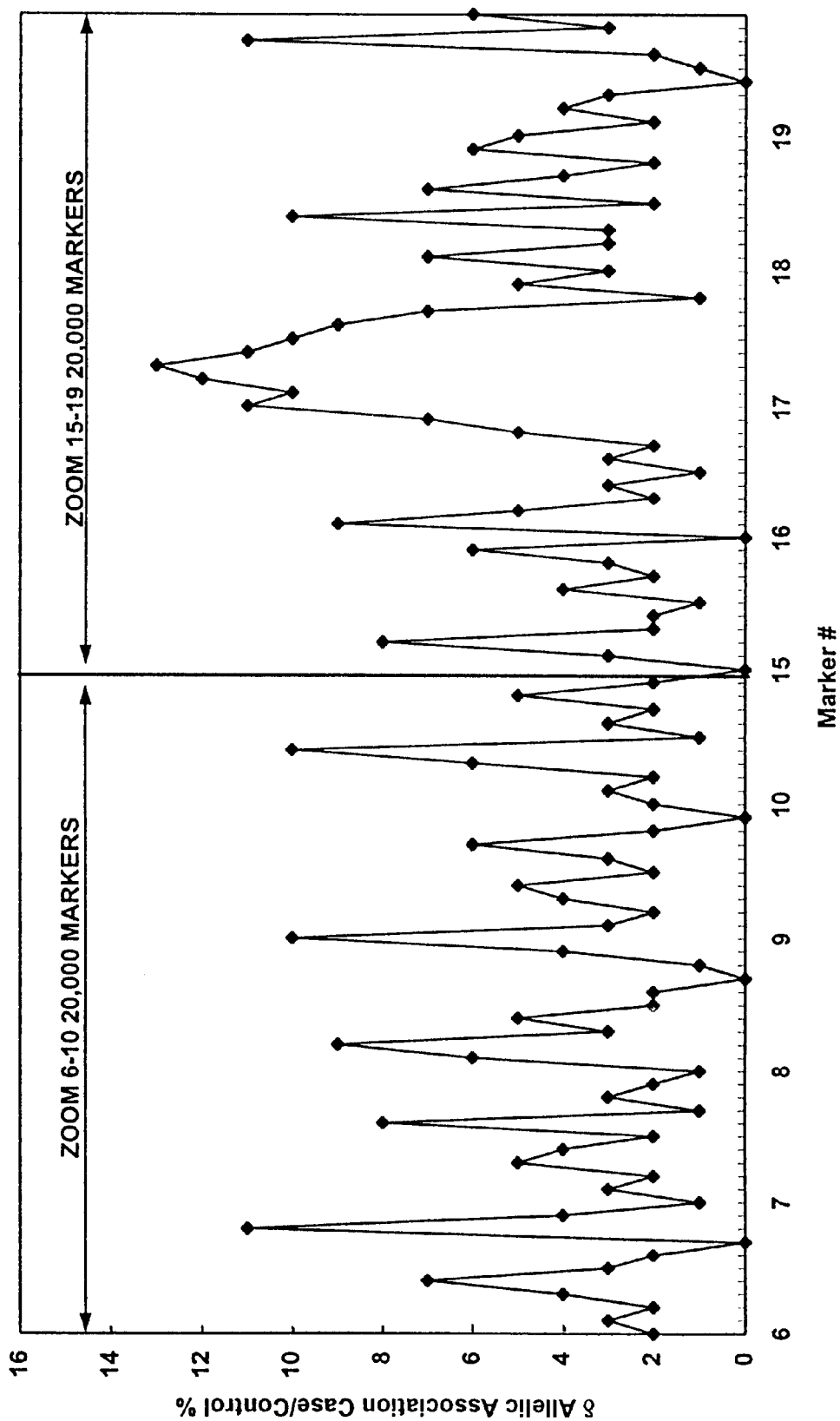
FIG. 6 is a hypothetical association analysis conducted with a map comprising about 60,000 biallelic markers.

FIGS. 4, 5, and 6 provide a simulated illustration of the above principles. As illustrated in FIG. 4, an association analysis conducted with a map comprising about 3,000 biallelic markers yields a group of points. However, when an association analysis is performed using a denser map which includes additional biallelic markers, the points become broad peaks indicative of the location of a gene associated with a detectable trait. For example, the biallelic markers used in the initial association analysis may be obtained from a map comprising about 20,000 biallelic markers, as illustrated by the simulation results shown in FIG. 5. In some embodiments, one or more of the biallelic markers of SEQ ID Nos. 1 to 3908, 1 to 2260, 2261 to 3374, 3735 to 3908 or the sequences complementary thereto are used in the association analysis.

In the simulated results of FIG. 4, the association analysis with 3,000 markers suggests peaks near markers 9 and 17.

Next, a second analysis is performed using additional markers in the vicinity of markers 9 and 17, as illustrated in the simulated results of FIG. 5, using a map of about 20,000 markers. This step again indicates an association in the close vicinity of marker 17, since more markers in this region show an association with the trait. However, none of the additional markers around marker 9 shows a significant association with the trait, which makes marker 9 a potential false positive. In some embodiments, one or more of the biallelic markers selected from the group consisting of SEQ ID Nos. 1 to 3908, 1 to 2260, 2261 to 3374, 3735 to 3908 or the sequences complementary thereto are used in the second analysis. In order to further test the validity of these two suspected associations, a third analysis may be obtained with a map comprising about 60,000 biallelic markers. In some embodiments, one or more of the biallelic markers selected from the group consisting of SEQ ID Nos: 1 to 3908, 1 to 2260, 2261 to 3374, 3735 to 3908 or the sequences complementary thereto are used in the third association analysis. In the simulated results of FIG. 6, more markers lying around marker 17 exhibit a high degree of association with the detectable trait. Conversely, no association is confirmed in the vicinity of marker 9. The genomic region surrounding marker 17 can thus be considered a candidate region for the potential trait of this simulation.

Example 7

Haplotype Analysis: Identification of Biallelic Markers Delineating a Genomic Region Associated with Alzheimer's Disease (AD)

As shown in Table 3 within Example 5, at an average map density of one marker per 40 kb only one marker (99-365-344) out of five random biallelic markers from a ca. 200 kb genomic region around the Apo E gene showed a clear association to Alzheimer's disease (delta allelic frequency in cases and controls=18%; p value=6.9 E-10). The allelic frequencies of the other four random markers were not significantly different between Alzheimer's disease cases and controls (p-values≧E-01). However, since linkage disequilibrium can usually be detected between markers located further apart than an average 40 kb as previously discussed, one should expect that, performing an association study with a local excerpt of a biallelic marker map covering ca. 200 kb with an average inter-marker distance of ca. 40 kb should allow the identification of more than one biallelic marker associated with Alzheimer's disease.

A haplotype analysis was thus performed using the biallelic markers 99-344-439; 99-355-219; 99-359-308; 99-365-344; and 99-366-274 (of SEQ ID Nos: 3909 to 3919).

In a first step, marker 99-365-344 that was already found associated with Alzheimer's disease was not included in the haplotype study. Only biallelic markers 99-344-439, 99-355-219, 99-359-308, and 99-366-274, which did not show any significant association with Alzheimer's disease when taken individually, were used. This first haplotype analysis measured frequencies of all possible two-, three-, or four-marker haplotypes in the Alzheimer's disease case and control populations. As shown in FIG. 7, there was one haplotype among all the potential different haplotypes based on the four individually non-significant markers ("haplotype 8", TAGG comprising SEQ ID No. 3910 with the T allele of marker 99-366-274, SEQ ID No. 3909 with the A allele of marker 99-344-439, SEQ ID No. 3911 with the G allele of marker 99-359-308 and SEQ ID No. 3912 which is the G allele of marker 99-355-219), that was present at statistically significant different frequencies in the Alzheimer's disease case and control populations (D=12%; p value=2.05 E-06). Moreover, a significant difference was already observed for a three-marker haplotype included in the above mentioned "haplotype 8" ("haplotype 7", TGG, D=10%; p value=4.76 E-05). Haplotype 7 comprises SEQ ID No. 3910 with the T allele of marker 99-366-274, SEQ ID No. 3911 with the G allele of marker 99-359-308 and SEQ ID No. 3912 with the G allele of marker 99-355-219). The haplotype association analysis thus clearly increased the statistical power of the individual marker association studies by more than four orders of magnitude when compared to single-marker analysis from p values≧E-01 for the individual markers to p value<2 E-06 for the four-marker "haplotype 8". See Table 3.

Figure 8:
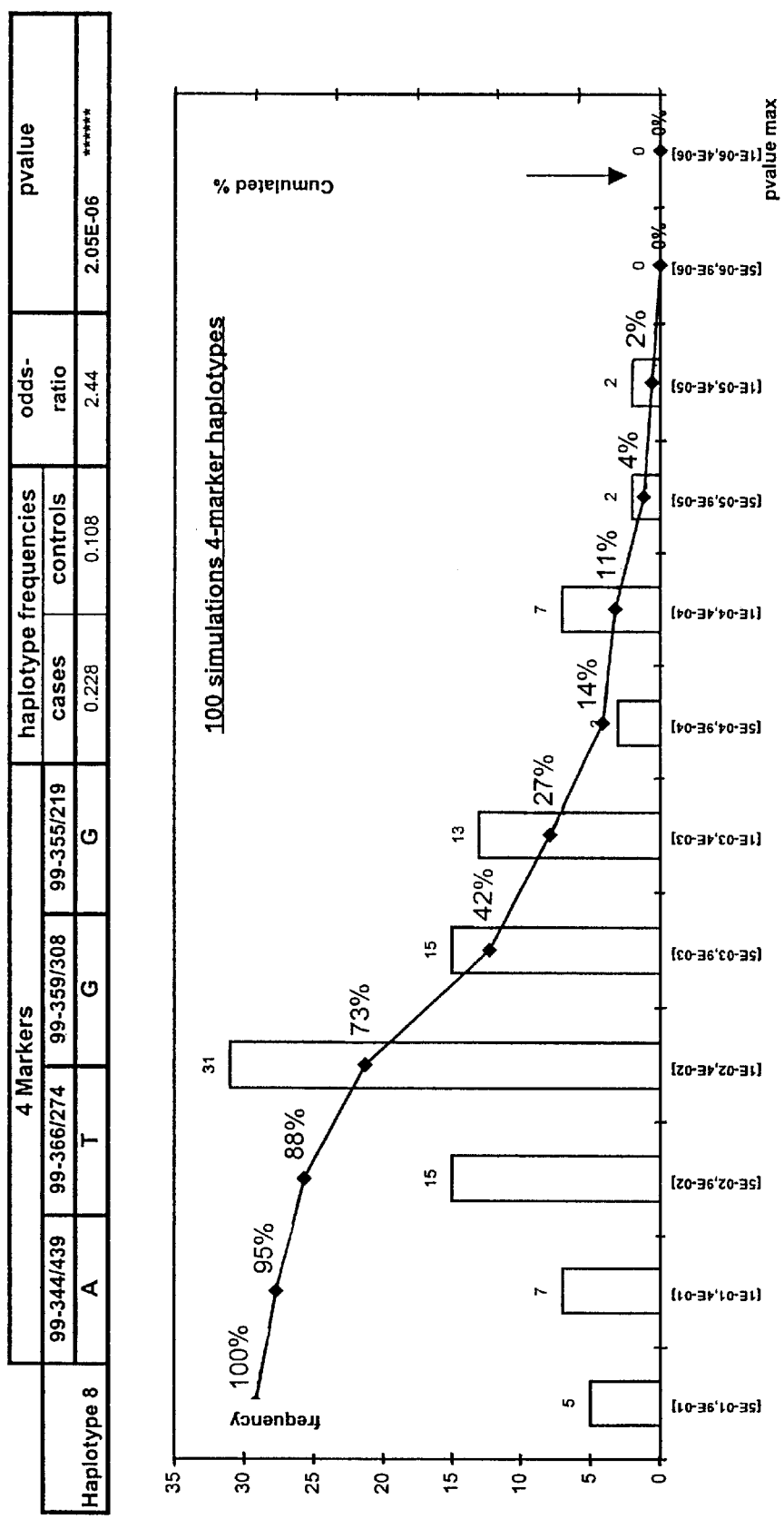
FIG. 8 is a simulated haplotype analysis using the biallelic markers in the Apo E region included in the haplotype analysis of FIG. 7.

The significance of the values obtained for this haplotype association analysis was evaluated by the following computer simulation. The genotype data from the Alzheimer's disease cases and the unaffected controls were pooled and randomly allocated to two groups which contained the same number of individuals as the case/control groups used to produce the data summarized in FIG. 7. A four-marker haplotype analysis (99-344-439; 99-355-219; 99-359-308; and 99-366-274) was run on these artificial groups. This experiment was reiterated 100 times and the results are shown in FIG. 8. No haplotype among those generated was found for which the p-value of the frequency difference between both populations was more significant than 1 E-05. In addition, only 4% of the generated haplotypes showed p-values lower than 1 E-04. Since both these p-value thresholds are less significant than the 2 E-06 p-value showed by "haplotype 8", this haplotype can be considered significantly associated with Alzheimer's disease.

In a second step, marker 99-365-344 was included in the haplotype analyzes. The frequency differences between the affected and non affected populations was calculated for all two-, three-, four- or five-marker haplotypes involving markers: 99-344-439; 99-355-219; 99-359-308; 99-366-274; and 99-365-344. The most significant p-values obtained in each category of haplotype (involving two, three, four or five markers) were examined depending on which markers were involved or not within the haplotype. This showed that all haplotypes which included marker 99-36S-344 showed a significant association with Alzheimer's disease (p-values in the range of E-04 to E-11).

An additional way of evaluating the significance of the values obtained in the haplotype association analysis was to perform a similar Alzheimer's disease case-control study on biallelic markers generated from BACs containing inserts corresponding to genomic regions derived from chromosomes 13 or 21 and not known to be involved in Alzheimer's disease. Performing similar haplotype and individual association analyzes as those described above and in Example 10 did not generate any significant association results (all p-values for haplotype analyzes were less significant than E-03; all p-values for single marker association studies were less significant than E-02).

Example 8

Genotyping of Biallelic Markers Using Microsequencing Procedures

Several microsequencing protocols conducted in liquid phase are well known to those skilled in the art. A first possible detection analysis allowing the allele characterization of the microsequencing reaction products relies on detecting fluorescent ddNTP-extended microsequencing primers after gel electrophoresis. A first alternative to this approach consists in performing a liquid phase microsequencing reaction, the analysis of which may be carried out in solid phase.

For example, the microsequencing reaction may be performed using 5'-biotinylated oligonucleotide primers and fluorescein-dideoxynucleotides. The biotinylated oligonucleotide is annealed to the target nucleic acid sequence immediately adjacent to the polymorphic nucleotide position of interest. It is then specifically extended at its 3'-end following a PCR cycle, wherein the labeled dideoxynucleotide analog complementary to the polymorphic base is incorporated. The biotinylated primer is then captured on a microtiter plate coated with streptavidin. The analysis is thus entirely carried out in a microtiter plate format. The incorporated ddNTP is detected by a fluorescein antibody—alkaline phosphatase conjugate.

In practice this microsequencing analysis is performed as follows. 20 $\mu$l of the microsequencing reaction is added to 80 $\mu$l of capture buffer (SSC 2x, 2.5% PEG 8000, 0.25 M Tris pH7.5, 1.8% BSA, 0.05% Tween 20) and incubated for 20 minutes on a microtiter plate coated with streptavidin (Boehringer). The plate is rinsed once with washing buffer (0.1 M Tris pH 7.5, 0.1 M NaCl, 0.1% Tween 20). 100 $\mu$l of anti-fluorescein antibody conjugated with phosphatase alkaline, diluted 1/5000 in washing buffer containing 1.8% BSA is added to the microtiter plate. The antibody is incubated on the microtiter plate for 20 minutes. After washing the microtiter plate four times, 100 $\mu$l of 4-methylumbelliferyl phosphate (Sigma) diluted to 0.4 mg/ml in 0.1 M diethanolamine pH 9.6, 10mM $MgCl_2$ are added. The detection of the microsequencing reaction is carried out on a fluorimeter (Dynatech) after 20 minutes of incubation.

As another alternative, solid phase microsequencing reactions have been developed, for which either the oligonucleotide microsequencing primers or the PCR-amplified products derived from the DNA fragment of interest are immobilized. For example, immobilization can be carried out via an interaction between biotinylated DNA and streptavidin-coated microtitration wells or avidin-coated polystyrene particles.

As a further alternative, the PCR reaction generating the amplicons to be genotyped can be performed directly in solid phase conditions, following procedures such as those described in WO 96/13609, the disclosure of which is incorporated herein by reference in its entirety.

In such solid phase microsequencing reactions, incorporated ddNTPs can either be radiolabeled (see Syvänen, *Clin. Chim. Acta.* 226:225–236 (1994), the disclosure of which is incorporated herein by reference in its entirety) or linked to fluorescein (see Livak and Hainer, *Hum. Metat.* 3:379–385 (1994), the disclosure of which is incorporated herein by reference in its entirety). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate).

Other possible reporter-detection couples for use in the above microsequencing procedures include:

ddNTP linked to dinitrophenyl (DNP) and anti-DNP alkaline phosphatase conjugate (see Harju et al., *Clin Chem*:39(11Pt 1):2282–2287 (1993), incorporated herein by reference in its entirety)

biotinylated ddNTP and horseradish peroxidase-conjugated streptavidin with o-phenylenediamine as a substrate (see WO 92/15712, incorporated herein by reference in its entirety).

A diagnosis kit based on fluorescein-linked ddNTP with antifluorescein antibody conjugated with alkaline phosphatase has been commercialized under the name PRONTO by GamidaGen Ltd.

As yet another alternative microsequencing procedure, Nyren et al. (*Anal. Biochem.* 208:171–175 (1993), the disclosure of which is incorporated herein by reference in its entirety) have described a solid-phase DNA sequencing procedure that relies on the detection of DNA polymerase activity by an enzymatic luminometric inorganic pyrophosphate detection assay (ELIDA). In this procedure, the PCR-amplified products are biotinylated and immobilized on beads. The microsequencing primer is annealed and four aliquots of this mixture are separately incubated with DNA polymerase and one of the four different ddNTPs. After the reaction, the resulting fragments are washed and used as substrates in a primer extension reaction with all four dNTPs present. The progress of the DNA-directed polymerization reactions is monitored with the ELIDA. Incorporation of a ddNTP in the first reaction prevents the formation of pyrophosphate during the subsequent dNTP reaction. In contrast, no ddNTP incorporation in the first reaction gives extensive pyrophosphate release during the dNTP reaction and this leads to generation of light throughout the ELIDA reactions. From the ELIDA results, the identity of the first base after the primer is easily deduced.

It will be appreciated that several parameters of the above-described microsequencing procedures may be successfully modified by those skilled in the art without undue experimentation. In particular, high throughput improvements to these procedures may be elaborated, following principles such as those described further below.

Example 9

Sequence Analysis

DNA sequences, such as BAC inserts, containing the region carrying the candidate gene associated with the detectable trait are sequenced and their sequence is analyzed using automated software which eliminates repeat sequences while retaining potential gene sequences. The potential gene sequences are compared to numerous databases to identify potential exons using a set of scoring algorithms such as trained Hidden Markov Models, statistical analysis models (including promoter prediction tools) and the GRAIL neural network. Preferred databases for use in this analysis, the construction and use of which are further detailed in Example 17, include the following:

NRPU (Non-Redundant Protein-Unique) database: NRPU is a non-redundant merge of the publicly available NBRF/PIR, Genpept, and SwissProt databases. Homologies found with NRPU allow the identification of regions potentially coding for already known proteins or related to known proteins (translated exons).

NREST (Non-Redundant EST database): NREST is a merge of the EST subsection of the publicly available GenBank database. Homologies found with NREST allow the location of potentially transcribed regions (translated or non-translated exons).

NRN (Non-Redundant Nucleic acid database): NRN is a merge of GenBank, EMBL and their daily updates.

Any sequence giving a positive hit with NRPU, NREST or an "excellent" score using GRAIL or/and other scoring algorithms is considered a potential functional region, and is then considered a candidate for genomic analysis.

While this first screening allows the detection of the "strongest" exons, a semi-automatic scan is further applied to the remaining sequences in the context of the sequence assembly. That is, the sequences neighboring a 5' site or an exon are submitted to another round of bioinformatics analysis with modified parameters. In this way, new exon candidates are generated for genomic analysis.

Using the above procedures, genes associated with detectable traits may be identified.

Example 10

YAC Contig Construction in the Candidate Genomic Region

Substantial amounts of LOH data supported the hypothesis that genes associated with distinct cancer types are located within a particular region of the human genome. More specifically, this region was likely to harbor a gene associated with prostate cancer.

Association studies were performed as described below in order to identify this prostate cancer gene. First, a YAC contig which contains the candidate genomic region was constructed as follows. The CEPH-Genethon YAC map for the entire human genome (Chumakov et al. (1995), supra) was used for detailed contig building in the genomic region containing genetic markers known to map in the candidate genomic region. Screening data available for several publicly available genetic markers were used to select a set of CEPH YACs localized within the candidate region. This set of YACs was tested by PCR with the above mentioned genetic markers as well as with other publicly available markers supposedly located within the candidate region. As a result of these studies, a YAC STS contig map was generated around genetic markers known to map in this genomic region. Two CEPH YACs were found to constitute a minimal tiling path in this region, with an estimated size of ca. 2 Megabases.

During this mapping effort, several publicly known STS markers were precisely located within the contig.

Example 11 below describes the identification of sets of biallelic markers within the candidate genomic region.

Example 11

BAC Contig Construction and Biallelic Markers Isolation Within the Candidate Chromosomal Region Next, a BAC contig covering the candidate genomic region was constructed as follows. BAC libraries were obtained as described in Woo et al., *Nucleic Acids Res.* 22:4922–4931 (1994), the disclosure of which is incorporated herein by reference in its entirety. Briefly, the two whole human genome BamHI and HindIII libraries already described in related WIPO application No. PCT/IB98/00193 were constructed using the pBeloBAC11 vector (Kim et al. (1996), supra).

The BAC libraries were then screened with all of the above mentioned STSs, following the procedure described in Example 1 above.

The ordered BACs selected by STS screening and verified by FISH, were assembled into contigs and new markers were generated by partial sequencing of insert ends from some of them. These markers were used to fill the gaps in the contig of BAC clones covering the candidate chromosomal region having an estimated size of 2 megabases.

Figure 9:
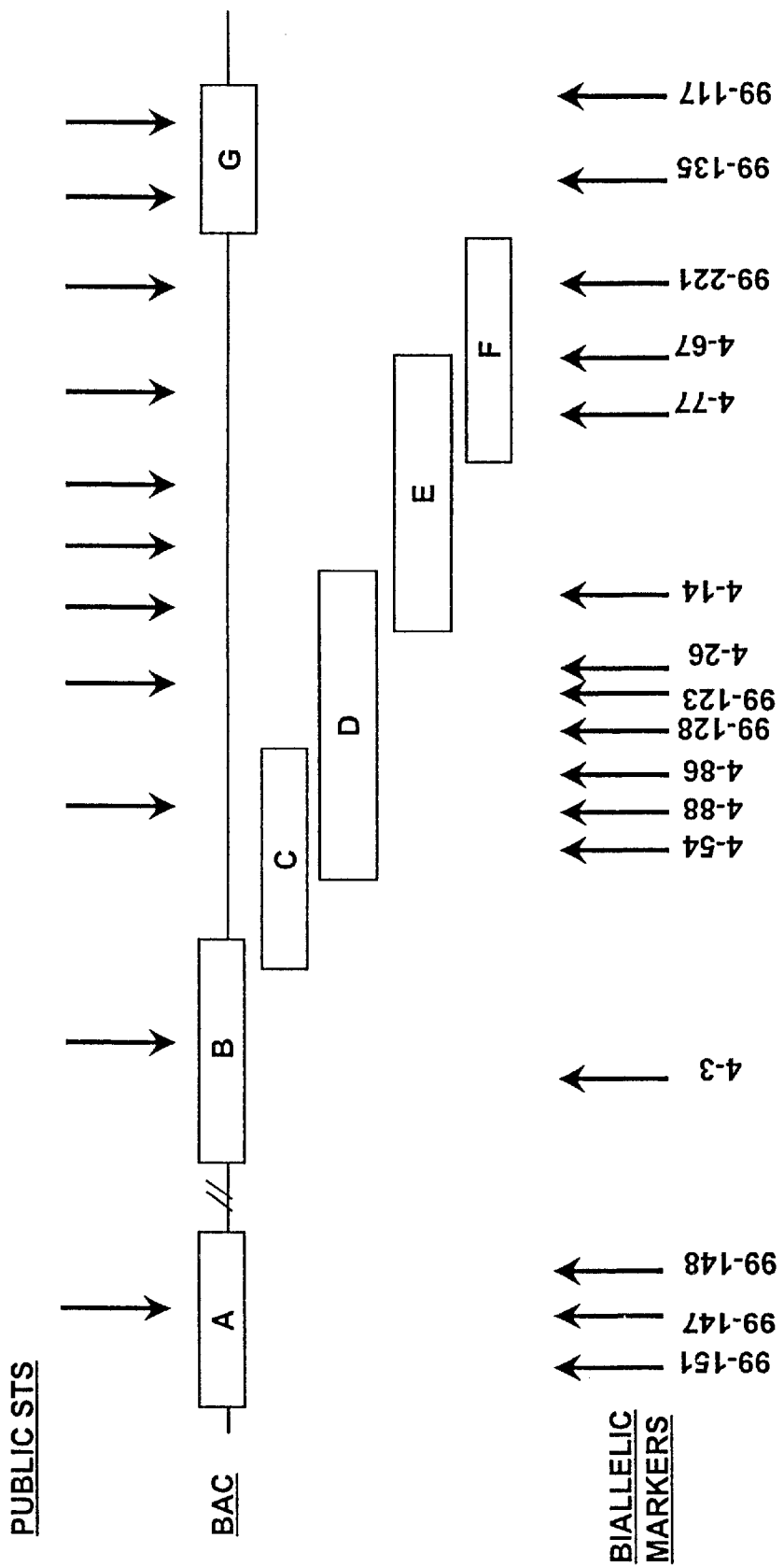
FIG. 9 shows a minimal array of overlapping clones which was chosen for further studies of biallelic markers associated with prostate cancer, the positions of STS markers known to map in the candidate genomic region along the contig, and the locations of biallelic markers along the BAC contig harboring a genomic region harboring a candidate gene associated with prostate cancer which were identified using the methods of the present invention.

FIG. 9 illustrates a minimal array of overlapping clones which was chosen for further studies, and the positions of the publicly known STS markers along said contig.

Selected BAC clones from the contig were subcloned and sequenced, essentially following the procedures described in related WIPO application No. PCT/IB98/00193.

Biallelic markers lying along the contig were identified following the processes described in related WIPO application No. PCT/IB98/00193, the disclosure of which is incorporated herein by reference in its entirety.

FIG. 9 shows the locations of the biallelic markers along the BAC contig. This first set of markers corresponds to a medium density map of the candidate locus, with an inter-marker distance averaging 50 kb–150 kb.

A second set of biallelic markers was then generated as described above in order to provide a very high-density map of the region identified using the first set of markers which can be used to conduct association studies, as explained below. This very high density map has markers spaced on average every 2–50 kb.

The biallelic markers were then used in association studies. DNA samples were obtained from individuals suffering from prostate cancer and unaffected individuals as described in Example 12.

Example 12

Collection of DNA Samples from Affected and Non-affected Individuals

Prostate cancer patients were recruited according to clinical inclusion criteria based on pathological or radical prostatectomy records. Control cases included in this study were both ethnically- and age-matched to the affected cases; they were checked for both the absence of all clinical and biological criteria defining the presence or the risk of prostate cancer, and for the absence of related familial prostate cancer cases. Both affected and control individuals were all unrelated.

The two following groups of independent individuals were used in the association studies. The first group, comprising individuals suffering from prostate cancer, contained 185 individuals. Of these 185 cases of prostate cancer, 47 cases were sporadic and 138 cases were familial. The control group contained 104 non-diseased individuals.

Haplotype analysis was conducted using additional diseased (total samples: 281) and control samples (total samples: 130), from individuals recruited according to similar criteria.

DNA was extracted from peripheral venous blood of all individuals as described in related WIPO application No. PCT/IB98/00193.

The frequencies of the biallelic markers in each population were determined as described in Example 13.

Example 13

Genotyping Affected and Control Individuals

Genotyping was performed using the following microsequencing procedure. Amplification was performed on each DNA sample using primers designed as previously explained. The pairs of primers of SEQ ID Nos.: 7849 to 7860 and 11780 to 11791 were used to generate amplicons harboring the biallelic markers of SEQ ID Nos: 3915 to 3926 or the sequences complementary thereto (markers 99-123-381, 4-26-29, 4-14-240, 4-77-151, 99-217-277, 4-67-40, 99-213-164, 99-221-377, 99-135-196, 99-1482-32, 4-73-134, and 4-65-324) using the protocols described in related WIPO application No. PCT/IB98/00193.

Microsequencing primers were designed for each of the biallelic markers, as previously described. After purification of the amplification products, the microsequencing reaction mixture was prepared by adding, in a 20 μl final volume: 10 pmol microsequencing oligonucleotide, 1 U Thermosequenase (Amersham E79000G), 1.25 μl Thermosequenase buffer (260 mM Tris HCl pH 9.5, 65 mM $MgCl_2$), and the two appropriate fluorescent ddNTPs (Perkin Elmer, Dye Terminator Set 401095) complementary to the nucleotides at the polymorphic site of each biallelic marker tested, following the manufacturer's recommendations. After 4 minutes at 94° C., 20 PCR cycles of 15 sec at 55° C., 5 sec at 72° C., and 10 sec at 94° C. were carried out in a Tetrad PTC-225 thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized as homozygous or heterozygous based on the height ratio.

Association analyzes were then performed using the biallelic markers as described below.

Example 14

Association Analysis

Figure 10:
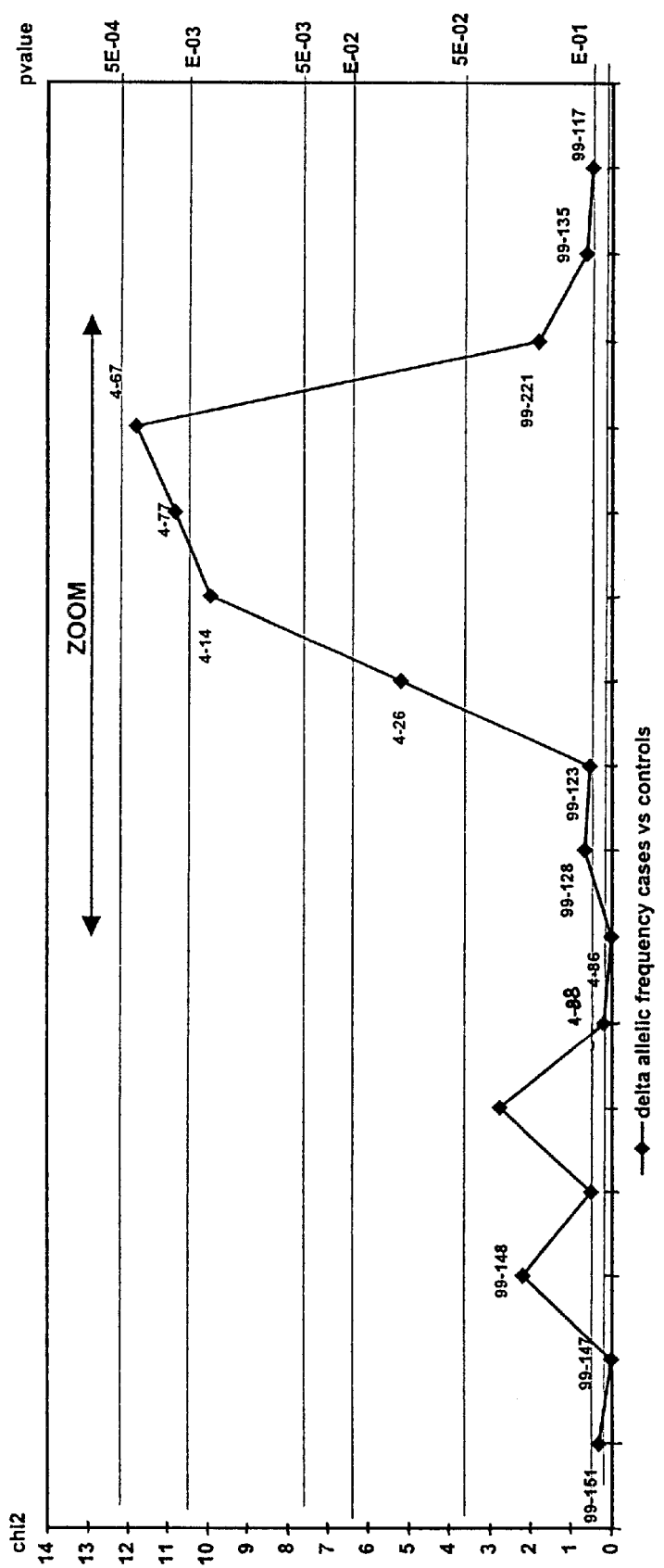
FIG. 10 is a rough localization of a candidate gene for prostate cancer which was obtained by determining the frequencies of the biallelic markers of FIG. 9 in affected and unaffected populations.

Association studies were run in two successive steps. In a first step, a rough localization of the candidate gene was achieved by determining the frequencies of the biallelic markers of FIG. 9 in the affected and unaffected populations. The results of this rough localization are shown in FIG. 10. This analysis indicated that a gene responsible for prostate cancer was located near the biallelic marker designated 4-67.

In a second phase of the analysis, the position of the gene responsible for prostate cancer was further refined using the very high density set of markers including the markers of SEQ ID Nos: 3915 to 3926 or the sequences complementary thereto (markers 99-123-381, 4-26-29, 4-14-240, 4-77-151, 99-217-277, 4-67-40, 99-213-164, 99-221-377, 99-135-196, 99-1482-32, 4-73-134, and 4-65-324).

Figure 11:
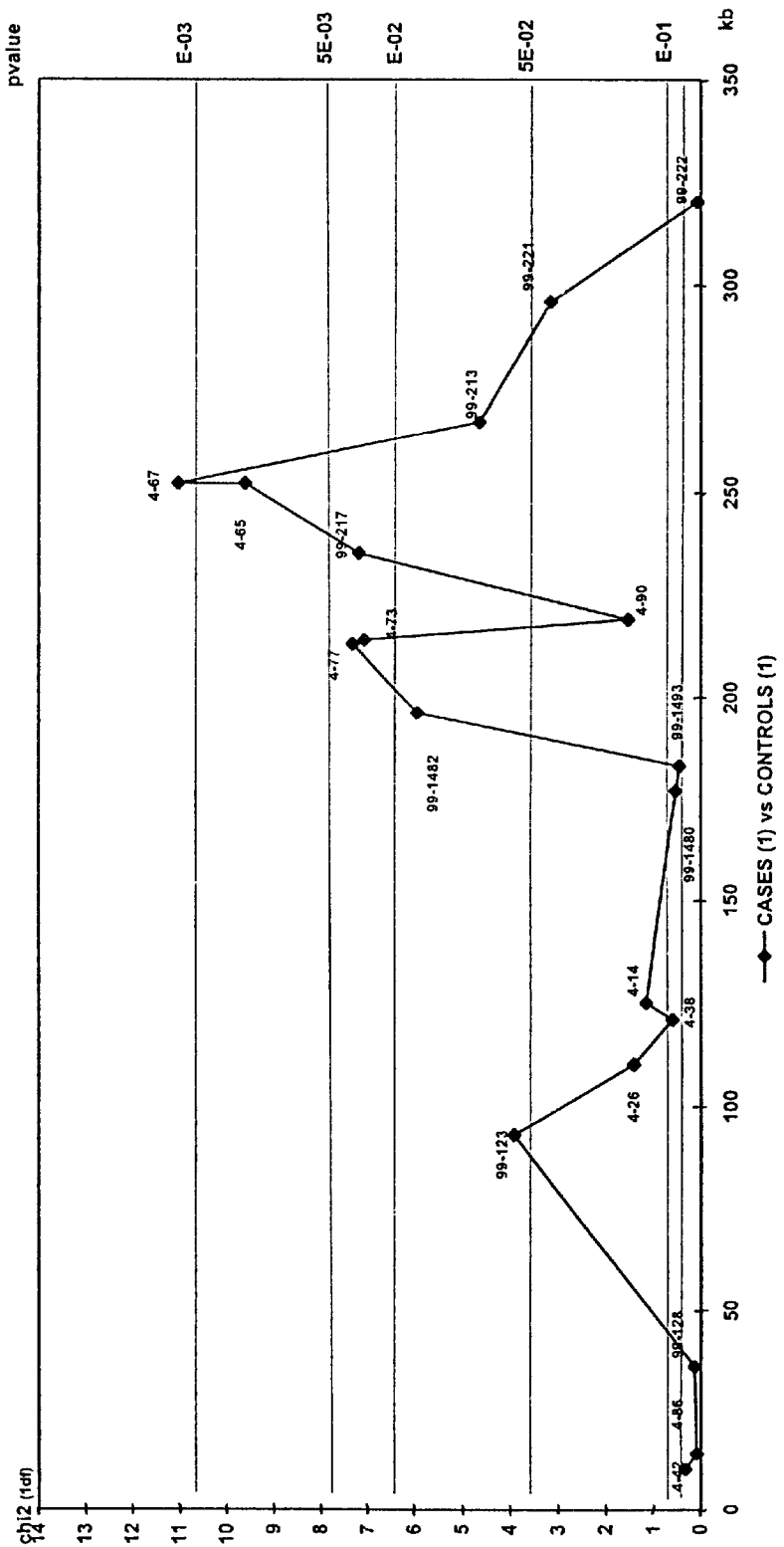
FIG. 11 is a further refinement of the localization of the candidate gene for prostate cancer using additional biallelic markers which were not included in the rough localization illustrated in FIG. 10.

As shown in FIG. 11, the second phase of the analysis confirmed that the gene responsible for prostate cancer was near the biallelic marker designated 4-67-40, most probably within a ca. 150 kb region comprising the marker.

A haplotype analysis was also performed as described in Example 15.

Example 15

Haplotype Analysis

The allelic frequencies of each of the alleles of biallelic markers 99-123-381, 4-26-29, 4-14-240, 4-77-151, 99-217-277, 4-67-40, 99-213-164, 99-221-377, and 99-135-196 were determined in the affected and unaffected populations. Table 4 lists the internal identification numbers of the markers used in the haplotype analysis (SEQ ID Nos: 3915–3923), the alleles of each marker, the most frequent allele in both unaffected individuals and individuals suffering from prostate cancer, the least frequent allele in both unaffected individuals and individuals suffering from prostate cancer, and the frequencies of the least frequent alleles in each population.

TABLE 4

| Markers | Polymorphic base * | Frequency of least frequent allele ** | |
|---|---|---|---|
| | | Cases | Controls |
| 99-123-381 | C/T | 0.35 | 0.3 |
| 4-26-29 | A/G | 0.39 | 0.45 |
| 4-14-240 | C/T | 0.35 | 0.41 |
| 4-77-151 | C/G | 0.33 | 0.24 |
| 99-217-277 | C/T | 0.31 | 0.23 |
| 4-67-40 | C/T | 0.26 | 0.16 |
| 99-213-164 | T/C | 0.45 | 0.38 |
| 99-221-377 | C/A | 0.43 | 0.43 |
| 99-135-196 | A/G | 0.25 | 0.3 |

\* most frequent allele/least frequent allele
\*\* standard deviations
0.023 to 0.031 for controls;
0.018 to 0.021 for cases Among all the theoretical potential different haplotypes based on 2 to 9 markers, 11 haplotypes showing a strong association with prostate cancer were selected. The results of these haplotype analyzes are shown in FIG. 12.

FIGS. 11 and 12 aggregate association analysis results with sequencing results—generated following the procedures further described in Example 16, which permitted the physical order and the distance between markers to be estimated.

The significance of the values obtained in FIG. 12 are underscored by the following results of computer simulations. For the computer simulations, the data from the affected individuals and the unaffected controls were pooled and randomly allocated to two groups which contained the same number of individuals as the affected and unaffected groups used to compile the data summarized in FIG. 12. A haplotype analysis was run on these artificial groups for the six markers included in haplotype 5 of FIG. 12. This experiment was reiterated 100 times and the results are shown in FIG. 13. Among 100 iterations, only 5% of the obtained haplotypes are present with a p-value less significant than E-04 as compared to the p-value of 9E-07 for haplotype 5 of FIG. 12. Furthermore, for haplotype 5 of FIG. 12, only 6% of the obtained haplotypes have a significance level below $5^{E-}03$, while none of them show a significance level below 5E-03.

Thus, using the data of FIG. 13 and evaluating the associations for single marker alleles or for haplotypes will permit estimation of the risk a corresponding carrier has to develop prostate cancer. It will be appreciated that significance thresholds of relative risks will be more finely assessed according to the population tested.

Diagnostic techniques for determining an individual's risk of developing prostate cancer may be implemented as described below for the markers in the maps of the present invention, including the markers of SEQ ID Nos: 3915 to 3923 (markers 99-123-381, 4-26-29, 4-14-240, 4-77-151, 99-217-277, 4-67-40, 99-213-164, 99-221-377, and 99-135-196).

The above haplotype analysis indicated that 171 kb of genomic DNA between biallelic markers 4-14-240 and 99-221-377 totally or partially contains a gene responsible for prostate cancer. Therefore, the protein coding sequences lying within this region were characterized to locate the gene associated with prostate cancer. This analysis, described in further detail below, revealed a single protein coding sequence in the 171 kb genomic region, which was designated as the PG1 gene.

Example 16

Identification of the Genomic Sequence in the Candidate Region

Template DNA for sequencing the PG1 gene was obtained as follows. BACs E and F from FIG. 9 were subcloned as previously described. Plasmid inserts were first amplified by PCR on PE 9600 thermocyclers (Perkin-Elmer), using appropriate primers, AmpliTaqGold (Perkin-Elmer), dNTms (Boehringer), buffer and cycling conditions as recommended by the Perkin-Elmer Corporation.

PCR products were then sequenced using automatic ABI Prism 377 sequencers (Perkin Elmer, Applied Biosystems Division, Foster City, Calif.). Sequencing reactions were performed using PE 9600 thermocyclers (Perkin Elmer) with standard dye-primer chemistry and ThermoSequenase (Amersham Life Science). The primers were labeled with the JOE, FAM, ROX and TAMRA dyes. The dNTPs and ddNTPs used in the sequencing reactions were purchased from Boehringer. Sequencing buffer, reagent concentrations and cycling conditions were as recommended by Amersham.

Following the sequencing reaction, the samples were precipitated with EtOH, resuspended in formamide loading buffer, and loaded on a standard 4% acrylamide gel. Electrophoresis was performed for 2.5 hours at 3000V on an ABI 377 sequencer, and the sequence data were collected and analyzed using the ABI Prism DNA Sequencing Analysis Software, version 2.1.2.

The sequence data obtained as described above were transferred to a proprietary database, where quality control and validation steps were performed. A proprietary base-caller flagged suspect peaks, taking into account the shape of the peaks, the inter-peak resolution, and the noise level. The proprietary base-caller also performed an automatic trimming. Any stretch of 25 or fewer bases having more than 4 suspect peaks was considered unreliable and was discarded.

The sequence fragments from BAC subclones isolated as described above were assembled using Gap4 software from R. Staden (Bonfield et al. 1995). This software allows the reconstruction of a single sequence from sequence fragments. The sequence deduced from the alignment of different fragments is called the consensus sequence. Directed sequencing techniques (primer walking) were used to complete sequences and link contigs.

Potential functional sequences were then identified as described in Example 17.

Example 17

Identification of Functional Sequences

Potential exons in BAC-derived human genomic sequences were located by homology searches on protein, nucleic acid and EST (Expressed Sequence Tags) public databases. Main public databases were locally reconstructed as mentioned in Example 9. The protein database, NRPU (Non-redundant Protein Unique) is formed by a non-redundant fusion of the Genpept (Benson et al., *Nucleic Acids Res*. 24:1–5 (1996), the disclosure of which is incorporated herein by reference in its entirety), Swissprot (Bairoch, A. and Apweiler, R., *Nucleic Acids Res*. 24:21–25 (1996), the disclosure of which is incorporated herein by reference in its entirety) and PIR/NBRF (George et al., *Nucleic Acids Res*. 24:17–20 (1996), the disclosure of which is incorporated herein by reference in its entirety) databases. Redundant data were eliminated by using the NRDB software (Benson et al. (1996), supra) and internal repeats were masked with the XNU software (Benson et al., supra). Homologies found using the NRPU database allowed the identification of sequences corresponding to potential coding exons related to known proteins.

The EST local database is composed by the gbest section (1-9) of GenBank (Benson et al. (1996), supra), and thus contains all publicly available transcript fragments. Homologies found with this database allowed the localization of potentially transcribed regions.

The local nucleic acid database contained all sections of GenBank and EMBL (Rodriguez-Tome et al., *Nucleic Acids Res*. 24:6–12 (1996), the disclosure of which is incorporated herein by reference in its entirety) except the EST sections. Redundant data were eliminated as previously described.

Similarity searches in protein or nucleic acid databases were performed using the BLAST software (Altschul et al., *J. Mol. Biol*. 215:403–410 (1990), the disclosure of which is incorporated herein by reference in its entirety). Alignments were refined using the Fasta software, and multiple alignments used Clustal W. Homology thresholds were adjusted for each analysis based on the length and the complexity of the tested region, as well as on the size of the reference database.

Potential exon sequences identified as above were used as probes to screen cDNA libraries. Extremities of positive clones were sequenced and the sequence stretches were positioned on the genomic sequence determined above. Primers were then designed using the results from these alignments in order to enable the cloning of cDNAs derived from the gene associated with prostate cancer that was identified using the above procedures.

The obtained cDNA molecules were then sequenced and results of Northern blot analysis of prostate mRNAs supported the existence of a major cDNA having a 5–6 kb length. The structure of the gene associated with prostate cancer was evaluated as described in Example 18.

Example 18

Analysis of Gene Structure

The intron/exon structure of the gene was finally completely deduced by aligning the mRNA sequence from the cDNA obtained as described above and the genomic DNA sequence obtained as described above. This alignment permitted the determination of the positions of the introns and exons, the positions of the start and end nucleotides defining each of the at least 8 exons, the locations and phases of the 5' and 3' splice sites, the position of the stop codon, and the position of the polyadenylation site to be determined in the genomic sequence. This analysis also yielded the positions of the coding region in the mRNA, and the locations of the polyadenylation signal and polyA stretch in the mRNA.

The gene identified as described above comprises at least 8 exons and spans more than 52 kb. A G/C rich putative promoter region was identified upstream of the coding sequence. A CCAAT in the putative promoter was also identified. The promoter region was identified as described in Prestridge, D. S., Predicting Pol II Promoter Sequences Using Transcription Factor Binding Sites, *J. Mol. Biol*. 249:923–932 (1995), the disclosure of which is incorporated herein by reference in its entirety.

Additional analysis using conventional techniques, such as a 5'RACE reaction using the Marathon-Ready human prostate cDNA kit from Clontech (Catalog. No. PT1156-1), may be performed to confirm that the 5' of the cDNA obtained above is the authentic 5' end in the mRNA.

Alternatively, the 5' sequence of the transcript can be determined by conducting a PCR amplification with a series of primers extending from the 5' end of the identified coding region.

Example 19

Detection of Biallelic Markers in the Candidate Gene: DNA Extraction

Donors were unrelated and healthy. They presented a sufficient diversity for being representative of a French heterogeneous population. The DNA from 100 individuals was extracted and tested for the detection of the biallelic markers.

30 ml of peripheral venous blood were taken from each donor in the presence of EDTA. Cells (pellet) were collected after centrifugation for 10 minutes at 2000 rpm. Red cells were lysed by a lysis solution (50 ml final volume: 10 mM Tris pH7.6; 5 mM $MgCl_{2;\ 10}$ mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:

3 ml TE 10-2 (Tris-HCl 10 mM, EDTA 2 mM)/NaCl 0.4 M

200 µl SDS 10%

500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm. For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 µg/ml DNA).

To determine the presence of proteins in the DNA solution, the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

Example 20

Detection of the Biallelic Markers: Amplification of Genomic DNA by PCR

The amplification of specific genomic sequences of the DNA samples of Example 19 was carried out on the pool of DNA obtained previously using the amplification primers of SEQ ID Nos: 7861 to 7865 and 11792 to 11796. In addition, 50 individual samples were similarly amplified.

PCR assays were performed using the following protocol:

| | |
|---|---|
| Final volume | 25 µl |
| DNA | 2 ng/µl |
| MgCl2 | 2 mM |
| dNTP (each) | 200 µM |
| primer (each) | 2.9 ng/µl |
| Ampli Taq Gold DNA polymerase | 0.05 unit/µl |
| PCR buffer (10x = 0.1 M TrisHCl pH 8.3 0.5 M KCl | 1x |

Pairs of first primers were designed to amplify the promoter region, exons, and 3' end of the candidate asthma-associated gene using the sequence information of the candidate gene and the OSP software (Hillier & Green, 1991). These first primers were about 20 nucleotides in length and contained a common oligonucleotide tail upstream of the specific bases targeted for amplification which was useful for sequencing. The synthesis of these primers was performed following the phosphoramidite method, on a GENSET UFPS 24.1 synthesizer.

DNA amplification was performed on a Genius II thermocycler. After heating at 94° C. for 10 min, 40 cycles were performed. Each cycle comprised: 30 sec at 94° C., 55° C. for 1 min, and 30 sec at 72° C. For final elongation, 7 min at 72° C. ended the amplification. The quantities of the amplification products obtained were determined on 96-well microtiter plates, using a fluorometer and Picogreen as intercalant agent (Molecular Probes).

Example 21

Detection of the Biallelic Markers Sequencing of Amplified Genomic DNA and Identification of Polymorphisms The sequencing of the amplified DNA obtained in Example 20 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were analyzed as formerly described.

The sequence data were further evaluated using the above mentioned polymorphism analysis software designed to detect the presence of biallelic markers among the pooled amplified fragments. The polymorphism search was based on the presence of superimposed peaks in the electrophoresis pattern resulting from different bases occurring at the same position as described previously.

Six fragments of amplification were analyzed. In these segments, 8 biallelic markers were detected (SEQ ID Nos: 3927 to 3934). The localization of the biallelic markers, the polymorphic bases of each allele, and the frequencies of the most frequent alleles was as shown in Table 5.

TABLE 5

| Amplicon | Marker Name | Origin of DNA | Localization gene | Polymorphism | Frequency |
|---|---|---|---|---|---|
| 1 | 10-204-326 | Ind. | Promoter | A/G | 96.2 (G) |
| 2 | 10-32-357 | Pool | Intron 1 | A/C | 67.7 (C) |
| 3 | 10-33-175 | Ind. | Exon 2 | C/T | 97.3 (C) |
| 3 | 10-33-234 | Pool | Intron 2 | A/C | 56.7 (C) |
| 3 | 10-33-327 | Ind. | Intron 2 | C/T | 75.3 (T) |
| 5 | 10-35-358 | Pool | Intron 4 | C/G | 67.9 (G) |
| 5 | 10-35-390 | Ind. | Intron 4 | C/T | 82 (C) |
| 6 | 10-36-164 | Ind. | Exon 5 | A/G | 99.5 (G) |

Allelic frequencies were determined in a population of random blood donors from French Caucasian origin. Their wide range is due to the fact that, besides screening a pool of 100 individuals to generate biallelic markers as described above, polymorphism searches were also conducted in an individual testing format for 50 samples. This strategy was chosen here to provide a potential shortcut towards the identification of putative causal mutations in the association studies using them. As the 10-36-164 biallelic marker (SEQ ID No: 3933) was found in only one individual, this marker was not considered in the association studies.

The fourth fragment of amplification carrying exon 3 (not shown in the Table) was not polymorphic in the tested samples (1 pool+50 individuals).

Example 22

Validation of the Polymorphisms Through Microsequencing

The biallelic markers identified in Example 21 were further confirmed and their respective frequencies were determined through microsequencing. Microsequencing was carried out for each individual DNA sample described in Example 19.

Amplification from genomic DNA of individuals was performed by PCR as described above for the detection of the biallelic markers with the same set of PCR primers described above.

The preferred primers used in microsequencing had about 19 nucleotides in length and hybridized just upstream of the considered polymorphic base. Five primers hybridized with the non-coding strand of the gene. For the biallelic markers 10-204-326, 10-35-358 and 10-36-164, primers hybridized with the coding strand of the gene.

The microsequencing reaction was performed as described in Example 13.

Example 23

Association Study Between Asthma and the Biallelic Markers of the Candidate Gene Collection of DNA Samples from Affected and Non-Affected Individuals The asthmatic population used to perform association studies in order to establish whether the candidate gene was an asthma-causing gene consisted of 298 individuals. More than 90% of these 298 asthmatic individuals had a Caucasian ethnic background.

The control population consisted of 373 unaffected individuals, among which 279 French (at least 70% were of Caucasian origin) and 94 American (at least 90% were of Caucasian origin).

DNA samples were obtained from asthmatic and non-asthmatic individuals as described above.

Example 24

Association Study Between Asthma and the Biallelic Markers of the Candidate Gene Genotyping of Affected and Control Individuals The general strategy to perform the association studies was to individually scan the DNA samples from all individuals in each of the populations described above in order to establish the allele frequencies of the above described biallelic markers in each of these populations.

Allelic frequencies of the above-described biallelic markers in each population were determined by performing microsequencing reactions on amplified fragments obtained by genomic PCR performed on the DNA samples from each individual. Genomic PCR and microsequencing were performed as detailed above in Examples 20 and 22 using the described amplification and microsequencing primers.

Example 25

Association study Between Asthma and the Biallelic Markers of the Candidate Gene Table 6 shows the results of the association study between five biallelic markers in the candidate gene and asthma.

TABLE 6

| | Allelic frequencies (%) | | | |
|---|---|---|---|---|
| Markers | Asthmatics 298 individuals | Controls 373 individuals | Frequency diff. | P value |
| 10-32-357 | A 38.6 | A 29.8 | 8.8 | $7.34 \times 10^{-4}$ |
| 10-33-234 | A 49 | A 44.3 | 4.7 | $8.86 \times 10^{-2}$ |
| 10-33-327 | T 78.5 | T 74.6 | 3.9 | $1.0 \times 10^{-1}$ |
| 10-35-358 | G 72.3 | G 66.9 | 5.4 | $3.59 \times 10^{-2}$ |
| 10-35-390 | T 30.4 | T 20.3 | 10.1 | $2.33 \times 10^{-5}$ |

As shown in Table 6, markers 10-32-357 and 10-35-390 presented a strong association with asthma, this association being highly significant (p value=$7.34 \times 10^{-4}$ for marker 10-32-357 and $2.33 \times 10^{-5}$ for marker 10-35-390).

Three markers showed moderate association when tested independently, namely 10-33-234, 10-33-327,10–35-358.

It is worth mentioning that allelic frequencies for each of the biallelic markers of Table 7 were separately measured within the French control population (279 individuals) and the American control population (94 individuals). The differences in allele frequencies between the two populations were between 1% and 7%, with p-values above 10-1. These data confirmed that the combined French/American control population (373 individuals) was homogeneous enough to be used as a control population for the present association study.

Example 26

Association Studies: Haplotype Frequency Analysis

As already shown, one way of increasing the statistical power of individual markers, is by performing haplotype association analysis. A haplotype analysis for association of markers in the candidate gene and asthma was performed by estimating the frequencies of all possible haplotypes for biallelic markers 10-32-357, 10-33-234, 10-33-327, 10-35-358 and 10-35-390 in the asthmatic and control populations described in Example 25 (Table 6), and comparing these frequencies by means of a chi square statistical test (one degree of freedom). Haplotype estimations were performed by applying the Expectation-Maximization (EM) algorithm (Excoffier L & Slatkin M, 1995, *Mol.Biol.Evol.* 12:921–927, the disclosure of which is incorporated herein by reference in its entirety), using the EM-HAPLO program (Hawley Ma., Pakstis A J & Kidd K K, 1994, Am.J.Phys.Anthropol. 18:104, the disclosure of which is incorporated herein by reference in its entirety).

The results of such haplotype analysis are shown in Table 7.

TABLE 7

| | Haplotype frequencies | | | | | | | | |
|---|---|---|---|---|---|---|---|---|---|
| Markers | 10-32-357 | 10-33-234 | 10-33-327 | 10-35-358 | 10-35-390 | Asthm. | Controls | Odds ratio | P value |
| Frequency diff. | 8.8 | 4.7 | 3.9 | 5.4 | 10.1 | | | | |
| P value | $7.34 \times 10^{-4}$ | $8.86 \times 10^{-2}$ | $1.0 \times 10^{-1}$ | $3.59 \times 10^{-2}$ | $2.33 \times 10^{-5}$ | | | | |
| Haplotype 1 5 | A | T | | | | 0.2 | 0.11 | 2.02 | $8.47 \times 10^{-6}$ |
| Haplotype 2 | A | T | G | | | 0.27 | 0.18 | 1.68 | $2.81 \times 10^{-4}$ |
| Haplotype 3 | A | A | T | G | T | 0.18 | 0.09 | 2.22 | $3.95 \times 10^{-5}$ |

A two-marker haplotype covering markers 10-32-357 and 10-35-390 (haplotype 1, AT alleles respectively) presented a p value of $8.47 \times 10-6$, an odds ratio of 2.02 and haplotype frequencies of 0.2 for asthmatic and 0.11 for control populations respectively.

A three-marker haplotype covering markers 10-33-234, 10-33-327 and 10-35-358 (haplotype 2, ATG alleles respectively) presented a p value of $2.81 \times 10-4$, an odds ratio of 1.68 and haplotype frequencies of 0.27 for asthmatic and 0.18 for control populations respectively.

A five-marker haplotype covering markers 10-32-357, 10-33-234, 10-33-327, 10-35-358 and 10-35-390 (haplotype 3, AATGT alleles respectively) presented a p value of $3.95 \times 10-5$, an odds ratio of 2.22 and haplotype frequencies of 0.18 for asthmatic and 0.09 for control populations respectively.

Haplotype association analysis thus increased the statistical power of the individual marker association studies when compared to single-marker analysis (from p values between $10^{-1}$ and $2 \times 10^{-5}$ for the individual markers to p values between $3 \times 10^{-4}$ and $8 \times 10^{-6}$ for the three-marker haplotype, haplotype 2).

The significance of the values obtained for the haplotype association analysis was evaluated by the following computer simulation test. The genotype data from the asthmatic and control individuals were pooled and randomly allocated to two groups which contained the same number of individuals as the trait-positive and trait-negative groups used to produce the data summarized in Table 7. A haplotype analysis was then run on these artificial groups for the three haplotypes presented in Table 6. This experiment was reiterated 1000 times and the results are shown in Table 8.

TABLE 8

| Haplotype | Chi-Square Average | Chi-Square | Permutation Test Maximal Chi-Square | P value |
|---|---|---|---|---|
| Haplotype 1 (A---T) | 19.70 | 1.2 | 11.6 | $1.0 \times 10^{-3}$ |
| Haplotype 2 (-ATG-) | 13.49 | 1.2 | 10.5 | $1.0 \times 10^{-3}$ |
| Haplotype 3 (AATGT) | 16.66 | 1.2 | 9.3 | $1.0 \times 10^{-3}$ |

The results in Table 8 show that among 1000 iterations only 1‰ of the obtained haplotypes has a p value comparable to the one obtained in Table 4.

These results clearly validate the statistical significance of the haplotypes obtained (haplotypes 1, 2 and 3, Table 7).

Example 27

Extraction of DNA 30 ml of blood are taken from the individuals in the presence of EDTA. Cells (pellet) are collected after centrifugation for 10 minutes at 2000 rpm. Red cells are lysed by a lysis solution (50 ml final volume: 10 mM Tris pH7.6; 5 mM MgCl$_2$; 10 mM NaCl). The solution is centrifuged (10 minutes, 2000 rpm) as many times as necessary to eliminate the residual red cells present in the supernatant, after resuspension of the pellet in the lysis solution.

The pellet of white cells is lysed overnight at 42° C. with 3.7 ml of lysis solution composed of:

3 ml TE 10-2 (Tris-HCl 10 mM, EDTA 2 mM)/NaCl 0.4 M

200 µl SDS 10%

500 µl K-proteinase (2 mg K-proteinase in TE 10-2/NaCl 0.4 M).

For the extraction of proteins, 1 ml saturated NaCl (6M) (1/3.5 v/v) is added. After vigorous agitation, the solution is centrifuged for 20 minutes at 10000 rpm. For the precipitation of DNA, 2 to 3 volumes of 100% ethanol are added to the previous supernatant, and the solution is centrifuged for 30 minutes at 2000 rpm. The DNA solution is rinsed three times with 70% ethanol to eliminate salts, and centrifuged for 20 minutes at 2000 rpm. The pellet is dried at 37° C., and resuspended in 1 ml TE 10-1 or 1 ml water. The DNA concentration is evaluated by measuring the OD at 260 nm (1 unit OD=50 µg/ml DNA).

To evaluate the presence of proteins in the DNA solution, the OD 260/OD 280 ratio is determined. Only DNA preparations having a OD 260/OD 280 ratio between 1.8 and 2 are used in the subsequent steps described below.

Once genomic DNA from every individual in the given population has been extracted, it is preferred that a fraction of each DNA sample is separated, after which a pool of DNA is constituted by assembling equivalent DNA amounts of the separated fractions into a single one.

Although this invention has been described in terms of certain preferred embodiments, other embodiments which will be apparent to those of ordinary skill in the art of view of the disclosure herein are also within the scope of this invention. Accordingly, the scope of the invention is intended to be defined only by reference to the appended claims.

TABLE 1

| SEQ ID No. | Marker Name | Allele 1$^{ST}$ | Allele 2$^{ND}$ | Preferred microseq. primer | Amplification primer Upstream (PU) | Amplification primer Downstream (RP) |
|---|---|---|---|---|---|---|
| 1 | 99-109-224 | G | C | S | 3935 | 7866 |
| 2 | 99-1126-384 | A | G | S | 3936 | 7867 |
| 3 | 99-114-68 | G | C | S | 3937 | 7868 |
| 4 | 99-1151-516 | A | C | S | 3938 | 7869 |
| 5 | 99-1165-159 | C | T | S | 3939 | 7870 |
| 6 | 99-1167-201 | A | G | A | 3940 | 7871 |
| 7 | 99-117-205 | C | T | S | 3941 | 7872 |
| 8 | 99-118-92 | C | T | S | 3942 | 7873 |
| 9 | 99-1217-332 | C | T | A | 3943 | 7874 |
| 10 | 99-1233-183 | A | G | S | 3944 | 7875 |
| 11 | 99-12478-263 | G | T | A | 3945 | 7876 |
| 12 | 99-12487-301 | A | C | S | 3946 | 7877 |
| 13 | 99-12497-155 | C | T | S | 3947 | 7878 |
| 14 | 99-12503-44 | G | C | S | 3948 | 7879 |
| 15 | 99-12504-402 | A | T | S | 3949 | 7880 |
| 16 | 99-12505-374 | A | G | A | 3950 | 7881 |
| 17 | 99-12506-199 | G | T | A | 3951 | 7882 |
| 18 | 99-12509-423 | C | T | S | 3952 | 7883 |
| 19 | 99-12513-146 | G | C | S | 3953 | 7884 |
| 20 | 99-12514-170 | G | C | S | 3954 | 7885 |
| 21 | 99-12515-205 | G | C | S | 3955 | 7886 |
| 22 | 99-12516-524 | A | G | A | 3956 | 7887 |
| 23 | 99-12518-325 | C | T | S | 3957 | 7888 |
| 24 | 99-12523-255 | C | T | S | 3958 | 7889 |
| 25 | 99-12525-277 | C | T | S | 3959 | 7890 |
| 26 | 99-12526-317 | C | T | S | 3960 | 7891 |
| 27 | 99-12527-292 | A | G | A | 3961 | 7892 |
| 28 | 99-12531-30 | C | T | S | 3962 | 7893 |
| 29 | 99-12532-199 | A | T | S | 3963 | 7894 |
| 30 | 99-12534-207 | A | C | S | 3964 | 7895 |
| 31 | 99-12535-362 | A | C | S | 3965 | 7896 |
| 32 | 99-12537-340 | G | C | S | 3966 | 7897 |
| 33 | 99-12538-142 | A | C | S | 3967 | 7898 |
| 34 | 99-12539-287 | C | T | S | 3968 | 7899 |
| 35 | 99-12540-426 | C | T | S | 3969 | 7900 |

TABLE 1-continued

| SEQ ID No. | Marker Name | Preferred Allele 1ST | 2ND | microseq. primer | Amplification primer Upstream (PU) | Downstream (RP) |
|---|---|---|---|---|---|---|
| 36 | 99-12541-307 | C | T | S | 3970 | 7901 |
| 37 | 99-12545-121 | A | G | A | 3971 | 7902 |
| 38 | 99-12548-88 | A | G | A | 3972 | 7903 |
| 39 | 99-12558-167 | C | T | S | 3973 | 7904 |
| 40 | 99-12562-291 | C | T | S | 3974 | 7905 |
| 41 | 99-12564-354 | A | T | S | 3975 | 7906 |
| 42 | 99-12565-273 | C | T | S | 3976 | 7907 |
| 43 | 99-12575-248 | G | C | S | 3977 | 7908 |
| 44 | 99-12576-325 | C | T | S | 3978 | 7909 |
| 45 | 99-12580-268 | A | G | A | 3979 | 7910 |
| 46 | 99-12585-85 | A | C | S | 3980 | 7911 |
| 47 | 99-12593-103 | A | C | S | 3981 | 7912 |
| 48 | 99-12600-283 | G | C | S | 3982 | 7913 |
| 49 | 99-12608-71 | C | T | S | 3983 | 7914 |
| 50 | 99-12610-106 | C | T | S | 3984 | 7915 |
| 51 | 99-12611-311 | G | T | A | 3985 | 7916 |
| 52 | 99-12613-366 | A | G | A | 3986 | 7917 |
| 53 | 99-12615-235 | A | C | S | 3987 | 7918 |
| 54 | 99-12617-412 | G | C | S | 3988 | 7919 |
| 55 | 99-12618-211 | C | T | S | 3989 | 7920 |
| 56 | 99-12619-367 | A | G | A | 3990 | 7921 |
| 57 | 99-12621-114 | A | G | A | 3991 | 7922 |
| 58 | 99-12624-61 | A | T | S | 3992 | 7923 |
| 59 | 99-1263-276 | A | G | S | 3993 | 7924 |
| 60 | 99-12632-165 | C | T | S | 3994 | 7925 |
| 61 | 99-12637-62 | C | T | S | 3995 | 7926 |
| 62 | 99-12639-311 | G | C | S | 3996 | 7927 |
| 63 | 99-12640-179 | C | T | A | 3997 | 7928 |
| 64 | 99-12650-200 | C | T | A | 3998 | 7929 |
| 65 | 99-12651-297 | G | C | S | 3999 | 7930 |
| 66 | 99-12652-459 | A | G | S | 4000 | 7931 |
| 67 | 99-12654-278 | G | T | A | 4001 | 7932 |
| 68 | 99-12656-303 | C | T | A | 4002 | 7933 |
| 69 | 99-12658-206 | A | G | A | 4003 | 7934 |
| 70 | 99-12661-92 | G | T | A | 4004 | 7935 |
| 71 | 99-12668-329 | C | T | A | 4005 | 7936 |
| 72 | 99-1268-177 | A | G | A | 4006 | 7937 |
| 73 | 99-12733-366 | G | C | S | 4007 | 7938 |
| 74 | 99-12738-57 | G | C | S | 4008 | 7939 |
| 75 | 99-12740-354 | C | T | A | 4009 | 7940 |
| 76 | 99-12749-286 | A | G | S | 4010 | 7941 |
| 77 | 99-12750-369 | A | T | S | 4011 | 7942 |
| 78 | 99-12751-406 | C | T | A | 4012 | 7943 |
| 79 | 99-12755-421 | A | G | S | 4013 | 7944 |
| 80 | 99-12756-344 | A | C | S | 4014 | 7945 |
| 81 | 99-12757-240 | A | G | S | 4015 | 7946 |
| 82 | 99-12759-420 | G | T | A | 4016 | 7947 |
| 83 | 99-12777-71 | A | G | S | 4017 | 7948 |
| 84 | 99-12782-76 | A | C | S | 4018 | 7949 |
| 85 | 99-12794-299 | G | C | S | 4019 | 7950 |
| 86 | 99-128-60 | C | T | S | 4020 | 7951 |
| 87 | 99-12816-101 | G | C | S | 4021 | 7952 |
| 88 | 99-12817-358 | C | T | A | 4022 | 7953 |
| 89 | 99-12819-165 | A | G | S | 4023 | 7954 |
| 90 | 99-12826-408 | A | T | S | 4024 | 7955 |
| 91 | 99-12831-345 | A | C | S | 4025 | 7956 |
| 92 | 99-12836-387 | C | T | A | 4026 | 7957 |
| 93 | 99-12842-305 | C | T | A | 4027 | 7958 |
| 94 | 99-12843-337 | A | G | S | 4028 | 7959 |
| 95 | 99-12844-130 | A | G | S | 4029 | 7960 |
| 96 | 99-12847-37 | A | G | S | 4030 | 7961 |
| 97 | 99-12848-204 | A | G | S | 4031 | 7962 |
| 98 | 99-12852-260 | A | G | S | 4032 | 7963 |
| 99 | 99-12856-183 | A | C | S | 4033 | 7964 |
| 100 | 99-12878-291 | C | T | S | 4034 | 7965 |
| 101 | 99-12880-282 | C | T | S | 4035 | 7966 |
| 102 | 99-12884-248 | A | G | A | 4036 | 7967 |
| 103 | 99-12885-261 | A | C | S | 4037 | 7968 |
| 104 | 99-12898-364 | C | T | S | 4038 | 7969 |
| 105 | 99-12899-307 | C | T | S | 4039 | 7970 |
| 106 | 99-1290-291 | C | T | S | 4040 | 7971 |
| 107 | 99-12900-165 | G | C | S | 4041 | 7972 |
| 108 | 99-12901-316 | A | G | A | 4042 | 7973 |
| 109 | 99-12903-381 | C | T | S | 4043 | 7974 |
| 110 | 99-12907-295 | A | G | A | 4044 | 7975 |
| 111 | 99-12908-369 | G | C | S | 4045 | 7976 |
| 112 | 99-12913-197 | C | T | S | 4046 | 7977 |
| 113 | 99-12914-227 | G | T | A | 4047 | 7978 |
| 114 | 99-12924-273 | G | C | S | 4048 | 7979 |
| 115 | 99-12925487 | C | T | S | 4049 | 7980 |
| 116 | 99-12926-332 | C | T | A | 4050 | 7981 |
| 117 | 99-12931-173 | A | G | S | 4051 | 7982 |
| 118 | 99-12948-61 | A | T | S | 4052 | 7983 |
| 119 | 99-12952-199 | G | C | S | 4053 | 7984 |
| 120 | 99-12956-43 | C | T | A | 4054 | 7985 |
| 121 | 99-12957-448 | C | T | A | 4055 | 7986 |
| 122 | 99-12961-318 | A | G | S | 4056 | 7987 |
| 123 | 99-12962-181 | A | G | S | 4057 | 7988 |
| 124 | 99-12963-255 | C | T | A | 4058 | 7989 |
| 125 | 99-12964-230 | C | T | A | 4059 | 7990 |
| 126 | 99-13021-124 | C | T | S | 4060 | 7991 |
| 127 | 99-13036-313 | A | C | S | 4061 | 7992 |
| 128 | 99-13045-385 | A | C | S | 4062 | 7993 |
| 129 | 99-13051-235 | A | G | S | 4063 | 7994 |
| 130 | 99-13061-100 | C | T | S | 4064 | 7995 |
| 131 | 99-13064-328 | C | T | S | 4065 | 7996 |
| 132 | 99-13065-311 | C | T | S | 4066 | 7997 |
| 133 | 99-13070-207 | G | T | A | 4067 | 7998 |
| 134 | 99-13098-369 | A | G | S | 4068 | 7999 |
| 135 | 99-13106-251 | A | G | S | 4069 | 8000 |
| 136 | 99-13115-106 | C | T | A | 4070 | 8001 |
| 137 | 99-13121-198 | A | G | S | 4071 | 8002 |
| 138 | 99-13130-75 | A | G | S | 4072 | 8003 |
| 139 | 99-13133-341 | A | G | S | 4073 | 8004 |
| 140 | 99-13134-79 | A | G | S | 4074 | 8005 |
| 141 | 99-13165-216 | A | G | S | 4075 | 8006 |
| 142 | 99-13178-252 | C | T | A | 4076 | 8007 |
| 143 | 99-13192-272 | A | G | S | 4077 | 8008 |
| 144 | 99-13193-453 | C | T | A | 4078 | 8009 |
| 145 | 99-13201-154 | C | T | A | 4079 | 8010 |
| 146 | 99-13213-79 | A | G | S | 4080 | 8011 |
| 147 | 99-13215-109 | C | T | A | 4081 | 8012 |
| 148 | 99-13218-103 | G | C | S | 4082 | 8013 |
| 149 | 99-13219-378 | A | G | S | 4083 | 8014 |
| 150 | 99-13222-274 | C | T | A | 4084 | 8015 |
| 151 | 99-13224-351 | C | T | S | 4085 | 8016 |
| 152 | 99-13227-270 | A | C | S | 4086 | 8017 |
| 153 | 99-13229-192 | G | T | A | 4087 | 8018 |
| 154 | 99-13232-494 | G | C | S | 4088 | 8019 |
| 155 | 99-13237-44 | G | T | S | 4089 | 8020 |
| 156 | 99-13238-276 | A | G | S | 4090 | 8021 |
| 157 | 99-13241-49 | C | T | A | 4091 | 8022 |
| 158 | 99-13246-251 | A | G | S | 4092 | 8023 |
| 159 | 99-13250-439 | C | T | A | 4093 | 8024 |
| 160 | 99-13251-118 | G | T | A | 4094 | 8025 |
| 161 | 99-13258-232 | G | T | A | 4095 | 8026 |
| 162 | 99-13260-358 | G | C | S | 4096 | 8027 |
| 163 | 99-13262-376 | G | C | S | 4097 | 8028 |
| 164 | 99-13269-144 | A | G | S | 4098 | 8029 |
| 165 | 99-13270-309 | G | T | A | 4099 | 8030 |
| 166 | 99-13271-163 | A | G | S | 4100 | 8031 |
| 167 | 99-13272-151 | A | G | S | 4101 | 8032 |
| 168 | 99-13273-144 | A | C | S | 4102 | 8033 |
| 169 | 99-13276-168 | C | T | A | 4103 | 8034 |
| 170 | 99-13279-301 | A | G | S | 4104 | 8035 |
| 171 | 99-13286-58 | A | G | S | 4105 | 8036 |
| 172 | 99-13287-298 | C | T | A | 4106 | 8037 |
| 173 | 99-13294-281 | A | G | S | 4107 | 8038 |
| 174 | 99-13296-330 | C | T | A | 4108 | 8039 |
| 175 | 99-13320-352 | A | G | S | 4109 | 8040 |
| 176 | 99-13332-259 | C | T | A | 4110 | 8041 |
| 177 | 99-13334-136 | A | C | S | 4111 | 8042 |
| 178 | 99-13336-364 | A | G | S | 4112 | 8043 |
| 179 | 99-13339-335 | G | C | S | 4113 | 8044 |
| 180 | 99-13354-225 | A | G | S | 4114 | 8045 |
| 181 | 99-13368-221 | C | T | A | 4115 | 8046 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 182 | 99-13394-42 | A | G | S | 4116 | 8047 |
| 183 | 99-13395-110 | C | T | A | 4117 | 8048 |
| 184 | 99-13396-258 | G | C | S | 4118 | 8049 |
| 185 | 99-134-362 | G | T | A | 4119 | 8050 |
| 186 | 99-13401-106 | A | C | A | 4120 | 8051 |
| 187 | 99-13404-373 | A | G | S | 4121 | 8052 |
| 188 | 99-13406-279 | G | T | A | 4122 | 8053 |
| 189 | 99-1342-51 | C | T | A | 4123 | 8054 |
| 190 | 99-13429-188 | A | C | S | 4124 | 8055 |
| 191 | 99-13439-327 | A | G | S | 4125 | 8056 |
| 192 | 99-13443-275 | C | T | A | 4126 | 8057 |
| 193 | 99-13450-276 | A | G | S | 4127 | 8058 |
| 194 | 99-13457-138 | G | C | S | 4128 | 8059 |
| 195 | 99-1346-503 | C | T | S | 4129 | 8060 |
| 196 | 99-13462-263 | A | G | S | 4130 | 8061 |
| 197 | 99-13486-358 | A | G | S | 4131 | 8062 |
| 198 | 99-13489-396 | C | T | A | 4132 | 8063 |
| 199 | 99-13499-445 | A | G | S | 4133 | 8064 |
| 200 | 99-13502-118 | C | T | S | 4134 | 8065 |
| 201 | 99-13509-388 | A | G | A | 4135 | 8066 |
| 202 | 99-1351-264 | A | T | S | 4136 | 8067 |
| 203 | 99-13515-428 | C | T | S | 4137 | 8068 |
| 204 | 99-13525-395 | C | T | S | 4138 | 8069 |
| 205 | 99-13526-368 | C | T | S | 4139 | 8070 |
| 206 | 99-13531-449 | A | T | S | 4140 | 8071 |
| 207 | 99-13536-134 | C | T | S | 4141 | 8072 |
| 208 | 99-13540-338 | G | C | S | 4142 | 8073 |
| 209 | 99-13541-85 | A | G | A | 4143 | 8074 |
| 210 | 99-13545-215 | C | T | S | 4144 | 8075 |
| 211 | 99-13552-172 | A | C | S | 4145 | 8076 |
| 212 | 99-13553-390 | A | C | S | 4146 | 8077 |
| 213 | 99-13555-402 | A | G | A | 4147 | 8078 |
| 214 | 99-1356-500 | A | T | S | 4148 | 8079 |
| 215 | 99-13567-258 | C | T | S | 4149 | 8080 |
| 216 | 99-13586-230 | G | T | A | 4150 | 8081 |
| 217 | 99-13588-238 | A | C | S | 4151 | 8082 |
| 218 | 99-13589-362 | A | G | A | 4152 | 8083 |
| 219 | 99-1359-355 | C | T | S | 4153 | 8084 |
| 220 | 99-13591-360 | G | C | S | 4154 | 8085 |
| 221 | 99-13592-304 | A | C | S | 4155 | 8086 |
| 222 | 99-13596-69 | A | C | S | 4156 | 8087 |
| 223 | 99-13598-260 | G | C | S | 4157 | 8088 |
| 224 | 99-13600-305 | A | G | S | 4158 | 8089 |
| 225 | 99-13601-360 | A | G | S | 4159 | 8090 |
| 226 | 99-13605-208 | C | T | A | 4160 | 8091 |
| 227 | 99-13606-83 | G | C | S | 4161 | 8092 |
| 228 | 99-1362-126 | A | G | A | 4162 | 8093 |
| 229 | 99-13624-415 | C | T | A | 4163 | 8094 |
| 230 | 99-13638-354 | A | G | S | 4164 | 8095 |
| 231 | 99-13644-439 | G | C | S | 4165 | 8096 |
| 232 | 99-13647-278 | C | T | A | 4166 | 8097 |
| 233 | 99-13652-407 | G | C | S | 4167 | 8098 |
| 234 | 99-13663-218 | C | T | A | 4168 | 8099 |
| 235 | 99-13666-275 | A | T | S | 4169 | 8100 |
| 236 | 99-1367-287 | A | G | A | 4170 | 8101 |
| 237 | 99-13671-396 | C | T | A | 4171 | 8102 |
| 238 | 99-13678-251 | C | T | A | 4172 | 8103 |
| 239 | 99-13679-285 | C | T | A | 4173 | 8104 |
| 240 | 99-1368-299 | C | T | S | 4174 | 8105 |
| 241 | 99-13684-488 | A | C | S | 4175 | 8106 |
| 242 | 99-13687-316 | A | G | S | 4176 | 8107 |
| 243 | 99-1373-358 | A | T | S | 4177 | 8108 |
| 244 | 99-1376-196 | A | T | S | 4178 | 8109 |
| 245 | 99-13790-129 | C | T | A | 4179 | 8110 |
| 246 | 99-13798-284 | A | G | S | 4180 | 8111 |
| 247 | 99-13831-102 | A | G | S | 4181 | 8112 |
| 248 | 99-13832-226 | C | T | A | 4182 | 8113 |
| 249 | 99-13835-39 | G | C | S | 4183 | 8114 |
| 250 | 99-1385-91 | G | C | A | 4184 | 8115 |
| 251 | 99-13853-256 | C | T | A | 4185 | 8116 |
| 252 | 99-13854-363 | C | T | A | 4186 | 8117 |
| 253 | 99-13860-368 | C | T | A | 4187 | 8118 |
| 254 | 99-13861-227 | A | G | S | 4188 | 8119 |
| 255 | 99-13866-198 | C | T | A | 4189 | 8120 |
| 256 | 99-13868-240 | C | T | A | 4190 | 8121 |
| 257 | 99-1387-462 | C | T | A | 4191 | 8122 |
| 258 | 99-13876-55 | A | G | S | 4192 | 8123 |
| 259 | 99-13878-385 | A | C | S | 4193 | 8124 |
| 260 | 99-1388-242 | A | G | A | 4194 | 8125 |
| 261 | 99-13880-185 | A | G | S | 4195 | 8126 |
| 262 | 99-13883-103 | A | G | S | 4196 | 8127 |
| 263 | 99-13887-190 | C | T | A | 4197 | 8128 |
| 264 | 99-13888-332 | C | T | A | 4198 | 8129 |
| 265 | 99-13892-338 | A | G | S | 4199 | 8130 |
| 266 | 99-13897-431 | G | T | A | 4200 | 8131 |
| 267 | 99-1391-204 | C | T | S | 4201 | 8132 |
| 268 | 99-13912-89 | C | T | A | 4202 | 8133 |
| 269 | 99-13913-278 | A | G | S | 4203 | 8134 |
| 270 | 99-13914-169 | A | G | S | 4204 | 8135 |
| 271 | 99-1392-200 | C | T | S | 4205 | 8136 |
| 272 | 99-13920-172 | A | G | S | 4206 | 8137 |
| 273 | 99-13925-97 | A | G | S | 4207 | 8138 |
| 274 | 99-13929-201 | A | C | S | 4208 | 8139 |
| 275 | 99-13932-229 | C | T | A | 4209 | 8140 |
| 276 | 99-1394-271 | A | G | A | 4210 | 8141 |
| 277 | 99-13956-119 | G | C | S | 4211 | 8142 |
| 278 | 99-13960-142 | C | T | A | 4212 | 8143 |
| 279 | 99-13962-339 | A | G | S | 4213 | 8144 |
| 280 | 99-13980-150 | C | T | A | 4214 | 8145 |
| 281 | 99-13996-123 | A | G | S | 4215 | 8146 |
| 282 | 99-13997-181 | C | T | A | 4216 | 8147 |
| 283 | 99-13998-421 | C | T | A | 4217 | 8148 |
| 284 | 99-140-130 | C | T | S | 4218 | 8149 |
| 285 | 99-14004-328 | G | C | S | 4219 | 8150 |
| 286 | 99-14005-344 | C | T | A | 4220 | 8151 |
| 287 | 99-14009-133 | C | T | A | 4221 | 8152 |
| 288 | 99-14010-165 | C | T | A | 4222 | 8153 |
| 289 | 99-14013-125 | C | T | A | 4223 | 8154 |
| 290 | 99-14025-459 | A | G | S | 4224 | 8155 |
| 291 | 99-1404-135 | A | G | S | 4225 | 8156 |
| 292 | 99-14046-270 | A | G | S | 4226 | 8157 |
| 293 | 99-14050-295 | G | T | A | 4227 | 8158 |
| 294 | 99-14068-214 | C | T | A | 4228 | 8159 |
| 295 | 99-14072-363 | C | T | A | 4229 | 8160 |
| 296 | 99-14080-436 | G | T | A | 4230 | 8161 |
| 297 | 99-14083-346 | A | G | S | 4231 | 8162 |
| 298 | 99-14087-429 | G | T | A | 4232 | 8163 |
| 299 | 99-14090-398 | A | T | S | 4233 | 8164 |
| 300 | 99-14094-274 | A | T | S | 4234 | 8165 |
| 301 | 99-14119-101 | C | T | S | 4235 | 8166 |
| 302 | 99-14120-283 | A | G | A | 4236 | 8167 |
| 303 | 99-14127-127 | A | G | A | 4237 | 8168 |
| 304 | 99-1413-137 | G | C | S | 4238 | 8169 |
| 305 | 99-14135-375 | C | T | S | 4239 | 8170 |
| 306 | 99-14139-321 | A | T | S | 4240 | 8171 |
| 307 | 99-14140-310 | A | G | A | 4241 | 8172 |
| 308 | 99-14145-220 | G | C | S | 4242 | 8173 |
| 309 | 99-14147-369 | A | G | A | 4243 | 8174 |
| 310 | 99-14149-351 | G | C | S | 4244 | 8175 |
| 311 | 99-1416-589 | A | G | A | 4245 | 8176 |
| 312 | 99-14161-267 | A | G | A | 4246 | 8177 |
| 313 | 99-14162-180 | C | T | S | 4247 | 8178 |
| 314 | 99-14166-217 | G | C | S | 4248 | 8179 |
| 315 | 99-14175-380 | A | G | S | 4249 | 8180 |
| 316 | 99-14179-191 | A | G | S | 4250 | 8181 |
| 317 | 99-14186-424 | A | G | S | 4251 | 8182 |
| 318 | 99-14197-144 | A | G | S | 4252 | 8183 |
| 319 | 99-14203-268 | A | C | S | 4253 | 8184 |
| 320 | 99-14204-468 | G | T | A | 4254 | 8185 |
| 321 | 99-14220-351 | A | G | S | 4255 | 8186 |
| 322 | 99-1423-361 | A | C | S | 4256 | 8187 |
| 323 | 99-14250-381 | A | G | S | 4257 | 8188 |
| 324 | 99-14254-305 | G | T | A | 4258 | 8189 |
| 325 | 99-14256-133 | C | T | A | 4259 | 8190 |
| 326 | 99-1426-185 | C | T | S | 4260 | 8191 |
| 327 | 99-14260-261 | C | T | A | 4261 | 8192 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 328 | 99-14277-73 | A | G | S | 4262 | 8193 |
| 329 | 99-14282-334 | A | C | S | 4263 | 8194 |
| 330 | 99-14285-381 | C | T | A | 4264 | 8195 |
| 331 | 99-14286-220 | G | T | A | 4265 | 8196 |
| 332 | 99-14309-259 | C | T | S | 4266 | 8197 |
| 333 | 99-14315-405 | A | C | S | 4267 | 8198 |
| 334 | 99-14329-205 | G | C | S | 4268 | 8199 |
| 335 | 99-14331-64 | A | G | S | 4269 | 8200 |
| 336 | 99-14332-437 | C | T | A | 4270 | 8201 |
| 337 | 99-14343-408 | A | G | S | 4271 | 8202 |
| 338 | 99-14345-139 | C | T | A | 4272 | 8203 |
| 339 | 99-14356-141 | A | G | S | 4273 | 8204 |
| 340 | 99-1437-325 | C | T | S | 4274 | 8205 |
| 341 | 99-14385-117 | A | T | S | 4275 | 8206 |
| 342 | 99-14392-431 | A | C | S | 4276 | 8207 |
| 343 | 99-14393-190 | C | T | A | 4277 | 8208 |
| 344 | 99-144-392 | C | T | S | 4278 | 8209 |
| 345 | 99-14405-105 | A | G | S | 4279 | 8210 |
| 346 | 99-1442-224 | G | T | A | 4280 | 8211 |
| 347 | 99-14444-193 | G | C | S | 4281 | 8212 |
| 348 | 99-14446-337 | A | G | S | 4282 | 8213 |
| 349 | 99-14452-263 | C | T | S | 4283 | 8214 |
| 350 | 99-14459-44 | G | C | S | 4284 | 8215 |
| 351 | 99-14468-247 | C | T | A | 4285 | 8216 |
| 352 | 99-14470-243 | A | G | S | 4286 | 8217 |
| 353 | 99-14492-322 | C | T | A | 4287 | 8218 |
| 354 | 99-14497-220 | A | G | S | 4288 | 8219 |
| 355 | 99-14505-250 | C | T | A | 4289 | 8220 |
| 356 | 99-14518-57 | C | T | A | 4290 | 8221 |
| 357 | 99-1453-204 | C | T | S | 4291 | 8222 |
| 358 | 99-14553-224 | C | T | S | 4292 | 8223 |
| 359 | 99-14562-402 | A | G | S | 4293 | 8224 |
| 360 | 99-14566-320 | C | T | A | 4294 | 8225 |
| 361 | 99-14574-310 | G | C | S | 4295 | 8226 |
| 362 | 99-14581-365 | C | T | A | 4296 | 8227 |
| 363 | 99-14591-172 | G | C | S | 4297 | 8228 |
| 364 | 99-14595-210 | C | T | A | 4298 | 8229 |
| 365 | 99-14596-174 | C | T | A | 4299 | 8230 |
| 366 | 99-14597-85 | G | C | S | 4300 | 8231 |
| 367 | 99-14598-91 | C | T | A | 4301 | 8232 |
| 368 | 99-14599-220 | C | T | A | 4302 | 8233 |
| 369 | 99-14600-207 | A | G | S | 4303 | 8234 |
| 370 | 99-14601-448 | C | T | A | 4304 | 8235 |
| 371 | 99-14607-267 | C | T | A | 4305 | 8236 |
| 372 | 99-14609-467 | G | T | A | 4306 | 8237 |
| 373 | 99-14610-351 | A | C | S | 4307 | 8238 |
| 374 | 99-14611-241 | G | C | S | 4308 | 8239 |
| 375 | 99-14612-100 | G | C | S | 4309 | 8240 |
| 376 | 99-14614-248 | A | G | S | 4310 | 8241 |
| 377 | 99-14615-65 | A | G | S | 4311 | 8242 |
| 378 | 99-14616-35 | A | G | S | 4312 | 8243 |
| 379 | 99-14618-147 | G | C | S | 4313 | 8244 |
| 380 | 99-14619-325 | A | C | S | 4314 | 8245 |
| 381 | 99-1462-238 | G | C | S | 4315 | 8246 |
| 382 | 99-14620-253 | C | T | A | 4316 | 8247 |
| 383 | 99-14621-96 | G | C | S | 4317 | 8248 |
| 384 | 99-14622-276 | C | T | A | 4318 | 8249 |
| 385 | 99-14626-307 | A | G | S | 4319 | 8250 |
| 386 | 99-14627-272 | C | T | A | 4320 | 8251 |
| 387 | 99-14628-312 | A | C | S | 4321 | 8252 |
| 388 | 99-14629-274 | A | G | S | 4322 | 8253 |
| 389 | 99-14630-75 | C | T | A | 4323 | 8254 |
| 390 | 99-14634-350 | A | G | S | 4324 | 8255 |
| 391 | 99-14635-296 | G | C | S | 4325 | 8256 |
| 392 | 99-14637-366 | G | C | S | 4326 | 8257 |
| 393 | 99-14638-276 | A | G | S | 4327 | 8258 |
| 394 | 99-14643-27 | C | T | S | 4328 | 8259 |
| 395 | 99-14644-395 | G | C | S | 4329 | 8260 |
| 396 | 99-14647-227 | C | T | A | 4330 | 8261 |
| 397 | 99-14651-205 | A | G | S | 4331 | 8262 |
| 398 | 99-14652-120 | A | G | S | 4332 | 8263 |
| 399 | 99-14653-138 | C | T | A | 4333 | 8264 |
| 400 | 99-14662-352 | A | G | S | 4334 | 8265 |
| 401 | 99-14664-289 | C | T | A | 4335 | 8266 |
| 402 | 99-14665-199 | A | G | S | 4336 | 8267 |
| 403 | 99-14669-238 | A | G | S | 4337 | 8268 |
| 404 | 99-14671-175 | C | T | A | 4338 | 8269 |
| 405 | 99-14676-313 | A | T | S | 4339 | 8270 |
| 406 | 99-14677-358 | G | C | S | 4340 | 8271 |
| 407 | 99-14678-75 | G | C | S | 4341 | 8272 |
| 408 | 99-14679-241 | C | T | A | 4342 | 8273 |
| 409 | 99-14468-435 | C | T | S | 4343 | 8274 |
| 410 | 99-1469-47 | G | C | S | 4344 | 8275 |
| 411 | 99-14690-84 | G | T | A | 4345 | 8276 |
| 412 | 99-14692-46 | A | G | S | 4346 | 8277 |
| 413 | 99-14699-149 | C | T | A | 4347 | 8278 |
| 414 | 99-147-181 | A | G | A | 4348 | 8279 |
| 415 | 99-14701-264 | A | G | S | 4349 | 8280 |
| 416 | 99-14704-59 | A | C | S | 4350 | 8281 |
| 417 | 99-14708-142 | G | T | A | 4351 | 8282 |
| 418 | 99-14676-571 | C | T | S | 4352 | 8283 |
| 419 | 99-14710-107 | C | T | A | 4353 | 8284 |
| 420 | 99-14712-163 | C | T | A | 4354 | 8285 |
| 421 | 99-14714-237 | C | T | S | 4355 | 8286 |
| 422 | 99-14717-132 | A | G | S | 4356 | 8287 |
| 423 | 99-1472-435 | A | G | A | 4357 | 8288 |
| 424 | 99-14722-272 | C | T | A | 4358 | 8289 |
| 425 | 99-14729-284 | A | T | S | 4359 | 8290 |
| 426 | 99-14733-26 | A | T | S | 4360 | 8291 |
| 427 | 99-14735-328 | A | G | S | 4361 | 8292 |
| 428 | 99-1474-156 | G | T | A | 4362 | 8293 |
| 429 | 99-14746-377 | A | G | S | 4363 | 8294 |
| 430 | 99-14753-194 | G | T | A | 4364 | 8295 |
| 431 | 99-14756-270 | A | T | S | 4365 | 8296 |
| 432 | 99-1476-172 | G | C | S | 4366 | 8297 |
| 433 | 99-14761-194 | A | G | S | 4367 | 8298 |
| 434 | 99-14773-383 | G | T | A | 4368 | 8299 |
| 435 | 99-14776-79 | G | C | S | 4369 | 8300 |
| 436 | 99-14777-100 | C | T | S | 4370 | 8301 |
| 437 | 99-14782-152 | G | C | S | 4371 | 8302 |
| 438 | 99-14784-212 | A | G | S | 4372 | 8303 |
| 439 | 99-14785-92 | A | C | S | 4373 | 8304 |
| 440 | 99-14786-59 | A | G | S | 4374 | 8305 |
| 441 | 99-1479-158 | C | T | S | 4375 | 8306 |
| 442 | 99-14792-43 | C | T | S | 4376 | 8307 |
| 443 | 99-14796-227 | C | T | A | 4377 | 8308 |
| 444 | 99-14799-57 | A | G | S | 4378 | 8309 |
| 445 | 99-148-182 | A | G | A | 4379 | 8310 |
| 446 | 99-14480-290 | G | T | A | 4380 | 8311 |
| 447 | 99-14802-60 | A | T | S | 4381 | 8312 |
| 448 | 99-14803-157 | C | T | A | 4382 | 8313 |
| 449 | 99-14804-216 | A | G | S | 4383 | 8314 |
| 450 | 99-14805-58 | A | G | S | 4384 | 8315 |
| 451 | 99-14806-108 | G | C | S | 4385 | 8316 |
| 452 | 99-14807-150 | G | C | S | 4386 | 8317 |
| 453 | 99-1481-285 | G | T | A | 4387 | 8318 |
| 454 | 99-14810-407 | C | T | A | 4388 | 8319 |
| 455 | 99-14812-189 | G | C | S | 4389 | 8320 |
| 456 | 99-14817-323 | C | T | A | 4390 | 8321 |
| 457 | 99-14818-430 | A | G | S | 4391 | 8322 |
| 458 | 99-14819-278 | G | C | S | 4392 | 8323 |
| 459 | 99-14820-76 | A | T | S | 4393 | 8324 |
| 460 | 99-14821-48 | C | T | A | 4394 | 8325 |
| 461 | 99-14826-238 | G | T | A | 4395 | 8326 |
| 462 | 99-14828-214 | C | T | A | 4396 | 8327 |
| 463 | 99-14833-226 | A | T | S | 4397 | 8328 |
| 464 | 99-1484-328 | G | C | S | 4398 | 8329 |
| 465 | 99-14843-195 | G | T | A | 4399 | 8330 |
| 466 | 99-14844-143 | C | T | A | 4400 | 8331 |
| 467 | 99-1485-251 | G | T | A | 4401 | 8332 |
| 468 | 99-14850-136 | A | G | S | 4402 | 8333 |
| 469 | 99-14856-260 | A | G | S | 4403 | 8334 |
| 470 | 99-14861-387 | A | G | S | 4404 | 8335 |
| 471 | 99-14862-171 | A | T | S | 4405 | 8336 |
| 472 | 99-14865-386 | A | G | S | 4406 | 8337 |
| 473 | 99-14867-160 | A | T | S | 4407 | 8338 |

TABLE 1-continued

| SEQ ID No. | Marker Name | Allele 1ST | 2ND | Preferred microseq. primer | Amplification primer Upstream (PU) | Downstream (RP) |
|---|---|---|---|---|---|---|
| 474 | 99-14872-326 | A | G | S | 4408 | 8339 |
| 475 | 99-14873453 | C | T | A | 4409 | 8340 |
| 476 | 99-14875-411 | C | T | A | 4410 | 8341 |
| 477 | 99-14879-398 | G | C | S | 4411 | 8342 |
| 478 | 99-14881-231 | C | T | A | 4412 | 8343 |
| 479 | 99-14882-382 | G | C | S | 4413 | 8344 |
| 480 | 99-14883-123 | G | C | S | 4414 | 8345 |
| 481 | 99-1489-76 | A | C | S | 4415 | 8346 |
| 482 | 99-14890-358 | G | T | A | 4416 | 8347 |
| 483 | 99-14892-237 | A | G | S | 4417 | 8348 |
| 484 | 99-14894-52 | A | G | S | 4418 | 8349 |
| 485 | 99-14895-343 | C | T | A | 4419 | 8350 |
| 486 | 99-14897-356 | C | T | A | 4420 | 8351 |
| 487 | 99-1490-381 | C | T | S | 4421 | 8352 |
| 488 | 99-14907-411 | G | T | A | 4422 | 8353 |
| 489 | 99-1493-280 | A | G | A | 4423 | 8354 |
| 490 | 99-14937-42 | A | C | S | 4424 | 8355 |
| 491 | 99-14939-240 | A | C | S | 4425 | 8356 |
| 492 | 99-1494-598 | A | G | A | 4426 | 8357 |
| 493 | 99-14940-224 | A | G | S | 4427 | 8358 |
| 494 | 99-14950-346 | A | T | S | 4428 | 8359 |
| 495 | 99-14959-81 | A | T | S | 4429 | 8360 |
| 496 | 99-14961-193 | G | C | S | 4430 | 8361 |
| 497 | 99-14962-120 | A | G | S | 4431 | 8362 |
| 498 | 99-14966-187 | A | G | S | 4432 | 8363 |
| 499 | 99-14970-352 | A | G | S | 4433 | 8364 |
| 500 | 99-14978-200 | G | T | A | 4434 | 8365 |
| 501 | 99-1498-120 | C | T | S | 4435 | 8366 |
| 502 | 99-14983-186 | G | T | A | 4436 | 8367 |
| 503 | 99-14984-35 | C | T | A | 4437 | 8368 |
| 504 | 99-15005-169 | C | T | A | 4438 | 8369 |
| 505 | 99-15007-369 | A | G | S | 4439 | 8370 |
| 506 | 99-1501-296 | A | G | A | 4440 | 8371 |
| 507 | 99-15016-293 | C | T | A | 4441 | 8372 |
| 508 | 99-15018-270 | A | G | S | 4442 | 8373 |
| 509 | 99-15019-408 | A | G | S | 4443 | 8374 |
| 510 | 99-15021-189 | A | G | S | 4444 | 8375 |
| 511 | 99-15030-271 | A | C | S | 4445 | 8376 |
| 512 | 99-15039-277 | G | T | A | 4446 | 8377 |
| 513 | 99-1504-252 | A | G | A | 4447 | 8378 |
| 514 | 99-15043-175 | A | G | S | 4448 | 8379 |
| 515 | 99-15046-54 | C | T | A | 4449 | 8380 |
| 516 | 99-1506-505 | C | T | S | 4450 | 8381 |
| 517 | 99-15072-64 | C | T | A | 4451 | 8382 |
| 518 | 99-15087-77 | C | T | A | 4452 | 8383 |
| 519 | 99-15098-367 | C | T | A | 4453 | 8384 |
| 520 | 99-151-94 | A | G | A | 4454 | 8385 |
| 521 | 99-15100-363 | C | T | A | 4455 | 8386 |
| 522 | 99-15101-154 | G | C | S | 4456 | 8387 |
| 523 | 99-15106-451 | C | T | A | 4457 | 8388 |
| 524 | 99-15107-228 | A | G | S | 4458 | 8389 |
| 525 | 99-15112-358 | C | T | A | 4459 | 8390 |
| 526 | 99-15118-69 | A | G | S | 4460 | 8391 |
| 527 | 99-15123-180 | C | T | A | 4461 | 8392 |
| 528 | 99-15128-349 | C | T | A | 4462 | 8393 |
| 529 | 99-15129-279 | C | T | A | 4463 | 8394 |
| 530 | 99-15135-231 | A | G | S | 4464 | 8395 |
| 531 | 99-15137-386 | A | G | S | 4465 | 8396 |
| 532 | 99-1515-402 | A | G | A | 4466 | 8397 |
| 533 | 99-15160-270 | A | G | S | 4467 | 8398 |
| 534 | 99-15164-67 | C | T | A | 4468 | 8399 |
| 535 | 99-15193-143 | G | T | A | 4469 | 8400 |
| 536 | 99-15195-377 | A | C | S | 4470 | 8401 |
| 537 | 99-15199-179 | C | T | A | 4471 | 8402 |
| 538 | 99-1520-143 | C | T | S | 4472 | 8403 |
| 539 | 99-15200-196 | A | G | S | 4473 | 8404 |
| 540 | 99-15202-357 | G | C | S | 4474 | 8405 |
| 541 | 99-1521-457 | G | C | S | 4475 | 8406 |
| 542 | 99-1525-102 | C | T | A | 4476 | 8407 |
| 543 | 99-15290-343 | G | T | A | 4477 | 8408 |
| 544 | 99-15296-326 | G | C | S | 4478 | 8409 |
| 545 | 99-15302-371 | G | T | A | 4479 | 8410 |
| 546 | 99-15307-251 | C | T | A | 4480 | 8411 |
| 547 | 99-15310-385 | A | G | S | 4481 | 8412 |
| 548 | 99-15325-95 | A | G | A | 4482 | 8413 |
| 549 | 99-15328-328 | C | T | A | 4483 | 8414 |
| 550 | 99-1533-471 | G | T | A | 4484 | 8415 |
| 551 | 99-15330-301 | G | C | S | 4485 | 8416 |
| 552 | 99-15335-313 | A | G | S | 4486 | 8417 |
| 553 | 99-15339-378 | C | T | A | 4487 | 8418 |
| 554 | 99-15345-376 | G | T | A | 4488 | 8419 |
| 555 | 99-1535-241 | C | T | S | 4489 | 8420 |
| 556 | 99-1537-243 | G | T | A | 4490 | 8421 |
| 557 | 99-15374-99 | A | G | S | 4491 | 8422 |
| 558 | 99-15377-206 | A | G | S | 4492 | 8423 |
| 559 | 99-15382-388 | G | T | A | 4493 | 8424 |
| 560 | 99-15393-177 | A | T | S | 4494 | 8425 |
| 561 | 99-15406-220 | A | C | S | 4495 | 8426 |
| 562 | 99-15425-132 | C | T | A | 4496 | 8427 |
| 563 | 99-15441-337 | A | C | S | 4497 | 8428 |
| 564 | 99-15446-339 | A | G | S | 4498 | 8429 |
| 565 | 99-15457-171 | A | C | S | 4499 | 8430 |
| 566 | 99-15458-308 | C | T | A | 4500 | 8431 |
| 567 | 99-15473-339 | A | C | S | 4501 | 8432 |
| 568 | 99-15486-309 | A | C | S | 4502 | 8433 |
| 569 | 99-15489-305 | G | C | S | 4503 | 8434 |
| 570 | 99-1549-124 | A | G | A | 4504 | 8435 |
| 571 | 99-15490-398 | A | C | S | 4505 | 8436 |
| 572 | 99-15493-197 | A | G | S | 4506 | 8437 |
| 573 | 99-15500-77 | A | G | S | 4507 | 8438 |
| 574 | 99-15502-250 | G | C | S | 4508 | 8439 |
| 575 | 99-15503-85 | G | T | A | 4509 | 8440 |
| 576 | 99-15507-248 | C | T | A | 4510 | 8441 |
| 577 | 99-15508-259 | C | T | A | 4511 | 8442 |
| 578 | 99-15511-278 | A | G | S | 4512 | 8443 |
| 579 | 99-15516-155 | A | G | S | 4513 | 8444 |
| 580 | 99-15524-224 | C | T | A | 4514 | 8445 |
| 581 | 99-15526-324 | A | T | S | 4515 | 8446 |
| 582 | 99-15527-154 | A | G | S | 4516 | 8447 |
| 583 | 99-15528-333 | A | G | S | 4517 | 8448 |
| 584 | 99-1553-544 | A | C | S | 4518 | 8449 |
| 585 | 99-15543-55 | C | T | A | 4519 | 8450 |
| 586 | 99-15545-282 | A | G | S | 4520 | 8451 |
| 587 | 99-15557-50 | A | G | S | 4521 | 8452 |
| 588 | 99-1557-251 | C | T | S | 4522 | 8453 |
| 589 | 99-15574-261 | G | T | A | 4523 | 8454 |
| 590 | 99-15575-278 | G | T | A | 4524 | 8455 |
| 591 | 99-1558-26 | C | T | S | 4525 | 8456 |
| 592 | 99-15595-41 | A | G | A | 4526 | 8457 |
| 593 | 99-15596-64 | C | T | S | 4527 | 8458 |
| 594 | 99-15599-252 | A | G | S | 4528 | 8459 |
| 595 | 99-15605-221 | A | G | S | 4529 | 8460 |
| 596 | 99-15606-326 | C | T | A | 4530 | 8461 |
| 597 | 99-15625-299 | G | C | S | 4531 | 8462 |
| 598 | 99-15627-324 | A | C | S | 4532 | 8463 |
| 599 | 99-15636-159 | A | G | S | 4533 | 8464 |
| 600 | 99-15638-65 | C | T | A | 4534 | 8465 |
| 601 | 99-15648-83 | A | G | S | 4535 | 8466 |
| 602 | 99-15659-332 | G | C | S | 4536 | 8467 |
| 603 | 99-1568-240 | A | T | S | 4537 | 8468 |
| 604 | 99-15705-110 | C | T | S | 4538 | 8469 |
| 605 | 99-15717-120 | C | T | A | 4539 | 8470 |
| 606 | 99-15718-234 | C | T | A | 4540 | 8471 |
| 607 | 99-1572-440 | C | T | S | 4541 | 8472 |
| 608 | 99-15728-334 | A | T | S | 4542 | 8473 |
| 609 | 99-15739-113 | C | T | A | 4543 | 8474 |
| 610 | 99-15744-344 | C | T | A | 4544 | 8475 |
| 611 | 99-15747-185 | C | T | A | 4545 | 8476 |
| 612 | 99-15748-360 | A | C | S | 4546 | 8477 |
| 613 | 99-15756-54 | C | T | A | 4547 | 8478 |
| 614 | 99-15758-119 | C | T | A | 4548 | 8479 |
| 615 | 99-15762-455 | A | G | S | 4549 | 8480 |
| 616 | 99-1577-105 | A | G | A | 4550 | 8481 |
| 617 | 99-15774-268 | A | G | S | 4551 | 8482 |
| 618 | 99-15776-158 | C | T | A | 4552 | 8483 |
| 619 | 99-1578-496 | C | T | S | 4553 | 8484 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 620 | 99-15798-86 | C | T | A | 4554 | 8485 |
| 621 | 99-15803-52 | A | G | S | 4555 | 8486 |
| 622 | 99-15805-327 | A | G | S | 4556 | 8487 |
| 623 | 99-1582430 | C | T | S | 4557 | 8488 |
| 624 | 99-15826-407 | G | T | A | 4558 | 8489 |
| 625 | 99-15830-282 | A | G | S | 4559 | 8490 |
| 626 | 99-1585-373 | C | T | S | 4560 | 8491 |
| 627 | 99-1587-281 | A | G | A | 4561 | 8492 |
| 628 | 99-15891-215 | A | G | S | 4562 | 8493 |
| 629 | 99-15910-116 | A | C | S | 4563 | 8494 |
| 630 | 99-15916-270 | A | G | S | 4564 | 8495 |
| 631 | 99-15925-331 | C | T | A | 4565 | 8496 |
| 632 | 99-15947-109 | C | T | A | 4566 | 8497 |
| 633 | 99-15965-67 | A | G | S | 4567 | 8498 |
| 634 | 99-15966-87 | C | T | A | 4568 | 8499 |
| 635 | 99-15968-59 | A | G | S | 4569 | 8500 |
| 636 | 99-1597-162 | A | G | A | 4570 | 8501 |
| 637 | 99-15970-56 | A | G | S | 4571 | 8502 |
| 638 | 99-15973-73 | C | T | A | 4572 | 8503 |
| 639 | 99-15981-298 | A | G | S | 4573 | 8504 |
| 640 | 99-15985-354 | A | G | S | 4574 | 8505 |
| 641 | 99-15992-145 | A | C | S | 4575 | 8506 |
| 642 | 99-15996-361 | G | T | A | 4576 | 8507 |
| 643 | 99-16003-91 | G | C | S | 4577 | 8508 |
| 644 | 99-16005-314 | C | T | A | 4578 | 8509 |
| 645 | 99-1601-402 | A | T | S | 4579 | 8510 |
| 646 | 99-1602-200 | G | C | S | 4580 | 8511 |
| 647 | 99-16022-325 | A | G | S | 4581 | 8512 |
| 648 | 99-16023-160 | G | C | S | 4582 | 8513 |
| 649 | 99-16030-317 | A | G | S | 4583 | 8514 |
| 650 | 99-1605-112 | A | G | A | 4584 | 8515 |
| 651 | 99-1607-373 | A | G | A | 4585 | 8516 |
| 652 | 99-1611-382 | A | G | A | 4586 | 8517 |
| 653 | 99-16121-51 | C | T | A | 4587 | 8518 |
| 654 | 99-16128-88 | C | T | A | 4588 | 8519 |
| 655 | 99-16129-69 | C | T | A | 4589 | 8520 |
| 656 | 99-16139-79 | A | G | S | 4590 | 8521 |
| 657 | 99-16140-324 | A | G | S | 4591 | 8522 |
| 658 | 99-1615-118 | A | G | A | 4592 | 8523 |
| 659 | 99-16166-331 | A | G | S | 4593 | 8524 |
| 660 | 99-16167-130 | G | C | S | 4594 | 8525 |
| 661 | 99-16188-76 | A | G | S | 4595 | 8526 |
| 662 | 99-16192-217 | A | C | S | 4596 | 8527 |
| 663 | 99-16198-203 | A | T | S | 4597 | 8528 |
| 664 | 99-16202-240 | A | G | S | 4598 | 8529 |
| 665 | 99-16205-255 | A | G | S | 4599 | 8530 |
| 666 | 99-16210-217 | A | T | S | 4600 | 8531 |
| 667 | 99-1622-158 | G | C | S | 4601 | 8532 |
| 668 | 99-16221-161 | G | C | S | 4602 | 8533 |
| 669 | 99-16227-270 | A | G | S | 4603 | 8534 |
| 670 | 99-1623-145 | C | T | S | 4604 | 8535 |
| 671 | 99-16247-447 | A | G | S | 4605 | 8536 |
| 672 | 99-16254-304 | A | G | S | 4606 | 8537 |
| 673 | 99-16260-277 | A | G | S | 4607 | 8538 |
| 674 | 99-16262-232 | C | T | A | 4608 | 8539 |
| 675 | 99-16265-88 | G | C | S | 4609 | 8540 |
| 676 | 99-16279-409 | G | T | A | 4610 | 8541 |
| 677 | 99-16308-315 | A | G | S | 4611 | 8542 |
| 678 | 99-16346-433 | C | T | A | 4612 | 8543 |
| 679 | 99-16366-425 | A | T | S | 4613 | 8544 |
| 680 | 99-16637-345 | C | T | S | 4614 | 8545 |
| 681 | 99-16375-469 | C | T | A | 4615 | 8546 |
| 682 | 99-1638-571 | C | T | S | 4616 | 8547 |
| 683 | 99-16386-484 | G | C | S | 4617 | 8548 |
| 684 | 99-16396-174 | C | T | A | 4618 | 8549 |
| 685 | 99-16399-135 | A | C | S | 4619 | 8550 |
| 686 | 99-16403-273 | A | G | S | 4620 | 8551 |
| 687 | 99-16407-260 | A | C | S | 4621 | 8552 |
| 688 | 99-16409-58 | A | T | S | 4622 | 8553 |
| 689 | 99-16414-297 | A | C | S | 4623 | 8554 |
| 690 | 99-16445-444 | C | T | A | 4624 | 8555 |
| 691 | 99-16466-419 | A | C | S | 4625 | 8556 |
| 692 | 99-16474-299 | G | T | A | 4626 | 8557 |
| 693 | 99-16500-380 | A | T | S | 4627 | 8558 |
| 694 | 99-16505-368 | G | C | S | 4628 | 8559 |
| 695 | 99-16526-375 | A | C | S | 4629 | 8560 |
| 696 | 99-16528-194 | C | T | A | 4630 | 8561 |
| 697 | 99-16531-251 | A | G | S | 4631 | 8562 |
| 698 | 99-16535-344 | C | T | A | 4632 | 8563 |
| 699 | 99-16559-90 | A | G | S | 4633 | 8564 |
| 700 | 99-16562-182 | A | G | S | 4634 | 8565 |
| 701 | 99-16563-263 | G | C | S | 4635 | 8566 |
| 702 | 99-16564-118 | A | G | S | 4636 | 8567 |
| 703 | 99-16568-283 | G | T | A | 4637 | 8568 |
| 704 | 99-16569-65 | A | G | S | 4638 | 8569 |
| 705 | 99-16658-474 | C | T | S | 4639 | 8570 |
| 706 | 99-16611-318 | A | C | S | 4640 | 8571 |
| 707 | 99-1664-289 | C | T | S | 4641 | 8572 |
| 708 | 99-16655-135 | C | T | S | 4642 | 8573 |
| 709 | 99-16657-361 | A | G | S | 4643 | 8574 |
| 710 | 99-16677-346 | C | T | S | 4644 | 8575 |
| 711 | 99-16683-465 | A | C | S | 4645 | 8576 |
| 712 | 99-16692-343 | G | T | A | 4646 | 8577 |
| 713 | 99-16697-149 | A | C | S | 4647 | 8578 |
| 714 | 99-16708-273 | A | G | A | 4648 | 8579 |
| 715 | 99-16740-391 | G | T | A | 4649 | 8580 |
| 716 | 99-16768-54 | A | T | S | 4650 | 8581 |
| 717 | 99-16801-374 | C | T | S | 4651 | 8582 |
| 718 | 99-16827-356 | A | G | A | 4652 | 8583 |
| 719 | 99-16838-212 | C | T | S | 4653 | 8584 |
| 720 | 99-16841-120 | A | T | S | 4654 | 8585 |
| 721 | 99-16842-362 | A | G | A | 4655 | 8586 |
| 722 | 99-16845-234 | A | G | A | 4656 | 8587 |
| 723 | 99-16847-405 | A | G | A | 4657 | 8588 |
| 724 | 99-16855-84 | G | C | S | 4658 | 8589 |
| 725 | 99-16867-193 | C | T | S | 4659 | 8590 |
| 726 | 99-16873-407 | G | C | S | 4660 | 8591 |
| 727 | 99-16886-198 | G | T | A | 4661 | 8592 |
| 728 | 99-16891-264 | C | j | A | 4662 | 8593 |
| 729 | 99-16894-85 | C | T | A | 4663 | 8594 |
| 730 | 99-16895-56 | A | C | S | 4664 | 8595 |
| 731 | 99-16903-53 | A | G | S | 4665 | 8596 |
| 732 | 99-16905-281 | C | T | A | 4666 | 8597 |
| 733 | 99-16906-114 | A | G | S | 4667 | 8598 |
| 734 | 99-16913-94 | A | G | S | 4668 | 8599 |
| 735 | 99-16914-412 | A | G | S | 4669 | 8600 |
| 736 | 99-16929-479 | A | C | S | 4670 | 8601 |
| 737 | 99-16930-306 | C | T | A | 4671 | 8602 |
| 738 | 99-16933-33 | A | G | S | 4672 | 8603 |
| 739 | 99-16946-157 | A | C | S | 4673 | 8604 |
| 740 | 99-16948-390 | A | T | S | 4674 | 8605 |
| 741 | 99-16952-248 | A | C | S | 4675 | 8606 |
| 742 | 99-16975-253 | G | C | S | 4676 | 8607 |
| 743 | 99-16979-274 | A | G | S | 4677 | 8608 |
| 744 | 99-16990-155 | C | T | A | 4678 | 8609 |
| 745 | 99-16994-63 | A | G | S | 4679 | 8610 |
| 746 | 99-17001-311 | C | T | A | 4680 | 8611 |
| 747 | 99-17008-420 | C | T | S | 4681 | 8612 |
| 748 | 99-1701-39 | A | G | A | 4682 | 8613 |
| 749 | 99-17013-217 | G | T | A | 4683 | 8614 |
| 750 | 99-17016-258 | A | G | A | 4684 | 8615 |
| 751 | 99-17028-56 | A | G | A | 4685 | 8616 |
| 752 | 99-17045-267 | A | G | A | 4686 | 8617 |
| 753 | 99-17048-207 | A | C | S | 4687 | 8618 |
| 754 | 99-17052-71 | A | G | A | 4688 | 8619 |
| 755 | 99-17062-102 | A | G | S | 4689 | 8620 |
| 756 | 99-17065-230 | A | G | S | 4690 | 8621 |
| 757 | 99-17084-191 | A | G | S | 4691 | 8622 |
| 758 | 99-1709-597 | G | C | S | 4692 | 8623 |
| 759 | 99-17094-132 | C | T | S | 4693 | 8624 |
| 760 | 99-17095-424 | A | G | S | 4694 | 8625 |
| 761 | 99-1710-249 | G | C | S | 4695 | 8626 |
| 762 | 99-17103-142 | C | T | A | 4696 | 8627 |
| 763 | 99-17105-147 | A | G | S | 4697 | 8628 |
| 764 | 99-17112-191 | C | T | A | 4698 | 8629 |
| 765 | 99-17122-255 | G | C | S | 4699 | 8630 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 766 | 99-17123-320 | C | T | A | 4700 | 8631 |
| 767 | 99-17133-327 | A | T | S | 4701 | 8632 |
| 768 | 99-17134-82 | C | T | A | 4702 | 8633 |
| 769 | 99-17136-384 | A | G | S | 4703 | 8634 |
| 770 | 99-17154-256 | A | G | S | 4704 | 8635 |
| 771 | 99-17157-33 | A | G | S | 4705 | 8636 |
| 772 | 99-17159-280 | A | G | S | 4706 | 8637 |
| 773 | 99-17164-252 | G | C | S | 4707 | 8638 |
| 774 | 99-17165-359 | A | G | S | 4708 | 8639 |
| 775 | 99-17169-485 | A | T | S | 4709 | 8640 |
| 776 | 99-17176-315 | A | G | S | 4710 | 8641 |
| 777 | 99-17180-309 | A | G | S | 4711 | 8642 |
| 778 | 99-17204-105 | A | G | S | 4712 | 8643 |
| 779 | 99-17205-68 | C | T | A | 4713 | 8644 |
| 780 | 99-17213-128 | C | T | A | 4714 | 8645 |
| 781 | 99-1723-101 | A | G | A | 4715 | 8646 |
| 782 | 99-17253-394 | G | T | A | 4716 | 8647 |
| 783 | 99-17262-65 | G | T | A | 4717 | 8648 |
| 784 | 99-17274-353 | A | G | A | 4718 | 8649 |
| 785 | 99-17282-138 | A | T | S | 4719 | 8650 |
| 786 | 99-17306-27 | C | T | A | 4720 | 8651 |
| 787 | 99-17315-86 | A | T | S | 4721 | 8652 |
| 788 | 99-17343-305 | A | G | S | 4722 | 8653 |
| 789 | 99-17347-160 | C | T | A | 4723 | 8654 |
| 790 | 99-17351-259 | G | T | A | 4724 | 8655 |
| 791 | 99-17352-284 | C | T | A | 4725 | 8656 |
| 792 | 99-17357-244 | C | T | A | 4726 | 8657 |
| 793 | 99-17363-245 | A | G | S | 4727 | 8658 |
| 794 | 99-17365-188 | A | G | S | 4728 | 8659 |
| 795 | 99-17375-363 | G | C | S | 4729 | 8660 |
| 796 | 99-1738-72 | A | G | A | 4730 | 8661 |
| 797 | 99-17389-164 | G | T | A | 4731 | 8662 |
| 798 | 99-1739-135 | A | C | S | 4732 | 8663 |
| 799 | 99-17409-293 | C | T | S | 4733 | 8664 |
| 800 | 99-17412-296 | C | T | A | 4734 | 8665 |
| 801 | 99-17416-310 | A | G | S | 4735 | 8666 |
| 802 | 99-17418-41 | A | T | S | 4736 | 8667 |
| 803 | 99-17420-380 | A | G | S | 4737 | 8668 |
| 804 | 99-17428-129 | A | G | S | 4738 | 8669 |
| 805 | 99-17450-352 | A | G | S | 4739 | 8670 |
| 806 | 99-17464-376 | C | T | A | 4740 | 8671 |
| 807 | 99-17476-141 | A | C | S | 4741 | 8672 |
| 808 | 99-17481-171 | C | T | A | 4742 | 8673 |
| 809 | 99-17483-282 | G | T | A | 4743 | 8674 |
| 810 | 99-17490-199 | A | G | S | 4744 | 8675 |
| 811 | 99-17491-362 | C | T | A | 4745 | 8676 |
| 812 | 99-17495-100 | A | C | S | 4746 | 8677 |
| 813 | 99-17496-301 | A | C | S | 4747 | 8678 |
| 814 | 99-17498-312 | C | T | A | 4748 | 8679 |
| 815 | 99-17499-62 | A | G | S | 4749 | 8680 |
| 816 | 99-17520-31 | C | T | A | 4750 | 8681 |
| 817 | 99-17522-423 | A | G | S | 4751 | 8682 |
| 818 | 99-17523-116 | A | C | S | 4752 | 8683 |
| 819 | 99-17529-210 | A | G | S | 4753 | 8684 |
| 820 | 99-17557-358 | C | T | A | 4754 | 8685 |
| 821 | 99-17563-102 | G | C | S | 4755 | 8686 |
| 822 | 99-17588-501 | A | G | S | 4756 | 8687 |
| 823 | 99-17610-44 | A | G | S | 4757 | 8688 |
| 824 | 99-17629-89 | G | T | A | 4758 | 8689 |
| 825 | 99-1764-65 | G | C | S | 4759 | 8690 |
| 826 | 99-17647-79 | A | G | S | 4760 | 8691 |
| 827 | 99-1765-171 | C | T | S | 4761 | 8692 |
| 828 | 99-17656-239 | A | G | S | 4762 | 8693 |
| 829 | 99-17658-167 | A | G | S | 4763 | 8694 |
| 830 | 99-17662-126 | C | T | A | 4764 | 8695 |
| 831 | 99-17663-29 | A | G | S | 4765 | 8696 |
| 832 | 99-17677-251 | A | G | A | 4766 | 8697 |
| 833 | 99-17680-451 | C | T | S | 4767 | 8698 |
| 834 | 99-17683-286 | A | G | A | 4768 | 8699 |
| 835 | 99-17687-373 | C | T | S | 4769 | 8700 |
| 836 | 99-17700-191 | G | C | S | 4770 | 8701 |
| 837 | 99-17702-57 | G | T | A | 4771 | 8702 |
| 838 | 99-17718-259 | C | T | S | 4772 | 8703 |
| 839 | 99-17720-224 | G | C | S | 4773 | 8704 |
| 840 | 99-17728-310 | A | C | S | 4774 | 8705 |
| 841 | 99-17773-343 | C | T | S | 4775 | 8706 |
| 842 | 99-17740-227 | G | C | S | 4776 | 8707 |
| 843 | 99-17775-187 | A | G | A | 4777 | 8708 |
| 844 | 99-17758-292 | A | G | A | 4778 | 8709 |
| 845 | 99-17762-327 | A | G | A | 4779 | 8710 |
| 846 | 99-17773-392 | C | T | S | 4780 | 8711 |
| 847 | 99-17774-276 | C | T | S | 4781 | 8712 |
| 848 | 99-17775-286 | C | T | S | 4782 | 8713 |
| 849 | 99-17776-114 | A | T | S | 4783 | 8714 |
| 850 | 99-17779-117 | A | C | S | 4784 | 8715 |
| 851 | 99-17792-144 | C | T | S | 4785 | 8716 |
| 852 | 99-17798-345 | C | T | S | 4786 | 8717 |
| 853 | 99-17802-338 | A | G | A | 4787 | 8718 |
| 854 | 99-17808-398 | G | C | S | 4788 | 8719 |
| 855 | 99-1781-129 | A | G | A | 4789 | 8720 |
| 856 | 99-17810-366 | C | T | S | 4790 | 8721 |
| 857 | 99-17816-377 | G | C | S | 4791 | 8722 |
| 858 | 99-17820-316 | A | G | A | 4792 | 8723 |
| 859 | 99-17821-109 | A | G | S | 4793 | 8724 |
| 860 | 99-17827-106 | A | C | S | 4794 | 8725 |
| 861 | 99-17829-412 | G | C | S | 4795 | 8726 |
| 862 | 99-17833-108 | G | T | A | 4796 | 8727 |
| 863 | 99-17845-286 | A | G | A | 4797 | 8728 |
| 864 | 99-17854-229 | C | T | S | 4798 | 8729 |
| 865 | 99-17856-308 | G | C | S | 4799 | 8730 |
| 866 | 99-17857-251 | A | G | A | 4800 | 8731 |
| 867 | 99-17863-257 | A | G | A | 4801 | 8732 |
| 868 | 99-17864-202 | G | T | A | 4802 | 8733 |
| 869 | 99-17866-124 | C | T | S | 4803 | 8734 |
| 870 | 99-17889-148 | G | C | S | 4804 | 8735 |
| 871 | 99-17890-58 | C | T | S | 4805 | 8736 |
| 872 | 99-17899-140 | A | G | A | 4806 | 8737 |
| 873 | 99-17913-222 | G | T | A | 4807 | 8738 |
| 874 | 99-17920-382 | A | G | A | 4808 | 8739 |
| 875 | 99-1793-225 | A | T | S | 4809 | 8740 |
| 876 | 99-17938-131 | A | G | A | 4810 | 8741 |
| 877 | 99-17945-63 | A | T | S | 4811 | 8742 |
| 878 | 99-17946-69 | A | C | S | 4812 | 8743 |
| 879 | 99-17952-370 | C | T | S | 4813 | 8744 |
| 880 | 99-1796-184 | A | T | S | 4814 | 8745 |
| 881 | 99-17971-78 | A | G | A | 4815 | 8746 |
| 882 | 99-17976-132 | G | C | S | 4816 | 8747 |
| 883 | 99-17989-85 | A | G | A | 4817 | 8748 |
| 884 | 99-17991-412 | A | T | S | 4818 | 8749 |
| 885 | 99-17992-404 | A | G | A | 4819 | 8750 |
| 886 | 99-18004-125 | C | T | S | 4820 | 8751 |
| 887 | 99-18007-159 | C | T | S | 4821 | 8752 |
| 888 | 99-18030-54 | A | T | S | 4822 | 8753 |
| 889 | 99-18038-384 | G | C | S | 4823 | 8754 |
| 890 | 99-18046-65 | A | T | S | 4824 | 8755 |
| 891 | 99-18053-328 | A | G | S | 4825 | 8756 |
| 892 | 99-18054-392 | A | C | S | 4826 | 8757 |
| 893 | 99-18056-354 | A | G | S | 4827 | 8758 |
| 894 | 99-18057-55 | A | C | S | 4828 | 8759 |
| 895 | 99-18060-203 | G | T | A | 4829 | 8760 |
| 896 | 99-18062-187 | A | G | A | 4830 | 8761 |
| 897 | 99-18069-282 | C | T | A | 4831 | 8762 |
| 898 | 99-18079-46 | G | C | S | 4832 | 8763 |
| 899 | 99-1808-291 | A | T | S | 4833 | 8764 |
| 900 | 99-18080-378 | G | T | A | 4834 | 8765 |
| 901 | 99-18085-94 | A | G | S | 4835 | 8766 |
| 902 | 99-18086-434 | A | G | S | 4836 | 8767 |
| 903 | 99-18087-152 | C | T | A | 4837 | 8768 |
| 904 | 99-18091-47 | G | C | S | 4838 | 8769 |
| 905 | 99-18096-198 | C | T | A | 4839 | 8770 |
| 906 | 99-18109-159 | C | T | A | 4840 | 8771 |
| 907 | 99-1813-310 | C | T | S | 4841 | 8772 |
| 908 | 99-18130-258 | A | G | S | 4842 | 8773 |
| 909 | 99-1814-245 | A | G | A | 4843 | 8774 |
| 910 | 99-18171-95 | G | T | A | 4844 | 8775 |
| 911 | 99-18172-284 | A | G | S | 4845 | 8776 |

TABLE 1-continued

| SEQ ID No. | Marker Name | Preferred Allele 1ST | 2ND | microseq. primer | Amplification primer Upstream (PU) | Downstream (RP) |
|---|---|---|---|---|---|---|
| 912 | 99-18179-185 | G | T | A | 4846 | 8777 |
| 913 | 99-18198-203 | C | T | A | 4847 | 8778 |
| 914 | 99-18201-23 | A | G | S | 4848 | 8779 |
| 915 | 99-18206-76 | A | G | S | 4849 | 8780 |
| 916 | 99-18210-30 | G | C | S | 4850 | 8781 |
| 917 | 99-18213-185 | A | G | S | 4851 | 8782 |
| 918 | 99-18214-86 | A | C | S | 4852 | 8783 |
| 919 | 99-18221-207 | C | T | A | 4853 | 8784 |
| 920 | 99-1823-157 | A | G | A | 4854 | 8785 |
| 921 | 99-1824-226 | A | G | A | 4855 | 8786 |
| 922 | 99-18242-369 | A | G | S | 4856 | 8787 |
| 923 | 99-18253-407 | C | T | S | 4857 | 8788 |
| 924 | 99-18255-259 | A | T | S | 4858 | 8789 |
| 925 | 99-18258-45 | G | C | S | 4859 | 8790 |
| 926 | 99-18268-460 | A | G | A | 4860 | 8791 |
| 927 | 99-18272-287 | G | C | S | 4861 | 8792 |
| 928 | 99-18276-390 | A | G | S | 4862 | 8793 |
| 929 | 99-18288-205 | A | G | A | 4863 | 8794 |
| 930 | 99-18289-36 | C | T | S | 4864 | 8795 |
| 931 | 99-18303-79 | C | T | S | 4865 | 8796 |
| 932 | 99-18306-377 | A | G | A | 4866 | 8797 |
| 933 | 99-18307-371 | A | C | S | 4867 | 8798 |
| 934 | 99-18310-262 | C | T | S | 4868 | 8799 |
| 935 | 99-18312-58 | C | T | S | 4869 | 8800 |
| 936 | 99-18341-95 | G | T | A | 4870 | 8801 |
| 937 | 99-18344-284 | A | G | A | 4871 | 8802 |
| 938 | 99-18345-107 | C | T | S | 4872 | 8803 |
| 939 | 99-18371-433 | A | T | S | 4873 | 8804 |
| 940 | 99-18373-27 | A | G | A | 4874 | 8805 |
| 941 | 99-18375-237 | A | G | A | 4875 | 8806 |
| 942 | 99-18379-485 | C | T | S | 4876 | 8807 |
| 943 | 99-18386-177 | A | T | S | 4877 | 8808 |
| 944 | 99-18394-132 | G | T | A | 4878 | 8809 |
| 945 | 99-18402-255 | C | T | S | 4879 | 8810 |
| 946 | 99-18406-155 | A | G | A | 4880 | 8811 |
| 947 | 99-18414-204 | A | C | S | 4881 | 8812 |
| 948 | 99-18418-127 | G | C | S | 4882 | 8813 |
| 949 | 99-1842-78 | C | T | S | 4883 | 8814 |
| 950 | 99-18423-336 | A | G | A | 4884 | 8815 |
| 951 | 99-18427-314 | C | T | S | 4885 | 8816 |
| 952 | 99-18438-398 | C | T | S | 4886 | 8817 |
| 953 | 99-18442-283 | C | T | S | 4887 | 8818 |
| 954 | 99-18444-185 | C | T | S | 4888 | 8819 |
| 955 | 99-18458-191 | A | G | A | 4889 | 8820 |
| 956 | 99-18470-119 | A | T | S | 4890 | 8821 |
| 957 | 99-18478-101 | A | G | A | 4891 | 8822 |
| 958 | 99-18486-49 | A | G | A | 4892 | 8823 |
| 959 | 99-18487-236 | C | T | S | 4893 | 8824 |
| 960 | 99-18488-273 | A | G | A | 4894 | 8825 |
| 961 | 99-1849-421 | C | T | S | 4895 | 8826 |
| 962 | 99-18536-290 | G | T | A | 4896 | 8827 |
| 963 | 99-18542-232 | A | C | S | 4897 | 8828 |
| 964 | 99-18551-389 | G | C | S | 4898 | 8829 |
| 965 | 99-18561-371 | A | C | S | 4899 | 8830 |
| 966 | 99-18573-363 | G | T | A | 4900 | 8831 |
| 967 | 99-18582-422 | A | G | A | 4901 | 8832 |
| 968 | 99-18588-175 | A | C | S | 4902 | 8833 |
| 969 | 99-18596-83 | A | G | A | 4903 | 8834 |
| 970 | 99-18597-415 | C | T | S | 4904 | 8835 |
| 971 | 99-18599-347 | A | G | A | 4905 | 8836 |
| 972 | 99-1860-281 | A | G | A | 4906 | 8837 |
| 973 | 99-18602-241 | A | G | A | 4907 | 8838 |
| 974 | 99-18606-324 | C | T | S | 4908 | 8839 |
| 975 | 99-1861-191 | G | C | S | 4909 | 8840 |
| 976 | 99-18612-184 | C | T | S | 4910 | 8841 |
| 977 | 99-18618-455 | C | T | S | 4911 | 8842 |
| 978 | 99-18620-125 | C | T | S | 4912 | 8843 |
| 979 | 99-18637-281 | C | T | A | 4913 | 8844 |
| 980 | 99-18638-164 | C | T | A | 4914 | 8845 |
| 981 | 99-18640-458 | C | T | A | 4915 | 8846 |
| 982 | 99-18648-71 | C | T | A | 4916 | 8847 |
| 983 | 99-18666-483 | G | T | A | 4917 | 8848 |
| 984 | 99-18667-392 | G | C | S | 4918 | 8849 |
| 985 | 99-18669-223 | G | C | S | 4919 | 8850 |
| 986 | 99-18715-172 | A | G | A | 4920 | 8851 |
| 987 | 99-18719-225 | C | T | S | 4921 | 8852 |
| 988 | 99-18720-235 | C | T | S | 4922 | 8853 |
| 989 | 99-18721-442 | A | G | A | 4923 | 8854 |
| 990 | 99-18724-409 | C | T | S | 4924 | 8855 |
| 991 | 99-18729-377 | A | T | S | 4925 | 8856 |
| 992 | 99-18873-193 | C | T | A | 4926 | 8857 |
| 993 | 99-18744-170 | A | G | A | 4927 | 8858 |
| 994 | 99-18745-423 | A | G | A | 4928 | 8859 |
| 995 | 99-18747-72 | C | T | S | 4929 | 8860 |
| 996 | 99-18751-217 | G | T | A | 4930 | 8861 |
| 997 | 99-18755-267 | C | T | S | 4931 | 8862 |
| 998 | 99-18774-69 | G | T | A | 4932 | 8863 |
| 999 | 99-18775-161 | G | T | A | 4933 | 8864 |
| 1000 | 99-18777-130 | C | T | S | 4934 | 8865 |
| 1001 | 99-18802-308 | G | C | S | 4935 | 8866 |
| 1002 | 99-18808-155 | C | T | S | 4936 | 8867 |
| 1003 | 99-18814-275 | G | C | S | 4937 | 8868 |
| 1004 | 99-18822-289 | C | T | A | 4938 | 8869 |
| 1005 | 99-18822-368 | C | T | S | 4939 | 8870 |
| 1006 | 99-18826-378 | C | T | S | 4940 | 8871 |
| 1007 | 99-18827-92 | A | G | A | 4941 | 8872 |
| 1008 | 99-18883-121 | G | T | A | 4942 | 8873 |
| 1009 | 99-18847-263 | C | T | S | 4943 | 8874 |
| 1010 | 99-18853-64 | G | T | A | 4944 | 8875 |
| 1011 | 99-18855-173 | A | G | A | 4945 | 8876 |
| 1012 | 99-18860-308 | C | T | S | 4946 | 8877 |
| 1013 | 99-18861-23 | C | T | S | 4947 | 8878 |
| 1014 | 99-18888-162 | C | T | S | 4948 | 8879 |
| 1015 | 99-18890-125 | C | T | A | 4949 | 8880 |
| 1016 | 99-18895-67 | A | C | S | 4950 | 8881 |
| 1017 | 99-18974-99 | A | G | A | 4951 | 8882 |
| 1018 | 99-18976-135 | A | T | S | 4952 | 8883 |
| 1019 | 99-18982-345 | C | T | S | 4953 | 8884 |
| 1020 | 99-18986-248 | G | C | S | 4954 | 8885 |
| 1021 | 99-18987-191 | A | G | A | 4955 | 8886 |
| 1022 | 99-18995-300 | C | T | S | 4956 | 8887 |
| 1023 | 99-18996-388 | A | G | A | 4957 | 8888 |
| 1024 | 99-19008-237 | C | T | S | 4958 | 8889 |
| 1025 | 99-19013-384 | C | T | S | 4959 | 8890 |
| 1026 | 99-19016-51 | A | G | A | 4960 | 8891 |
| 1027 | 99-1909-387 | G | T | A | 4961 | 8892 |
| 1028 | 99-1910-94 | C | T | S | 4962 | 8893 |
| 1029 | 99-1916-91 | G | T | A | 4963 | 8894 |
| 1030 | 99-1917-434 | A | T | S | 4964 | 8895 |
| 1031 | 99-19253-102 | A | G | A | 4965 | 8896 |
| 1032 | 99-19256-149 | C | T | S | 4966 | 8897 |
| 1033 | 99-1934-272 | A | G | A | 4967 | 8898 |
| 1034 | 99-1936-289 | C | T | S | 4968 | 8899 |
| 1035 | 99-1944-379 | C | T | S | 4969 | 8900 |
| 1036 | 99-1947-205 | A | G | S | 4970 | 8901 |
| 1037 | 99-1948-49 | G | C | S | 4971 | 8902 |
| 1038 | 99-1953-287 | A | G | A | 4972 | 8903 |
| 1039 | 99-1955-443 | A | G | A | 4973 | 8904 |
| 1040 | 99-1960-424 | A | T | S | 4974 | 8905 |
| 1041 | 99-1964-53 | C | T | S | 4975 | 8906 |
| 1042 | 99-1977-440 | A | G | S | 4976 | 8907 |
| 1043 | 99-1997-139 | G | T | A | 4977 | 8908 |
| 1044 | 99-19999-92 | C | T | S | 4978 | 8909 |
| 1045 | 99-2000-240 | G | T | A | 4979 | 8910 |
| 1046 | 99-20000-252 | A | G | A | 4980 | 8911 |
| 1047 | 99-2001-177 | A | G | S | 4981 | 8912 |
| 1048 | 99-20011-229 | C | T | S | 4982 | 8913 |
| 1049 | 99-20018-244 | G | C | S | 4983 | 8914 |
| 1050 | 99-20023-386 | A | T | S | 4984 | 8915 |
| 1051 | 99-2003-509 | G | C | S | 4985 | 8916 |
| 1052 | 99-20032-90 | G | T | A | 4986 | 8917 |
| 1053 | 99-20033-186 | G | T | A | 4987 | 8918 |
| 1054 | 99-20035-283 | A | C | S | 4988 | 8919 |
| 1055 | 99-2004-35 | C | T | S | 4989 | 8920 |
| 1056 | 99-2005-466 | G | C | S | 4990 | 8921 |
| 1057 | 99-20057-166 | C | T | S | 4991 | 8922 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 1058 | 99-20061-56 | C | T | S | 4992 | 8923 |
| 1059 | 99-20062-181 | A | G | A | 4993 | 8924 |
| 1060 | 99-2007-278 | C | T | S | 4994 | 8925 |
| 1061 | 99-20074-154 | A | C | S | 4995 | 8926 |
| 1062 | 99-20090-81 | A | C | S | 4996 | 8927 |
| 1063 | 99-2010-363 | C | T | A | 4997 | 8928 |
| 1064 | 99-20110-65 | G | T | A | 4998 | 8929 |
| 1065 | 99-2012-243 | A | G | A | 4999 | 8930 |
| 1066 | 99-20154-451 | A | T | S | 5000 | 8931 |
| 1067 | 99-20156-212 | A | G | A | 5001 | 8932 |
| 1068 | 99-20198-54 | C | T | S | 5002 | 8933 |
| 1069 | 99-2020-281 | C | T | A | 5003 | 8934 |
| 1070 | 99-20208-176 | A | G | A | 5004 | 8935 |
| 1071 | 99-2022-200 | A | C | S | 5005 | 8936 |
| 1072 | 99-2024-132 | A | G | A | 5006 | 8937 |
| 1073 | 99-2025-234 | C | T | A | 5007 | 8938 |
| 1074 | 99-20250-362 | A | T | S | 5008 | 8939 |
| 1075 | 99-2027-296 | A | G | S | 5009 | 8940 |
| 1076 | 99-20294-274 | C | T | S | 5010 | 8941 |
| 1077 | 99-20303-127 | C | T | S | 5011 | 8942 |
| 1078 | 99-20313-311 | A | G | A | 5012 | 8943 |
| 1079 | 99-20320-321 | C | T | S | 5013 | 8944 |
| 1080 | 99-20326-130 | A | G | A | 5014 | 8945 |
| 1081 | 99-20332-432 | A | G | A | 5015 | 8946 |
| 1082 | 99-20335-48 | C | T | S | 5016 | 8947 |
| 1083 | 99-20340-161 | A | G | A | 5017 | 8948 |
| 1084 | 99-20348-403 | A | G | A | 5018 | 8949 |
| 1085 | 99-2035-323 | C | T | S | 5019 | 8950 |
| 1086 | 99-20353-229 | A | G | A | 5020 | 8951 |
| 1087 | 99-20357-359 | A | T | S | 5021 | 8952 |
| 1088 | 99-2036-168 | A | T | S | 5022 | 8953 |
| 1089 | 99-2037-470 | C | T | S | 5023 | 8954 |
| 1090 | 99-20385-215 | C | T | S | 5024 | 8955 |
| 1091 | 99-2041-141 | A | G | A | 5025 | 8956 |
| 1092 | 99-2042-439 | G | C | S | 5026 | 8957 |
| 1093 | 99-20420-274 | C | T | S | 5027 | 8958 |
| 1094 | 99-20423-430 | C | T | S | 5028 | 8959 |
| 1095 | 99-20424-330 | C | T | S | 5029 | 8960 |
| 1096 | 99-20428-271 | C | T | S | 5030 | 8961 |
| 1097 | 99-2043-220 | A | T | S | 5031 | 8962 |
| 1098 | 99-2046-275 | A | G | A | 5032 | 8963 |
| 1099 | 99-20469-213 | C | T | S | 5033 | 8964 |
| 1100 | 99-2048-267 | G | C | S | 5034 | 8965 |
| 1101 | 99-20480-233 | C | T | S | 5035 | 8966 |
| 1102 | 99-20481-131 | G | C | S | 5036 | 8967 |
| 1103 | 99-20485-269 | A | G | A | 5037 | 8968 |
| 1104 | 99-20493-238 | G | T | A | 5038 | 8969 |
| 1105 | 99-20499-364 | A | T | S | 5039 | 8970 |
| 1106 | 99-20504-90 | A | G | A | 5040 | 8971 |
| 1107 | 99-20508-456 | C | T | S | 5041 | 8972 |
| 1108 | 99-2051-360 | A | C | S | 5042 | 8973 |
| 1109 | 99-20511-221 | C | T | S | 5043 | 8974 |
| 1110 | 99-20514-71 | A | G | A | 5044 | 8975 |
| 1111 | 99-20518-456 | A | G | A | 5045 | 8976 |
| 1112 | 99-2052-376 | G | T | A | 5046 | 8977 |
| 1113 | 99-20527-220 | A | T | S | 5047 | 8978 |
| 1114 | 99-2053-386 | A | G | A | 5048 | 8979 |
| 1115 | 99-20531-285 | A | C | S | 5049 | 8980 |
| 1116 | 99-2054-93 | A | G | S | 5050 | 8981 |
| 1117 | 99-20542-248 | A | G | A | 5051 | 8982 |
| 1118 | 99-20549-141 | A | G | A | 5052 | 8983 |
| 1119 | 99-2055-236 | A | G | A | 5053 | 8984 |
| 1120 | 99-20552-37 | C | T | S | 5054 | 8985 |
| 1121 | 99-2056-474 | C | T | S | 5055 | 8986 |
| 1122 | 99-20561-126 | G | T | A | 5056 | 8987 |
| 1123 | 99-20565-190 | C | T | S | 5057 | 8988 |
| 1124 | 99-20566-376 | A | G | A | 5058 | 8989 |
| 1125 | 99-20567-268 | C | T | S | 5059 | 8990 |
| 1126 | 99-20568-284 | A | C | S | 5060 | 8991 |
| 1127 | 99-2058-168 | G | T | A | 5061 | 8992 |
| 1128 | 99-20581-125 | A | T | S | 5062 | 8993 |
| 1129 | 99-20594-103 | G | C | S | 5063 | 8994 |
| 1130 | 99-2060-322 | A | T | S | 5064 | 8995 |
| 1131 | 99-2061-257 | A | C | S | 5065 | 8996 |
| 1132 | 99-20616-287 | C | T | S | 5066 | 8997 |
| 1133 | 99-20623-354 | C | T | S | 5067 | 8998 |
| 1134 | 99-2063-451 | A | G | A | 5068 | 8999 |
| 1135 | 99-20639-257 | C | T | S | 5069 | 9000 |
| 1136 | 99-20642-382 | A | G | A | 5070 | 9001 |
| 1137 | 99-20651-108 | A | G | A | 5071 | 9002 |
| 1138 | 99-20656-171 | C | T | S | 5072 | 9003 |
| 1139 | 99-20659-289 | C | T | S | 5073 | 9004 |
| 1140 | 99-20675-407 | G | C | S | 5074 | 9005 |
| 1141 | 99-20677-289 | C | T | S | 5075 | 9006 |
| 1142 | 99-20683-98 | A | C | S | 5076 | 9007 |
| 1143 | 99-20688-310 | A | G | A | 5077 | 9008 |
| 1144 | 99-20723-206 | C | T | S | 5078 | 9009 |
| 1145 | 99-20726-494 | A | G | A | 5079 | 9010 |
| 1146 | 99-20732-413 | G | C | S | 5080 | 9011 |
| 1147 | 99-20738-89 | G | C | S | 5081 | 9012 |
| 1148 | 99-20739-335 | A | G | A | 5082 | 9013 |
| 1149 | 99-2074-273 | A | C | S | 5083 | 9014 |
| 1150 | 99-20746-369 | A | G | A | 5084 | 9015 |
| 1151 | 99-20747-322 | A | G | A | 5085 | 9016 |
| 1152 | 99-20766-117 | A | G | A | 5086 | 9017 |
| 1153 | 99-20768-469 | C | T | S | 5087 | 9018 |
| 1154 | 99-2077-510 | G | C | S | 5088 | 9019 |
| 1155 | 99-20771-171 | A | G | A | 5089 | 9020 |
| 1156 | 99-2078-348 | A | G | A | 5090 | 9021 |
| 1157 | 99-20797-262 | C | T | S | 5091 | 9022 |
| 1158 | 99-20798-87 | C | T | S | 5092 | 9023 |
| 1159 | 99-2080-33 | A | G | A | 5093 | 9024 |
| 1160 | 99-20802-358 | C | T | S | 5094 | 9025 |
| 1161 | 99-20814-222 | C | T | S | 5095 | 9026 |
| 1162 | 99-2082-284 | A | G | A | 5096 | 9027 |
| 1163 | 99-20823-49 | C | T | S | 5097 | 9028 |
| 1164 | 99-20828-131 | C | T | S | 5098 | 9029 |
| 1165 | 99-20830-449 | A | G | A | 5099 | 9030 |
| 1166 | 99-2084-504 | A | G | A | 5100 | 9031 |
| 1167 | 99-2085-172 | C | T | S | 5101 | 9032 |
| 1168 | 99-20850-374 | C | T | S | 5102 | 9033 |
| 1169 | 99-20853-29 | A | G | A | 5103 | 9034 |
| 1170 | 99-20856-158 | C | T | S | 5104 | 9035 |
| 1171 | 99-20867-393 | A | G | A | 5105 | 9036 |
| 1172 | 99-20872-325 | A | C | S | 5106 | 9037 |
| 1173 | 99-20883-234 | C | T | S | 5107 | 9038 |
| 1174 | 99-20887-420 | C | T | S | 5108 | 9039 |
| 1175 | 99-2089-84 | A | G | A | 5109 | 9040 |
| 1176 | 99-20895-36 | A | G | S | 5110 | 9041 |
| 1177 | 99-2092-323 | A | C | S | 5111 | 9042 |
| 1178 | 99-20928-66 | G | C | S | 5112 | 9043 |
| 1179 | 99-2093-278 | C | T | S | 5113 | 9044 |
| 1180 | 99-20938-256 | G | T | A | 5114 | 9045 |
| 1181 | 99-2094-129 | A | G | A | 5115 | 9046 |
| 1182 | 99-20950-251 | G | C | S | 5116 | 9047 |
| 1183 | 99-2098-102 | G | T | A | 5117 | 9048 |
| 1184 | 99-21012-277 | A | C | S | 5118 | 9049 |
| 1185 | 99-21021-273 | C | T | S | 5119 | 9050 |
| 1186 | 99-2103-270 | G | C | S | 5120 | 9051 |
| 1187 | 99-21035-279 | C | T | S | 5121 | 9052 |
| 1188 | 99-21064-278 | C | T | S | 5122 | 9053 |
| 1189 | 99-21070-272 | A | G | A | 5123 | 9054 |
| 1190 | 99-21079-169 | G | T | A | 5124 | 9055 |
| 1191 | 99-21084-496 | C | T | S | 5125 | 9056 |
| 1192 | 99-2109-276 | G | T | A | 5126 | 9057 |
| 1193 | 99-211-291 | A | G | S | 5127 | 9058 |
| 1194 | 99-21141-314 | A | G | A | 5128 | 9059 |
| 1195 | 99-21148-269 | A | G | A | 5129 | 9060 |
| 1196 | 99-21149-129 | A | G | A | 5130 | 9061 |
| 1197 | 99-21167-159 | C | T | S | 5131 | 9062 |
| 1198 | 99-21170-107 | C | T | S | 5132 | 9063 |
| 1199 | 99-21221-96 | A | T | S | 5133 | 9064 |
| 1200 | 99-2126-79 | A | T | S | 5134 | 9065 |
| 1201 | 99-21370-87 | C | T | S | 5135 | 9066 |
| 1202 | 99-2170-188 | G | C | S | 5136 | 9067 |
| 1203 | 99-2172-314 | A | G | S | 5137 | 9068 |

TABLE 1-continued

| SEQ ID No. | Marker Name | Allele 1ST | 2ND | Preferred microseq. primer | Amplification primer Upstream (PU) | Downstream (RP) |
|---|---|---|---|---|---|---|
| 1204 | 99-2173-289 | C | T | S | 5138 | 9069 |
| 1205 | 99-2179-303 | G | T | A | 5139 | 9070 |
| 1206 | 99-2193-225 | A | G | A | 5140 | 9071 |
| 1207 | 99-22011-342 | C | T | S | 5141 | 9072 |
| 1208 | 99-22015-219 | A | G | A | 5142 | 9073 |
| 1209 | 99-22022-145 | A | G | A | 5143 | 9074 |
| 1210 | 99-22027-410 | G | C | S | 5144 | 9075 |
| 1211 | 99-22036-314 | A | T | S | 5145 | 9076 |
| 1212 | 99-22038-381 | G | C | S | 5146 | 9077 |
| 1213 | 99-22044-431 | A | G | A | 5147 | 9078 |
| 1214 | 99-22048-259 | A | G | A | 5148 | 9079 |
| 1215 | 99-22051-261 | C | T | S | 5149 | 9080 |
| 1216 | 99-22066-139 | A | G | A | 5150 | 9081 |
| 1217 | 99-22072-80 | C | T | S | 5151 | 9082 |
| 1218 | 99-22073-381 | G | C | S | 5152 | 9083 |
| 1219 | 99-22078-350 | A | G | A | 5153 | 9084 |
| 1220 | 99-22087-150 | C | T | S | 5154 | 9085 |
| 1221 | 99-2209-111 | A | G | A | 5155 | 9086 |
| 1222 | 99-22091-289 | G | T | A | 5156 | 9087 |
| 1223 | 99-22096-276 | C | T | S | 5157 | 9088 |
| 1224 | 99-22100-265 | C | T | S | 5158 | 9089 |
| 1225 | 99-22102-238 | C | T | S | 5159 | 9090 |
| 1226 | 99-22122-54 | A | G | A | 5160 | 9091 |
| 1227 | 99-22125-126 | C | T | S | 5161 | 9092 |
| 1228 | 99-2214-148 | A | C | S | 5162 | 9093 |
| 1229 | 99-22147-359 | C | T | S | 5163 | 9094 |
| 1230 | 99-22160-331 | A | G | A | 5164 | 9095 |
| 1231 | 99-22167-79 | C | T | S | 5165 | 9096 |
| 1232 | 99-22172-304 | A | T | S | 5166 | 9097 |
| 1233 | 99-2218-219 | A | G | A | 5167 | 9098 |
| 1234 | 99-22189-248 | C | T | S | 5168 | 9099 |
| 1235 | 99-22219-245 | C | T | S | 5169 | 9100 |
| 1236 | 99-22191-339 | C | T | S | 5170 | 9101 |
| 1237 | 99-22192-383 | C | T | S | 5171 | 9102 |
| 1238 | 99-222-109 | C | T | S | 5172 | 9103 |
| 1239 | 99-2220-300 | A | G | A | 5173 | 9104 |
| 1240 | 99-22209-304 | A | C | S | 5174 | 9105 |
| 1241 | 99-22215-391 | A | G | A | 5175 | 9106 |
| 1242 | 99-22217-423 | G | C | S | 5176 | 9107 |
| 1243 | 99-2222-459 | C | T | S | 5177 | 9108 |
| 1244 | 99-22227-275 | A | T | S | 5178 | 9109 |
| 1245 | 99-22255-384 | A | G | A | 5179 | 9110 |
| 1246 | 99-22262-331 | C | T | S | 5180 | 9111 |
| 1247 | 99-22265-294 | A | C | S | 5181 | 9112 |
| 1248 | 99-22266-474 | C | T | S | 5182 | 9113 |
| 1249 | 99-2228-301 | A | G | A | 5183 | 9114 |
| 1250 | 99-2229-240 | G | T | A | 5184 | 9115 |
| 1251 | 99-22333-237 | C | T | S | 5185 | 9116 |
| 1252 | 99-22336-316 | C | T | S | 5186 | 9117 |
| 1253 | 99-22337-199 | A | C | S | 5187 | 9118 |
| 1254 | 99-2235-499 | G | C | S | 5188 | 9119 |
| 1255 | 99-22356-370 | A | C | S | 5189 | 9120 |
| 1256 | 99-22357-186 | C | T | S | 5190 | 9121 |
| 1257 | 99-2240-281 | C | T | S | 5191 | 9122 |
| 1258 | 99-22409-141 | C | T | S | 5192 | 9123 |
| 1259 | 99-2242-206 | C | T | S | 5193 | 9124 |
| 1260 | 99-2244-83 | A | G | A | 5194 | 9125 |
| 1261 | 99-22442-147 | G | T | A | 5195 | 9126 |
| 1262 | 99-22449-216 | G | C | S | 5196 | 9127 |
| 1263 | 99-22453-370 | A | T | S | 5197 | 9128 |
| 1264 | 99-22456-55 | A | C | S | 5198 | 9129 |
| 1265 | 99-2246-340 | A | G | A | 5199 | 9130 |
| 1266 | 99-2248-76 | C | T | S | 5200 | 9131 |
| 1267 | 99-22490-246 | A | G | A | 5201 | 9132 |
| 1268 | 99-22491-79 | G | T | A | 5202 | 9133 |
| 1269 | 99-2250-236 | C | T | S | 5203 | 9134 |
| 1270 | 99-22503-146 | C | T | S | 5204 | 9135 |
| 1271 | 99-22506-395 | C | T | S | 5205 | 9136 |
| 1272 | 99-22513-90 | A | G | A | 5206 | 9137 |
| 1273 | 99-22520-413 | G | C | S | 5207 | 9138 |
| 1274 | 99-22546-125 | C | T | S | 5208 | 9139 |
| 1275 | 99-22565-114 | A | G | A | 5209 | 9140 |
| 1276 | 99-22571-136 | C | T | S | 5210 | 9141 |
| 1277 | 99-22573-321 | A | G | A | 5211 | 9142 |
| 1278 | 99-22578-78 | C | T | S | 5212 | 9143 |
| 1279 | 99-22580-72 | A | T | S | 5213 | 9144 |
| 1280 | 99-22585-462 | G | C | S | 5214 | 9145 |
| 1281 | 99-22586-39 | A | G | S | 5215 | 9146 |
| 1282 | 99-22604-208 | G | T | A | 5216 | 9147 |
| 1283 | 99-22610-343 | A | G | A | 5217 | 9148 |
| 1284 | 99-22615-392 | C | T | S | 5218 | 9149 |
| 1285 | 99-22617-378 | C | T | S | 5219 | 9150 |
| 1286 | 99-22620-404 | C | T | S | 5220 | 9151 |
| 1287 | 99-22628-292 | A | G | A | 5221 | 9152 |
| 1288 | 99-22629-124 | C | T | S | 5222 | 9153 |
| 1289 | 99-22632-237 | G | C | S | 5223 | 9154 |
| 1290 | 99-22646-233 | A | G | A | 5224 | 9155 |
| 1291 | 99-22648-57 | C | T | S | 5225 | 9156 |
| 1292 | 99-22650-64 | A | C | S | 5226 | 9157 |
| 1293 | 99-22652-343 | A | G | A | 5227 | 9158 |
| 1294 | 99-22655-319 | A | T | S | 5228 | 9159 |
| 1295 | 99-22660-386 | A | G | A | 5229 | 9160 |
| 1296 | 99-22662-268 | A | G | A | 5230 | 9161 |
| 1297 | 99-22666-164 | C | T | S | 5231 | 9162 |
| 1298 | 99-22668-232 | G | T | A | 5232 | 9163 |
| 1299 | 99-22674-31 | C | T | S | 5233 | 9164 |
| 1300 | 99-22675-187 | A | G | A | 5234 | 9165 |
| 1301 | 99-22680-130 | C | T | S | 5235 | 9166 |
| 1302 | 99-22683-107 | A | G | A | 5236 | 9167 |
| 1303 | 99-2269-179 | A | G | A | 5237 | 9168 |
| 1304 | 99-22700-358 | A | G | A | 5238 | 9169 |
| 1305 | 99-22701-307 | C | T | S | 5239 | 9170 |
| 1306 | 99-2271-403 | A | G | A | 5240 | 9171 |
| 1307 | 99-22712-242 | A | G | A | 5241 | 9172 |
| 1308 | 99-22718-94 | A | T | S | 5242 | 9173 |
| 1309 | 99-2272-409 | G | T | A | 5243 | 9174 |
| 1310 | 99-22728-207 | A | G | A | 5244 | 9175 |
| 1311 | 99-2273-528 | C | T | S | 5245 | 9176 |
| 1312 | 99-22733-281 | G | C | S | 5246 | 9177 |
| 1313 | 99-22741-180 | A | G | A | 5247 | 9178 |
| 1314 | 99-2275-466 | C | T | S | 5248 | 9179 |
| 1315 | 99-2276-331 | C | T | S | 5249 | 9180 |
| 1316 | 99-22771-150 | A | G | A | 5250 | 9181 |
| 1317 | 99-22775-365 | C | T | S | 5251 | 9182 |
| 1318 | 99-2278-276 | A | G | A | 5252 | 9183 |
| 1319 | 99-22785-431 | A | T | S | 5253 | 9184 |
| 1320 | 99-22843-342 | G | T | A | 5254 | 9185 |
| 1321 | 99-22844-211 | A | G | A | 5255 | 9186 |
| 1322 | 99-22857-88 | C | T | S | 5256 | 9187 |
| 1323 | 99-22868-425 | A | C | S | 5257 | 9188 |
| 1324 | 99-22872-431 | C | T | S | 5258 | 9189 |
| 1325 | 99-2288-144 | C | T | S | 5259 | 9190 |
| 1326 | 99-22917-145 | G | T | A | 5260 | 9191 |
| 1327 | 99-22937-395 | C | T | S | 5261 | 9192 |
| 1328 | 99-22948-262 | C | T | S | 5262 | 9193 |
| 1329 | 99-22954-306 | A | C | S | 5263 | 9194 |
| 1330 | 99-22957-409 | A | G | A | 5264 | 9195 |
| 1331 | 99-22959-239 | A | G | A | 5265 | 9196 |
| 1332 | 99-22964-82 | C | T | S | 5266 | 9197 |
| 1333 | 99-22975-126 | C | T | S | 5267 | 9198 |
| 1334 | 99-23014-300 | A | G | A | 5268 | 9199 |
| 1335 | 99-23018-166 | A | G | A | 5269 | 9200 |
| 1336 | 99-23020-187 | G | T | A | 5270 | 9201 |
| 1337 | 99-23083-59 | C | T | S | 5271 | 9202 |
| 1338 | 99-23100-367 | A | G | A | 5272 | 9203 |
| 1339 | 99-23115-404 | G | C | S | 5273 | 9204 |
| 1340 | 99-23118-402 | A | G | A | 5274 | 9205 |
| 1341 | 99-2312-358 | C | T | S | 5275 | 9206 |
| 1342 | 99-23123-250 | A | G | A | 5276 | 9207 |
| 1343 | 99-23127-314 | G | C | S | 5277 | 9208 |
| 1344 | 99-23132-192 | A | G | A | 5278 | 9209 |
| 1345 | 99-23134-89 | A | G | A | 5279 | 9210 |
| 1346 | 99-2315-213 | A | G | A | 5280 | 9211 |
| 1347 | 99-23150-262 | A | C | S | 5281 | 9212 |
| 1348 | 99-2320-292 | C | T | S | 5282 | 9213 |
| 1349 | 99-23201-345 | C | T | S | 5283 | 9214 |

TABLE 1-continued

| SEQ ID No. | Marker Name | Preferred Allele 1ST | 2ND | microseq. primer | Amplification primer Upstream (PU) | Downstream (RP) |
|---|---|---|---|---|---|---|
| 1350 | 99-23202-185 | A | C | S | 5284 | 9215 |
| 1351 | 99-23204-262 | C | T | S | 5285 | 9216 |
| 1352 | 99-23207-281 | C | T | S | 5286 | 9217 |
| 1353 | 99-2321-82 | C | T | S | 5287 | 9218 |
| 1354 | 99-23228-176 | G | C | S | 5288 | 9219 |
| 1355 | 99-2324-338 | A | C | S | 5289 | 9220 |
| 1356 | 99-23266-146 | A | G | A | 5290 | 9221 |
| 1357 | 99-23269-263 | A | T | S | 5291 | 9222 |
| 1358 | 99-2328-535 | G | C | S | 5292 | 9223 |
| 1359 | 99-23299-424 | A | G | A | 5293 | 9224 |
| 1360 | 99-23302-326 | C | T | S | 5294 | 9225 |
| 1361 | 99-2331-639 | G | T | A | 5295 | 9226 |
| 1362 | 99-23312-93 | A | G | A | 5296 | 9227 |
| 1363 | 99-23317-51 | A | G | A | 5297 | 9228 |
| 1364 | 99-23322-49 | A | G | A | 5298 | 9229 |
| 1365 | 99-23326-120 | A | G | A | 5299 | 9230 |
| 1366 | 99-23328-292 | A | G | A | 5300 | 9231 |
| 1367 | 99-23333-157 | A | G | A | 5301 | 9232 |
| 1368 | 99-23334-443 | A | G | A | 5302 | 9233 |
| 1369 | 99-23359-99 | G | C | S | 5303 | 9234 |
| 1370 | 99-23381-412 | A | G | A | 5304 | 9235 |
| 1371 | 99-23387-404 | G | C | S | 5305 | 9236 |
| 1372 | 99-23413-242 | A | G | A | 5306 | 9237 |
| 1373 | 99-23415-131 | A | G | A | 5307 | 9238 |
| 1374 | 99-23417-128 | G | T | A | 5308 | 9239 |
| 1375 | 99-23437-347 | A | G | A | 5309 | 9240 |
| 1376 | 99-23440-274 | A | G | A | 5310 | 9241 |
| 1377 | 99-23444-203 | A | G | A | 5311 | 9242 |
| 1378 | 99-2345-28 | G | C | A | 5312 | 9243 |
| 1379 | 99-23451-78 | A | G | A | 5313 | 9244 |
| 1380 | 99-23452-306 | G | T | A | 5314 | 9245 |
| 1381 | 99-23454-317 | C | T | A | 5315 | 9246 |
| 1382 | 99-23460-199 | A | C | S | 5316 | 9247 |
| 1383 | 99-23462-192 | C | T | S | 5317 | 9248 |
| 1384 | 99-23463-118 | C | T | S | 5318 | 9249 |
| 1385 | 99-23469-288 | C | T | S | 5319 | 9250 |
| 1386 | 99-2347-207 | A | C | S | 5320 | 9251 |
| 1387 | 99-23473-35 | C | T | S | 5321 | 9252 |
| 1388 | 99-2348-127 | A | G | A | 5322 | 9253 |
| 1389 | 99-23488-239 | A | G | A | 5323 | 9254 |
| 1390 | 99-23492-151 | C | T | S | 5324 | 9255 |
| 1391 | 99-23496-94 | A | G | A | 5325 | 9256 |
| 1392 | 99-2351045 | A | G | A | 5326 | 9257 |
| 1393 | 99-23528-452 | C | T | S | 5327 | 9258 |
| 1394 | 99-2356-322 | A | G | A | 5328 | 9259 |
| 1395 | 99-2362-270 | A | G | A | 5329 | 9260 |
| 1396 | 99-2364-329 | G | C | S | 5330 | 9261 |
| 1397 | 99-2367-61 | A | G | A | 5331 | 9262 |
| 1398 | 99-2368-61 | A | G | A | 5332 | 9263 |
| 1399 | 99-23687-107 | C | T | A | 5333 | 9264 |
| 1400 | 99-237-151 | A | G | A | 5334 | 9265 |
| 1401 | 99-23714-196 | G | C | S | 5335 | 9266 |
| 1402 | 99-23737-186 | C | T | S | 5336 | 9267 |
| 1403 | 99-2375-114 | C | T | A | 5337 | 9268 |
| 1404 | 99-23773-199 | C | T | S | 5338 | 9269 |
| 1405 | 99-2378-200 | A | G | A | 5339 | 9270 |
| 1406 | 99-2381-394 | A | G | A | 5340 | 9271 |
| 1407 | 99-2409-298 | A | G | A | 5341 | 9272 |
| 1408 | 99-241-341 | A | T | S | 5342 | 9273 |
| 1409 | 99-2413-368 | A | G | A | 5343 | 9274 |
| 1410 | 99-2417-177 | C | T | S | 5344 | 9275 |
| 1411 | 99-2419-285 | C | T | S | 5345 | 9276 |
| 1412 | 99-24246-247 | C | T | A | 5346 | 9277 |
| 1413 | 99-24253-437 | A | G | S | 5347 | 9278 |
| 1414 | 99-24259-466 | A | T | S | 5348 | 9279 |
| 1415 | 99-24264-380 | G | C | S | 5349 | 9280 |
| 1416 | 99-24269-417 | C | T | A | 5350 | 9281 |
| 1417 | 99-24270-207 | G | T | A | 5351 | 9282 |
| 1418 | 99-24275-107 | A | G | S | 5352 | 9283 |
| 1419 | 99-24284-213 | A | T | S | 5353 | 9284 |
| 1420 | 99-24286-231 | A | G | S | 5354 | 9285 |
| 1421 | 99-24288-121 | A | G | S | 5355 | 9286 |
| 1422 | 99-24333-37 | A | G | S | 5356 | 9287 |
| 1423 | 99-24342-311 | C | T | A | 5357 | 9288 |
| 1424 | 99-24376-24 | A | G | S | 5358 | 9289 |
| 1425 | 99-24379-319 | C | T | S | 5359 | 9290 |
| 1426 | 99-24381-217 | A | G | S | 5360 | 9291 |
| 1427 | 99-24385-210 | A | T | S | 5361 | 9292 |
| 1428 | 99-24388-391 | A | T | S | 5362 | 9293 |
| 1429 | 99-24390-27 | A | G | S | 5363 | 9294 |
| 1430 | 99-24392-61 | A | C | S | 5364 | 9295 |
| 1431 | 99-24393-108 | A | G | S | 5365 | 9296 |
| 1432 | 99-2440-246 | C | T | S | 5366 | 9297 |
| 1433 | 99-24409-383 | A | G | S | 5367 | 9298 |
| 1434 | 99-24411-420 | G | C | S | 5368 | 9299 |
| 1435 | 99-24427-321 | A | G | S | 5369 | 9300 |
| 1436 | 99-24432-284 | A | C | S | 5370 | 9301 |
| 1437 | 99-24438-402 | A | G | S | 5371 | 9302 |
| 1438 | 99-24441-431 | C | T | A | 5372 | 9303 |
| 1439 | 99-24447-448 | A | T | S | 5373 | 9304 |
| 1440 | 99-2445-79 | C | T | S | 5374 | 9305 |
| 1441 | 99-24454-257 | G | C | S | 5375 | 9306 |
| 1442 | 99-24463-206 | A | G | S | 5376 | 9307 |
| 1443 | 99-24496-171 | C | T | A | 5377 | 9308 |
| 1444 | 99-24506-396 | A | G | S | 5378 | 9309 |
| 1445 | 99-24508-45 | G | C | S | 5379 | 9310 |
| 1446 | 99-24529-330 | A | G | S | 5380 | 9311 |
| 1447 | 99-24534-317 | G | C | S | 5381 | 9312 |
| 1448 | 99-24554-324 | A | G | A | 5382 | 9313 |
| 1449 | 99-24557-406 | G | T | A | 5383 | 9314 |
| 1450 | 99-24561-360 | A | T | S | 5384 | 9315 |
| 1451 | 99-24570-260 | G | C | S | 5385 | 9316 |
| 1452 | 99-24688-312 | C | T | A | 5386 | 9317 |
| 1453 | 99-24725-138 | A | G | S | 5387 | 9318 |
| 1454 | 99-24727-360 | A | G | S | 5388 | 9319 |
| 1455 | 99-24750-293 | C | T | A | 5389 | 9320 |
| 1456 | 99-24778-221 | C | T | A | 5390 | 9321 |
| 1457 | 99-24793-390 | C | T | A | 5391 | 9322 |
| 1458 | 99-24800-565 | G | T | S | 5392 | 9323 |
| 1459 | 99-25005-154 | A | C | S | 5393 | 9324 |
| 1460 | 99-25007-131 | A | T | S | 5394 | 9325 |
| 1461 | 99-25053-114 | A | G | S | 5395 | 9326 |
| 1462 | 99-25055-44 | A | G | S | 5396 | 9327 |
| 1463 | 99-25070-78 | C | T | A | 5397 | 9328 |
| 1464 | 99-25077-124 | A | G | S | 5398 | 9329 |
| 1465 | 99-25129-166 | C | T | A | 5399 | 9330 |
| 1466 | 99-25134-296 | A | G | S | 5400 | 9331 |
| 1467 | 99-2524-98 | A | G | A | 5401 | 9332 |
| 1468 | 99-25246-170 | C | T | A | 5402 | 9333 |
| 1469 | 99-25249-151 | G | T | A | 5403 | 9334 |
| 1470 | 99-2525-142 | A | G | S | 5404 | 9335 |
| 1471 | 99-25255-288 | C | T | A | 5405 | 9336 |
| 1472 | 99-25369-121 | C | T | S | 5406 | 9337 |
| 1473 | 99-25379-389 | C | T | S | 5407 | 9338 |
| 1474 | 99-25382-226 | A | C | S | 5408 | 9339 |
| 1475 | 99-25387-220 | G | T | A | 5409 | 9340 |
| 1476 | 99-25400-379 | C | T | S | 5410 | 9341 |
| 1477 | 99-25412-354 | G | T | A | 5411 | 9342 |
| 1478 | 99-25431-269 | A | C | S | 5412 | 9343 |
| 1479 | 99-25432-119 | C | T | S | 5413 | 9344 |
| 1480 | 99-25433-351 | A | G | S | 5414 | 9345 |
| 1481 | 99-25447-272 | A | G | S | 5415 | 9346 |
| 1482 | 99-25448-348 | G | T | A | 5416 | 9347 |
| 1483 | 99-25452-83 | C | T | A | 5417 | 9348 |
| 1484 | 99-25454-349 | G | T | A | 5418 | 9349 |
| 1485 | 99-25458-103 | G | C | S | 5419 | 9350 |
| 1486 | 99-25503-333 | A | T | S | 5420 | 9351 |
| 1487 | 99-25507-373 | C | T | A | 5421 | 9352 |
| 1488 | 99-25510-390 | A | C | S | 5422 | 9353 |
| 1489 | 99-25538-423 | A | C | S | 5423 | 9354 |
| 1490 | 99-25539-86 | C | T | A | 5424 | 9355 |
| 1491 | 99-25543-390 | A | G | S | 5425 | 9356 |
| 1492 | 99-25575-303 | C | T | A | 5426 | 9357 |
| 1493 | 99-25618-196 | A | C | S | 5427 | 9358 |
| 1494 | 99-25620-360 | C | T | A | 5428 | 9359 |
| 1495 | 99-25629-262 | A | G | S | 5429 | 9360 |

TABLE 1-continued

| SEQ ID No. | Marker Name | Allele 1ST | 2ND | Preferred microseq. primer | Amplification primer Upstream (PU) | Downstream (RP) |
|---|---|---|---|---|---|---|
| 1496 | 99-25657-314 | C | T | A | 5430 | 9361 |
| 1497 | 99-25672-97 | A | G | S | 5431 | 9362 |
| 1498 | 99-25676-211 | C | T | A | 5432 | 9363 |
| 1499 | 99-25678-307 | A | G | S | 5433 | 9364 |
| 1500 | 99-2570-218 | C | T | S | 5434 | 9365 |
| 1501 | 99-25712-418 | C | T | A | 5435 | 9366 |
| 1502 | 99-25716-393 | C | T | A | 5436 | 9367 |
| 1503 | 99-25717-252 | G | T | A | 5437 | 9368 |
| 1504 | 99-25725-80 | A | G | S | 5438 | 9369 |
| 1505 | 99-25732-152 | A | G | S | 5439 | 9370 |
| 1506 | 99-25745-36 | A | G | S | 5440 | 9371 |
| 1507 | 99-25781-275 | C | T | A | 5441 | 9372 |
| 1508 | 99-25836-106 | C | T | S | 5442 | 9373 |
| 1509 | 99-2597-34 | C | T | S | 5443 | 9374 |
| 1510 | 99-26001-224 | A | G | S | 5444 | 9375 |
| 1511 | 99-26002-93 | C | T | A | 5445 | 9376 |
| 1512 | 99-26042-310 | A | G | A | 5446 | 9377 |
| 1513 | 99-26080-152 | C | T | S | 5447 | 9378 |
| 1514 | 99-26082-48 | C | T | S | 5448 | 9379 |
| 1515 | 99-26099-119 | A | G | A | 5449 | 9380 |
| 1516 | 99-2610-121 | A | C | S | 5450 | 9381 |
| 1517 | 99-26105-273 | A | C | S | 5451 | 9382 |
| 1518 | 99-26116-191 | C | T | A | 5452 | 9383 |
| 1519 | 99-2615-83 | C | T | S | 5453 | 9384 |
| 1520 | 99-2620-227 | A | G | A | 5454 | 9385 |
| 1521 | 99-2624-407 | G | T | A | 5455 | 9386 |
| 1522 | 99-2625-70 | A | G | A | 5456 | 9387 |
| 1523 | 99-2637-28 | A | G | A | 5457 | 9388 |
| 1524 | 99-2662-407 | C | T | S | 5458 | 9389 |
| 1525 | 99-2669-233 | A | G | A | 5459 | 9390 |
| 1526 | 99-2675-121 | A | G | A | 5460 | 9391 |
| 1527 | 99-2683-388 | C | T | S | 5461 | 9392 |
| 1528 | 99-342-288 | A | C | S | 5462 | 9393 |
| 1529 | 99-370-205 | A | G | A | 5463 | 9394 |
| 1530 | 99-371-415 | C | T | S | 5464 | 9395 |
| 1531 | 99-388-405 | A | G | A | 5465 | 9396 |
| 1532 | 99-390-246 | G | T | S | 5466 | 9397 |
| 1533 | 99-393-448 | A | T | S | 5467 | 9398 |
| 1534 | 99-397-205 | A | G | A | 5468 | 9399 |
| 1535 | 99-400-102 | G | C | S | 5469 | 9400 |
| 1536 | 99-402-139 | A | G | A | 5470 | 9401 |
| 1537 | 99-404-114 | C | T | S | 5471 | 9402 |
| 1538 | 99-414-349 | G | C | S | 5472 | 9403 |
| 1539 | 99-417-241 | A | G | A | 5473 | 9404 |
| 1540 | 99-426-359 | G | T | S | 5474 | 9405 |
| 1541 | 99-429-115 | A | C | S | 5475 | 9406 |
| 1542 | 99-430-352 | C | T | S | 5476 | 9407 |
| 1543 | 99-435-41 | A | G | A | 5477 | 9408 |
| 1544 | 99-449-344 | G | T | S | 5478 | 9409 |
| 1545 | 99-4536-255 | A | G | A | 5479 | 9410 |
| 1546 | 99-4541-39 | G | T | A | 5480 | 9411 |
| 1547 | 99-4544-287 | A | G | A | 5481 | 9412 |
| 1548 | 99-4547-312 | C | T | S | 5482 | 9413 |
| 1549 | 99-4595-341 | A | T | S | 5483 | 9414 |
| 1550 | 99-4604-26 | A | T | S | 5484 | 9415 |
| 1551 | 994618-240 | C | T | S | 5485 | 9416 |
| 1552 | 99-4625-216 | C | T | S | 5486 | 9417 |
| 1553 | 99-4630-272 | A | G | A | 5487 | 9418 |
| 1554 | 99-4644-107 | A | T | S | 5488 | 9419 |
| 1555 | 99-465-443 | A | C | S | 5489 | 9420 |
| 1556 | 99-4655-145 | C | T | S | 5490 | 9421 |
| 1557 | 99-466-361 | C | T | S | 5491 | 9422 |
| 1558 | 99-4666-185 | C | T | S | 5492 | 9423 |
| 1559 | 99-4674-166 | A | G | A | 5493 | 9424 |
| 1560 | 99-4676-342 | A | G | S | 5494 | 9425 |
| 1561 | 99-4677-58 | C | T | S | 5495 | 9426 |
| 1562 | 99-4679-240 | C | T | A | 5496 | 9427 |
| 1563 | 99-4680-352 | C | T | S | 5497 | 9428 |
| 1564 | 99-4681-228 | A | G | A | 5498 | 9429 |
| 1565 | 99-4682-177 | C | T | S | 5499 | 9430 |
| 1566 | 99-4685-217 | A | G | A | 5500 | 9431 |
| 1567 | 99-4705-226 | G | C | S | 5501 | 9432 |
| 1568 | 99-4714-156 | A | G | A | 5502 | 9433 |
| 1569 | 99-472-70 | C | T | S | 5503 | 9434 |
| 1570 | 99-4725-251 | A | T | S | 5504 | 9435 |
| 1571 | 99-4756-236 | C | T | S | 5505 | 9436 |
| 1572 | 99-4761-279 | A | G | A | 5506 | 9437 |
| 1573 | 99-4777-302 | A | G | A | 5507 | 9438 |
| 1574 | 99-4777-137 | G | C | S | 5508 | 9439 |
| 1575 | 99-4790-305 | A | G | A | 5509 | 9440 |
| 1576 | 99-4796-325 | A | C | S | 5510 | 9441 |
| 1577 | 99-482-130 | C | T | S | 5511 | 9442 |
| 1578 | 99-4822-291 | A | G | A | 5512 | 9443 |
| 1579 | 994823-173 | G | T | A | 5513 | 9444 |
| 1580 | 99-483-424 | A | C | S | 5514 | 9445 |
| 1581 | 99-4836-206 | A | G | A | 5515 | 9446 |
| 1582 | 99-4838-424 | C | T | S | 5516 | 9447 |
| 1583 | 99-4840-368 | C | T | S | 5517 | 9448 |
| 1584 | 99-4844-102 | C | T | S | 5518 | 9449 |
| 1585 | 99-486-243 | C | T | S | 5519 | 9450 |
| 1586 | 99-4863-240 | C | T | S | 5520 | 9451 |
| 1587 | 99-4882-351 | A | T | S | 5521 | 9452 |
| 1588 | 99-4890-255 | G | T | A | 5522 | 9453 |
| 1589 | 99-4891-509 | A | C | S | 5523 | 9454 |
| 1590 | 99-4895-158 | C | T | S | 5524 | 9455 |
| 1591 | 99-490-202 | C | T | S | 5525 | 9456 |
| 1592 | 99-4924-254 | C | T | S | 5526 | 9457 |
| 1593 | 99-4928-102 | C | T | S | 5527 | 9458 |
| 1594 | 99-4950-196 | A | C | S | 5528 | 9459 |
| 1595 | 99-4951-36 | C | T | A | 5529 | 9460 |
| 1596 | 99-4956-236 | A | G | A | 5530 | 9461 |
| 1597 | 99-4966-298 | A | G | A | 5531 | 9462 |
| 1598 | 99-4968-273 | C | T | S | 5532 | 9463 |
| 1599 | 99-5016-206 | C | T | S | 5533 | 9464 |
| 1600 | 99-5029-240 | G | T | A | 5534 | 9465 |
| 1601 | 99-5032-232 | A | C | S | 5535 | 9466 |
| 1602 | 99-5036-40 | C | T | S | 5536 | 9467 |
| 1603 | 99-5038-181 | C | T | S | 5537 | 9468 |
| 1604 | 99-5043-111 | A | C | S | 5538 | 9469 |
| 1605 | 99-5099-245 | A | G | A | 5539 | 9470 |
| 1606 | 99-5101-284 | G | T | A | 5540 | 9471 |
| 1607 | 99-5104-160 | A | G | A | 5541 | 9472 |
| 1608 | 99-5107-184 | G | T | A | 5542 | 9473 |
| 1609 | 99-5108-144 | A | G | A | 5543 | 9474 |
| 1610 | 99-511-33 | C | T | S | 5544 | 9475 |
| 1611 | 99-5130-355 | C | T | S | 5545 | 9476 |
| 1612 | 99-5142-74 | C | T | S | 5546 | 9477 |
| 1613 | 99-5148-269 | G | C | S | 5547 | 9478 |
| 1614 | 99-5149-436 | C | T | S | 5548 | 9479 |
| 1615 | 99-5157-422 | G | C | S | 5549 | 9480 |
| 1616 | 99-5162461 | C | T | S | 5550 | 9481 |
| 1617 | 99-5168-220 | C | T | S | 5551 | 9482 |
| 1618 | 99-5184-146 | A | G | A | 5552 | 9483 |
| 1619 | 99-5186-455 | A | G | A | 5553 | 9484 |
| 1620 | 99-5189-412 | C | T | S | 5554 | 9485 |
| 1621 | 99-5193-430 | A | G | A | 5555 | 9486 |
| 1622 | 99-5194-145 | A | G | A | 5556 | 9487 |
| 1623 | 99-5199-108 | A | T | S | 5557 | 9488 |
| 1624 | 99-5202-145 | A | G | A | 5558 | 9489 |
| 1625 | 99-5224-293 | G | C | S | 5559 | 9490 |
| 1626 | 99-5225-198 | C | T | S | 5560 | 9491 |
| 1627 | 99-5226-215 | A | G | A | 5561 | 9492 |
| 1628 | 99-5247-158 | A | G | A | 5562 | 9493 |
| 1629 | 99-5252-252 | A | G | A | 5563 | 9494 |
| 1630 | 99-5265-288 | C | T | S | 5564 | 9495 |
| 1631 | 99-5290-322 | C | T | S | 5565 | 9496 |
| 1632 | 99-5291-331 | A | C | S | 5566 | 9497 |
| 1633 | 99-5294-362 | A | C | S | 5567 | 9498 |
| 1634 | 99-5306-93 | C | T | S | 5568 | 9499 |
| 1635 | 99-5308-341 | G | C | S | 5569 | 9500 |
| 1636 | 99-5312-273 | C | T | S | 5570 | 9501 |
| 1637 | 99-5326-332 | A | G | A | 5571 | 9502 |
| 1638 | 99-5338-151 | C | T | S | 5572 | 9503 |
| 1639 | 99-5355-165 | A | G | A | 5573 | 9504 |
| 1640 | 99-5356-100 | A | T | S | 5574 | 9505 |
| 1641 | 99-5360-151 | C | T | S | 5575 | 9506 |

TABLE 1-continued

| SEQ ID No. | Marker Name | Allele 1ST | 2ND | Preferred microseq. primer | Amplification primer Upstream (PU) | Downstream (RP) |
|---|---|---|---|---|---|---|
| 1642 | 99-5362-203 | C | T | S | 5576 | 9507 |
| 1643 | 99-5364-95 | C | T | A | 5577 | 9508 |
| 1644 | 99-5379-158 | A | G | A | 5578 | 9509 |
| 1645 | 99-5386-85 | A | G | A | 5579 | 9510 |
| 1646 | 99-5389-409 | A | G | A | 5580 | 9511 |
| 1647 | 99-5390-375 | C | T | S | 5581 | 9512 |
| 1648 | 99-5401-280 | C | T | S | 5582 | 9513 |
| 1649 | 99-5405-376 | C | T | S | 5583 | 9514 |
| 1650 | 99-5406-299 | A | T | S | 5584 | 9515 |
| 1651 | 99-5407-173 | C | T | S | 5585 | 9516 |
| 1652 | 99-5411-378 | C | T | S | 5586 | 9517 |
| 1653 | 99-5416-137 | A | G | A | 5587 | 9518 |
| 1654 | 99-5420-425 | G | C | S | 5588 | 9519 |
| 1655 | 99-5427-466 | A | G | A | 5589 | 9520 |
| 1656 | 99-5432-391 | G | C | S | 5590 | 9521 |
| 1657 | 99-5433-45 | C | T | S | 5591 | 9522 |
| 1658 | 99-5437-159 | A | G | A | 5592 | 9523 |
| 1659 | 99-5438-70 | C | T | S | 5593 | 9524 |
| 1660 | 99-5441-287 | C | T | S | 5594 | 9525 |
| 1661 | 99-5446-303 | C | T | S | 5595 | 9526 |
| 1662 | 99-5447-322 | A | G | A | 5596 | 9527 |
| 1663 | 99-5458-203 | C | T | S | 5597 | 9528 |
| 1664 | 99-5468-319 | A | C | S | 5598 | 9529 |
| 1665 | 99-5472-290 | C | T | S | 5599 | 9530 |
| 1666 | 99-5475-455 | A | G | A | 5600 | 9531 |
| 1667 | 99-5477-207 | A | C | S | 5601 | 9532 |
| 1668 | 99-5485-325 | A | G | A | 5602 | 9533 |
| 1669 | 99-5490-368 | C | T | S | 5603 | 9534 |
| 1670 | 99-5494-205 | A | G | A | 5604 | 9535 |
| 1671 | 99-5502-433 | A | C | S | 5605 | 9536 |
| 1672 | 99-5505-226 | C | T | S | 5606 | 9537 |
| 1673 | 99-5516-121 | C | T | S | 5607 | 9538 |
| 1674 | 99-5526-334 | C | T | S | 5608 | 9539 |
| 1675 | 99-5566-131 | A | G | A | 5609 | 9540 |
| 1676 | 99-5582-71 | G | C | S | 5610 | 9541 |
| 1677 | 99-5590-99 | C | T | S | 5611 | 9542 |
| 1678 | 99-5595-380 | A | G | A | 5612 | 9543 |
| 1679 | 99-5596-216 | A | G | A | 5613 | 9544 |
| 1680 | 99-5604-376 | A | G | A | 5614 | 9545 |
| 1681 | 99-5608-324 | A | G | A | 5615 | 9546 |
| 1682 | 99-5632-425 | A | G | A | 5616 | 9547 |
| 1683 | 99-5633-334 | A | G | A | 5617 | 9548 |
| 1684 | 99-5634-426 | C | T | S | 5618 | 9549 |
| 1685 | 99-5636-198 | C | T | S | 5619 | 9550 |
| 1686 | 99-5660-265 | G | C | S | 5620 | 9551 |
| 1687 | 99-5670-264 | C | T | S | 5621 | 9552 |
| 1688 | 99-5678-321 | A | G | A | 5622 | 9553 |
| 1689 | 99-5680-109 | A | G | A | 5623 | 9554 |
| 1690 | 99-5681-81 | C | T | S | 5624 | 9555 |
| 1691 | 99-5685-274 | A | T | S | 5625 | 9556 |
| 1692 | 99-5686-274 | G | C | S | 5626 | 9557 |
| 1693 | 99-5700-142 | G | C | S | 5627 | 9558 |
| 1694 | 99-5702-192 | C | T | S | 5628 | 9559 |
| 1695 | 99-5703-72 | C | T | S | 5629 | 9560 |
| 1696 | 99-5709-80 | A | G | A | 5630 | 9561 |
| 1697 | 99-5711-206 | C | T | S | 5631 | 9562 |
| 1698 | 99-5712-123 | A | T | S | 5632 | 9563 |
| 1699 | 99-5727-77 | C | T | S | 5633 | 9564 |
| 1700 | 99-5729-370 | A | G | A | 5634 | 9565 |
| 1701 | 99-5731-450 | G | T | A | 5635 | 9566 |
| 1702 | 99-5741-59 | A | G | A | 5636 | 9567 |
| 1703 | 99-5742-337 | C | T | S | 5637 | 9568 |
| 1704 | 99-5745-256 | G | C | S | 5638 | 9569 |
| 1705 | 99-5756-233 | A | G | A | 5639 | 9570 |
| 1706 | 99-576-421 | G | C | S | 5640 | 9571 |
| 1707 | 99-5760-164 | A | G | A | 5641 | 9572 |
| 1708 | 99-5770-275 | C | T | S | 5642 | 9573 |
| 1709 | 99-5781-110 | G | C | S | 5643 | 9574 |
| 1710 | 99-5795-234 | A | C | S | 5644 | 9575 |
| 1711 | 99-5813-34 | A | T | S | 5645 | 9576 |
| 1712 | 99-582-132 | A | G | S | 5646 | 9577 |
| 1713 | 99-5832-136 | C | T | S | 5647 | 9578 |
| 1714 | 99-5836-327 | C | T | S | 5648 | 9579 |
| 1715 | 99-5837-407 | C | T | S | 5649 | 9580 |
| 1716 | 99-5860-278 | A | G | A | 5650 | 9581 |
| 1717 | 99-5867-284 | G | T | A | 5651 | 9582 |
| 1718 | 99-5875-411 | A | G | A | 5652 | 9583 |
| 1719 | 99-5893-211 | A | G | A | 5653 | 9584 |
| 1720 | 99-5907-143 | C | T | S | 5654 | 9585 |
| 1721 | 99-5908-225 | A | G | A | 5655 | 9586 |
| 1722 | 99-5909-292 | C | T | S | 5656 | 9587 |
| 1723 | 99-5912-49 | A | G | A | 5657 | 9588 |
| 1724 | 99-5915-378 | A | G | A | 5658 | 9589 |
| 1725 | 99-5951-438 | C | T | S | 5659 | 9590 |
| 1726 | 99-5957-123 | G | C | S | 5660 | 9591 |
| 1727 | 99-596-228 | G | C | S | 5661 | 9592 |
| 1728 | 99-5968-382 | A | T | S | 5662 | 9593 |
| 1729 | 99-5979-96 | C | T | S | 5663 | 9594 |
| 1730 | 99-598-130 | A | G | A | 5664 | 9595 |
| 1731 | 99-6007-246 | A | C | S | 5665 | 9596 |
| 1732 | 99-6012-220 | G | T | A | 5666 | 9597 |
| 1733 | 99-602-258 | A | G | A | 5667 | 9598 |
| 1734 | 99-6038-286 | A | G | S | 5668 | 9599 |
| 1735 | 99-6042-134 | G | C | S | 5669 | 9600 |
| 1736 | 99-6051-251 | G | C | S | 5670 | 9601 |
| 1737 | 99-6067-247 | C | T | S | 5671 | 9602 |
| 1738 | 99-6069-41 | A | G | A | 5672 | 9603 |
| 1739 | 99-607-397 | A | G | A | 5673 | 9604 |
| 1740 | 99-6077-346 | C | T | S | 5674 | 9605 |
| 1741 | 99-6079-343 | A | G | A | 5675 | 9606 |
| 1742 | 99-608-183 | G | T | A | 5676 | 9607 |
| 1743 | 99-6080-99 | C | T | S | 5677 | 9608 |
| 1744 | 99-609-225 | A | T | S | 5678 | 9609 |
| 1745 | 99-6091-305 | A | G | A | 5679 | 9610 |
| 1746 | 99-6094-223 | C | T | S | 5680 | 9611 |
| 1747 | 99-6095-316 | A | G | A | 5681 | 9612 |
| 1748 | 99-6097-202 | G | T | A | 5682 | 9613 |
| 1749 | 99-610-250 | A | G | A | 5683 | 9614 |
| 1750 | 99-6112-275 | C | T | S | 5684 | 9615 |
| 1751 | 99-6117-221 | A | G | A | 5685 | 9616 |
| 1752 | 99-6122-100 | A | G | A | 5686 | 9617 |
| 1753 | 99-6131-166 | A | G | A | 5687 | 9618 |
| 1754 | 99-6135-319 | C | T | S | 5688 | 9619 |
| 1755 | 99-614-346 | G | C | S | 5689 | 9620 |
| 1756 | 99-6141-339 | C | T | S | 5690 | 9621 |
| 1757 | 99-615-387 | A | C | S | 5691 | 9622 |
| 1758 | 99-616-338 | A | G | A | 5692 | 9623 |
| 1759 | 99-6176-96 | A | G | A | 5693 | 9624 |
| 1760 | 99-6180-389 | G | T | A | 5694 | 9625 |
| 1761 | 99-6181-328 | A | C | S | 5695 | 9626 |
| 1762 | 99-6189-224 | A | G | A | 5696 | 9627 |
| 1763 | 99-619-141 | C | T | S | 5697 | 9628 |
| 1764 | 99-6191-252 | A | C | S | 5698 | 9629 |
| 1765 | 99-6193-88 | C | T | S | 5699 | 9630 |
| 1766 | 99-621-215 | A | G | A | 5700 | 9631 |
| 1767 | 99-6217-420 | C | T | S | 5701 | 9632 |
| 1768 | 99-622-95 | A | G | A | 5702 | 9633 |
| 1769 | 99-6253-308 | C | T | S | 5703 | 9634 |
| 1770 | 99-6257-226 | C | T | S | 5704 | 9635 |
| 1771 | 99-6261-172 | A | C | S | 5705 | 9636 |
| 1772 | 99-6278-391 | C | T | S | 5706 | 9637 |
| 1773 | 99-6294-184 | C | T | S | 5707 | 9638 |
| 1774 | 99-6298-280 | A | C | S | 5708 | 9639 |
| 1775 | 99-6300-106 | G | C | S | 5709 | 9640 |
| 1776 | 99-6310-217 | G | C | S | 5710 | 9641 |
| 1777 | 99-632-173 | C | T | S | 5711 | 9642 |
| 1778 | 99-6327-270 | A | C | S | 5712 | 9643 |
| 1779 | 99-6332-143 | C | T | S | 5713 | 9644 |
| 1780 | 99-6367-268 | A | C | S | 5714 | 9645 |
| 1781 | 99-6368-426 | A | G | A | 5715 | 9646 |
| 1782 | 99-6404-147 | A | G | A | 5716 | 9647 |
| 1783 | 99-6409-62 | C | T | S | 5717 | 9648 |
| 1784 | 99-6411-93 | A | G | A | 5718 | 9649 |
| 1785 | 99-6413-369 | C | T | S | 5719 | 9650 |
| 1786 | 99-6415-279 | C | T | S | 5720 | 9651 |
| 1787 | 99-6421-210 | C | T | S | 5721 | 9652 |

TABLE 1-continued

| SEQ ID No. | Marker Name | Preferred Allele 1ST | 2ND | microseq. primer | Amplification primer Upstream (PU) | Downstream (RP) |
|---|---|---|---|---|---|---|
| 1788 | 99-6423-90 | G | C | S | 5722 | 9653 |
| 1789 | 99-6426-413 | A | G | A | 5723 | 9654 |
| 1790 | 99-6427-190 | A | G | A | 5724 | 9655 |
| 1791 | 99-6435-343 | A | G | A | 5725 | 9656 |
| 1792 | 99-6437-77 | A | C | S | 5726 | 9657 |
| 1793 | 99-6440-318 | G | C | S | 5727 | 9658 |
| 1794 | 99-6447-178 | C | T | S | 5728 | 9659 |
| 1795 | 99-6456-165 | C | T | S | 5729 | 9660 |
| 1796 | 99-6459-201 | A | G | A | 5730 | 9661 |
| 1797 | 99-646-271 | C | T | S | 5731 | 9662 |
| 1798 | 99-6463-348 | A | C | S | 5732 | 9663 |
| 1799 | 99-6468-288 | A | G | A | 5733 | 9664 |
| 1800 | 99-6478-358 | A | G | A | 5734 | 9665 |
| 1801 | 99-6480-440 | A | G | A | 5735 | 9666 |
| 1802 | 99-6489-237 | G | T | A | 5736 | 9667 |
| 1803 | 99-649-422 | A | T | S | 5737 | 9668 |
| 1804 | 99-6496-340 | A | G | A | 5738 | 9669 |
| 1805 | 99-6511-176 | C | T | S | 5739 | 9670 |
| 1806 | 99-6525-196 | C | T | S | 5740 | 9671 |
| 1807 | 99-6527-95 | A | C | S | 5741 | 9672 |
| 1808 | 99-6529-519 | C | T | S | 5742 | 9673 |
| 1809 | 99-6539-298 | A | G | A | 5743 | 9674 |
| 1810 | 99-6557-401 | A | G | A | 5744 | 9675 |
| 1811 | 99-658-367 | A | G | A | 5745 | 9676 |
| 1812 | 99-6581-45 | C | T | S | 5746 | 9677 |
| 1813 | 99-6586-359 | A | G | A | 5747 | 9678 |
| 1814 | 99-6588-94 | C | T | S | 5748 | 9679 |
| 1815 | 99-6595-322 | G | C | S | 5749 | 9680 |
| 1816 | 99-6609-103 | C | T | S | 5750 | 9681 |
| 1817 | 99-6612-185 | G | T | A | 5751 | 9682 |
| 1818 | 99-6613-223 | G | C | S | 5752 | 9683 |
| 1819 | 99-6620-294 | A | C | S | 5753 | 9684 |
| 1820 | 99-6628-474 | A | C | S | 5754 | 9685 |
| 1821 | 99-6639-290 | C | T | S | 5755 | 9686 |
| 1822 | 99-6640-342 | A | T | S | 5756 | 9687 |
| 1823 | 99-6646-465 | A | G | A | 5757 | 9688 |
| 1824 | 99-6667-63 | C | T | S | 5758 | 9689 |
| 1825 | 99-6672-314 | G | T | A | 5759 | 9690 |
| 1826 | 99-6675-324 | A | G | A | 5760 | 9691 |
| 1827 | 99-6688-363 | A | G | A | 5761 | 9692 |
| 1828 | 99-669-291 | A | C | S | 5762 | 9693 |
| 1829 | 99-6697-80 | A | T | S | 5763 | 9694 |
| 1830 | 99-670-274 | A | G | A | 5764 | 9695 |
| 1831 | 99-6705-101 | C | T | S | 5765 | 9696 |
| 1832 | 99-6706-308 | C | T | S | 5766 | 9697 |
| 1833 | 99-6715-439 | C | T | S | 5767 | 9698 |
| 1834 | 99-6726-341 | A | T | S | 5768 | 9699 |
| 1835 | 99-6730-356 | A | G | A | 5769 | 9700 |
| 1836 | 99-6753-79 | A | C | S | 5770 | 9701 |
| 1837 | 99-6757-288 | G | T | A | 5771 | 9702 |
| 1838 | 99-676-357 | A | G | A | 5772 | 9703 |
| 1839 | 99-6781-263 | G | T | A | 5773 | 9704 |
| 1840 | 99-6790-378 | C | T | S | 5774 | 9705 |
| 1841 | 99-680-228 | A | G | A | 5775 | 9706 |
| 1842 | 99-6804-426 | A | G | A | 5776 | 9707 |
| 1843 | 99-6815-484 | G | C | S | 5777 | 9708 |
| 1844 | 99-6820-251 | A | G | A | 5778 | 9709 |
| 1845 | 99-6832-178 | C | T | S | 5779 | 9710 |
| 1846 | 99-6856-433 | A | G | A | 5780 | 9711 |
| 1847 | 99-6865-455 | C | T | S | 5781 | 9712 |
| 1848 | 99-6866-130 | A | G | A | 5782 | 9713 |
| 1849 | 99-6869-256 | A | G | A | 5783 | 9714 |
| 1850 | 99-6876-229 | C | T | S | 5784 | 9715 |
| 1851 | 99-689-219 | C | T | S | 5785 | 9716 |
| 1852 | 99-6893-392 | C | T | S | 5786 | 9717 |
| 1853 | 99-6895-144 | A | T | S | 5787 | 9718 |
| 1854 | 99-6938-347 | G | T | A | 5788 | 9719 |
| 1855 | 99-694-236 | G | T | A | 5789 | 9720 |
| 1856 | 99-6940-464 | A | G | A | 5790 | 9721 |
| 1857 | 99-6942-313 | A | C | S | 5791 | 9722 |
| 1858 | 99-6951-410 | G | T | A | 5792 | 9723 |
| 1859 | 99-6956-58 | C | T | S | 5793 | 9724 |
| 1860 | 99-6957-137 | G | C | S | 5794 | 9725 |
| 1861 | 99-6960-412 | A | T | S | 5795 | 9726 |
| 1862 | 99-6962-34 | G | C | S | 5796 | 9727 |
| 1863 | 99-6979-64 | C | T | S | 5797 | 9728 |
| 1864 | 99-6986-157 | A | G | A | 5798 | 9729 |
| 1865 | 99-6988-236 | A | C | S | 5799 | 9730 |
| 1866 | 99-6989-397 | A | G | A | 5800 | 9731 |
| 1867 | 99-6996-217 | C | T | S | 5801 | 9732 |
| 1868 | 99-700-123 | A | G | A | 5802 | 9733 |
| 1869 | 99-7000-235 | G | C | S | 5803 | 9734 |
| 1870 | 99-7004-304 | A | G | A | 5804 | 9735 |
| 1871 | 99-7013-250 | C | T | S | 5805 | 9736 |
| 1872 | 99-7024-122 | G | T | A | 5806 | 9737 |
| 1873 | 99-7025-226 | C | T | S | 5807 | 9738 |
| 1874 | 99-7026-247 | C | T | S | 5808 | 9739 |
| 1875 | 99-7047-225 | C | T | S | 5809 | 9740 |
| 1876 | 99-7056-49 | A | G | A | 5810 | 9741 |
| 1877 | 99-708-243 | C | T | S | 5811 | 9742 |
| 1878 | 99-7084-187 | C | T | S | 5812 | 9743 |
| 1879 | 99-7090-294 | A | G | A | 5813 | 9744 |
| 1880 | 99-7093-36 | A | C | S | 5814 | 9745 |
| 1881 | 99-7098-382 | A | G | A | 5815 | 9746 |
| 1882 | 99-7103-155 | C | T | S | 5816 | 9747 |
| 1883 | 99-7104-187 | A | G | A | 5817 | 9748 |
| 1884 | 99-7107-143 | A | G | A | 5818 | 9749 |
| 1885 | 99-7114-31 | A | G | A | 5819 | 9750 |
| 1886 | 99-7119-278 | A | G | A | 5820 | 9751 |
| 1887 | 99-7129-335 | A | C | S | 5821 | 9752 |
| 1888 | 99-7131-259 | C | T | S | 5822 | 9753 |
| 1889 | 99-7136-329 | C | T | S | 5823 | 9754 |
| 1890 | 99-7137-420 | C | T | S | 5824 | 9755 |
| 1891 | 99-7140-355 | A | G | A | 5825 | 9756 |
| 1892 | 99-7141-395 | A | G | A | 5826 | 9757 |
| 1893 | 99-7144-261 | C | j | S | 5827 | 9758 |
| 1894 | 99-7148-262 | C | T | S | 5828 | 9759 |
| 1895 | 99-7167-438 | A | G | A | 5829 | 9760 |
| 1896 | 99-7172-441 | A | G | A | 5830 | 9761 |
| 1897 | 99-7177-81 | C | T | S | 5831 | 9762 |
| 1898 | 99-718-261 | A | G | A | 5832 | 9763 |
| 1899 | 99-7183-338 | A | G | A | 5833 | 9764 |
| 1900 | 99-7193-228 | G | C | S | 5834 | 9765 |
| 1901 | 99-72-109 | C | T | S | 5835 | 9766 |
| 1902 | 99-7212-346 | C | T | S | 5836 | 9767 |
| 1903 | 99-7214-109 | C | T | S | 5837 | 9768 |
| 1904 | 99-7218-444 | C | T | S | 5838 | 9769 |
| 1905 | 99-7234-101 | A | T | S | 5839 | 9770 |
| 1906 | 99-724-246 | A | G | A | 5840 | 9771 |
| 1907 | 99-7252-279 | C | T | S | 5841 | 9772 |
| 1908 | 99-7274-172 | C | T | S | 5842 | 9773 |
| 1909 | 99-7275-150 | C | T | S | 5843 | 9774 |
| 1910 | 99-7276-286 | A | G | A | 5844 | 9775 |
| 1911 | 99-7293-201 | A | G | A | 5845 | 9776 |
| 1912 | 99-73-140 | C | T | S | 5846 | 9777 |
| 1913 | 99-7311-179 | A | G | A | 5847 | 9778 |
| 1914 | 99-7312-177 | A | G | A | 5848 | 9779 |
| 1915 | 99-7323-178 | A | C | S | 5849 | 9780 |
| 1916 | 99-7326-94 | G | C | S | 5850 | 9781 |
| 1917 | 99-7334-350 | C | T | S | 5851 | 9782 |
| 1918 | 99-734-126 | C | T | S | 5852 | 9783 |
| 1919 | 99-7349-384 | G | C | S | 5853 | 9784 |
| 1920 | 99-7356-176 | A | G | A | 5854 | 9785 |
| 1921 | 99-7363-474 | C | T | S | 5855 | 9786 |
| 1922 | 99-737-372 | A | G | A | 5856 | 9787 |
| 1923 | 99-7373-339 | A | G | A | 5857 | 9788 |
| 1924 | 99-7374-230 | A | G | A | 5858 | 9789 |
| 1925 | 99-7375-210 | C | T | S | 5859 | 9790 |
| 1926 | 99-7376-157 | A | T | S | 5860 | 9791 |
| 1927 | 99-7380-255 | A | G | A | 5861 | 9792 |
| 1928 | 99-7387-414 | C | T | S | 5862 | 9793 |
| 1929 | 99-7391-356 | C | T | S | 5863 | 9794 |
| 1930 | 99-7396-228 | A | T | S | 5864 | 9795 |
| 1931 | 99-7402-110 | C | T | S | 5865 | 9796 |
| 1932 | 99-7405-92 | C | T | S | 5866 | 9797 |
| 1933 | 99-7406-380 | A | G | A | 5867 | 9798 |

TABLE 1-continued

| SEQ ID No. | Marker Name | Preferred Allele 1ST | 2ND | microseq. primer | Amplification primer Upstream (PU) | Downstream (RP) |
|---|---|---|---|---|---|---|
| 1934 | 99-7417-440 | C | T | S | 5868 | 9799 |
| 1935 | 99-7429-204 | G | T | A | 5869 | 9800 |
| 1936 | 99-7447-281 | G | C | S | 5870 | 9801 |
| 1937 | 99-7453-405 | C | T | S | 5871 | 9802 |
| 1938 | 99-7454-35 | G | C | S | 5872 | 9803 |
| 1939 | 99-747-252 | A | G | A | 5873 | 9804 |
| 1940 | 99-7475-179 | G | T | A | 5874 | 9805 |
| 1941 | 99-7480-66 | A | G | A | 5875 | 9806 |
| 1942 | 99-7492-275 | C | T | S | 5876 | 9807 |
| 1943 | 99-7493-249 | G | C | S | 5877 | 9808 |
| 1944 | 99-7502-382 | A | T | S | 5878 | 9809 |
| 1945 | 99-7504-342 | A | C | S | 5879 | 9810 |
| 1946 | 99-7520-222 | A | G | A | 5880 | 9811 |
| 1947 | 99-7524-130 | A | G | A | 5881 | 9812 |
| 1948 | 99-7543-467 | A | G | A | 5882 | 9813 |
| 1949 | 99-755-83 | A | T | S | 5883 | 9814 |
| 1950 | 99-7598-388 | A | G | A | 5884 | 9815 |
| 1951 | 99-760-261 | C | T | S | 5885 | 9816 |
| 1952 | 99-7604-309 | A | G | A | 5886 | 9817 |
| 1953 | 99-7605-62 | G | C | S | 5887 | 9818 |
| 1954 | 99-7608-388 | C | T | S | 5888 | 9819 |
| 1955 | 99-7610-444 | C | T | S | 5889 | 9820 |
| 1956 | 99-7611-156 | A | G | A | 5890 | 9821 |
| 1957 | 99-7614-28 | A | T | S | 5891 | 9822 |
| 1958 | 99-763-240 | A | G | A | 5892 | 9823 |
| 1959 | 99-7642-191 | A | G | A | 5893 | 9824 |
| 1960 | 99-7643-350 | C | T | S | 5894 | 9825 |
| 1961 | 99-7650-187 | G | C | S | 5895 | 9826 |
| 1962 | 99-7671-33 | G | C | S | 5896 | 9827 |
| 1963 | 99-7677-107 | C | T | S | 5897 | 9828 |
| 1964 | 99-7688-325 | C | T | S | 5898 | 9829 |
| 1965 | 99-7692-340 | A | G | A | 5899 | 9830 |
| 1966 | 99-77-318 | A | C | A | 5900 | 9831 |
| 1967 | 99-7706-303 | A | G | A | 5901 | 9832 |
| 1968 | 99-771-391 | A | G | A | 5902 | 9833 |
| 1969 | 99-7710-318 | C | T | S | 5903 | 9834 |
| 1970 | 99-7712-176 | C | T | S | 5904 | 9835 |
| 1971 | 99-7721-379 | A | C | A | 5905 | 9836 |
| 1972 | 99-7727-65 | C | T | S | 5906 | 9837 |
| 1973 | 99-7728-334 | A | G | A | 5907 | 9838 |
| 1974 | 99-7732-122 | C | T | S | 5908 | 9839 |
| 1975 | 99-7737-264 | A | G | A | 5909 | 9840 |
| 1976 | 99-7744-255 | G | C | S | 5910 | 9841 |
| 1977 | 99-7745-305 | G | C | S | 5911 | 9842 |
| 1978 | 99-7749-123 | C | T | S | 5912 | 9843 |
| 1979 | 99-7751-450 | A | G | A | 5913 | 9844 |
| 1980 | 99-7753-199 | G | C | S | 5914 | 9845 |
| 1981 | 99-7754-119 | G | T | A | 5915 | 9846 |
| 1982 | 99-7759-63 | G | T | A | 5916 | 9847 |
| 1983 | 99-7762-227 | A | G | A | 5917 | 9848 |
| 1984 | 99-7764-161 | A | G | A | 5918 | 9849 |
| 1985 | 99-7775-313 | C | T | A | 5919 | 9850 |
| 1986 | 99-7784-31 | C | T | S | 5920 | 9851 |
| 1987 | 99-7789-404 | G | T | A | 5921 | 9852 |
| 1988 | 99-7792-173 | C | T | A | 5922 | 9853 |
| 1989 | 99-7796-130 | G | C | S | 5923 | 9854 |
| 1990 | 99-7803-253 | A | G | A | 5924 | 9855 |
| 1991 | 99-781-64 | A | G | A | 5925 | 9856 |
| 1992 | 99-7840-281 | A | C | S | 5926 | 9857 |
| 1993 | 99-785-360 | A | G | A | 5927 | 9858 |
| 1994 | 99-7868-204 | A | G | A | 5928 | 9859 |
| 1995 | 99-7869-135 | G | C | S | 5929 | 9860 |
| 1996 | 99-7870-316 | A | C | S | 5930 | 9861 |
| 1997 | 99-7877-363 | A | G | A | 5931 | 9862 |
| 1998 | 99-7882-43 | A | G | A | 5932 | 9863 |
| 1999 | 99-7883-411 | G | C | S | 5933 | 9864 |
| 2000 | 99-7884-151 | G | T | A | 5934 | 9865 |
| 2001 | 99-7893-226 | A | G | A | 5935 | 9866 |
| 2002 | 99-7898-43 | A | T | S | 5936 | 9867 |
| 2003 | 99-7900-452 | A | G | A | 5937 | 9868 |
| 2004 | 99-791-236 | C | T | S | 5938 | 9869 |
| 2005 | 99-7917-429 | A | C | S | 5939 | 9870 |
| 2006 | 99-794-393 | G | C | S | 5940 | 9871 |
| 2007 | 99-7949-301 | A | G | A | 5941 | 9872 |
| 2008 | 99-795-211 | C | T | S | 5942 | 9873 |
| 2009 | 99-7967-152 | C | T | S | 5943 | 9874 |
| 2010 | 99-797-238 | C | T | S | 5944 | 9875 |
| 2011 | 99-7985-178 | G | C | S | 5945 | 9876 |
| 2012 | 99-7988-389 | C | T | S | 5946 | 9877 |
| 2013 | 99-8002-49 | A | G | A | 5947 | 9878 |
| 2014 | 99-8010-124 | C | T | S | 5948 | 9879 |
| 2015 | 99-8012-420 | A | G | A | 5949 | 9880 |
| 2016 | 99-8013-122 | A | G | A | 5950 | 9881 |
| 2017 | 99-8016-267 | A | G | A | 5951 | 9882 |
| 2018 | 99-8025-306 | A | C | S | 5952 | 9883 |
| 2019 | 99-8027-265 | C | T | S | 5953 | 9884 |
| 2020 | 99-8028-87 | A | T | S | 5954 | 9885 |
| 2021 | 99-8030-411 | G | C | S | 5955 | 9886 |
| 2022 | 99-8046-263 | A | G | A | 5956 | 9887 |
| 2023 | 99-8051-125 | A | G | A | 5957 | 9888 |
| 2024 | 99-806-152 | C | T | S | 5958 | 9889 |
| 2025 | 99-8063-174 | C | T | S | 5959 | 9890 |
| 2026 | 99-8067-79 | A | G | A | 5960 | 9891 |
| 2027 | 99-8068-258 | C | T | S | 5961 | 9892 |
| 2028 | 99-8081-340 | C | T | S | 5962 | 9893 |
| 2029 | 99-8088-247 | A | C | S | 5963 | 9894 |
| 2030 | 99-8089-246 | A | G | A | 5964 | 9895 |
| 2031 | 99-8095-164 | G | T | A | 5965 | 9896 |
| 2032 | 99-81-227 | C | T | S | 5966 | 9897 |
| 2033 | 99-810-117 | A | G | A | 5967 | 9898 |
| 2034 | 99-8102-124 | C | T | S | 5968 | 9899 |
| 2035 | 99-8120-354 | A | G | A | 5969 | 9900 |
| 2036 | 99-8128-302 | C | T | S | 5970 | 9901 |
| 2037 | 99-8141-65 | A | C | S | 5971 | 9902 |
| 2038 | 99-8161-230 | A | G | A | 5972 | 9903 |
| 2039 | 99-8162-210 | C | T | S | 5973 | 9904 |
| 2040 | 99-8164-397 | A | G | S | 5974 | 9905 |
| 2041 | 99-8170-163 | C | T | S | 5975 | 9906 |
| 2042 | 99-8173-352 | C | T | S | 5976 | 9907 |
| 2043 | 99-8181-228 | A | T | S | 5977 | 9908 |
| 2044 | 99-8186-76 | G | T | A | 5978 | 9909 |
| 2045 | 99-8188-369 | G | T | A | 5979 | 9910 |
| 2046 | 99-8192-168 | C | T | S | 5980 | 9911 |
| 2047 | 99-8219-373 | A | G | A | 5981 | 9912 |
| 2048 | 99-8245-192 | G | C | S | 5982 | 9913 |
| 2049 | 99-8255-365 | A | G | A | 5983 | 9914 |
| 2050 | 99-8256-148 | A | G | A | 5984 | 9915 |
| 2051 | 99-8266-393 | A | G | A | 5985 | 9916 |
| 2052 | 99-827-359 | C | T | S | 5986 | 9917 |
| 2053 | 99-8272-122 | G | C | S | 5987 | 9918 |
| 2054 | 99-8276-65 | A | C | S | 5988 | 9919 |
| 2055 | 99-8278-412 | A | G | A | 5989 | 9920 |
| 2056 | 99-8279-252 | A | T | S | 5990 | 9921 |
| 2057 | 99-828-259 | C | T | S | 5991 | 9922 |
| 2058 | 99-8287-122 | A | C | S | 5992 | 9923 |
| 2059 | 99-8289-179 | G | C | S | 5993 | 9924 |
| 2060 | 99-8290-174 | A | G | A | 5994 | 9925 |
| 2061 | 99-8292-240 | A | G | A | 5995 | 9926 |
| 2062 | 99-8294-408 | A | G | A | 5996 | 9927 |
| 2063 | 99-8308-237 | A | C | S | 5997 | 9928 |
| 2064 | 99-8313-107 | A | G | A | 5998 | 9929 |
| 2065 | 99-8318-50 | A | G | A | 5999 | 9930 |
| 2066 | 99-8328-298 | C | T | S | 6000 | 9931 |
| 2067 | 99-8338-212 | G | C | S | 6001 | 9932 |
| 2068 | 99-8340-364 | C | T | S | 6002 | 9933 |
| 2069 | 99-8341-99 | A | G | A | 6003 | 9934 |
| 2070 | 99-8342-33 | A | C | S | 6004 | 9935 |
| 2071 | 99-8353-291 | A | C | S | 6005 | 9936 |
| 2072 | 99-8360-401 | C | T | S | 6006 | 9937 |
| 2073 | 99-8361-103 | C | T | S | 6007 | 9938 |
| 2074 | 99-8367-239 | C | T | S | 6008 | 9939 |
| 2075 | 99-8369-276 | G | T | A | 6009 | 9940 |
| 2076 | 99-8377-429 | C | T | S | 6010 | 9941 |
| 2077 | 99-8378-69 | A | G | A | 6011 | 9942 |
| 2078 | 99-8379-337 | C | T | S | 6012 | 9943 |
| 2079 | 99-8381-114 | C | T | S | 6013 | 9944 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 2080 | 99-8383-158 | G | T | A | 6014 | 9945 |
| 2081 | 99-8385-244 | A | G | A | 6015 | 9946 |
| 2082 | 99-840-68 | A | C | S | 6016 | 9947 |
| 2083 | 99-8402-113 | G | C | S | 6017 | 9948 |
| 2084 | 99-8414-183 | A | T | S | 6018 | 9949 |
| 2085 | 99-8441-298 | A | C | S | 6019 | 9950 |
| 2086 | 99-8442-95 | C | T | S | 6020 | 9951 |
| 2087 | 99-8453-358 | A | G | A | 6021 | 9952 |
| 2088 | 99-8454-152 | C | T | S | 6022 | 9953 |
| 2089 | 99-8456-266 | A | C | S | 6023 | 9954 |
| 2090 | 99-8457-239 | C | T | S | 6024 | 9955 |
| 2091 | 99-8470-275 | A | G | A | 6025 | 9956 |
| 2092 | 99-8472-152 | G | C | S | 6026 | 9957 |
| 2093 | 99-8476-216 | A | G | A | 6027 | 9958 |
| 2094 | 99-8478-385 | G | T | A | 6028 | 9959 |
| 2095 | 99-8487-245 | C | T | S | 6029 | 9960 |
| 2096 | 99-8491-339 | A | G | A | 6030 | 9961 |
| 2097 | 99-8499-107 | C | T | S | 6031 | 9962 |
| 2098 | 99-8505-269 | A | G | A | 6032 | 9963 |
| 2099 | 99-851-237 | C | T | S | 6033 | 9964 |
| 2100 | 99-8510-44 | A | C | S | 6034 | 9965 |
| 2101 | 99-8514-434 | C | T | S | 6035 | 9966 |
| 2102 | 99-8530-209 | A | G | A | 6036 | 9967 |
| 2103 | 99-854-415 | C | T | S | 6037 | 9968 |
| 2104 | 99-8546-116 | C | T | S | 6038 | 9969 |
| 2105 | 99-8571-396 | A | G | A | 6039 | 9970 |
| 2106 | 99-8575-401 | C | T | S | 6040 | 9971 |
| 2107 | 99-8576-321 | A | G | A | 6041 | 9972 |
| 2108 | 99-8578-407 | A | C | S | 6042 | 9973 |
| 2109 | 99-8581-443 | C | T | S | 6043 | 9974 |
| 2110 | 99-8583-146 | A | C | S | 6044 | 9975 |
| 2111 | 99-8588-369 | A | G | A | 6045 | 9976 |
| 2112 | 99-8590-287 | A | G | A | 6046 | 9977 |
| 2113 | 99-860-419 | C | T | S | 6047 | 9978 |
| 2114 | 99-8600-393 | A | T | S | 6048 | 9979 |
| 2115 | 99-8609-434 | G | T | A | 6049 | 9980 |
| 2116 | 99-8611-383 | A | G | A | 6050 | 9981 |
| 2117 | 99-862-233 | A | C | S | 6051 | 9982 |
| 2118 | 99-8626-133 | C | T | S | 6052 | 9983 |
| 2119 | 99-8632-413 | A | G | A | 6053 | 9984 |
| 2120 | 99-8638-107 | C | T | S | 6054 | 9985 |
| 2121 | 99-8641-418 | C | T | S | 6055 | 9986 |
| 2122 | 99-8648-169 | A | T | S | 6056 | 9987 |
| 2123 | 99-8654-157 | A | G | A | 6057 | 9988 |
| 2124 | 99-8655-77 | C | T | S | 6058 | 9989 |
| 2125 | 99-8658-168 | A | G | A | 6059 | 9990 |
| 2126 | 99-866-160 | C | T | S | 6060 | 9991 |
| 2127 | 99-8662-192 | A | C | S | 6061 | 9992 |
| 2128 | 99-8663-39 | C | T | S | 6062 | 9993 |
| 2129 | 99-8665-182 | A | C | S | 6063 | 9994 |
| 2130 | 99-8671-143 | A | G | A | 6064 | 9995 |
| 2131 | 99-8695-147 | A | T | S | 6065 | 9996 |
| 2132 | 99-870-379 | C | T | S | 6066 | 9997 |
| 2133 | 99-8703-42 | C | T | S | 6067 | 9998 |
| 2134 | 99-8715-315 | A | G | A | 6068 | 9999 |
| 2135 | 99-8725-240 | A | G | A | 6069 | 10000 |
| 2136 | 99-8732-105 | A | G | A | 6070 | 10001 |
| 2137 | 99-8744-283 | A | G | A | 6071 | 10002 |
| 2138 | 99-8748-239 | C | T | S | 6072 | 10003 |
| 2139 | 99-8755-402 | C | T | S | 6073 | 10004 |
| 2140 | 99-8761-163 | A | G | A | 6074 | 10005 |
| 2141 | 99-8775-410 | C | T | S | 6075 | 10006 |
| 2142 | 99-8778-416 | A | G | A | 6076 | 10007 |
| 2143 | 99-8780-454 | C | T | S | 6077 | 10008 |
| 2144 | 99-8796-142 | G | T | A | 6078 | 10009 |
| 2145 | 99-8799-211 | A | G | A | 6079 | 10010 |
| 2146 | 99-88-216 | A | G | S | 6080 | 10011 |
| 2147 | 99-8800-250 | C | T | S | 6081 | 10012 |
| 2148 | 99-8802-119 | A | G | A | 6082 | 10013 |
| 2149 | 99-8804-83 | A | C | S | 6083 | 10014 |
| 2150 | 99-8812-220 | A | G | A | 6084 | 10015 |
| 2151 | 99-8827-400 | C | T | S | 6085 | 10016 |
| 2152 | 99-8831-41 | C | T | S | 6086 | 10017 |
| 2153 | 99-8835-400 | A | G | A | 6087 | 10018 |
| 2154 | 99-8849-167 | A | G | A | 6088 | 10019 |
| 2155 | 99-8857-96 | A | T | S | 6089 | 10020 |
| 2156 | 99-8866-150 | A | G | S | 6090 | 10021 |
| 2157 | 99-8867-278 | A | T | S | 6091 | 10022 |
| 2158 | 99-8872-391 | A | T | S | 6092 | 10023 |
| 2159 | 99-8885-447 | A | G | A | 6093 | 10024 |
| 2160 | 99-8887-397 | A | G | A | 6094 | 10025 |
| 2161 | 99-8894-123 | A | G | A | 6095 | 10026 |
| 2162 | 99-8895-272 | A | T | S | 6096 | 10027 |
| 2163 | 99-8901-283 | A | G | A | 6097 | 10028 |
| 2164 | 99-8905-184 | G | C | S | 6098 | 10029 |
| 2165 | 99-8910-170 | C | T | S | 6099 | 10030 |
| 2166 | 99-8923-138 | C | T | S | 6100 | 10031 |
| 2167 | 99-8924-415 | A | T | S | 6101 | 10032 |
| 2168 | 99-8960-426 | A | C | S | 6102 | 10033 |
| 2169 | 99-8963-409 | A | C | S | 6103 | 10034 |
| 2170 | 99-8974-386 | C | T | S | 6104 | 10035 |
| 2171 | 99-8978-52 | A | G | A | 6105 | 10036 |
| 2172 | 99-8992-43 | A | G | A | 6106 | 10037 |
| 2173 | 99-9015-255 | A | G | A | 6107 | 10038 |
| 2174 | 99-9020-110 | G | T | A | 6108 | 10039 |
| 2175 | 99-9026-273 | A | G | A | 6109 | 10040 |
| 2176 | 99-9029-132 | A | G | A | 6110 | 10041 |
| 2177 | 99-9047-183 | A | G | A | 6111 | 10042 |
| 2178 | 99-9053-311 | A | C | S | 6112 | 10043 |
| 2179 | 99-9059-197 | A | T | S | 6113 | 10044 |
| 2180 | 99-9061-309 | A | G | A | 6114 | 10045 |
| 2181 | 99-9064-194 | A | G | A | 6115 | 10046 |
| 2182 | 99-9079-158 | A | G | A | 6116 | 10047 |
| 2183 | 99-9084-200 | A | G | A | 6117 | 10048 |
| 2184 | 99-9092-167 | A | G | A | 6118 | 10049 |
| 2185 | 99-9097-342 | A | G | A | 6119 | 10050 |
| 2186 | 99-9105-68 | G | T | A | 6120 | 10051 |
| 2187 | 99-9118-393 | C | T | S | 6121 | 10052 |
| 2188 | 99-9120-197 | C | T | S | 6122 | 10053 |
| 2189 | 99-9126-25 | G | C | S | 6123 | 10054 |
| 2190 | 99-913-140 | A | G | A | 6124 | 10055 |
| 2191 | 99-9141-307 | G | C | S | 6125 | 10056 |
| 2192 | 99-9152-154 | C | T | S | 6126 | 10057 |
| 2193 | 99-9157-329 | A | C | S | 6127 | 10058 |
| 2194 | 99-9175-329 | A | G | A | 6128 | 10059 |
| 2195 | 99-9204-245 | C | T | S | 6129 | 10060 |
| 2196 | 99-921-285 | C | T | S | 6130 | 10061 |
| 2197 | 99-924-93 | A | G | A | 6131 | 10062 |
| 2198 | 99-9240-109 | C | T | S | 6132 | 10063 |
| 2199 | 99-9250-450 | G | T | A | 6133 | 10064 |
| 2200 | 99-9254-404 | A | G | A | 6134 | 10065 |
| 2201 | 99-926-98 | G | T | A | 6135 | 10066 |
| 2202 | 99-9263-283 | A | G | A | 6136 | 10067 |
| 2203 | 99-9271-70 | G | T | A | 6137 | 10068 |
| 2204 | 99-9274-246 | C | T | S | 6138 | 10069 |
| 2205 | 99-9276-163 | C | T | S | 6139 | 10070 |
| 2206 | 99-9355-134 | C | T | S | 6140 | 10071 |
| 2207 | 99-9368-223 | A | G | A | 6141 | 10072 |
| 2208 | 99-937-125 | A | T | S | 6142 | 10073 |
| 2209 | 99-9372-298 | A | C | S | 6143 | 10074 |
| 2210 | 99-9381-429 | A | G | A | 6144 | 10075 |
| 2211 | 99-9385-387 | C | T | S | 6145 | 10076 |
| 2212 | 99-9389-363 | A | G | A | 6146 | 10077 |
| 2213 | 99-9395-133 | C | T | S | 6147 | 10078 |
| 2214 | 99-9401-80 | A | G | A | 6148 | 10079 |
| 2215 | 99-9402-263 | C | T | S | 6149 | 10080 |
| 2216 | 99-9404-338 | A | T | S | 6150 | 10081 |
| 2217 | 99-9405-421 | A | G | A | 6151 | 10082 |
| 2218 | 99-941-265 | A | T | S | 6152 | 10083 |
| 2219 | 99-9410-205 | C | T | S | 6153 | 10084 |
| 2220 | 99-9412-202 | C | T | S | 6154 | 10085 |
| 2221 | 99-9417-151 | C | T | S | 6155 | 10086 |
| 2222 | 99-942-381 | C | T | S | 6156 | 10087 |
| 2223 | 99-9420-318 | C | T | S | 6157 | 10088 |
| 2224 | 99-9421-51 | A | G | A | 6158 | 10089 |
| 2225 | 99-9422-41 | A | G | A | 6159 | 10090 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 2226 | 99-9423-394 | A | G | A | 6160 | 10091 |
| 2227 | 99-9424-229 | A | G | A | 6161 | 10092 |
| 2228 | 99-9427-454 | C | T | S | 6162 | 10093 |
| 2229 | 99-9446-394 | A | G | A | 6163 | 10094 |
| 2230 | 99-9448-292 | C | T | S | 6164 | 10095 |
| 2231 | 99-9462-362 | A | G | A | 6165 | 10096 |
| 2232 | 99-9471-230 | A | G | A | 6166 | 10097 |
| 2233 | 99-949-214 | A | G | A | 6167 | 10098 |
| 2234 | 99-9491-388 | A | G | A | 6168 | 10099 |
| 2235 | 99-9493-455 | G | C | S | 6169 | 10100 |
| 2236 | 99-9499-111 | A | T | S | 6170 | 10101 |
| 2237 | 99-950-418 | C | T | S | 6171 | 10102 |
| 2238 | 99-9513-285 | A | G | A | 6172 | 10103 |
| 2239 | 99-952-252 | G | C | S | 6173 | 10104 |
| 2240 | 99-9527-211 | C | T | S | 6174 | 10105 |
| 2241 | 99-9531-340 | C | T | S | 6175 | 10106 |
| 2242 | 99-9538-395 | A | G | A | 6176 | 10107 |
| 2243 | 99-954-45 | A | C | S | 6177 | 10108 |
| 2244 | 99-9542-164 | G | T | A | 6178 | 10109 |
| 2245 | 99-9545-100 | A | C | S | 6179 | 10110 |
| 2246 | 99-9554-345 | A | C | S | 6180 | 10111 |
| 2247 | 99-9555-348 | C | T | S | 6181 | 10112 |
| 2248 | 99-9556-349 | A | G | A | 6182 | 10113 |
| 2249 | 99-9567-229 | C | T | A | 6183 | 10114 |
| 2250 | 99-9572-240 | C | T | A | 6184 | 10115 |
| 2251 | 99-9577-284 | C | T | A | 6185 | 10116 |
| 2252 | 99-9579-363 | G | C | S | 6186 | 10117 |
| 2253 | 99-958-92 | C | T | A | 6187 | 10118 |
| 2254 | 99-9587-338 | A | G | S | 6188 | 10119 |
| 2255 | 99-961-150 | C | T | S | 6189 | 10120 |
| 2256 | 99-963-395 | A | G | A | 6190 | 10121 |
| 2257 | 99-965-165 | C | T | S | 6191 | 10122 |
| 2258 | 99-967-306 | C | T | S | 6192 | 10123 |
| 2259 | 99-976-246 | C | T | S | 6193 | 10124 |
| 2260 | 99-979-343 | A | C | S | 6194 | 10125 |
| 2261 | 99-10000-518 | G | A | S | 6195 | 10126 |
| 2262 | 99-10016-115 | T | A | S | 6196 | 10127 |
| 2263 | 99-10027-378 | G | A | S | 6197 | 10128 |
| 2264 | 99-10028-93 | C | G | S | 6198 | 10129 |
| 2265 | 99-10031-130 | T | C | A | 6199 | 10130 |
| 2266 | 99-10046-199 | T | C | S | 6200 | 10131 |
| 2267 | 99-10064-252 | T | C | S | 6201 | 10132 |
| 2268 | 99-10066-465 | G | T | A | 6202 | 10133 |
| 2269 | 99-10067-168 | G | A | A | 6203 | 10134 |
| 2270 | 99-10078-341 | T | C | S | 6204 | 10135 |
| 2271 | 99-10104-464 | C | A | S | 6205 | 10136 |
| 2272 | 99-10106-247 | G | T | A | 6206 | 10137 |
| 2273 | 99-10108-419 | G | A | S | 6207 | 10138 |
| 2274 | 99-10118-323 | T | C | A | 6208 | 10139 |
| 2275 | 99-10126-413 | C | T | A | 6209 | 10140 |
| 2276 | 99-10127-506 | A | T | S | 6210 | 10141 |
| 2277 | 99-10137-195 | T | G | A | 6211 | 10142 |
| 2278 | 99-10142-293 | G | A | S | 6212 | 10143 |
| 2279 | 99-10143-111 | A | G | S | 6213 | 10144 |
| 2280 | 99-10146-202 | T | A | S | 6214 | 10145 |
| 2281 | 99-10149-291 | T | C | A | 6215 | 10146 |
| 2282 | 99-10151-340 | G | A | S | 6216 | 10147 |
| 2283 | 99-10153-267 | A | G | S | 6217 | 10148 |
| 2284 | 99-10155423 | C | G | S | 6218 | 10149 |
| 2285 | 99-10173-122 | A | G | S | 6219 | 10150 |
| 2286 | 99-10179-48 | G | A | S | 6220 | 10151 |
| 2287 | 99-1018-244 | A | C | A | 6221 | 10152 |
| 2288 | 99-10183-166 | G | T | A | 6222 | 10153 |
| 2289 | 99-10185-402 | C | A | S | 6223 | 10154 |
| 2290 | 99-10188-116 | G | A | S | 6224 | 10155 |
| 2291 | 99-10201-115 | C | T | A | 6225 | 10156 |
| 2292 | 99-10207-173 | A | G | S | 6226 | 10157 |
| 2293 | 99-10211-380 | A | G | S | 6227 | 10158 |
| 2294 | 99-10216-336 | A | C | S | 6228 | 10159 |
| 2295 | 99-10220-312 | C | A | S | 6229 | 10160 |
| 2296 | 99-10223-153 | T | A | S | 6230 | 10161 |
| 2297 | 99-10224-223 | T | A | S | 6231 | 10162 |
| 2298 | 99-10234-334 | A | G | S | 6232 | 10163 |
| 2299 | 99-1024-403 | G | A | S | 6233 | 10164 |
| 2300 | 99-10245-197 | A | G | S | 6234 | 10165 |
| 2301 | 99-10256-41 | A | G | S | 6235 | 10166 |
| 2302 | 99-10264-82 | G | A | S | 6236 | 10167 |
| 2303 | 99-10266-290 | T | A | S | 6237 | 10168 |
| 2304 | 99-10267-409 | A | C | S | 6238 | 10169 |
| 2305 | 99-10303-406 | C | T | A | 6239 | 10170 |
| 2306 | 99-10304-88 | A | G | S | 6240 | 10171 |
| 2307 | 99-10312-155 | C | T | A | 6241 | 10172 |
| 2308 | 99-10318-230 | C | T | A | 6242 | 10173 |
| 2309 | 99-10330-432 | G | A | S | 6243 | 10174 |
| 2310 | 99-10332-89 | C | T | A | 6244 | 10175 |
| 2311 | 99-10345-182 | T | G | A | 6245 | 10176 |
| 2312 | 99-10353-285 | G | T | A | 6246 | 10177 |
| 2313 | 99-10364-331 | A | G | S | 6247 | 10178 |
| 2314 | 99-10369-41 | T | C | A | 6248 | 10179 |
| 2315 | 99-10374-343 | C | T | A | 6249 | 10180 |
| 2316 | 99-10381-328 | T | A | S | 6250 | 10181 |
| 2317 | 99-10389-114 | G | T | A | 6251 | 10182 |
| 2318 | 99-10390-172 | A | G | S | 6252 | 10183 |
| 2319 | 99-10414-128 | C | T | A | 6253 | 10184 |
| 2320 | 99-10434-121 | G | T | S | 6254 | 10185 |
| 2321 | 99-10436-162 | C | T | A | 6255 | 10186 |
| 2322 | 99-10438-281 | C | A | S | 6256 | 10187 |
| 2323 | 99-10446-425 | G | C | S | 6257 | 10188 |
| 2324 | 99-10451-188 | A | T | S | 6258 | 10189 |
| 2325 | 99-10452-306 | A | G | S | 6259 | 10190 |
| 2326 | 99-10457-310 | T | C | A | 6260 | 10191 |
| 2327 | 99-10470-405 | A | C | S | 6261 | 10192 |
| 2328 | 99-10471-88 | C | T | A | 6262 | 10193 |
| 2329 | 99-10473-259 | T | C | A | 6263 | 10194 |
| 2330 | 99-10474-223 | G | C | S | 6264 | 10195 |
| 2331 | 99-10481-217 | C | T | A | 6265 | 10196 |
| 2332 | 99-10487-57 | T | C | A | 6266 | 10197 |
| 2333 | 99-10488-146 | G | C | S | 6267 | 10198 |
| 2334 | 99-10491-300 | C | T | A | 6268 | 10199 |
| 2335 | 99-10499-102 | T | G | A | 6269 | 10200 |
| 2336 | 99-10502-160 | T | C | A | 6270 | 10201 |
| 2337 | 99-10506-307 | A | C | S | 6271 | 10202 |
| 2338 | 99-10507-216 | C | T | A | 6272 | 10203 |
| 2339 | 99-10509-122 | T | G | A | 6273 | 10204 |
| 2340 | 99-1051-284 | G | A | A | 6274 | 10205 |
| 2341 | 99-10513-347 | T | C | A | 6275 | 10206 |
| 2342 | 99-10514-546 | G | T | A | 6276 | 10207 |
| 2343 | 99-10521-296 | C | T | A | 6277 | 10208 |
| 2344 | 99-10522-395 | A | C | A | 6278 | 10209 |
| 2345 | 99-10536-90 | C | A | S | 6279 | 10210 |
| 2346 | 99-10539-208 | G | A | S | 6280 | 10211 |
| 2347 | 99-10542-326 | C | T | A | 6281 | 10212 |
| 2348 | 99-10543-278 | A | T | S | 6282 | 10213 |
| 2349 | 99-1055-140 | C | T | S | 6283 | 10214 |
| 2350 | 99-10557-276 | T | C | A | 6284 | 10215 |
| 2351 | 99-10567-233 | A | G | S | 6285 | 10216 |
| 2352 | 99-10570-107 | G | A | S | 6286 | 10217 |
| 2353 | 99-10573-375 | G | A | S | 6287 | 10218 |
| 2354 | 99-10575-416 | T | C | A | 6288 | 10219 |
| 2355 | 99-10576-351 | A | G | S | 6289 | 10220 |
| 2356 | 99-10577-36 | T | C | A | 6290 | 10221 |
| 2357 | 99-10581-354 | G | C | S | 6291 | 10222 |
| 2358 | 99-10589-360 | A | C | S | 6292 | 10223 |
| 2359 | 99-10601-463 | C | G | S | 6293 | 10224 |
| 2360 | 99-10606-92 | G | A | S | 6294 | 10225 |
| 2361 | 99-10608-353 | C | T | A | 6295 | 10226 |
| 2362 | 99-10613-277 | C | G | S | 6296 | 10227 |
| 2363 | 99-10618-404 | A | T | S | 6297 | 10228 |
| 2364 | 99-10626-196 | G | C | S | 6298 | 10229 |
| 2365 | 99-10630-236 | G | A | S | 6299 | 10230 |
| 2366 | 99-10632-55 | A | T | S | 6300 | 10231 |
| 2367 | 99-10634-141 | G | A | S | 6301 | 10232 |
| 2368 | 99-10643-161 | T | C | A | 6302 | 10233 |
| 2369 | 99-10659-208 | C | T | A | 6303 | 10234 |
| 2370 | 99-10661-153 | G | A | S | 6304 | 10235 |
| 2371 | 99-10662-397 | C | T | A | 6305 | 10236 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 2372 | 99-10667-251 | G | C | S | 6306 | 10237 |
| 2373 | 99-10675-109 | A | G | S | 6307 | 10238 |
| 2374 | 99-1068-309 | C | T | S | 6308 | 10239 |
| 2375 | 99-10683-117 | A | G | S | 6309 | 10240 |
| 2376 | 99-10689-419 | A | G | S | 6310 | 10241 |
| 2377 | 99-10692-377 | G | A | S | 6311 | 10242 |
| 2378 | 99-10694-446 | C | T | A | 6312 | 10243 |
| 2379 | 99-10695-161 | C | T | A | 6313 | 10244 |
| 2380 | 99-1070-342 | C | T | S | 6314 | 10245 |
| 2381 | 99-10702-261 | G | A | S | 6315 | 10246 |
| 2382 | 99-10706-228 | T | C | A | 6316 | 10247 |
| 2383 | 99-10708-28 | G | A | S | 6317 | 10248 |
| 2384 | 99-10709-460 | G | A | S | 6318 | 10249 |
| 2385 | 99-10715-43 | A | G | S | 6319 | 10250 |
| 2386 | 99-10719-455 | C | T | S | 6320 | 10251 |
| 2387 | 99-10720-63 | A | G | S | 6321 | 10252 |
| 2388 | 99-10731-195 | C | T | S | 6322 | 10253 |
| 2389 | 99-10735-238 | T | C | A | 6323 | 10254 |
| 2390 | 99-1074-127 | G | A | A | 6324 | 10255 |
| 2391 | 99-10741-421 | A | C | S | 6325 | 10256 |
| 2392 | 99-10743-315 | T | A | S | 6326 | 10257 |
| 2393 | 99-1075-314 | G | A | A | 6327 | 10258 |
| 2394 | 99-10752-366 | A | G | S | 6328 | 10259 |
| 2395 | 99-1076-116 | C | T | A | 6329 | 10260 |
| 2396 | 99-10769-291 | A | C | S | 6330 | 10261 |
| 2397 | 99-10771-266 | A | C | S | 6331 | 10262 |
| 2398 | 99-10775-331 | A | G | S | 6332 | 10263 |
| 2399 | 99-10776-447 | T | A | S | 6333 | 10264 |
| 2400 | 99-1079-237 | C | G | S | 6334 | 10265 |
| 2401 | 99-1081-159 | A | T | S | 6335 | 10266 |
| 2402 | 99-10816-272 | G | A | S | 6336 | 10267 |
| 2403 | 99-1082-180 | T | A | S | 6337 | 10268 |
| 2404 | 99-10839-239 | C | T | A | 6338 | 10269 |
| 2405 | 99-10842-232 | A | G | S | 6339 | 10270 |
| 2406 | 99-10843-114 | A | G | S | 6340 | 10271 |
| 2407 | 99-10856-246 | C | G | S | 6341 | 10272 |
| 2408 | 99-10861-96 | T | C | A | 6342 | 10273 |
| 2409 | 99-10862-397 | T | C | A | 6343 | 10274 |
| 2410 | 99-10864-418 | C | G | S | 6344 | 10275 |
| 2411 | 99-10870-234 | G | A | S | 6345 | 10276 |
| 2412 | 99-10874-69 | G | A | S | 6346 | 10277 |
| 2413 | 99-10879-386 | A | G | S | 6347 | 10278 |
| 2414 | 99-10887-214 | A | G | S | 6348 | 10279 |
| 2415 | 99-10890-201 | T | G | A | 6349 | 10280 |
| 2416 | 99-10894-35 | T | C | A | 6350 | 10281 |
| 2417 | 99-10898-209 | G | T | A | 6351 | 10282 |
| 2418 | 99-10904-111 | C | T | A | 6352 | 10283 |
| 2419 | 99-10905-85 | C | T | A | 6353 | 10284 |
| 2420 | 99-1091-446 | C | T | S | 6354 | 10285 |
| 2421 | 99-10927-388 | G | C | S | 6355 | 10286 |
| 2422 | 99-10929-298 | T | A | S | 6356 | 10287 |
| 2423 | 99-10930-95 | A | T | S | 6357 | 10288 |
| 2424 | 99-10937-64 | T | C | A | 6358 | 10289 |
| 2425 | 99-10944-83 | G | A | S | 6359 | 10290 |
| 2426 | 99-10951-434 | T | C | A | 6360 | 10291 |
| 2427 | 99-10959-113 | C | T | A | 6361 | 10292 |
| 2428 | 99-10964-89 | T | C | A | 6362 | 10293 |
| 2429 | 99-10965-174 | C | A | S | 6363 | 10294 |
| 2430 | 99-10966-113 | G | A | S | 6364 | 10295 |
| 2431 | 99-10974-193 | T | A | S | 6365 | 10296 |
| 2432 | 99-10978-393 | T | A | S | 6366 | 10297 |
| 2433 | 99-10979-156 | T | A | S | 6367 | 10298 |
| 2434 | 99-10988-242 | T | A | S | 6368 | 10299 |
| 2435 | 99-10992-98 | G | A | S | 6369 | 10300 |
| 2436 | 99-11000-163 | A | G | S | 6370 | 10301 |
| 2437 | 99-11001-393 | C | T | A | 6371 | 10302 |
| 2438 | 99-11003-361 | G | A | S | 6372 | 10303 |
| 2439 | 99-11006-426 | C | T | A | 6373 | 10304 |
| 2440 | 99-11007-68 | T | C | A | 6374 | 10305 |
| 2441 | 99-11014-194 | C | A | S | 6375 | 10306 |
| 2442 | 99-11034-317 | C | T | A | 6376 | 10307 |
| 2443 | 99-11035-299 | C | T | A | 6377 | 10308 |
| 2444 | 99-11037-218 | C | A | S | 6378 | 10309 |
| 2445 | 99-1105-127 | A | C | S | 6379 | 10310 |
| 2446 | 99-1J051-154 | A | T | S | 6380 | 10311 |
| 2447 | 99-11063-111 | G | C | S | 6381 | 10312 |
| 2448 | 99-11074-187 | A | G | S | 6382 | 10313 |
| 2449 | 99-11075-311 | G | A | S | 6383 | 10314 |
| 2450 | 99-11089-424 | C | A | S | 6384 | 10315 |
| 2451 | 99-11094-427 | G | A | A | 6385 | 10316 |
| 2452 | 99-11099-179 | A | G | S | 6386 | 10317 |
| 2453 | 99-11103-88 | A | T | S | 6387 | 10318 |
| 2454 | 99-11106-117 | C | T | A | 6388 | 10319 |
| 2455 | 99-11110-375 | C | T | A | 6389 | 10320 |
| 2456 | 99-11115-133 | A | G | S | 6390 | 10321 |
| 2457 | 99-11119-132 | T | C | A | 6391 | 10322 |
| 2458 | 99-11128-162 | A | G | 8 | 6392 | 10323 |
| 2459 | 99-11136-374 | G | A | S | 6393 | 10324 |
| 2460 | 99-11142-139 | T | C | A | 6394 | 10325 |
| 2461 | 99-11143-443 | A | C | S | 6395 | 10326 |
| 2462 | 99-11144-137 | G | A | S | 6396 | 10327 |
| 2463 | 99-11148-369 | A | C | S | 6397 | 10328 |
| 2464 | 99-11158-255 | C | T | A | 6398 | 10329 |
| 2465 | 99-11163-293 | C | G | S | 6399 | 10330 |
| 2466 | 99-11164-298 | C | T | A | 6400 | 10331 |
| 2467 | 99-11168-197 | G | A | S | 6401 | 10332 |
| 2468 | 99-11175-348 | A | C | S | 6402 | 10333 |
| 2469 | 99-11179-239 | C | T | A | 6403 | 10334 |
| 2470 | 99-11180-148 | A | G | S | 6404 | 10335 |
| 2471 | 99-11183-166 | G | A | S | 6405 | 10336 |
| 2472 | 99-11191-86 | A | G | S | 6406 | 10337 |
| 2473 | 99-11210-235 | G | A | S | 6407 | 10338 |
| 2474 | 99-11214-188 | T | G | A | 6408 | 10339 |
| 2475 | 99-11218-174 | G | A | S | 6409 | 10340 |
| 2476 | 99-11236-63 | C | T | A | 6410 | 10341 |
| 2477 | 99-11247-86 | C | G | S | 6411 | 10342 |
| 2478 | 99-11248-404 | A | G | S | 6412 | 10343 |
| 2479 | 99-11252-263 | T | A | S | 6413 | 10344 |
| 2480 | 99-11255-375 | G | A | S | 6414 | 10345 |
| 2481 | 99-11260-422 | C | T | A | 6415 | 10346 |
| 2482 | 99-11261-255 | G | A | S | 6416 | 10347 |
| 2483 | 99-11293-125 | G | A | S | 6417 | 10348 |
| 2484 | 99-11313-95 | G | A | S | 6418 | 10349 |
| 2485 | 99-11320-29 | C | T | A | 6419 | 10350 |
| 2486 | 99-11326-356 | A | G | S | 6420 | 10351 |
| 2487 | 99-11340-89 | C | T | A | 6421 | 10352 |
| 2488 | 99-11346-222 | T | C | A | 6422 | 10353 |
| 2489 | 99-11350-116 | A | G | S | 6423 | 10354 |
| 2490 | 99-11356-187 | A | T | S | 6424 | 10355 |
| 2491 | 99-11362-334 | C | T | A | 6425 | 10356 |
| 2492 | 99-11369-112 | C | G | S | 6426 | 10357 |
| 2493 | 99-11372-162 | C | A | 8 | 6427 | 10358 |
| 2494 | 99-11377-384 | A | G | S | 6428 | 10359 |
| 2495 | 99-11381-256 | C | G | S | 6429 | 10360 |
| 2496 | 99-11385-245 | C | T | A | 6430 | 10361 |
| 2497 | 99-11413-239 | A | G | S | 6431 | 10362 |
| 2498 | 99-1143-340 | G | A | S | 6432 | 10363 |
| 2499 | 99-11430-162 | C | A | S | 6433 | 10364 |
| 2500 | 99-11431-333 | A | G | S | 6434 | 10365 |
| 2501 | 99-11449-297 | A | G | S | 6435 | 10366 |
| 2502 | 99-11464-236 | C | G | S | 6436 | 10367 |
| 2503 | 99-11466-107 | T | C | A | 6437 | 10368 |
| 2504 | 99-11485-396 | T | A | S | 6438 | 10369 |
| 2505 | 99-11492-360 | A | T | S | 6439 | 10370 |
| 2506 | 99-11499-45 | G | A | S | 6440 | 10371 |
| 2507 | 99-11505-92 | A | G | S | 6441 | 10372 |
| 2508 | 99-11506-224 | G | C | S | 6442 | 10373 |
| 2509 | 99-11520-170 | A | G | S | 6443 | 10374 |
| 2510 | 99-11521-146 | G | T | A | 6444 | 10375 |
| 2511 | 99-11522-313 | C | T | A | 6445 | 10376 |
| 2512 | 99-11528-137 | A | T | S | 6446 | 10377 |
| 2513 | 99-11530-388 | G | A | S | 6447 | 10378 |
| 2514 | 99-11533-375 | C | G | S | 6448 | 10379 |
| 2515 | 99-11535-193 | G | T | A | 6449 | 10380 |
| 2516 | 99-11543-415 | A | T | S | 6450 | 10381 |
| 2517 | 99-11545-180 | T | C | A | 6451 | 10382 |

TABLE 1-continued

| SEQ ID No. | Marker Name | Allele 1ST | 2ND | Preferred microseq. primer | Amplification primer Upstream (PU) | Downstream (RP) |
|---|---|---|---|---|---|---|
| 2518 | 99-11555-397 | C | T | A | 6452 | 10383 |
| 2519 | 99-11559-81 | C | A | S | 6453 | 10384 |
| 2520 | 99-11563-183 | A | G | S | 6454 | 10385 |
| 2521 | 99-11565-305 | C | A | S | 6455 | 10386 |
| 2522 | 99-11566-385 | G | A | S | 6456 | 10387 |
| 2523 | 99-11580-97 | A | G | S | 6457 | 10388 |
| 2524 | 99-11584-69 | A | G | 8 | 6458 | 10389 |
| 2525 | 99-11587-202 | A | G | S | 6459 | 10390 |
| 2526 | 99-11592-297 | A | G | S | 6460 | 10391 |
| 2527 | 99-11600-48 | A | G | S | 6461 | 10392 |
| 2528 | 99-11601-441 | C | T | A | 6462 | 10393 |
| 2529 | 99-11602-93 | G | A | S | 6463 | 10394 |
| 2530 | 99-11604-396 | T | C | A | 6464 | 10395 |
| 2531 | 99-11611-259 | A | G | S | 6465 | 10396 |
| 2532 | 99-11613-315 | T | C | A | 6466 | 10397 |
| 2533 | 99-11620-149 | A | C | S | 6467 | 10398 |
| 2534 | 99-11635-363 | C | T | A | 6468 | 10399 |
| 2535 | 99-11643-378 | C | T | A | 6469 | 10400 |
| 2536 | 99-11645-157 | C | T | A | 6470 | 10401 |
| 2537 | 99-11658-275 | G | A | S | 6471 | 10402 |
| 2538 | 99-11668-308 | T | C | A | 6472 | 10403 |
| 2539 | 99-11669-394 | C | T | A | 6473 | 10404 |
| 2540 | 99-11670-486 | G | T | A | 6474 | 10405 |
| 2541 | 99-11685-200 | T | C | A | 6475 | 10406 |
| 2542 | 99-11697-345 | C | T | A | 6476 | 10407 |
| 2543 | 99-11700-326 | T | C | A | 6477 | 10408 |
| 2544 | 99-11704-23 | T | C | A | 6478 | 10409 |
| 2545 | 99-11705-302 | G | T | A | 6479 | 10410 |
| 2546 | 99-11723-211 | A | T | S | 6480 | 10411 |
| 2547 | 99-11743-233 | C | T | A | 6481 | 10412 |
| 2548 | 99-11745-256 | A | G | S | 6482 | 10413 |
| 2549 | 99-11746-238 | A | G | S | 6483 | 10414 |
| 2550 | 99-11780-292 | G | T | A | 6484 | 10415 |
| 2551 | 99-11785-167 | A | G | S | 6485 | 10416 |
| 2552 | 99-11786-98 | G | T | A | 6486 | 10417 |
| 2553 | 99-11787-281 | G | A | S | 6487 | 10418 |
| 2554 | 99-11788-69 | G | A | S | 6488 | 10419 |
| 2555 | 99-11789-348 | A | C | S | 6489 | 10420 |
| 2556 | 99-11797-147 | A | G | S | 6490 | 10421 |
| 2557 | 99-11810-289 | A | C | S | 6491 | 10422 |
| 2558 | 99-11811-158 | A | G | S | 6492 | 10423 |
| 2559 | 99-1182-310 | G | A | A | 6493 | 10424 |
| 2560 | 99-11823-118 | G | A | S | 6494 | 10425 |
| 2561 | 99-11824-90 | T | A | S | 6495 | 10426 |
| 2562 | 99-1183-182 | G | A | A | 6496 | 10427 |
| 2563 | 99-11830-334 | C | G | S | 6497 | 10428 |
| 2564 | 99-11831-321 | C | T | A | 6498 | 10429 |
| 2565 | 99-11839-223 | C | T | A | 6499 | 10430 |
| 2566 | 99-11842-197 | T | C | A | 6500 | 10431 |
| 2567 | 99-1185-317 | T | G | A | 6501 | 10432 |
| 2568 | 99-11851-45 | C | G | S | 6502 | 10433 |
| 2569 | 99-11857-368 | G | A | S | 6503 | 10434 |
| 2570 | 99-1186-249 | G | A | A | 6504 | 10435 |
| 2571 | 99-11861-254 | C | T | A | 6505 | 10436 |
| 2572 | 99-11877-237 | T | C | A | 6506 | 10437 |
| 2573 | 99-11880-90 | G | C | S | 6507 | 10438 |
| 2574 | 99-11882-120 | A | G | S | 6508 | 10439 |
| 2575 | 99-11894-470 | G | A | S | 6509 | 10440 |
| 2576 | 99-11917-129 | A | G | S | 6510 | 10441 |
| 2577 | 99-11922-206 | G | A | S | 6511 | 10442 |
| 2578 | 99-11930-395 | C | T | A | 6512 | 10443 |
| 2579 | 99-11966-288 | A | G | S | 6513 | 10444 |
| 2580 | 99-11989-233 | C | A | S | 6514 | 10445 |
| 2581 | 99-11993-468 | C | T | A | 6515 | 10446 |
| 2582 | 99-12000-355 | T | C | A | 6516 | 10447 |
| 2583 | 99-12005-282 | C | T | A | 6517 | 10448 |
| 2584 | 99-12017-203 | G | T | A | 6518 | 10449 |
| 2585 | 99-1202-340 | C | T | S | 6519 | 10450 |
| 2586 | 99-12028-121 | T | C | A | 6520 | 10451 |
| 2587 | 99-1203-272 | A | G | A | 6521 | 10452 |
| 2588 | 99-12038-420 | C | T | A | 6522 | 10453 |
| 2589 | 99-12039-389 | C | T | A | 6523 | 10454 |
| 2590 | 99-12048-300 | A | G | S | 6524 | 10455 |
| 2591 | 99-12049-245 | A | G | S | 6525 | 10456 |
| 2592 | 99-12050-459 | A | G | S | 6526 | 10457 |
| 2593 | 99-12061-211 | A | G | S | 6527 | 10458 |
| 2594 | 99-12062-94 | G | A | S | 6528 | 10459 |
| 2595 | 99-12068-348 | T | C | A | 6529 | 10460 |
| 2596 | 99-12087-45 | C | T | A | 6530 | 10461 |
| 2597 | 99-1211-59 | C | T | A | 6531 | 10462 |
| 2598 | 99-12130-72 | G | A | S | 6532 | 10463 |
| 2599 | 99-12133-294 | T | C | A | 6533 | 10464 |
| 2600 | 99-12135-288 | C | A | S | 6534 | 10465 |
| 2601 | 99-12152-332 | A | G | S | 6535 | 10466 |
| 2602 | 99-12158-148 | A | G | S | 6536 | 10467 |
| 2603 | 99-12168-256 | C | T | A | 6537 | 10468 |
| 2604 | 99-12171-93 | G | A | S | 6538 | 10469 |
| 2605 | 99-12178-423 | C | T | A | 6539 | 10470 |
| 2606 | 99-12181-226 | T | C | A | 6540 | 10471 |
| 2607 | 99-12186-229 | C | T | A | 6541 | 10472 |
| 2608 | 99-12198-289 | A | G | S | 6542 | 10473 |
| 2609 | 99-12199-246 | T | C | A | 6543 | 10474 |
| 2610 | 99-12203-356 | C | G | S | 6544 | 10475 |
| 2611 | 99-12224-368 | A | G | S | 6545 | 10476 |
| 2612 | 99-12228-184 | C | T | A | 6546 | 10477 |
| 2613 | 99-12241-380 | T | G | A | 6547 | 10478 |
| 2614 | 99-12253-145 | T | C | A | 6548 | 10479 |
| 2615 | 99-12265-324 | A | T | S | 6549 | 10480 |
| 2616 | 99-12267-161 | G | T | A | 6550 | 10481 |
| 2617 | 99-12268-54 | G | A | S | 6551 | 10482 |
| 2618 | 99-12270-408 | T | G | A | 6552 | 10483 |
| 2619 | 99-12271-298 | G | A | S | 6553 | 10484 |
| 2620 | 99-12275-214 | A | T | S | 6554 | 10485 |
| 2621 | 99-12299-433 | T | G | A | 6555 | 10486 |
| 2622 | 99-12303-460 | C | T | A | 6556 | 10487 |
| 2623 | 99-12335-394 | C | T | A | 6557 | 10488 |
| 2624 | 99-12338-83 | T | C | A | 6558 | 10489 |
| 2625 | 99-12344-171 | G | C | S | 6559 | 10490 |
| 2626 | 99-12347-490 | G | C | S | 6560 | 10491 |
| 2627 | 99-12348-74 | T | G | A | 6561 | 10492 |
| 2628 | 99-12352-124 | T | G | A | 6562 | 10493 |
| 2629 | 99-12356-272 | T | C | A | 6563 | 10494 |
| 2630 | 99-12361-88 | T | C | A | 6564 | 10495 |
| 2631 | 99-12368-335 | A | C | S | 6565 | 10496 |
| 2632 | 99-12370-67 | G | A | S | 6566 | 10497 |
| 2633 | 99-12384-135 | G | A | S | 6567 | 10498 |
| 2634 | 99-12388-466 | G | A | S | 6568 | 10499 |
| 2635 | 99-12393-326 | A | G | S | 6569 | 10500 |
| 2636 | 99-12399-180 | C | T | A | 6570 | 10501 |
| 2637 | 99-12412-381 | T | C | A | 6571 | 10502 |
| 2638 | 99-12415-509 | A | G | S | 6572 | 10503 |
| 2639 | 99-12444-400 | A | G | S | 6573 | 10504 |
| 2640 | 99-12465-227 | G | A | A | 6574 | 10505 |
| 2641 | 99-12468-236 | G | T | A | 6575 | 10506 |
| 2642 | 99-12470-288 | G | A | A | 6576 | 10507 |
| 2643 | 99-12522-196 | T | C | S | 6577 | 10508 |
| 2644 | 99-12561-278 | C | G | S | 6578 | 10509 |
| 2645 | 99-12570-265 | G | A | A | 6579 | 10510 |
| 2646 | 99-12595-313 | C | T | S | 6580 | 10511 |
| 2647 | 99-12596-334 | T | C | S | 6581 | 10512 |
| 2648 | 99-12598-191 | C | A | S | 6582 | 10513 |
| 2649 | 99-12602-212 | G | T | A | 6583 | 10514 |
| 2650 | 99-12605-365 | C | T | S | 6584 | 10515 |
| 2651 | 99-12607-384 | A | G | A | 6585 | 10516 |
| 2652 | 99-12664-222 | C | A | S | 6586 | 10517 |
| 2653 | 99-12696-116 | T | C | 8 | 6587 | 10518 |
| 2654 | 99-12960-443 | G | A | S | 6588 | 10519 |
| 2655 | 99-12965-451 | C | T | A | 6589 | 10520 |
| 2656 | 99-12969-128 | C | T | A | 6590 | 10521 |
| 2657 | 99-12970-339 | A | G | S | 6591 | 10522 |
| 2658 | 99-12973-162 | G | A | S | 6592 | 10523 |
| 2659 | 99-13074-132 | T | C | A | 6593 | 10524 |
| 2660 | 99-13077-340 | C | T | A | 6594 | 10525 |
| 2661 | 99-1311-59 | C | G | S | 6595 | 10526 |
| 2662 | 99-13113-234 | G | A | S | 6596 | 10527 |
| 2663 | 99-13205-67 | T | A | S | 6597 | 10528 |

TABLE 1-continued

| SEQ ID No. | Marker Name | Allele 1ST | 2ND | Preferred microseq. primer | Amplification primer Upstream (PU) | Downstream (RP) |
|---|---|---|---|---|---|---|
| 2664 | 99-1326-203 | C | T | A | 6598 | 10529 |
| 2665 | 99-1333-123 | C | G | S | 6599 | 10530 |
| 2666 | 99-1335-195 | A | G | A | 6600 | 10531 |
| 2667 | 99-13350-376 | T | G | A | 6601 | 10532 |
| 2668 | 99-13376-288 | A | T | S | 6602 | 10533 |
| 2669 | 99-13473-135 | C | T | A | 6603 | 10534 |
| 2670 | 99-13530-325 | T | C | S | 6604 | 10535 |
| 2671 | 99-13563-83 | C | T | S | 6605 | 10536 |
| 2672 | 99-13579-242 | G | C | S | 6606 | 10537 |
| 2673 | 99-13609-327 | T | C | A | 6607 | 10538 |
| 2674 | 99-13621-358 | T | C | S | 6608 | 10539 |
| 2675 | 99-1370-401 | A | G | S | 6609 | 10540 |
| 2676 | 99-13864-64 | G | T | A | 6610 | 10541 |
| 2677 | 99-13938-286 | T | C | A | 6611 | 10542 |
| 2678 | 99-13943-247 | T | C | A | 6612 | 10543 |
| 2679 | 99-13948-182 | T | A | S | 6613 | 10544 |
| 2680 | 99-13966-334 | T | C | A | 6614 | 10545 |
| 2681 | 99-14002-395 | C | G | S | 6615 | 10546 |
| 2682 | 99-14022-347 | C | T | A | 6616 | 10547 |
| 2683 | 99-14042-464 | G | A | S | 6617 | 10548 |
| 2684 | 99-14045-353 | T | C | A | 6618 | 10549 |
| 2685 | 99-14074-326 | C | T | A | 6619 | 10550 |
| 2686 | 99-14093-333 | T | C | A | 6620 | 10551 |
| 2687 | 99-14105-357 | G | C | S | 6621 | 10552 |
| 2688 | 99-14107-175 | A | G | S | 6622 | 10553 |
| 2689 | 99-14111-346 | C | G | S | 6623 | 10554 |
| 2690 | 99-14177-226 | A | G | S | 6624 | 10555 |
| 2691 | 99-14198-374 | T | G | A | 6625 | 10556 |
| 2692 | 99-14225-345 | T | C | A | 6626 | 10557 |
| 2693 | 99-14228-387 | C | G | S | 6627 | 10558 |
| 2694 | 99-14410-373 | T | C | A | 6628 | 10559 |
| 2695 | 99-14413-383 | T | G | A | 6629 | 10560 |
| 2696 | 99-14415-106 | C | T | A | 6630 | 10561 |
| 2697 | 99-14424-353 | G | A | S | 6631 | 10562 |
| 2698 | 99-14473-243 | A | C | S | 6632 | 10563 |
| 2699 | 99-14476-377 | T | G | A | 6633 | 10564 |
| 2700 | 99-14481-386 | T | C | A | 6634 | 10565 |
| 2701 | 99-14489-415 | G | T | A | 6635 | 10566 |
| 2702 | 99-14673-334 | A | G | S | 6636 | 10567 |
| 2703 | 99-14705-290 | A | G | S | 6637 | 10568 |
| 2704 | 99-14739-205 | C | G | S | 6638 | 10569 |
| 2705 | 99-14743-418 | C | T | A | 6639 | 10570 |
| 2706 | 99-14944-119 | A | C | S | 6640 | 10571 |
| 2707 | 99-14949-472 | G | A | S | 6641 | 10572 |
| 2708 | 99-15000-259 | C | T | A | 6642 | 10573 |
| 2709 | 99-15067-278 | T | C | A | 6643 | 10574 |
| 2710 | 99-15192-224 | C | T | A | 6644 | 10575 |
| 2711 | 99-15369-90 | C | T | A | 6645 | 10576 |
| 2712 | 99-15423-223 | G | A | S | 6646 | 10577 |
| 2713 | 99-15471-316 | G | T | A | 6647 | 10578 |
| 2714 | 99-15538-250 | T | C | A | 6648 | 10579 |
| 2715 | 99-15588-430 | A | G | S | 6649 | 10580 |
| 2716 | 99-15615-368 | G | A | A | 6650 | 10581 |
| 2717 | 99-15653-359 | G | A | S | 6651 | 10582 |
| 2718 | 99-15654-122 | G | A | S | 6652 | 10583 |
| 2719 | 99-15724-147 | C | T | A | 6653 | 10584 |
| 2720 | 99-15784-28 | G | T | A | 6654 | 10585 |
| 2721 | 99-1591-235 | G | A | A | 6655 | 10586 |
| 2722 | 99-15963-394 | A | G | S | 6656 | 10587 |
| 2723 | 99-15984-100 | A | G | S | 6657 | 10588 |
| 2724 | 99-16017-426 | C | T | A | 6658 | 10589 |
| 2725 | 99-16026-359 | G | A | S | 6659 | 10590 |
| 2726 | 99-1624-377 | G | A | A | 6660 | 10591 |
| 2727 | 99-16241-126 | T | G | A | 6661 | 10592 |
| 2728 | 99-16259-304 | A | C | S | 6662 | 10593 |
| 2729 | 99-16284-389 | T | C | A | 6663 | 10594 |
| 2730 | 99-16343-30 | T | C | A | 6664 | 10595 |
| 2731 | 99-16401-88 | C | T | A | 6665 | 10596 |
| 2732 | 99-16406-349 | C | T | A | 6666 | 10597 |
| 2733 | 99-16422-240 | A | G | S | 6667 | 10598 |
| 2734 | 99-16428-275 | C | T | A | 6668 | 10599 |
| 2735 | 99-16430-358 | T | G | A | 6669 | 10600 |
| 2736 | 99-16432-114 | T | A | S | 6670 | 10601 |
| 2737 | 99-16647-382 | T | C | A | 6671 | 10602 |
| 2738 | 99-16661-147 | G | A | S | 6672 | 10603 |
| 2739 | 99-16686-82 | A | C | S | 6673 | 10604 |
| 2740 | 99-16714-82 | G | A | A | 6674 | 10605 |
| 2741 | 99-16735-210 | A | G | A | 6675 | 10606 |
| 2742 | 99-16739-245 | G | A | A | 6676 | 10607 |
| 2743 | 99-16751-318 | A | T | S | 6677 | 10608 |
| 2744 | 99-16752-78 | C | G | S | 6678 | 10609 |
| 2745 | 99-16754-63 | A | G | A | 6679 | 10610 |
| 2746 | 99-16758-60 | G | T | A | 6680 | 10611 |
| 2747 | 99-16761-370 | A | G | A | 6681 | 10612 |
| 2748 | 99-16769-459 | G | A | A | 6682 | 10613 |
| 2749 | 99-16771-222 | C | A | S | 6683 | 10614 |
| 2750 | 99-16772-36 | T | C | S | 6684 | 10615 |
| 2751 | 99-16774-183 | G | T | A | 6685 | 10616 |
| 2752 | 99-16776-275 | C | G | S | 6686 | 10617 |
| 2753 | 99-16794-291 | A | T | S | 6687 | 10618 |
| 2754 | 99-16797-385 | G | A | A | 6688 | 10619 |
| 2755 | 99-16815-282 | G | A | A | 6689 | 10620 |
| 2756 | 99-16835-413 | G | A | A | 6690 | 10621 |
| 2757 | 99-16909-151 | T | C | A | 6691 | 10622 |
| 2758 | 99-17024-215 | C | T | S | 6692 | 10623 |
| 2759 | 99-17046-162 | A | C | S | 6693 | 10624 |
| 2760 | 99-17075-173 | C | T | A | 6694 | 10625 |
| 2761 | 99-17107-271 | G | T | A | 6695 | 10626 |
| 2762 | 99-17162-81 | G | T | A | 6696 | 10627 |
| 2763 | 99-17167-55 | A | G | S | 6697 | 10628 |
| 2764 | 99-17214-451 | T | C | A | 6698 | 10629 |
| 2765 | 99-17254-339 | G | A | A | 6699 | 10630 |
| 2766 | 99-17402-339 | G | A | S | 6700 | 10631 |
| 2767 | 99-17492-271 | T | C | A | 6701 | 10632 |
| 2768 | 99-17519-116 | G | A | S | 6702 | 10633 |
| 2769 | 99-17581-374 | G | A | A | 6703 | 10634 |
| 2770 | 99-17716-400 | C | T | S | 6704 | 10635 |
| 2771 | 99-18122-403 | C | T | A | 6705 | 10636 |
| 2772 | 99-18126-160 | A | T | S | 6706 | 10637 |
| 2773 | 99-18127-283 | A | G | S | 6707 | 10638 |
| 2774 | 99-18141-152 | T | C | A | 6708 | 10639 |
| 2775 | 99-18190-317 | G | A | S | 6709 | 10640 |
| 2776 | 99-18321-371 | T | C | S | 6710 | 10641 |
| 2777 | 99-1833-56 | T | C | S | 6711 | 10642 |
| 2778 | 99-18334-485 | A | G | A | 6712 | 10643 |
| 2779 | 99-18396-324 | A | C | S | 6713 | 10644 |
| 2780 | 99-18471-410 | A | G | A | 6714 | 10645 |
| 2781 | 99-18528-195 | G | A | A | 6715 | 10646 |
| 2782 | 99-18576-182 | A | C | S | 6716 | 10647 |
| 2783 | 99-18581-34 | T | C | S | 6717 | 10648 |
| 2784 | 99-18645-309 | G | A | S | 6718 | 10649 |
| 2785 | 99-18696-213 | T | C | S | 6719 | 10650 |
| 2786 | 99-18698-346 | C | G | S | 6720 | 10651 |
| 2787 | 99-18710-208 | C | T | S | 6721 | 10652 |
| 2788 | 99-18717-319 | T | A | S | 6722 | 10653 |
| 2789 | 99-18718-362 | C | G | S | 6723 | 10654 |
| 2790 | 99-18771-300 | C | T | S | 6724 | 10655 |
| 2791 | 99-1879-393 | G | A | A | 6725 | 10656 |
| 2792 | 99-18886-50 | T | A | S | 6726 | 10657 |
| 2793 | 99-18944-242 | C | T | S | 6727 | 10658 |
| 2794 | 99-19023-347 | T | C | S | 6728 | 10659 |
| 2795 | 99-19027-222 | A | G | A | 6729 | 10660 |
| 2796 | 99-19033-208 | G | T | A | 6730 | 10661 |
| 2797 | 99-19040-395 | A | G | A | 6731 | 10662 |
| 2798 | 99-19041-87 | A | G | A | 6732 | 10663 |
| 2799 | 99-19048-487 | C | T | S | 6733 | 10664 |
| 2800 | 99-19050-251 | T | C | S | 6734 | 10665 |
| 2801 | 99-19053-241 | T | A | S | 6735 | 10666 |
| 2802 | 99-19055-264 | T | C | A | 6736 | 10667 |
| 2803 | 99-19059-347 | C | A | A | 6737 | 10668 |
| 2804 | 99-19069-44 | C | T | A | 6738 | 10669 |
| 2805 | 99-19095-106 | T | C | S | 6739 | 10670 |
| 2806 | 99-19096-317 | A | G | A | 6740 | 10671 |
| 2807 | 99-19104-66 | T | C | S | 6741 | 10672 |
| 2808 | 99-19105-114 | A | G | A | 6742 | 10673 |
| 2809 | 99-19108-156 | C | T | S | 6743 | 10674 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 2810 | 99-19110-175 | A | G | A | 6744 | 10675 |
| 2811 | 99-19122-58 | A | G | A | 6745 | 10676 |
| 2812 | 99-19123-242 | A | G | A | 6746 | 10677 |
| 2813 | 99-19130-86 | T | C | S | 6747 | 10678 |
| 2814 | 99-19137-156 | C | T | S | 6748 | 10679 |
| 2815 | 99-19142-245 | T | C | S | 6749 | 10680 |
| 2816 | 99-19154-146 | C | T | S | 6750 | 10681 |
| 2817 | 99-19155-75 | A | G | A | 6751 | 10682 |
| 2818 | 99-19167-269 | A | G | A | 6752 | 10683 |
| 2819 | 99-19170-193 | A | G | A | 6753 | 10684 |
| 2820 | 99-19171-120 | G | A | S | 6754 | 10685 |
| 2821 | 99-19175-150 | G | A | A | 6755 | 10686 |
| 2822 | 99-19177-425 | C | T | S | 6756 | 10687 |
| 2823 | 99-19178-163 | T | C | S | 6757 | 10688 |
| 2824 | 99-19210-502 | A | G | A | 6758 | 10689 |
| 2825 | 99-19219-316 | G | A | A | 6759 | 10690 |
| 2826 | 99-19220-220 | T | C | S | 6760 | 10691 |
| 2827 | 99-19223-238 | C | T | S | 6761 | 10692 |
| 2828 | 99-19226-169 | A | G | A | 6762 | 10693 |
| 2829 | 99-19228-319 | G | A | A | 6763 | 10694 |
| 2830 | 99-19236-409 | G | A | A | 6764 | 10695 |
| 2831 | 99-19241-362 | C | T | S | 6765 | 10696 |
| 2832 | 99-19242-254 | G | A | A | 6766 | 10697 |
| 2833 | 99-19283-172 | A | G | A | 6767 | 10698 |
| 2834 | 99-19295-95 | C | j | S | 6768 | 10699 |
| 2835 | 99-19304-270 | T | C | S | 6769 | 10700 |
| 2836 | 99-19305-367 | A | C | S | 6770 | 10701 |
| 2837 | 99-19309-296 | T | C | S | 6771 | 10702 |
| 2838 | 99-19312-34 | G | A | A | 6772 | 10703 |
| 2839 | 99-19324-214 | A | G | A | 6773 | 10704 |
| 2840 | 99-19330-274 | G | T | A | 6774 | 10705 |
| 2841 | 99-19347-228 | G | A | A | 6775 | 10706 |
| 2842 | 99-19348-229 | T | C | S | 6776 | 10707 |
| 2843 | 99-19351-360 | A | T | S | 6777 | 10708 |
| 2844 | 99-19368-92 | C | A | S | 6778 | 10709 |
| 2845 | 99-19375-434 | G | A | A | 6779 | 10710 |
| 2846 | 99-19381-249 | G | A | A | 6780 | 10711 |
| 2847 | 99-19383-432 | G | C | S | 6781 | 10712 |
| 2848 | 99-19384-63 | G | A | A | 6782 | 10713 |
| 2849 | 99-19418-61 | G | A | A | 6783 | 10714 |
| 2850 | 99-19420-86 | A | T | S | 6784 | 10715 |
| 2851 | 99-19426-250 | G | A | A | 6785 | 10716 |
| 2852 | 99-19431-249 | A | G | A | 6786 | 10717 |
| 2853 | 99-19438-261 | T | A | S | 6787 | 10718 |
| 2854 | 99-19442-48 | G | A | A | 6788 | 10719 |
| 2855 | 99-19444-350 | T | C | S | 6789 | 10720 |
| 2856 | 99-19450-440 | C | A | S | 6790 | 10721 |
| 2857 | 99-19453-250 | G | T | A | 6791 | 10722 |
| 2858 | 99-19457-182 | T | C | S | 6792 | 10723 |
| 2859 | 99-19460-346 | G | T | A | 6793 | 10724 |
| 2860 | 99-19461-282 | T | C | S | 6794 | 10725 |
| 2861 | 99-19464-165 | A | G | A | 6795 | 10726 |
| 2862 | 99-19466-406 | C | T | S | 6796 | 10727 |
| 2863 | 99-19474-266 | G | T | S | 6797 | 10728 |
| 2864 | 99-19475-113 | G | C | S | 6798 | 10729 |
| 2865 | 99-19477-208 | T | C | S | 6799 | 10730 |
| 2866 | 99-19504-468 | T | C | S | 6800 | 10731 |
| 2867 | 99-19528-278 | C | T | S | 6801 | 10732 |
| 2868 | 99-19529-118 | A | G | A | 6802 | 10733 |
| 2869 | 99-19532-207 | G | T | A | 6803 | 10734 |
| 2870 | 99-19538-272 | A | G | A | 6804 | 10735 |
| 2871 | 99-19544-329 | G | A | A | 6805 | 10736 |
| 2872 | 99-19546-473 | G | A | A | 6806 | 10737 |
| 2873 | 99-19550-397 | G | T | A | 6807 | 10738 |
| 2874 | 99-19553-52 | T | C | S | 6808 | 10739 |
| 2875 | 99-19557-152 | A | G | A | 6809 | 10740 |
| 2876 | 99-19560-289 | G | T | A | 6810 | 10741 |
| 2877 | 99-19562-227 | G | A | A | 6811 | 10742 |
| 2878 | 99-19566-337 | C | G | S | 6812 | 10743 |
| 2879 | 99-19568-273 | C | T | S | 6813 | 10744 |
| 2880 | 99-19575-299 | A | G | A | 6814 | 10745 |
| 2881 | 99-19578-307 | A | G | A | 6815 | 10746 |
| 2882 | 99-19580-323 | C | T | S | 6816 | 10747 |
| 2883 | 99-19584-352 | C | T | S | 6817 | 10748 |
| 2884 | 99-19588-438 | G | A | A | 6818 | 10749 |
| 2885 | 99-19589-118 | C | T | S | 6819 | 10750 |
| 2886 | 99-19601-95 | T | G | A | 6820 | 10751 |
| 2887 | 99-19624-48 | C | G | S | 6821 | 10752 |
| 2888 | 99-19634-149 | A | G | A | 6822 | 10753 |
| 2889 | 99-19639-225 | A | G | A | 6823 | 10754 |
| 2890 | 99-19645-339 | A | G | A | 6824 | 10755 |
| 2891 | 99-19650-338 | G | C | S | 6825 | 10756 |
| 2892 | 99-19651-133 | A | C | S | 6826 | 10757 |
| 2893 | 99-19664-328 | G | A | A | 6827 | 10758 |
| 2894 | 99-19673-125 | C | G | S | 6828 | 10759 |
| 2895 | 99-19678-269 | G | C | S | 6829 | 10760 |
| 2896 | 99-19685-39 | A | T | S | 6830 | 10761 |
| 2897 | 99-19697-304 | C | T | S | 6831 | 10762 |
| 2898 | 99-19703-75 | C | G | S | 6832 | 10763 |
| 2899 | 99-19705-128 | T | C | S | 6833 | 10764 |
| 2900 | 99-19709-299 | T | G | A | 6834 | 10765 |
| 2901 | 99-19711-169 | G | T | A | 6835 | 10766 |
| 2902 | 99-19722-150 | T | C | S | 6836 | 10767 |
| 2903 | 99-19731-244 | A | G | A | 6837 | 10768 |
| 2904 | 99-19732-385 | T | A | S | 6838 | 10769 |
| 2905 | 99-19736-62 | G | A | A | 6839 | 10770 |
| 2906 | 99-19745-330 | C | T | S | 6840 | 10771 |
| 2907 | 99-19749-158 | G | A | A | 6841 | 10772 |
| 2908 | 99-19752-88 | T | C | S | 6842 | 10773 |
| 2909 | 99-19753-300 | G | A | A | 6843 | 10774 |
| 2910 | 99-19756-85 | T | C | S | 6844 | 10775 |
| 2911 | 99-19764-177 | T | C | S | 6845 | 10776 |
| 2912 | 99-19769-227 | C | T | S | 6846 | 10777 |
| 2913 | 99-19780-179 | A | G | A | 6847 | 10778 |
| 2914 | 99-19785-140 | A | G | A | 6848 | 10779 |
| 2915 | 99-19790-398 | G | A | A | 6849 | 10780 |
| 2916 | 99-19791-103 | G | T | A | 6850 | 10781 |
| 2917 | 99-19795-199 | A | G | A | 6851 | 10782 |
| 2918 | 99-19796-256 | T | G | A | 6852 | 10783 |
| 2919 | 99-19807-396 | C | T | S | 6853 | 10784 |
| 2920 | 99-19813-55 | C | T | S | 6854 | 10785 |
| 2921 | 99-19818-156 | C | T | S | 6855 | 10786 |
| 2922 | 99-19826-285 | G | A | A | 6856 | 10787 |
| 2923 | 99-19839-223 | A | G | A | 6857 | 10788 |
| 2924 | 99-19851-40 | C | G | S | 6858 | 10789 |
| 2925 | 99-19858-91 | C | T | S | 6859 | 10790 |
| 2926 | 99-19860-68 | A | G | A | 6860 | 10791 |
| 2927 | 99-19864-112 | T | C | S | 6861 | 10792 |
| 2928 | 99-19871-422 | T | C | S | 6862 | 10793 |
| 2929 | 99-19872-136 | G | A | A | 6863 | 10794 |
| 2930 | 99-19875-99 | A | G | A | 6864 | 10795 |
| 2931 | 99-19876-394 | A | C | S | 6865 | 10796 |
| 2932 | 99-19890-235 | A | C | S | 6866 | 10797 |
| 2933 | 99-19896-142 | G | T | A | 6867 | 10798 |
| 2934 | 99-19901-383 | C | T | S | 6868 | 10799 |
| 2935 | 99-19906-136 | C | G | S | 6869 | 10800 |
| 2936 | 99-19911-90 | G | C | S | 6870 | 10801 |
| 2937 | 99-19916-380 | T | C | S | 6871 | 10802 |
| 2938 | 99-19922-42 | G | A | A | 6872 | 10803 |
| 2939 | 99-19923-383 | G | A | A | 6873 | 10804 |
| 2940 | 99-19933-251 | A | G | A | 6874 | 10805 |
| 2941 | 99-19937-235 | A | G | A | 6875 | 10806 |
| 2942 | 99-19944-306 | T | A | S | 6876 | 10807 |
| 2943 | 99-19951-313 | A | T | S | 6877 | 10808 |
| 2944 | 99-20038-204 | T | C | S | 6878 | 10809 |
| 2945 | 99-20072-277 | A | T | S | 6879 | 10810 |
| 2946 | 99-20226-32 | T | C | S | 6880 | 10811 |
| 2947 | 99-20228-290 | T | C | S | 6881 | 10812 |
| 2948 | 99-20234-101 | C | G | S | 6882 | 10813 |
| 2949 | 99-20537-433 | G | C | S | 6883 | 10814 |
| 2950 | 99-20733-79 | G | A | A | 6884 | 10815 |
| 2951 | 99-20815-363 | A | T | S | 6885 | 10816 |
| 2952 | 99-20896-383 | A | G | A | 6886 | 10817 |
| 2953 | 99-20958-373 | A | G | A | 6887 | 10818 |
| 2954 | 99-21057-337 | T | C | S | 6888 | 10819 |
| 2955 | 99-21059-118 | T | C | S | 6889 | 10820 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 2956 | 99-21110-304 | C | G | S | 6890 | 10821 |
| 2957 | 99-21123-62 | C | T | S | 6891 | 10822 |
| 2958 | 99-21133-169 | G | A | A | 6892 | 10823 |
| 2959 | 99-21181-413 | A | G | A | 6893 | 10824 |
| 2960 | 99-21192-164 | T | A | S | 6894 | 10825 |
| 2961 | 99-21227-295 | T | C | S | 6895 | 10826 |
| 2962 | 99-21229-81 | G | A | A | 6896 | 10827 |
| 2963 | 99-21240-419 | C | T | S | 6897 | 10828 |
| 2964 | 99-21242-57 | T | A | S | 6898 | 10829 |
| 2965 | 99-21244-495 | G | A | A | 6899 | 10830 |
| 2966 | 99-21252-77 | T | C | S | 6900 | 10831 |
| 2967 | 99-21267-111 | C | T | S | 6901 | 10832 |
| 2968 | 99-21284-322 | G | A | A | 6902 | 10833 |
| 2969 | 99-21293-252 | A | G | A | 6903 | 10834 |
| 2970 | 99-21307-370 | A | G | A | 6904 | 10835 |
| 2971 | 99-21310-416 | A | G | A | 6905 | 10836 |
| 2972 | 99-21312-319 | C | A | S | 6906 | 10837 |
| 2973 | 99-21323-142 | A | G | A | 6907 | 10838 |
| 2974 | 99-21327-94 | A | G | A | 6908 | 10839 |
| 2975 | 99-21328-173 | C | T | S | 6909 | 10840 |
| 2976 | 99-21329-518 | A | G | A | 6910 | 10841 |
| 2977 | 99-21342-350 | T | C | S | 6911 | 10842 |
| 2978 | 99-21346-290 | G | A | A | 6912 | 10843 |
| 2979 | 99-21360-343 | A | G | A | 6913 | 10844 |
| 2980 | 99-21361-97 | G | T | A | 6914 | 10845 |
| 2981 | 99-21377-73 | C | T | S | 6915 | 10846 |
| 2982 | 99-21378-303 | T | C | S | 6916 | 10847 |
| 2983 | 99-21391-418 | G | A | A | 6917 | 10848 |
| 2984 | 99-21401-117 | T | C | S | 6918 | 10849 |
| 2985 | 99-21423-302 | T | C | S | 6919 | 10850 |
| 2986 | 99-21433-238 | T | G | A | 6920 | 10851 |
| 2987 | 99-21441-420 | A | G | A | 6921 | 10852 |
| 2988 | 99-21444-227 | T | C | S | 6922 | 10853 |
| 2989 | 99-21448-361 | A | G | A | 6923 | 10854 |
| 2990 | 99-21461-375 | C | T | S | 6924 | 10855 |
| 2991 | 99-21463-258 | A | G | A | 6925 | 10856 |
| 2992 | 99-21465-58 | C | A | S | 6926 | 10857 |
| 2993 | 99-21486-88 | C | A | S | 6927 | 10858 |
| 2994 | 99-21492-310 | C | T | S | 6928 | 10859 |
| 2995 | 99-21502-211 | G | A | A | 6929 | 10860 |
| 2996 | 99-21508-131 | C | A | S | 6930 | 10861 |
| 2997 | 99-21510-466 | T | A | S | 6931 | 10862 |
| 2998 | 99-21512-165 | A | T | S | 6932 | 10863 |
| 2999 | 99-21516-293 | G | T | A | 6933 | 10864 |
| 3000 | 99-21533-445 | C | T | S | 6934 | 10865 |
| 3001 | 99-21560-376 | G | A | A | 6935 | 10866 |
| 3002 | 99-21561-41 | T | C | S | 6936 | 10867 |
| 3003 | 99-21566-152 | C | T | S | 6937 | 10868 |
| 3004 | 99-21578-105 | T | C | S | 6938 | 10869 |
| 3005 | 99-21580-141 | A | G | A | 6939 | 10870 |
| 3006 | 99-21591-181 | T | G | A | 6940 | 10871 |
| 3007 | 99-21592-43 | C | T | S | 6941 | 10872 |
| 3008 | 99-21607-114 | A | G | A | 6942 | 10873 |
| 3009 | 99-21615-133 | C | T | S | 6943 | 10874 |
| 3010 | 99-21657-161 | T | C | S | 6944 | 10875 |
| 3011 | 99-21664-278 | G | T | A | 6945 | 10876 |
| 3012 | 99-21666-96 | C | A | S | 6946 | 10877 |
| 3013 | 99-21673-106 | A | T | S | 6947 | 10878 |
| 3014 | 99-21674-245 | G | C | S | 6948 | 10879 |
| 3015 | 99-21687-313 | G | A | A | 6949 | 10880 |
| 3016 | 99-21690-162 | A | G | A | 6950 | 10881 |
| 3017 | 99-21693-368 | C | T | S | 6951 | 10882 |
| 3018 | 99-21699-149 | G | C | S | 6952 | 10883 |
| 3019 | 99-21703-36 | G | A | A | 6953 | 10884 |
| 3020 | 99-21705-306 | T | G | A | 6954 | 10885 |
| 3021 | 99-21707-429 | C | T | S | 6955 | 10886 |
| 3022 | 99-21710-272 | C | G | S | 6956 | 10887 |
| 3023 | 99-21733-323 | G | C | S | 6957 | 10888 |
| 3024 | 99-21734-183 | C | T | S | 6958 | 10889 |
| 3025 | 99-21742-337 | G | A | A | 6959 | 10890 |
| 3026 | 99-21745-455 | T | C | S | 6960 | 10891 |
| 3027 | 99-21756-230 | T | G | A | 6961 | 10892 |
| 3028 | 99-21759-21 | T | G | A | 6962 | 10893 |
| 3029 | 99-21762-135 | A | C | S | 6963 | 10894 |
| 3030 | 99-21763-52 | A | G | A | 6964 | 10895 |
| 3031 | 99-21765-111 | A | T | S | 6965 | 10896 |
| 3032 | 99-21767-392 | T | A | S | 6966 | 10897 |
| 3033 | 99-21771-144 | G | A | A | 6967 | 10898 |
| 3034 | 99-21775-466 | A | T | S | 6968 | 10899 |
| 3035 | 99-21787-348 | A | G | A | 6969 | 10900 |
| 3036 | 99-21790-161 | G | A | A | 6970 | 10901 |
| 3037 | 99-21791-364 | T | C | S | 6971 | 10902 |
| 3038 | 99-21800-310 | A | G | A | 6972 | 10903 |
| 3039 | 99-21801-123 | T | C | S | 6973 | 10904 |
| 3040 | 99-21804-310 | T | C | S | 6974 | 10905 |
| 3041 | 99-21810-222 | G | A | A | 6975 | 10906 |
| 3042 | 99-21811-209 | T | C | S | 6976 | 10907 |
| 3043 | 99-21827-155 | T | C | S | 6977 | 10908 |
| 3044 | 99-21829-261 | C | T | S | 6978 | 10909 |
| 3045 | 99-21831-311 | A | G | A | 6979 | 10910 |
| 3046 | 99-21838-153 | A | G | A | 6980 | 10911 |
| 3047 | 99-21844-165 | G | A | A | 6981 | 10912 |
| 3048 | 99-21846-327 | C | T | S | 6982 | 10913 |
| 3049 | 99-21874-311 | G | T | A | 6983 | 10914 |
| 3050 | 99-21880-331 | C | T | S | 6984 | 10915 |
| 3051 | 99-21881-152 | T | C | S | 6985 | 10916 |
| 3052 | 99-21889-219 | G | A | A | 6986 | 10917 |
| 3053 | 99-21893-388 | G | A | A | 6987 | 10918 |
| 3054 | 99-21896-345 | A | G | A | 6988 | 10919 |
| 3055 | 99-21898-102 | T | A | S | 6989 | 10920 |
| 3056 | 99-21901-331 | G | A | A | 6990 | 10921 |
| 3057 | 99-21913-483 | A | G | A | 6991 | 10922 |
| 3058 | 99-21916-359 | A | G | A | 6992 | 10923 |
| 3059 | 99-21917-84 | G | C | S | 6993 | 10924 |
| 3060 | 99-21919-38 | A | G | A | 6994 | 10925 |
| 3061 | 99-21921-338 | T | C | S | 6995 | 10926 |
| 3062 | 99-21943-413 | C | T | S | 6996 | 10927 |
| 3063 | 99-21948-237 | C | T | S | 6997 | 10928 |
| 3064 | 99-21950-107 | G | C | S | 6998 | 10929 |
| 3065 | 99-21952-76 | T | C | A | 6999 | 10930 |
| 3066 | 99-21968-150 | G | A | A | 7000 | 10931 |
| 3067 | 99-21969-425 | T | G | A | 7001 | 10932 |
| 3068 | 99-22008-325 | C | T | S | 7002 | 10933 |
| 3069 | 99-22098-101 | C | G | S | 7003 | 10934 |
| 3070 | 99-22155-199 | T | C | S | 7004 | 10935 |
| 3071 | 99-22181-171 | G | A | A | 7005 | 10936 |
| 3072 | 99-22187-261 | C | T | S | 7006 | 10937 |
| 3073 | 99-22190-369 | T | C | S | 7007 | 10938 |
| 3074 | 99-22202-58 | T | C | S | 7008 | 10939 |
| 3075 | 99-22204-391 | T | C | S | 7009 | 10940 |
| 3076 | 99-22206-455 | C | G | S | 7010 | 10941 |
| 3077 | 99-22213-333 | T | A | S | 7011 | 10942 |
| 3078 | 99-22355-213 | T | A | S | 7012 | 10943 |
| 3079 | 99-22363-268 | A | G | A | 7013 | 10944 |
| 3080 | 99-22375-353 | G | A | A | 7014 | 10945 |
| 3081 | 99-22405-335 | C | T | S | 7015 | 10946 |
| 3082 | 99-2251-151 | G | A | A | 7016 | 10947 |
| 3083 | 99-22530-48 | C | T | S | 7017 | 10948 |
| 3084 | 99-22537-280 | A | G | A | 7018 | 10949 |
| 3085 | 99-22567-243 | C | G | S | 7019 | 10950 |
| 3086 | 99-22572-72 | A | G | A | 7020 | 10951 |
| 3087 | 99-22593-64 | C | T | S | 7021 | 10952 |
| 3088 | 99-22706-367 | T | C | S | 7022 | 10953 |
| 3089 | 99-22729-352 | T | A | S | 7023 | 10954 |
| 3090 | 99-22768-113 | G | T | A | 7024 | 10955 |
| 3091 | 99-22814-349 | C | T | S | 7025 | 10956 |
| 3092 | 99-22818-33 | C | T | S | 7026 | 10957 |
| 3093 | 99-22826-311 | C | T | S | 7027 | 10958 |
| 3094 | 99-22851-121 | A | G | A | 7028 | 10959 |
| 3095 | 99-23113-388 | C | T | S | 7029 | 10960 |
| 3096 | 99-23188-227 | T | C | S | 7030 | 10961 |
| 3097 | 99-23240-326 | C | A | S | 7031 | 10962 |
| 3098 | 99-23246-66 | A | G | A | 7032 | 10963 |
| 3099 | 99-23248-308 | A | G | A | 7033 | 10964 |
| 3100 | 99-23249-262 | A | G | A | 7034 | 10965 |
| 3101 | 99-23274-182 | C | T | S | 7035 | 10966 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 3102 | 99-2333-423 | T | G | A | 7036 | 10967 |
| 3103 | 99-2341-485 | C | T | S | 7037 | 10968 |
| 3104 | 99-2342-217 | C | T | S | 7038 | 10969 |
| 3105 | 99-23427-283 | G | A | A | 7039 | 10970 |
| 3106 | 99-23442-190 | T | C | S | 7040 | 10971 |
| 3107 | 99-23544-340 | C | A | S | 7041 | 10972 |
| 3108 | 99-23549-78 | G | A | A | 7042 | 10973 |
| 3109 | 99-23558-98 | A | G | A | 7043 | 10974 |
| 3110 | 99-23565-252 | G | C | S | 7044 | 10975 |
| 3111 | 99-23589-198 | A | C | S | 7045 | 10976 |
| 3112 | 99-23590-205 | C | T | S | 7046 | 10977 |
| 3113 | 99-23621-189 | G | A | A | 7047 | 10978 |
| 3114 | 99-23641-159 | G | A | A | 7048 | 10979 |
| 3115 | 99-23652-244 | G | A | A | 7049 | 10980 |
| 3116 | 99-23696-164 | C | T | S | 7050 | 10981 |
| 3117 | 99-23701-104 | C | T | S | 7051 | 10982 |
| 3118 | 99-23702-437 | G | A | A | 7052 | 10983 |
| 3119 | 99-2371-93 | A | C | S | 7053 | 10984 |
| 3120 | 99-23711-455 | C | T | S | 7054 | 10985 |
| 3121 | 99-23730-202 | T | C | S | 7055 | 10986 |
| 3122 | 99-23736-314 | G | A | S | 7056 | 10987 |
| 3123 | 99-23813-476 | C | T | S | 7057 | 10988 |
| 3124 | 99-23821-176 | G | C | S | 7058 | 10989 |
| 3125 | 99-23844-382 | A | C | S | 7059 | 10990 |
| 3126 | 99-23858-51 | G | T | A | 7060 | 10991 |
| 3127 | 99-23860-146 | G | C | S | 7061 | 10992 |
| 3128 | 99-23876-265 | A | C | S | 7062 | 10993 |
| 3129 | 99-23878-400 | C | A | S | 7063 | 10994 |
| 3130 | 99-23880-268 | G | A | A | 7064 | 10995 |
| 3131 | 99-23887-103 | G | A | A | 7065 | 10996 |
| 3132 | 99-23889-342 | A | G | A | 7066 | 10997 |
| 3133 | 99-23894-339 | T | C | S | 7067 | 10998 |
| 3134 | 99-23895-40 | T | C | S | 7068 | 10999 |
| 3135 | 99-23902-103 | T | C | S | 7069 | 11000 |
| 3136 | 99-23912-116 | G | C | S | 7070 | 11001 |
| 3137 | 99-23915-69 | A | G | A | 7071 | 11002 |
| 3138 | 99-23918-179 | T | C | S | 7072 | 11003 |
| 3139 | 99-23934-353 | G | A | A | 7073 | 11004 |
| 3140 | 99-23936-216 | T | C | S | 7074 | 11005 |
| 3141 | 99-23938-414 | G | A | A | 7075 | 11006 |
| 3142 | 99-23943-245 | A | G | A | 7076 | 11007 |
| 3143 | 99-23960-298 | T | C | A | 7077 | 11008 |
| 3144 | 99-23965-360 | C | T | A | 7078 | 11009 |
| 3145 | 99-23977-141 | G | A | S | 7079 | 11010 |
| 3146 | 99-23987-115 | C | T | A | 7080 | 11011 |
| 3147 | 99-23988-441 | C | T | A | 7081 | 11012 |
| 3148 | 99-23995-407 | A | G | S | 7082 | 11013 |
| 3149 | 99-24000-316 | C | T | S | 7083 | 11014 |
| 3150 | 99-24003-172 | T | C | A | 7084 | 11015 |
| 3151 | 99-24004-200 | A | G | S | 7085 | 11016 |
| 3152 | 99-24007-362 | T | C | A | 7086 | 11017 |
| 3153 | 99-24020-379 | C | A | S | 7087 | 11018 |
| 3154 | 99-24038-103 | C | T | A | 7088 | 11019 |
| 3155 | 99-24063-363 | T | C | S | 7089 | 11020 |
| 3156 | 99-24073-384 | G | A | A | 7090 | 11021 |
| 3157 | 99-24075-45 | T | G | A | 7091 | 11022 |
| 3158 | 99-24079-268 | C | A | S | 7092 | 11023 |
| 3159 | 99-24084-110 | G | A | A | 7093 | 11024 |
| 3160 | 99-24092-209 | A | G | A | 7094 | 11025 |
| 3161 | 99-24096-386 | T | A | S | 7095 | 11026 |
| 3162 | 99-24105-247 | C | T | S | 7096 | 11027 |
| 3163 | 99-24113-332 | A | G | A | 7097 | 11028 |
| 3164 | 99-24117-169 | A | G | A | 7098 | 11029 |
| 3165 | 99-24119-368 | T | G | A | 7099 | 11030 |
| 3166 | 99-24123-125 | A | G | A | 7100 | 11031 |
| 3167 | 99-24140-394 | G | A | A | 7101 | 11032 |
| 3168 | 99-24148-332 | A | C | S | 7102 | 11033 |
| 3169 | 99-24152-268 | C | T | S | 7103 | 11034 |
| 3170 | 99-24155-271 | A | C | S | 7104 | 11035 |
| 3171 | 99-24156-107 | C | T | S | 7105 | 11036 |
| 3172 | 99-24167-85 | A | C | S | 7106 | 11037 |
| 3173 | 99-24175-218 | A | G | A | 7107 | 11038 |
| 3174 | 99-24180-390 | A | G | A | 7108 | 11039 |
| 3175 | 99-24182-326 | C | A | S | 7109 | 11040 |
| 3176 | 99-24185-446 | T | C | S | 7110 | 11041 |
| 3177 | 99-24187-142 | A | G | A | 7111 | 11042 |
| 3178 | 99-24190-231 | G | C | S | 7112 | 11043 |
| 3179 | 99-24202-433 | C | G | S | 7113 | 11044 |
| 3180 | 99-24204-486 | T | C | S | 7114 | 11045 |
| 3181 | 99-24208-292 | T | A | S | 7115 | 11046 |
| 3182 | 99-24210-111 | G | A | A | 7116 | 11047 |
| 3183 | 99-24217-206 | T | C | S | 7117 | 11048 |
| 3184 | 99-24225-439 | A | G | A | 7118 | 11049 |
| 3185 | 99-24228-386 | G | C | S | 7119 | 11050 |
| 3186 | 99-24232-419 | A | G | A | 7120 | 11051 |
| 3187 | 99-24234-352 | A | G | S | 7121 | 11052 |
| 3188 | 99-24369-263 | G | C | S | 7122 | 11053 |
| 3189 | 99-24397-315 | G | C | S | 7123 | 11054 |
| 3190 | 99-24408-202 | A | G | S | 7124 | 11055 |
| 3191 | 99-2441-512 | A | G | A | 7125 | 11056 |
| 3192 | 99-24412-279 | C | T | A | 7126 | 11057 |
| 3193 | 99-24415-85 | T | C | A | 7127 | 11058 |
| 3194 | 99-24470-168 | G | A | S | 7128 | 11059 |
| 3195 | 99-24472-179 | A | G | S | 7129 | 11060 |
| 3196 | 99-24480-44 | A | C | S | 7130 | 11061 |
| 3197 | 99-24485-55 | G | T | A | 7131 | 11062 |
| 3198 | 99-24490-363 | A | G | S | 7132 | 11063 |
| 3199 | 99-24492-351 | C | G | S | 7133 | 11064 |
| 3200 | 99-24581-253 | G | A | S | 7134 | 11065 |
| 3201 | 99-24591-33 | T | C | A | 7135 | 11066 |
| 3202 | 99-24592-55 | C | T | A | 7136 | 11067 |
| 3203 | 99-24745-413 | T | C | A | 7137 | 11068 |
| 3204 | 99-24753-182 | G | A | S | 7138 | 11069 |
| 3205 | 99-24768-233 | C | T | S | 7139 | 11070 |
| 3206 | 99-24855-180 | C | T | A | 7140 | 11071 |
| 3207 | 99-24863-199 | C | T | A | 7141 | 11072 |
| 3208 | 99-24867-219 | G | A | S | 7142 | 11073 |
| 3209 | 99-24871-435 | A | G | S | 7143 | 11074 |
| 3210 | 99-24889-311 | T | A | S | 7144 | 11075 |
| 3211 | 99-24897-276 | C | G | S | 7145 | 11076 |
| 3212 | 99-24904-187 | T | C | A | 7146 | 11077 |
| 3213 | 99-24909-440 | A | G | S | 7147 | 11078 |
| 3214 | 99-24917-250 | G | A | S | 7148 | 11079 |
| 3215 | 99-24930-299 | A | G | A | 7149 | 11080 |
| 3216 | 99-24936-332 | G | T | A | 7150 | 11081 |
| 3217 | 99-24965-416 | G | C | S | 7151 | 11082 |
| 3218 | 99-24966-423 | C | T | A | 7152 | 11083 |
| 3219 | 99-25020-395 | C | G | S | 7153 | 11084 |
| 3220 | 99-25362-247 | T | C | S | 7154 | 11085 |
| 3221 | 99-25394-261 | T | C | S | 7155 | 11086 |
| 3222 | 99-25406-54 | G | C | S | 7156 | 11087 |
| 3223 | 99-25446-121 | C | A | S | 7157 | 11088 |
| 3224 | 99-25496-221 | C | T | A | 7158 | 11089 |
| 3225 | 99-25497-242 | G | A | S | 7159 | 11090 |
| 3226 | 99-2559-253 | T | G | A | 7160 | 11091 |
| 3227 | 99-25654-281 | G | A | S | 7161 | 11092 |
| 3228 | 99-2566-112 | A | G | A | 7162 | 11093 |
| 3229 | 99-2567-329 | T | G | A | 7163 | 11094 |
| 3230 | 99-2571-242 | G | A | A | 7164 | 11095 |
| 3231 | 99-25738-218 | C | T | A | 7165 | 11096 |
| 3232 | 99-25755-364 | A | G | S | 7166 | 11097 |
| 3233 | 99-25834-70 | T | G | A | 7167 | 11098 |
| 3234 | 99-25843-256 | A | C | S | 7168 | 11099 |
| 3235 | 99-26051-273 | G | A | A | 7169 | 11100 |
| 3236 | 99-26058-275 | G | C | S | 7170 | 11101 |
| 3237 | 99-26074-400 | A | C | S | 7171 | 11102 |
| 3238 | 99-26076-376 | G | A | A | 7172 | 11103 |
| 3239 | 99-2630-67 | G | A | A | 7173 | 11104 |
| 3240 | 99-2633-129 | C | A | S | 7174 | 11105 |
| 3241 | 99-2634-341 | G | A | A | 7175 | 11106 |
| 3242 | 99-2636-64 | A | T | S | 7176 | 11107 |
| 3243 | 99-2642-255 | A | G | A | 7177 | 11108 |
| 3244 | 99-2645-118 | T | G | A | 7178 | 11109 |
| 3245 | 99-2647-368 | G | A | A | 7179 | 11110 |
| 3246 | 99-2649-107 | T | A | S | 7180 | 11111 |
| 3247 | 99-2711-269 | A | G | A | 7181 | 11112 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 3248 | 99-2712-52 | C | T | S | 7182 | 11113 |
| 3249 | 99-2718-202 | C | T | S | 7183 | 11114 |
| 3250 | 99-2719-419 | T | C | S | 7184 | 11115 |
| 3251 | 99-2726-364 | C | G | S | 7185 | 11116 |
| 3252 | 99-2734-400 | T | G | A | 7186 | 11117 |
| 3253 | 99-2740-351 | T | G | A | 7187 | 11118 |
| 3254 | 99-2752-213 | C | G | S | 7188 | 11119 |
| 3255 | 99-2760-182 | A | G | A | 7189 | 11120 |
| 3256 | 99-2761-223 | A | G | A | 7190 | 11121 |
| 3257 | 99-2765-279 | A | G | A | 7191 | 11122 |
| 3258 | 99-2790-217 | T | C | S | 7192 | 11123 |
| 3259 | 99-2797-399 | C | T | S | 7193 | 11124 |
| 3260 | 99-2816-62 | G | A | A | 7194 | 11125 |
| 3261 | 99-2817-88 | G | C | A | 7195 | 11126 |
| 3262 | 99-2819-108 | A | G | A | 7196 | 11127 |
| 3263 | 99-2820-199 | A | G | A | 7197 | 11128 |
| 3264 | 99-2832-152 | C | T | S | 7198 | 11129 |
| 3265 | 99-2868-277 | G | C | S | 7199 | 11130 |
| 3266 | 99-2870-70 | A | G | A | 7200 | 11131 |
| 3267 | 99-2881-61 | T | A | S | 7201 | 11132 |
| 3268 | 99-2895-47 | A | G | A | 7202 | 11133 |
| 3269 | 99-2903-265 | A | T | S | 7203 | 11134 |
| 3270 | 99-2906-80 | C | T | S | 7204 | 11135 |
| 3271 | 99-2914-48 | A | G | A | 7205 | 11136 |
| 3272 | 99-2922-171 | G | A | A | 7206 | 11137 |
| 3273 | 99-2924-183 | T | C | S | 7207 | 11138 |
| 3274 | 99-2926-184 | G | A | A | 7208 | 11139 |
| 3275 | 99-2928-52 | G | A | A | 7209 | 11140 |
| 3276 | 99-2938-83 | T | C | S | 7210 | 11141 |
| 3277 | 99-2943-230 | T | G | A | 7211 | 11142 |
| 3278 | 99-2944-351 | C | T | S | 7212 | 11143 |
| 3279 | 99-295-355 | T | C | S | 7213 | 11144 |
| 3280 | 99-2954-160 | C | G | S | 7214 | 11145 |
| 3281 | 99-2956-239 | C | T | S | 7215 | 11146 |
| 3282 | 99-2970-318 | G | C | S | 7216 | 11147 |
| 3283 | 99-2978-135 | C | A | S | 7217 | 11148 |
| 3284 | 99-2981-53 | T | C | S | 7218 | 11149 |
| 3285 | 99-2988-243 | C | T | S | 7219 | 11150 |
| 3286 | 99-2989-345 | C | A | S | 7220 | 11151 |
| 3287 | 99-2991-256 | G | A | A | 7221 | 11152 |
| 3288 | 99-2995-168 | C | T | S | 7222 | 11153 |
| 3289 | 99-2999-371 | C | T | S | 7223 | 11154 |
| 3290 | 99-3013-250 | A | T | S | 7224 | 11155 |
| 3291 | 99-3018-50 | A | G | A | 7225 | 11156 |
| 3292 | 99-3019-316 | A | T | S | 7226 | 11157 |
| 3293 | 99-3020-369 | A | G | A | 7227 | 11158 |
| 3294 | 99-3021-290 | A | G | A | 7228 | 11159 |
| 3295 | 99-3044-216 | C | T | S | 7229 | 11160 |
| 3296 | 99-3045-108 | C | T | S | 7230 | 11161 |
| 3297 | 99-3046-91 | T | C | S | 7231 | 11162 |
| 3298 | 99-3047-395 | G | A | A | 7232 | 11163 |
| 3299 | 99-3058-420 | T | A | S | 7233 | 11164 |
| 3300 | 99-306-119 | G | A | A | 7234 | 11165 |
| 3301 | 99-3061-369 | A | G | A | 7235 | 11166 |
| 3302 | 99-3106-272 | G | A | A | 7236 | 11167 |
| 3303 | 99-3108-156 | A | T | S | 7237 | 11168 |
| 3304 | 99-3109-402 | G | A | A | 7238 | 11169 |
| 3305 | 99-3110-321 | C | T | S | 7239 | 11170 |
| 3306 | 99-312-311 | C | T | S | 7240 | 11171 |
| 3307 | 99-3129-113 | T | A | S | 7241 | 11172 |
| 3308 | 99-3132-158 | A | G | A | 7242 | 11173 |
| 3309 | 99-3144-112 | A | G | A | 7243 | 11174 |
| 3310 | 99-3147-24 | C | G | S | 7244 | 11175 |
| 3311 | 99-3153-190 | C | T | S | 7245 | 11176 |
| 3312 | 99-3154-110 | T | C | S | 7246 | 11177 |
| 3313 | 99-3156-251 | T | C | S | 7247 | 11178 |
| 3314 | 99-3167-227 | A | G | A | 7248 | 11179 |
| 3315 | 99-3195-71 | G | A | A | 7249 | 11180 |
| 3316 | 99-3217-274 | G | A | A | 7250 | 11181 |
| 3317 | 99-3224-232 | A | G | A | 7251 | 11182 |
| 3318 | 99-3231-109 | T | A | S | 7252 | 11183 |
| 3319 | 99-3234-274 | A | C | S | 7253 | 11184 |
| 3320 | 99-325-226 | A | C | S | 7254 | 11185 |
| 3321 | 99-3266-193 | G | A | A | 7255 | 11186 |
| 3322 | 99-3276-195 | C | A | S | 7256 | 11187 |
| 3323 | 99-3279-337 | T | C | S | 7257 | 11188 |
| 3324 | 99-3293-300 | T | G | A | 7258 | 11189 |
| 3325 | 99-3296-101 | T | A | S | 7259 | 11190 |
| 3326 | 99-3299-211 | C | T | S | 7260 | 11191 |
| 3327 | 99-3305-272 | A | C | S | 7261 | 11192 |
| 3328 | 99-3335-53 | C | T | S | 7262 | 11193 |
| 3329 | 99-3337-294 | C | T | S | 7263 | 11194 |
| 3330 | 99-3342-103 | G | A | A | 7264 | 11195 |
| 3331 | 99-3347-226 | T | A | S | 7265 | 11196 |
| 3332 | 99-3349-124 | A | C | S | 7266 | 11197 |
| 3333 | 99-3353-350 | T | C | S | 7267 | 11198 |
| 3334 | 99-3356-345 | A | G | A | 7268 | 11199 |
| 3335 | 99-3368-277 | C | T | S | 7269 | 11200 |
| 3336 | 99-3373-253 | C | G | S | 7270 | 11201 |
| 3337 | 99-3374-274 | G | A | A | 7271 | 11202 |
| 3338 | 99-3385-197 | C | T | S | 7272 | 11203 |
| 3339 | 99-3390-328 | G | A | A | 7273 | 11204 |
| 3340 | 99-3391-160 | C | T | S | 7274 | 11205 |
| 3341 | 99-3393-245 | A | G | A | 7275 | 11206 |
| 3342 | 99-3398-196 | T | C | S | 7276 | 11207 |
| 3343 | 99-3399-449 | C | T | S | 7277 | 11208 |
| 3344 | 99-3400-83 | G | A | A | 7278 | 11209 |
| 3345 | 99-3414-112 | G | A | A | 7279 | 11210 |
| 3346 | 99-3415-215 | G | A | A | 7280 | 11211 |
| 3347 | 99-3426-270 | C | T | S | 7281 | 11212 |
| 3348 | 99-3428-366 | A | G | A | 7282 | 11213 |
| 3349 | 99-3445-239 | G | C | S | 7283 | 11214 |
| 3350 | 99-3453-138 | A | G | A | 7284 | 11215 |
| 3351 | 99-3460-337 | C | T | S | 7285 | 11216 |
| 3352 | 99-3462-117 | C | T | S | 7286 | 11217 |
| 3353 | 99-3468-272 | A | G | A | 7287 | 11218 |
| 3354 | 99-3469-313 | C | G | S | 7288 | 11219 |
| 3355 | 99-3473-309 | C | G | S | 7289 | 11220 |
| 3356 | 99-3474-272 | A | G | S | 7290 | 11221 |
| 3357 | 99-3478-199 | G | A | A | 7291 | 11222 |
| 3358 | 99-3479-293 | T | C | S | 7292 | 11223 |
| 3359 | 99-3482-225 | A | G | A | 7293 | 11224 |
| 3360 | 99-3483-252 | T | C | S | 7294 | 11225 |
| 3361 | 99-3485-245 | T | A | S | 7295 | 11226 |
| 3362 | 99-3511-130 | G | A | A | 7296 | 11227 |
| 3363 | 99-3519-374 | G | A | A | 7297 | 11228 |
| 3364 | 99-3522-210 | A | G | A | 7298 | 11229 |
| 3365 | 99-3523-270 | A | C | S | 7299 | 11230 |
| 3366 | 99-3524-403 | T | A | S | 7300 | 11231 |
| 3367 | 99-3542-336 | G | T | A | 7301 | 11232 |
| 3368 | 99-3556-129 | T | G | A | 7302 | 11233 |
| 3369 | 99-3563-121 | C | T | S | 7303 | 11234 |
| 3370 | 99-3580-122 | C | G | S | 7304 | 11235 |
| 3371 | 99-3588-188 | T | A | S | 7305 | 11236 |
| 3372 | 99-3589-203 | C | T | S | 7306 | 11237 |
| 3373 | 99-3596-147 | C | T | S | 7307 | 11238 |
| 3374 | 99-36-69 | C | T | S | 7308 | 11239 |
| 3375 | 99-3601-226 | T | C | S | 7309 | 11240 |
| 3376 | 99-3603-80 | T | A | S | 7310 | 11241 |
| 3377 | 99-3604-91 | A | G | A | 7311 | 11242 |
| 3378 | 99-3619-330 | C | T | S | 7312 | 11243 |
| 3379 | 99-3620-314 | G | A | A | 7313 | 11244 |
| 3380 | 99-3628-31 | G | A | A | 7314 | 11245 |
| 3381 | 99-3629-219 | G | A | A | 7315 | 11246 |
| 3382 | 99-3631-159 | C | T | S | 7316 | 11247 |
| 3383 | 99-3638-259 | A | C | S | 7317 | 11248 |
| 3384 | 99-3641-230 | C | A | S | 7318 | 11249 |
| 3385 | 99-3666-280 | G | A | A | 7319 | 11250 |
| 3386 | 99-3667-190 | G | A | A | 7320 | 11251 |
| 3387 | 99-3677-196 | T | A | S | 7321 | 11252 |
| 3388 | 99-3680-274 | C | G | S | 7322 | 11253 |
| 3389 | 99-3689-50 | A | G | A | 7323 | 11254 |
| 3390 | 99-3690-355 | G | C | S | 7324 | 11255 |
| 3391 | 99-3699-230 | G | A | A | 7325 | 11256 |
| 3392 | 99-3702-226 | T | A | S | 7326 | 11257 |
| 3393 | 99-3703-331 | C | T | S | 7327 | 11258 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 3394 | 99-3705-195 | G | A | A | 7328 | 11259 |
| 3395 | 99-3709-366 | T | C | S | 7329 | 11260 |
| 3396 | 99-3717-68 | A | G | A | 7330 | 11261 |
| 3397 | 99-3728-341 | T | C | S | 7331 | 11262 |
| 3398 | 99-3739-215 | G | A | A | 7332 | 11263 |
| 3399 | 99-3746-337 | C | G | S | 7333 | 11264 |
| 3400 | 99-3749-174 | C | T | S | 7334 | 11265 |
| 3401 | 99-3752-210 | C | T | S | 7335 | 11266 |
| 3402 | 99-3760-59 | A | G | A | 7336 | 11267 |
| 3403 | 99-3761-329 | C | T | S | 7337 | 11268 |
| 3404 | 99-3764-198 | C | T | S | 7338 | 11269 |
| 3405 | 99-3765-279 | A | G | A | 7339 | 11270 |
| 3406 | 99-377-306 | G | A | S | 7340 | 11271 |
| 3407 | 99-3773-337 | T | C | S | 7341 | 11272 |
| 3408 | 99-3774-351 | A | G | A | 7342 | 11273 |
| 3409 | 99-3775-98 | G | A | A | 7343 | 11274 |
| 3410 | 99-3778-97 | T | A | S | 7344 | 11275 |
| 3411 | 99-3789-293 | A | G | A | 7345 | 11276 |
| 3412 | 99-3792-294 | A | G | A | 7346 | 11277 |
| 3413 | 99-3802-197 | C | T | S | 7347 | 11278 |
| 3414 | 99-3805-125 | A | G | A | 7348 | 11279 |
| 3415 | 99-3812-243 | T | G | A | 7349 | 11280 |
| 3416 | 99-3813-122 | T | C | S | 7350 | 11281 |
| 3417 | 99-3857-261 | A | G | A | 7351 | 11282 |
| 3418 | 99-3862-153 | A | G | A | 7352 | 11283 |
| 3419 | 99-3875-138 | A | C | S | 7353 | 11284 |
| 3420 | 99-3888-309 | G | A | A | 7354 | 11285 |
| 3421 | 99-3893-108 | A | C | S | 7355 | 11286 |
| 3422 | 99-3941-107 | A | G | A | 7356 | 11287 |
| 3423 | 99-3944-247 | G | T | A | 7357 | 11288 |
| 3424 | 99-3953-77 | G | A | A | 7358 | 11289 |
| 3425 | 99-3954-362 | G | C | S | 7359 | 11290 |
| 3426 | 99-3978-146 | C | T | S | 7360 | 11291 |
| 3427 | 99-3981-156 | A | G | A | 7361 | 11292 |
| 3428 | 99-3992-185 | C | T | S | 7362 | 11293 |
| 3429 | 99-4001-330 | C | T | S | 7363 | 11294 |
| 3430 | 99-4009-232 | C | T | S | 7364 | 11295 |
| 3431 | 99-4025-300 | C | T | S | 7365 | 11296 |
| 3432 | 99-4052-415 | G | T | A | 7366 | 11297 |
| 3433 | 99-4064-346 | A | C | S | 7367 | 11298 |
| 3434 | 99-4065-20 | A | G | A | 7368 | 11299 |
| 3435 | 99-4073-307 | C | A | S | 7369 | 11300 |
| 3436 | 99-4076-255 | G | A | A | 7370 | 11301 |
| 3437 | 99-4077-230 | T | C | S | 7371 | 11302 |
| 3438 | 99-4078-212 | G | C | S | 7372 | 11303 |
| 3439 | 99-4079-389 | A | G | A | 7373 | 11304 |
| 3440 | 99-4119-307 | C | T | S | 7374 | 11305 |
| 3441 | 99-4120-253 | C | T | S | 7375 | 11306 |
| 3442 | 99-4122-23 | T | C | S | 7376 | 11307 |
| 3443 | 99-4125-192 | C | A | S | 7377 | 11308 |
| 3444 | 99-4131-288 | T | C | S | 7378 | 11309 |
| 3445 | 99-4138-360 | A | C | S | 7379 | 11310 |
| 3446 | 99-4139-128 | C | T | S | 7380 | 11311 |
| 3447 | 99-4140-254 | C | T | S | 7381 | 11312 |
| 3448 | 99-4182-113 | A | G | A | 7382 | 11313 |
| 3449 | 99-4193-384 | A | G | A | 7383 | 11314 |
| 3450 | 99-4194-336 | T | C | S | 7384 | 11315 |
| 3451 | 99-4199-339 | G | A | A | 7385 | 11316 |
| 3452 | 99-4201-501 | G | T | A | 7386 | 11317 |
| 3453 | 99-4202-223 | T | C | S | 7387 | 11318 |
| 3454 | 99-4203-110 | T | C | S | 7388 | 11319 |
| 3455 | 99-4207-210 | G | A | A | 7389 | 11320 |
| 3456 | 99-4218-24 | G | A | A | 7390 | 11321 |
| 3457 | 99-4220-241 | T | C | S | 7391 | 11322 |
| 3458 | 99-4225-339 | T | C | S | 7392 | 11323 |
| 3459 | 99-4231-139 | T | C | S | 7393 | 11324 |
| 3460 | 99-4232-105 | A | G | A | 7394 | 11325 |
| 3461 | 99-4233-261 | A | G | A | 7395 | 11326 |
| 3462 | 99-4238-181 | T | C | S | 7396 | 11327 |
| 3463 | 99-4251-311 | T | C | S | 7397 | 11328 |
| 3464 | 99-4266-313 | A | G | A | 7398 | 11329 |
| 3465 | 99-4272-418 | G | A | S | 7399 | 11330 |
| 3466 | 99-4283-257 | G | A | A | 7400 | 11331 |
| 3467 | 99-4284-200 | A | C | S | 7401 | 11332 |
| 3468 | 99-4285-370 | C | T | S | 7402 | 11333 |
| 3469 | 99-4290-131 | G | A | A | 7403 | 11334 |
| 3470 | 99-4293-344 | C | T | S | 7404 | 11335 |
| 3471 | 99-4296-156 | T | A | S | 7405 | 11336 |
| 3472 | 99-4312-338 | A | G | A | 7406 | 11337 |
| 3473 | 99-4323-311 | T | C | S | 7407 | 11338 |
| 3474 | 99-4325-87 | T | C | S | 7408 | 11339 |
| 3475 | 99-4332-136 | C | A | S | 7409 | 11340 |
| 3476 | 99-4335-371 | C | G | S | 7410 | 11341 |
| 3477 | 99-4336-171 | C | T | S | 7411 | 11342 |
| 3478 | 99-4337-369 | A | G | A | 7412 | 11343 |
| 3479 | 99-4339-180 | T | C | S | 7413 | 11344 |
| 3480 | 99-4358-133 | A | G | A | 7414 | 11345 |
| 3481 | 99-4364-360 | C | T | S | 7415 | 11346 |
| 3482 | 99-4398-167 | T | A | S | 7416 | 11347 |
| 3483 | 99-4399-228 | T | A | S | 7417 | 11348 |
| 3484 | 99-4404-384 | G | A | A | 7418 | 11349 |
| 3485 | 99-4406-115 | A | G | A | 7419 | 11350 |
| 3486 | 99-4435-203 | A | G | A | 7420 | 11351 |
| 3487 | 99-4448-174 | T | C | S | 7421 | 11352 |
| 3488 | 99-4455-357 | T | A | S | 7422 | 11353 |
| 3489 | 99-4458-59 | A | G | A | 7423 | 11354 |
| 3490 | 99-4467-39 | T | C | S | 7424 | 11355 |
| 3491 | 99-4468-130 | C | A | S | 7425 | 11356 |
| 3492 | 99-4483-333 | C | T | S | 7426 | 11357 |
| 3493 | 99-4534-158 | T | C | S | 7427 | 11358 |
| 3494 | 99-4567-424 | T | C | A | 7428 | 11359 |
| 3495 | 99-4575-226 | C | T | S | 7429 | 11360 |
| 3496 | 99-4580-296 | G | A | A | 7430 | 11361 |
| 3497 | 99-4589-169 | C | T | S | 7431 | 11362 |
| 3498 | 99-4614-72 | A | C | S | 7432 | 11363 |
| 3499 | 99-4619-267 | A | C | S | 7433 | 11364 |
| 3500 | 99-4636-62 | C | T | S | 7434 | 11365 |
| 3501 | 994649-251 | T | A | S | 7435 | 11366 |
| 3502 | 99-468-271 | T | C | S | 7436 | 11367 |
| 3503 | 99-4688-442 | C | G | S | 7437 | 11368 |
| 3504 | 99-4691-400 | A | G | A | 7438 | 11369 |
| 3505 | 99-4692-372 | T | G | A | 7439 | 11370 |
| 3506 | 99-4715-280 | G | A | A | 7440 | 11371 |
| 3507 | 99-4736-164 | C | T | S | 7441 | 11372 |
| 3508 | 99-4744-72 | G | T | A | 7442 | 11373 |
| 3509 | 99-4746-160 | G | T | A | 7443 | 11374 |
| 3510 | 99-4748-76 | C | T | S | 7444 | 11375 |
| 3511 | 99-4755-84 | C | A | S | 7445 | 11376 |
| 3512 | 99-4758-66 | G | A | A | 7446 | 11377 |
| 3513 | 99-4772-80 | C | A | S | 7447 | 11378 |
| 3514 | 99-4791-198 | G | A | S | 7448 | 11379 |
| 3515 | 99-4792-298 | G | A | A | 7449 | 11380 |
| 3516 | 99-4799-209 | C | A | S | 7450 | 11381 |
| 3517 | 99-480-373 | G | A | A | 7451 | 11382 |
| 3518 | 99-4810-454 | A | G | A | 7452 | 11383 |
| 3519 | 99-4825-253 | A | G | A | 7453 | 11384 |
| 3520 | 99-4832-314 | G | A | A | 7454 | 11385 |
| 3521 | 99-4837-337 | C | T | S | 7455 | 11386 |
| 3522 | 99-4856-363 | G | A | A | 7456 | 11387 |
| 3523 | 99-4871-375 | C | T | S | 7457 | 11388 |
| 3524 | 99-4874-285 | C | T | S | 7458 | 11389 |
| 3525 | 99-4885-366 | A | G | A | 7459 | 11390 |
| 3526 | 99-49-41 | G | A | A | 7460 | 11391 |
| 3527 | 99-4903-395 | A | G | A | 7461 | 11392 |
| 3528 | 99-499-294 | C | T | S | 7462 | 11393 |
| 3529 | 99-5059-256 | T | C | S | 7463 | 11394 |
| 3530 | 99-5074-454 | T | C | S | 7464 | 11395 |
| 3531 | 99-5076-173 | C | T | S | 7465 | 11396 |
| 3532 | 99-5098-29 | G | A | A | 7466 | 11397 |
| 3533 | 99-51-263 | G | C | S | 7467 | 11398 |
| 3534 | 99-5112-188 | C | T | S | 7468 | 11399 |
| 3535 | 99-515-151 | T | C | S | 7469 | 11400 |
| 3536 | 99-5166-223 | C | T | S | 7470 | 11401 |
| 3537 | 99-5167-321 | A | T | S | 7471 | 11402 |
| 3538 | 99-5176-230 | T | C | S | 7472 | 11403 |
| 3539 | 99-5240-419 | C | T | S | 7473 | 11404 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 3540 | 99-5329-269 | G | T | S | 7474 | 11405 |
| 3541 | 99-5339-196 | A | G | A | 7475 | 11406 |
| 3542 | 99-5347-394 | T | C | S | 7476 | 11407 |
| 3543 | 99-5397-353 | G | C | A | 7477 | 11408 |
| 3544 | 99-55-233 | C | A | S | 7478 | 11409 |
| 3545 | 99-5549-289 | A | G | A | 7479 | 11410 |
| 3546 | 99-5569-237 | A | G | A | 7480 | 11411 |
| 3547 | 99-5575-330 | C | T | S | 7481 | 11412 |
| 3548 | 99-5602-372 | G | C | S | 7482 | 11413 |
| 3549 | 99-5671-333 | T | C | S | 7483 | 11414 |
| 3550 | 99-568-101 | G | A | S | 7484 | 11415 |
| 3551 | 99-5688-116 | A | G | A | 7485 | 11416 |
| 3552 | 99-5689-391 | G | C | S | 7486 | 11417 |
| 3553 | 99-5715-224 | T | G | A | 7487 | 11418 |
| 3554 | 99-5718-82 | A | G | A | 7488 | 11419 |
| 3555 | 99-5723-291 | A | G | A | 7489 | 11420 |
| 3556 | 99-5747-278 | T | C | S | 7490 | 11421 |
| 3557 | 99-5775-154 | C | T | S | 7491 | 11422 |
| 3558 | 99-5828-235 | T | C | S | 7492 | 11423 |
| 3559 | 99-5846-383 | C | T | S | 7493 | 11424 |
| 3560 | 99-5861-151 | G | A | A | 7494 | 11425 |
| 3561 | 99-59-137 | A | C | S | 7495 | 11426 |
| 3562 | 99-5930-449 | T | A | A | 7496 | 11427 |
| 3563 | 99-5931-330 | G | A | A | 7497 | 11428 |
| 3564 | 99-5967-165 | C | T | S | 7498 | 11429 |
| 3565 | 99-5987-135 | A | G | A | 7499 | 11430 |
| 3566 | 99-5996-279 | T | C | S | 7500 | 11431 |
| 3567 | 99-6001-372 | T | G | A | 7501 | 11432 |
| 3568 | 99-6020-477 | A | G | A | 7502 | 11433 |
| 3569 | 99-6047-225 | T | A | S | 7503 | 11434 |
| 3570 | 99-6071-272 | A | G | A | 7504 | 11435 |
| 3571 | 99-6076-394 | A | T | S | 7505 | 11436 |
| 3572 | 99-6096-354 | C | G | S | 7506 | 11437 |
| 3573 | 99-6103-356 | T | C | S | 7507 | 11438 |
| 3574 | 99-6124-125 | T | C | S | 7508 | 11439 |
| 3575 | 99-6173-229 | T | G | A | 7509 | 11440 |
| 3576 | 99-634-278 | T | A | A | 7510 | 11441 |
| 3577 | 99-6401-64 | A | G | A | 7511 | 11442 |
| 3578 | 99-6538-193 | G | A | A | 7512 | 11443 |
| 3579 | 99-6549-275 | A | G | A | 7513 | 11444 |
| 3580 | 99-6564-236 | G | C | S | 7514 | 11445 |
| 3581 | 99-6574-150 | T | G | A | 7515 | 11446 |
| 3582 | 99-6583-289 | A | G | A | 7516 | 11447 |
| 3583 | 99-6591-236 | T | C | S | 7517 | 11448 |
| 3584 | 99-6597-213 | A | G | A | 7518 | 11449 |
| 3585 | 99-6603-47 | A | G | A | 7519 | 11450 |
| 3586 | 99-6707-405 | G | A | A | 7520 | 11451 |
| 3587 | 99-6720-186 | C | G | S | 7521 | 11452 |
| 3588 | 99-6809-317 | C | T | S | 7522 | 11453 |
| 3589 | 99-6834-307 | G | A | A | 7523 | 11454 |
| 3590 | 99-6837-253 | C | A | S | 7524 | 11455 |
| 3591 | 99-6878-317 | C | T | S | 7525 | 11456 |
| 3592 | 99-6888-188 | T | G | A | 7526 | 11457 |
| 3593 | 99-6919-372 | G | A | A | 7527 | 11458 |
| 3594 | 99-6922-169 | T | C | S | 7528 | 11459 |
| 3595 | 99-6974-417 | A | G | A | 7529 | 11460 |
| 3596 | 99-6978-149 | C | G | S | 7530 | 11461 |
| 3597 | 99-6984-287 | G | C | S | 7531 | 11462 |
| 3598 | 99-6998-86 | T | C | S | 7532 | 11463 |
| 3599 | 99-7032-416 | T | A | S | 7533 | 11464 |
| 3600 | 99-7048-342 | C | T | S | 7534 | 11465 |
| 3601 | 99-7060-512 | A | G | A | 7535 | 11466 |
| 3602 | 99-7086-91 | G | C | S | 7536 | 11467 |
| 3603 | 99-7117-266 | T | A | S | 7537 | 11468 |
| 3604 | 99-7203-286 | T | C | A | 7538 | 11469 |
| 3605 | 99-7268-383 | T | C | S | 7539 | 11470 |
| 3606 | 99-7281-131 | T | C | A | 7540 | 11471 |
| 3607 | 99-7282-145 | G | T | A | 7541 | 11472 |
| 3608 | 99-7296-429 | T | C | A | 7542 | 11473 |
| 3609 | 99-7344-203 | C | T | S | 7543 | 11474 |
| 3610 | 99-7377-370 | T | C | S | 7544 | 11475 |
| 3611 | 99-7394-398 | A | G | A | 7545 | 11476 |
| 3612 | 99-7412-288 | C | T | S | 7546 | 11477 |
| 3613 | 99-7422-375 | C | T | S | 7547 | 11478 |
| 3614 | 99-7430-548 | T | A | S | 7548 | 11479 |
| 3615 | 99-7442-390 | T | C | S | 7549 | 11480 |
| 3616 | 99-7481-268 | A | G | A | 7550 | 11481 |
| 3617 | 99-7696-215 | C | T | S | 7551 | 11482 |
| 3618 | 99-7702-225 | C | T | S | 7552 | 11483 |
| 3619 | 99-7772-185 | C | T | S | 7553 | 11484 |
| 3620 | 99-7815-70 | A | T | S | 7554 | 11485 |
| 3621 | 99-7818-342 | G | A | A | 7555 | 11486 |
| 3622 | 99-7860-320 | T | G | A | 7556 | 11487 |
| 3623 | 99-7886-350 | G | C | S | 7557 | 11488 |
| 3624 | 99-7944-130 | A | T | S | 7558 | 11489 |
| 3625 | 99-7945-106 | G | A | A | 7559 | 11490 |
| 3626 | 99-7976-324 | A | G | A | 7560 | 11491 |
| 3627 | 99-8000-88 | C | T | S | 7561 | 11492 |
| 3628 | 99-8006-241 | C | T | S | 7562 | 11493 |
| 3629 | 99-8038-47 | T | C | S | 7563 | 11494 |
| 3630 | 99-8055-299 | A | G | A | 7564 | 11495 |
| 3631 | 99-8059-59 | A | G | A | 7565 | 11496 |
| 3632 | 99-8061-106 | C | T | S | 7566 | 11497 |
| 3633 | 99-8109-168 | A | G | A | 7567 | 11498 |
| 3634 | 99-8115-238 | T | G | A | 7568 | 11499 |
| 3635 | 99-8166-370 | T | C | S | 7569 | 11500 |
| 3636 | 99-8226-78 | T | G | A | 7570 | 11501 |
| 3637 | 99-8232-303 | A | G | A | 7571 | 11502 |
| 3638 | 99-824-359 | C | T | S | 7572 | 11503 |
| 3639 | 99-8274-70 | A | G | A | 7573 | 11504 |
| 3640 | 99-8359-153 | T | A | S | 7574 | 11505 |
| 3641 | 99-8630-298 | G | A | A | 7575 | 11506 |
| 3642 | 99-8659-399 | T | A | S | 7576 | 11507 |
| 3643 | 99-8679-371 | T | G | A | 7577 | 11508 |
| 3644 | 99-8690-117 | T | C | S | 7578 | 11509 |
| 3645 | 99-8751-299 | C | T | S | 7579 | 11510 |
| 3646 | 99-8795-58 | G | A | A | 7580 | 11511 |
| 3647 | 99-882-250 | C | A | S | 7581 | 11512 |
| 3648 | 99-887-344 | G | T | A | 7582 | 11513 |
| 3649 | 99-8875-283 | G | A | A | 7583 | 11514 |
| 3650 | 99-892-77 | T | C | S | 7584 | 11515 |
| 3651 | 99-8936-202 | T | C | S | 7585 | 11516 |
| 3652 | 99-8952-319 | G | C | S | 7586 | 11517 |
| 3653 | 99-896-83 | T | C | S | 7587 | 11518 |
| 3654 | 99-899-252 | G | C | S | 7588 | 11519 |
| 3655 | 99-9072-32 | G | C | S | 7589 | 11520 |
| 3656 | 99-9076-357 | C | T | S | 7590 | 11521 |
| 3657 | 99-9077-52 | T | C | S | 7591 | 11522 |
| 3658 | 99-9089-155 | T | A | S | 7592 | 11523 |
| 3659 | 99-9113-277 | C | A | S | 7593 | 11524 |
| 3660 | 99-9145-438 | A | G | A | 7594 | 11525 |
| 3661 | 99-9164-365 | T | C | S | 7595 | 11526 |
| 3662 | 99-9308-416 | A | G | A | 7596 | 11527 |
| 3663 | 99-9316-399 | A | G | A | 7597 | 11528 |
| 3664 | 99-9343-71 | C | T | S | 7598 | 11529 |
| 3665 | 99-9362-282 | T | C | S | 7599 | 11530 |
| 3666 | 99-9363-143 | G | A | A | 7600 | 11531 |
| 3667 | 99-9375-337 | G | C | S | 7601 | 11532 |
| 3668 | 99-9380-292 | T | C | S | 7602 | 11533 |
| 3669 | 99-9607-402 | C | T | A | 7603 | 11534 |
| 3670 | 99-9620-241 | C | T | S | 7604 | 11535 |
| 3671 | 99-9623-330 | T | C | S | 7605 | 11536 |
| 3672 | 99-9633-32 | T | C | S | 7606 | 11537 |
| 3673 | 99-9636-423 | T | C | S | 7607 | 11538 |
| 3674 | 99-9658-42 | T | G | A | 7608 | 11539 |
| 3675 | 99-9662-213 | T | C | A | 7609 | 11540 |
| 3676 | 99-9666-363 | T | C | A | 7610 | 11541 |
| 3677 | 99-9668-185 | C | T | A | 7611 | 11542 |
| 3678 | 99-9680-363 | A | G | S | 7612 | 11543 |
| 3679 | 99-9696-292 | T | C | A | 7613 | 11544 |
| 3680 | 99-9697-375 | A | C | S | 7614 | 11545 |
| 3681 | 99-9700-289 | C | T | A | 7615 | 11546 |
| 3682 | 99-9704-445 | T | C | A | 7616 | 11547 |
| 3683 | 99-9706-448 | C | T | A | 7617 | 11548 |
| 3684 | 99-9709-115 | T | C | A | 7618 | 11549 |
| 3685 | 99-9710-242 | C | A | S | 7619 | 11550 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 3686 | 99-9714-302 | T | C | S | 7620 | 11551 |
| 3687 | 99-9717-449 | A | G | A | 7621 | 11552 |
| 3688 | 99-9726-190 | T | C | S | 7622 | 11553 |
| 3689 | 99-974-231 | A | G | A | 7623 | 11554 |
| 3690 | 99-9745-284 | G | A | A | 7624 | 11555 |
| 3691 | 99-9751-134 | A | T | S | 7625 | 11556 |
| 3692 | 99-9765-237 | A | G | S | 7626 | 11557 |
| 3693 | 99-9774-392 | A | T | S | 7627 | 11558 |
| 3694 | 99-9778-360 | A | G | S | 7628 | 11559 |
| 3695 | 99-9781-174 | T | C | A | 7629 | 11560 |
| 3696 | 99-9785-141 | T | C | A | 7630 | 11561 |
| 3697 | 99-9810-257 | A | T | S | 7631 | 11562 |
| 3698 | 99-9811-369 | C | T | A | 7632 | 11563 |
| 3699 | 99-9820-483 | C | T | A | 7633 | 11564 |
| 3700 | 99-9822-257 | A | T | S | 7634 | 11565 |
| 3701 | 99-9829-367 | G | A | S | 7635 | 11566 |
| 3702 | 99-983-278 | G | A | A | 7636 | 11567 |
| 3703 | 99-9832-128 | T | C | A | 7637 | 11568 |
| 3704 | 99-9833-167 | A | G | S | 7638 | 11569 |
| 3705 | 99-9835-217 | C | T | A | 7639 | 11570 |
| 3706 | 99-9837-275 | A | G | S | 7640 | 11571 |
| 3707 | 99-9839-416 | G | C | S | 7641 | 11572 |
| 3708 | 99-9840-192 | C | T | A | 7642 | 11573 |
| 3709 | 99-9847-25 | A | G | S | 7643 | 11574 |
| 3710 | 99-9849-291 | G | A | S | 7644 | 11575 |
| 3711 | 99-9852-276 | T | C | A | 7645 | 11576 |
| 3712 | 99-9854-316 | G | C | S | 7646 | 11577 |
| 3713 | 99-9856-252 | C | T | A | 7647 | 11578 |
| 3714 | 99-9859-132 | C | A | S | 7648 | 11579 |
| 3715 | 99-9866-365 | T | C | A | 7649 | 11580 |
| 3716 | 99-990-356 | T | A | S | 7650 | 11581 |
| 3717 | 99-9906-280 | G | C | S | 7651 | 11582 |
| 3718 | 99-9908-423 | T | A | S | 7652 | 11583 |
| 3719 | 99-991-157 | A | G | A | 7653 | 11584 |
| 3720 | 99-9915-281 | T | G | A | 7654 | 11585 |
| 3721 | 99-9920-245 | T | C | A | 7655 | 11586 |
| 3722 | 99-9921-365 | T | C | A | 7656 | 11587 |
| 3723 | 99-9922-154 | C | T | A | 7657 | 11588 |
| 3724 | 99-9926-454 | G | A | S | 7658 | 11589 |
| 3725 | 99-9928-454 | C | T | A | 7659 | 11590 |
| 3726 | 99-9929-144 | G | A | S | 7660 | 11591 |
| 3727 | 99-9935-418 | G | A | S | 7661 | 11592 |
| 3728 | 99-9941-426 | T | A | S | 7662 | 11593 |
| 3729 | 99-995-251 | A | C | S | 7663 | 11594 |
| 3730 | 99-996-210 | T | C | S | 7664 | 11595 |
| 3731 | 99-9986-202 | T | C | S | 7665 | 11596 |
| 3732 | 99-9988-111 | T | G | A | 7666 | 11597 |
| 3733 | 99-9994-226 | C | A | S | 7667 | 11598 |
| 3734 | 99-9995-50 | C | T | S | 7668 | 11599 |
| 3735 | 99-10069-366 | A | T | S | 7669 | 11600 |
| 3736 | 99-10074-266 | A | G | A | 7670 | 11601 |
| 3737 | 99-10129-177 | A | G | S | 7671 | 11602 |
| 3738 | 99-10198-271 | A | G | S | 7672 | 11603 |
| 3739 | 99-10306-345 | C | T | A | 7673 | 11604 |
| 3740 | 99-10307-115 | A | G | S | 7674 | 11605 |
| 3741 | 99-10326-149 | C | T | A | 7675 | 11606 |
| 3742 | 99-10393-179 | A | G | S | 7676 | 11607 |
| 3743 | 99-10685-454 | A | C | S | 7677 | 11608 |
| 3744 | 99-10857-217 | C | T | A | 7678 | 11609 |
| 3745 | 99-10948-281 | C | T | A | 7679 | 11610 |
| 3746 | 99-11104-329 | A | G | S | 7680 | 11611 |
| 3747 | 99-11116-199 | C | T | A | 7681 | 11612 |
| 3748 | 99-11117-282 | A | G | S | 7682 | 11613 |
| 3749 | 99-11121-461 | A | G | S | 7683 | 11614 |
| 3750 | 99-11124-363 | C | T | A | 7684 | 11615 |
| 3751 | 99-11172-373 | C | T | A | 7685 | 11616 |
| 3752 | 99-11206-379 | C | T | A | 7686 | 11617 |
| 3753 | 99-11303-223 | C | T | A | 7687 | 11618 |
| 3754 | 99-11307-168 | G | T | A | 7688 | 11619 |
| 3755 | 99-11325-188 | A | G | S | 7689 | 11620 |
| 3756 | 99-11365-273 | C | T | A | 7690 | 11621 |
| 3757 | 99-11389-268 | A | T | S | 7691 | 11622 |
| 3758 | 99-11395-376 | A | G | S | 7692 | 11623 |
| 3759 | 99-11500-50 | C | T | S | 7693 | 11624 |
| 3760 | 99-11571-88 | G | T | S | 7694 | 11625 |
| 3761 | 99-11710-452 | A | G | S | 7695 | 11626 |
| 3762 | 99-1173-208 | A | T | S | 7696 | 11627 |
| 3763 | 99-11735-215 | C | T | A | 7697 | 11628 |
| 3764 | 99-11864-218 | A | C | S | 7698 | 11629 |
| 3765 | 99-1187-293 | G | C | S | 7699 | 11630 |
| 3766 | 99-11872-228 | C | T | A | 7700 | 11631 |
| 3767 | 99-11878-212 | C | T | A | 7701 | 11632 |
| 3768 | 99-11905-202 | G | C | S | 7702 | 11633 |
| 3769 | 99-11932-48 | C | T | A | 7703 | 11634 |
| 3770 | 99-11964-158 | A | C | S | 7704 | 11635 |
| 3771 | 99-12164-412 | C | T | A | 7705 | 11636 |
| 3772 | 99-12227-278 | G | C | S | 7706 | 11637 |
| 3773 | 99-12417-447 | A | G | S | 7707 | 11638 |
| 3774 | 99-12459-119 | G | T | A | 7708 | 11639 |
| 3775 | 99-12521-212 | C | T | S | 7709 | 11640 |
| 3776 | 99-12569-95 | A | G | A | 7710 | 11641 |
| 3777 | 99-1298-430 | A | G | S | 7711 | 11642 |
| 3778 | 99-1315-105 | G | C | S | 7712 | 11643 |
| 3779 | 99-13154-74 | C | T | A | 7713 | 11644 |
| 3780 | 99-13155-134 | A | G | S | 7714 | 11645 |
| 3781 | 99-13249-461 | C | T | A | 7715 | 11646 |
| 3782 | 99-13794-147 | G | C | S | 7716 | 11647 |
| 3783 | 99-14899-215 | A | C | S | 7717 | 11648 |
| 3784 | 99-16351-44 | C | T | A | 7718 | 11649 |
| 3785 | 99-16436-382 | A | G | S | 7719 | 11650 |
| 3786 | 99-16753-387 | G | C | S | 7720 | 11651 |
| 3787 | 99-1807-300 | A | G | A | 7721 | 11652 |
| 3788 | 99-19032-132 | A | C | S | 7722 | 11653 |
| 3789 | 99-19212-369 | C | T | S | 7723 | 11654 |
| 3790 | 99-19273-219 | A | G | A | 7724 | 11655 |
| 3791 | 99-19279-356 | C | T | S | 7725 | 11656 |
| 3792 | 99-19541-172 | A | G | A | 7726 | 11657 |
| 3793 | 99-19552-214 | G | T | A | 7727 | 11658 |
| 3794 | 99-21051-435 | C | T | S | 7728 | 11659 |
| 3795 | 99-21246-20 | C | T | S | 7729 | 11660 |
| 3796 | 99-21387-465 | C | T | S | 7730 | 11661 |
| 3797 | 99-21407-352 | A | G | A | 7731 | 11662 |
| 3798 | 99-21418-83 | C | T | S | 7732 | 11663 |
| 3799 | 99-21419-85 | C | T | S | 7733 | 11664 |
| 3800 | 99-21430-308 | C | T | S | 7734 | 11665 |
| 3801 | 99-21435-96 | A | G | A | 7735 | 11666 |
| 3802 | 99-21446-240 | C | T | S | 7736 | 11667 |
| 3803 | 99-21452-173 | A | G | A | 7737 | 11668 |
| 3804 | 99-21488-376 | G | T | A | 7738 | 11669 |
| 3805 | 99-21489-227 | C | T | S | 7739 | 11670 |
| 3806 | 99-21496-248 | C | T | S | 7740 | 11671 |
| 3807 | 99-21519-446 | A | G | A | 7741 | 11672 |
| 3808 | 99-21618-178 | A | G | A | 7742 | 11673 |
| 3809 | 99-21725-371 | C | T | S | 7743 | 11674 |
| 3810 | 99-21773-155 | A | C | S | 7744 | 11675 |
| 3811 | 99-21781-252 | A | G | A | 7745 | 11676 |
| 3812 | 99-21820-230 | A | G | A | 7746 | 11677 |
| 3813 | 99-21822-50 | A | G | A | 7747 | 11678 |
| 3814 | 99-21939-170 | A | T | S | 7748 | 11679 |
| 3815 | 99-22404-59 | A | G | A | 7749 | 11680 |
| 3816 | 99-22594-395 | A | G | A | 7750 | 11681 |
| 3817 | 99-22679-148 | A | C | S | 7751 | 11682 |
| 3818 | 99-23095-184 | G | C | S | 7752 | 11683 |
| 3819 | 99-23370-249 | C | T | S | 7753 | 11684 |
| 3820 | 99-23568-395 | G | C | S | 7754 | 11685 |
| 3821 | 99-23824-339 | C | T | S | 7755 | 11686 |
| 3822 | 99-23969-316 | C | T | A | 7756 | 11687 |
| 3823 | 99-24032-138 | A | T | S | 7757 | 11688 |
| 3824 | 99-24048-286 | C | T | S | 7758 | 11689 |
| 3825 | 99-24074-190 | A | G | A | 7759 | 11690 |
| 3826 | 99-24082-408 | A | C | S | 7760 | 11691 |
| 3827 | 99-24104-308 | G | T | A | 7761 | 11692 |
| 3828 | 99-24138-224 | A | G | A | 7762 | 11693 |
| 3829 | 99-24172-116 | C | T | S | 7763 | 11694 |
| 3830 | 99-24267-190 | A | C | S | 7764 | 11695 |
| 3831 | 99-24949-289 | C | T | A | 7765 | 11696 |

TABLE 1-continued

| SEQ ID No. | Marker Name | Allele 1ST | Allele 2ND | Preferred microseq. primer | Amplification primer Upstream (PU) | Amplification primer Downstream (RP) |
|---|---|---|---|---|---|---|
| 3832 | 99-253-97 | A | G | A | 7766 | 11697 |
| 3833 | 99-2694-411 | A | G | A | 7767 | 11698 |
| 3834 | 99-2697-336 | A | G | A | 7768 | 11699 |
| 3835 | 99-2720-280 | A | G | A | 7769 | 11700 |
| 3836 | 99-2851-105 | G | C | S | 7770 | 11701 |
| 3837 | 99-2889-197 | C | T | S | 7771 | 11702 |
| 3838 | 99-3072-323 | A | G | A | 7772 | 11703 |
| 3839 | 99-3089-49 | A | G | A | 7773 | 11704 |
| 3840 | 99-3157-203 | G | T | A | 7774 | 11705 |
| 3841 | 99-3210-341 | G | T | A | 7775 | 11706 |
| 3842 | 99-3218-344 | A | G | A | 7776 | 11707 |
| 3843 | 99-3251-254 | G | T | A | 7777 | 11708 |
| 3844 | 99-3298-158 | C | T | A | 7778 | 11709 |
| 3845 | 99-3300-433 | A | G | A | 7779 | 11710 |
| 3846 | 99-3364-247 | A | T | S | 7780 | 11711 |
| 3847 | 99-3427-271 | A | G | A | 7781 | 11712 |
| 3848 | 99-3484-96 | A | G | A | 7782 | 11713 |
| 3849 | 99-3537-196 | A | G | A | 7783 | 11714 |
| 3850 | 99-3568-156 | G | T | A | 7784 | 11715 |
| 3851 | 99-3592-325 | A | G | A | 7785 | 11716 |
| 3852 | 99-3602-245 | C | T | S | 7786 | 11717 |
| 3853 | 99-3608-264 | A | G | A | 7787 | 11718 |
| 3854 | 99-3643-352 | A | G | A | 7788 | 11719 |
| 3855 | 99-3770-363 | C | T | S | 7789 | 11720 |
| 3856 | 99-3772-266 | A | G | A | 7790 | 11721 |
| 3857 | 99-3790-361 | A | G | A | 7791 | 11722 |
| 3858 | 99-3818-255 | A | G | A | 7792 | 11723 |
| 3859 | 99-3863-328 | A | G | A | 7793 | 11724 |
| 3860 | 99-3879-245 | A | G | A | 7794 | 11725 |
| 3861 | 99-3882-312 | C | T | S | 7795 | 11726 |
| 3862 | 99-3883-329 | C | T | S | 7796 | 11727 |
| 3863 | 99-3884-355 | G | C | S | 7797 | 11728 |
| 3864 | 99-3894-333 | C | T | S | 7798 | 11729 |
| 3865 | 99-3936-352 | A | G | S | 7799 | 11730 |
| 3866 | 99-3946-236 | A | G | A | 7800 | 11731 |
| 3867 | 99-4029-174 | C | T | S | 7801 | 11732 |
| 3868 | 99-4036-308 | C | T | S | 7802 | 11733 |
| 3869 | 99-4102-109 | A | G | A | 7803 | 11734 |
| 3870 | 99-4110-180 | A | G | A | 7804 | 11735 |
| 3871 | 99-4111-259 | A | G | A | 7805 | 11736 |
| 3872 | 99-4126-366 | A | G | A | 7806 | 11737 |
| 3873 | 99-4157-72 | A | G | A | 7807 | 11738 |
| 3874 | 99-4228-168 | C | T | S | 7808 | 11739 |
| 3875 | 99-4239-328 | A | G | A | 7809 | 11740 |
| 3876 | 99-4254-307 | A | G | A | 7810 | 11741 |
| 3877 | 99-4264-228 | C | T | S | 7811 | 11742 |
| 3878 | 99-4311-146 | A | G | A | 7812 | 11743 |
| 3879 | 99-4381-385 | C | T | S | 7813 | 11744 |
| 3880 | 99-4403-194 | A | C | S | 7814 | 11745 |
| 3881 | 99-4524-296 | A | G | A | 7815 | 11746 |
| 3882 | 99-4582-359 | G | T | A | 7816 | 11747 |
| 3883 | 99-4611-151 | C | T | S | 7817 | 11748 |
| 3884 | 99-4689-375 | A | T | S | 7818 | 11749 |
| 3885 | 994762-114 | A | G | A | 7819 | 11750 |
| 3886 | 99-4878-107 | C | T | S | 7820 | 11751 |
| 3887 | 99-5075-219 | C | T | A | 7821 | 11752 |
| 3888 | 99-5190-277 | A | G | A | 7822 | 11753 |
| 3889 | 99-5605-90 | G | T | A | 7823 | 11754 |
| 3890 | 99-5882-105 | C | T | S | 7824 | 11755 |
| 3891 | 99-5977-241 | C | T | S | 7825 | 11756 |
| 3892 | 99-5993-323 | C | T | S | 7826 | 11757 |
| 3893 | 99-5994-205 | G | T | S | 7827 | 11758 |
| 3894 | 99-6827-399 | A | G | A | 7828 | 11759 |
| 3895 | 99-7076-198 | C | T | S | 7829 | 11760 |
| 3896 | 99-7215-279 | C | T | S | 7830 | 11761 |
| 3897 | 99-8206-133 | A | G | A | 7831 | 11762 |
| 3898 | 99-8614-236 | A | G | A | 7832 | 11763 |
| 3899 | 99-889-153 | G | C | S | 7833 | 11764 |
| 3900 | 99-9450-70 | A | T | S | 7834 | 11765 |
| 3901 | 99-9609-220 | C | T | A | 7835 | 11766 |
| 3902 | 99-9612-324 | A | G | S | 7836 | 11767 |
| 3903 | 99-9616-136 | A | G | A | 7837 | 11768 |
| 3904 | 99-9683-49 | A | G | S | 7838 | 11769 |
| 3905 | 99-9907-88 | C | T | A | 7839 | 11770 |
| 3906 | 99-993-218 | C | T | S | 7840 | 11771 |
| 3907 | 99-24069-351 | C | T | S | 7841 | 11772 |
| 3908 | 99-3855-279 | G | C | A | 7842 | 11773 |
| 3909 | 99-344-439 | G | A | A | 7843 | 11774 |
| 3910 | 99-366-274 | C | T | S | 7844 | 11775 |
| 3911 | 99-359-308 | A | G | A | 7845 | 11776 |
| 3912 | 99-355-219 | A | G | A | 7846 | 11777 |
| 3913 | 99-365-344 | C | T | S | 7847 | 11778 |
| 3914 | 99-2452-54 | C | T | S | 7848 | 11779 |
| 3915 | 99-123-381 | C | T | S | 7849 | 11780 |
| 3916 | 4-26-29 | A | G | A | 7850 | 11781 |
| 3917 | 4-14-240 | C | T | S | 7851 | 11782 |
| 3918 | 4-77-151 | G | C | S | 7852 | 11783 |
| 3919 | 99-217-277 | C | T | S | 7853 | 11784 |
| 3920 | 4-67-40 | C | T | S | 7854 | 11785 |
| 3921 | 99-213-164 | A | G | A | 7855 | 11786 |
| 3922 | 99-221-377 | A | C | S | 7856 | 11787 |
| 3923 | 99-135-196 | A | G | A | 7857 | 11788 |
| 3924 | 99-1482-32 | A | C | S | 7858 | 11789 |
| 3925 | 4-73-134 | G | C | S | 7859 | 11790 |
| 3926 | 4-65-324 | C | T | S | 7860 | 11791 |
| 3927 | 10-32-357 | A | C | S | 7861 | 11792 |
| 3928 | 10-33-175 | T | C | S | 7862 | 11793 |
| 3929 | 10-33-234 | A | C | S | 7862 | 11793 |
| 3930 | 10-33-327 | C | T | S | 7862 | 11793 |
| 3931 | 10-35-358 | G | C | A | 7863 | 11794 |
| 3932 | 10-35-390 | T | C | S | 7863 | 11794 |
| 3933 | 10-36-164 | A | G | A | 7864 | 11795 |
| 3934 | 10-204-326 | A | G | A | 7865 | 11796 |

TABLE 9

| SEQ ID No. | Marker Name | Chromosomal Localization | Adjacent STS (including aliases) |
|---|---|---|---|
| 2 | 9-1126-384 | 10p12.1–p11.2 | g12982/WI-15761/EST230735/RH51226/R45505 |
|  |  |  | g26880/SRGC-2047/Z24310 |
|  |  |  | g26882/SHGC-14408 |
|  |  |  | g4194/AFMa109xe1/D10S1641/ |
| 9 | 9-1217-332 | 21q11.2–q21 | g7903/D21S1880/ |
| 59 | 9-1263-276 | 21q21 | g7833/D21S177 |
|  |  |  | g7957/D21S409/ |

TABLE 9-continued

| SEQ ID No. | Marker Name | Chromosomal Localization | Adjacent STS (including aliases) |
|---|---|---|---|
| 236 | 9-1367-287 | 1q43 | g401/D1S2483/G04024<br>g428/EST386335/RH50010/SGC35175/ |
| 238 | 9-13678-251 | 1q43 | g15623/D1S547/GATA4A09<br>g17350/RH1290/SHGC-477<br>g17708/RH11033/D29436/D29436<br>g18500/RH26479/R65593<br>g319/EST161941/RH50228/RH64454/SGC33718/T91820<br>g405/D1S1707/G02394<br>g408/AFM214xe11/Z66804<br>g417/D1S2421/WI-9317/D29955/RH49709<br>g420/WI-15754/RH49799<br>g426/WI-13731/RH49867/RH64343/R44970/ |
| 239 | 9-13679-285 | 1q43 | g15623/D1S547/GATA4A09<br>g17350/RH1290/SHGC-477<br>g17708/RH11033/D29436/D29436<br>g18500/RH26479/R65593<br>g319/EST161941/RH50228/RH64454/SGC33718/T91820<br>g405/D1S1707/G02394<br>g408/AFM214xe11/Z66804<br>g417/D1S2421/WI-9317/D29955/RH49709<br>g420/WI-15754/RH49799<br>g426/WI-13731/RH49867/RH64343/R44970/ |
| 240 | 9-1368-299 | 1q43 | g401/D1S2483/G04024<br>g428/EST386335/RH50010/SGC35175/ |
| 241 | 9-13684-488 | 1q43 | g15623/D1S547/GATA4A09<br>g17350/RH1290/SHGC-477<br>g17708/RH11033/D29436/D29436<br>g18500/RH26479/R65593<br>g319/EST161941/RH50228/RH64454/SGC33718/T91820<br>g405/D1S1707/G02394<br>g408/AFM214xe11/Z66804<br>g417/D1S2421/WI-9317/D29955/RH49709<br>g420/WI-15754/RH49799<br>g426/WI-13731/RH49867/RH64343/R44970/ |
| 242 | 9-13687-316 | 1q43 | g15623/D1S547/GATA4A09<br>g17350/RH1290/SHGC-477<br>g17708/RH11033/D29436/D29436<br>g18500/RH26479/R65593<br>g319/EST161941/RH50228/RH64454/SGC33718/T91820<br>g405/D1S1707/G02394<br>g408/AFM214xe11/Z66804<br>g417/D1S2421/WI-9317/D29955/RH49709<br>g420/WI-15754/RH49799<br>g426/WI-13731/RH49867/RH64343/R44970 |
| 243 | 9-1373-358 | 1q43 | g401/D1S2483/G04024<br>g428/EST386335/RH50010/SGC35175/ |
| 244 | 9-1376-196 | 1q43 | g401/D1S2483/G04024<br>g428/EST386335/RH50010/SGC35175/ |
| 245 | 9-13790-129 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RR49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 246 | 9-13798-284 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 250 | 9-1385-91 | 1q43 | g313/D1S3401/G04332<br>g404/D1S3450/G11836/ |
| 257 | 9-1387-462 | 1q43 | g313/D1S3401/G04332<br>g404/D1S3450/G11836/ |
| 260 | 9-1388-242 | 1q43 | g313/D1S3401/G04332<br>g404/D1S3450/G11836/ |
| 267 | 9-1391-204 | 1q43 | g313/D1S3401/G04332<br>g404/D1S3450/G11836/ |
| 271 | 9-1392-200 | 1q43 | g313/D1S3401/G04332<br>g404/D1S3450/G11836/ |

TABLE 9-continued

| SEQ ID No. | Marker Name | Chromosomal Localization | Adjacent STS (including aliases) |
|---|---|---|---|
| 276 | 9-1394-271 | 1q43 | g313/D1S3401/G04332<br>g404/D1S3450/G11836/ |
| 304 | 9-1413-137 | 1q43;5q34 | g410/D1S180/ |
| 311 | 9-1416-589 | 1q43;5q34 | g410/D1S180/ |
| 328 | 9-14277-73 | 1q43 | g416/D1S3481/G13394/ |
| 329 | 9-14282-334 | 1q43 | g416/D1S3481/G13394/ |
| 330 | 9-14285-381 | 1q43 | g416/D1S3481/G13394/ |
| 331 | 9-14286-220 | 1q43 | g416/D1S3481/G13394/ |
| 332 | 9-14309-259 | 2q35 | g1392/AFM119xc7/D2S126<br>g4167/AFMa104yd5/D2S2148/ |
| 333 | 9-14315-405 | 2q35 | g1392/AFM119xc7/D2S126<br>g4167/AFMa104yd5/D2S2148/ |
| 334 | 9-14329-205 | 2q35 | g1392/AFM119xc7/D2S126<br>g4167/AFMa104yd5/D2S2148/ |
| 335 | 9-14331-64 | 2q35 | g1392/AFM119xc7/D2S126<br>g4167/AFMa104yd5/D2S2148/ |
| 336 | 9-14332-437 | 2q35 | g1392/AFM119xc7/D2S126<br>g4167/AFMa104yd5/D2S2148/ |
| 340 | 9-1437-325 | 1q43 | g18377/RH25341/D29955<br>g425/WI-12765/RH50388/RH63951/Z39518/ |
| 346 | 9-1442-224 | 1q43 | g18377/RH25341/D29955<br>g425/WI-12765/RH50388/RH63951/Z39518/ |
| 351 | 9-14468-247 | 2q32 | g650/RH18030/RH70596/ |
| 352 | 9-14470-243 | 2q32 | g650/RH18030/RH70596/ |
| 353 | 9-14492-322 | 2q33 | g1453/AFM135xf12/D2S2396/ |
| 354 | 9-14497-220 | 2q33 | g1453/AFM135xf12/D2S2396/ |
| 355 | 9-14505-250 | 5q31.3 | g2885/AFM282wd5/D5S638/ |
| 356 | 9-14518-57 | 11p15.5–p15.4 | g6052/AFMb355za9/D11S4177/ |
| 357 | 9-1453-204 | 4p14 | g3928/AFMa061zh9/D4S3040/ |
| 381 | 9-1462-238 | 8p23.2–p23.1 | g480/WI-9756/G05400/ |
| 409 | 9-1468-435 | 8p23.2–p23.1 | g480/WI-9756/G05400/ |
| 410 | 9-1469-47 | 8p23.2–p23.1 | g480/WI-9756/G05400/ |
| 418 | 9-1471-571 | 8p23.2–p23.1 | g480/WI-9756/G05400/ |
| 423 | 9-1472-435 | 8p23.2–p23.1 | g480/WI-9756/G05400/ |
| 428 | 9-1474-156 | 8p23.2–p23.1 | g480/WI-9756/G05400/ |
| 432 | 9-1476-172 | 8p23.2–p23.1 | g480/WI-9756/G05400/ |
| 494 | 9-14950-346 | 5q31.1–q31.2 | g1446/AFM127xh4/D5S402/ |
| 495 | 9-14959-81 | 1q43 | g423/WI-18277/RH49873<br>g424/WI-11392/RH49759/RH63907/T87504/ |
| 496 | 9-14961-193 | 1q43 | g423/WI-18277/RH49873<br>g424/WI-11392/RH49759/RH63907/T87504/ |
| 497 | 9-14962-120 | 1q43 | g423/WI-18277/RH49873<br>g424/WI-11392/RH49759/RR63907/T87504/ |
| 498 | 9-14966-187 | 1q43 | g423/WI-18277/RH49873<br>g424/WI-11392/RH49759/RH63907/T87504/ |
| 499 | 9-14970-352 | 2q33 | g3108/AFM297ve9/D252336<br>g648/EST180027/RH56357/SGC34048/R09731/ |
| 500 | 9-14978-200 | 2q33 | g3108/AFM297ve9/D2S2336<br>g648/EST180027/RH56357/SGC34048/R09731/ |
| 502 | 9-14983-186 | 2q33 | g3108/AFM297ve9/D2S2336<br>g648/EST180027/RH56357/SGC34048/R09731/ |
| 503 | 9-14984-35 | 2q33 | g3108/AFM297ve9/D252336<br>g648/EST180027/RH56357/SGC34048/R09731/ |
| 504 | 9-15005-169 | 1q42.3–q43 | g427/AFMa111yd5/Z67285/ |
| 505 | 9-15007-369 | 1q42.3–q43 | g427/AFMa111yd5/Z67285/ |
| 507 | 9-15016-293 | 2p24 | g2364/AFM234vg5/D25309/ |
| 508 | 9-15018-270 | 2p24 | g2364/AFM234vg5/D25309/ |
| 509 | 9-15019-408 | 2p24 | g2364/AFM234vg5/D25309/ |
| 510 | 9-15021-189 | 2p24 | g2364/AFM234vg5/D25309/ |
| 511 | 9-15030-271 | 2q33.3–q34 | g24928/SHGC-1643/Z24076<br>g2972/AFM289vf5/D2S346/ |
| 512 | 9-15039-277 | 2q33.3–q34 | g24928/SHGC-1643/Z24076<br>g2972/AFM289vf5/D2S346/ |
| 514 | 9-15043-175 | 2q33.3–q34 | g24928/SHGC-1643/Z24076<br>g2972/AFM289vf5/D2S346/ |
| 515 | 9-15046-54 | 2q33.3–q34 | g24928/SHGC-1643/Z24076<br>g2972/AFM289vf5/D2S346/ |
| 543 | 9-15290-343 | 5q31.3 | g1094/AFM042xd12/D5S393/ |
| 544 | 9-15296-326 | 5q31.3 | g1094/AFM042xd12/D5S393/ |
| 545 | 9-15302-371 | 5q31.3 | g1094/AFM042xd12/D5S393/ |
| 546 | 9-15307-251 | 2q34–q35 | g1698/AFM172xg3/D2S137<br>g19419/RH56366/R00076/SGC33908/RH56366<br>g885/WI-17547/EST253706/R76848/ |
| 547 | 9-15310-385 | 2q34–q35 | g1698/AFM172xg3/D2S137<br>g19419/RH56366/R00076/SGC33908/RH56366<br>g885/WI-17547/EST253706/R76848/ |

TABLE 9-continued

| SEQ ID No. | Marker Name | Chromosomal Localization | Adjacent STS (including aliases) |
|---|---|---|---|
| 548 | 9-15325-95 | 2q34–q35 | g1698/AFM172xg3/D2S137<br>g19419/RH56366/R00076/SGC33908/RH56366<br>g885/WI-17547/EST253706/R76848/ |
| 549 | 9-15328-328 | 2q34–q35 | g1698/AFM172xg3/D2S137<br>g19419/RH56366/R00076/SGC33908/RH56366<br>g885/WI-17547/EST253706/R76848/ |
| 551 | 9-15330-301 | 2q34–q35 | g1698/AFM172xg3/D2S137<br>g19419/RH56366/R00076/SGC33908/RH56366<br>g885/WI-17547/EST253706/R76848/ |
| 552 | 9-15335-313 | 1q43 | g422/WI-15487/RH50392/RH64322/R39926<br>g431/WI-31075/RH50186/RH64283/SGC31075/ |
| 553 | 9-15339-378 | 1q43 | g422/WI-15487/RH50392/RH64322/R39926<br>g431/WI-31075/RH50186/RH64283/SGC31075/ |
| 554 | 9-15345-376 | 11p15.5–p15.4 | g6052/AFMb355za9/D11S4177/ |
| 570 | 9-1549-124 | 1q43 | g1385/AFM116xf8/D1S304<br>g407/AFM151XB8/Z66679/ |
| 584 | 9-1553-544 | 1q43 | g1385/AFM116xf8/D1S304<br>g407/AFM151XB8/Z66679/ |
| 588 | 9-1557-251 | 1q43 | g1385/AFM116xf8/D1S304<br>g407/AFM151XB8/Z66679/ |
| 591 | 9-1558-26 | 1q43 | g1385/AFM116xf8/D1S304<br>g407/AFM151XB8/Z66679/ |
| 597 | 9-15625-299 | 1q43 | g17455/AFMa045zc5<br>g309/WI-14972/RH50726/RH64224<br>g311/WI-14095/RH50061/RH64366/R55784<br>g403/WI-7199/RH49904/M30269<br>g406/AFM093XG5/Z66633/ |
| 598 | 9-15627-324 | 1q43 | g17455/AFMa045zc5<br>g309/WI-14972/RH50726/RH64224<br>g311/WI-14095/RH50061/RH64366/R55784<br>g403/WI-7199/RH49904/M30269<br>g406/AFM093XG5/Z66633/ |
| 599 | 9-15636-159 | 1q43 | g17455/AFMa045zc5<br>g309/WI-14972/RH50726/RH64224<br>g311/WI-14095/RH50061/RH64366/R55784<br>g403/WI-7199/RH49904/M30269<br>g406/AFM093XG5/Z66633/ |
| 600 | 9-15638-65 | Xp11.22–p11.21 | g4806/AFMa230vc1/DXS8032/ |
| 601 | 9-15648-83 | Xp11.22–p11.21 | g4806/AFMa230vc1/DXS8032/ |
| 602 | 9-15659-332 | Xp21.3–p21.2 | g3025/AFM292wb9/DXS1218/ |
| 603 | 9-1568-240 | 1q43 | g1385/AFM116xf8/D1S304<br>g407/AFM151XB8/Z66679/ |
| 607 | 9-1572-440 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 616 | 9-1577-105 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 619 | 9-1578-496 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |

TABLE 9-continued

| SEQ ID No. | Marker Name | Chromosomal Localization | Adjacent STS (including aliases) |
|---|---|---|---|
| 623 | 9-1582-430 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 626 | 9-1585-373 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 627 | 9-1587-281 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 629 | 9-1590-116 | 16q13;2q21 | g12752/WI-15065/EST284024/RH54840<br>g15308/D16S2966/UTR-01731<br>g23548/RH54739/R50764/WI-14274/ |
| 630 | 9-15916-270 | 16q13;2q21 | g12752/WI-15065/EST284024/RH54840<br>g15308/D16S2966/UTR-01731<br>g23548/RH54739/R50764/WI-14274/ |
| 631 | 9-15925-331 | 16q13;2q21 | g12752/WI-15065/EST284024/RH54840<br>g15308/D16S2966/UTR-01731<br>g23548/RH54739/R50764/WI-14274/ |
| 632 | 9-15947-109 | 16q13;2q21 | g12752/WI-15065/EST284024/RH54840<br>g15308/D16S2966/UTR-01731<br>g23548/RH54739/R50764/WI-14274/ |
| 636 | 9-1597-162 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 645 | 9-1601-402 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa24Swd5/D1S2678<br>g4901/AFMa247wg9/D1S2680/ |
| 646 | 9-1602-200 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 647 | 9-16022-325 | 5q31.3–q32 | g1166/AFM066xf11/D5S396<br>g20471/RH60098/WI-10312/ |
| 648 | 9-16023-160 | 5q31.3–q32 | g1166/AFM066xf11/D5S396<br>g20471/RH60098/WI-10312/ |
| 649 | 9-16030-317 | 5q31.3–q32 | g1166/AFM066xf11/D5S396<br>g20471/RH60098/WI-10312/ |

TABLE 9-continued

| SEQ ID No. | Marker Name | Chromosomal Localization | Adjacent STS (including aliases) |
|---|---|---|---|
| 650 | 9-1605-112 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 651 | 9-1607-373 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 652 | 9-1611-382 | 1q43 | g313/D1S3401/G04332<br>g404/D1S3450/G11836/ |
| 658 | 9-1615-118 | 1q43 | g313/D1S3401/G04332<br>g404/D1S3450/G11836/ |
| 667 | 9-1622-158 | 1q43 | g2259/AFM218zb6/D1S321/ |
| 670 | 9-1623-145 | 1q43 | g2259/AFM218zb6/D1S321/ |
| 677 | 9-16308-315 | 15q23 | g27865/D15S1242/ |
| 680 | 9-1637-345 | 1q43 | g2259/AFM218zb6/D1S321/ |
| 682 | 9-1638-571 | 1q43 | g2259/AFM218zb6/D1S321/ |
| 748 | 9-1701-39 | 8p23.2–p23.1 | g480/WI-9756/G05400/ |
| 758 | 9-1709-597 | 8p23.2–p23.1 | g480/WI-9756/G05400/ |
| 761 | 9-1710-249 | 8p23.2–p23.1 | g480/WI-9756/G05400/ |
| 908 | 9-18130-258 | 20p12 | g1846/AFM197xb12/D20S112/ |
| 931 | 9-18303-79 | 2q35 | g16358/WI-15771/EST226018/WI-15771/RH56329/<br>R54614<br>g879/EST387886/RH56672/SGC32531<br>g895/WI-15771/EST226018/R54614<br>g897/WI-19704<br>g900/WI-20003/RH56649/T19369/ |
| 936 | 9-18341-95 | 2q35 | g11465/WI-11020/EST206594/WI-11020/RH56985/<br>R36533<br>g24950/SHGC-6253/G02482<br>g891/EST165729/SGC33785/T95608<br>g892/RH56759/NIB1635/T16652<br>g893/WI-11020/EST206594/R36533<br>g894/WI-14333/EST228327/RH57030/R44333<br>g896/WI-22153/RH56193/ |
| 937 | 9-18344-284 | 2q35 | g11465/WI-11020/EST206594/WI-11020/RH56985/<br>R36533<br>g24950/SHGC-6253/G02482<br>g891/EST165729/SGC33785/T95608<br>g892/RH56759/NIB1635/T16652<br>g893/WI-11020/EST206594/R36533<br>g894/WI-14333/EST228327/RH57030/R44333<br>g896/WI-22153/RH56193/ |
| 938 | 9-18345-107 | 2q35 | g11465/WI-11020/EST206594/WI-11020/RH56985/<br>R36533<br>g24950/SHGC-6253/G02482<br>g891/EST165729/SGC33785/T95608<br>g892/RH56759/NIB1635/T16652<br>g893/WI-11020/EST206594/R36533<br>g894/WI-14333/EST228327/RH57030/R44333<br>g896/WI-22153/RH56193/ |
| 939 | 9-18371-433 | 2q33 | g678/WI-14342/R43945/ |
| 940 | 9-18373-27 | 2q33 | g678/WI-14342/R43945/ |
| 941 | 9-18375-237 | 2q33 | g678/WI-14342/R43945/ |
| 942 | 9-18379-485 | 2q33 | g678/WI-14342/R43945/ |
| 973 | 9-18602-241 | 1q42.3–q43 | g312/D1S3398/G04103/ |
| 974 | 9-18606-324 | 1q42.3–q43 | g312/D1S3398/G04103/ |
| 976 | 9-18612-184 | 1q42.3–q43 | g312/D1S3398/G04103/ |
| 977 | 9-18618-455 | 2q34 | g5200/AFMa351zd1/D2S2242/ |
| 978 | 9-18620-125 | 2q34 | g5200/AFMa351zd1/D2S2242/ |
| 982 | 9-18648-71 | 2q34–q35 | g2044/AFM205yb4/D2S295/ |
| 986 | 9-18715-172 | 17q23–q24 | g1684/AFM168xd12/D17S794/ |
| 987 | 9-18719-225 | 2q34–q35 | g6159/AFMc009yh1/D2S2322/ |
| 988 | 9-18720-235 | 2q34–q35 | g6159/AFMc009yh1/D2S2322/ |
| 989 | 9-18721-442 | 2q34–q35 | g6159/AFMc009yh1/D2S2322/ |
| 993 | 9-18744-170 | 2p13–p12;2q35 | g731/D2S2722/ |

TABLE 9-continued

| SEQ ID No. | Marker Name | Chromosomal Localization | Adjacent STS (including aliases) |
|---|---|---|---|
| 994 | 9-18745-423 | 2p13–p12;2q35 | g731/D2S2722/ |
| 995 | 9-18747-72 | 2p13–p12;2q35 | g731/D2S2722/ |
| 1002 | 9-18808-155 | 11q23–q24 | g4760/AFMa222xc5/D11S4104/ |
| 1003 | 9-18814-275 | 18q12.3–q21.1 | g1510/AFM147yf2/D18S1094/ |
| 1017 | 9-18974-99 | 8p23.1 | g21326/RH62553/T03554/IB46 g23/SHGC-9737/G13478 g26491/SHGC-33472/R01769/ |
| 1018 | 9-18976-135 | 8p23.1 | g21326/RH62553/T03554/IB46 g23/SHGC-9737/G13478 g26491/SHGC-33472/R01769/ |
| 1019 | 9-18982-345 | 8p23.1 | g21326/RH62553/T03554/IB46 g23/SHGC-9737/G13478 g26491/SHGC-33472/R01769/ |
| 1020 | 9-18986-248 | 8p23.1 | g21326/RH62553/T03554/IB46 g23/SHGC-9737/G13478 g26491/SHGC-33472/R01769/ |
| 1021 | 9-18987-191 | 4q12–q13.1 | g3031/AFM292xe1/D4S1592 g3712/AFMa044tf1/D4S3019/ |
| 1022 | 9-18995-300 | 4q12–q13.1 | g3031/AFM292xe1/D4S1592 g3712/AFMa044tf1/D4S3019/ |
| 1023 | 9-18996-388 | 4q12–q13.1 | g3031/AFM292xe1/D4S1592 g3712/AFMa044tf1/D4S3019/ |
| 1031 | 9-19253-102 | 4q12 | g11759/WI-11762/EST183347/RH59610/R12768 g14673/D452603/MR10551 g20013/RH59475/SGC35370/ |
| 1032 | 9-19256-149 | 4q12 | g11759/WI-11762/EST183347/RH59610/R12768 g14673/D4S2603/MR10551 g20013/RH59475/SGC35370/ |
| 1041 | 9-1964-53 | 1q43 | g15623/D1S547/GATA4A09 g17350/RH1290/SHGC-477 g17708/RH11033/D29436/D29436 g18500/RH26479/R65593 g319/EST161941/RH50228/RH64454/SGC33718/ T91820 g405/D1S1707/G02394 g408/AFM214xe11/Z66804 g417/D1S2421/WI-9317/D29955/RH49709 g420/WI-15754/RH49799 g426/WI-13731/RH49867/RH64343/R44970/ |
| 1042 | 9-1977-440 | 1q43 | g15623/D1S547/GATA4A09 g17350/RH1290/SHGC-477 g17708/RH11033/D29436/D29436 g18500/RH26479/R65593 g319/EST161941/RH50228/RH64454/SGC33718/ T91820 g405/D1S1707/G02394 g408/AFM214xe11/Z66804 g417/D1S2421/WI-9317/D29955/RH49709 g420/WI-15754/RH49799 g426/WI-13731/RH49867/RH64343/R44970/ |
| 1044 | 9-19999-92 | 4p14;8p22 | g1951/AFM200yc7/D4S1547/ |
| 1046 | 9-20000-252 | 4p14;8p22 | g1951/AFM200yc7/D4S1547/ |
| 1076 | 9-20294-274 | 4p14 | g5753/AFMb319ze5/D4S2974/ |
| 1077 | 9-20303-127 | 4p14 | g5753/AFMb319ze5/D4S2974/ |
| 1078 | 9-20313-311 | 4p14 | g5753/AFMb319ze5/D4S2974/ |
| 1079 | 9-20320-321 | 4p14 | g19996/RH59112/R77106/SGC34270/ |
| 1080 | 9-20326-130 | 4p14 | g19996/RH59112/R77106/SGC34270/ |
| 1081 | 9-20332-432 | 4p14 | g19996/RH59112/R77106/SGC34270/ |
| 1082 | 9-20335-48 | 4p14 | g19996/RH59112/R77106/SGC34270/ |
| 1083 | 9-20340-161 | 4p14 | g19996/RH59112/R77106/SGC34270/ |
| 1090 | 9-20385-215 | 4p14;8p22 | g1951/AFM200yc7/D4S1547/ |
| 1099 | 9-20469-213 | 4p14 | g12593/WI-14683/EST283388/RH59148 g25359/SHGC4-1576/Z23989/ |
| 1101 | 9-20480-233 | 4p14 | g12593/WI-14683/EST283388/RH59148 g25359/SHGC4-1576/Z23989/ |
| 1102 | 9-20481-131 | 4p14 | g12593/WI-14683/EST283388/RH59148 g25359/SHGC4-1576/Z23989/ |
| 1103 | 9-20485-269 | 4p14 | g12593/WI-14683/EST283388/RH59148 g25359/SHGC4-1576/Z23989/ |
| 1104 | 9-20493-238 | 4p14 | g12593/WI-14683/EST283388/RH59148 g25359/SRGC4-1576/Z23989/ |
| 1105 | 9-20499-364 | 4p14 | g12593/WI-14683/EST283388/RH59148 g25359/SHGC4-1576/Z23989/ |
| 1106 | 9-20504-90 | 4p14 | g12593/WI-14683/EST283388/RH59148 g25359/SHGC4-1576/Z23989/ |

TABLE 9-continued

| SEQ ID No. | Marker Name | Chromosomal Localization | Adjacent STS (including aliases) |
|---|---|---|---|
| 1107 | 9-20508-456 | 4p14 | g12593/WI-14683/EST283388/RH59148 g25359/SRGC4-1576/Z23989/ |
| 1109 | 9-20511-221 | 4p14 | g12593/WI-14683/EST283388/RH59148 g25359/SHGC4-1576/Z23989/ |
| 1110 | 9-20514-71 | 4p14 | g12593/WI-14683/EST283388/RH59148 g25359/SHGC4-1576/Z23989/ |
| 1180 | 9-20938-256 | 6q22.1–q22.2 | g2096/AFM207xb6/D6S412/ |
| 1182 | 9-20950-251 | 2p21–p16 | g19180/RH56202/L47574/WI-18791/ |
| 1184 | 9-21012-277 | 6q12–q13 | g6016/AFMb352wc1/D6S1659/ |
| 1185 | 9-21021-273 | 6q12–q13 | g6016/AFMb352wc1/D6S1659/ |
| 1198 | 9-2117-107 | 21q22.1 | g1505/AFM147xb12/D21S260 g7678/D21S12 g7852/D21S1824 g7867/D21S1839/ |
| 1199 | 9-21221-96 | 3p24.3–p25.1 | g24997/D3S4113/ |
| 1221 | 9-2209-111 | 10p12.1–p11.2 | g1397/AFM119xh12/D10S197/ |
| 1228 | 9-2214-148 | 10p12.1–p11.2 | g1397/AFM119xh12/D10S197/ |
| 1233 | 9-2218-219 | 10p12.1–p11.2 | g1397/AFM119xh12/D10S197/ |
| 1235 | 9-2219-245 | 10p12.1–p11.2 | g1397/AFM119xb12/D10S197/ |
| 1239 | 9-2220-300 | 10p12.1–p11.2 | g1397/AFM119xh12/D10S197/ |
| 1240 | 9-2209-304 | 11q22.3–q23.1 | g22439/RH51746/WI-14282/ |
| 1243 | 9-2222-459 | 10p12.1–p11.2 | g1397/AFM119xh12/D10S197/ |
| 1245 | 9-22255-384 | 20q13.1–q13.2 | g17162/WI-31010/EST384826/RH57250/RH64058/SGC31010/ |
| 1246 | 9-22262-331 | 19q13.1 | g11280/TIGR-A005D28/RH55812 g11653/WI-11537/EST180053/RH56022/R09757/ |
| 1249 | 9-2228-301 | 21q21 | g7672/D21S11/ |
| 1250 | 9-2229-240 | 21q21 | g7672/D21S11/ |
| 1254 | 9-2235-499 | 21q21 | g7672/D21S11/ |
| 1257 | 9-2240-281 | 21q22.1 | g7689/D21S1230/ |
| 1259 | 9-2242-206 | 21q22.1 | g7689/D21S1230/ |
| 1260 | 9-2244-83 | 21q22.1 | g7689/D21S1230/ |
| 1261 | 9-22442-147 | 1p31.3–p31.2 | g18161/RH17161 g18429/RH25834/Z45206/ |
| 1262 | 9-22449-216 | 1p31.3–p31.2 | g18161/RH17161 g18429/RH25834/Z45206/ |
| 1263 | 9-22453-370 | 1p31.3–p31.2 | g18161/RH17161 g18429/RH25834/Z45206/ |
| 1264 | 9-22456-55 | 1p31.3–p31.2 | g18161/RH17161 g18429/RH25834/Z45206/ |
| 1265 | 9-2246-340 | 21q22.1 | g7689/D21S1230/ |
| 1266 | 9-2248-76 | 21q22.1 | g7689/D21S1230/ |
| 1269 | 9-2250-236 | 21q22.1 | g7689/D21S1230/ |
| 1274 | 9-22546-125 | 3q26.2–q26.3 | g16578 g19824/RH58812/R39509/WI-11077/ |
| 1275 | 9-22565-114 | 14q24.3–q31 | g23143/RH53688/G04281/WI-3377 g27731/D14S929/ |
| 1276 | 9-22571-136 | 14q24.3–q31 | g23143/RH53688/G04281/WI-3377 g27731/D14S929/ |
| 1282 | 9-22604-208 | 1p32.1–p31.3 | g11032/RH49618/NIB551/T17225 g12546/WI-14549/EST42945/RH50683/T17225/ |
| 1283 | 9-22610-343 | 15q21 | g12995/WI-15792/EST265261/RH54066 g27831/SHGC-9535/ |
| 1284 | 9-22615-392 | 15q21 | g12995/WI-15792/EST265261/RH54066 g27831/SHGC-9535/ |
| 1285 | 9-22617-378 | 15q21 | g12995/WI-15792/EST265261/RH54066 g27831/SHGC-9535/ |
| 1286 | 9-22620-404 | 19q13.4 | g12950/WI-15666/EST230907/RH55986/R44502/ |
| 1287 | 9-22628-292 | 15q24 | g16003/WI-20012/EST48352/RH54344/T28573 g23432/RH54202/WI-7231/ |
| 1288 | 9-22629-124 | 15q24 | g16003/WI-20012/EST48352/RH54344/T28573 g23432/RH54202/WI-7231/ |
| 1289 | 9-22632-237 | 15q24 | g16003/WI-20012/EST48352/RH54344/T28573 g23432/RH54202/WI-7231/ |
| 1290 | 9-22646-233 | 6q21 | g5686/AFMb312yc1/D6S1635/ |
| 1291 | 9-22648-57 | 6q21 | g5686/AFMb312yc1/D6S1635/ |
| 1292 | 9-22650-64 | 6q21 | g5686/AFMb312yc1/D6S1635/ |
| 1293 | 9-22652-343 | 8q24.2 | g5926/AFMb340xd5/D8S1783/ |
| 1294 | 9-22655-319 | 8q24.2 | g5926/AFMb340xd5/D8S1783/ |
| 1295 | 9-22660-386 | 8q24.2 | g5926/AFMb340xd5/D8S1783/ |
| 1296 | 9-22662-268 | 8q24.2 | g5926/AFMb340xd5/D8S1783/ |
| 1297 | 9-22666-164 | 4p15.3–p15.2 | g19966/RH58930/L14153/D4S1267/ |
| 1298 | 9-22668-232 | 4p15.3–p15.2 | g19966/RH58930/L14153/D4S1267/ |
| 1299 | 9-22674-31 | 4p15.3–p15.2 | g19966/RH58930/L14153/D4S1267/ |
| 1300 | 9-22675-187 | 4p15.3–p15.2 | g19966/RH58930/L14153/D4S1267/ |
| 1301 | 9-22680-130 | 18p11.31 | g23841/RH55516/G03618/WI-4219/ |

TABLE 9-continued

| SEQ ID No. | Marker Name | Chromosomal Localization | Adjacent STS (including aliases) |
|---|---|---|---|
| 1302 | 9-22683-107 | 18p11.31 | g23841/RH55516/G03618/WI-4219/ |
| 1304 | 9-22700-358 | 11q23.1–q23.2; 5q11.2 | g27251/SHGC-2090/Z24364/RH13666 g3346/AFM320Xh1/D11S1347/ |
| 1305 | 9-22701-307 | 11q23.1–q23.2; 5q11.2 | g27251/SHGC12090/Z24364/RH13666 g3346/AFM320xh1/D11S1347/ |
| 1312 | 9-22733-281 | 2q35 | g19425/RH56275/H62242/SGC32398/RH56275/ |
| 1313 | 9-22741-180 | 2q34–q35 | g6159/AFMc009yh1/D2S2322/ |
| 1316 | 9-22771-150 | 2q35 | g24953/SRGC-971/Z17049 g4193/AFMa109wg5/D2S2151/ |
| 1317 | 9-22775-365 | 2q35 | g24953/SHGC-971/Z17049 g4193/AFMa109wg5/D2S2151/ |
| 1319 | 9-22785-431 | 2q35 | g24953/SHGC-971/Z17049 g4193/AFMa109wg5/D2S2151/ |
| 1320 | 9-22843-342 | 2q35 | g874/WI-12463/EST195179/R25134/ |
| 1321 | 9-22844-211 | 2q35 | g874/WI-12463/EST195179/R25134/ |
| 1323 | 9-22868-425 | 2q33 | g1453/AFM135xf12/D2S2396/ |
| 1324 | 9-22872-431 | 2q33 | g1453/AFM135xf12/D2S2396/ |
| 1325 | 9-2288-144 | 21q21.3 | g5554/AFMb291yb9/D21S1896 g7754/D21S1435/ |
| 1326 | 9-22917-145 | 2q32.3–q33 | g6130/AFMc005wb9/D2S2318/ |
| 1328 | 9-22948-262 | 2p23 | g10323/AFMB353WF1/w2082/ |
| 1329 | 9-22954-306 | 2p23 | g10323/AFMB353WF1/w2082/ |
| 1330 | 9-22957-409 | 2p23 | g10323/AFMB353WF1/w2082/ |
| 1331 | 9-22959-239 | 2p23 | g10323/AFMB353WF1/w2082/ |
| 1332 | 9-22964-82 | 11p15.5–p15.4 | g6052/AFMb355za9/D11S4177/ |
| 1333 | 9-22975-126 | 11p15.5–p15.4 | g6052/AFMb355za9/D11S4177/ |
| 1334 | 9-23014-300 | 2q34–q35 | g2044/AFM205yb4/D2S295/ |
| 1335 | 9-23018-166 | 2q34–q35 | g2044/AFM205yb4/D2S295/ |
| 1336 | 9-23020-187 | 1q43 | g422/WI-15487/RH50392/RH64322/R39926 g431/WI-31075/RH50186/RH64283/SGC31075/ |
| 1337 | 9-23083-59 | 1p34.2–p34.1 | g18865/RH33933/G07594/SHGC-4031/ |
| 1338 | 9-23100-367 | 9q33–q34.1 | g15044/D9S1698/HSC0VC072/ |
| 1339 | 9-23115-404 | 22q12;2p23 | g19151/RH57021/R95095/SGC33508 g19152/RH56155/WI-10842/ |
| 1340 | 9-23118-402 | 22q12;2p23 | g19151/RH57021/R95095/SGC33508 g19152/RH56155/WI-10842/ |
| 1341 | 9-2312-358 | 21q21.2 | g7697/D21S1240/ |
| 1342 | 9-23123-250 | 3p21.1–p14.3 | g2744/AFM268wg9/D3S1578/ |
| 1343 | 9-23127-314 | 3p21.1–p14.3 | g2744/AFM268wg9/D3S1578/ |
| 1344 | 9-23132-192 | 3p21.1–p14.3 | g2744/AFM268wg9/D3S1578/ |
| 1345 | 9-23134-89 | 3p21.1–p14.3 | g2744/AFM268wg9/D3S1578/ |
| 1346 | 9-2315-213 | 21q21.2 | g7697/D21S1240/ |
| 1347 | 9-23150-262 | 18q23 | g13666/WI-18089/EST355463/RH55492 g28291/SHGC-17251/ |
| 1348 | 9-2320-292 | 21q21.2 | g7697/D21S1240/ |
| 1349 | 9-23201-345 | 4q31.1–q31.2 | g16662/WI-15195/EST308096/RH59447 g25614/D4S507 g6094/AFMb361zg5/D4S2998/ |
| 1350 | 9-23202-185 | 4q31.1–q31.2 | g16662/WI-15195/EST308096/RH59447 g25614/D4S507 g6094/AFMb361zg5/D4S2998/ |
| 1351 | 9-23204-262 | 4q31.1–q31.2 | g16662/WI-15195/EST308096/RH59447 g25614/D4S507 g6094/AFMb361zg5/D4S2998/ |
| 1352 | 9-23207-281 | 4q31.1–q31.2 | g16662/WI-15195/EST308096/RH59447 g25614/D4S507 g6094/AFMb361zg5/D4S2998/ |
| 1353 | 9-2321-82 | 21q21.2 | g7697/D21S1240/ |
| 1354 | 9-23228-176 | 2q21 | g19179/RH56626/T10467/SGC32727 g19285/RH56961/R51826/SGC31844/ |
| 1355 | 9-2324-338 | 21q21.2 | g7697/D21S1240/ |
| 1358 | 9-2328-535 | 10p11.2 | g1912/AFM199zb6/D10S213/ |
| 1359 | 9-23299-424 | 3q21 | g5752/AFMb319yf1/D3S3646/ |
| 1360 | 9-23302-326 | 3q21 | g5752/AFMb319yf1/D3S3646/ |
| 1361 | 9-2331-639 | 21q22.1 | g7774/D21S1677 g7876/D21S1853 g7877/D21S1854 g7886/D21S1865 g7887/D21S1866/ |
| 1362 | 9-23312-93 | 3q21 | g5752/AFMb319yf1/D3S3646/ |
| 1363 | 9-23317-51 | 1q32.1 | g5230/AFMb002ya5/D1S2716/ |
| 1364 | 9-23322-49 | 1q32.1 | g5230/AFMb002ya5/D1S2716/ |
| 1365 | 9-23326-120 | 1q32.1 | g5230/AFMb002ya5/D1S2716/ |
| 1366 | 9-23328-292 | 1q32.1 | g5230/AFMb002ya5/D1S2716/ |
| 1367 | 9-23333-157 | 9p22 | g10403/D9S921/GATA-D9S921 g26676/SHGC-3751/Z16707/RH13288/ |

TABLE 9-continued

| SEQ ID No. | Marker Name | Chromosomal Localization | Adjacent STS (including aliases) |
|---|---|---|---|
| 1368 | 9-23334-443 | 9p22 | g10403/D9S921/GATA-D9S921 g26676/SHGC-3751/Z16707/RH13288/ |
| 1369 | 9-23359-99 | 2q35 | g878/RH56992/SGC35345/ |
| 1370 | 9-23381-412 | 2q34 | g5200/AFMa351zd1/D2S2242/ |
| 1371 | 9-23387-404 | 2q34 | g5200/AFMa351zd1/D2S2242 / |
| 1372 | 9-23413-242 | 11q23.3–q24 | g2707/AFM265wa9/D11S1328/ |
| 1373 | 9-23415-131 | 11q23.3–q24 | g2707/AFM265wa9/D11S1328/ |
| 1374 | 9-23417-128 | 11q23.3–q24 | g2707/AFM265wa9/D11S1328/ |
| 1378 | 9-2345-28 | 13p13–q11; 14p13–q11.1; 15p13–q11.1; 16p11.1–q11.2; 1p11–q12; 21p13–q11.1; 3p11–q11.1; 9p11–q12; Yq12 | g6058/AFMb356wg1/D21S1904 g7727/D21S13 g7737/D21S1416 g7750/D21S1431/ |
| 1383 | 9-23462-192 | 1q21.1–q21.2 | g17255/RH421/Z24671/SHGC-1599/RH13725 g19054/RH36179/H47260/stSG12720/ |
| 1384 | 9-23463-118 | 1q21.1–q21.2 | g17255/RH421/Z24671/SHGC-1599/RH13725 g19054/RH36179/H47260/stSG12720/ |
| 1386 | 9-2347-207 | 13p13–q11; 14p13–q11.1; 15p13–q11.1; 16p11.1–q11.2; 1p11–q12; 21p13–q11.1; 3p11–q11.1; 9p11–q12; Yq12 | g6058/AFMb356wg1/D21S1904 g7727/D21S13 g7737/D21S1416 g7750/D21S1431/ |
| 1388 | 9-2348-127 | 13p13–q11; 14p13–q11.1; 15p13–q11.1; 16p11.1–q11.2; 1p11–q12; 21p13–q11.1; 3p11–q11.1; 9p11–q12; Yq12 | g6058/AFMb356wg1/D21S1904 g7727/D21S13 g7737/D21S1416 g7750/D21S1431/ |
| 1394 | 9-2356-322 | 13p13–q11;14p13–q11.1;15p13–q11.1;16p11.1–q11.2;1p11–q12;21p13–q11.1;3p11–q11.1;9p11–q12;Yq12 | g6058/AFMb3S6wg1/D21S1904 g7727/D21S13 g7737/D21S1416 g7750/D21S1431/ |
| 1395 | 9-2362-270 | 21q21–q22.1 | g7899/D21S1877 g7904/D21S1881/ |
| 1396 | 9-2364-329 | 21q21–q22.1 | g7899/D21S1877 g7904/D21S1881/ |
| 1397 | 9-2367-61 | 21q21–q22.1 | g7899/D21S1877 g7904/D21S1881/ |
| 1398 | 9-2368-61 | 21q21–q22.1 | g7899/D21S1877 g7904/D21S1881/ |
| 1399 | 9-23687-107 | 2q34 | g2193/AFM212ze9/D2S157/ |
| 1400 | 9-237-151 | 21q22.3 | g7967/D21S49/ |
| 1401 | 9-23714-196 | 15q23 | g27865/D15S1242/ |
| 1403 | 9-2375-114 | 21q11.2 | g7010/D21S258 g7029/AFMa083xe1/ |
| 1405 | 9-2378-200 | 21q11.2 | g7010/D21S258 g7029/AFMa083xe1/ |
| 1406 | 9-2381-394 | 21q11.2 | g7010/D21S258 g7029/AFMa083xe1/ |
| 1409 | 9-2413-368 | 21q22.1 | g7798/D21S1700 g7879/D21S1856/ |
| 1410 | 9-2417-177 | 21q22.1 | g7798/D21S1700 g7879/D21S1856/ |
| 1411 | 9-2419-285 | 21q22.1 | g7798/D21S1700 g7879/D21S1856/ |
| 1412 | 9-24246-247 | 2q33 | g649/Mch4 g651/RH15884/T91183/ |
| 1413 | 9-24253-437 | 2q35 | g15152/D2S2592/UTR-05171/ |
| 1414 | 9-24259-466 | 2q35 | g15152/D2S2592/UTR-05171/ |
| 1415 | 9-24264-380 | 2q35 | g15152/D2S2592/UTR-05171/ |

TABLE 9-continued

| SEQ ID No. | Marker Name | Chromosomal Localization | Adjacent STS (including aliases) |
|---|---|---|---|
| 1416 | 9-24269-417 | 2q33–q34 | g2141/AFM210yf10/D2S155/ |
| 1417 | 9-24270-207 | 2q33–q34 | g2141/AFM210yf10/D2S155/ |
| 1419 | 9-24284-213 | 2q33–q34 | g732/RH56861/ |
| 1420 | 9-24286-231 | 2q33–q34 | g732/RH56861/ |
| 1421 | 9-24288-121 | 2q33–q34 | g732/RH56861/ |
| 1422 | 9-24333-37 | 2q34 | g882/EST141512/RH56286/SGC33506/T79149/ |
| 1423 | 9-24342-311 | 2q35 | g679/EST250412/RH56354/SGC31996/ |
| 1424 | 9-24376-24 | 7q11.23–q21.1 | g11961/WI-12513/EST251317/RH61608/R74459/ |
| 1425 | 9-24379-319 | 7q11.23–q21.1 | g11961/WI-12513/EST251317/RH61608/R74459/ |
| 1429 | 9-24390-27 | 10q11.2 | g21928/RH51060/SGC38063/ |
| 1430 | 9-24392-61 | 10q11.2 | g21928/RH51060/SGC38063/ |
| 1431 | 9-24393-108 | 10q11.2 | g21928/RH51060/SGC38063/ |
| 1433 | 9-24409-383 | 14q24.3 | g23123/RH53961/T40920/SGC32981/SHGC-32981/ |
| 1434 | 9-24411-420 | 14q24.3 | g23123/RH53961/T40920/SGC32981/SHGC-32981/ G27696/G25597/EST91724 g27725/SHGC-942/Z16981/RH49039/ |
| 1435 | 9-24427-321 | 5q34 | g1927/AFM200vf6/D5S619/ |
| 1436 | 9-24432-284 | 5q34 | g1927/AFM200vf6/D5S619/ |
| 1439 | 9-24447-448 | 1p31.3–p31.2 | g14348/D1S2161/MR7398 g18605/RH27953/G07842/ |
| 1441 | 9-24454-257 | 1p31.3–p31.2 | g14348/D1S2161/MR7398 g18605/RH27953/G07842/ |
| 1442 | 9-24463-206 | 21q21–q22.1 | g24227/RH57563/H92581/WI-22816 g7742/D21S1422 |
| 1443 | 9-24496-171 | 11q23.3–q24 | g22500/RH52371/H30529/SGC30738 |
| 1444 | 9-24506-396 | 4q25 | g20076/RH59480/Z15005/WI-6987 g20078/RH59042/T16396/WI-13405/ |
| 1445 | 9-24508-45 | 4q25 | g20076/RH59480/Z15005/WI-6987 g20078/RH59042/T16396/WI-13405/ |
| 1446 | 9-24529-330 | 2q35 | g16358/WI-15771/EST226018/WI-15771/RH56329/ R54614 g879/EST387886/RH56672/SGC32531 g895/WI-15771/EST226018/R54614 g897/WI-19704 g900/WI-20003/RH56649/T19369/ |
| 1447 | 9-24534-317 | 2q35 | g16358/WI-15771/EST226018/WI-15771/RH56329/ R54614 g879/EST387886/RH56672/SGC32531 g895/WI-15771/EST226018/R54614 g897/WI-19704 g900/WI-20003/RH56649/T19369/ |
| 1448 | 9-24554-324 | 2q35 | g875/WI-12994/HSC2KC082 g876/WI-17411/EST240716/RH56866/R63961/ |
| 1449 | 9-24557-406 | 2q35 | g5212/AFMa357wc9/D2S2244/ |
| 1450 | 9-24561-360 | 2q35 | g13275/WI-16791/EST159864/WI-16791/RH56414/ T89743 g889/WI-16791/EST159864/T89743/ |
| 1451 | 9-24570-260 | 6q26 | g15128/D6S1951/UTR-00083/ |
| 1453 | 9-24725-138 | 16q21–q22; 7p11.1–q11.1 | g12359/WI-13905/EST227346/RH54662/R49366 g16052/WI-20039/EST59759/RH54768/T33895 g27992/SHGC-11618/T56923/ |
| 1454 | 9-24727-360 | 16q21–q22; 7p11.1–q11.1 | g12359/WI-13905/EST227346/RH54662/R49366 g16052/WI-20039/EST59759/RH54768/T33895 g27992/SHGC-11618/T56923/ |
| 1455 | 9-24750-293 | 11q23.1–q23.2 | g15768 g22459/RH52046/H86791/SGC31226/ |
| 1456 | 9-24778-221 | 7q22 | g491/WI-6368/RH61376/ |
| 1457 | 9-24793-390 | 7q22 | g491/WI-6368/RH61376/ |
| 1458 | 9-24800-565 | 7q22 | g491/WI-6368/RH61376/ |
| 1461 | 9-25053-114 | 2q33–q34 | g6158/AFMc009wh1/D2S2321/ |
| 1462 | 9-25055-44 | 2q33–q34 | g6158/AFMc009wh1/D2S2321/ |
| 1463 | 9-25070-78 | 2q33–q34 | g6158/AFMc009wh1/D2S2321/ |
| 1467 | 9-2524-98 | 21q22.3 | g7967/D21S49/ |
| 1468 | 9-25246-170 | 13q34 | g15911 g712/RH17028/ |
| 1469 | 9-25249-151 | 13q34 | g15911 g712/RH17028/ |
| 1470 | 9-2525-142 | 21q22.3 | g7967/D21S49/ |
| 1471 | 9-25255-288 | 13q34 | g15911 g712/RH17028/ |
| 1472 | 9-25369-121 | 15q21 | g23347/RH54301/G05439/WI-9836 g23349/RH54281/H92576/SGC32630/ |
| 1478 | 9-25431-269 | 2q33–q34 | g881/WI-18179/EST362695/ |
| 1479 | 9-25432-119 | 2q33–q34 | g881/WI-18179/EST362695/ |
| 1480 | 9-25433-351 | 2q33–q34 | g881/WI-18179/EST362695/ |

TABLE 9-continued

| SEQ ID No. | Marker Name | Chromosomal Localization | Adjacent STS (including aliases) |
|---|---|---|---|
| 1481 | 9-25447-272 | 1q44 | g17338/RH1233/SHGC-269 g18240/RH17889/R98962/R98962 g18593/RH27933/RH64496/ |
| 1482 | 9-25448-348 | 18q11.2 | g10695/CHLC.GATA84D10/CHLC.GATA85D10.P19280/ G08009/GATA-P19280/ |
| 1483 | 9-25452-83 | 18q11.2 | g10695/CHLC.GATA85D10/CHLC.GATA85D10.P19280/ G08009/GATA-P19280/ |
| 1484 | 9-25454-349 | 18q11.2 | g10695/CHLC.GATA85D10/CHLC.GATA85D10.P19280/ G08009/GATA-P19280/ |
| 1500 | 9-2570-218 | 21q22.3 | g24258/RH57551/R48588/SGC34143 g24259/RH57619/H53556/SGC34732/ |
| 1502 | 9-25716-393 | 13q34 | g866/WI-13756/RH53429/R46080/ |
| 1503 | 9-25717-252 | 13q34 | g866/WI-13756/RH53429/R46080/ |
| 1507 | 9-25781-275 | 19q13.2 | g11925/WI-12417/EST276107/RH55689/ |
| 1509 | 9-2597-34 | 21q22.2 | g7732/D21S1411/ |
| 1510 | 9-26001-224 | 3q27–q28 | g11074/RH58557/Z22625/T40957 g19863/RH58270/H61445/SGC34843/ |
| 1511 | 9-26002-93 | 3q27–q28 | g11074/RH58557/Z22625/T40957 g19863/RH58270/H61445/SGC34843/ |
| 1512 | 9-26042-310 | 2q23 | g1807/AFM191wg9/D2S142/ |
| 1513 | 9-26080-152 | 11q24;5q15 | g4300/AFMa124wg5/D5S1957/ |
| 1514 | 9-26082-48 | 11q24;5q15 | g4300/AFMa124wg5/D5S1957/ |
| 1515 | 9-26099-119 | 1p22 | g17899/RH12743/R47991/stSG4580/ |
| 1517 | 9-26105-273 | 2q35 | g19425/RH56275/H62242/SGC32398/RH56275/ |
| 1518 | 9-26116-191 | 5q21–q22 | g13747/WI-18306/EST374223/RH59791 g20406/RH60017/H10223/SGC32412/ |
| 1521 | 9-2624-407 | 21q22.2 | g16433 g24246/RH57580/SGC32448 g28577/SHGC-10474 g28580/SHGC-10477 g7818/D21S1725E/ |
| 1522 | 9-2625-70 | 21q22.2 | g16433 g24246/RH57580/SGC32448 g28577/SHGC-10474 g28580/SHGC-10477 g7818/D21S1725E/ |
| 1523 | 9-2637-28 | 21q22.2 | g16433 g24246/RH57580/SGC32448 g28577/SHGC-10474 g28580/SHGC-10477 g7818/D21S1725E/ |
| 1528 | 9-342-288 | 19q13.2–q13.3 | g448/RH11470/RH1669/ |
| 1544 | 9-449-344 | 10p12.1–p11.2 | g3518/AFM338ta5/D10S600/ |
| 1545 | 9-4536-255 | 15q14–q15 | g15965/WI-11934/EST197813/RH54176/R27768 g15966/WI-19599/ |
| 1546 | 9-4541-39 | 1p36.2–p36.1 | g316/EST47321/D19656/RH50110/SGC32758 g414/WI-12386/RH50879/RH63782/ |
| 1547 | 9-4544-287 | 1p36.2–p36.1 | g316/EST47321/D19656/RH50110/SGC32758 g414/WI-12386/RH50879/RH63782/ |
| 1548 | 9-4547-312 | 1p36.2–p36.1 | g316/EST47321/D19656/RH50110/SGC32758 g414/WI-12386/RH50879/RH63782/ |
| 1549 | 9-4595-341 | 1q43 | g314/WI-10464/ |
| 1550 | 9-4604-26 | 1q43 | g314/WI-10464/ |
| 1555 | 9-465-443 | 10p12.1–p11.2 | g1621/AFM164tg9/D10S204/ |
| 1557 | 9-466-361 | 10p12.1–p11.2 | g1621/AFM164tg9/D10S204/ |
| 1569 | 9-472-70 | 10p11.2 | g2598/AFM254xb1/D10S224/ |
| 1591 | 9-490-202 | 10p12.1–p11.2 | g5171/AFMa346zd5/D10S1695 g5966/AFMb345ya9/D10S1732/ |
| 1594 | 9-4950-196 | 1q43 | g416/D1S3481/G13394/ |
| 1595 | 9-4951-36 | 1q43 | g416/D1S3481/G13394/ |
| 1599 | 9-5016-206 | 7q11.23–q21.1 | g1970/AFM203vb6/D7S634/ |
| 1600 | 9-5029-240 | 7q11.23–q21.1 | g1970/AFM203vb6/D7S634/ |
| 1605 | 9-5099-245 | 7q11.23–q21.1 | g2935/AFM286xf9/D7S669/ |
| 1606 | 9-5101-284 | 7q11.23–q21.1 | g2935/AFM286xf9/D7S669/ |
| 1607 | 9-5104-160 | 7q11.23–q21.1 | g2935/AFM286xf9/D7S669/ |
| 1608 | 9-5107-184 | 7q11.23–q21.1 | g2935 /AFM286xf9/D7S669/ |
| 1609 | 9-5108-144 | 7q11.23–q21.1 | g2935/AFM286xf9/D7S669/ |
| 1610 | 9-511-33 | 10p12.1–p11.2 | g4171/AFMa106vf5/D10S1639/ |
| 1633 | 9-5294-362 | 2q33 | g4971/AFMa285zb9/D2S2214 g4987/AFMa289xc1/D2S2217/ |
| 1634 | 9-5306-93 | 2q33 | g4971/AFMa285zb9/D2S2214 g4987/AFMa289xc1/D2S2217/ |
| 1635 | 9-5308-341 | 2q33 | g4971/AFMa285zb9/D2S2214 g4987/AFMa289xc1/D2S2217/ |
| 1636 | 9-5312-273 | 2q33 | g4971/AFMa285zb9/D2S2214 g4987/AFMa289xc1/D2S2217/ |

TABLE 9-continued

| SEQ ID No. | Marker Name | Chromosomal Localization | Adjacent STS (including aliases) |
|---|---|---|---|
| 1639 | 9-5355-165 | 1q43 | g430/RH50609/RH71064/SGC35584/ |
| 1640 | 9-5356-100 | 1q43 | g430/RH50609/RH71064/SGC35584/ |
| 1641 | 9-5360-151 | 1q43 | g430/RH50609/RH71064/SGC35584/ |
| 1642 | 9-5362-203 | 1q43 | g430/RH50609/RH71064/SGC35584/ |
| 1643 | 9-5364-95 | 1q43 | g430/RH50609/RH71064/SGC35584/ |
| 1644 | 9-5379-158 | 2p13 | g681/WI-9025/ |
| 1645 | 9-5386-85 | 2p13 | g681/WI-9025/ |
| 1654 | 9-5420-425 | 1q43 | g496/WI-20654/TWIK1/EST/RH50086/T89039/ |
| 1655 | 9-5427-466 | 1q43 | g496/WI-20654/TWIK1/EST/RH50086/T89039/ |
| 1656 | 9-5432-391 | 1q43 | g496/WI-20654/TWIK1/EST/RH50086/T89039/ |
| 1657 | 9-5433-45 | 1q43 | g496/WI-20654/TWIK1/EST/RH50086/T89039/ |
| 1658 | 9-5437-159 | 1q43 | g496/WI-20654/TWIK1/EST/RH50086/T89039/ |
| 1659 | 9-5438-70 | 1q43 | g496/WI-20654/TWIK1/EST/RH50086/T89039/ |
| 1660 | 9-5441-287 | 1q43 | g496/WI-20654/TWIK1/EST/RH50086/T89039/ |
| 1661 | 9-5446-303 | 1q43 | g496/WI-20654/TWIK1/EST/RH50086/T89039/ |
| 1662 | 9-5447-322 | 1q43 | g496/WI-20654/TWIK1/EST/RH50086/T89039/ |
| 1663 | 9-5458-203 | 2q32.3 | g2869/AFM280wd5/D2S342/ |
| 1664 | 9-5468-319 | 2q33.3–q34 | g1197/AFM074xg9/D2S307 g24934/SHGC-3548/Z23329/ |
| 1665 | 9-5472-290 | 2q34–q35 | g4057/AFMa082xc5/D2S2382 g680/D2S2606/XRCC5?/ |
| 1666 | 9-5475-455 | 2q34–q35 | g4057/AFMa082xc5/D2S2382 g680/D2S2606/XRCC5?/ |
| 1667 | 9-5477-207 | 2q34–q35 | g4057/AFMa082xc5/D2S2382 g680/D2S2606/XRCC5?/ |
| 1668 | 9-5485-325 | 2q34–q35 | g4057/AFMa082xc5/D2S2382 g680/D2S2606/XRCC5?/ |
| 1669 | 9-5490-368 | 2q34–q35 | g4057/AFMa082xc5/D2S2382 g680/D2S2606/XRCC5?/ |
| 1670 | 9-5494-205 | 2q34–q35 | g4057/AFMa082xc5/D2S2382 g680/D2S2606/XRCC5?/ |
| 1671 | 9-5502-433 | 2q34–q35 | g4057/AFMa082xc5/D2S2382 g680/D2S2606/XRCC5?/ |
| 1672 | 9-5505-226 | 2q33 | g19410/RH56788/H90757/SGC35219 g50057/RH67919 g733/WI-8988/D2S2634/G07066/ |
| 1673 | 9-5516-121 | 2q33 | g19410/RH56788/H90757/SGC35219 g50057/RH67919 g733/WI-8988/D2S2634/G07066/ |
| 1674 | 9-5526-334 | 2q33 | g19410/RH56788/H90757/SGC35219 g50057/RH67919 g733/WI-8988/D2S2634/G07066/ |
| 1675 | 9-5566-131 | 2q33 | g675/RH18054/ |
| 1676 | 9-5582-71 | 2q34–q35 | g19417/RH56312/R44983/SGC31824 g646/RH56681/SGC33209/R02572 g647/D2S2635 g887/WI-10220/EST135001/T72644/ |
| 1677 | 9-5590-99 | 2q34–q35 | g19417/RH56312/R44983/SGC31824 g646/RH56681/SGC33209/R02572 g647/D2S2635 g887/WI-10220/EST135001/T72644/ |
| 1678 | 9-5595-380 | 2q34–q35 | g19417/RH56312/R44983/SGC31824 g646/RH56681/SGC33209/R02572 g647/D2S2635 g887/WI-10220/EST135001/T72644/ |
| 1679 | 9-5596-216 | 2q34–q35 | g19417/RH56312/R44983/SGC31824 g646/RH56681/SGC33209/R02572 g647/D2S2635 g887/WI-10220/EST135001/T72644/ |
| 1680 | 9-5604-376 | 2q34–q35 | g19417/RH56312/R44983/SGC31824 g646/RH56681/SGC33209/R02572 g647/D2S2635 g887/WI-10220/EST135001/T72644/ |
| 1681 | 9-5608-324 | 2q34–q35 | g19417/RH56312/R44983/SGC31824 g646/RH56681/SGC33209/R02572 g647/D2S2635 g887/WI-10220/EST135001/T72644/ |
| 1753 | 9-6131-166 | 2q33 | g4971/AFMa285zb9/D2S2214 g4987/AFMa289xc1/D2S2217/ |
| 1754 | 9-6135-319 | 2q33 | g4971/AFMa285zb9/D2S2214 g4987/AFMa289xc1/D2S2217/ |
| 1756 | 9-6141-339 | 2q33 | g4971/AFMa285zb9/D2S2214 g4987/AFMa289xc1/D2S2217/ |
| 1759 | 9-6176-96 | 2q33.3–q34 | g1197/AFM074xg9/D2S307 g24934/SHGC-3548/Z23329/ |

TABLE 9-continued

| SEQ ID No. | Marker Name | Chromosomal Localization | Adjacent STS (including aliases) |
|---|---|---|---|
| 1760 | 9-6180-389 | 2q33.3–q34 | g1197/AFM074xg9/D2S307 g24934/SHGC-3548/Z23329/ |
| 1761 | 9-6181-328 | 2q33.3–q34 | g1197/AFM074xg9/D2S307 g24934/SHGC-3548/Z23329/ |
| 1762 | 9-6189-224 | 2p13 | g681/WI-9025/ |
| 1764 | 9-6191-252 | 2p13 | g681/WI-9025/ |
| 1765 | 9-6193-88 | 2p13 | g681/WI-9025/ |
| 1767 | 9-6217-420 | 2q32.3 | g2869/AFM280wd5/D2S342/ |
| 1769 | 9-6253-308 | 1q42.3–q43 | g498/WI-21544/EST/RH50234/R54815/ |
| 1770 | 9-6257-226 | 1q42.3–q43 | g498/WI-21544/EST/RH50234/R54815/ |
| 1771 | 9-6261-172 | 1q42.3–q43 | g498/WI-21544/EST/RH50234/R54815/ |
| 1772 | 9-6278-391 | 2q35 | g2382/AFM234xb8/D2S164 g5267/AFMb009zd5/D2S2248/ |
| 1773 | 9-6294-184 | 2q35 | g2382/AFM234xb8/D2S164 g5267/AFMb009zd5/D2S2248/ |
| 1774 | 9-6298-280 | 2q35 | g2382/AFM234xb8/D2S164 g5267/AFMb009zd5/D2S2248/ |
| 1775 | 9-6300-106 | 2q35 | g2382/AFM234xb8/D2S164 g5267/AFMb009zd5/D2S2248/ |
| 1776 | 9-6310-217 | 1q42.3–q43 | g498/WI-21544/EST/RH50234/R54815/ |
| 1782 | 9-6404-147 | 9q34.2 | g2548/AFM248wf1/D9S179 g26813/SHGC-3659/Z17118/ |
| 1783 | 9-6409-62 | 9q34.2 | g2548/AFM248wf1/D9S179 g26813/SHGC-3659/Z17118/ |
| 1784 | 9-6411-93 | 9q34.2 | g2548/AFM248wf1/D9S179 g26813/SHGC3659/Z17118/ |
| 1785 | 9-6413-369 | 9q34.2 | g2548/AFM248wf1/D9S179 g26813/SHGC-3659/Z17118/ |
| 1881 | 9-7098-382 | 11q23.3–q24 | g2274/AFM220xh6/D11S924 g5211/AFMa357wa5/D11S4129 g5947/AFMb342ze9/D11S4171/ |
| 1882 | 9-7103-155 | 11q23.3–q24 | g2274/AFM220xh6/D11S924 g5211/AFMa357wa5/D11S4129 g5947/AFMb342ze9/D11S4171/ |
| 1883 | 9-7104-187 | 11q23.3–q24 | g2274/AFM220xh6/D11S924 g5211/AFMa357wa5/D11S4129 g5947/AFMb342ze9/D11S4171/ |
| 1884 | 9-7107-143 | 11q23.3–q24 | g2274/AFM220xh6/D11S924 g5211/AFMa357wa5/D11S4129 g5947/AFMb342ze9/D11S4171/ |
| 1885 | 9-7114-31 | 11q23.3–q24 | g2274/AFM220xh6/D11S924 g5211/AFMa357wa5/D11S4129 g5947/AFMb342ze9/D11S4171/ |
| 1886 | 9-719-278 | 10q25.3–q26.1 | g5771/AFMb320zb5/D10S1722/ |
| 1892 | 9-7141-395 | 8p21 | g12037/WI-12748/RH62389/G13379/HSC2SC022/ |
| 1895 | 9-7167-438 | 1q43–q44 | g1317/AFM102xe3/D1S204 g5995/AFMb349xb9/D1S2785/ |
| 1896 | 9-7172-441 | 1q43–q44 | g1317/AFM102xe3/D1S204 g5995/AFMb349xb9/D1S2785/ |
| 1897 | 9-7177-81 | 1q43 | g12003/WI-12648/EST332992/RH49763/RH63832/R92197/ |
| 1899 | 9-7183-338 | 1q43 | g12003/WI-12648/EST332992/RH49763/RH63832/R92197/ |
| 1900 | 9-7193-228 | 1q43 | g12003/WI-12648/EST332992/RH49763/RH63832/R92197/ |
| 1902 | 9-7212-346 | 1q43 | g12003/WI-12648/EST332992/RH49763/RH63832/R92197/ |
| 1903 | 9-7214-109 | 8p21 | g12037/WI-12748/RH62389/G13379/HSC25C022/ |
| 1904 | 9-7218-444 | 8p21 | g12037/WI-12748/RH62389/G13379/HSC25C022/ |
| 1905 | 9-7234-101 | 11q23–q24 | g11907/WI-112357/EST142002/RH51673/T79639 g5745/AFMb318z19/D11S4157/ |
| 1907 | 9-7252-279 | 11q23.3 | g4523/AFMa162wf5/D11S4089/ |
| 1962 | 9-7671-33 | 11q24 | g5238/AFMb004z19/D11S4132/ |
| 1963 | 9-7677-107 | 11q24 | g5238/AFMb004z19/D11S4132/ |
| 1964 | 9-7688-325 | 11q23.3–q24 | g2707/AFM265wa9/D11S1328/ |
| 1965 | 9-7692-340 | 11q23.3–q24 | g2707/AFM265wa9/D11S1328/ |
| 1967 | 9-7706-303 | 11q24 | g5443/AFMb066zg9/D11S4144/ |
| 1969 | 9-7710-318 | 12q14–q15 | g5395/AFMb043wd1/D12S1649/ |
| 1970 | 9-7712-176 | 12q14–q15 | g5395/AFMb043wd1/D12S1649/ |
| 1971 | 9-7721-379 | 12q14–q15 | g5395/AFMb043wd1/D12S1649/ |
| 1972 | 9-7727-65 | 14q13; 15q13–q14 | g6091/AFMb361yh9/D14S1034/ |
| 1973 | 9-7728-334 | 14q13; 15q13–q14 | g6091/AFMb361yh9/D14S1034/ |
| 1974 | 9-7732-122 | 14q13; 15q13–q14 | g6091/AFMb361yh9/D14S1034/ |

TABLE 9-continued

| SEQ ID No. | Marker Name | Chromosomal Localization | Adjacent STS (including aliases) |
|---|---|---|---|
| 1975 | 9-7737-264 | 2q32.1–q32.2 | g19365/RH56584/SGC31527 g19370/RH57027/R78360/SGC34224 g2101/AFM207xg1/D2S152/ |
| 1976 | 9-7744-255 | 2q32.1–q32.2 | g19365/RH56584/SGC31527 g19370/RH57027/R78360/SGC34224 g2101/AFM207xg1/D2S152/ |
| 1977 | 9-7745-305 | 2q32.1–q32.2 | g19365/RH56584/SGC31527 g19370/RH57027/R78360/SGC34224 g2101/AFM207xg1/D2S152/ |
| 1978 | 9-7749-123 | 2q32.1–q32.2 | g19365/RH56584/SGC31527 g19370/RH57027/R78360/SGC34224 g2101/AFM207xg1/D2S152/ |
| 1979 | 9-7751-450 | 2q33 | g5710/AFMb315xd5/D2S2287/ |
| 1980 | 9-7753-199 | 2q33 | g5710/AFMb315xd5/D2S2287/ |
| 1981 | 9-7754-119 | 2q33 | g5710/AFMb315xd5/D2S2287/ |
| 1982 | 9-7759-63 | 2q33 | g5710/AFMb315xd5/D2S2287/ |
| 1983 | 9-7762-227 | 2q33 | g5710/AFMb315xd5/D2S2287/ |
| 1984 | 9-7764-161 | 2q33 | g5710/AFMb315xd5/D2S2287/ |
| 1985 | 9-7775-313 | 14q32.2 | g27781/SHGC-1408/Z23999/ |
| 1986 | 9-7784-31 | 11q23.3–q24 | g2623/AFM256za5/D11S936 g3466/AFM331yc5/D11S1353/ |
| 1987 | 9-7789-404 | 11q23.3–q24 | g2623/AFM256za5/D11S936 g3466/AFM331yc5/D11S1353/ |
| 1988 | 9-7792-173 | 11q23.3–q24 | g2623/AFM256za5/D11S936 g3466/AFM331yc5/D11S1353/ |
| 1989 | 9-7796-130 | 2q32.3–q33 | g6130/AFMc005wb9/D2S2318/ |
| 1990 | 9-7803-253 | 2q32.3–q33 | g6130/AFMc005wb9/D2S2318/ |
| 1992 | 9-7840-281 | 2q31–q32.1 | g5604/AFMb297xc1/D2S2273/ |
| 1994 | 9-7868-204 | 2q34–q35 | g2794/AFM273va9/D2S334/ |
| 1995 | 9-7869-135 | 2q34–q35 | g2794/AFM273va9/D2S334/ |
| 1996 | 9-7870-316 | 2q34–q35 | g2794/AFM273va9/D2S334/ |
| 1997 | 9-7877-363 | 2q34–q35 | g2794/AFM273va9/D2S334/ |
| 1998 | 9-7882-43 | 2q35 | g2211/AFM214ye1/D2S301/ |
| 1999 | 9-7883-411 | 2q35 | g2211/AFM214ye1/D2S301/ |
| 2000 | 9-7884-151 | 2q35 | g2211/AFM214ye1/D2S301/ |
| 2001 | 9-7893-226 | 2q35 | g2211/AFM214ye1/D2S301/ |
| 2002 | 9-7898-43 | 2q33–q34 | g3773/AFMa050ya5/D2S2358/ |
| 2003 | 9-7900-452 | 2q33–q34 | g3773/AFMa050ya5/D2S2358/ |
| 2005 | 9-7917-429 | 2q33–q34 | g3773/AFMa050ya5/D2S2358/ |
| 2024 | 9-806-152 | 13p13–q11; 14p13–q11.1; 15p13–q11.1; 1p11–q12; 21p13; 22p13–q11.1; 9p11–q12 | g7719/D21S1277/ |
| 2033 | 9-810-117 | 13p13–q11; 14p13–q11.1; 15p13–q12; 21p13; 22p13–q11.1; 9p11–q12 | g7719/D21S1277/ |
| 2087 | 9-8453-358 | 2q32.2 | g5488/AFMb082ye1/D2S2262/ |
| 2088 | 9-8454-152 | 2q32.2 | g5488/AFMb082ye1/D2S2262/ |
| 2089 | 9-8456-266 | 2q32.2 | g5488/AFMb082ye1/D2S2262/ |
| 2090 | 9-8457-239 | 2q32.2 | g5488/AFMb082ye1/D2S2262/ |
| 2091 | 9-8470-275 | 2q32.2 | g5488/AFMb082ye1/D2S2262/ |
| 2092 | 9-8472-152 | 2q32.2 | g5488/AFMb082ye1/D2S2262/ |
| 2093 | 9-8476-216 | 2q34 | g2193/AFM212ze9/D2S157/ |
| 2094 | 9-8478-385 | 2q34 | g2193/AFM212ze9/D2S157/ |
| 2095 | 9-8487-245 | 2q34 | g2193/AFM212ze9/D2S157/ |
| 2096 | 9-8491-339 | 2q34 | g2193/AFM212ze9/D2S157/ |
| 2097 | 9-8499-107 | 2q34 | g2193/AFM212ze9/D2S157/ |
| 2098 | 9-8505-269 | 2q36 | g643/T95608/SGC33785/EST165729/RH56667 g676/WI-11020/R36533/ |
| 2100 | 9-8510-44 | 2q36 | g643/T95608/SGC33785/EST165729/RH56667 g676/WI-11020/R36533/ |
| 2101 | 9-8514-434 | 2q36 | g643/T95608/SGC33785/EST165729/RH56667 g676/WI-11020/R36533/ |
| 2102 | 9-8530-209 | 2q36 | g643/T95608/SGC33785/EST165729/RH56667 g676/WI-11020/R36533/ |
| 2110 | 9-8583-146 | 14q13 | g3541/AFM340zd9/D14S1049/ |
| 2111 | 9-8588-369 | 14q13 | g3541/AFM340zd9/D14S1049/ |
| 2112 | 9-8590-287 | 14q13 | g3541/AFM340zd9/D14S1049/ |
| 2196 | 9-921-285 | 13q31.1 | g14575/D13S1196/MR8039 g8824/D13S1196/WI5275/ |

TABLE 9-continued

| SEQ ID No. | Marker Name | Chromosomal Localization | Adjacent STS (including aliases) |
|---|---|---|---|
| 2197 | 9-924-93 | 13q31.1 | g14575/D13S1196/MR8039 g8824/D13S1196/WI5275/ |
| 2200 | 9-9254-404 | 2q33.3 | g1909/AFM199yf2/D2S2237/ |
| 2201 | 9-926-98 | 13q31.1 | g14575/D13S1196/MR8039 g8824/D13S1196/WI5275/ |
| 2202 | 9-9263-283 | 2q33.3 | g1909/AFM199yf2/D2S2237/ |
| 2203 | 9-9271-70 | 2q33.3 | g1909/AFM199yf2/D2S2237/ |
| 2204 | 9-9274-246 | 2q33.3 | g1909/AFM199yf2/D2S2237/ |
| 2205 | 9-9276-163 | 2q33.3 | g1909/AFM199yf2/D2S2237/ |
| 2208 | 9-937-125 | 13q31.1 | g14575/D13S1196/MR8039 g8824/D13S1196/WI5275/ |
| 2218 | 9-941-265 | 13q31.1 | g14575/D13S1196/MR8039 g8824/D13S1196/WI5275/ |
| 2222 | 9-942-381 | 13q31.1 | g14575/D13S1196/MR8039 g8824/D13S1196/WI5275/ |
| 2233 | 9-949-214 | 13q31.1 | g14575/D13S1196/MR8039 g8824/D13S1196/WI5275/ |
| 2237 | 9-950-418 | 13q31.3 | g2255/AFM218yf10/D13S265 g8812/WI10332/ |
| 2239 | 9-952-252 | 13q31.3 | g2255/AFM218yf10/D13S265 g8812/WI10332/ |
| 2243 | 9-954-45 | 13q31.3 | g2255/AFM218yf10/D13S265 g8812/WI10332/ |
| 2253 | 9-958-92 | 13q31.3 | g2255/AFM218yf10/D13S265 g8812/WI10332/ |
| 2255 | 9-961-150 | 13q31.3 | g2255/AFM218yf10/D13S265 g8812/WI10332/ |
| 2256 | 9-963-395 | 13q22.3–q31.1 | g2243/AFM218xd12/D13S264 g2474/AFM240wh2/D13S170/ |
| 2257 | 9-965-165 | 13q22.3–q31.1 | g2243/AFM218xd12/D13S264 g2474/AFM240wh2/D13S170/ |
| 2258 | 9-967-306 | 13q22.3–q31.1 | g2243/AFM218xd12/D13S264 g2474/AFM240wh2/D13S170/ |
| 2259 | 9-976-246 | 13q22.3–q31.1 | g2243/AFM218xd12/D13S264 g2474/AFM240wh2/D13S170/ |
| 2260 | 9-979-343 | 13q22.3–q31.1 | g2243/AFM218xd12/D13S264 g2474/AFM240wh2/D13S170/ |
| 2420 | 9-1091-446 | 21q22.1–q22.2 | g7006/D21S211 g7724/D21S1283/ |
| 2445 | 9-1105-127 | 13p13–q11; 14p13–q11.1; 15p13–q12; 21p13–q11.1; 22p13–q11.1; 3p11–q11.2; 4p11–q11; 9p11–q12 | g9370/AFMG51E07/G51E07/ |
| 2585 | 9-1202-340 | 21q22.3 | g7781/D21S1684 g7882/D21S1859 g7889/D21S1868 g7893/D21S1871 g7897/D21S1875/ |
| 2587 | 9-1203-272 | 21q22.3 | g7781/D21S1684 g7882/D21S1859 g7889/D21S1868 g7893/D21S1871 g7897/D21S1875/ |
| 2597 | 9-1211-59 | 21q22.3 | g7781/D21S1684 g7882/D21S1859 g7889/D21S1868 g7893/D21S1871 g7897/D21S1875/ |
| 2655 | 9-12965-451 | 5q32 | g1840/AFM196xc7/D5S479/ |
| 2656 | 9-12969-128 | 5q32 | g1840/AFM196xc7/D5S479/ |
| 2657 | 9-12970-339 | 5q32 | g1840/AFM196xc7/D5S479/ |
| 2658 | 9-12973-162 | 5q32 | g1840/AFM196xc7/D5S479/ |
| 2675 | 9-1370-401 | 1q43 | g401/D1S2483/G04024 g428/EST386335/R1150010/SGC35175/ |
| 2706 | 9-14944-119 | 5q30.1–q31.2 | g1446/AFM127xh4/D5S4021 |
| 2707 | 9-14949-472 | 5q31.1–q31.2 | g1446/AFM127xh4/D5S4021 |
| 2708 | 9-15000-259 | 1q42.3–q43 | g427/AFMa111yd5/Z67285/ |
| 2717 | 9-15653-359 | Xp21.3–p21.2 | g3025/AFM292wb9/DXS1218/ |
| 2718 | 9-15654-122 | Xp21.3–p21.2 | g3025/AFM292wb9/DXS1218/ |

TABLE 9-continued

| SEQ ID No. | Marker Name | Chromosomal Localization | Adjacent STS (including aliases) |
|---|---|---|---|
| 2721 | 9-1591-235 | 1q43 | g1262/AFM088xe5/D1S2850 |
| | | | g17846/RH12368/stSG3536 |
| | | | g18893/RH34172/L18266/SHGC-4752 |
| | | | g307/WI-11654/RH50099/RH63795/R10130 |
| | | | g317/EST382595/RH49984/SGC34592 |
| | | | g402/D1S1680/G09467 |
| | | | g421/WI-12850/RH50542/Z41492 |
| | | | g4882/AFMa245wd5/D1S2678 |
| | | | g4901/AFMa247wg9/D1S2680/ |
| 2725 | 9-16026-359 | 5q31.3–q32 | g1166/AFM066xf11/D5S396 |
| | | | g20471/RH60098/WI-10312/ |
| 2726 | 9-1624-377 | 1q43 | g2259/AFM218zb6/D1S321/ |
| 2771 | 9-18122-403 | 20p12 | g1846/AFM197xb12/D20S112/ |
| 2772 | 9-18126-160 | 20p12 | g1846/AFM197xb12/D20S112/ |
| 2773 | 9-18127-283 | 20p12 | g1846/AFM197xb12/D20S112/ |
| 2774 | 9-18141-152 | 17p12 | g1854/AFM197xh6/D17S9221 |
| 2778 | 9-18334-485 | 2q35 | g11465/WI-11020/EST206594/WI-11020/RH56985/R36533 |
| | | | g24950/SHGC-6253/G02482 |
| | | | g891/EST165729/SGC33785/T95608 |
| | | | g892/RH56759/NIB1635/T16652 |
| | | | g893/WI-11020/EST206594/R36533 |
| | | | g894/WI-14333/EST228327/RH57030/R44333 |
| | | | g896/WI-22153/RH56193/ |
| 2784 | 9-18645-309 | 2q34–q35 | g2044/AFM205yb4/D2S295/ |
| 2785 | 9-18696-213 | 17q12 | g23714/RH55113/G04954/WI-5770/ |
| 2786 | 9-18698-346 | 11q23–q24 | g4760/AFMa222xc5/D11S4104/ |
| 2787 | 9-18710-208 | 17q23–q24 | g1684/AFM168xd12/D17S794/ |
| 2788 | 9-18717-319 | 17q23–q24 | g1684/AFM168xd12/D17S794/ |
| 2789 | 9-18718-362 | 17q23–q24 | g1684/AFM168xd12/D17S794/ |
| 2793 | 9-18944-242 | 6p21.2–p21.1 | g10052/AFM165YD12/ |
| 2794 | 9-19023-347 | 6p21.2–p21.1 | g10052/AFM165YD12/ |
| 2795 | 9-19027-222 | 6p21.2–p21.1 | g10052/AFM165YD12/ |
| 2796 | 9-19033-208 | 17p13 | g23660/RH54938/G05471/WI-9926/ |
| 2839 | 9-19324-214 | 5q32 | g11857/WI-12096/EST115160/WI-12096/RH59849/T61077 |
| | | | g20484/RH60414/H11651/SGC32445 |
| | | | g2482/AFM240xg3/D5S500 |
| | | | g653/WI-12096/T61077/ |
| 2840 | 9-19330-274 | 5q32 | g11857/WI-12096/EST115160/WI-12096/RH59849/T61077 |
| | | | g20484/RH60414/H11651/SGC32445 |
| | | | g2482/AFM240xg3/D5S500 |
| | | | 245 |
| | | | g653/WI-12096/T61077/ |
| 2946 | 9-20226-32 | 6p22.3 | g26006/SHGC-13860/T55234/ |
| 2947 | 9-20228-290 | 6p22.3 | g26006/SHGC-13860/T55234/ |
| 2948 | 9-20234-101 | 6p22.3 | g26006/SHGC-13860/T55234/ |
| 2953 | 9-20958-373 | 22q12.3–q13.1 | g24314/RH57665/T87617/WI-20641/ |
| 2954 | 9-21057-337 | 21q22.3 | g1183/AFM071xa1/D21S1912 |
| | | | g7874/D21S1851 |
| | | | g7918/D21S1930/ |
| 2955 | 9-21059-118 | 21q22.3 | g1183/AFM071xa1/D21S1912 |
| | | | g7874/D21S1851 |
| | | | g7918/D21S1930/ |
| 2961 | 9-21227-295 | 3p24.3–p25.1 | g24997/D3S4113/ |
| 3074 | 9-22202-58 | 11q22.3–q23.1 | g22439/RH51746/WI-14282/ |
| 3075 | 9-22204-391 | 11q22.3–q23.1 | g22439/RH51746/WI-14282/ |
| 3076 | 9-22206-455 | 11q22.3–q23.1 | g22439/RH51746/WI-14282/ |
| 3082 | 9-2251-151 | 21q22.1 | g7689/D21S1230/ |
| 3083 | 9-22530-48 | 6p22.1–p21.3 | g1070/AFM031yh12/D6S258/ |
| 3084 | 9-22537-280 | 6p22.1–p21.3 | g1070/AFM031yh12/D6S258/ |
| 3085 | 9-22567-243 | 14q24.3–q31 | g23143/RH53688/G04281/WI-3377 |
| | | | g27731/D14S929/ |
| 3086 | 9-22572-72 | 14q24.3–q31 | g23143/RH53688/G04281/WI-3377 |
| | | | g27731/D14S929/ |
| 3089 | 9-22729-352 | 2q35 | g19425/RH56275/H62242/SGC32398/RH56275/ |
| 3090 | 9-22768-113 | 2q35 | g24953/SHGC-971/Z17049 |
| | | | g4193/AFMa109wg5/D2S2151/ |
| 3091 | 9-22814-349 | 21q21.1 | g7005/D21S172 |
| | | | g7814/D21S1721E/ |
| 3092 | 9-22818-33 | 21q21.1 | g7005/D21S172 |
| | | | g7814/D21S1721E/ |
| 3093 | 9-22826-311 | 21q21.1 | g7005/D21S172 |
| | | | g7814/D21S1721E/ |

TABLE 9-continued

| SEQ ID No. | Marker Name | Chromosomal Localization | Adjacent STS (including aliases) |
|---|---|---|---|
| 3095 | 9-23113-388 | 22q12;2p23 | g19151/RH57021/R95095/SGC33508 g19152/RH56155/WI-10842/ |
| 3102 | 9-2333-423 | 21q22.1 | g7774/D21S1677 g7876/D21S1853 g7877/D21S1854 g7886/D21S1865 g7887/D21S1866/ |
| 3103 | 9-2341-485 | 21q22.1 | g7774/D21S1677 g7876/D21S1853 g7877/D21S1854 g7886/D21S1865 g7887/D21S1866/ |
| 3104 | 9-2342-217 | 21q22.1 | g7774/D21S1677 g7876/D21S1853 g7877/D21S1854 g7886/D21S1865 g7887/D21S1866/ |
| 3105 | 9-23427-283 | Xp11.22–p11.21 | g4806/AFMa230vc1/DXS8032/ |
| 3116 | 9-23696-164 | 5q31.2 | g1948/AFM200ya9/D5S414 g20384/AFM240yf6 g25905/SHGC-11406/T50434 g25906/SHGC-893/Z16886/ |
| 3117 | 9-23701-104 | 5q31.2 | g1948/AFM200ya9/D5S414 g20384/AFM240yf6 g25905/SHGC-11406/T50434 g25906/SHGC-893/Z16886/ |
| 3118 | 9-23702-437 | 5q31.2 | g1948/AFM200ya9/D5S414 g20384/AFM240yf6 g25905/SHGC-11406/T50434 g25906/SHGC-893/Z16886/ |
| 3119 | 9-2371-93 | 21q22.1 | g7798/D21S1700 g7879/D21S1856/ |
| 3120 | 9-23711-455 | 15q23 | g27865/D15S1242/ |
| 3121 | 9-23730-202 | 15q23 | g27865/D15S1242/ |
| 3188 | 9-24369-263 | 7q11.23–q21.1 | g11961/WI-12513/EST25131/RH61608/R74459/ |
| 3189 | 9-24397-315 | 11q22.3–q23.1 | g15763/WI-30893/RH52168/ |
| 3190 | 9-24408-202 | 14q24.3 | g23123/RH53961/T40920/SGC32981/SHGC-32981/ G27696/G25597/EST91724 g27725/SHGC-942/Z16981/RH49039/ |
| 3192 | 9-24412-279 | 1q24–q25 | g18536/RH26850/Z38322/ |
| 3193 | 9-24415-85 | 1q24–q25 | g18536/RH26850/Z38322/ |
| 3194 | 9-24470-168 | Xq22.2 | g24379/RH63325/G04441/WI-3796/ |
| 3195 | 9-24472-179 | Xq22.2 | g24379/RH63325/G04441/WI-3796/ |
| 3196 | 9-24480-44 | Xq22.2 | g24379/RH63325/G04441/WI-3796/ |
| 3197 | 9-24485-55 | Xp22.1 | g24364/RH63434/R59327/SGC31861/ |
| 3198 | 9-24490-363 | Xp22.1 | g24364/RH63434/R59327/SGC31861/ |
| 3199 | 9-24492-351 | Xp22.1 | g24364/RH63434/R59327/SGC31861/ |
| 3200 | 9-24581-253 | 22q11.2–q12 | g24283/RH57762/R54799/WI-21996 g24289/RH57833/G03738/WI-373/ |
| 3201 | 9-24591-33 | 22q11.2–q12 | g24283/RH57762/R54799/WI-21996 g24289/RH57833/G03738/WI-373/ |
| 3202 | 9-24592-55 | 4q26–q27 | g20097/RH59095/H50674/WI-18054/ |
| 3203 | 9-24745-413 | 11q23.1–q23.2 | g15768 g22459/RH52046/H86791/SGC31226/ |
| 3204 | 9-24753-182 | 11q23.1–q23.2 | g15768 g22459/RH52046/H86791/SGC31226/ |
| 3205 | 9-24768-233 | 22q13 | g775/stSG5976/RH27889/ |
| 3220 | 9-25362-247 | 17q12–q21 | g2174/AFM211zd12/D17S1842/ |
| 3223 | 9-25446-121 | 15q14 | g15961/WI-7216/RH54415/G06453/G00-679-062/ UTR-03037/M99564/ |
| 3224 | 9-25496-221 | 2q37.1 | g19470/RH56828/T54332/SGC33096 g24961/SHGC-1072/Z17274/RH13453/ |
| 3225 | 9-25497-242 | 21q22.2 g16433 | g16433 g24246/RH57580/SGC32448 g28577/SHGC-10474 g28580/SHGC-10477 g7818/D21S1725E/ |
| 3226 | 9-2559-253 | 21q22.3 g24258 | g24258/RH57551/R48588/SGC34143 g24259/RH57619/H53556/SGC34732/ |
| 3228 | 9-2566-112 | 21q22.3 g24258 | g24258/RH57551/R48588/SGC34143 g24259/RH57619/H53556/SGC34732/ |
| 3229 | 9-2567-329 | 21q22.3 g24258 | G24258/RH57551/R48588/SGC34143 g24259/RH57619/H53556/SGC34732/ |
| 3230 | 9-2571-242 | 21q22.3 g24258 | g24258/RH57551/R48588/SGC34143 g24259/RH57619/H53556/SGC34732/ |
| 3235 | 9-26051-273 | 10p12.1–p11.2 | g21912/RH51110/SGC31510/WICGR/ |

TABLE 9-continued

| SEQ ID No. | Marker Name | Chromosomal Localization | Adjacent STS (including aliases) |
|---|---|---|---|
| 3236 | 9-26058-275 | 19q13.1 g3203 | g3203/AFM304zg1/D19S417/ |
| 3237 | 9-26074-400 | 6p22 | g13490/WI-17546/EST261382/RH61086 g20682/RH60603/R26060/WI-11794/RH37391/ |
| 3238 | 9-26076-376 | 6p22 | g13490/WI-17546/EST261382/RH61086 g20682/RH60603/R26060/WI-11794/RH37391/ |
| 3239 | 9-2630-67 | 21q22.2 g16433 | g16433 g24246/RH57580/SGC32448 g28577/SHGC-10474 g28580/SHGC-10477 g7818/D21S1725E/ |
| 3240 | 9-2633-129 | 21q22.2 g16433 | g16433 g24246/RH57580/SGC32448 g28577/SHGC-10474 g28580/SHGC-10477 g7818/D21S1725E/ |
| 3241 | 9-2634-341 | 21q22.2 g16433 | g16433 g24246/RH57580/SGC32448 g28577/SRGC-10474 g28580/SHGC-10477 g7818/D21S1725E/ |
| 3242 | 9-2636-64 | 21q22.2 g16433 | g16433 g24246/RH57580/SGC32448 g28577/SHGC-10474 g28580/SHGC-10477 g7818/D21S1725E/ |
| 3243 | 9-2642-255 | 21q22.2 g16433 | g16433 g24246/RH57580/SGC32448 g28577/SRGC-10474 g28580/SRGC-10477 g7818/D21S1725E/ |
| 3244 | 9-2645-118 | 21q22.1 g2908 | g2908/AFM283xh9/D21S1255 g7915/D21S1928/ |
| 3245 | 9-2647-368 | 21q22.1 g2908 | g2908/AFM283xh9/D21S1255 g7915/D21S1928/ |
| 3246 | 9-2649-107 | 21q22.1 g2908 | g2908/AFM283xh9/D21S1255 g7915/D21S1928/ |
| 3493 | 9-4534-158 | 15q14–q15 | g15965/WI-11934/EST197813/RH54176/R27768 g15966/WI-19599/ |
| 3497 | 9-4589-169 | 1q43 | g314/WI-10464/ |
| 3502 | 9-468-271 | 10p11.2 g2598 | g2598/AFM254xb1/D10S224/ |
| 3527 | 9-4903-395 | 21q21.1 g7005 | g7005/D21S172 g7814/D21S1721E/ |
| 3528 | 9-499-294 | 10p12.1–p11.2 | g4171/AFMa106vf5/D10S1639/ |
| 3532 | 9-5098-29 | 7q11.23–q21.1 | g2935/AFM286xf9/D7S669/ |
| 3534 | 9-5112-188 | 7q11.23–q21.1 | g2935/AFM286xf9/D7S669/ |
| 3545 | 9-5549-289 | 2q33 | g675/RH18054/ |
| 3546 | 9-5569-237 | 2q33 | g675/RH18054/ |
| 3547 | 9-5575-330 | 2q34–q35 | g19417/RH56312/R44983/SGC31824 g646/RH56681/SGC33209/R02572 g647/D2S2635 g887/WI-10220/EST135001/T72644/ |
| 3548 | 9-5602-372 | 2q34–q35 | g19417/RH56312/R44983/SGC31824 g646/RH56681/SGC33209/R02572 g647/D2S2635 g887/WI-10220/EST135001/T72644/ |
| 3550 | 9-568-101 | 21q22.1–q22.2 | g2421/AFM238wc3/D21S267 g28563/SHGC-3796/Z17065/ |
| 3577 | 9-6401-64 | 9q34.2 | g2548/AFM248wf1/D9S179 g26813/SHGC-3659/Z17118/ |
| 3603 | 9-7117-266 | 10q25.3–q26.1 | g5771/AFMb320zb5/D10S1722/ |
| 3604 | 9-7203-286 | 1q43 | g12003/WI-12648/EST332992/RH49763/RH63832/R92197/ |
| 3617 | 9-7696-215 | 11q24 | g5443/AFMb066zg9/D11S4144/ |
| 3618 | 9-7702-225 | 11q24 | g5443/AFMb066zg9/D11S4144/ |
| 3619 | 9-7772-185 | 14q32.2 g27781 | g27781/SHGC-1408/Z23999/ |
| 3622 | 9-7860-320 | 2q34–q35 | g2794/AFM273va9/D2S334/ |
| 3623 | 9-7886-350 | 2q35 | g2211/AFM214ye1/D2S301/ |
| 3663 | 9-9316-399 | 2q34–q35 | g12748/WI-15052/EST283445/RH56222 g19413/AFMb299wb5/ |
| 3689 | 9-974-231 | 13q22.3–q31.1 | g2243/AFM218xd12/D13S264 g2474/AFM240wh2/D13S170/ |

TABLE 9-continued

| SEQ ID No. | Marker Name | Chromosomal Localization | Adjacent STS (including aliases) |
|---|---|---|---|
| 3782 | 9-13794-147 | 1q43 | g1262/AFM088xe5/D1S2850<br>g17846/RH12368/stSG3536<br>g18893/RH34172/L18266/SHGC-4752<br>g307/WI-11654/RH50099/RH63795/R10130<br>g317/EST382595/RH49984/SGC34592<br>g402/D1S1680/G09467<br>g421/WI-12850/RH50542/Z41492<br>g4882/AFMa245wd5/D1S2678<br>g4901/AFMa247wg9/D1S2680/ |
| 3788 | 9-19032-132 | 17p13 | g23660/RH54938/G05471/WI-9926/ |
| 3794 | 9-21051-435 | 21q22.3 g1183 | g1183/AFM071xa1/D21S1912<br>g7874/D21S1851<br>g7918/D21S1930/ |
| 3817 | 9-22679-148 | 18p11.31 | g23841/RH55516/G03618/WI-4219/ |
| 3818 | 9-23095-184 | 1q21–q22 | g17211/RH75/D19615/ |
| 3819 | 9-23370-249 | 2q35 | g16359/WI-19704/ |
| 3830 | 9-24267-190 | 2q33–q34 | g2141/AFM210yf10/D2S155/ |
| 3832 | 9-253-97 | 21q22.1 g24236 | g24236/RH57620/H16797/SGC32169<br>g2978/AFM289xh1/D21S1910/ |
| 3889 | 9-5605-90 | 2q34–q35 | g19417/RH56312/R44983/SGC31824<br>g646/RH56681/SGC33209/R02572<br>g647/D2S2635<br>g887/WI-10220/EST135001/T726441 |
| 3896 | 9-7215-279 | 8p21 | g12037/WI-12748/RH62389/G13379/HSC25C022/ |
| 3909 | 9-344-439 | 19q13.2–q13.3 | g448/RH11470/RH1669/ |
| 3910 | 9-366-274 | 19q13.2–q13.3 | g448/RH11470/RH1669/ |
| 3911 | 9-359-308 | 19q13.2–q13.3 | g448/RH11470/RH1669/ |
| 3912 | 9-355-219 | 19q13.2–q13.3 | g448/RH11470/RH1669/ |
| 3913 | 9-365-344 | 19q13.2–q13.3 | g448/RH11470/RH1669/ |

TABLE 10

| SEQ ID No. | Marker Name | Chromosomal Localization | Adjacent STS |
|---|---|---|---|
| 232 | 99-13647-278 | 11q12 | g403/WI-7199/RH49904/M30269<br>g406/AFM093XG5/Z66633<br>g416/D1S3481/G13394<br>g496/WI-20654/TWIK1/EST/RH50086/T89039/ |
| 233 | 99-13652-407 | 11q12 | g403/WI-7199/RH49904/M30269<br>g406/AFM093XGS/Z66633<br>g416/D1S3481/G13394<br>g496/WI-20654/TWIK1/EST/RH50086/T89039/ |
| 234 | 99-13663-218 | 11q12 | g403/WI-7199/RH49904/M30269<br>g406/AFM093XG5/Z66633<br>g416/D1S3481/G13394<br>g496/WI-20654/TWIK1/EST/RH50086/T89039/ |
| 235 | 99-13666-275 | 11q12 | g403/WI-7199/RH49904/M30269<br>g406/AFM093XGS/Z66633<br>g416/D1S3481/G13394<br>g496/WI-20654/TWIK1/EST/RH50086/T89039/ |
| 237 | 99-13671-396 | 11q12 | g403/WI-7199/RH49904/M30269<br>g406/AFM093XG5/Z66633<br>g416/D1S3481/G13394<br>g496/WI-20654/TWIK1/EST/RH50086/T89039/ |
| 322 | 99-1423-361 | 2p15-p14 | g411/AFMa045xa9/ |
| 326 | 99-1426-185 | 2p15-p14 | g411/AFMa045xa9/ |
| 517 | 99-15072-64 | 2q32-q33 | g27160/RH11834/ |
| 518 | 99-15087-77 | 2q32-q33 | g27160/RH11834/ |
| 550 | 99-1533-471 | 2p15-p14 | g411/AFMa045xa9/ |
| 555 | 99-1535-241 | 2p15-p14 | g411/AFMa045xa9/ |
| 556 | 99-1537-243 | 2p15-p14 | g411/AFMa045xa9/ |
| 592 | 99-15595-41 | 2q32.1-q32.2 | g313/D1S3401/G04332/ |
| 593 | 99-15596-64 | 2q32.1-q32.2 | g313/D1S3401/G04332/ |
| 594 | 99-15599-252 | 2q32.1-q32.2 | g313/D1S3401/G04332/ |
| 595 | 99-15605-221 | 2q32.1-q32.2 | g313/D1S3401/G04332/ |
| 596 | 99-15606-326 | 2q32.1-q32.2 | g313/D1S3401/G04332/ |
| 604 | 99-15705-110 | 15q23-q24 | g1484/AFM143xd12/D25128/ |
| 605 | 99-15717-120 | 15q23-q24 | g1484/AFM143xd12/D2S128/ |
| 606 | 99-15718-234 | 15q23-q24 | g1484/AFM143xd12/D2S128/ |
| 628 | 99-15891-215 | Xq26.3 | g8814/WI-14718/ |
| 699 | 99-16559-90 | | g2862/AFM278yd1/D6S444/ |
| 700 | 99-16562-182 | | g2862/AFM278yd1/D6S444/ |
| 701 | 99-16563-263 | | g2862/AFM278yd1/D6S444/ |
| 702 | 99-16564-118 | | g2862/AFM278yd1/D6S444/ |

TABLE 10-continued

| SEQ ID No. | Marker Name | Chromosomal Localization | Adjacent STS |
|---|---|---|---|
| 901 | 99-18085-94 | 3p23-p22 | g6189/AFMc013ye9/D4S3001/ |
| 902 | 99-18086-434 | 3p23-p22 | g6189/AFMc013ye9/D4S3001/ |
| 903 | 99-18087-152 | 3p23-p22 | g6189/AFMc013ye9/D4S3001/ |
| 923 | 99-18253-407 | | g22462/RH52139 g4351/AFMa130we1/D11S3178/ |
| 924 | 99-18255-259 | | g22462/RH52139 g4351/AFMa130we1/D11S3178/ |
| 929 | 99-18288-205 | | g4651/AFMa202zc1/D4S2923/ |
| 930 | 99-18289-36 | | g4651/AFMa202zc1/D4S2923/ |
| 932 | 99-18306-377 | | g10904/RH60078/ |
| 933 | 99-18307-371 | | g10904/RH60078/ |
| 934 | 99-18310-262 | | g10904/RH60078/ |
| 935 | 99-18312-58 | | g10904/RH60078/ |
| 964 | 99-18551-389 | | g1461/AFM136xd2/D5S403 g25942/SHGC-758/ |
| 967 | 99-18582-422 | | g10470/D5S1491 g22231/RH52188/ |
| 968 | 99-18588-175 | | g26653/SHGC-1005/Z17109 g3397/AFM324td5/D5S671/ |
| 969 | 99-18596-83 | | g26653/SHGC-1005/Z17109 g3397/AFM324td5/D5S671/ |
| 970 | 99-18597-415 | | g26653/SHGC-1005/Z17109 g3397/AFM324td5/D5S671/ |
| 971 | 99-18599-347 | | g26653/SHGC-1005/Z17109 g3397/AFM324td5/D5S671/ |
| 983 | 99-18666-483 | | g11811/WI-11885/ |
| 984 | 99-18667-392 | | g11811/WI-11885/ |
| 985 | 99-18669-223 | | g11811/WI-11885/ |
| 996 | 99-18751-217 | 1q22 | g8823/WI-4658/ |
| 997 | 99-18755-267 | 1q22 | g8823/WI-4658/ |
| 998 | 99-18774-69 | | g11451/D5S2428/10859/ |
| 999 | 99-18775-161 | | g11451/D5S2428/10859/ |
| 1000 | 99-18777-130 | | g11451/D5S2428/10859/ |
| 1001 | 99-18802-308 | | g13318/WI-16922/ |
| 1005 | 99-18822-368 | 6p21.1-p12 | g1552/AFM155ye1/D2S280/ |
| 1006 | 99-18826-378 | 6p21.1-p12 | g1552/AFM155ye1/D2S280/ |
| 1007 | 99-18827-92 | 6p21.1-p12 | g1552/AFM155ye1/D2S280/ |
| 1009 | 99-18847-263 | 6q24 | g2318/AFM224zf4/D2S161/ |
| 1010 | 99-18853-64 | | g13318/WI-16922/ |
| 1011 | 99-18855-173 | | g13318/WI-16922/ |
| 1012 | 99-18860-308 | | g13318/WI-16922/ |
| 1024 | 99-19008-237 | | g3339/AFM319zf9/D2S377/ |
| 1025 | 99-19013-384 | | g3339/AFM319zf9/D2S377/ |
| 1026 | 99-19016-51 | | g3339/AFM319zf9/D2S377/ |
| 1084 | 99-20348-403 | | g15529/WI-30719/RH64237/ |
| 1086 | 99-20353-229 | | g15529/WI-30719/RH64237/ |
| 1087 | 99-20357-359 | | g25667/SHGC-12669 g5998/AFMb349yf9/D4S2992/ |
| 1194 | 99-21141-314 | 6q23 | g1323/AFM105xc1/D2S318/105xc1/ |
| 1195 | 99-21148-269 | 6q23 | g1323/AFM105xc1/D2S318/105xc1/ |
| 1196 | 99-21149-129 | 6q23 | g1323/AFM105xc1/D2S318/105xc1/ |
| 1197 | 99-21167-159 | 6q23 | g1323/AFM105xc1/D2S318/105xc1/ |
| 1230 | 99-22160-331 | 13q22 | g17798/RH12008/ |
| 1231 | 99-22167-79 | 13q22 | g17798/RH12008/ |
| 1232 | 99-22172-304 | 13q22 | g17798/RH12008/ |
| 1234 | 99-22189-248 | 2q13-q14 | g1050/AFM026wh7/D12S1595/026wh7 g28792/SHGC-37555/ |
| 1236 | 99-22191-339 | 2q13-q14 | g1050/AFM026wh7/D12S1595/026wh7 g28792/SHGC-37555/ |
| 1237 | 99-22192-383 | 2q13-q14 | g1050/AFM026wh7/D12S1595/026wh7 g28792/SHGC-37555/ |
| 1241 | 99-22215-391 | 18p11.31 | g15435/D15S1203/WI-9767 g16860/WI-20135/ |
| 1242 | 99-22217-423 | 18p11.31 | g15435/D15S1203/WI-9767 g16860/WI-20135/ |
| 1244 | 99-22227-275 | 18p11.31 | g15435/D15S1203/WI-9767 g16860/WI-20135/ |
| 1247 | 99-22265-294 | 16 | g3692/AFMa041yb5/D16S3125/ |
| 1248 | 99-22266-474 | 16 | g3692/AFMa041yb5/D16S3125/ |
| 1251 | 99-22333-237 | | g4979/AFMa286ze9/D5S1994/ |
| 1252 | 99-22336-316 | | g4979/AFMa286ze9/D5S1994/ |
| 1253 | 99-22337-199 | | g4979/AFMa286ze9/D5S1994/ |
| 1255 | 99-22356-370 | | g11856/WI-12093/ |
| 1256 | 99-22357-186 | | g11856/WI-12093/ |
| 1258 | 99-22409-141 | | g11856/WI-12093/ |

TABLE 10-continued

| SEQ ID No. | Marker Name | Chromosomal Localization | Adjacent STS |
|---|---|---|---|
| 1267 | 99-22490-246 | 13q14.1 g16914 | WI-18828/ |
| 1268 | 99-22491-79 | 13q14.1 g16914 | WI-18828/ |
| 1270 | 99-22503-146 | 13q14.1 g16914 | WI-18828/ |
| 1271 | 99-22506-395 | 1p32.1-p31.3 | g20699/RH61218/ |
| 1272 | 99-22513-90 | 1p32.1-p31.3 | g20699/RH61218/ |
| 1273 | 99-22520-413 | 19q12-q13.1 | g18667/RH29813/ |
| 1307 | 99-22712-242 | 11q14-q21 | g10031/AFM115YB6/w1773 g19151/RH57021/R95095/SGC33508/ |
| 1308 | 99-22718-94 | 11q14-q21 | g10031/AFM115YB6/w1773 g19151/RH57021/R95095/SGC33508/ |
| 1310 | 99-22728-207 | 11q14-q21 | g10031/AFM115YB6/w1773 g19151/RH57021/R95095/SGC33508/ |
| 1322 | 99-22857-88 | 12q22 | g2972/AFM289vfS/D2S346/ |
| 1356 | 99-23266-146 | 5q13 | g12748/WI-15052/EST283445/RH56222/ |
| 1357 | 99-23269-263 | 5q13 | g12748/WI-15052/EST283445/RH56222/ |
| 1385 | 99-23469-288 | 14q31 | g20668/RH60581/ |
| 1387 | 99-23473-35 | 14q31 | g20668/RH60581/ |
| 1389 | 99-23488-239 | 2q32.3-q33 | g24198/RH57320/SGC30627/ |
| 1390 | 99-23492-151 | 2q32.3-q33 | g24198/RH57320/SGC30627/ |
| 1391 | 99-23496-94 | 2q32.3-q33 | g24198/RH57320/SGC30627/ |
| 1392 | 99-23510-45 | 8q21.1-q21.2 | g6072/AFMb359wh1/D11S4179/ |
| 1393 | 99-23528-452 | 8q21.1-q21.2 | g6072/AFMb359wh1/D11S4179/ |
| 1426 | 99-24381-217 | 4q34-q35 | g13574/WI-17820/ |
| 1427 | 99-24385-210 | 4q34-q35 | g13574/WI-17820/ |
| 1428 | 99-24388-391 | 4q34-q35 | g13574/WI-17820/ |
| 1437 | 99-24438-402 | 10p12-p11.2 | g15056/WI-7090 g18656/RH29333 g3307/AFM317yc5/D7S685/ |
| 1438 | 99-24441-431 | 10p12-p11.2 | g15056/WI-7090 g18656/RH29333 g3307/AFM317ycS/D7S685/ |
| 1459 | 99-25005-154 | 6p25 | g1147/AFM059yg5/D4S2988/059yg5/ |
| 1460 | 99-25007-131 | 6p25 | g1147/AFM059yg5/D4S2988/059yg5/ |
| 1465 | 99-25129-166 | | g6011/AFMb351xf9/D5S2050/ |
| 1466 | 99-25134-296 | | g6011/AFMb351xf9/D5S2050/ |
| 1473 | 99-25379-389 | | g2028/AFM205wh8/D5S417/ |
| 1474 | 99-25382-226 | | g2028/AFM205wh8/D5S417/ |
| 1475 | 99-25387-220 | | g2028/AFM205wh8/D5S417/ |
| 1476 | 99-25400-379 | | g25712/SHGC-1789 g25713/SHGC-6395 g2753/AFM268zd9/D5S630/ |
| 1477 | 99-25412-354 | | g11977/WI-12573 g13670/WI-18094/ |
| 1485 | 99-25458-103 | 14q31 | g13865/WI-18706/ |
| 1486 | 99-25503-333 | 5q22-q23.1 | g6127/AFMc003zg5/D3S3681/ |
| 1487 | 99-25507-373 | 15q15 | g19212/RH57152 g20451/RH59692/ |
| 1488 | 99-25510-390 | 15q15 | g19212/RH57152 g20451/RH59692/ |
| 1492 | 99-25575-303 | | g15433/D3S3958/WI-9747 g6236/AFMc024yd1/D3S3692/ |
| 1493 | 99-25618-196 | | g10319/AFMB346XE9/w2056 g4935/AFMa275zh1/D3S3588/ |
| 1494 | 99-25620-360 | | g10319/AFMB346XE9/w2056 g4935/AFMa275zh1/D3S3588/ |
| 1495 | 99-25629-262 | | g10319/AFMB346XE9/w2056 g4935/AFMa275zh1/D3S3588/ |
| 1496 | 99-25657-314 | | g5177/AFMa348yd9/D4S2955/ |
| 1497 | 99-25672-97 | | g10965/RH59124/ |
| 1498 | 99-25676-211 | | g10965/RH59124/ |
| 1499 | 99-25678-307 | | g10965/RH59124/ |
| 1501 | 99-25712-418 | | g11689/WI-11614 g13669/WI-18093/ |
| 1504 | 99-25725-80 | | g14391/D4S2653/WI-4583/ |
| 1505 | 99-25732-152 | | g14391/D4S2653/WI-4583/ |
| 1506 | 99-25745-36 | | g11645/WI-11521 g22536/RH52006/WI-6398/ |
| 1573 | 99-477-302 | 11q22.3-q23.1 | g5966/AFMb345ya9/D10S1732/ |
| 1577 | 99-482-130 | 11q22.3-q23.1 | g5966/AFMb345ya9/D10S1732/ |
| 1580 | 99-483-424 | 11q22.3-q23.1 | g5966/AFMb345ya9/D10S1732/ |
| 1585 | 99-486-243 | 11q22.3-q23.1 | g5966/AFMb345ya9/D10S1732/ |
| 1592 | 99-4924-254 | 3q13.3 | g1572/AFM157xg9/D2S2178/ |
| 1593 | 99-4928-102 | 3q13.3 | g1572/AFM157xg9/D2S2178/ |

TABLE 10-continued

| SEQ ID No. | Marker Name | Chromosomal Localization | Adjacent STS |
|---|---|---|---|
| 1778 | 99-6327-270 | 7q31.1 | g5753/AFMb319ze5/D4S2974/ |
| 1779 | 99-6332-143 | 7q31.1 | g5753/AFMb319ze5/D4S2974/ |
| 1786 | 99-6415-279 | 9q33 | g407/AFM151XB8/Z66679/ |
| 1787 | 99-6421-210 | 9q33 | g407/AFM151XB8/Z66679/ |
| 1788 | 99-6423-90 | 9q33 | g407/AFM151XB8/Z66679/ |
| 1789 | 99-6426-413 | 9q33 | g407/AFM151XB8/Z66679/ |
| 1790 | 99-6427-190 | 9q33 | g407/AFM151XB8/Z66679/ |
| 1800 | 99-6478-358 | 8q13 | g775/stSG5976/RH27889/ |
| 1801 | 99-6480-440 | 8q13 | g775/stSG5976/RH27889/ |
| 1802 | 99-6489-237 | 8q13 | g775/stSG5976/RH27889/ |
| 1887 | 99-7129-335 | 11q21 | g1453/AFM135xf12/D2S2396/ |
| 1888 | 99-7131-259 | 11q21 | g1453/AFM135xf12/D2S2396/ |
| 1889 | 99-7136-329 | 11q21 | g1453/AFM135xf12/D2S2396/ |
| 1890 | 99-7137-420 | 11q21 | g1453/AFM135xf12/D2S2396/ |
| 1891 | 99-7140-355 | 11q21 | g1453/AFM135xf12/D2S2396/ |
| 2104 | 99-8546-116 | 12q22 | g2972/AFM289vf5/D2S346/ |
| 2105 | 99-8571-396 | 12q15 | g1392/AFM119xc7/D2S126/ |
| 2106 | 99-8575-401 | 12q15 | g1392/AFM119xc7/D2S126/ |
| 2107 | 99-8576-321 | 12q15 | g1392/AFM119xc7/D2S126/ |
| 2108 | 99-8578-407 | 12q15 | g1392/AFM119xc7/D2S126/ |
| 2109 | 99-8581-443 | 12q15 | g1392/AFM119xc7/D2S126/ |
| 2190 | 99-913-140 | 7p22 | g2474/AFM240wh2/D13S170/ |
| 2709 | 99-15067-278 | 2q32-q33 | g27160/RH11834/ |
| 2716 | 99-15615-368 | 2q32.1-q32.2 | g313/D1S3401/G04332/ |
| 2729 | 99-16284-389 | Xq26.3 | g8814/WI-14718/ |
| 2776 | 99-18321-371 | | g2237/AFM217yel/D5S627 g4093/AFMa084zc1/D5S2113/ |
| 2782 | 99-18576-182 | | g10470/D5S1491 g22231/RH52188/ |
| 2783 | 99-18581-34 | | g10470/D5S1491 g22231/RH52188/ |
| 2790 | 99-18771-300 | | g11451/D5S2428/10859/ |
| 2956 | 99-21110-304 | | g3373/AFM323vc1/D11S1348/ |
| 2957 | 99-21123-62 | | g3373/AFM323vc1/D11S1348/ |
| 2958 | 99-21133-169 | | g3373/AFM323vc1/D11S1348/ |
| 3071 | 99-22181-171 | 4q23-q24 | g20693/RH61180/ |
| 3072 | 99-22187-261 | 13q13 | g15285/D1S3356/WI-8997 g19004/RH35464/ |
| 3073 | 99-22190-369 | 2q13-q14 | g1050/AFM026wh7/D12S1595/026wh7 g28792/SHGC-37555/ |
| 3077 | 99-22213-333 | 18p11.31 | g15435/D15S1203/WI-9767 g16860/WI-20135/ |
| 3078 | 99-22355-213 | | g11856/WI-12093/ |
| 3087 | 99-22593-64 | | g11914/WI-12390 g12081/WI-12941 g13404/WI-17166/ |
| 3088 | 99-22706-367 | 11q14-q21 | g10031/AFM115YB6/w1773 g19151/RH57021/R95095/SGC33508/ |
| 3094 | 99-22851-121 | 12q22 | g2972/AFM289vf5/D25346/ |
| 3096 | 99-23188-227 | 6p22.1-p21.3 | g19258/RH56674/ |
| 3097 | 99-23240-326 | 1q43;Xq25 | g18121/RH16765 g24533/RH63274/WI-9960 g28803/SHGC-16321 g495/WI-20605/RH50893/ |
| 3098 | 99-23246-66 | 6q27 | g1752/AFM184xb10/D8S1178/ |
| 3099 | 99-23248-308 | 6q27 | g1752/AFM184xb10/D8S1178/ |
| 3100 | 99-23249-262 | 6q27 | g1752/AFM184xb10/D8S1178/ |
| 3101 | 99-23274-182 | 2q33-q34 | g11967/WI-12530/ |
| 3219 | 99-25020-395 | 7q31.3 | g10580/D6S1053/ |
| 3221 | 99-25394-261 | | g25712/SHGC-1789 g25713/SHGC-6395 g2753/AFM268zd9/D5S630/ |
| 3222 | 99-25406-54 | | g11977/WI-12573 g13670/WI-18094/ |
| 3227 | 99-25654-281 | | g5177/AFMa348yd9/D4S2955/ |
| 3231 | 99-25738-218 | | g11645/WI-11521 g22536/RH52006/WI-6398/ |
| 3517 | 99-480-373 | 11q22.3-q23.1 | g5966/AFMb345ya9/D10S1732/ |
| 3575 | 99-6173-229 | 11q13.3;3q22;4p16;7p22;8p23.1 | g8817/WI-3139/ |
| 3620 | 99-7815-70 | | g316/EST47321/D19656/RH50110/SGC32758/ |
| 3621 | 99-7818-342 | 9q34.1 | g316/E5T47321/D19656/RH50110/SGC32758/ |
| 3816 | 99-22594-395 | 9q34.1 | g11914/WI-12390 g12081/WI-12941 g13404/WI-17166/ |

TABLE 11

| SEQ ID No | Marker Name | Localization |
|---|---|---|
| 1 | 99-109-224 | 8p23 |
| 4 | 99-1151-516 | 6p21.3–p21.2 |
| 10 | 99-1233-183 | 8p23 |
| 14 | 99-12503-44 | 8p23 |
| 15 | 99-12504-402 | 8p23 |
| 16 | 99-12505-374 | 8p23 |
| 17 | 99-12506-199 | 8p23 |
| 18 | 99-12509-423 | 8p23 |
| 19 | 99-12513-146 | 8p23 |
| 20 | 99-12514-170 | 8p23 |
| 21 | 99-12515-205 | 8p23 |
| 22 | 99-12516-524 | 8p23 |
| 23 | 99-12518-325 | 8p23 |
| 24 | 99-12523-255 | 8p23 |
| 25 | 99-12525-277 | 8p23 |
| 26 | 99-12526-317 | 8p23 |
| 27 | 99-12527-292 | 8p23 |
| 28 | 99-12531-30 | 8p23 |
| 29 | 99-12532-199 | 8p23 |
| 30 | 99-12534-207 | 8p23 |
| 31 | 99-12535-362 | 8p23 |
| 32 | 99-12537-340 | 8p23 |
| 33 | 99-12538-142 | 8p23 |
| 34 | 99-12539-287 | 8p23 |
| 35 | 99-12540-426 | 8p23 |
| 36 | 99-12541-307 | 8p23 |
| 37 | 99-12545-121 | 8p23 |
| 38 | 99-12548-88 | 8p23 |
| 39 | 99-12558-167 | 8p23 |
| 40 | 99-12562-291 | 8p23 |
| 41 | 99-12564-354 | 8p23 |
| 42 | 99-12565-273 | 8p23 |
| 43 | 99-12575-248 | 8p23 |
| 44 | 99-12576-325 | 8p23 |
| 45 | 99-12580-268 | 8p23 |
| 46 | 99-12585-85 | 8p23 |
| 47 | 99-12593-103 | 8p23 |
| 48 | 99-12600-283 | 8p23 |
| 49 | 99-12608-71 | 8p23 |
| 50 | 99-12610-106 | 8p23 |
| 51 | 99-12611-311 | 8p23 |
| 52 | 99-12613-366 | 8p23 |
| 53 | 99-12615-235 | 8p23 |
| 54 | 99-12617-412 | 8p23 |
| 55 | 99-12618-211 | 8p23 |
| 56 | 99-12619-367 | 8p23 |
| 57 | 99-12621-114 | 8p23 |
| 58 | 99-12624-61 | 8p23 |
| 60 | 99-12632-165 | 8p23 |
| 61 | 99-12637-62 | 8p23 |
| 62 | 99-12639-311 | 8p23 |
| 63 | 99-12640-179 | 8p23 |
| 64 | 99-12650-200 | 8p23 |
| 65 | 99-12651-297 | 8p23 |
| 66 | 99-12652-459 | 8p23 |
| 67 | 99-12654-278 | 8p23 |
| 68 | 99-12656-303 | 8p23 |
| 69 | 99-12658-206 | 8p23 |
| 70 | 99-12661-92 | 8p23 |
| 71 | 99-12668-329 | 8p23 |
| 72 | 99-1268-177 | 1q43 |
| 73 | 99-12733-366 | 8p23 |
| 74 | 99-12738-57 | 8p23 |
| 75 | 99-12740-354 | 8p23 |
| 76 | 99-12749-286 | 8p23 |
| 77 | 99-12750-369 | 8p23 |
| 78 | 99-12751-406 | 8p23 |
| 79 | 99-12755-421 | 8p23 |
| 80 | 99-12756-344 | 8p23 |
| 81 | 99-12757-240 | 8p23 |
| 82 | 99-12759-420 | 8p23 |
| 83 | 99-12777-71 | 8p23 |
| 84 | 99-12782-76 | 8p23 |
| 85 | 99-12794-299 | 8p23 |
| 86 | 99-128-60 | 8p23 |
| 87 | 99-12816-101 | 8p23 |
| 88 | 99-12817-358 | 8p23 |
| 89 | 99-12819-165 | 8p23 |
| 90 | 99-12826-408 | 8p23 |
| 91 | 99-12831-345 | 8p23 |
| 92 | 99-12836-387 | 8p23 |
| 93 | 99-12842-305 | 8p23 |
| 94 | 99-12843-337 | 8p23 |
| 95 | 99-12844-130 | 8p23 |
| 96 | 99-12847-37 | 8p23 |
| 97 | 99-12848-204 | 8p23 |
| 98 | 99-12852-260 | 8p23 |
| 99 | 99-12856-183 | 8p23 |
| 100 | 99-12878-291 | 8p23 |
| 101 | 99-12880-282 | 8p23 |
| 102 | 99-12884-248 | 8p23 |
| 103 | 99-12885-261 | 8p23 |
| 104 | 99-12898-364 | 8p23 |
| 105 | 99-12899-307 | 8p23 |
| 106 | 99-1290-291 | 1q43 |
| 107 | 99-12900-165 | 8p23 |
| 108 | 99-12901-316 | 8p23 |
| 109 | 99-12903-381 | 8p23 |
| 110 | 99-12907-295 | 8p23 |
| 111 | 99-12908-369 | 8p23 |
| 112 | 99-12913-197 | 8p23 |
| 113 | 99-12914-227 | 8p23 |
| 114 | 99-12924-273 | 8p23 |
| 115 | 99-12925-487 | 8p23 |
| 116 | 99-12926-332 | 8p23 |
| 117 | 99-12931-173 | 8p23 |
| 118 | 99-12948-61 | 8p23 |
| 119 | 99-12952-199 | 8p23 |
| 120 | 99-12956-43 | 8p23 |
| 121 | 99-12957-448 | 8p23 |
| 122 | 99-12961-318 | 8p23 |
| 123 | 99-12962-181 | 8p23 |
| 124 | 99-12963-255 | 8p23 |
| 125 | 99-12964-230 | 8p23 |
| 189 | 99-1342-51 | 1q43 |
| 195 | 99-1346-503 | 1q43 |
| 202 | 99-1351-264 | 1q43 |
| 214 | 99-1356-500 | 1q43 |
| 219 | 99-1359-355 | 8p23.2–23.1 |
| 228 | 99-1362-126 | 8p23.2–23.1 |
| 291 | 99-1404-135 | 1q43 |
| 341 | 99-14385-117 | 3q27 |
| 342 | 99-14392-431 | 3q27 |
| 343 | 99-14393-190 | 3q27 |
| 345 | 99-14405-105 | 3q27 |
| 358 | 99-14553-224 | 1q42.3 |
| 359 | 99-14562-402 | 1q42.3 |
| 360 | 99-14566-320 | 1q42.3 |
| 361 | 99-14574-310 | 1q42.3 |
| 362 | 99-14581-365 | 8p23 |
| 363 | 99-14591-172 | 8p23 |
| 364 | 99-14595-210 | 8p23 |
| 365 | 99-14596-174 | 8p23 |
| 366 | 99-14597-85 | 8p23 |
| 367 | 99-14598-91 | 8p23 |
| 368 | 99-14599-220 | 8p23 |
| 369 | 99-14600-207 | 8p23 |
| 370 | 99-14601-448 | 8p23 |
| 371 | 99-14607-267 | 8p23 |
| 372 | 99-14609-467 | 8p23 |
| 373 | 99-14610-351 | 8p23 |
| 374 | 99-14611-241 | 8p23 |
| 375 | 99-14612-100 | 8p23 |
| 376 | 99-14614-248 | 8p23 |
| 377 | 99-14615-65 | 8p23 |
| 378 | 99-14616-35 | 8p23 |
| 379 | 99-14618-147 | 8p23 |
| 380 | 99-14619-325 | 8p23 |
| 382 | 99-14620-253 | 8p23 |
| 383 | 99-14621-96 | 8p23 |
| 384 | 99-14622-276 | 8p23 |
| 385 | 99-14626-307 | 8p23 |
| 386 | 99-14627-272 | 8p23 |
| 387 | 99-14628-312 | 8p23 |

TABLE 11-continued

| SEQ ID No | Marker Name | Localization |
|---|---|---|
| 388 | 99-14629-274 | 8p23 |
| 389 | 99-14630-75 | 8p23 |
| 390 | 99-14634-350 | 8p23 |
| 391 | 99-14635-296 | 8p23 |
| 392 | 99-14637-366 | 8p23 |
| 393 | 99-14638-276 | 8p23 |
| 394 | 99-14643-27 | 8p23 |
| 395 | 99-14644-395 | 8p23 |
| 396 | 99-14647-227 | 8p23 |
| 397 | 99-14651-205 | 8p23 |
| 398 | 99-14652-120 | 8p23 |
| 399 | 99-14653-138 | 8p23 |
| 400 | 99-14622-352 | 8p23 |
| 401 | 99-14664-289 | 8p23 |
| 402 | 99-14665-199 | 8p23 |
| 403 | 99-14669-238 | 8p23 |
| 404 | 99-14671-175 | 8p23 |
| 405 | 99-14676-313 | 8p23 |
| 406 | 99-14677-358 | 8p23 |
| 407 | 99-14678-75 | 8p23 |
| 408 | 99-14679-241 | 8p23 |
| 411 | 99-14690-84 | 8p23 |
| 412 | 99-14692-46 | 8p23 |
| 413 | 99-14699-149 | 8p23 |
| 414 | 99-147-181 | 8p23.3–p23.2 |
| 415 | 99-14701-264 | 8p23 |
| 416 | 99-14704-59 | 8p23 |
| 417 | 99-14708-142 | 8p23 |
| 419 | 99-14710-107 | 8p23 |
| 420 | 99-14712-163 | 8p23 |
| 421 | 99-14714-237 | 8p23 |
| 422 | 99-14717-132 | 8p23 |
| 424 | 99-14722-272 | 8p23 |
| 425 | 99-14729-284 | 8p23 |
| 426 | 99-14733-26 | 8p23 |
| 427 | 99-14735-328 | 8p23 |
| 429 | 99-14746-377 | 8p23 |
| 430 | 99-14753-194 | 8p23 |
| 431 | 99-14756-270 | 8p23 |
| 433 | 99-14761-194 | 8p23 |
| 434 | 99-14773-383 | 8p23 |
| 435 | 99-14776-79 | 8p23 |
| 436 | 99-14777-100 | 8p23 |
| 437 | 99-14782-152 | 8p23 |
| 438 | 99-14784-212 | 8p23 |
| 439 | 99-14785-92 | 8p23 |
| 440 | 99-14786-59 | 8p23 |
| 441 | 99-1479-158 | 8p23 |
| 442 | 99-14792-43 | 8p23 |
| 443 | 99-14796-227 | 8p23 |
| 444 | 99-14799-57 | 8p23 |
| 445 | 99-148-182 | 8p23.3–p23.2 |
| 446 | 99-1480-290 | 8p23 |
| 447 | 99-14802-60 | 8p23 |
| 448 | 99-14803-157 | 8p23 |
| 449 | 99-14804-216 | 8p23 |
| 450 | 99-14805-58 | 8p23 |
| 451 | 99-14806-108 | 8p23 |
| 452 | 99-14807-150 | 8p23 |
| 453 | 99-1481-285 | 8p23 |
| 454 | 99-14810-407 | 8p23 |
| 455 | 99-14812-189 | 8p23 |
| 456 | 99-14817-323 | 8p23 |
| 457 | 99-14818-430 | 8p23 |
| 458 | 99-14819-278 | 8p23 |
| 459 | 99-14820-76 | 8p23 |
| 460 | 99-14821-48 | 8p23 |
| 461 | 99-14826-238 | 8p23 |
| 462 | 99-14828-214 | 8p23 |
| 463 | 99-14833-226 | 8p23 |
| 464 | 99-1484-328 | 8p23 |
| 465 | 99-14843-195 | 8p23 |
| 466 | 99-14844-143 | 8p23 |
| 467 | 99-1485-251 | 8p23 |
| 468 | 99-14850-136 | 8p23 |
| 469 | 99-14856-260 | 8p23 |
| 470 | 99-14861-387 | 8p23 |
| 471 | 99-14862-171 | 8p23 |
| 472 | 99-14865-386 | 8p23 |
| 473 | 99-14867-160 | 8p23 |
| 474 | 99-14872-326 | 8p23 |
| 475 | 99-14873-453 | 8p23 |
| 476 | 99-14875-411 | 8p23 |
| 477 | 99-14879-398 | 8p23 |
| 478 | 99-14881-231 | 8p23 |
| 479 | 99-14882-382 | 8p23 |
| 480 | 99-14883-123 | 8p23 |
| 481 | 99-1489-76 | 8p23 |
| 482 | 99-14890-358 | 8p23 |
| 483 | 99-14892-237 | 8p23 |
| 484 | 99-14894-52 | 8p23 |
| 485 | 99-14895-343 | 8p23 |
| 486 | 99-14897-356 | 8p23 |
| 487 | 99-1490-381 | 8p23 |
| 488 | 99-14907-411 | 8p23.1 |
| 489 | 99-1493-280 | 8p23 |
| 490 | 99-14937-42 | 11p15.1–p14 |
| 491 | 99-14939-240 | 11p15.1–p14 |
| 492 | 99-1494-598 | 8p23 |
| 493 | 99-14940-224 | 11p15.1–p14 |
| 501 | 99-1498-120 | 1q43 |
| 506 | 99-1501-296 | 1q43 |
| 513 | 99-1504-252 | 1q43 |
| 516 | 99-1506-505 | 1q43 |
| 519 | 99-15098-367 | 1q43 |
| 520 | 99-151-94 | 8p23.3–p23.2 |
| 521 | 99-15100-363 | 1q43 |
| 522 | 99-15101-154 | 1q43 |
| 523 | 99-15106-451 | 1q43 |
| 524 | 99-15107-228 | 1q43 |
| 525 | 99-15112-358 | 1q43 |
| 526 | 99-15118-69 | 1q43 |
| 527 | 99-15123-180 | 1q43 |
| 528 | 99-15128-349 | 1q43 |
| 529 | 99-15129-279 | 1q43 |
| 530 | 99-15135-231 | 1q43 |
| 531 | 99-15137-386 | 1q43 |
| 532 | 99-1515-402 | 1q43 |
| 533 | 99-15160-270 | 1q43 |
| 534 | 99-15164-67 | 1q43 |
| 538 | 99-1520-143 | 1q43 |
| 541 | 99-1521-457 | 1q43 |
| 542 | 99-1525-102 | 1q43 |
| 705 | 99-1658-474 | 1q43 |
| 707 | 99-1664-289 | 1q43 |
| 904 | 99-18091-47 | 14q24.2 |
| 905 | 99-18096-198 | 14q24.2 |
| 906 | 99-18109-159 | 6q24 |
| 919 | 99-18221-207 | 5q13 |
| 922 | 99-18242-369 | 5q13 |
| 925 | 99-18258-45 | 2q35 |
| 926 | 99-18268-460 | 2q35 |
| 927 | 99-18272-287 | 2q35 |
| 928 | 99-18276-390 | 2q35 |
| 965 | 99-18561-371 | 2q35 |
| 966 | 99-18573-363 | 2q35 |
| 1043 | 99-1997-139 | 8p23.2 |
| 1045 | 99-2000-240 | 8p23.2 |
| 1047 | 99-2001-177 | 8p23.2 |
| 1048 | 99-20011-229 | 3q21–q22 |
| 1049 | 99-20018-244 | 3q21–q22 |
| 1051 | 99-2003-509 | 8p23.2 |
| 1055 | 99-2004-35 | 8p23.2 |
| 1056 | 99-2005-466 | 8p23.2 |
| 1060 | 99-2007-278 | 8p23.2 |
| 1063 | 99-2010-363 | 8p23.2 |
| 1065 | 99-2012-243 | 8p23.2 |
| 1069 | 99-2020-281 | 8p23.2 |
| 1071 | 99-2022-200 | 8p23.2 |
| 1072 | 99-2024-132 | 8p23.2 |
| 1073 | 99-2025-234 | 8p23.2 |
| 1074 | 99-20250-362 | 4q21.1–q21.2 |
| 1075 | 99-2027-296 | 8p23.2 |
| 1085 | 99-2035-323 | 8p23.2 |

TABLE 11-continued

| SEQ ID No | Marker Name | Localization |
|---|---|---|
| 1088 | 99-2036-168 | 8p23.2 |
| 1089 | 99-2037-470 | 8p23.2 |
| 1091 | 99-2041-141 | 8p23.2 |
| 1092 | 99-2042-439 | 8p23.2 |
| 1093 | 99-20420-274 | 4p14 |
| 1094 | 99-20423-430 | 4p14 |
| 1095 | 99-20424-330 | 4p14 |
| 1096 | 99-20428-271 | 4p14 |
| 1097 | 99-2043-220 | 8p23.2 |
| 1098 | 99-2046-275 | 8p23.2 |
| 1100 | 99-2048-267 | 8p23.2 |
| 1108 | 99-2051-360 | 8p23.2 |
| 1112 | 99-2052-376 | 8p23.2 |
| 1114 | 99-2053-386 | 8p23.2 |
| 1116 | 99-2054-93 | 8p23.2 |
| 1119 | 99-2055-236 | 8p23.2 |
| 1121 | 99-2056-474 | 8p23.2 |
| 1127 | 99-2058-168 | 8p23.2 |
| 1130 | 99-2060-322 | 8p23.2 |
| 1131 | 99-2061-257 | 8p23 |
| 1134 | 99-2063-451 | 8p23 |
| 1149 | 99-2074-273 | 8p23 |
| 1154 | 99-2077-510 | 8p23 |
| 1156 | 99-2078-348 | 8p23 |
| 1159 | 99-2080-33 | 8p23 |
| 1162 | 99-2082-284 | 8p23 |
| 1166 | 99-2084-504 | 8p23 |
| 1167 | 99-2085-172 | 8p23 |
| 1175 | 99-2089-84 | 8p23 |
| 1177 | 99-2092-323 | 8p23 |
| 1179 | 99-2093-278 | 8p23 |
| 1181 | 99-2094-129 | 8p23 |
| 1183 | 99-2098-102 | 21q21 |
| 1186 | 99-2103-270 | 21q21 |
| 1187 | 99-21035-279 | 2q11.2 |
| 1188 | 99-21064-278 | 1q43 |
| 1189 | 99-21070-272 | 1q43 |
| 1190 | 99-21079-169 | 1q43 |
| 1191 | 99-21084-496 | 1q43 |
| 1192 | 99-2109-276 | 21q21 |
| 1193 | 99-211-291 | 8p23 |
| 1200 | 99-2126-79 | 8p23 |
| 1201 | 99-21370-87 | 22q11.2 |
| 1202 | 99-2170-188 | 8p23 |
| 1203 | 99-2172-314 | 8p23 |
| 1204 | 99-2173-289 | 8p23 |
| 1205 | 99-2179-303 | 8p23 |
| 1206 | 99-2193-225 | 8p23 |
| 1238 | 99-222-109 | 8p23 |
| 1277 | 99-22573-321 | 2q34–q35 |
| 1278 | 99-22578-78 | 2q34–q35 |
| 1279 | 99-22580-72 | 2q34–q35 |
| 1280 | 99-22585-462 | 2q34–q35 |
| 1281 | 99-22586-39 | 2q34–q35 |
| 1303 | 99-2269-179 | 21q22.1 |
| 1306 | 99-2271-403 | 21q22.1 |
| 1309 | 99-2272-409 | 21q22.1 |
| 1311 | 99-2273-528 | 21q22.1 |
| 1314 | 99-2275-466 | 21q22.1 |
| 1315 | 99-2276-331 | 21q22.1 |
| 1318 | 99-2278-276 | 21q22.1 |
| 1327 | 99-22937-395 | 14q24.2 |
| 1375 | 99-23437-347 | 2q34–q35 |
| 1376 | 99-23440-274 | 2q34–q35 |
| 1377 | 99-23444-203 | 2q34–q35 |
| 1379 | 99-23451-78 | 2q34–q35 |
| 1380 | 99-23452-306 | 2q34–q35 |
| 1381 | 99-23454-317 | 2q34–q35 |
| 1382 | 99-23460-199 | 2q34–q35 |
| 1402 | 99-23737-186 | 5q13 |
| 1404 | 99-23773-199 | 9q34.3 |
| 1407 | 99-2409-298 | 3 |
| 1408 | 99-241-341 | 21q21 |
| 1418 | 99-24275-107 | 2q33–q34 |
| 1432 | 99-2440-246 | 1q21.1–q21.2 |
| 1440 | 99-2445-79 | 1q21.1–q21.2 |
| 1452 | 99-24688-312 | 21q22.1 |
| 1464 | 99-25077-124 | 3p21.3 |
| 1489 | 99-25538-423 | 8p11.1–q11 |
| 1490 | 99-25539-86 | 8p11.1–q11 |
| 1491 | 99-25543-390 | 8p11.1–q11 |
| 1516 | 99-2610-121 | 21q22.1 |
| 1519 | 99-2615-83 | 21q22.1 |
| 1520 | 99-2620-227 | 21q22.1 |
| 1524 | 99-2662-407 | 1q43 |
| 1525 | 99-2669-233 | 1q43 |
| 1526 | 99-2675-121 | 1q43 |
| 1527 | 99-2683-388 | 1q43 |
| 1558 | 99-4666-185 | 8p23 |
| 1559 | 99-4674-166 | 8p23 |
| 1560 | 99-4676-342 | 8p23 |
| 1561 | 99-4677-58 | 8p23 |
| 1562 | 99-4679-240 | 8p23 |
| 1563 | 99-4680-352 | 8p23 |
| 1564 | 99-4681-228 | 8p23 |
| 1570 | 99-4725-251 | 1q23–q24 |
| 1596 | 99-4956-236 | 4q13.1–q13.2 |
| 1597 | 99-4966-298 | 4q13.1–q13.2 |
| 1598 | 99-4968-273 | 4q13.1–q13.2 |
| 1601 | 99-5032-232 | 4q31.3 |
| 1602 | 99-5036-40 | 2q12 |
| 1603 | 99-5038-181 | 2q12 |
| 1604 | 99-5043-111 | 2q12 |
| 1637 | 99-5326-332 | 3q25.1 |
| 1638 | 99-5338-151 | 6p12 |
| 1646 | 99-5389-409 | 1q43 |
| 1647 | 99-5390-375 | 1q43 |
| 1648 | 99-5401-280 | 1q43 |
| 1649 | 99-5405-376 | 1q43 |
| 1650 | 99-5406-299 | 1q43 |
| 1651 | 99-5407-173 | 1q43 |
| 1652 | 99-5411-378 | 1q43 |
| 1653 | 99-5416-137 | 1q43 |
| 1706 | 99-576-421 | 8p23 |
| 1712 | 99-582-132 | 8p23 |
| 1727 | 99-596-228 | 8p23 |
| 1730 | 99-598-130 | 8p23 |
| 1733 | 99-602-258 | 8p23 |
| 1739 | 99-607-397 | 8p23 |
| 1742 | 99-608-183 | 8p23 |
| 1744 | 99-609-225 | 8p23 |
| 1749 | 99-610-250 | 8p23 |
| 1755 | 99-614-346 | 8p23 |
| 1757 | 99-615-387 | 8p23 |
| 1758 | 99-616-338 | 8p23 |
| 1763 | 99-619-141 | 8p23 |
| 1766 | 99-621-215 | 8p23 |
| 1768 | 99-622-95 | 8p23 |
| 1791 | 99-6435-343 | 9q32 |
| 1792 | 99-6437-77 | 9q32 |
| 1793 | 99-6440-318 | 9q32 |
| 1794 | 99-6447-178 | 10q24.3–q25.1 |
| 1795 | 99-6456-165 | 10p15 |
| 1796 | 99-6459-201 | 10p15 |
| 1798 | 99-6463-348 | 10p15 |
| 1799 | 99-6468-288 | 10p15 |
| 1805 | 99-6511-176 | 10q26.3 |
| 1878 | 99-7084-187 | 10q26.2 |
| 1879 | 99-7090-294 | 10q26.2 |
| 1880 | 99-7093-36 | 10q26.2 |
| 1893 | 99-7144-261 | 1q43 |
| 1894 | 99-7148-262 | 1q43 |
| 1901 | 99-72-109 | 8p23 |
| 1912 | 99-73-140 | 8p23 |
| 1966 | 99-77-318 | 8p23 |
| 2032 | 99-81-227 | 8p23 |
| 2052 | 99-827-359 | 13 |
| 2057 | 99-828-259 | 13 |
| 2082 | 99-840-68 | 13 |
| 2099 | 99-851-237 | 13q31 |
| 2103 | 99-854-415 | 13q31 |
| 2113 | 99-860-419 | 13q31 |
| 2117 | 99-862-233 | 13q31 |
| 2126 | 99-866-160 | 13q31 |

TABLE 11-continued

| SEQ ID No | Marker Name | Localization |
|---|---|---|
| 2132 | 99-870-379 | 13q31 |
| 2146 | 99-88-216 | 8p23 |
| 2198 | 99-9240-109 | 2q33–q34 |
| 2199 | 99-9250-450 | 2q33–q34 |
| 2261 | 99-10000-518 | 4q25 |
| 2262 | 99-10016-115 | 4q21 |
| 2263 | 99-10027-378 | 4q25 |
| 2264 | 99-10028-93 | 4q25 |
| 2265 | 99-10031-130 | 4q25 |
| 2266 | 99-10046-199 | 4q25 |
| 2267 | 99-10064-252 | 4q25 |
| 2268 | 99-10066-465 | 4q25 |
| 2269 | 99-10067-168 | 4q25 |
| 2270 | 99-10078-341 | 4q25 |
| 2271 | 99-10104-464 | 4q21 |
| 2272 | 99-10106-247 | 4q21 |
| 2273 | 99-10108-419 | 4q21 |
| 2274 | 99-10118-323 | 4q25 |
| 2275 | 99-10126-413 | 4q25 |
| 2276 | 99-10127-506 | 4q25 |
| 2277 | 99-10137-195 | 4 |
| 2278 | 99-10142-293 | 4 |
| 2279 | 99-10143-111 | 4 |
| 2280 | 99-10146-202 | 4 |
| 2281 | 99-10149-291 | 4 |
| 2282 | 99-10151-340 | 4 |
| 2283 | 99-10153-267 | 4 |
| 2284 | 99-10155-423 | 4 |
| 2285 | 99-10173-122 | 4q25 |
| 2286 | 99-10179-48 | 4q25 |
| 2287 | 99-1018-244 | 16p13.1 |
| 2288 | 99-10183-166 | 4q25 |
| 2289 | 99-10185-402 | 4q25 |
| 2290 | 99-10188-116 | 4q25 |
| 2291 | 99-10201-115 | 4q25 |
| 2292 | 99-10207-173 | 4q25 |
| 2293 | 99-10211-380 | 4q25 |
| 2294 | 99-10216-336 | 4q25 |
| 2295 | 99-10220-312 | 4q25 |
| 2296 | 99-10223-153 | 4q25 |
| 2297 | 99-10224-223 | 4q25 |
| 2298 | 99-10234-334 | 4q25 |
| 2299 | 99-1024-403 | 16p13.1 |
| 2300 | 99-10245-197 | 5q |
| 2301 | 99-10256-41 | 5p |
| 2302 | 99-10264-82 | 5p |
| 2303 | 99-10266-290 | 5q |
| 2304 | 99-10267-409 | 5q |
| 2305 | 99-10303-406 | 5q31 |
| 2306 | 99-10304-88 | 5q31 |
| 2307 | 99-10312-155 | 5q |
| 2308 | 99-10318-230 | 6p22.2–22.3 |
| 2309 | 99-10330-432 | 6p22.2–22.3 |
| 2310 | 99-10332-89 | 6p22.2–22.3 |
| 2311 | 99-10345-182 | 6p24 |
| 2312 | 99-10353-285 | 6p24 |
| 2313 | 99-10364-331 | 6q21–22.1 |
| 2314 | 99-10369-41 | 6q21–22.1 |
| 2315 | 99-10374-343 | 6p22.3–24.3 |
| 2316 | 99-10381-328 | 6p22.1–22.3 |
| 2317 | 99-10389-114 | 6p22.1–22.3 |
| 2318 | 99-10390-172 | 6p22.3–24.1 |
| 2319 | 99-10414-128 | 6p22.3–24.1 |
| 2320 | 99-10434-121 | 6q27 |
| 2321 | 99-10436-162 | 6q27 |
| 2322 | 99-10438-281 | 6q27 |
| 2323 | 99-10446-425 | 6q21 |
| 2324 | 99-10451-188 | 6q21 |
| 2325 | 99-10452-306 | 6q21 |
| 2326 | 99-10457-310 | 6q21 |
| 2327 | 99-10470-405 | 6p25 |
| 2328 | 99-10471-88 | 6p25 |
| 2329 | 99-10473-259 | 6p25 |
| 2330 | 99-10474-223 | 6p25 |
| 2331 | 99-10481-217 | 6p22.3–23 |
| 2332 | 99-10487-57 | 6q16.1–16.3 |
| 2333 | 99-10488-146 | 6q16.1–16.3 |
| 2334 | 99-10491-300 | 6q16.1–16.3 |
| 2335 | 99-10499-102 | 6q27 |
| 2336 | 99-10502-161 | 6q27 |
| 2337 | 99-10506-307 | 6q27 |
| 2338 | 99-10507-216 | 6p23–25.1 |
| 2339 | 99-10509-122 | 6p23–25.1 |
| 2340 | 99-1051-284 | 16p13.1 |
| 2341 | 99-10513-347 | 6p23–25.1 |
| 2342 | 99-10514-546 | 6p23–25.1 |
| 2343 | 99-10521-296 | 6q16 |
| 2344 | 99-10522-395 | 6q16 |
| 2345 | 99-10536-90 | 6p22.3–23 |
| 2346 | 99-10539-208 | 6p22.3–23 |
| 2347 | 99-10542-326 | 6p22.3–23 |
| 2348 | 99-10543-278 | 6p22.3–23 |
| 2349 | 99-1055-140 | 16p13.1 |
| 2350 | 99-10557-276 | 6q23.1–23.3 |
| 2351 | 99-10567-233 | 6q22 |
| 2352 | 99-10570-107 | 6q22 |
| 2353 | 99-10573-375 | 6p21 |
| 2354 | 99-10575-416 | 6p21 |
| 2355 | 99-10576-351 | 6p21 |
| 2356 | 99-10577-36 | 6p21 |
| 2357 | 99-10581-354 | 6p21 |
| 2358 | 99-10589-360 | 6p21 |
| 2359 | 99-10601-463 | 6p21 |
| 2360 | 99-10606-92 | 6q27 |
| 2361 | 99-10608-353 | 6q27 |
| 2362 | 99-10613-277 | 6q27 |
| 2363 | 99-10618-404 | 6q27 |
| 2364 | 99-10626-196 | 6q22.2–22.33 |
| 2365 | 99-10630-236 | 6q22.2–22.33 |
| 2366 | 99-10632-55 | 6q21–22 |
| 2367 | 99-10634-141 | 6q21–22 |
| 2368 | 99-10643-161 | 6q21–22 |
| 2369 | 99-10659-208 | 6q26–q27 |
| 2370 | 99-10661-153 | 6q26–q27 |
| 2371 | 99-10662-397 | 6q26–q27 |
| 2372 | 99-10667-251 | 6q26–q27 |
| 2373 | 99-10675-109 | 6p24 |
| 2374 | 99-1068-309 | 16p11.2–p12 |
| 2375 | 99-10683-117 | 6p24 |
| 2376 | 99-10689-419 | 6p24 |
| 2377 | 99-10692-377 | 6q22 |
| 2378 | 99-10694-446 | 6q22 |
| 2379 | 99-10695-161 | 6q22 |
| 2380 | 99-1070-342 | 16p11.2–p12 |
| 2381 | 99-10702-261 | 6q22 |
| 2382 | 99-10706-228 | 6q16.1–21 |
| 2383 | 99-10708-28 | 6q16.1–21 |
| 2384 | 99-10709-460 | 6q16.1–21 |
| 2385 | 99-10715-43 | 6q16.1–21 |
| 2386 | 99-10719-455 | 6q22 |
| 2387 | 99-10720-63 | 6q22 |
| 2388 | 99-10731-195 | 6q22.1–6q22.33 |
| 2389 | 99-10735-238 | 6q22.1–6q22.33 |
| 2390 | 99-1074-127 | 16p13.11 |
| 2391 | 99-10741-421 | 6q22.1–6q22.33 |
| 2392 | 99-10743-315 | 6q22.1–6q22.33 |
| 2393 | 99-1075-314 | 16p13.11 |
| 2394 | 99-10752-366 | 7q31 |
| 2395 | 99-1076-116 | 16p13.11 |
| 2396 | 99-10769-291 | 7p15–p21 |
| 2397 | 99-10771-266 | 7p15–p21 |
| 2398 | 99-10775-331 | 7p15–p21 |
| 2399 | 99-10776-447 | 7p15–p21 |
| 2400 | 99-1079-237 | 16p13.11 |
| 2401 | 99-1081-159 | 16p13.11 |
| 2402 | 99-10816-272 | 7q21 |
| 2403 | 99-1082-180 | 16p13.11 |
| 2404 | 99-10839-239 | 7q31 |
| 2405 | 99-10842-232 | 7p15–p21 |
| 2406 | 99-10843-114 | 7p15–p21 |
| 2407 | 99-10856-246 | 7q31 |
| 2408 | 99-10861-96 | 7q31 |
| 2409 | 99-10862-397 | 7q31 |
| 2410 | 99-10864-418 | 7p21 |

TABLE 11-continued

| SEQ ID No | Marker Name | Localization |
|---|---|---|
| 2411 | 99-10870-234 | 7p21 |
| 2412 | 99-10874-69 | 7p21 |
| 2413 | 99-10879-386 | 7q21–q22 |
| 2414 | 99-10887-214 | 7q21–q22 |
| 2415 | 99-10890-201 | 7p15–p21 |
| 2416 | 99-10894-35 | 7p15–p21 |
| 2417 | 99-10898-209 | 7p15 |
| 2418 | 99-10904-111 | 7p15 |
| 2419 | 99-10905-85 | 7p15 |
| 2421 | 99-10927-388 | 7q11.2–q21 |
| 2422 | 99-10929-298 | 7q11.2–q21 |
| 2423 | 99-10930-95 | 7q11.2–q21 |
| 2424 | 99-10937-64 | 7q11.2–q21 |
| 2425 | 99-10944-83 | 7p15–p21 |
| 2426 | 99-10951-434 | 7p15–p21 |
| 2427 | 99-10959-113 | 7q21–q22 |
| 2428 | 99-10964-89 | 7q11.23–q21 |
| 2429 | 99-10965-174 | 7q11.23–q21 |
| 2430 | 99-10966-113 | 7q11.23–q21 |
| 2431 | 99-10974-193 | 7q11.23–q21 |
| 2432 | 99-10978-393 | 7q11.23–q21 |
| 2433 | 99-10979-156 | 7q11.23–q21 |
| 2434 | 99-10988-242 | 7q11.23–q21 |
| 2435 | 99-10992-98 | 7q31 |
| 2436 | 99-11000-163 | 7q31 |
| 2437 | 99-11001-393 | 7q31 |
| 2438 | 99-11003-361 | 7q31 |
| 2439 | 99-11006-426 | 7p15 |
| 2440 | 99-11007-68 | 7p15 |
| 2441 | 99-11014-194 | 7p15 |
| 2442 | 99-11034-317 | 7q11.23–q21.1 |
| 2443 | 99-11035-299 | 7q11.23–q21.1 |
| 2444 | 99-11037-218 | 7q11.23–q21.1 |
| 2446 | 99-11051-154 | 7q31 |
| 2447 | 99-11063-111 | 7q31 |
| 2448 | 99-11074-187 | 7q31 |
| 2449 | 99-11075-311 | 7q31 |
| 2450 | 99-11089-424 | 7p15–p21 |
| 2451 | 99-11094-427 | 7p15–p21 |
| 2452 | 99-11099-179 | 7p15–p21 |
| 2453 | 99-11103-88 | 7p15–p21 |
| 2454 | 99-11106-117 | 7p15–p21 |
| 2455 | 99-11110-375 | 7p15–p21 |
| 2456 | 99-11115-133 | 7p15–p21 |
| 2457 | 99-11119-132 | 8q21 |
| 2458 | 99-11128-162 | 8q21 |
| 2459 | 99-11136-374 | 8q21 |
| 2460 | 99-11142-139 | 8q21 |
| 2461 | 99-11143-443 | 8q21 |
| 2462 | 99-11144-137 | 8q21 |
| 2463 | 99-11148-369 | 11 |
| 2464 | 99-11158-255 | 11 |
| 2465 | 99-11163-293 | 11p11.2 |
| 2466 | 99-11164-298 | 11p11.2 |
| 2467 | 99-11168-197 | 11p11.2 |
| 2468 | 99-11175-348 | 11q25 |
| 2469 | 99-11179-239 | 11q25 |
| 2470 | 99-11180-148 | 11q25 |
| 2471 | 99-11183-166 | 11q25 |
| 2473 | 99-11210-235 | 11p14.3 |
| 2474 | 99-11214-188 | 11p14.3 |
| 2475 | 99-11218-174 | 11p14.3 |
| 2476 | 99-11236-63 | 11 |
| 2477 | 99-11247-86 | 11 |
| 2478 | 99-11248-404 | 11 |
| 2479 | 99-11252-263 | 11 |
| 2480 | 99-11255-375 | 12q24 |
| 2481 | 99-11260-422 | 12q24 |
| 2482 | 99-11261-255 | 12q24 |
| 2483 | 99-11293-125 | 12q |
| 2484 | 99-11313-95 | 15 |
| 2485 | 99-11320-29 | 15 |
| 2486 | 99-11326-356 | 16p11.2 |
| 2487 | 99-11340-89 | 16p11.2 |
| 2488 | 99-11346-222 | 16p11.2 |
| 2489 | 99-11350-116 | 16p11.2–p12 |
| 2490 | 99-11356-187 | 16p11.2–p12 |
| 2491 | 99-11362-334 | 16p11.2–p12 |
| 2492 | 99-11369-112 | 16p12–p13.1 |
| 2493 | 99-11372-162 | 16p12–p13.1 |
| 2494 | 99-11377-384 | 16p12–p13.1 |
| 2495 | 99-1381-256 | 16p12–p13.1 |
| 2496 | 99-11385-245 | 16p12.2–p12 |
| 2497 | 99-11413-239 | 16p11.2 |
| 2498 | 99-1143-340 | 6p21.3–p21.2 |
| 2499 | 99-11430-162 | 16p11.2 |
| 2500 | 99-11431-333 | 16p11.2 |
| 2501 | 99-11449-297 | 16p11.2 |
| 2502 | 99-11464-236 | 16p12.3 |
| 2503 | 99-11466-107 | 16p12.3 |
| 2504 | 99-11485-396 | 6p12 |
| 2505 | 99-11492-360 | 16p13.2–13.3 |
| 2506 | 99-11499-45 | 16p13.2–13.3 |
| 2507 | 99-11505-92 | 16p13.2–13.3 |
| 2508 | 99-11506-224 | 16p13.2–13.3 |
| 2509 | 99-11520-170 | 16p11.2–12 |
| 2510 | 99-11521-146 | 16p11.2–12 |
| 2511 | 99-11522-313 | 16p11.2–12 |
| 2512 | 99-11528-137 | 16p13.11 |
| 2513 | 99-11530-388 | 16p13.11 |
| 2514 | 99-11533-375 | 16p13.11 |
| 2515 | 99-11535-193 | 16p13.3 |
| 2516 | 99-11543-415 | 16p13.3 |
| 2517 | 99-11545-180 | 16p13.3 |
| 2518 | 99-11555-397 | 16p13.3 |
| 2519 | 99-11559-81 | 17 |
| 2520 | 99-11563-183 | 17 |
| 2521 | 99-11565-305 | 17 |
| 2522 | 99-11566-385 | 17 |
| 2523 | 99-11580-97 | 17 |
| 2524 | 99-11584-69 | 17 |
| 2525 | 99-11587-202 | 17 |
| 2526 | 99-11592-297 | 17 |
| 2527 | 99-11600-48 | 17 |
| 2528 | 99-11601-441 | 17 |
| 2529 | 99-11602-93 | 17 |
| 2530 | 99-11604-396 | 17 |
| 2531 | 99-11611-259 | 17 |
| 2532 | 99-11613-315 | 17 |
| 2533 | 99-11620-149 | 17 |
| 2534 | 99-11635-363 | 17 |
| 2535 | 99-11643-378 | 17 |
| 2536 | 99-11645-157 | 17 |
| 2537 | 99-11658-275 | 17 |
| 2538 | 99-11668-308 | 17 |
| 2539 | 99-11669-394 | 17 |
| 2540 | 99-11670-486 | 17 |
| 2541 | 99-11685-200 | 17 |
| 2542 | 99-11697-345 | 17 |
| 2543 | 99-11700-326 | 17 |
| 2544 | 99-11704-23 | 17 |
| 2545 | 99-11705-302 | 17 |
| 2546 | 99-11723-211 | 17 |
| 2547 | 99-11743-233 | 17 |
| 2548 | 99-11745-256 | 17 |
| 2549 | 99-11746-238 | 17 |
| 2550 | 99-11780-292 | 17 |
| 2551 | 99-11785-167 | 17 |
| 2552 | 99-11786-98 | 17 |
| 2553 | 99-11787-281 | 17 |
| 2554 | 99-11788-69 | 17 |
| 2555 | 99-11789-348 | 17 |
| 2556 | 99-11797-147 | 17 |
| 2557 | 99-11810-289 | 17 |
| 2558 | 99-11811-158 | 17 |
| 2559 | 99-1182-310 | 17 |
| 2560 | 99-11823-118 | 17 |
| 2561 | 99-11824-90 | 17 |
| 2562 | 99-1183-182 | 6 |
| 2563 | 99-11830-334 | 17 |
| 2564 | 99-11831-321 | 17 |
| 2565 | 99-11839-223 | 17 |
| 2566 | 99-11842-197 | 17 |
| 2567 | 99-1185-317 | 6 |

TABLE 11-continued

| SEQ ID No | Marker Name | Localization |
|---|---|---|
| 2568 | 99-11851-45 | 17 |
| 2569 | 99-11857-368 | 22 |
| 2570 | 99-1186-249 | 6 |
| 2571 | 99-11861-254 | 22 |
| 2572 | 99-11877-237 | 22q12–13 |
| 2573 | 99-11880-90 | 22q12–13 |
| 2574 | 99-11882-120 | 22q12–13 |
| 2575 | 99-11894-470 | 22q12-qter |
| 2576 | 99-11917-129 | 22q11.2-qter |
| 2577 | 99-11922-206 | 22q11.2-qter |
| 2578 | 99-11930-395 | 22q12.1 |
| 2579 | 99-11966-288 | 22 |
| 2580 | 99-11989-233 | Xp22 |
| 2581 | 99-11993-468 | X |
| 2582 | 99-12000-355 | X |
| 2583 | 99-12005-282 | X |
| 2584 | 99-12017-203 | Xp22 |
| 2586 | 99-12028-121 | Xp22 |
| 2588 | 99-12038-420 | X |
| 2589 | 99-12039-389 | X |
| 2590 | 99-12048-300 | X |
| 2591 | 99-12049-245 | X |
| 2592 | 99-12050-459 | X |
| 2593 | 99-12061-211 | X |
| 2594 | 99-12062-94 | X |
| 2595 | 99-12068-348 | X |
| 2596 | 99-12087-45 | X |
| 2598 | 99-12130-72 | X |
| 2599 | 99-12133-294 | X |
| 2600 | 99-12135-288 | X |
| 2601 | 99-12152-332 | X |
| 2602 | 99-12158-148 | X |
| 2603 | 99-12168-256 | X |
| 2604 | 99-12171-93 | X |
| 2605 | 99-12178-423 | X |
| 2606 | 99-12181-226 | X |
| 2607 | 99-12186-229 | X |
| 2608 | 99-12198-289 | X |
| 2609 | 99-12199-246 | X |
| 2610 | 99-12203-356 | X |
| 2611 | 99-12224-368 | Xq23 |
| 2612 | 99-12228-184 | Xq23 |
| 2613 | 99-12241-380 | Xq23 |
| 2614 | 99-12253-145 | Xq27–Xq28 |
| 2615 | 99-12265-324 | Xq21 |
| 2616 | 99-12267-161 | Xq21 |
| 2617 | 99-12268-54 | Xq21 |
| 2618 | 99-12270-408 | Xq21 |
| 2619 | 99-12271-298 | Xp11.3–p11.4 |
| 2620 | 99-12275-214 | Xp11.3–p11.4 |
| 2621 | 99-12299-433 | X |
| 2622 | 99-12303-460 | X |
| 2623 | 99-12335-394 | Xq21.1–Xq21.3 |
| 2624 | 99-12338-83 | Xq21.1–Xq21.3 |
| 2625 | 99-12344-171 | Xq21.1–Xq21.3 |
| 2626 | 99-12347-490 | Xp11.23–11.4 |
| 2627 | 99-12348-74 | Xp11.23–11.4 |
| 2628 | 99-12352-124 | Xp11.23–11.4 |
| 2629 | 99-12356-272 | Xp11.23–11.4 |
| 2630 | 99-12361-88 | Xp11.4 |
| 2631 | 99-12368-335 | Xp11.4 |
| 2632 | 99-12370-67 | Xp11.4 |
| 2633 | 99-12384-135 | Xq21 |
| 2634 | 99-12388-466 | Xq21 |
| 2635 | 99-12393-326 | Xq21 |
| 2636 | 99-12399-180 | Xq21.1–21.33 |
| 2637 | 99-12412-381 | Xq22 |
| 2638 | 99-12415-509 | Xq22 |
| 2639 | 99-12444-400 | Xq21.1 |
| 2640 | 99-12465-227 | Xq28 |
| 2641 | 99-12468-236 | Xq28 |
| 2642 | 99-12470-288 | Xq28 |
| 2643 | 99-12522-196 | 8p23 |
| 2644 | 99-12561-278 | 8p23 |
| 2645 | 99-12570-265 | 8p23 |
| 2646 | 99-12595-313 | 8p23 |
| 2647 | 99-12596-334 | 8p23 |
| 2648 | 99-12598-191 | 8p23 |
| 2649 | 99-12602-212 | 8p23 |
| 2650 | 99-12605-365 | 8p23 |
| 2651 | 99-12607-384 | 8p23 |
| 2652 | 99-12664-222 | 8p23 |
| 2653 | 99-12696-116 | 8p23 |
| 2654 | 99-12960-443 | 8p23 |
| 2661 | 99-1311-59 | X |
| 2664 | 99-1326-203 | X |
| 2665 | 99-1333-123 | X |
| 2666 | 99-1335-195 | X |
| 2694 | 99-14410-373 | 19q13.1 |
| 2695 | 99-14413-383 | 19q13.1 |
| 2696 | 99-14415-106 | 19q13.1 |
| 2697 | 99-14424-353 | 19q13.1 |
| 2698 | 99-14473-243 | 5q31.2 |
| 2699 | 99-14476-377 | 5q31.2 |
| 2700 | 99-14481-386 | 5q31.2 |
| 2701 | 99-14489-415 | 5q31.2 |
| 2702 | 99-14673-334 | 8p23 |
| 2703 | 99-14705-290 | 8p23 |
| 2704 | 99-14739-205 | 8p23 |
| 2705 | 99-14743-418 | 8p23 |
| 2733 | 99-16422-240 | 15q14 |
| 2734 | 99-16428-275 | 15q14 |
| 2735 | 99-16430-358 | 15q14 |
| 2736 | 99-16432-114 | 15q14 |
| 2797 | 99-19040-395 | 1q42–43 |
| 2798 | 99-19041-87 | 1q42–43 |
| 2799 | 99-19048-487 | 1q42–43 |
| 2800 | 99-19050-251 | 1q42–43 |
| 2801 | 99-19053-241 | 1q24–25 |
| 2802 | 99-19055-264 | 1q24–25 |
| 2803 | 99-19059-347 | 1q24–25 |
| 2804 | 99-19069-44 | 1p35.1–p36.21 |
| 2805 | 99-19095-106 | 1q24 |
| 2806 | 99-19096-317 | 1q24 |
| 2807 | 99-19104-66 | 1q24.1–25.3 |
| 2808 | 99-19105-114 | 1q24.1–25.3 |
| 2809 | 99-19108-156 | 1q24.1–25.3 |
| 2810 | 99-19110-175 | 1q24–25 |
| 2811 | 99-19122-58 | 1q24–25 |
| 2812 | 99-19123-242 | 1q24 |
| 2813 | 99-19130-86 | 1q24 |
| 2814 | 99-19137-156 | 1q32.3.–41 |
| 2815 | 99-19142-245 | 1q32.3.–41 |
| 2816 | 99-19154-146 | 1q32.2–q41 |
| 2817 | 99-19155-75 | 1q32.2–q41 |
| 2818 | 99-19167-269 | 1p34.3–36.13 |
| 2819 | 99-19170-193 | 1p34.3–36.13 |
| 2820 | 99-19171-120 | 1p34.3–36.13 |
| 2821 | 99-19175-150 | 1p34.3–36.13 |
| 2822 | 99-19177-425 | 1q24.1–25.2 |
| 2823 | 99-19178-163 | 1q24.1–25.2 |
| 2824 | 99-19210-502 | 1q32.1–32.3 |
| 2825 | 99-19219-316 | 1q32.1–32.3 |
| 2826 | 99-19220-220 | 1p34.4–36.13 |
| 2827 | 99-19223-238 | 1p34.4–36.13 |
| 2828 | 99-19226-169 | 1p34.4–36.13 |
| 2829 | 99-19228-319 | 1p34.4–36.13 |
| 2830 | 99-19236-409 | 3p13–3p14.2 |
| 2831 | 99-19241-362 | 3p13–3p14.2 |
| 2832 | 99-19242-254 | 3p13–3p14.2 |
| 2833 | 99-19283-172 | 1q32.1–32.3 |
| 2834 | 99-19295-95 | 1 |
| 2835 | 99-19304-270 | 1p36.21–36.33 |
| 2836 | 99-19305-367 | 1p36.21–36.33 |
| 2837 | 99-19309-296 | 1p36.21–36.33 |
| 2838 | 99-19312-34 | 1q24.1–24.3 |
| 2841 | 99-19347-228 | 1q24 |
| 2842 | 99-19348-229 | 1q24 |
| 2843 | 99-19351-360 | 1q24 |
| 2844 | 99-19368-92 | 8q21 |
| 2845 | 99-19375-434 | 8q21 |
| 2846 | 99-19381-249 | 8q21 |
| 2847 | 99-19383-432 | 8q21 |
| 2848 | 99-19384-63 | 8q21 |

TABLE 11-continued

| SEQ ID No | Marker Name | Localization |
| --- | --- | --- |
| 2849 | 99-19418-61 | 7p14–p15 |
| 2850 | 99-19420-86 | 7p14–p15 |
| 2851 | 99-19426-250 | 7p14–p15 |
| 2852 | 99-19431-249 | 7p14–p15 |
| 2853 | 99-19438-261 | 7q31 |
| 2854 | 99-19442-48 | 7q31 |
| 2855 | 99-19444-350 | 7q31 |
| 2856 | 99-19450-440 | 7p15.3–p21 |
| 2857 | 99-19453-250 | 7p15.3–p21 |
| 2858 | 99-19457-182 | 7p15.3–p21 |
| 2859 | 99-19460-346 | 7p21–p22 |
| 2860 | 99-19461-282 | 7p21–p22 |
| 2861 | 99-19464-165 | 7p21–p22 |
| 2862 | 99-19466-406 | 7p21–p22 |
| 2863 | 99-19474-266 | 7p21–p22 |
| 2864 | 99-19475-113 | 7p21–p22 |
| 2865 | 99-19477-208 | 7p21–p22 |
| 2866 | 99-19504-468 | 7q31–q32 |
| 2867 | 99-19528-278 | 7p12–p14 |
| 2868 | 99-19529-118 | 7p12–p14 |
| 2869 | 99-19532-207 | 7p12–p14 |
| 2870 | 99-19538-272 | 7p21 |
| 2871 | 99-19544-329 | 7p21–p22 |
| 2872 | 99-19546-473 | 7p21–p22 |
| 2873 | 99-19550-397 | 7p21–p22 |
| 2874 | 99-19553-52 | 7p21 |
| 2875 | 99-19557-152 | 7p21 |
| 2876 | 99-19560-289 | 7p21 |
| 2877 | 99-19562-227 | 7p21 |
| 2878 | 99-19566-337 | 7q34–q36 |
| 2879 | 99-19568-273 | 7q34–q36 |
| 2880 | 99-19575-299 | 7p15–p21 |
| 2881 | 99-19578-307 | 7p15–p21 |
| 2882 | 99-19580-323 | 7p15–p21 |
| 2883 | 99-19584-352 | 7q21.1–q31.1 |
| 2884 | 99-19588-438 | 7q21.1–q31.1 |
| 2885 | 99-19589-118 | 7q21.1–q31.1 |
| 2886 | 99-19601-95 | 7q21 |
| 2887 | 99-19624-48 | 7q21–q31.1 |
| 2888 | 99-19634-149 | 7q21–q31.1 |
| 2889 | 99-19639-225 | 7q11.23–q21.1 |
| 2890 | 99-19645-339 | 7q11.23–q21.1 |
| 2891 | 99-19650-338 | 7q11 |
| 2892 | 99-19651-133 | 7q11 |
| 2893 | 99-19664-328 | 7p14–p15 |
| 2894 | 99-19673-125 | 7p21–p22 |
| 2895 | 99-19678-269 | 7p21–p22 |
| 2896 | 99-19685-39 | 7q21.2–q31.1 |
| 2897 | 99-19697-304 | 7q21 |
| 2898 | 99-19703-75 | 7q21 |
| 2899 | 99-19705-128 | 7q21 |
| 2900 | 99-19709-299 | 7p14–p15 |
| 2901 | 99-19711-169 | 7p14–p15 |
| 2902 | 99-19722-150 | 7p12–p14 |
| 2903 | 99-19731-244 | 7p12–p14 |
| 2904 | 99-19732-385 | 7p12–p14 |
| 2905 | 99-19736-62 | 7p12–p14 |
| 2906 | 99-19745-330 | 7q22–q31.1 |
| 2907 | 99-19749-158 | 7p11.2–p12 |
| 2908 | 99-19752-88 | 7p11.2–p12 |
| 2909 | 99-19753-300 | 7p11.2–p12 |
| 2910 | 99-19756-85 | 7p11.2–p12 |
| 2911 | 99-19764-177 | 7p14–p15 |
| 2912 | 99-19769-227 | 7p14–p15 |
| 2913 | 99-19780-179 | 7p14–p15 |
| 2914 | 99-19785-140 | 7p14–p15 |
| 2915 | 99-19790-398 | 7p12–p14 |
| 2916 | 99-19791-103 | 7p12–p14 |
| 2917 | 99-19795-199 | 7p12–p14 |
| 2918 | 99-19796-256 | 7p12–p14 |
| 2919 | 99-19807-396 | 7q31 |
| 2920 | 99-19813-55 | 7p14–p15 |
| 2921 | 99-19818-156 | 7p14–p15 |
| 2922 | 99-19826-285 | 7q21 |
| 2923 | 99-19839-223 | 7p15–p21 |
| 2924 | 99-19851-40 | 7q31 |
| 2925 | 99-19858-91 | 7p12–p14 |
| 2926 | 99-19860-68 | 7p12–p14 |
| 2927 | 99-19864-112 | 7p12–p14 |
| 2928 | 99-19871-422 | 7p12–p14 |
| 2929 | 99-19872-136 | 7q31 |
| 2930 | 99-19875-99 | 7q31 |
| 2931 | 99-19876-394 | 7q31 |
| 2932 | 99-19890-235 | 7q11.23–q21.1 |
| 2933 | 99-19896-142 | 7p13–p14 |
| 2934 | 99-19901-383 | 7p13–p14 |
| 2935 | 99-19906-136 | 7p21 |
| 2936 | 99-19911-90 | 7p21 |
| 2937 | 99-19916-380 | 7p21 |
| 2938 | 99-19922-42 | 7q22–q31.1 |
| 2939 | 99-19923-383 | 7q22–q31.1 |
| 2940 | 99-19933-251 | 7p15–p21 |
| 2941 | 99-19937-235 | 7p15–p21 |
| 2942 | 99-19944-306 | 7q21–q22 |
| 2943 | 99-19951-313 | 7q21–q22 |
| 2959 | 99-21181-413 | 12q24 |
| 2960 | 99-21192-164 | 12q24 |
| 2962 | 99-21229-81 | Xq26.1–27.2 |
| 2963 | 99-21240-419 | 1q24 |
| 2964 | 99-21242-57 | 1q24 |
| 2965 | 99-21244-495 | 1q24 |
| 2966 | 99-21252-77 | Xp22.11–22.32 |
| 2967 | 99-21267-111 | Xq21.1–21.33 |
| 2969 | 99-21293-252 | 7p15–p21 |
| 2970 | 99-21307-370 | 5q31 |
| 2971 | 99-21310-416 | 5q31 |
| 2972 | 99-21312-319 | 5q31 |
| 2973 | 99-21323-142 | 16p12 |
| 2974 | 99-21327-94 | 4 |
| 2975 | 99-21328-173 | 4 |
| 2976 | 99-21329-518 | 4 |
| 2977 | 99-21342-350 | 7p15 |
| 2978 | 99-21346-290 | Xq23 |
| 2979 | 99-21360-343 | 22q11.2 |
| 2980 | 99-21361-97 | 22q11.2 |
| 2981 | 99-21377-73 | 22q11.2 |
| 2982 | 99-21378-303 | 22q11.2 |
| 2983 | 99-21391-418 | 22q11.2 |
| 2984 | 99-21401-117 | 22q11.2 |
| 2985 | 99-21423-302 | 22q11.2 |
| 2986 | 99-21433-238 | 22q11.2 |
| 2987 | 99-21441-420 | 22q11.2 |
| 2988 | 99-21444-227 | 22q11.2 |
| 2989 | 99-21448-361 | 22q11.2 |
| 2990 | 99-21461-375 | 22q12.1-qter |
| 2991 | 99-21463-258 | 22q12.1-qter |
| 2992 | 99-21465-58 | 22q12.1-qter |
| 2993 | 99-21486-88 | 17 |
| 2994 | 99-21492-310 | 17 |
| 2995 | 99-21502-211 | 17 |
| 2996 | 99-21508-131 | 17 |
| 2997 | 99-21510-466 | 17 |
| 2998 | 99-21512-165 | 17 |
| 2999 | 99-21516-293 | 17 |
| 3000 | 99-21533-445 | 17 |
| 3001 | 99-21560-376 | 19p12 |
| 3002 | 99-21561-41 | 19p12 |
| 3003 | 99-21566-152 | 19p12 |
| 3004 | 99-21578-105 | 17 |
| 3005 | 99-21580-141 | 17 |
| 3006 | 99-21591-181 | 22q11.2 |
| 3007 | 99-21592-43 | 22q11.2 |
| 3008 | 99-21607-114 | 22q11.2 |
| 3009 | 99-21615-133 | 22q11.2 |
| 3010 | 99-21657-161 | 17 |
| 3011 | 99-21664-278 | 17 |
| 3012 | 99-21666-96 | 17 |
| 3013 | 99-21673-106 | 17 |
| 3014 | 99-21674-245 | 17 |
| 3015 | 99-21687-313 | 21q22.2 |
| 3016 | 99-21690-162 | 21q22.2 |
| 3017 | 99-21693-368 | 21q22.2 |
| 3018 | 99-21699-149 | 21q22.2 |
| 3019 | 99-21703-36 | 21 |

TABLE 11-continued

| SEQ ID No | Marker Name | Localization |
|---|---|---|
| 3020 | 99-21705-306 | 21 |
| 3021 | 99-21707-429 | 21 |
| 3022 | 99-21710-272 | 21 |
| 3023 | 99-21733-323 | 21q22.3 |
| 3024 | 99-21734-183 | 21q22.3 |
| 3025 | 99-21742-337 | 21q22.3 |
| 3026 | 99-21745-455 | 21q22.3 |
| 3027 | 99-21756-230 | 21q22.3 |
| 3028 | 99-21759-21 | 21q22.3 |
| 3029 | 99-21762-135 | 21q22.3 |
| 3030 | 99-21763-52 | 21q22.3 |
| 3031 | 99-21765-111 | 22q11.2–12.2 |
| 3032 | 99-21767-392 | 22q11.2–12.2 |
| 3033 | 99-21771-144 | 22q11.2–12.2 |
| 3034 | 99-21775-466 | 22q12 |
| 3035 | 99-21787-348 | 22q12.1–12.3 |
| 3036 | 99-21790-161 | 22q12.1–12.3 |
| 3037 | 99-21791-364 | 22q12.1–12.3 |
| 3038 | 99-21800-310 | 22q11.2–12.1 |
| 3039 | 99-21801-123 | 22q11.2–12.1 |
| 3040 | 99-21804-310 | 22q11.2–12.1 |
| 3041 | 99-21810-222 | 22q11.2–12.1 |
| 3042 | 99-21811-209 | 22q13.31–13.32 |
| 3043 | 99-21827-155 | 22q13.31–13.32 |
| 3044 | 99-21829-261 | 22q13.31–33 |
| 3045 | 99-21831-311 | 22q13.31–33 |
| 3046 | 99-21838-153 | 22q13.31–33 |
| 3047 | 99-21844-165 | 22q12.1 |
| 3048 | 99-21846-327 | 22q12.1 |
| 3049 | 99-21874-311 | 20 |
| 3050 | 99-21880-331 | 20 |
| 3051 | 99-21881-152 | 20 |
| 3052 | 99-21889-219 | 20p12 |
| 3053 | 99-21893-388 | 20p12 |
| 3054 | 99-21896-345 | 20p12 |
| 3055 | 99-21898-102 | 20p12 |
| 3056 | 99-21901-331 | 20p12 |
| 3057 | 99-21913-483 | 20p12 |
| 3058 | 99-21916-359 | 22q12.1–12.3 |
| 3059 | 99-21917-84 | 22q12.1–12.3 |
| 3060 | 99-21919-38 | 22q12.1–12.3 |
| 3061 | 99-21921-338 | 22q12.1–12.3 |
| 3062 | 99-21943-413 | 20q12–13.12 |
| 3063 | 99-21948-237 | 20q12–13.12 |
| 3064 | 99-21950-107 | 20q12–13.12 |
| 3065 | 99-21952-76 | 20q12–13.2 |
| 3066 | 99-21968-150 | 20q12–13.1 |
| 3067 | 99-21969-425 | 20q12–13.1 |
| 3079 | 99-22363-268 | X |
| 3080 | 99-22375-353 | X |
| 3081 | 99-22405-335 | 16p13.11 |
| 3106 | 99-23442-190 | 2q34–q35 |
| 3107 | 99-23544-340 | 10q25 |
| 3108 | 99-23549-78 | 10q25 |
| 3109 | 99-23558-98 | 10q25 |
| 3110 | 99-23565-252 | 10q25 |
| 3111 | 99-23589-198 | 10 |
| 3112 | 99-23590-205 | 10 |
| 3113 | 99-23621-189 | 10 |
| 3114 | 99-23641-159 | 10 |
| 3115 | 99-23652-244 | 10 |
| 3122 | 99-23736-314 | 5q13 |
| 3123 | 99-23813-476 | 12q13.1 |
| 3124 | 99-23821-176 | 12q13.1 |
| 3125 | 99-23844-382 | 12q24 |
| 3126 | 99-23858-51 | 12q13.1 |
| 3127 | 99-23860-146 | 12q13.1 |
| 3128 | 99-23876-265 | 2 |
| 3129 | 99-23878-400 | 2 |
| 3130 | 99-23880-268 | 2 |
| 3131 | 99-23887-103 | 12q24 |
| 3132 | 99-23889-342 | 12q24 |
| 3133 | 99-23894-339 | 12q13 |
| 3134 | 99-23895-40 | 12q13 |
| 3135 | 99-23902-103 | 12q24.1 |
| 3136 | 99-23912-116 | 12q24.1 |
| 3137 | 99-23915-69 | 12q24.1 |
| 3138 | 99-23918-179 | 12q24.1 |
| 3139 | 99-23934-353 | 12p13.3 |
| 3140 | 99-23936-216 | 12p13.3 |
| 3141 | 99-23938-414 | 12p13.3 |
| 3142 | 99-23943-245 | 12p13.3 |
| 3143 | 99-23960-298 | 12 |
| 3144 | 99-23965-360 | 12 |
| 3145 | 99-23977-141 | 13q12–13 |
| 3146 | 99-23987-115 | 13q12–13 |
| 3147 | 99-23988-441 | 13q12–13 |
| 3148 | 99-23995-407 | 4q25 |
| 3149 | 99-24000-316 | 4q25 |
| 3150 | 99-24003-172 | 4p16 |
| 3151 | 99-24004-200 | 4p16 |
| 3152 | 99-24007-362 | 4p16 |
| 3153 | 99-24020-379 | 4 |
| 3154 | 99-24038-103 | 4 |
| 3155 | 99-24063-363 | 4 |
| 3156 | 99-24073-384 | 4 |
| 3157 | 99-24075-45 | 4 |
| 3158 | 99-24079-268 | 4 |
| 3159 | 99-24084-110 | 4 |
| 3160 | 99-24092-209 | 4 |
| 3161 | 99-24096-386 | 4 |
| 3162 | 99-24105-247 | 4 |
| 3163 | 99-24113-332 | 4 |
| 3164 | 99-24117-169 | 4 |
| 3165 | 99-24119-368 | 4 |
| 3166 | 99-24123-125 | 4 |
| 3167 | 99-24140-394 | 4 |
| 3168 | 99-24148-332 | 4 |
| 3169 | 99-24152-268 | 4 |
| 3170 | 99-24155-271 | 4 |
| 3171 | 99-24156-107 | 4 |
| 3172 | 99-24167-85 | 4 |
| 3173 | 99-24175-218 | 4 |
| 3174 | 99-24180-390 | 4 |
| 3175 | 99-24182-326 | 4q25 |
| 3176 | 99-24185-446 | 4q25 |
| 3177 | 99-24187-142 | 4q25 |
| 3178 | 99-24190-231 | 4q25 |
| 3179 | 99-24202-433 | 4q25 |
| 3180 | 99-24204-486 | 4 |
| 3181 | 99-24208-292 | 4 |
| 3182 | 99-24210-111 | 4 |
| 3183 | 99-24217-206 | 4 |
| 3184 | 99-24225-439 | 4 |
| 3185 | 99-24228-386 | 4 |
| 3186 | 99-24232-419 | 4 |
| 3187 | 99-24234-352 | 4 |
| 3191 | 99-2441-512 | 1q21.1–q21.2 |
| 3206 | 99-24855-180 | 6q21 |
| 3207 | 99-24863-199 | 6q21 |
| 3208 | 99-24867-219 | 6q27 |
| 3209 | 99-24871-435 | 6q27 |
| 3210 | 99-24889-311 | 4 |
| 3211 | 99-24897-276 | 4q25 |
| 3212 | 99-24904-187 | 4q25 |
| 3213 | 99-24909-440 | 22q11.2 |
| 3214 | 99-24917-250 | 7q22–q31 |
| 3215 | 99-24930-299 | 17 |
| 3216 | 99-24936-332 | 17 |
| 3217 | 99-24965-416 | 11p15.5 |
| 3218 | 99-24966-423 | 11p15.5 |
| 3251 | 99-2726-364 | 21 |
| 3252 | 99-2734-400 | 21q22.2 |
| 3253 | 99-2740-351 | 17 |
| 3254 | 99-2752-213 | 17 |
| 3255 | 99-2760-182 | 21 |
| 3256 | 99-2761-223 | 21 |
| 3257 | 99-2765-279 | 21 |
| 3258 | 99-2790-217 | 21 |
| 3259 | 99-2797-399 | 21 |
| 3260 | 99-2816-62 | 21 |
| 3261 | 99-2817-88 | 21 |
| 3262 | 99-2819-108 | 21 |
| 3263 | 99-2820-199 | 21 |

TABLE 11-continued

| SEQ ID No | Marker Name | Localization |
|---|---|---|
| 3264 | 99-2832-152 | 21 |
| 3267 | 99-2881-61 | 22q12 |
| 3268 | 99-2895-47 | 7q21–7q22 |
| 3269 | 99-2903-265 | 7q21–7q22 |
| 3270 | 99-2906-80 | 7q21–7q22 |
| 3271 | 99-2914-48 | 7q21–7q22 |
| 3272 | 99-2922-171 | 7q21–7q22 |
| 3273 | 99-2924-183 | 7q21–7q22 |
| 3274 | 99-2926-184 | 7q21–7q22 |
| 3275 | 99-2928-52 | 7q21–7q22 |
| 3276 | 99-2938-83 | 7q31.2 |
| 3277 | 99-2943-230 | 13q12–13q13 |
| 3278 | 99-2944-351 | 13q12–13q13 |
| 3279 | 99-295-355 | 8 |
| 3280 | 99-2954-160 | 3p21.3 |
| 3281 | 99-2956-239 | 3p21.3 |
| 3282 | 99-2970-318 | 7q21–7q22 |
| 3283 | 99-2978-135 | 7q21–7q22 |
| 3284 | 99-2981-53 | 7q21–7q22 |
| 3285 | 99-2988-243 | 7q31–q32 |
| 3286 | 99-2989-345 | 7q31–q32 |
| 3287 | 99-2991-256 | 7q31–q32 |
| 3288 | 99-2995-168 | 7q31–q32 |
| 3289 | 99-2999-371 | 7q31–q32 |
| 3290 | 99-3013-250 | Xq23 |
| 3291 | 99-3018-50 | Xq23 |
| 3292 | 99-3019-316 | Xq23 |
| 3293 | 99-3020-369 | Xq23 |
| 3294 | 99-3021-290 | Xq23 |
| 3295 | 99-3044-216 | 5p15.2 |
| 3296 | 99-3045-108 | 5p15.2 |
| 3297 | 99-3046-91 | 5p15.2 |
| 3298 | 99-3047-395 | 5p15.2 |
| 3299 | 99-3058-420 | 7q22 |
| 3301 | 99-3061-369 | 7q22 |
| 3302 | 99-3106-272 | 7q22 |
| 3303 | 99-3108-156 | 7q22 |
| 3304 | 99-3109-402 | 7q22 |
| 3305 | 99-3110-321 | 7q22 |
| 3306 | 99-312-311 | 8q24 |
| 3307 | 99-3129-113 | 19 |
| 3308 | 99-3132-158 | 19 |
| 3309 | 99-3144-112 | 19 |
| 3310 | 99-3147-24 | 19 |
| 3311 | 99-3153-190 | 19 |
| 3312 | 99-3154-110 | 19 |
| 3313 | 99-3156-251 | 19 |
| 3314 | 99-3167-227 | 19 |
| 3315 | 99-3195-71 | 10q25-qter |
| 3316 | 99-3217-274 | Xp22.1 |
| 3317 | 99-3224-232 | Xp22.1 |
| 3318 | 99-3231-109 | Xp22.1 |
| 3319 | 99-3234-274 | Xp22.1 |
| 3320 | 99-325-226 | 8q24.3 |
| 3321 | 99-3266-193 | 4p16.3 |
| 3322 | 99-3276-195 | 22q11.2-qter |
| 3323 | 99-3279-337 | 4p16.3 |
| 3324 | 99-3293-300 | 4p16.3 |
| 3325 | 99-3296-101 | 4p16.3 |
| 3326 | 99-3299-211 | 4p16.3 |
| 3327 | 99-3305-272 | 22q11.2-qter |
| 3328 | 99-3335-53 | 4p16.3 |
| 3329 | 99-3337-294 | 4p16.3 |
| 3330 | 99-3342-103 | 4p16.3 |
| 3331 | 99-3347-226 | 22q11.2-qter |
| 3332 | 99-3349-124 | 22 |
| 3333 | 99-3353-350 | 22q11.2-qter |
| 3334 | 99-3356-345 | 22q11.2-qter |
| 3335 | 99-3368-277 | 4p16.3 |
| 3336 | 99-3373-253 | 4p16.3 |
| 3337 | 99-3374-274 | 4p16.3 |
| 3338 | 99-3385-197 | 16p13.3 |
| 3339 | 99-3390-328 | 16p13.3 |
| 3340 | 99-3391-160 | 16p13.3 |
| 3341 | 99-3393-245 | 22q11.2-qter |
| 3342 | 99-3398-196 | 4p16.3 |
| 3343 | 99-3399-449 | 4p16.3 |
| 3344 | 99-3400-83 | 4p16.3 |
| 3345 | 99-3414-112 | 22q11.2-qter |
| 3346 | 99-3415-215 | 22q11.2-qter |
| 3347 | 99-3426-270 | 4p16.3 |
| 3348 | 99-3428-366 | 4p16.3 |
| 3349 | 99-3445-239 | 22q11.2-qter |
| 3350 | 99-3453-138 | 22q11.2-qter |
| 3351 | 99-3460-337 | 22q12 |
| 3352 | 99-3462-117 | 13q12–13 |
| 3353 | 99-3468-272 | 13q12–13 |
| 3354 | 99-3469-313 | 13q12–13 |
| 3355 | 99-3473-309 | 13q12–13 |
| 3356 | 99-3474-272 | 13q12–13 |
| 3357 | 99-3478-199 | 22 |
| 3358 | 99-3479-293 | 22 |
| 3359 | 99-3482-225 | 22q11.2-qter |
| 3360 | 99-3483-252 | 22q11.2-qter |
| 3361 | 99-3485-245 | 22q11.2-qter |
| 3362 | 99-3511-130 | 4p16.3 |
| 3363 | 99-3519-374 | 13q12–13 |
| 3364 | 99-3522-210 | 13q12–13 |
| 3365 | 99-3523-270 | 13q12–13 |
| 3366 | 99-3524-403 | 13q12–13 |
| 3367 | 99-3542-336 | 13q12–13 |
| 3368 | 99-3556-129 | 13q12–13 |
| 3369 | 99-3563-121 | 22 |
| 3370 | 99-3580-122 | 22 |
| 3371 | 99-3588-188 | 22q12 |
| 3372 | 99-3589-203 | 22q12-qter |
| 3373 | 99-3596-147 | 22q12 |
| 3374 | 99-36-69 | 1q23 |
| 3375 | 99-3601-226 | 22q12 |
| 3376 | 99-3603-80 | 22q12 |
| 3377 | 99-3604-91 | 22q12 |
| 3378 | 99-3619-330 | 22q12 |
| 3379 | 99-3620-314 | 22q12 |
| 3380 | 99-3628-31 | 6p21.3 |
| 3381 | 99-3629-219 | 6p21.3 |
| 3382 | 99-3631-159 | 6p21.3 |
| 3383 | 99-3638-259 | 22 |
| 3384 | 99-3641-230 | 22 |
| 3385 | 99-3666-280 | 16p13.3 |
| 3386 | 99-3667-190 | 16p13.3 |
| 3387 | 99-3677-196 | 22q11.2-qter |
| 3388 | 99-3680-274 | 22q11.2-qter |
| 3389 | 99-3689-50 | 22q12 |
| 3390 | 99-3690-355 | 22q12 |
| 3391 | 99-3699-230 | 22q12 |
| 3392 | 99-3702-226 | 22q12 |
| 3393 | 99-3703-331 | 22q12 |
| 3394 | 99-3705-195 | X |
| 3395 | 99-3709-366 | X |
| 3396 | 99-3717-68 | 22 |
| 3397 | 99-3728-341 | 11 |
| 3398 | 99-3739-215 | 22 |
| 3399 | 99-3746-337 | 6p21.3 |
| 3400 | 99-3749-174 | 6p21.3 |
| 3401 | 99-3752-210 | 6p21.3 |
| 3402 | 99-3760-59 | 6q21 |
| 3403 | 99-3761-329 | 6q21 |
| 3404 | 99-3764-198 | 6q21 |
| 3405 | 99-3765-279 | 6q21 |
| 3407 | 99-3773-337 | 6p21.3 |
| 3408 | 99-3774-351 | 6p21.3 |
| 3409 | 99-3775-98 | 6p21.3 |
| 3410 | 99-3778-97 | 13q12–13 |
| 3411 | 99-3789-293 | 3q12–13 |
| 3412 | 99-3792-294 | 16p13.3 |
| 3413 | 99-3802-197 | 13q12–13 |
| 3414 | 99-3805-125 | 13q12–13 |
| 3415 | 99-3812-243 | 22 |
| 3416 | 99-3813-122 | 22 |
| 3417 | 99-3857-261 | 17q22–q24 |
| 3418 | 99-3862-153 | 17q22–q24 |
| 3419 | 99-3875-138 | 8p12–q11.2 |
| 3420 | 99-3888-309 | Xp21.2 |
| 3421 | 99-3893-108 | 12q13 |

TABLE 11-continued

| SEQ ID No | Marker Name | Localization |
|---|---|---|
| 3424 | 99-3953-77 | 19q13.2–13.3 |
| 3425 | 99-3954-362 | 19q13.2–13.3 |
| 3426 | 99-3978-146 | X |
| 3427 | 99-3981-156 | X |
| 3428 | 99-3992-185 | 17q21 |
| 3429 | 99-4001-330 | 20q13.2-qter |
| 3430 | 99-4009-232 | 4q11–22 |
| 3431 | 99-4025-300 | 12pter–p12 |
| 3432 | 99-4052-415 | 6p25–p24 |
| 3433 | 99-4064-346 | Xp21.3–p21.1 |
| 3434 | 99-4065-20 | 11p15.5 |
| 3435 | 99-4073-307 | 11p15.5 |
| 3436 | 99-4076-255 | 22q11 |
| 3437 | 99-4077-230 | 22q11 |
| 3438 | 99-4078-212 | 22q11 |
| 3439 | 99-4079-389 | 22q11 |
| 3440 | 99-4119-307 | 10 |
| 3441 | 99-4120-253 | 10 |
| 3442 | 99-4122-23 | 16p13.13–13.2 |
| 3443 | 99-4125-192 | 16p13.13–13.2 |
| 3445 | 99-4138-360 | 12q24-qter |
| 3446 | 99-4139-128 | 12q24-qter |
| 3447 | 99-4140-254 | 12q24-qter |
| 3448 | 99-4182-113 | 12p13 |
| 3449 | 99-4193-384 | 1 |
| 3450 | 99-4194-336 | 1 |
| 3451 | 99-4199-339 | 4q |
| 3452 | 99-4201-501 | 4q |
| 3453 | 99-4202-223 | 11p15 |
| 3454 | 99-4203-110 | 11p15 |
| 3455 | 99-4207-210 | 22q12 |
| 3456 | 99-4218-24 | 22q12 |
| 3457 | 99-4220-241 | 22q12 |
| 3458 | 99-4225-339 | X |
| 3459 | 99-4231-139 | 17p13.3 |
| 3460 | 99-4232-105 | 17p13.3 |
| 3461 | 99-4233-261 | 12p12–13 |
| 3462 | 99-4238-181 | Xp21.2 |
| 3463 | 99-4251-311 | 12p12–13 |
| 3466 | 99-4283-257 | 19q13.1 |
| 3467 | 99-4284-200 | 12p12–p13 |
| 3468 | 99-4285-370 | 12p12–p13 |
| 3469 | 99-4290-131 | 12p12–13 |
| 3470 | 99-4293-344 | 12p12–13 |
| 3471 | 99-4296-156 | 8q24 |
| 3472 | 99-4312-338 | 4q11–12 |
| 3473 | 99-4323-311 | 5q33.3–q34 |
| 3474 | 99-4325-87 | 11q24 |
| 3475 | 99-4332-136 | 3p14.2 |
| 3476 | 99-4335-371 | 3p14.2 |
| 3477 | 99-4336-171 | 3p14.2 |
| 3478 | 99-4337-369 | 3p14.2 |
| 3479 | 99-4339-180 | 3p14.2 |
| 3481 | 99-4364-360 | Xp22 |
| 3482 | 99-4398-167 | 13q12–13q13 |
| 3483 | 99-4399-228 | 13q12–13q13 |
| 3484 | 99-4404-384 | Xp22.1–22.2 |
| 3485 | 99-4406-115 | Xp22.1–22.2 |
| 3486 | 99-4435-203 | 12p13 |
| 3487 | 99-4448-174 | 16p13.11 |
| 3488 | 99-4455-357 | 16p13.11 |
| 3489 | 99-4458-59 | 16p13.11 |
| 3490 | 99-4467-39 | 16p13 |
| 3491 | 99-4468-130 | 16p13 |
| 3492 | 99-4483-333 | 12p15 |
| 3494 | 99-4567-424 | 19 |
| 3495 | 99-4575-226 | 19 |
| 3496 | 99-4580-296 | 19 |
| 3535 | 99-515-151 | 21q22 |
| 3540 | 99-5329-269 | 6p12 |
| 3541 | 99-5339-196 | 6p12 |
| 3542 | 99-5347-394 | 1q43 |
| 3543 | 99-5397-353 | 1q43 |
| 3602 | 99-7086-91 | 10q26.2 |
| 3638 | 99-824-359 | 13 |
| 3647 | 99-882-250 | 1q23 |
| 3648 | 99-887-344 | 1q23 |
| 3650 | 99-892-77 | 1q23 |
| 3653 | 99-896-83 | 1q23 |
| 3654 | 99-899-252 | 6 |
| 3662 | 99-9308-416 | 5q31.3 |
| 3669 | 99-9607-402 | 1 |
| 3670 | 99-9620-241 | 1 |
| 3671 | 99-9623-330 | 1 |
| 3672 | 99-9633-32 | 1 |
| 3673 | 99-9636-423 | 1 |
| 3674 | 99-9658-42 | 1p35.2–36.13 |
| 3675 | 99-9662-213 | 1p35.2–36.13 |
| 3676 | 99-9666-363 | 1p35.2–36.13 |
| 3677 | 99-9668-185 | 1p35.2–36.13 |
| 3678 | 99-9680-363 | 1q23–25 |
| 3679 | 99-9696-292 | 1q24 |
| 3680 | 99-9697-375 | 1q24 |
| 3681 | 99-9700-289 | 1q24 |
| 3682 | 99-9704-445 | 1q24 |
| 3683 | 99-9706-448 | 1q24 |
| 3684 | 99-9709-115 | 1q24 |
| 3685 | 99-9710-242 | 1q24 |
| 3686 | 99-9714-302 | 1p36.13–36.22 |
| 3687 | 99-9717-449 | 1p36.13–36.22 |
| 3688 | 99-9726-190 | 1p36.21 |
| 3690 | 99-9745-284 | 1q23–24 |
| 3691 | 99-9751-134 | 1q24–q25 |
| 3692 | 99-9765-237 | 1p36.12–36.13 |
| 3693 | 99-9774-392 | 1p36.12–36.13 |
| 3694 | 99-9778-360 | 1p36.12–36.13 |
| 3695 | 99-9781-174 | 1p36.12–36.13 |
| 3696 | 99-9785-141 | 1q23.1–24.3 |
| 3697 | 99-9810-257 | 1p36.2–36.3 |
| 3698 | 99-9811-369 | 1p36.2–36.3 |
| 3699 | 99-9820-483 | 1p36.2–36.3 |
| 3700 | 99-9822-257 | 1p36.2–36.3 |
| 3701 | 99-9829-367 | 1q24–1q25 |
| 3702 | 99-983-278 | 11 |
| 3703 | 99-9832-128 | 1q24–1q25 |
| 3704 | 99-9833-167 | 1q24–1q25 |
| 3705 | 99-9835-217 | 1q24–1q25 |
| 3706 | 99-9837-275 | 1q23–1q24 |
| 3707 | 99-9839-416 | 1q23–1q24 |
| 3708 | 99-9840-192 | 1q23–1q24 |
| 3709 | 99-9847-25 | 2q1 |
| 3710 | 99-9849-291 | 2q1 |
| 3711 | 99-9852-276 | 2q1 |
| 3712 | 99-9854-316 | 2q1 |
| 3713 | 99-9856-252 | 3 |
| 3714 | 99-9859-132 | 3 |
| 3715 | 99-9866-365 | 3 |
| 3716 | 99-990-356 | 11 |
| 3717 | 99-9906-280 | 4q25 |
| 3718 | 99-9908-423 | 4q25 |
| 3719 | 99-991-157 | 16p13.11 |
| 3720 | 99-9915-281 | 4q25 |
| 3721 | 99-9920-245 | 4q25 |
| 3722 | 99-9921-365 | 4q25 |
| 3723 | 99-9922-154 | 4q25 |
| 3724 | 99-9926-454 | 4q25 |
| 3725 | 99-9928-454 | 4q25 |
| 3726 | 99-9929-144 | 4q25 |
| 3727 | 99-9935-418 | 4q25 |
| 3728 | 99-9941-426 | 4q25 |
| 3729 | 99-995-251 | 16p13.11 |
| 3730 | 99-996-210 | 16p13 |
| 3731 | 99-9986-202 | 4q25 |
| 3732 | 99-9988-111 | 4q25 |
| 3733 | 99-9994-226 | 4q25 |
| 3734 | 99-9995-50 | 4q25 |
| 3735 | 99-10069-366 | 4q25 |
| 3736 | 99-10074-266 | 4q25 |
| 3737 | 99-10129-177 | 4q25 |
| 3738 | 99-10198-271 | 4q25 |
| 3739 | 99-10306-345 | 5q |
| 3740 | 99-10307-115 | 5q |
| 3741 | 99-10326-149 | 6p22.2–22.3 |
| 3742 | 99-10393-179 | 6p22.3–24.1 |

TABLE 11-continued

| SEQ ID No | Marker Name | Localization |
|---|---|---|
| 3743 | 99-10685-454 | 6p24 |
| 3744 | 99-10857-217 | 7q31 |
| 3745 | 99-10948-281 | 7p15–p21 |
| 3746 | 99-11104-329 | 7p15–p21 |
| 3747 | 99-11116-199 | 8q21 |
| 3748 | 99-11117-282 | 8q21 |
| 3749 | 99-11121-461 | 8q21 |
| 3750 | 99-11124-363 | 8q21 |
| 3751 | 99-11172-373 | 11p11.2 |
| 3752 | 99-11206-379 | 11p14.3 |
| 3753 | 99-11303-223 | 15 |
| 3754 | 99-11307-168 | 15 |
| 3755 | 99-11325-188 | 16p11.2 |
| 3756 | 99-11365-273 | 16p11.2–p12 |
| 3757 | 99-11389-268 | 6p12.2–p12 |
| 3758 | 99-11395-376 | 16p12.2–p12 |
| 3759 | 99-11500-50 | 16p13.2–13.3 |
| 3760 | 99-11571-88 | 17 |
| 3761 | 99-11710-452 | 17 |
| 3762 | 99-1173-208 | 17 |
| 3763 | 99-11735-215 | 17 |
| 3764 | 99-11864-218 | 22 |
| 3765 | 99-1187-293 | 6 |
| 3766 | 99-11872-228 | 22 |
| 3767 | 99-11878-212 | 22q12–13 |
| 3768 | 99-11905-202 | 22q12-qter |
| 3769 | 99-11932-48 | 22q12.1 |
| 3770 | 99-11964-158 | 22 |
| 3771 | 99-12164-412 | X |
| 3772 | 99-12227-278 | Xq23 |
| 3773 | 99-12417-447 | Xq22 |
| 3774 | 99-12459-119 | Xq28 |
| 3775 | 99-12521-212 | 8p23 |
| 3776 | 99-12569-95 | 8p23 |
| 3777 | 99-1298-430 | X |
| 3778 | 99-1315-105 | X |
| 3783 | 99-14899-215 | 8p23.1 |
| 3789 | 99-19212-369 | 1q32.1–32.3 |
| 3790 | 99-19273-219 | 1p36.1–36.2 |
| 3791 | 99-19279-356 | 1q32.1–32.3 |
| 3792 | 99-19541-172 | 7p21 |
| 3793 | 99-19552-214 | 7p21–p22 |
| 3795 | 99-21246-20 | 1q24 |
| 3796 | 99-21387-465 | 22q11.2 |
| 3797 | 99-21407-352 | 22q11.2 |
| 3798 | 99-21418-83 | 22q11.2 |
| 3799 | 99-21419-85 | 22q11.2 |
| 3800 | 99-21430-308 | 22q11.2 |
| 3801 | 99-21435-96 | 22q11.2 |
| 3802 | 99-21446-240 | 22q11.2 |
| 3803 | 99-21452-173 | 22q11.2 |
| 3804 | 99-21488-376 | 17 |
| 3805 | 99-21489-227 | 17 |
| 3806 | 99-21496-248 | 17 |
| 3807 | 99-21519-446 | 17 |
| 3808 | 99-21618-178 | 22q11.2 |
| 3809 | 99-21725-371 | 21q22.3 |
| 3810 | 99-21773-155 | 22q12 |
| 3811 | 99-21781-252 | 22q12 |
| 3812 | 99-21820-230 | 22q13.31–13.32 |
| 3813 | 99-21822-50 | 22q13.31–13.32 |
| 3814 | 99-21939-170 | 20q12–13.12 |
| 3815 | 99-22404-59 | 16p13.11 |
| 3820 | 99-23568-395 | 10 |
| 3821 | 99-23824-339 | 12q13.1 |
| 3822 | 99-23969-316 | 12 |
| 3823 | 99-24032-138 | 4 |
| 3824 | 99-24048-286 | 4 |
| 3825 | 99-24074-190 | 4 |
| 3826 | 99-24082-408 | 4 |
| 3827 | 99-24104-308 | 4 |
| 3828 | 99-24138-224 | 4 |
| 3829 | 99-24172-116 | 4 |
| 3831 | 99-24949-289 | 17 |
| 3833 | 99-2694-411 | 1q43 |
| 3834 | 99-2697-336 | 1q43 |
| 3836 | 99-2851-105 | 1p13.3 |
| 3837 | 99-2889-197 | 22q13 |
| 3838 | 99-3072-323 | 7q21–7q22 |
| 3839 | 99-3089-49 | 7q21–7q22 |
| 3840 | 99-3157-203 | 19 |
| 3841 | 99-3210-341 | Xp22.1 |
| 3842 | 99-3218-344 | Xp22.1 |
| 3843 | 99-3251-254 | 4p16.3 |
| 3844 | 99-3298-158 | 4p16.3 |
| 3845 | 99-3300-433 | 22q11.2-qter |
| 3846 | 99-3364-247 | 22q11.2-qter |
| 3847 | 99-3427-271 | 4p16.3 |
| 3848 | 99-3484-96 | 22q11.2-qter |
| 3849 | 99-3537-196 | 22q12 |
| 3850 | 99-3568-156 | 22q12 |
| 3851 | 99-3592-325 | 22q12-qter |
| 3852 | 99-3602-245 | 22q12 |
| 3853 | 99-3608-264 | 22q11.2-qter |
| 3854 | 99-3643-352 | 9q34 |
| 3855 | 99-3770-363 | 6p21.3 |
| 3856 | 99-3772-266 | 6p21.3 |
| 3857 | 99-3790-361 | 13q12–13 |
| 3858 | 99-3818-255 | 22 |
| 3859 | 99-3863-328 | 7q22–q24 |
| 3860 | 99-3879-245 | 17q11.2 |
| 3861 | 99-3882-312 | 17q11.2 |
| 3862 | 99-3883-329 | 17q11.2 |
| 3863 | 99-3884-355 | 17q11.2 |
| 3864 | 99-3894-333 | 12q13 |
| 3865 | 99-3936-352 | Xq27.3–q28 |
| 3867 | 99-4029-174 | 12pter–p12 |
| 3869 | 99-4102-109 | 9q34 |
| 3870 | 99-4110-180 | 21q22.1 |
| 3871 | 99-4111-259 | 21q22.1 |
| 3872 | 99-4126-366 | 16p13.13–13.2 |
| 3873 | 99-4157-72 | 16p11.1 |
| 3874 | 99-4228-168 | 17p13.3 |
| 3875 | 99-4239-328 | Xp21.2 |
| 3876 | 99-4254-307 | 7q11.23 |
| 3878 | 99-4311-146 | 4q11–12 |
| 3879 | 99-4381-385 | Xq22.1–22.2 |
| 3880 | 99-4403-194 | Xp22.1–22.2 |
| 3881 | 99-4524-296 | 8 |
| 3882 | 99-4582-359 | 19 |
| 3899 | 99-889-153 | 1q23 |
| 3901 | 99-9609-220 | 1p36.2–36.3 |
| 3902 | 99-9612-324 | 1p36.2–36.3 |
| 3903 | 99-9616-136 | 1p36.2–36.3 |
| 3904 | 99-9683-49 | 1q23–25 |
| 3905 | 99-9907-88 | 4q25 |
| 3906 | 99-993-218 | 16p13.11 |
| 3907 | 99-24069-351 | 4 |
| 3908 | 99-3855-279 | 17q22–q24 |
| 3915 | 99-123-381 | 8p23 |
| 3916 | 4-26-29 | 8p23 |
| 3917 | 4-14-240 | 8p23 |
| 3918 | 4-77-151 | 8p23 |
| 3919 | 99-217-277 | 8p23 |
| 3920 | 4-67-40 | 8p23 |
| 3921 | 99-213-164 | 8p23 |
| 3922 | 99-221-377 | 8p23 |
| 3924 | 99-1482-32 | 8p23 |
| 3925 | 4-73-134 | 8p23 |
| 3926 | 4-65-324 | 8p23 |
| 3927 | 10-32-357 | 13q13 |
| 3928 | 10-33-175 | 13q13 |
| 3929 | 10-33-234 | 13q13 |
| 3930 | 10-33-327 | 13q13 |
| 3931 | 10-35-358 | 13q13 |
| 3932 | 10-35-390 | 13q13 |
| 3933 | 10-36-164 | 13q13 |
| 3934 | 10-204-326 | 13q13 |

SEQUENCE LISTING

The patent contains a lengthy "Sequence Listing" section. A copy of the "Sequence Listing" is available in electronic form from the USPTO web site (http://seqdata.uspto.gov/sequence.html?DocID=6537751B1). An electronic copy of the "Sequence Listing" will also be available from the USPTO upon request and payment of the fee set forth in 37 CFR 1.19(b)(3).

What is claimed is:

1. A method of determining whether an individual is at an increased risk for developing Alzheimer's disease comprising:
   (a) obtaining a biological sample comprising a nucleic acid from said individual;
   (b) determining the identity of a biallelic marker at position 24 of SEQ ID NO: 3913 within said biological sample;
   (c) evaluating whether an individual is at increased risk of Alzheimer's disease;
   wherein the presence of a T at position 24 of SEQ ID NO: 3913 is indicative of an increased risk to Alzheimer's disease.

2. A method according to claim 1, wherein the identity of the nucleotides at said biallelic marker is determined for both copies of said biallelic marker present in said subject's genome.

3. A method according to claim 1, further comprising amplifying a portion of said sequence comprising the biallelic marker prior to said determining step.

4. A method according to claim 3, wherein said amplifying is performed by PCR.

5. A method according to claim 3, wherein said determining is performed by a hybridization assay, a sequencing assay, a microsequencing assay, or an enzyme-based mismatch detection assay.

* * * * *

UNITED STATES PATENT AND TRADEMARK OFFICE
CERTIFICATE OF CORRECTION

PATENT NO. : 6,537,751 B1
DATED : March 25, 2003
INVENTOR(S) : Daniel Cohen, Ilya Chumakov and Marta Blumenfeld It is certified that error appears in the above-identified patent and that said Letters Patent is hereby corrected as shown below:

Column 15,
Line 56, "Markers Polynucleotides" should read -- Markers
                                                   Polynucleotides --.

Column 32,
Line 11, "ddNTT's" should read -- ddNTPs --.
Line 13, "(such asp-nitrophenyl" should read -- (such as $p$-nitrophenyl --.

Column 46,
Line 56, "phenotypes" should read -- phenotype $j$ --.

Column 47,
Line 55, "$\theta 4=$—"should read -- $\theta 4 = - - $ --.
Line 57, "$\theta 3=-+$" should read -- $\theta 3 = - + $ --.
Line 59, "$\theta 2=-+$" should read -- $\theta 2 = + - $ --.

Column 48,
Line 32, "with $D_{aiaj}<0$" should read -- with $D_{aiaj}>0$ --.

Column 74,
Line 59, "For % example," should read -- For example, --.

Column 91,
Lines 44-45, "p value<2" should read -- p value $\leq 2$ --.

Column 92,
Line 8, "99-36S-344" should read -- 99-365-344 --.

Column 98,
Line 11, "$5^{E-}03$" should read -- $5^{E}$-03 --.
Line 44, "dNTms" should read -- dNTPs --.

Column 100,
Line 55, "$_{10}$ mM" should read -- 10 mM --.

Column 101,
Line 62, "Markers Sequencing" should read -- "Sequencing"-- should be on a new line.

Columns 103-104,
Table 7, "Haplotype 1    should read    -- Haplotype 1
        5                                  Haplotype 2 --
          Haplotype 2"

UNITED STATES PATENT AND TRADEMARK OFFICE
CERTIFICATE OF CORRECTION

PATENT NO. : 6,537,751 B1
DATED : March 25, 2003
INVENTOR(S) : Daniel Cohen, Ilya Chumakov and Marta Blumenfeld It is certified that error appears in the above-identified patent and that said Letters Patent is hereby corrected as shown below:

<u>Column 104,</u>
Lines 46-47, "Hawley Ma.," should read -- Hawley ME, --.

<u>Column 108,</u>
Sequence ID No 115, "99-12925487" should read -- 99-12925-487 --.

<u>Column 115,</u>
Sequence ID No 623, "99-1582430" should read -- 99-1582-430 --.

<u>Column 116,</u>
Sequence ID No 728, $2^{nd}$ Allele, "j" should read -- T --.

<u>Column 125,</u>
Sequence ID No 1392, "99-2351045" should read -- 99-23510-45 --.

<u>Column 127,</u>
Sequence ID No 1551, "994618-240" should read -- 99-4618-240 --.

<u>Column 128,</u>
Sequence ID No 1579, "994823-173" should read -- 99-4823-173 --.
Sequence ID No 1616, "99-5162461" should read -- 99-5162-461 --.

<u>Column 132,</u>
Sequence ID No 1893, $2^{nd}$ allele, "j" should read -- T --.

<u>Column 137,</u>
Sequence ID No 2284, "99-10155423" should read -- 99-10155-423 --.

<u>Column 140,</u>
Sequence ID No 2446, "99-1J051-154" should read -- 99-11051-154 --.
Sequence ID No 2458, primer, "8" should read -- S --.
Sequence ID No 2493, primer, "8" should read -- S --.

<u>Column 141,</u>
Sequence ID No 2524, primer, "8" should read -- S --.

<u>Column 142,</u>
Sequence ID No 2653, primer, "8" should read -- S --.

<u>Column 145,</u>
Sequence ID No 2834, $2^{nd}$ allele, "j" should read -- T --.

UNITED STATES PATENT AND TRADEMARK OFFICE
CERTIFICATE OF CORRECTION

PATENT NO. : 6,537,751 B1
DATED : March 25, 2003
INVENTOR(S) : Daniel Cohen, Ilya Chumakov and Marta Blumenfeld It is certified that error appears in the above-identified patent and that said Letters Patent is hereby corrected as shown below:

<u>Column 154,</u>
Sequence ID No 3501, "994649-251" should read -- 99-4649-251 --.

<u>Column 159,</u>
Sequence ID No 3885, "994762-114" should read -- 99-4762-114 --.

<u>Column 160,</u>
Table 9, Sequence ID No 2, line 2, "SRGC" should read -- SHGC --.

<u>Columns 161-162,</u>
Sequence ID No 242, last line, "R44970" should read -- R44970/ --.
Sequence ID No 245, line 5, "RR49984" should read -- RH49984 --.

<u>Columns 163-164,</u>
Sequence ID No 332, line 1, "/D25126" should read -- /D2S126 --.
Sequence ID No 497, line 2, "/RR63907/" should read -- /RH63907/ --.
Sequence ID Nos 499 and 503, line 1, "/D252336" should read -- /D2S2336 --.
Sequence ID Nos 507, 508, 509 and 510, "/D25309/" should read -- /D2S309/ --.

<u>Column 167-168,</u>
Sequence ID No 629, marker name, "9-1590-116" should read -- 9-15910-116 --.
Sequence ID No 645, line 8, "AFMa24Swd5" should read -- AFMa245wd5 --.

<u>Columns 171-172,</u>
Sequence ID No 1031, line 2, "D452603" should read -- D4S2603 --.
Sequence ID No 1104, line 2, "/SRGC4-" should read -- /SHGC4- --.

<u>Columns 173-174,</u>
Sequence ID No 1107, line 2, "/SRGC4-" should read -- /SHGC4 --.
Sequence ID No 1235, "/AFM119xb12/" should read -- /AFM119xh12/ --.

<u>Columns 175-176,</u>
Sequence ID No 1304, line 2, "/AFM320Xh1/" should read -- /AFM320xh1/ --.
Sequence ID No 1305, line 1, "/SHGC12090/" should read -- /SHGC-2090/ --.
Sequence ID No 1367, line 1, "/D95921/" should read -- /D9S921 --.

<u>Columns 177 -178,</u>
Sequence ID No 1394, line 1, "/AFMb3S6wg1/" should read -- /AFMb356wg1/ --.

UNITED STATES PATENT AND TRADEMARK OFFICE
CERTIFICATE OF CORRECTION

PATENT NO.    : 6,537,751 B1
DATED         : March 25, 2003
INVENTOR(S)   : Daniel Cohen, Ilya Chumakov and Marta Blumenfeld It is certified that error appears in the above-identified patent and that said Letters Patent is hereby corrected as shown below:

Column 179-180,
Sequence ID No 1433, (lines 2 and 3 omitted), should read -- G27696 / 625597 / EST91724 g27725 / SHGC-942 / Z16981 / RH49039 --.
Sequence ID No 1443, (line 2 omitted), should read -- g27270 / SHGC-3645 / Z17001 / RH13384/ --.

Columns 181-182,
Sequence ID No 1482, line 1, "/CHLC.GATA84D10/" should read -- /CHLC.GATA85D10 --.
Sequence ID No 1633, line 1, "/AFMa28Szb9/" should read -- /AFMa285zb9/ --.

Columns 185-186,
Sequence ID No 1784 line 2, "/SHGC3659/" should read -- SHGC-3659 --.
Sequence ID No 1881, line 1, "/Dl1S5924/" should read -- D11S924 --.
Sequence ID No 1886, marker name, "9-719-278" should read -- 9-7119-278 --.
Sequence ID No 1892, "/HSC2SC022/" should read -- /HSC25CO22/ --.
Sequence 1D No 1905, line 1, "/WI-112357/" should read -- WI-12357/ --.
Sequence ID No 1905, line 2, "/AFMb318z19/" should read -- /AFMb318zf9/ --.
Sequence ID Nos 1962 and 1963, "/AFMb004z19/" should read -- /AFMb004zf9/ --.

Columns 187-188,
Sequence ID No 2033, line 3, "15p13-q12;" should read -- 15p13-q11.1;1p11-q12; --.

Columns 189-190,
Sequence ID No 2445, line 3, "15p13-q12;" should read -- 15p13-q1 l.l;lp11-q12; --.
Sequence ID No 2675, line 2, "/R1150010/" should read -- /RH50010/ --.
Sequence ID No 2706, Column 3, "5q30.1" should read -- 5q31.1 --.
Sequence ID Nos 2706 and 2707, "/D5S4021" should read -- /D5S402/ --.

Columns 191-192,
Sequence ID No 2774, "/D17S9221" should read -- D17S922/ --.
Sequence ID No 2840, Lines 4-6,
"g2482/AFM240xg3/D5S500                    -- g2482/AFM240xg3/D5S500
245                        should read       g653/WI-12096/T61077/ --.
g653/WI-12096/T61077/"

Columns 193-194,
Sequence ID No 3188, "/EST25131/" should read -- /EST251317/ --.

Columns 195-196,
Sequence ID Nos 3241 and 3243, line 3, "/SRGC-" should read -- SHGC --.

UNITED STATES PATENT AND TRADEMARK OFFICE
CERTIFICATE OF CORRECTION

PATENT NO.    : 6,537,751 B1
DATED         : March 25, 2003
INVENTOR(S)   : Daniel Cohen, Ilya Chumakov and Marta Blumenfeld It is certified that error appears in the above-identified patent and that said Letters Patent is hereby corrected as shown below:

Columns 197-198,
Sequence ID No 3889, line 4, "/T726441" should read -- /T72644/ --.
Sequence ID Nos 233 and 235, Line 2, "/AFM093XGS/" should read -- /AFM093XG5/ --.
Sequence ID No 604, "/D25128/" should read -- /D2S128/ --.

Columns 199-200,
Sequence ID No 1005, "/D25280/" should read -- /D2S280/ --.
Sequence ID No 1196, "/D25318/" should read -- /D2S318/ --.

Columns 201-202,
Sequence ID No 1322, "/AFM289vfS" should read -- /AFM289vf5/ --.
Sequence ID No 1438, line 3, "/AFM317ycS/" should read -- /AFM317yc5/ --.

Columns 203-204,
Sequence ID No 3094, "/D25346" should read -- /D2S346/ --.

Column 214,
Sequence ID No 2495, "99-1381-256" should read -- 99-11381-256 --.

Column 222,
Sequence ID No 3411, "3q12-13" should read -- 13q12-13 --.

Column 225,
Sequence ID No 3757, "6p12.2-p12" should read -- 16p12.2-p12 --.

Signed and Sealed this

Sixteenth Day of December, 2003

JAMES E. ROGAN
*Director of the United States Patent and Trademark Office*